US011377440B2

(12) United States Patent
Fosbenner et al.

(10) Patent No.: US 11,377,440 B2
(45) Date of Patent: Jul. 5, 2022

(54) MODULATORS OF STIMULATOR OF INTERFERON GENES (STING)

(71) Applicant: GlaxoSmithKline Intellectual Property Development Limited, Middlesex (GB)

(72) Inventors: David T. Fosbenner, Collegeville, PA (US); Todd L. Graybill, Collegeville, PA (US); Jianxing Kang, Collegeville, PA (US); Bryan W. King, Collegeville, PA (US); Yunfeng Lan, Collegeville, PA (US); Lara Kathryn Leister, Collegeville, PA (US); Mukesh K. Mahajan, Collegeville, PA (US); John F. Mehlmann, Collegeville, PA (US); Angel I. Morales-Ramos, Collegeville, PA (US); George Scott Pesiridis, Collegeville, PA (US); Joshi M. Ramanjulu, Collegeville, PA (US); Joseph J. Romano, Collegeville, PA (US); Stuart Paul Romeril, Collegeville, PA (US); Mark J. Schulz, Collegeville, PA (US); Huiqiang Zhou, Collegeville, PA (US); Junya Qu, Collegeville, PA (US)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 26 days.

(21) Appl. No.: 16/652,221

(22) PCT Filed: Oct. 4, 2018

(86) PCT No.: PCT/IB2018/057726
§ 371 (c)(1),
(2) Date: Mar. 30, 2020

(87) PCT Pub. No.: WO2019/069270
PCT Pub. Date: Apr. 11, 2019

(65) Prior Publication Data
US 2020/0291001 A1 Sep. 17, 2020

Related U.S. Application Data

(60) Provisional application No. 62/568,420, filed on Oct. 5, 2017.

(51) Int. Cl.
C07D 403/14 (2006.01)
C07D 401/14 (2006.01)
C07D 405/14 (2006.01)

(52) U.S. Cl.
CPC ......... C07D 403/14 (2013.01); C07D 401/14 (2013.01); C07D 405/14 (2013.01)

(58) Field of Classification Search
CPC ... C07D 403/14; C07D 405/14; C07D 401/14
(Continued)

(56) References Cited

U.S. PATENT DOCUMENTS

| 10,189,820 B2 * | 1/2019 | Mehlmann | C07D 498/18 |
|---|---|---|---|
| 10,981,901 B1 * | 4/2021 | Romano | C07D 405/14 |
| 2021/0139473 A1 * | 5/2021 | Charnley | A61P 31/20 |

FOREIGN PATENT DOCUMENTS

| CA | 2 906 137 A1 | 3/2017 |
|---|---|---|
| WO | 2015185565 | * 10/2015 |
| WO | WO 2015/185565 A1 | 12/2015 |
| WO | WO 2017/049401 A1 | 3/2017 |

(Continued)

OTHER PUBLICATIONS

International Search Report for International Application No. PCT/IB2018/057726, dated Jan. 29, 2019.
(Continued)

Primary Examiner — Kahsay Habte
(74) Attorney, Agent, or Firm — Stanek Lemon Crouse & Meeks, PA

(57) ABSTRACT

Disclosed are compounds having the formula: (I) wherein q, r, s, A, B, C, $R^{A1}$, $R^{A2}$, $R^{B1}$, $R^{B2}$, $R^{C1}$, $R^{C2}$, $R^3$, $R^4$, $R^5$, $R^6$, $R^{14}$, $R^{15}$, $R^{16}$, $R^{17}$, $R^x$, and $R^y$ are as defined herein, or a tautomer thereof, or a salt, particularly a pharmaceutically acceptable salt, thereof.

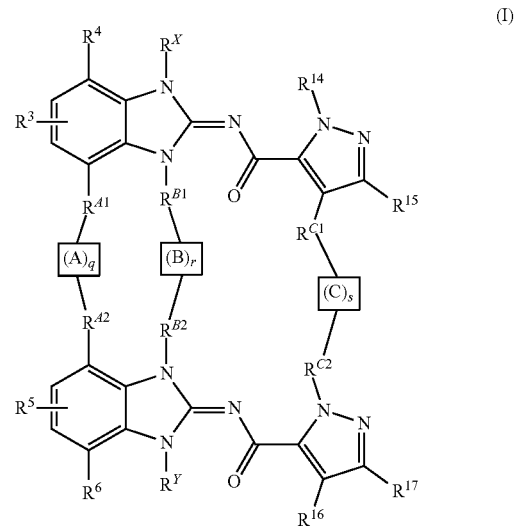

19 Claims, No Drawings

(58) Field of Classification Search
USPC .................................................. 514/234.5
See application file for complete search history.

(56) References Cited

FOREIGN PATENT DOCUMENTS

WO     WO 2017/175147 A1    10/2017
WO     WO 2017/175156 A1    10/2017

OTHER PUBLICATIONS

Written Opinion of the International Searching Authority for International Application No. PCT/IB2018/057726, dated Jan. 29, 2019.

* cited by examiner

MODULATORS OF STIMULATOR OF INTERFERON GENES (STING)

RELATED APPLICATION

The present application claims priority from U.S. Provisional Application No. 62/568,420 filed on Oct. 5, 2017, the entire contents of which is incorporated herein by reference.

FIELD OF THE INVENTION

The present invention relates to heterocyclic amides that are useful as modulators of transmembrane protein 173 (TMEM173), which is also known as STING (Stimulator of Interferon Genes)) and methods of making and using the same.

BACKGROUND OF THE INVENTION

Vertebrates are constantly threatened by the invasion of microorganisms and have evolved mechanisms of immune defense to eliminate infective pathogens. In mammals, this immune system comprises two branches; innate immunity and adaptive immunity. The innate immune system is the first line of defense which is initiated by Pattern Recognition Receptors (PRRs) which detect ligands from the pathogens as well as damage associated molecular patterns (Takeuchi O. et al, *Cell,* 2010: 140, 805-820). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signaling molecule in the innate immune response to cytosolic nucleic acids (Ishikawa H and Barber G N, *Nature,* 2008: 455, 674-678; WO2013/1666000). Activation of STING results in up-regulation of IRF3 and NFκB pathways leading to induction of Interferon-β and other cytokines. STING is critical for responses to cytosolic DNA of pathogen or host origin, and of unusual nucleic acids called Cyclic Dinucleotides (CDNs)

CDNs were first identified as bacterial secondary messengers responsible for controlling numerous responses in the prokaryotic cell. Bacterial CDNs, such as c-di-GMP are symmetrical molecules characterized by two 3',5' phosphodiester linkages.

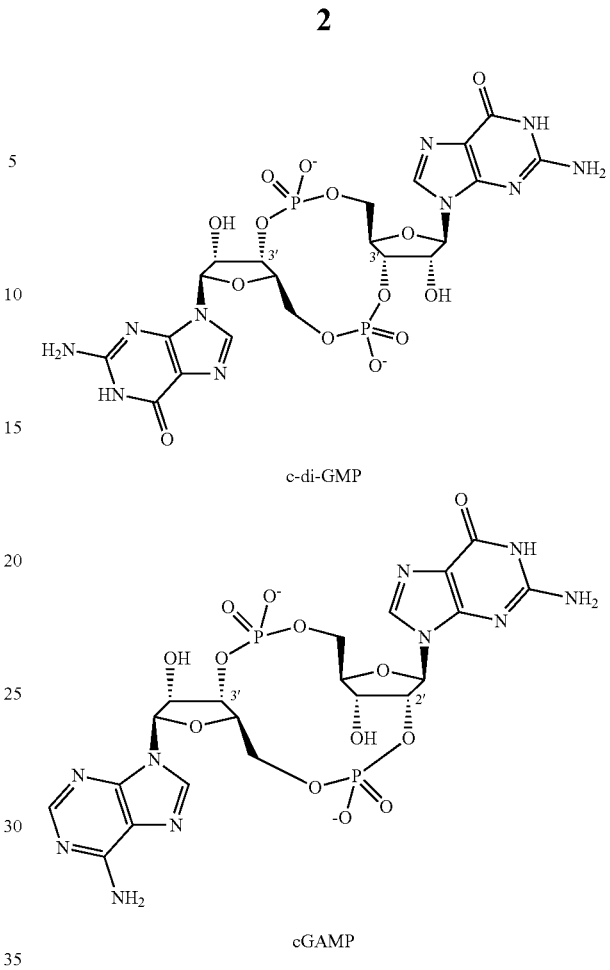

c-di-GMP cGAMP

Direct activation of STING by bacterial CDNs has recently been confirmed through X-ray crystallography (Burdette D L and Vance R E, *Nature Immunology,* 2013: 14, 19-26). Bacterial CDNs and their analogues have consequently attracted interest as potential vaccine adjuvants (Libanova R. et al, *Microbial Biotechnology* 2012: 5, 168-176; WO2007/054279, WO2005/087238).

More recently, the response to cytosolic DNA has been elucidated and shown to involve generation, by an enzyme called cyclic GMP-AMP synthase (cGAS, previously known as C6orf150 or MB21 D1), of a novel mammalian CDN signaling molecule identified as cGAMP, which then activates STING. Unlike bacterial CDNs, cGAMP is an unsymmetrical molecule characterized by its mixed 2',5' and 3',5' phosphodiester linkages. (Gao P et al, *Cell,* 2013: 153, 1094-1107). Interaction of cGAMP (II) with STING has also been demonstrated by X-ray crystallography (Cai X et al, *Molecular Cell,* 2014: 54, 289-296).

Interferon was first described as a substance which could protect cells from viral infection (Isaacs & Lindemann, *J. Virus Interference. Proc. R. Soc. Lon. Ser. B. Biol. Sci.* 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could modulate the innate immune response, including the activation or inhibition of type I interferon production and other cytokines, could become an important strategy for the treatment or prevention of human diseases including viral infections and autoimmune disease. This type of immunomodulatory strategy has the potential to identify compounds which may be useful not only in infectious diseases innate immunity but also in cancer (Zitvogel, L., et al., *Nature Reviews Immunology*, 2015 15(7), p405-414), allergic diseases (Moisan J. et al, *Am. J. Physiol. Lung Cell Mol. Physiol.*, 2006: 290, L987-995), neurodegenerative diseases such as amyotrophic lateral sclerosis and multiple sclerosis (Lemos, H. et al., *J. Immunol.*, 2014: 192(12), 5571-8; Cirulli, E. et al., *Science*, 2015: 347(6229), 1436-41; Freischmidt, A., et al., *Nat. Neurosci.*, 18(5), 631-6), other inflammatory conditions such as irritable bowel disease (Rakoff-Nahoum S., *Cell.*, 2004, 23, 118(2): 229-41), and as vaccine adjuvants (Persing et al. *Trends Microbiol.* 2002: 10(10 Suppl), S32-7 and Dubensky et al., *Therapeutic Advances in Vaccines*, published on line Sep. 5, 2013).

STING is essential for antimicrobial host defense, including protection against a range of DNA and RNA viruses and bacteria (reviewed in Barber et al. *Nat. Rev. Immunol.* 2015: 15(2): 87-103, Ma and Damania, *Cell Host & Microbe*, 2016: 19(2) 150-158). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm et al., *Nat Comm.* 2016: 7:10680; Ma et al, *PNAS* 2015: 112(31) E4306-E4315; Wu et al, *Cell Host Microbe* 2015: 18(3) 333-44; Liu et al, *J Virol* 2016: 90(20) 9406-19; Chen et al., *Protein Cell* 2014: 5(5) 369-81; Lau et al, *Science* 2013: 350(6260) 568-71; Ding et al, *J Hepatol* 2013: 59(1) 52-8; Nitta et al, *Hepatology* 2013 57(1) 46-58; Sun et al, *PloS One* 2012: 7(2) e30802; Aguirre et al, *PloS Pathog* 2012: 8(10) e1002934; Ishikawa et al, *Nature* 2009: 461(7265) 788-92). Thus, small molecule activation of STING could be beneficial for treatment of these infectious diseases.

In contrast, increased and prolonged type I IFN production is associated with a variety of chronic infections, including Mycobacteria (Collins et al, *Cell Host Microbe* 2015: 17(6) 820-8); Wassermann et al., *Cell Host Microbe* 2015: 17(6) 799-810; Watson et al., *Cell Host Microbe* 2015: 17(6) 811-9), Franciscella (Storek et al., *J Immunol.* 2015: 194(7) 3236-45; Jin et al., *J Immunol.* 2011: 187(5) 2595-601), Chlamydia (Prantner et al., *J Immunol* 2010: 184(5) 2551-60; *Plasmodium* (Sharma et al., *Immunity* 2011: 35(2) 194-207. and HIV (Herzner et al., *Nat Immunol* 2015 16(10) 1025-33; Gao et al., *Science* 2013: 341(6148) 903-6. Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow Y J, et al., *Nat. Genet.* 2006; 38(8) 38917-920, Stetson D B, et al., *Cell* 2008; 134 587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber J. P. et al *J Immunol* 2010: 185, 813-817).

Compounds that bind to STING and act as agonist have been shown to induce type 1 interferons and other cytokines on incubation with human PBMCs. Compounds which induce human interferons may be useful in the treatment of various disorders, for example the treatment of allergic diseases and other inflammatory conditions for example allergic rhinitis and asthma, the treatment of infectious diseases, neurodegenerative disease, pre-cancerous syndromes and cancer, and may also be useful as immugenic composition or vaccine adjuvants. Compounds that bind to STING may act as antagonists and could be useful in the treatment of inflammation, for example of autoimmune diseases, metabolic disease, neuroinflammation and inflammation in the heart that lead to cardiac disease (such as myocardial infarction) as suggested by recent studies. (Ridker et al., *N ENG J Med* 2017, 377 (12), 1119-1131; King et al., *Nat Med.* 2017 December; 23(12):1481-1487.) Based on recent studies, it is believed that inhibiting cGas or STING may be used to treat or prevent metabolic disease (such as insulin resistance, Nonalcoholic fatty liver disease (NAFLD)/Nonalcoholic steatohepatitis (NASH), obesity, diabetes, high blood pressure, fatty liver and cardiovascular diseases. (Qiao. Et al., *Metabolism Clinical and Experimental* (2007), 81, 13-24; Bai et al., *PNAS* (2017), 114, no. 46, 12196-12201; Iracheta et al., *Journal of Biological Chemistry* (2016) 52, 26794-26805; Cruz. et al., *Molecular Metabolism* (2018) 1-11, Patrasek et al., *Proc Natl Acad Sci* (2013), 110(41):16544-9, Mao et al., *Arterioscler Thromb Vasc Biol.* (2017) 37(5): 920-929)

It is envisaged that targeting STING with activation or inhibiting agents may be a promising approach for treating diseases and conditions in which modulation for the type 1 IFN pathway is beneficial, including inflammatory, allergic and autoimmune diseases, infectious diseases, cancer, pre-cancerous syndromes, tumor metastasis, metabolic disease, cardiovascular disease and as immugenic composition or vaccine adjuvants.

Skin cancers and various skin viral infections involve immune privileged environment and activation of local immune response to the lesions may be a topical therapeutic approach. STING agonists may be used for treating viral warts, superficial skin cancers and premalignant actinic keratoses. By a dual mechanism of action, STING activation (e.g., via microneedle patch delivery or topical formulation) may be used to control HPV directly via antiviral type I interferon production and indirectly by enhancing the adaptive immune response downstream of innate immune activation. STING agonist can activate the innate immune response in the lesion and drive the anti-HPV T-cell response.

Recent evidence has indicated that spontaneous activation of the STING pathway within tumor-resident dendritic cells leads to type I IFN production and adaptive immune responses against tumors. Furthermore, activation of this pathway in antigen presenting cells (APCs) within the tumor microenvironment drives the subsequent T-cell priming against tumor-associated antigens. Corrales and Gajewski, *Clin Cancer Res;* 21(21); 4774-9, 2015.

International Patent Applications WO2014/093936, WO2014/189805, WO2013/185052, U.S. 2014/0341976, WO 2015/077354, WO2015/185565, PCT/IB2017/051945 and GB 1501462.4 disclose certain cyclic di-nucleotides and their use in inducing an immune response via activation of STING. International Patent Applications WO2017/106740 describes the use of cyclic-di-nucleotide and related scaffold that measurably inhibit STING signaling and methods of identifying potent inhibitors of STING signaling. International Patent Application WO 2017/175147 and WO 2017/175156 describes the use of heterocyclic amides and their anaglogues as STING modulators.

The compounds of this invention modulate the activity of STING, and accordingly, may provide a beneficial therapeutic impact in treatment of diseases, disorders and/or conditions in which modulation of STING (Stimulator of Interferon Genes) is beneficial, for example for inflammation, allergic and autoimmune diseases, metabolic disease, cardiovascular disease, infectious diseases, cancer, pre-cancerous syndromes and as vaccine adjuvants.

SUMMARY OF THE INVENTION

The invention is directed to a compound according to Formula (I):

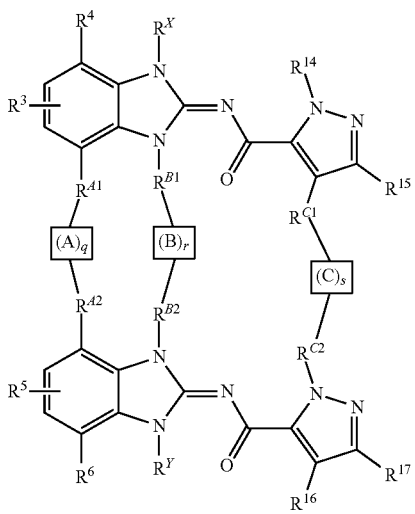

(I)

wherein:
  q is 0 or 1;
  r is 0 or 1;
  s is 0 or 1;
    wherein q+r+s=1 or 2;
  when q is 0, $R^{A1}$ and $R^{A2}$ are each independently H, halogen, hydroxy, —O—P(O)(OH)$_2$, —O—P(O)(R$^I$)(R$^{II}$), —N(R$^e$)(R$^f$), —CO$_2$R$^f$, —N(R$^f$)COR$^b$, —N(R$^g$)SO$_2$(C$_1$-C$_4$alkyl)-N(R$^e$)(R$^f$), —N(R$^g$)CO(C$_1$-C$_4$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
    wherein the (C$_1$-C$_6$alkyl) of said optionally substituted (C$_1$-C$_6$alkyl), optionally substituted (C$_1$-C$_6$alkyl) oxy-, optionally substituted (C$_1$-C$_6$alkyl)amino- and optionally substituted (C$_1$-C$_6$alkyl)(C$_1$-C$_4$alkyl) amino- is optionally substituted by 1-4 substituents each independently selected from hydroxy, —O—P(O)(OH)$_2$, —O—P(O)(R$^I$)(R$^{II}$),
  C$_1$-C$_4$alkoxy-, —N(R$^e$)(R$^f$), —CO$_2$(R$^f$), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from C$_1$-C$_4$alkyl, halogen, hydroxy, —O—P(O)(OH)$_2$, —O—P(O)(R$^I$)(R$^{II}$), amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$)(R$^{II}$), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$)(R$^{II}$), —C$_1$-C$_4$alkyl-(C$_1$-C$_4$alkoxy) and C$_1$-C$_4$alkoxy-(C$_1$-C$_4$alkoxy)-;
  when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, option ally substituted 4-6 membered heterocycloalkyl, optionally substituted phenyl, optionally substituted 5-6 membered heteroaryl, or optionally substituted 9-10 membered heteroaryl,
    wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(R$^I$)(R$^{II}$), —OR$^c$, —NH$_2$, —NR$^c$R$^e$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;
  when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;
  when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-,
    wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —O—P(O)(OH)$_2$, —O—P(O)(R$^I$)(R$^{II}$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$)(R$^{II}$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_1$-C$_4$alkoxy)-, —(C$_1$-C$_4$alkoxyl)-O—P(O)(OH)$_2$, —(C$_1$-C$_4$alkoxyl)-O—P(O)(R$^I$)(R$^{II}$) and C$_1$-C$_4$alkoxy-(C$_1$-C$_4$alkoxy)-;

when r is 1, R$^{B1}$ and R$^{B2}$ are each independently —CR$^d$R$^f$—, and B, taken together with R$^{B1}$ and R$^{B2}$, forms a linking group, wherein B is a bond or B is -halo(C$_1$-C$_{10}$alkyl)-, optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted C$_3$-C$_6$cycloalkyl, optionally substituted phenyl, optionally substituted 4-6 membered heterocycloalkyl, optionally substituted 5-6 membered heteroaryl, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl)-C$_1$-C$_4$alkyl-, wherein the alkyl moiety of said optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl-C$_1$-C$_4$alkyl)- is optionally substituted by 1-4 substituents each independently selected from —C$_1$-C$_4$alkyl, halogen, halo(C$_1$-C$_4$alkyl), —OH, —O—P(O)(OH)$_2$, —O—P(O)(R$^I$)(R$^{II}$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted C$_3$-C$_6$cycloalkyl, optionally substituted phenyl, optionally substituted 4-6 membered heterocycloalkyl, optionally substituted 5-6 membered heteroaryl, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl)-C$_1$-C$_4$alkyl- is optionally substituted by 1-4 substituents each independently selected from halogen, hydroxy, —O—P(O)(OH)$_2$, —O—P(O)(R$^I$)(R$^{II}$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy) O—P(O)(OH)$_2$, —(C$_2$-C$_4$alkoxy)-O—P(O)(R$^I$)(R$^{II}$), and C$_1$-C$_4$alkoxy-(C$_1$-C$_4$alkoxy)-;

when s is 1, R$^{C1}$ and R$^{C2}$ are each independently —CH$_2$—, and C, taken together with R$^{C1}$ and R$^{C2}$ forms a linking group, wherein C is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1 or 2 substituents each independently selected from halogen, halo(C$_1$-C$_4$alkyl), —OH, —O—P(O)(OH)$_2$, —O—P(O)(R$^I$)(R$^{II}$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_5$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$)(R$^{II}$), amino, (C$_1$-C$_4$alkyl)amino-, (C$_1$-

$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I$)($R^{II}$), and $C_1$-$C_4$alkoxy-($C_1$-$C_4$alkoxy)-;

$R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^4$ and $R^6$ are each independently selected from H, halogen, halo($C_1$-$C_6$alkyl), halo($C_1$-$C_6$alkoxy)-,
hydroxy, —O—P(O)(OH)$_2$, —O—P(O)($R^I$)($R^{II}$), —NH$_2$, —$NR^cR^c$, —$NR^cR^d$, —$COR^c$, —$CO_2R^c$, —N($R^d$)$COR^c$, —N($R^d$)$SO_2R^c$, —N($R^g$)$SO_2$($C_1$-$C_2$alkyl)-N($R^h$)($R^f$), —N($R^g$)CO($C_1$-$C_2$alkyl)-N($R^h$)($R^f$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected
from —OH, —O—P(O)(OH)$_2$, —O—P(O)($R^I$)($R^{II}$), —$OR^c$, —NH$_2$, —$NR^cR^c$, —$NR^cR^d$, —CO$_2$H, —$CO_2R^c$, —$OCOR^c$, —CO$_2$H, —$CO_2R^c$, —$SOR^c$, —$SO_2R^c$, —CONH$_2$, —$CONR^cR^d$, —SO$_2$NH$_2$, —$SO_2NR^cR^d$, —OCONH$_2$, —$OCONR^cR^d$, —$NR^d$-$COR^c$, —$NR^d SOR^c$, —$NR^d CO_2R^c$, —$NR^d SO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, —($C_1$-$C_4$alkyl)-O—P(O)(OH)$_2$, —($C_1$-$C_4$alkoxyl)-O—P(O)($R^I$)($R^{II}$), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxyl)-O—P(O)($R^I$)($R^{II}$), $C_1$-$C_4$alkoxy-($C_1$-$C_4$alkoxy)-, —$COR^d$, —CON($R^d$)($R^f$), and $CO_2R^d$;

$R^{14}$ is optionally substituted $C_1$-$C_4$alkyl, wherein said optionally substituted $C_1$-$C_4$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;

$R^{16}$ is H, halogen, or $C_1$-$C_4$alkyl;

$R^{15}$ and $R^{17}$ are each independently H, cyclopropyl, or $C_1$-$C_4$alkyl;

$R^a$ is H, —$R^c$, —$COR^c$, —CO$_2$H, —$CO_2R^c$, —$SOR^c$, —$SO_2R^c$, —CONH$_2$, —$CONR^cR^d$, —SO$_2$NH$_2$, or —$SO_2NR^cR^d$;

each $R^b$ is independently $C_1$-$C_4$alkyl,
halo($C_1$-$C_4$alkyl), —($C_1$-$C_4$alkyl)-OH, —($C_1$-$C_4$alkyl)-O—P(O)(OH)$_2$, —($C_1$-$C_4$alkoxyl)-O—P(O)($R^I$)($R^{II}$), —($C_1$-$C_4$alkyl)-O—($C_1$-$C_4$alkyl), —($C_1$-$C_4$alkyl)-N($R^e$)(R), —($C_1$-$C_4$alkyl)-O—CO($C_1$-$C_4$alkyl), or —($C_1$-$C_4$alkyl)-CO—O—($C_1$-$C_4$alkyl);

each $R^c$ is independently $C_1$-$C_4$alkyl,
halo($C_1$-$C_4$alkyl), —($C_1$-$C_4$alkyl)-OH, —($C_1$-$C_4$alkyl)-O—P(O)(OH)$_2$, —($C_1$-$C_4$alkoxyl)-O—P(O)($R^I$)($R^{II}$), —($C_1$-$C_4$alkyl)-O—($C_1$-$C_4$alkyl), —($C_1$-$C_4$alkyl)-N($R^e$)(R), —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl,
wherein the $C_3$-$C_6$cycloalkyl, phenyl, 4-6 membered heterocycloalkyl, 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, —O—P(O)(OH)$_2$, —O—P(O)($R^I$)($R^{II}$), amino, —($C_1$-$C_4$alkyl)NH$_2$, ($C_1$-$C_4$alkyl)amino-, ($C_1$-$C_4$alkyl)($C_1$-$C_4$alkyl)amino-, —$C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxyl)-O—P(O)(OH)$_2$, —($C_2$-$C_4$alkoxyl)-O—P(O)($R^I$)($R^{II}$), $C_1$-$C_4$alkoxy-($C_1$-$C_4$alkoxy)-, —$COR^d$, —CON($R^d$)($R^f$), and $CO_2R^d$;

each $R^d$ is independently H or $C_1$-$C_4$alkyl;

each $R^e$ is independently H,
$C_1$-$C_4$alkyl, —CO($C_1$-$C_4$alkyl), —OCO($C_1$-$C_4$alkyl), —CO$_2$($C_1$-$C_4$alkyl), —($C_1$-$C_4$alkyl)NH$_2$, —($C_1$-$C_4$alkyl) $C_1$-$C_4$alkoxy, —CO-(optionally substituted 5-6 membered heterocycloalkyl), —CO($C_1$-$C_4$alkyl)-(optionally substituted 5-6 membered heterocycloalkyl), —CO (optionally substituted 5-6 membered heteroaryl), or —CO($C_1$-$C_4$alkyl)-(optionally substituted 5-6 membered heteroaryl),
wherein the optionally substituted 5-6 membered heterocycloalkyl or optionally substituted 5-6 membered heteroaryl is optionally substituted 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-

C₄alkoxy)-, —(C₂-C₄alkoxy) O—P(O)(OH)₂, —(C₂-C₄alkoxy)-O—P(O)(R$^I$)(R$^{II}$), C₁-C₄alkoxy-(C₁-C₄alkoxy)-, —COR$^d$, —CON(R$^d$)(R$^f$), and CO₂R$^d$;

each R$^f$ is independently H or C₁-C₄alkyl;

R$^g$ and R$^h$ are each independently H or C₁-C₄alkyl or R$^g$ and R$^h$, taken together with the atom or atoms through which they are connected, form a 5-6 membered ring;

and each occurrence of R$^I$ and R$^{II}$ are independently (C₁-C₆alkyl)oxy-; and at least one of R$^X$ or R$^Y$ is independently C₁-C₄alkyl and the other one is H, or both R$^X$ and R$^Y$ are independently C₁-C₄alkyl;

or a tautomer thereof;

or a salt thereof.

It is to be understood that the references herein to compounds of Formula (I), and salts thereof covers the compounds of Formula (I), as free bases, or as salts thereof, for example as pharmaceutically acceptable salts thereof. Thus, in one embodiment, the invention is directed to compounds of Formula (I), as the free base. In another embodiment, the invention is directed to compounds of Formula (I), and salts thereof. In a further embodiment, the invention is directed to compounds of Formula (I), and pharmaceutically acceptable salts thereof.

The compounds according to Formula (I), or salts, particularly pharmaceutically acceptable salts, thereof, are modulators of STING. Accordingly, this invention provides a compound of Formula (I) or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a STING-mediated disease or disorder, specifically, for use in the treatment of a disease mediated by agonism or antagonism of STING. The invention also provides a compound of Formula (I), or a salt thereof, particularly a pharmaceutically acceptable salt thereof, for use in the manufacture of a medicament for the treatment of a STING-mediated disease or disorder.

The invention is also directed to a method of modulating STING, which method comprises contacting a cell with a compound according to Formula (I), or a salt, particularly a pharmaceutically acceptable salt, thereof. The invention is further directed to a method of treating a STING-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Such STING-mediated diseases or disorders include inflammation, allergic and autoimmune diseases, infectious diseases, cancer, pre-cancerous syndromes, metabolic diseases, and cardiovascular diseases. In addition, modulators of STING may be useful as immugenic composition or vaccine adjuvants.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a STING-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE APPLICATION

According to one aspect of the present invention, this invention relates to compounds of Formula (I)

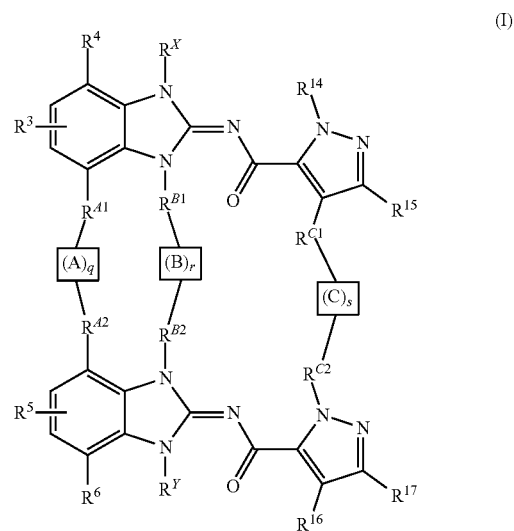

wherein:
q is 0 or 1;
r is 0 or 1;
s is 0 or 1;
wherein q+r+s=1 or 2;
when q is 0, R$^{A1}$ and R$^{A2}$ are each independently H, halogen, hydroxy, —O—P(O)(OH)₂, —(C₂-C₄alkoxy)-O—P(O)(R$^I$)(R$^{II}$), —N(R$^e$)(R$^f$), —CO₂R$^f$, —N(R$^f$)COR$^b$, —N(R$^g$)SO₂(C₁-C₄alkyl)-N(R$^e$)(R$^f$), —N(R$^g$)CO(C₁-C₄alkyl)-N(R$^h$)(R), optionally substituted (C₁-C₆alkyl), optionally substituted (C₁-C₆alkyl)oxy-, optionally substituted (C₁-C₆alkyl)amino-, and optionally substituted (C₁-C₆alkyl)(C₁-C₄alkyl)amino-,
wherein the (C₁-C₆alkyl) of said optionally substituted (C₁-C₆alkyl), optionally substituted (C₁-C₆alkyl)oxy-, optionally substituted (C₁-C₆alkyl)amino- and optionally substituted (C₁-C₆alkyl)(C₁-C₄alkyl)amino- is optionally substituted by 1-4 substituents each independently selected from
hydroxy, —O—P(O)(OH)₂, —(C₂-C₄alkoxy)-O—P(O)(R$^I$)(R$^{II}$),
C₁-C₄alkoxy-, —N(R$^e$)(R$^f$), —CO₂(R$^1$), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from C₁-C₄alkyl, halogen, hydroxy, —O—P(O)(OH)₂, —O—P(O)(R$^I$)(R$^{II}$), amino, (C₁-C₆alkyl)amino-, (C₁-C₆alkyl)(C₁-C₆alkyl)amino-, —(C₁-C₆alkyl)-NH₂, halo(C₁-C₆alkyl), hydroxy-(C₁-C₄alkyl)-, —(C₁-C₄alkyl)-O—P(O)(OH)₂, —(C₁-C₄alkoxyl)-O—P(O)(R$^I$)(R$^{II}$), halo(C₁-C₄alkoxy)-, C₁-C₄alkoxy-,
hydroxy-(C₂-C₄alkoxy)-, —(C₂-C₄alkoxy)-O—P(O)(OH)₂, —(C₂-C₄alkoxy)-O—P(O)(R$^I$)(R$^{II}$), —Ci-C₄alkyl-(C₁-C₄alkoxy) and C₁-C₄alkoxy-(C₁-C₄alkoxy)-;

when r is 0, $R^{B1}$ and $R^{B2}$ are each independently H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl, wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —O—P(O)(OH)$_2$, —O—P(O)($R^I$)($R^{II}$), —$OR^c$, —$NH_2$, —$NR^cR^c$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$;

when s is 0, $R^{C1}$ is H, halogen, or $C_1$-$C_4$alkyl and $R^{C2}$ is optionally substituted $C_1$-$C_4$alkyl, wherein said optionally substituted $C_1$-$C_4$alkyl group is optionally substituted by a substituent selected from —$OR^c$, —$NR^cR^d$, —$CO_2R^c$, —$CONR^cR^d$, —$SO_2NR^IR^d$, and —$OCONR^cR^d$;

when q is 1, $R^{A1}$ and $R^{A2}$ are each independently —$CH_2$—, —$NR^e$—, or —O—, and A, taken together with $R^{A1}$ and $R^{A2}$, forms a linking group, wherein A is -halo($C_1$-$C_{12}$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, halo($C_1$-$C_4$alkyl), —OH, —O—P(O)(OH)$_2$, —O—P(O)($R^I$)($R^{II}$), —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and the $C_3$-$C_6$cycloalkyl, phenyl, 4-6 membered heterocloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, —($C_1$-$C_4$alkoxyl)-O—P(O)(OH)$_2$, —($C_1$-$C_4$alkoxyl)-O—P(O)($R^I$)($R^{II}$), and $C_1$-$C_4$alkoxy-($C_1$-$C_4$alkoxy)-;

when r is 1, $R^{B1}$ and $R^{B2}$ are each independently —$CR^dR^f$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1-4 substituents each independently selected from —$C_1$-$C_4$alkyl, halogen, halo($C_1$-$C_4$alkyl), —OH, —O—P(O)(OH)$_2$, —O—P(O)($R^I$)($R^{II}$), —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)O—P(O)(OH)$_2$, —($C_2$-$C_4$alkoxyl)-O—P(O)($R^I$)($R^{II}$), and $C_1$-$C_4$alkoxy-($C_1$-$C_4$alkoxy)-;

when s is 1, $R^{C1}$ and $R^{C2}$ are each independently —CH$_2$—, and C, taken together with $R^{C1}$ and $R^{C2}$ forms a linking group, wherein C is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1 or 2 substituents each independently selected from halogen, halo(C$_1$-C$_4$alkyl), —OH, —O—P(O)(OH)$_2$, —O—P(O)(R$^I$)(R$^{II}$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$)(R$^{II}$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxyl)-O—P(O)(R$^I$)(R$^{II}$), and C$_1$-C$_4$alkoxy-(C$_1$-C$_4$alkoxy)-;

$R^3$ and $R^5$ are each independently —CON(R$^d$)(R$^f$), or one of $R^3$ and $R^5$ is —CON(R$^d$)(R$^f$), and the other of $R^3$ and $R^5$ is H, COOH or —CO$_2$(R$^c$);

$R^4$ and $R^6$ are each independently selected from H, halogen, halo(C$_1$-C$_6$alkyl), halo(C$_1$-C$_6$alkoxy)-, hydroxy, —O—P(O)(OH)$_2$, —O—P(O)(R$^I$)(R$^{II}$), —NH$_2$, —NR$^c$R$^c$, —NR$^c$R$^d$, —COR$^c$, —CO$_2$R$^c$, —N(R$^d$)COR$^c$, —N(R$^d$)SO$_2$R$^c$, —N(R$^g$)SO$_2$(C$_1$-C$_2$alkyl)-N(R$^h$)(R$^f$), —N(R$^g$)CO(C$_1$—C$_2$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-, wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from —OH, —O—P(O)(OH)$_2$, —O—P(O)(R$^I$)(R$^{II}$), —OR$^c$, —NH$_2$, —NR$^c$R$^c$, —NR$^c$R$^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$)(R$^{II}$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), hydroxy-(C$_1$-C$_4$alkyl)-, —(C$_1$-C$_4$alkyl)-O—P(O)(OH)$_2$, —(C$_1$-C$_4$alkoxyl)-O—P(O)(R$^I$)(R$^{II}$), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxyl)-O—P(O)(R$^I$)(R$^{II}$), —C$_1$-C$_4$alkoxy-(C$_1$-C$_4$alkoxy)-, —COR$^d$, —CON(R$^d$)(R$^f$), and —C$_2$R$^d$;

$R^{14}$ is optionally substituted C$_1$-C$_4$alkyl, wherein said optionally substituted C$_1$-C$_4$alkyl is optionally substituted by a substituent selected from —OR$^c$, —NR$^c$R$^d$, —CO$_2$R$^c$, —CONR$^c$R$^d$, —SO$_2$NR$^I$R$^d$, and —OCONR$^c$R$^d$;

$R^{16}$ is H, halogen, or C$_1$-C$_4$alkyl;

$R^{15}$ and $R^{17}$ are each independently H, cyclopropyl, or C$_1$-C$_4$alkyl;

$R^a$ is H, —R$^c$, —COR$^c$, —CO$_2$H, —CO$_2$R$^c$, —SOR$^c$, —SO$_2$R$^c$, —CONH$_2$, —CONR$^c$R$^d$, —SO$_2$NH$_2$, or —SO$_2$NR$^c$R$^d$;

each $R^b$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkoxyl)-O—P(O)(R$^I$)(R$^{II}$), —(C$_1$-C$_4$alkyl)-O—(C$_1$-C$_4$alkyl), —(C$_1$-C$_4$alkyl)-N(R$^e$)(R$^f$), —(C1-C4alkyl)-O—CO(C$_1$-C$_4$alkyl), or —(C1-C4alkyl)-CO—O—(C$_1$-C$_4$alkyl);

each $R^c$ is independently C$_1$-C$_4$alkyl, halo(C$_1$-C$_4$alkyl), —(C$_1$-C$_4$alkyl)-OH, —(C$_1$-C$_4$alkyl)-O—P(O)(OH)$_2$, —(C$_1$-C$_4$alkoxyl)-O—P(O)(R$^I$)(R$^{II}$), —(C$_1$-C$_4$alkyl)-O—(C$_1$-C$_4$alkyl), —(C$_1$-C$_4$alkyl)-N(R$^e$)(R$^f$), —(C$_1$-C$_4$alkyl)-O—CO(C$_1$-C$_4$alkyl), —(C$_1$-C$_4$alkyl)-CO—O—(C$_1$-C$_4$alkyl), optionally substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl, wherein the C$_3$-C$_6$cycloalkyl, phenyl, 4-6 membered heterocycloalkyl, 5-6 membered heteroaryl or optionally substituted 9-10 membered heteroaryl moiety of said substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, —O—P(O)(OH)$_2$, —O—P(O)(R$^I$)(R$^{II}$), amino, —($C_1$-$C_4$alkyl)NH$_2$, ($C_1$-$C_4$alkyl)amino-, ($C_1$-$C_4$alkyl)($C_1$-$C_4$alkyl)amino-, —$C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxyl)-O—P(O)(R$^I$)(R$^{II}$), $C_1$-$C_4$alkoxy-($C_1$-$C_4$alkoxy)-, —COR$^d$, —CON(R$^d$)(R$^f$), and CO$_2$R$^d$;

each R$^d$ is independently H or $C_1$-$C_4$alkyl;

each R$^e$ is independently H, $C_1$-$C_4$alkyl, —CO($C_1$-$C_4$alkyl), —OCO($C_1$-$C_4$alkyl), —CO$_2$($C_1$-$C_4$alkyl), —($C_1$-$C_4$alkyl)NH$_2$, —($C_1$-$C_4$alkyl) $C_1$-$C_4$alkoxy, —CO-(optionally substituted 5-6 membered heterocycloalkyl), —CO($C_1$-$C_4$alkyl)-(optionally substituted 5-6 membered heterocycloalkyl), —CO (optionally substituted 5-6 membered heteroaryl), or —CO($C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—P(O)(OH)$_2$, —O—P(O)(R$^I$)(R$^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy) O—P(O)(OH)$_2$, —($C_2$-$C_4$alkoxyl)-O—P(O)(R$^I$)(R$^{II}$), $C_1$-$C_4$alkoxy-($C_1$-$C_4$alkoxy)-, —COR$^d$, —CON(R$^d$)(R$^f$), and CO$_2$R$^d$;

each R$^f$ is independently H or $C_1$-$C_4$alkyl;

R$^g$ and R$^h$ are each independently H or $C_1$-$C_4$alkyl or R$^g$ and R$^h$, taken together with the atom or atoms through which they are connected, form a 5-6 membered ring;

and each occurrence of R$^I$ and R$^{II}$ are independently ($C_1$-$C_6$alkyl)oxy-; and at least one of R$^X$ or R$^Y$ is independently $C_1$-$C_4$alkyl and the other one is H, or both R$^X$ and R$^Y$ are independently $C_1$-$C_4$alkyl;

or a tautomer thereof;

or a salt thereof.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will be appreciated by those skilled in the art that the compounds of this invention may exist in other tautomeric forms including zwitterionic forms, or isomeric forms. All tautomeric (including zwitterionic forms) and isomeric forms of the formulas and compounds described herein are intended to be encompassed within the scope of the present invention.

It will also be appreciated by those skilled in the art that the compounds of this invention may exist in tautomeric (or isomeric) forms including, but not limited to, Formula (A), Formula (B) and/or Formula (C) or zwitterionic forms including, but not limited to, Formula (D) or Formula (E). In Formula (B), (C), (D) or (E), each occurrence of R is independently H or any appropriate substituent group on nitrogen, for example alkyl.

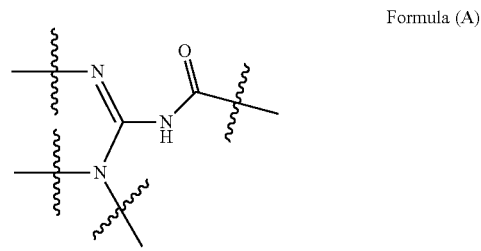

Formula (A)

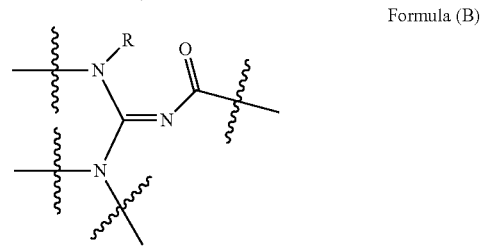

Formula (B)

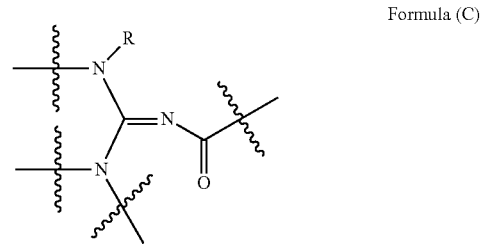

Formula (C)

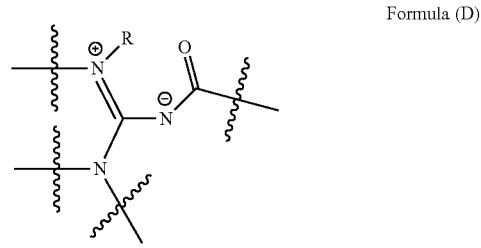

Formula (D)

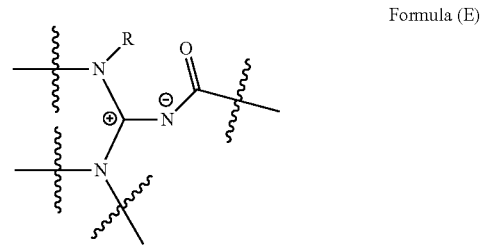

Formula (E)

The chemical names provided for the intermediate compounds and/or the compounds of this invention described herein may refer to any one of the tautomeric/isomeric representations of such compounds (in some instances, such alternate names are provided with the experimental). It is to be understood that any reference to a named compound (an intermediate compound or a compound of the invention) or a structurally depicted compound (an intermediate compound or a compound of the invention) is intended to encompass all tautomeric/isomeric forms including zwitterionic forms of such compounds and any mixture thereof.

As used herein, the term "alkyl" represents a saturated, straight or branched hydrocarbon group having the specified number of carbon atoms. The term "$C_1$-$C_4$alkyl" refers to a straight or branched alkyl moiety containing from 1 to 4 carbon atoms. Exemplary alkyls include, but are not limited to methyl, ethyl, n-propyl, isopropyl, n-butyl, isobutyl, s-butyl, t-butyl, pentyl and hexyl.

When a substituent term such as "alkyl" is used in combination with another substituent term, for example as in "hydroxy($C_1$-$C_4$alkyl)", the linking substituent term (e.g., alkyl) is intended to encompass a divalent moiety, wherein the point of attachment is through that linking substituent. Examples of "hydroxy($C_1$-$C_4$alkyl)" groups include, but are not limited to, hydroxymethyl, hydroxyethyl, and hydroxyisopropyl.

As used herein, the term "halo(alkyl)" represents a saturated, straight or branched hydrocarbon group having the specified number (n) of carbon atoms and one or more (up to 2n+1) halogen atoms. For example, the term "halo($C_1$-$C_4$alkyl)" represents a group having one or more halogen atoms, which may be the same or different, at one or more carbon atoms of an alkyl moiety containing from 1 to 4 carbon atoms. Examples of "halo($C_1$-$C_4$alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having the specified number of carbon atoms and at least 1 and up to 3 carbon-carbon double bonds. Examples include ethenyl and propenyl.

"Alkynyl" refers to straight or branched hydrocarbon group having the specified number of carbon atoms and at least 1 and up to 3 carbon-carbon triple bonds. Examples include ethynyl and propynyl.

"Alkoxy-" or "(alkyl)oxy-" refers to an "alkyl-oxy-" group, containing an alkyl moiety, having the specified number of carbon atoms, attached through an oxygen linking atom. For example, the term "$C_1$-$C_4$alkoxy-" represents a saturated, straight or branched hydrocarbon moiety having at least 1 and up to 4 carbon atoms attached through an oxygen linking atom. Exemplary "$C_1$-$C_4$alkoxy-" or "($C_1$-$C_4$alkyl)oxy-" groups include, but are not limited to, methoxy, ethoxy, n-propoxy, isopropoxy, n-butoxy, s-butoxy, and t-butoxy.

As used herein, the term "halo(alkoxy)-" represents a saturated, straight or branched hydrocarbon group having the specified number (n) of carbon atoms and one or more (up to 2n+1) halogen atoms, attached through an oxygen linking atom. For example, the term "halo($C_1$-$C_4$alkoxy)-" refers to a "haloalkyl-oxy-" group, containing a "halo($C_1$-$C_4$alkyl)" moiety attached through an oxygen linking atom. Exemplary "halo($C_1$-$C_4$alkoxy)-" groups include, but are not limited to, —$OCHF_2$ (difluoromethoxy), —$OCF_3$ (trifluoromethoxy), —$OCH_2CF_3$ (trifluoroethoxy), and —OCH$(CF_3)_2$ (hexafluoroisopropoxy).

A carbocyclic group or moiety is a cyclic group or moiety in which the ring members are carbon atoms, which may be saturated, partially unsaturated (non-aromatic) or fully unsaturated (aromatic).

"Cycloalkyl" refers to a non-aromatic, saturated, hydrocarbon ring group containing the specified number of carbon atoms in the ring. For example, the term "$C_3$-$C_6$cycloalkyl" refers to a cyclic group having from three to six ring carbon atoms. Exemplary "$C_3$-$C_6$cycloalkyl" groups include cyclopropyl, cyclobutyl, cyclopentyl, and cyclohexyl.

A heterocyclic group or moiety is a cyclic group or moiety having, as ring members, atoms of at least two different elements, which cyclic group or moiety may be saturated, partially unsaturated (non-aromatic) or fully unsaturated (aromatic).

"Heteroatom" refers to a nitrogen, sulfur, or oxygen atom, for example a nitrogen atom or an oxygen atom.

"Heterocycloalkyl" refers to a non-aromatic, monocyclic or bicyclic group containing 3-10 ring atoms and containing one or more (generally one or two) heteroatom ring members independently selected from oxygen, sulfur, and nitrogen. The point of attachment of a heterocycloalkyl group may be by any suitable carbon or nitrogen atom.

Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, and hexahydro-1H-1,4-diazepinyl.

Examples of "4-membered heterocycloalkyl" groups include oxetanyl, thietanyl and azetidinyl.

The term "5-6 membered heterocycloalkyl" represents a saturated, monocyclic group, containing 5 or 6 ring atoms, which includes one or two heteroatoms selected independently from oxygen, sulfur, and nitrogen. Illustrative examples of 5-6 membered heterocycloalkyl groups include, but are not limited to pyrrolidinyl, tetrahydrofuranyl, tetrahydrothienyl, tetrahydropyranyl, tetrahydrothiopyranyl, piperidinyl, piperazinyl, morpholinyl, and thiomorpholinyl.

"Heteroaryl" refers to an aromatic monocyclic or bicyclic group containing 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups containing either a phenyl ring fused to a heterocyclic moiety or a heteroaryl ring moiety fused to a carbocyclic moiety. The point of attachment of a heteroaryl group may be by any suitable carbon or nitrogen atom.

The term "5-6 membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, and oxadiazolyl. Selected 6-membered heteroaryl groups include pyridinyl (pyridyl), pyrazinyl, pyrimidinyl, pyridazinyl and triazinyl.

The term "9-10 membered heteroaryl" refers to an aromatic bicyclic group containing 9 or 10 ring atoms, including 1 to 4 heteroatoms independently selected from nitrogen, oxygen and sulfur. Examples of 9-membered heteroaryl (6,5-fused heteroaryl) groups include benzothienyl, benzofuranyl, indolyl, indolinyl (dihydroindolyl), isoindolyl, isoindolinyl, indazolyl, isobenzofuryl, 2,3-dihydrobenzofuryl, benzoxazolyl, benzoisoxazolyl, benzothiazolyl, benzoisothiazolyl, benzimidazolyl, benzoxadiazolyl, benzothiadiazolyl, benzotriazolyl, purinyl, imidazopyridinyl, pyrazolopyridinyl, triazolopyridinyl and 1,3-benzodioxolyl.

Examples of 10-membered heteroaryl (6,6-fused heteroaryl) groups include quinolinyl (quinolyl), isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, 1,2,3,4-tetrahydroquinolinyl (tetrahydroquinolinyl), 1,2,3,4-tetrahydroisoquinolinyl (tetrahydroisoquinolinyl), cinnolinyl, pteridinyl, and 2,3-dihydrobenzo[b][1,4]dioxinyl.

The terms "halogen" and "halo" refers to a halogen radical, for example, a fluoro, chloro, bromo, or iodo substituent.

"Oxo" represents a double-bonded oxygen moiety; for example, if attached directly to a carbon atom forms a carbonyl moiety (C=O).

"Hydroxy" or "hydroxyl" is intended to mean the radical —OH.

As used herein, the term "cyano" refers to a nitrile group, —C≡N.

As used herein, the term "optionally substituted" indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s) as defined in the substituent definitions (A, $R^3$, etc,) provided herein. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the terms "compound(s) of the invention" or "compound(s) of this invention" mean a compound of Formula (I) as defined herein, in any form, i.e., any tautomeric/isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi- hydrates)), and mixtures of various forms.

Accordingly, included within the present invention are the compounds of Formula (I), as defined herein, in any salt or non-salt form and any physical form thereof, and mixtures of various forms. While such are included within the present invention, it will be understood that the compounds of Formula (I), as defined herein, in any salt or non-salt form, and in any physical form thereof, may have varying levels of activity, different bioavailabilities and different handling properties for formulation purposes.

In one embodiment of the compounds of this invention, $R^3$ and $R^5$ are each independently —CON($R^d$)($R^f$), or one of $R^3$ and $R^5$ is —CON($R^d$)($R^f$), and the other of $R^3$ and $R^5$ is H or —CO$_2$($R^e$). In one embodiment, $R^3$ and $R^5$ are each independently —CON($R^d$)($R^f$). In another embodiment, one of $R^3$ and $R^5$ is —CON($R^d$)($R^f$) and the other of $R^3$ and $R^5$ is H. In a specific embodiment, $R^3$ and $R^5$ are each —CONH$_2$.

It is to be understood that when q is 0, A is absent and $R^{A1}$ and $R^{A2}$ are not connected. Similarly, it is to be understood that when r is 0, B is absent and $R^{B1}$ and $R^{B2}$ are not connected. Similarly, it is to be understood that when s is 0, C is absent and $R^{C1}$ and $R^{C2}$ are not connected.

In one embodiment of the compounds of this invention, q is 1, r is 0 and s is 0 (q+r+s=1) and the compound has Formula (I-A) or (I-a):

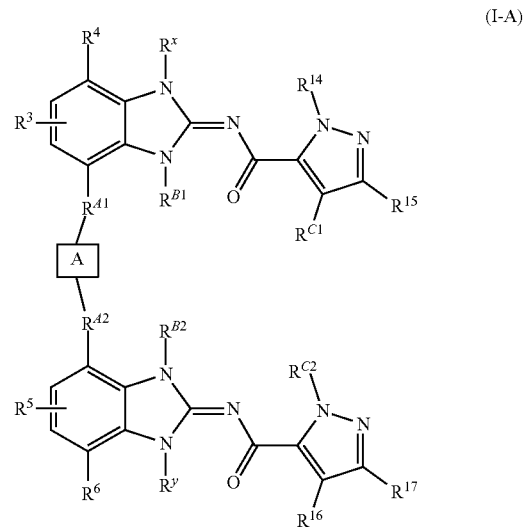

(I-A)

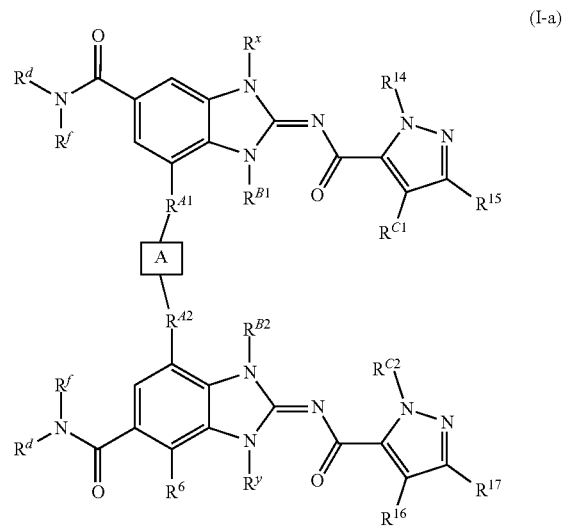

(I-a)

In one embodiment of the compounds of this invention, q is 0, r is 1 and s is 0 (q+r+s=1) and the compound has Formula (I-B) or (I-b):
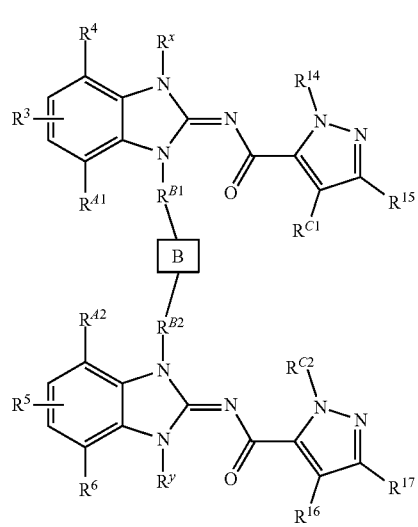
(I-B)
In one embodiment of the compounds of this invention, q is 0, r is 0 and s is 1 (q+r+s=1) and the compound has Formula (I-C) or (I-c):
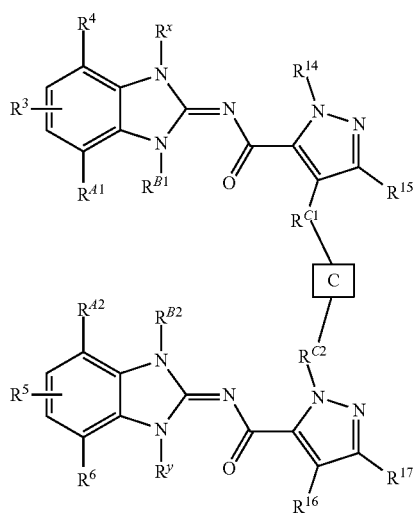
(I-C)
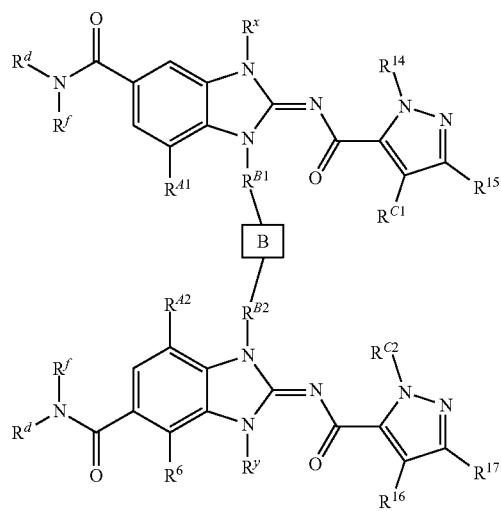
(I-b)
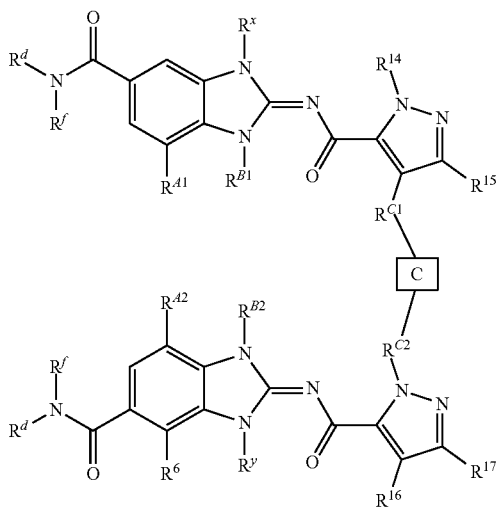
(I-c)

In one embodiment of the compounds of this invention, q is 1, r is 1 and s is 0 (q+r+s=2) and the compound has Formula (I-AB) or (I-ab):
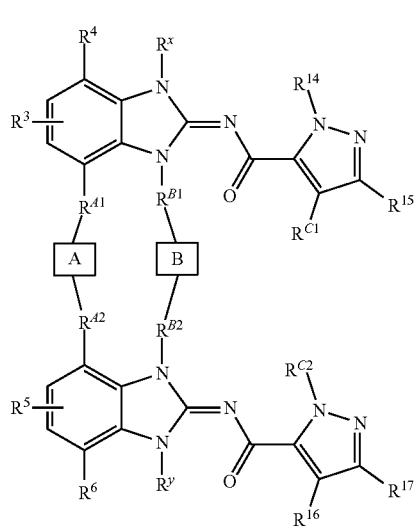
(I-AB)
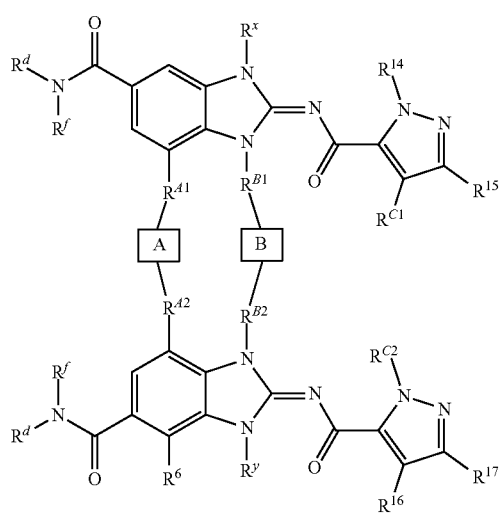
(I-ab)
In one embodiment of the compounds of this invention, q is 1, r is 0 and s is 1 (q+r+s=2) and the compound has Formula (I-AC) or (I-ac):
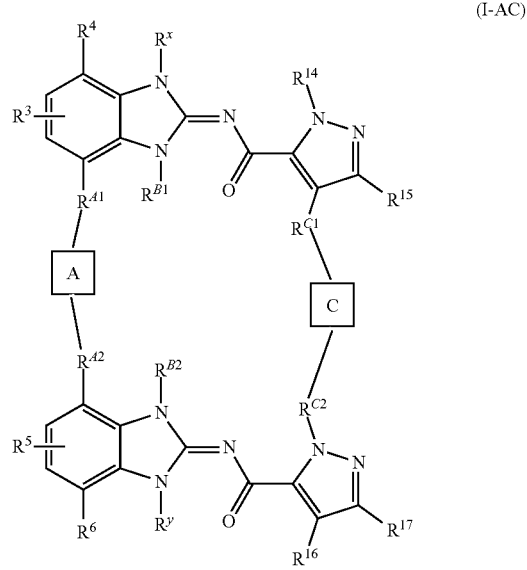
(I-AC)
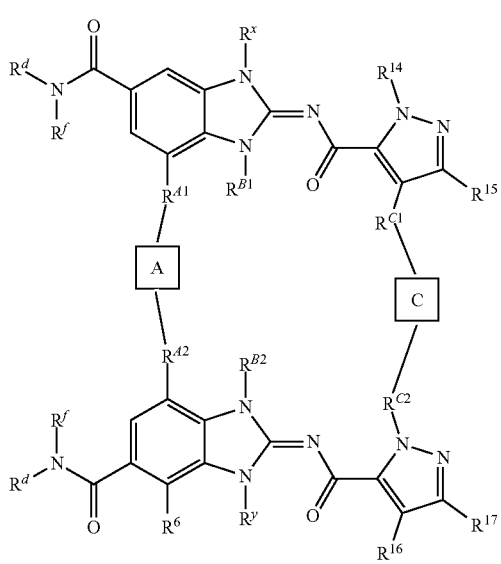
(I-ac)

In one embodiment of the compounds of this invention, q is 0, r is 1 and s is 1 (q+r+s=2) and the compound has Formula (I-BC) or (I-bc):

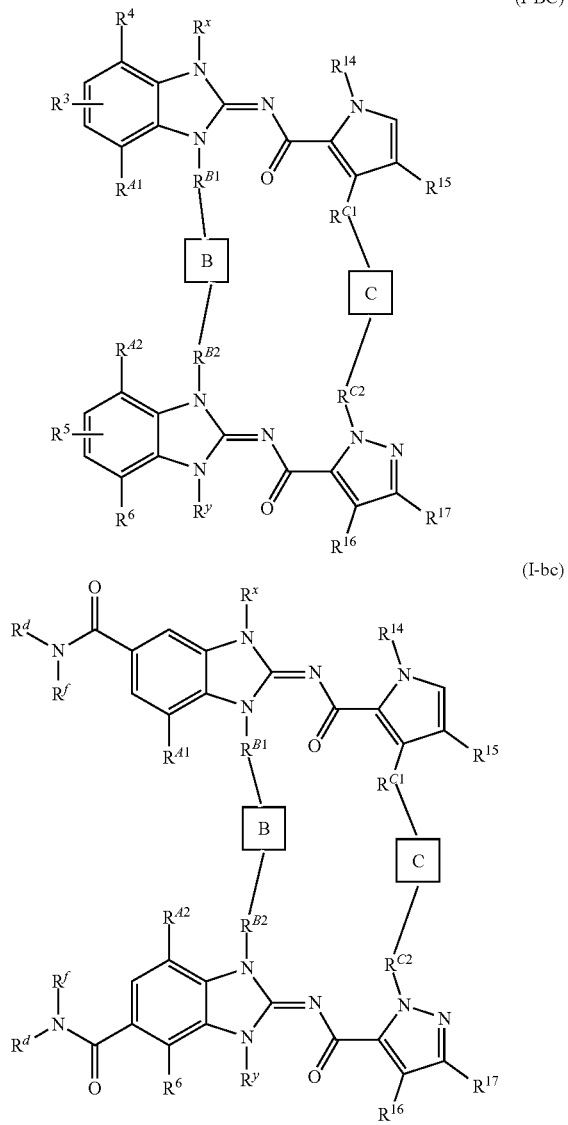

In one embodiment of the compounds of this invention, q is 0 and $R^{A1}$ and $R^{A2}$ are each independently H, halogen, hydroxy, —O—P(O)(OH)$_2$, —O—P(O)(R$^I$)(R$^{II}$), —N(R$^e$)(R$^f$), —CO$_2$R$^f$, —N(R$^f$)COR$^b$, —N(R$^g$)SO$_2$(C$_1$-C$_4$alkyl)-N(R$^e$)(R$^f$), —N(R$^g$)CO(C$_1$-C$_4$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-, wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxyl, —O—P(O)(OH)$_2$, —O—P(O)(R$^I$)(R$^{II}$), C$_1$-C$_4$alkoxy-, —N(R$^e$)(R$^f$), —CO$_2$(R$^1$), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)(R$^I$)(R$^{II}$), amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkoxyl)-O—P(O)(R$^I$)(R$^{II}$), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxyl)-O—P(O)(R$^I$)(R$^{II}$), and C$_1$-C$_4$alkoxy-(C$_1$-C$_4$alkoxy)-.

In one embodiment of the compounds of this invention, q is 0 and $R^{A1}$ and $R^{A2}$ are each independently H, hydroxy, —O—P(O)(OH)$_2$, —O—P(O)(R$^I$)(R$^{II}$), amino, (C$_1$-C$_4$alkyl)amino-, (C$_1$-C$_4$alkyl)(C$_1$-C$_4$alkyl)amino-, (C$_1$-C$_4$alkyl), hydroxy(C$_1$-C$_4$alkyl)-, amino(C$_1$-C$_4$alkyl)-, (C$_1$-C$_4$alkyl)amino(C$_1$-C$_4$alkyl)-, (C$_1$-C$_4$alkyl)(C$_1$-C$_4$alkyl)amino(C$_1$-C$_4$alkyl)-, C$_1$-C$_4$alkoxy-, hydroxy(C$_2$-C$_4$alkoxy)-, —(C$_2$-C$_4$alkoxy)-O—P(O)(OH)$_2$, —(C$_2$-C$_4$alkoxyl)-O—P(O)(R$^I$)(R$^{II}$), amino(C$_2$-C$_4$alkoxy)-, (C$_1$-C$_4$alkyl)amino(C$_2$-C$_4$alkoxy)-, (C$_1$-C$_4$alkyl)(C$_1$-C$_4$alkyl)amino(C$_2$-C$_4$alkoxy)-, 6-membered heterocycloalkyl-(C$_1$-C$_4$alkyl)-, phenyl(C$_1$-C$_4$alkoxy)-, (C$_1$-C$_4$alkyl)OCONH(C$_1$-C$_4$alkyl)-, hydroxy(C$_1$-C$_4$alkyl)amino-, -amino(C$_1$-C$_4$alkyl)-O—P(O)(OH)$_2$, -amino(C$_1$-C$_4$alkoxyl)-O—P(O)(R$^I$)(R$^{II}$), (C$_1$-C$_4$alkyl)CONH—, (C$_1$-C$_4$alkyl)CON(C$_1$-C$_4$alkyl)-, —CO$_2$H, —CO$_2$(C$_1$-C$_4$alkyl), amino(C$_1$-C$_4$alkyl)CONH—, (C$_1$-C$_4$alkyl)amino(C$_1$-C$_4$alkyl)CONH—, (C$_1$-C$_4$alkyl)(C$_1$-C$_4$alkyl)amino(C$_1$-C$_4$alkyl)CONH—, amino(C$_1$-C$_4$alkyl)CON(C$_1$-C$_4$alkyl)-, (C$_1$-C$_4$alkyl)amino(C$_1$-C$_4$alkyl)CON(C$_1$-C$_4$alkyl)-, hydroxy(C$_1$-C$_4$alkyl)CONH—, —NHCO(C$_1$-C$_4$alkyl)-O—P(O)(OH)$_2$, —NHCO(C$_1$-C$_4$alkyl)-O—P(O)(R$^I$)(R$^{II}$), (C$_1$-C$_4$alkyl)(C$_1$-C$_4$alkyl)amino(C$_1$-C$_4$alkyl)CON(C$_1$-C$_4$alkyl)-, hydroxy(C$_1$-C$_4$alkyl)CON(C$_1$-C$_4$alkyl)-, —(C$_1$-C$_4$alkyl)NCO(C$_1$-C$_4$alkyl)-O—P(O)(OH)$_2$, —(C$_1$-C$_4$alkyl) NCO (C$_1$-C$_4$alkyl) —O—P(O)(R$^I$)(R$^{II}$), HO$_2$C(C$_1$-C$_4$alkoxy)-, (C$_1$-C$_4$alkyl)OCO(C$_1$-C$_4$alkoxy)-, H$_2$NCO(C$_1$-C$_4$alkoxy)-, (C$_1$-C$_4$alkyl)HNCO(C$_1$-C$_4$alkoxy)-, (C$_1$-C$_4$alkyl)(C$_1$-C$_4$alkyl)NCO(C$_1$-C$_4$alkoxy)-, and —NHSO$_2$(C$_1$-C$_4$alkyl).

In one embodiment, q is 0 and $R^{A1}$ and $R^{A2}$ are each independently H, (C$_1$-C$_6$alkyl)oxy- or hydroxy(C$_2$-C$_6$alkyl)oxy-. In one embodiment, q is 0 and $R^{A1}$ and $R^{A2}$ are each independently H, (C$_1$-C$_6$alkyl)oxy-, hydroxy(C$_2$-C$_6$alkyl)oxy-, —(C$_2$-C$_4$alkoxy)-O—P(O)(OH)$_2$, —(C$_2$-C$_4$alkoxyl)-O—P(O)(R$^I$)(R$^{II}$), In one embodiment, q is 0 and $R^{A1}$ and $R^{A2}$ are each H. In selected embodiments, q is 0 and $R^{A1}$ and $R^{A2}$ are independently selected from H, —OCH$_2$CH$_2$CH$_2$OH and —OCH$_3$.

In one embodiment, q is 0 and $R^{A2}$ and $R^{A1}$ are each independently H, optionally substituted (C$_1$-C$_6$alkyl), or optionally substituted (C$_1$-C$_6$alkyl)oxy-, wherein C$_1$-C$_6$alkyl of said optionally substituted (C$_1$-C$_6$alkyl), or optionally substituted (C$_1$-C$_6$alkyl)oxy- is optionally substituted with 1-4 substituents each independently selected from the group consisting of hydroxyl, —O—P(O)(OH)$_2$, —O—P(O)(R$^I$)(R$^{II}$), C$_1$-C$_4$alkoxyl, —N(R$^e$)(R$^f$), —COOH, optionally substituted phenyl, and optionally substituted 5-6 membered heterocycloalkyl, and each R$^e$ is independently selected from H, C$_1$-C$_4$alkyl, —CO(C$_1$-C$_4$alkyl), —OCO(C$_1$-C$_4$alkyl), —(C$_1$-C$_4$alkyl)NH$_2$, —(C$_1$-C$_4$alkyl)C$_1$-C$_4$alkoxy, or —CO$_2$(C$_1$-C$_4$alkyl).

In one embodiment, q is 0 and $R^{A2}$ and $R^{A1}$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —O—P(O)(OH)$_2$, —O—P(O)($R^I$)($R^{II}$), —N($R^e$)($R^f$), $C_1$-$C_4$alkoxyl, phenyl, and optionally substituted 5-6 membered heterocycloalkyl containing at least one nitrogen or oxygen as a member of the ring, and each $R^e$ is each independently selected from H, $C_1$-$C_4$alkyl, —($C_1$-$C_4$alkyl)NH$_2$, or —($C_1$-$C_4$alkyl)$C_1$-$C_4$alkoxy.

In one embodiment, q is 0 and at least one of $R^{A2}$ or $R^{A1}$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl and morpholinyl and each $R^e$ is each independently selected from H, $C_1$-$C_4$alkyl, —($C_1$-$C_4$alkyl)NH$_2$, or —($C_1$-$C_4$alkyl)$C_1$-$C_4$alkoxy.

In one embodiment, q is 0 and at least one of $R^{A2}$ or $R^{A1}$ are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from tetrahydropyran, pyrrolidinyl, piperazinyl, piperidyl and morpholinyl, and each $R^e$ is each independently selected from H or $C_1$-$C_4$alkyl.

In one embodiment, q is 0 and $R^{A2}$ and $R^{A1}$ are each independently selected from H, hydroxy or optionally substituted ($C_1$-$C_6$alkyl)oxy-, and the $C_1$-$C_6$alkyl of said optionally substituted ($C_1$-$C_6$alkyl)oxy- is optionally substituted with hydroxy, phenyl or morpholinyl, wherein phenyl or morpholinyl are each optionally substituted by methyl or methoxy.

In one embodiment, q is 0, $R^{A1}$ and $R^{A2}$ are independently H, or optionally substituted ($C_1$-$C_6$alkyl)oxy-, wherein the alkyl of the optionally substituted ($C_1$-$C_6$alkyl)oxy- is optionally substituted with 1 substituent selected from the group consisting of hydroxy, optionally substituted phenyl, and optionally substituted 5-6 membered heterocycloalkyl, wherein the phenyl, and 5-6 membered heterocycloalkyl is optionally substituted with one substituent selected from the group consisting of $C_1$-$C_6$alkyl and $C_1$-$C_3$alkoxyl.

In one embodiment, q is 0, $R^{A1}$ and $R^{A2}$ are independently H, or optionally substituted ($C_1$-$C_6$alkyl)oxy-, wherein the alkyl of the optionally substituted ($C_1$-$C_6$alkyl)oxy- is optionally substituted with 1 substituent selected from the group consisting of hydroxy, optionally substituted phenyl, and optionally substituted morpholinyl, wherein the phenyl, and morpholinyl is optionally substituted with one substituent selected from the group consisting of $C_1$-$C_6$alkyl and $C_1$-$C_3$alkoxyl.

In one embodiment, q is 0, $R^{A1}$ and $R^{A2}$ are independently H, hydroxy or optionally substituted ($C_1$-$C_{12}$alkyl)oxy-,
  wherein the alkyl of optionally substituted ($C_1$-$C_{12}$alkyl) oxy- is optionally substituted by 1-4 substituents each independently selected from the group consisting of hydroxy, COOH, and optionally substituted phenyl,
    wherein said optionally substituted phenyl is optionally substituted by 1-4 substituents each independently selected from the group consisting of ($C_1$-$C_4$alkyl) oxy-.

In one embodiment, q is 0, one of $R^{A1}$ and $R^{A2}$ is H and the other one of $R^{A1}$ and $R^{A2}$ is hydroxy or optionally substituted ($C_1$-$C_4$alkyl)oxy-,
  wherein the alkyl of optionally substituted ($C_1$-$C_4$alkyl) oxy- is optionally substituted by 1-2 substituents each independently selected from the group consisting of hydroxy and optionally substituted phenyl,
    wherein said optionally substituted phenyl is optionally substituted by 1-2 substituents each independently of ($C_1$-$C_4$alkyl)oxy-.

In one embodiment, q is 0, $R^{A1}$ and $R^{A2}$ are both H.

In one embodiment, r is 0 and $R^{B1}$ and $R^{B2}$ are each H.

In another embodiment, r is 0 and $R^{B1}$ and $R^{B2}$ are each independently H, optionally substituted $C_1$-$C_6$alkyl, halo ($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted 5-6 membered heteroaryl or optionally substituted 9 membered heteroaryl.

In one embodiment of the compounds of this invention, s is 0 and $R^{C1}$ is H, halogen, or $C_1$-$C_4$alkyl and $R^{C2}$ is optionally substituted $C_1$-$C_4$alkyl, wherein said optionally substituted $C_1$-$C_4$alkyl group is optionally substituted by a substituent selected from —$OR^c$, —$NR^cR^d$, —$CO_2R^c$, —$CONR^cR^d$, —$SO_2NR^cR^d$, and —$OCONR^cR^d$.

In one embodiment of the compounds of this invention, when s is 0, $R^{C1}$ is H and $R^{C2}$ is $C_1$-$C_4$alkyl. In another embodiment, when s is 0, $R^1$ is $C_1$-$C_6$alkyl, specifically methyl. In another embodiment, when s is 0, $R^{C2}$ is $C_1$-$C_6$alkyl, specifically methyl or ethyl. In a selected embodiment, when s is 0, $R^{C2}$ is ethyl.

In one embodiment, q is 1 and A, taken together with $R^{A1}$ and $R^{A2}$, forms a 4-8 membered linking group. In a further embodiment, q is 1 and A, taken together with $R^{A1}$ and $R^{A2}$ forms a 4-6 membered linking group. In a still further embodiment, q is 1 and A, taken together with $R^{A1}$ and $R^{A2}$, forms a 5-membered linking group.

In another embodiment, q is 1, $R^{A1}$ and $R^{A2}$ are each independently —CH$_2$—, —$NR^e$—, or —O—, and A is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-$NR^a$—$C_1$-$C_4$alkyl- group, said substituted —$C_2$-$C_{10}$alkyl- group is substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl) amino-, halo($C_1$-$C_4$alkyl), halo($C_1$-$C_4$alkoxy)-, and $C_1$-$C_4$alkoxy-.

In another embodiment, q is 1, $R^{A1}$ and $R^{A2}$ are each independently —CH$_2$—, —$NR^e$—, or —O—, and A is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl) amino-, halo($C_1$-$C_4$alkyl), halo($C_1$-$C_4$alkoxy)-, and $C_1$-$C_4$alkoxy-.

In another embodiment, q is 1, $R^{A1}$ and $R^{A2}$ are each independently —CH$_2$—, —$NR^e$—, or —O—, and A is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl -, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)($R^I$)

($R^H$), amino, ($C_1$-$C_4$alkyl)amino-, ($C_1$-$C_4$alkyl)($C_1$-$C_4$alkyl) amino-, halo($C_1$-$C_4$alkyl), halo($C_1$-$C_4$alkoxy)-, and $C_1$-$C_4$alkoxy-.

In another embodiment, q is 1, $R^{A1}$ and $R^{A2}$ are each independently —CH$_2$— or —O—, and A is a —$C_2$-$C_4$alkyl-, —$C_2$-$C_4$alkenyl-, or —$C_2$-$C_4$alkynyl- group.

In selected embodiments, q is 1, $R^{A1}$ and $R^{A2}$ are each —O—, and A is —CH$_2$CH$_2$CH$_2$—, wherein A, taken together with $R^{A1}$ and $R^{A2}$, form a —OCH$_2$CH$_2$CH$_2$O— group.

In another embodiment, q is 1, $R^{A1}$ and $R^{A2}$ are each —O—, and A is —CH$_2$-phenyl-CH$_2$—, wherein A, taken together with $R^{A1}$ and $R^{A2}$, form a —OCH$_2$-phenyl-CH$_2$O— group. In a specific embodiment, q is 1, A, taken together with $R^{A1}$ and $R^{A2}$, form a —OCH$_2$-phenyl-CH$_2$O— group, wherein the —OCH$_2$— groups are located 1, 4 on the phenyl ring moiety.

The length of the linking groups defined herein represents the lowest number of atoms in a direct chain composed of —$R^{A1}$-A-$R^{A2}$— and/or —$R^{B1}$—B—$R^{B2}$— and/or $R^{C1}$—C—$R^{C2}$—. For example, when B is an optionally substituted phenyl, the linking group —$R^{B1}$—B—$R^{B2}$— may be represented as —(CH$_2$)-phenyl-(CH$_2$)—. This linking group is characterized as a 4-membered linking group when the 2 —(CH$_2$)— moieties are located on adjacent carbon atoms of the phenyl ring (1,2 substituted phenyl). In another embodiment, this linking group is characterized as a 6-membered linking group when the 2 —(CH$_2$)— moieties are substituted at para positions on the phenyl ring (1,4 substituted phenyl). It will be understood that any alkyl, alkenyl, or alkynyl group or moiety of A, B or C is a straight or branched-alkyl, alkenyl, or alkynyl group or moiety. For example, a —$R^{B1}$—B—$R^{B2}$— linking group, wherein B is —$C_1$-$C_{10}$alkyl- may contain an 8-membered linking group having a ($C_1$-$C_4$alkyl) branching group or 2-4 ($C_1$-$C_3$alkyl) branching groups, for example, 4 branching methyl groups (2 gem-dimethyl groups) or 2 branching methyl groups.

In one embodiment of the compounds of this invention, r is 1 and $R^{B1}$ and $R^{B2}$ are each independently —CH$_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1-4 substituents each independently selected from —$C_1$-$C_4$alkyl, halogen, halo($C_1$-$C_4$alkyl), —OH, —O—P(O)(OH)$_2$, —O—P(O)($R^I$)($R^H$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I$)($R^H$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In one embodiment of the compounds of this invention, r is 1, $R^B$i and $R^{B2}$ are each independently —CH$_2$—, and B, taken together with $R^{B1}$ and $R^{B2}$, forms a 2-6 membered linking group. In a further embodiment, r is 1, $R^{B1}$ and $R^{B2}$ are each independently —CH$_2$—, and B, taken together with $R^{B1}$ and $R^{B2}$, forms a 3-6 membered linking group. In a still further embodiment, r is 1, $R^{B1}$ and $R^{B2}$ are each independently —CH$_2$—, and B, taken together with $R^{B1}$ and $R^{B2}$, forms a 4-5 membered linking group.

In one embodiment of the compounds of this invention, r is 1, $R^{B1}$ and $R^{B2}$ are each independently —CR$^d$R$^f$—, and B, taken together with $R^{B1}$ and $R^{B2}$, forms a 2-6 membered linking group. In a further embodiment, r is 1, $R^{B1}$ and $R^{B2}$ are each independently —CH$_2$—, and B, taken together with $R^{B1}$ and $R^{B2}$, forms a 3-6 membered linking group. In a still further embodiment, r is 1, $R^{B1}$ and $R^{B2}$ are each independently —CH$_2$—, and B, taken together with $R^{B1}$ and $R^{B2}$, forms a 4-5 membered linking group.

In one embodiment, B is a bond.

In another embodiment, r is 1, $R^{B1}$ and $R^{B2}$ are each independently —CH$_2$—, and B is a substituted —$C_1$-$C_{10}$alkyl- group or is an unsubstituted —$C_1$-$C_{10}$alkyl-, —$C_2$-$C_{10}$alkenyl-, —$C_2$-$C_{10}$alkynyl-, —$C_1$-$C_6$alkyl-O—$C_1$-$C_6$alkyl-, or —$C_1$-$C_6$alkyl-NR$^a$—$C_1$-$C_6$alkyl- group, said substituted —$C_1$-$C_{10}$alkyl- group is substituted by 1-4 substituents each independently selected from —$C_1$-$C_4$alkyl, halogen, hydroxy, —O—P(O)(OH)$_2$, —O—P(O)($R^I$)($R^H$), amino, ($C_1$-$C_6$alkyl)amino-, ($C_1$-$C_6$alkyl)($C_1$-$C_6$alkyl)amino-, halo($C_1$-$C_6$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —NHCO($C_1$-$C_4$alkyl), optionally substituted phenyl, optionally substituted 5-6 membered heterocycloalkyl and optionally substituted 5-6 membered heteroaryl, wherein said optionally substituted phenyl, 5-6 membered heterocycloalkyl or 5-6 membered heteroaryl is optionally substituted by 1-4 substituents each independently selected from —$C_1$-$C_4$alkyl, halogen, hydroxy, —O—P(O)(OH)$_2$, —O—P(O)($R^I$R$^H$)$_2$, amino, ($C_1$-$C_6$alkyl)amino-, ($C_1$-$C_6$alkyl)($C_1$-$C_6$alkyl)amino-, halo($C_1$-$C_6$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-.

In another embodiment, r is 1, $R^{B1}$ and $R^{B2}$ are each independently —$CH_2$—, and B is a substituted —$C_1$-$C_6$alkyl- group or is an unsubstituted —$C_1$-$C_{10}$alkyl-, —$C_2$-$C_{10}$alkenyl-, —$C_2$-$C_{10}$alkynyl-, —$C_1$-$C_6$alkyl-O—$C_1$-$C_6$alkyl-, or —$C_1$-$C_6$alkyl-$NR^a$—$C_1$-$C_6$alkyl- group, said substituted —$C_1$-$C_{10}$alkyl- group is substituted by 1-4 substituents each independently selected from —$C_1$-$C_4$alkyl, halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —$CH_2$—, and B is a substituted —$C_1$-$C_6$alkyl- group or is an unsubstituted —$C_1$-$C_6$alkyl-, —$C_2$-$C_6$alkenyl-, —$C_2$-$C_6$alkynyl-, —$C_1$-$C_4$alkyl-O—$C_1$-$C_4$alkyl-, or —$C_1$-$C_4$alkyl-$NR^a$—$C_1$-$C_4$alkyl- group, said substituted —$C_1$-$C_6$alkyl- group is substituted by 1-4 substituents each independently selected from —$C_1$-$C_4$alkyl, halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —$CH_2$—, and B is a substituted —$C_1$-$C_6$alkyl- group or is an unsubstituted —$C_1$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_1$-$C_6$alkyl- group is substituted by 1-4 substituents each independently selected from —$C_1$-$C_4$alkyl, halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, r is 1, $R^{B1}$ and $R^{B2}$ are each independently —$CH_2$—, and B is a substituted —$C_2$-$C_4$alkyl- group or is an unsubstituted —$C_2$-$C_4$alkyl-, —$C_2$-$C_4$alkenyl-, —$C_2$-$C_4$alkynyl-, —$C_1$alkyl-O—$C_1$alkyl-, or -$C_6$alkyl-$NR^a$-$C_6$alkyl- group, said substituted —$C_2$-$C_4$alkyl- group is substituted by 1-4 substituents each independently selected from —$C_1$-$C_4$alkyl, halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In one embodiment, r is 1, $R^{B1}$ and $R^{B2}$ are each independently —$CR^dR^f$, $R^d$ and $R^f$ is H or methyl, and B is —CH=CH—, —CH($CH_3$)=CH($CH_3$)—, —$CH_2CH_2$—, —CH(OH)CH(OH)—, —CH($CH_3$)CH($CH_3$)—, —$CF_2$—$CF_2$—, or —$CH_2CH_2CH_2$—. In one embodiment, r is 1, $R^{B1}$ and $R^{B2}$ are each independently —$CR^dR^f$, $R^d$ and $R^f$ is H or methyl, and B is —CH=CH—, —$CH_2CH_2$—, —CH(OH)CH(OH)—. In these embodiments, r is 1, B, taken together with $R^{B1}$ and $R^{B2}$, form a —$CH_2$CH=CHCH$_2$—, —$CH_2CH_2CH_2CH_2$—, —$CH_2$CH(OH)CH(OH)CH$_2$—, or —$CH_2CH_2$N($CH_3$)CH$_2$CH$_2$— group. In these embodiments, r is 1, B, taken together with $R^{B1}$ and $R^{B2}$, form a —$CH_2$CH=CHCH$_2$—. In one embodiment, r is 1, B, taken together with $R^{B1}$ and $R^{B2}$, form —$CH_2CH_2CH_2CH_2$—.

In one embodiment of the compounds of this invention, s is 1 and $R^{C1}$ and $R^{C2}$ are each independently —$CH_2$—, and C, taken together with $R^{C1}$ and $R^{C2}$, forms a linking group, wherein C is -halo($C_1$-$C_{12}$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-$NR^a$—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —O—P(O)(OH)$_2$, —O—P(O)($R^I$)($R^{II}$), $OR^c$, —$NH_2$, —$NR^cR^d$, —$OCOR^C$, —$CO_2$H, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$,
and
the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxyl)-O—P(O)($R^I$)($R^{II}$), and $C_1$-$C_4$alkoxy-($C_1$-$C_4$alkoxy)-.

In one embodiment of the compounds of this invention, s is 1, $R^{C1}$ and $R^{C2}$ are each independently —$CH_2$—, and C, taken together with $R^{C1}$ and $R^{C2}$, forms a 4-8 membered linking group. In a further embodiment, s is 1 and C, taken together with $R^{C1}$ and $R^{C2}$, forms a 4-6 membered linking group. In a still further embodiment, s is 1 and C, taken together with $R^{C1}$ and $R^{C2}$ forms a 5-membered linking group.

In another embodiment, s is 1, $R^{C1}$ and $R^{C2}$ are each independently —$CH_2$—, and C is a substituted —$C_2$-$C_{10}$alkyl- group or is an unsubstituted —$C_2$-$C_{10}$alkyl-, —$C_2$-$C_{10}$alkenyl-, —$C_2$-$C_{10}$alkynyl-, —$C_1$-$C_4$alkyl-O—$C_1$-$C_4$alkyl-, or —$C_1$-$C_4$alkyl-$NR^a$—$C_1$-$C_4$alkyl- group, said substituted —$C_2$-$C_{10}$alkyl- group is substituted by 1-4 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a substituted —$C_2$-$C_6$alkyl- group or is an unsubstituted —$C_2$-$C_6$alkyl-, —$C_2$-$C_6$alkenyl-, —$C_2$-$C_6$alkynyl-, —$C_1$-$C_2$alkyl-O—$C_1$-$C_2$alkyl-, or —$C_1$-$C_2$alkyl-$NR^a$—$C_1$-$C_2$alkyl- group, said substituted —$C_2$-$C_6$alkyl- group is substituted by 1-2 substituents each independently selected from halogen, hydroxy, —O—P(O)(OH)$_2$, —O—P(O)($R^I$)($R^{II}$), amino, ($C_1$-$C_4$alkyl)amino-, ($C_1$-$C_4$alkyl)($C_1$-$C_4$alkyl)amino-, halo($C_1$-$C_4$alkyl), halo($C_1$-$C_4$alkoxy)-, and $C_1$-$C_4$alkoxy-.

In another embodiment, s is 1, $R^{C1}$ and $R^{C2}$ are each independently —$CH_2$—, and C is a —$C_2$-$C_4$alkyl-, —$C_2$-$C_4$alkenyl-, or —$C_2$-$C_4$alkynyl- group.

In selected embodiments, s is 1, $R^{C1}$ and $R^{C2}$ are each independently —$CH_2$—, and C is —$CH_2CH_2CH_2$—, wherein C, taken together with $R^{C1}$ and $R^{C2}$, form a —$CH_2CH_2CH_2CH_2CH_2$— group.

In one embodiment of the compounds of this invention, $R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^I$)($R^{II}$), —$NH_2$, —$NR^cR^c$, —$NR^cR^d$, —$COR^c$, —$CO_2R^c$, —N($R^d$)$COR^c$, —N($R^d$)$SO_2R^c$, —N($R^g$)$SO_2$($C_1$-$C_2$alkyl)-N($R^h$)($R^i$), —N($R^g$)CO($C_1$-$C_2$alkyl)-N($R^h$)($R^i$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-,
  wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected
    from —OH, —O—P(O)(OH)$_2$, —O—P(O)($R^I$)($R^{II}$), —$OR^c$, —$NH_2$, —$NR^cR^c$, —$NR^cR^d$, —$CO_2H$, —$CO_2R^c$ $OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^d$$COR^c$, —$NR^d SOR^c$, —$NR^d CO_2R^c$, —$NR^d SO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, —($C_1$-$C_4$alkyl)-O—P(O)(OH)$_2$, —($C_1$-$C_4$alkoxyl)-O—P(O)($R^I$)($R^{II}$), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxyl)-O—P(O)($R^I$)($R^{II}$), $C_1$-$C_4$alkoxy-($C_1$-$C_4$alkoxy)-, —$COR^d$, —CON($R^d$)($R^f$), and $CO_2R^d$.

In one embodiment, $R^4$ and $R^6$ are each H.

In one embodiment, $R^3$ and $R^5$ are independently selected from the group consisting of —CO—N($R^d$)($R^f$), and each $R^d$ and $R^f$ are independently H or $C_1$-$C_3$alkyl.

In one embodiment, $R^3$ and $R^5$ are $CONH_2$.

In one embodiment of the compounds of this invention, $R^{14}$ is optionally substituted $C_1$-$C_4$alkyl, wherein said optionally substituted $C_1$-$C_4$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$.

In one embodiment of the compounds of this invention, $R^{16}$ is H, halogen, or $C_1$-$C_4$alkyl.

In one embodiment of the compounds of this invention, $R^{15}$ and $R^{17}$ are each independently H, cyclopropyl, or $C_1$-$C_4$alkyl.

In one embodiment of the compounds of this invention, $R^{14}$, $R^{15}$, $R^{16}$, and $R^{17}$ are each independently H or $C_1$-$C_4$alkyl.

In one embodiment of this invention, $R^{16}$ is H.

In another embodiment, $R^{14}$, $R^{15}$, and $R^{17}$ are each independently $C_1$-$C_4$alkyl.

In another embodiment, $R^{14}$, $R^{15}$, and $R^{17}$ are each independently $C_1$-$C_3$alkyl, specifically, methyl or ethyl. In a selected embodiment, $R^{14}$ is ethyl.

In another embodiment, $R^{15}$ and $R^{17}$ are each methyl.

In one embodiment of the compounds of this invention, $R^a$ is H, —$R^c$, —$COR^c$, —$CO_2H$, —$CO_2R^c$, —$SOR^c$, —$SO_2R^c$, —$CONH_2$, —$CONR^cR^d$, —$SO_2NH_2$, or —$SO_2NR^IR^d$.

In another embodiment, $R^a$ is H, $C_1$-$C_4$alkyl, —CO($C_1$-$C_4$alkyl), —CO($C_1$-$C_4$alkyl)-OH, —CO($C_1$-$C_4$alkyl)-O—($C_1$-$C_4$alkyl), —CO($C_1$-$C_4$alkyl)-$NH_2$, —CO($C_1$-$C_4$alkyl)-NH($C_1$-$C_4$alkyl), or —CO($C_1$-$C_4$alkyl)-N($C_1$-$C_4$alkyl)($C_1$-$C_4$alkyl).

In one embodiment of the compounds of this invention, wherein $R^x$ and $R^y$ are each independently methyl or ethyl. In one embodiment of the compounds of this invention, wherein $R^x$ and $R^y$ are both methyl. In one embodiment of the compounds of this invention, the compounds of Formula (I) wherein one of $R^x$ and $R^y$ is methyl and the other one is H.

One embodiment of this invention is directed to a compound Formula (I), wherein:
  q+r+s=1 or 2;
  q is 0 and $R^{A1}$ and $R^{A2}$ are independently selected from H, —$OCH_2CH_2CH_2OH$ and —$OCH_3$; or
  q is 1, $R^{A1}$ and $R^{A2}$ are each —O—, and A is —$CH_2CH_2CH_2$—;
  r is 0 and $R^{B1}$ and $R^{B2}$ are each H; or
  r is 1, $R^{B1}$ and $R^{B2}$ are each independently —$CH_2$—, and B is —CH=CH—, —$CH_2CH_2$—, —CH(OH)CH(OH)—, or —$CH_2N(CH_3)CH_2$—;
  s is 0, $R^{C1}$ is methyl and $R^{C2}$ is ethyl; or
  s is 1, Rei and $R^{C2}$ are each independently —$CH_2$—, and C is —$CH_2CH_2CH_2$—;
  $R^3$ and $R^5$ are each —$CONH_2$;
  $R^4$ and $R^6$ are each H;
  $R^{14}$ is ethyl;
  $R^{15}$ is methyl;
  $R^{16}$ is H;
  $R^{17}$ is methyl,
or a salt, particularly a pharmaceutically acceptable salt, thereof.

In one embodiment of the compounds of this invention, $R^{14}$, $R^{15}$, $R^{c2}$ and $R^{17}$ are independently methyl or ethyl; one of $R^{A1}$ and $R^{A2}$ is H and the other one of $R^{A1}$ and $R^{A2}$ is optionally substituted ($C_1$-$C_4$alkyl)oxy-,
  wherein the alkyl of optionally substituted ($C_1$-$C_4$alkyl)oxy- is optionally substituted by 1-2 substituents each independently selected from the group consisting of hydroxy and optionally substituted phenyl,
    wherein said optionally substituted phenyl is optionally substituted by 1-2 substituents each independently selected from the group consisting of ($C_1$-$C_4$alkyl)oxy-;

$R^3$ and $R^5$ are both —CO—$NH_2$; and

B is substituted —$CH_2$—$CH_2$— or substituted —CH=CH—, wherein the substituted —$CH_2$—$CH_2$— or substituted —CH=CH— is substituted by 1-4 substituents each independently selected from the group consisting of fluoro and $C_{1-2}$alkyl; and at least one of $R^x$ or $R^y$ is independently $C_1$-$C_4$alkyl and the other one is H, or both $R^x$ and $R^y$ are independently $C_1$-$C_4$alkyl.

In one embodiment of this invention, the compound of invention is Formula (I-B')

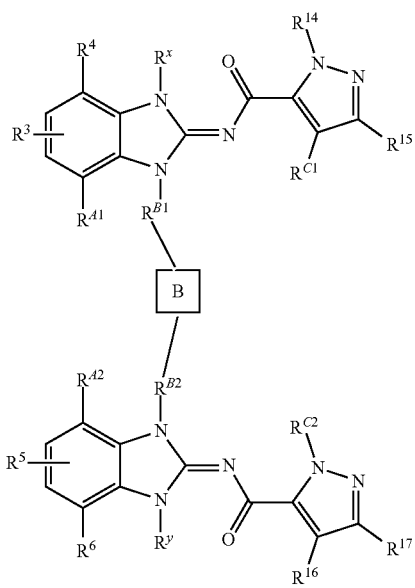

wherein $R^3$ and $R^5$ are each independently —CON($R^d$)($R^f$), or one of $R^3$ and $R^5$ is —CON($R^d$)($R^f$), and the other of $R^3$ and $R^5$ is H or —$CO_2$($R^c$);

$R^c$ is $C_1$-$C_4$alkyl;

$R^{B1}$ and $R^{B2}$ are each independently —$CR^dR^f$—;

B is -halo($C_1$-$C_5$alkyl), unsubstituted —$C_1$-$C_5$alkyl, or unsubstituted —$C_2$-$C_6$alkenyl-;

$R^{A2}$ and $R^{A1}$ are each independently H, halogen, hydroxyl, optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, $C_1$-$C_4$alkoxyl, —N($R^e$)($R^f$), —$CO_2$($R^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from $C_1$-$C_4$alkyl, halogen, hydroxy, —O—P(O)(OH)$_2$, —O—P(O)($R^I$)($R^{II}$), amino, ($C_1$-$C_6$alkyl)amino-, ($C_1$-$C_6$alkyl)($C_1$-$C_6$alkyl)amino-, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;

each $R^d$ is independently H or $C_1$-$C_4$alkyl;

$R^e$ is selected from H, ($C_1$-$C_4$alkyl), —CO($C_1$-$C_4$alkyl), —OCO($C_1$-$C_4$alkyl), or —$CO_2$($C_1$-$C_4$alkyl);

each $R^f$ is H or ($C_1$-$C_4$alkyl);

$R^4$ and $R^6$ are H;

$R^{14}$ is $C_1$-$C_4$alkyl;

$R^{C1}$ is H or $C_1$-$C_4$alkyl;

$R^{C2}$ is $C_1$-$C_4$alkyl;

$R^{15}$ is H or $C_1$-$C_4$alkyl;

$R^{16}$ is H or $C_1$-$C_4$alkyl;

$R^{17}$ is H or $C_1$-$C_4$alkyl; and each occurrence of $R^I$ and $R^{II}$ are independently ($C_1$-$C_6$alkyl)oxy-, at least one of $R^X$ or $R^y$ is independently $C_1$-$C_4$alkyl and the other one is H, or both $R^x$ and $R^y$ are independently $C_1$-$C_4$alkyl;

or a tautomer there of, or a salt thereof.

In one embodiment of this invention, the compound of invention is Formula (I-b'), Formula (I-b')

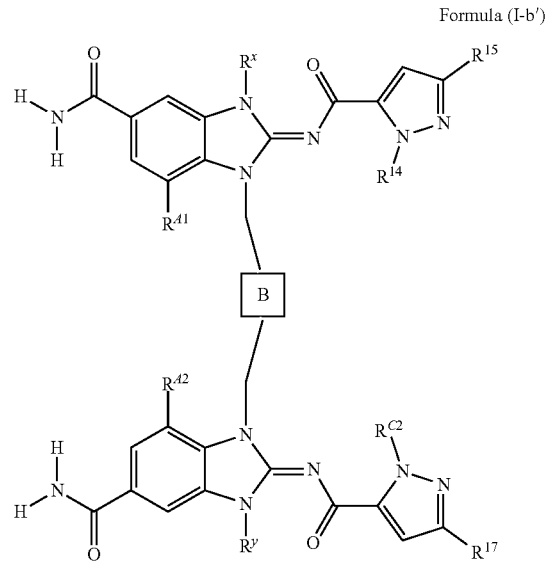

wherein

B is -halo($C_1$-$C_6$alkyl), unsubstituted —$C_1$-$C_5$alkyl, or unsubstituted —$C_2$-$C_6$alkenyl-;

$R^{A2}$ and $R^{A1}$ are each independently H, halogen, hydroxyl, —O—P(O)(OH)$_2$, —O—P(O)($R^I$)($R^{II}$), optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl) or optionally substituted ($C_1$-$C_6$alkyl)oxy- is optionally substituted with 1-4 substituents each independently selected from the group consisting of hydroxyl, $C_1$-$C_4$alkoxyl, —N($R^e$)($R^f$), —$CO_2$(R), optionally substituted phenyl, and optionally substituted 5-6 membered heterocycloalkyl, and wherein said optionally substituted phenyl, or 5-6 membered heterocycloalkyl is optionally substituted by 1-4 substituents each independently selected from $C_1$-$C_4$alkyl, halogen, hydroxy, —O—P(O)(OH)$_2$, —O—P(O)(R$^I$)(R$^{II}$), amino, (C$_1$-C$_6$alkyl)amino-, (C$_1$-C$_6$alkyl)(C$_1$-C$_6$alkyl)amino-, halo(C$_1$-C$_6$alkyl),
hydroxy-(C$_1$-C$_4$alkyl)-, —(C$_1$-C$_4$alkyl)-O—P(O)(OH)$_2$, —(C$_1$-C$_4$alkoxyl)-O—P(O)(R$^I$)(R$^{II}$), halo (C$_1$-C$_4$alkoxy)-, C$_1$-C$_4$alkoxy-,
hydroxy-(C$_2$-C$_4$alkoxy)-, —(C$_2$-C$_4$alkoxy)-O—P(O)(OH)$_2$, —(C$_2$-C$_4$alkoxyl)-O—P(O)(R$^I$)(R$^{II}$), —(C$_1$-C$_6$alkyl)-NH$_2$, —C$_1$-C$_4$alkyl-(C$_1$-C$_4$alkoxy) and C$_1$-C$_4$alkoxy-(C$_1$-C$_4$alkoxy)-;
R$^e$ is selected from H, (C$_1$-C$_4$alkyl), —CO(C$_1$-C$_4$alkyl), —OCO(C$_1$-C$_4$alkyl), —(C$_1$-C$_4$alkyl)-NH$_2$, —(C$_1$-C$_4$alkyl) C$_1$-C$_4$alkoxy, or —CO$_2$(C$_1$-C$_4$alkyl),
each R$^f$ is H or (C$_1$-C$_4$alkyl);
R$^{14}$ is C$_1$-C$_4$alkyl;
R$^{C2}$ is C$_1$-C$_4$alkyl;
R$^{15}$ is C$_1$-C$_4$alkyl; and
R$^{17}$ is C$_1$-C$_4$alkyl;
each occurrence of R$^I$ and R$^{II}$ are independently (C$_1$-C$_6$alkyl)oxy-,
at least one of R$^x$ or R$^y$ is independently C$_1$-C$_4$alkyl and the other one is H,
or both R$^x$ and R$^y$ are independently C$_1$-C$_4$alkyl;
or a tautomer thereof,
or a salt thereof.

In one embodiment, the compound of Formula (I-B'), or (I-b'), wherein R$^{A2}$ and R$^A$1 are each independently H, halogen, optionally substituted (C$_1$-C$_6$alkyl), or optionally substituted (C$_1$-C$_6$alkyl)oxy-, and the C$_1$-C$_6$alkyl of said optionally substituted (C$_1$-C$_6$alkyl), optionally substituted (C$_1$-C$_6$alkyl)oxy- is optionally substituted with 1-4 substituents each independently selected from the group consisting of hydroxyl, —O—P(O)(OH)$_2$, —O—P(O)(R$^I$)(R$^{II}$), —N(R$^e$)(R$^f$), C$_1$-C$_4$alkoxyl, phenyl, optionally substituted 5-6 membered heterocycloalkyl containing at least one nitrogen or oxygen as a member of the ring, each R$^e$ is independently selected from H, (C$_1$-C$_4$alkyl), —(C$_1$-C$_4$alkyl)-NH$_2$, or —(C$_1$-C$_4$alkyl) C$_1$-C$_4$alkoxy and each R$^f$ is independently H or (C$_1$-C$_4$alkyl).

In one embodiment, the compound of Formula (I-B') or (I-b'), wherein R$^{A2}$ and R$^A$1 are each independently H, halogen, optionally substituted (C$_1$-C$_6$alkyl), or optionally substituted (C$_1$-C$_6$alkyl)oxy-, and the C$_1$-C$_6$alkyl of said optionally substituted (C$_1$-C$_6$alkyl), optionally substituted (C$_1$-C$_6$alkyl)oxy- is optionally substituted with 1-4 substituents each independently selected from the group consisting of hydroxyl, —N(R$^e$)(R$^f$), C$_1$-C$_4$alkoxyl, phenyl, optionally substituted 5-6 membered heterocycloalkyl containing at least one nitrogen or oxygen as a member of the ring, and R$^e$ and R$^f$ are each independently H or (C$_1$-C$_4$alkyl).

In one embodiment, the compound of Formula (I-B') or (I-b') wherein at least one of R$^{A2}$ or R$^A$1 is independently H, halogen, optionally substituted (C$_1$-C$_6$alkyl), or optionally substituted (C$_1$-C$_6$alkyl)oxy-, and the C$_1$-C$_6$alkyl of said optionally substituted (C$_1$-C$_6$alkyl), optionally substituted (C$_1$-C$_6$alkyl)oxy- is optionally substituted with 1-4 substituents each independently selected from —N(R$^e$)(R$^f$), tetrahydropyran, pyrrolidinyl, piperazinyl, piperidyl and morpholinyl, each R$^e$ is independently selected from H, (C$_1$-C$_4$alkyl), —(C$_1$-C$_4$alkyl)-NH$_2$, or —(C$_1$-C$_4$alkyl) C$_1$-C$_4$alkoxy and each R$^f$ is independently H or (C$_1$-C$_4$alkyl).

In one embodiment, the compound of Formula (I-B') or (I-b'), wherein at least one of R$^{A2}$ or R$^A$1 is each independently H, halogen, optionally substituted (C$_1$-C$_6$alkyl), or optionally substituted (C$_1$-C$_6$alkyl)oxy-, and the C$_1$-C$_6$alkyl of said optionally substituted (C$_1$-C$_6$alkyl), optionally substituted (C$_1$-C$_6$alkyl)oxy- is optionally substituted with 1-4 substituents each independently selected from —N(R$^e$)(R$^f$), tetrahydropyran, pyrrolidinyl, piperazinyl, piperidyl or morpholinyl, and R$^e$ and R$^f$ are each independently H or (C$_1$-C$_4$alkyl).

In one embodiment, the compounds of Formula (I-B') or (I-b'), wherein R$^x$ and R$^y$ are each independently methyl or ethyl. In another embodiment, the compounds of Formula (I-B') or (I-b'), wherein R$^x$ and R$^y$ are both methyl. In a further embodiment, the compounds of Formula (I-B') or (I-b'), wherein one of R$^x$ and R$^y$ is methyl and the other one is H.

In one embodiment, the compound of Formula (I-B') or (I-b'), wherein
B is unsubstituted —C$_1$-C$_5$alkyl, or unsubstituted —C$_2$-C$_6$alkenyl-;
R$^{A2}$ and R$^A$1 are each independently H, halogen, optionally substituted (C$_1$-C$_6$alkyl), or optionally substituted (C$_1$-C$_6$alkyl)oxy-,
wherein C$_1$-C$_6$alkyl of said optionally substituted (C$_1$-C$_6$alkyl), or optionally substituted (C$_1$-C$_6$alkyl)oxy- is optionally substituted with 1-2 substituents each independently selected from the group consisting of hydroxyl, C$_1$-C$_4$alkoxyl, —N(R$^e$)(R$^f$), —CO$_2$(R$^f$), unsubstituted phenyl and unsubstituted 5-6 membered heterocycloalkyl,
R$^e$ is H, (C$_1$-C$_4$alkyl), —CO(C$_1$-C$_4$alkyl), —OCO(C$_1$-C$_4$alkyl), or —CO$_2$(C$_1$-C$_4$alkyl),
each occurrence of R$^f$ is H or (C$_1$-C$_4$alkyl);
R$^{14}$ is C$_1$-C$_4$alkyl;
R$^{C2}$ is C$_1$-C$_4$alkyl;
R$^{15}$ is C$_1$-C$_4$alkyl; and
R$^{17}$ is C$_1$-C$_4$alkyl;
each occurrence of R$^I$ and R$^{II}$ are independently (C$_1$-C$_6$alkyl)oxy-,
at least one of R$^x$ or R$^y$ is independently C$_1$-C$_2$alkyl and the other one is H,
or both R$^x$ and R$^y$ are independently C$_1$-C$_2$alkyl;
or a tautomer thereof,
or a salt thereof.

In one embodiment, the compound of Formula (I-b'), wherein
B is unsubstituted —C$_2$-C$_6$alkenyl-;
R$^{A2}$ and R$^A$1 are each independently H, optionally substituted (C$_1$-C$_6$alkyl), or optionally substituted (C$_1$-C$_6$alkyl)oxy-,
wherein C$_1$-C$_6$alkyl of said optionally substituted (C$_1$-C$_6$alkyl), or optionally substituted (C$_1$-C$_6$alkyl)oxy- is optionally substituted with 1 substituents each independently selected from the group consisting of hydroxyl, C$_1$-C$_4$alkoxyl, unsubstituted 5-6 membered heterocycloalkyl,
R$^{14}$ is C$_1$-C$_4$alkyl;
R$^{C2}$ is C$_1$-C$_4$alkyl;
R$^{15}$ is C$_1$-C$_4$alkyl; and
R$^{17}$ is C$_1$-C$_4$alkyl;
at least one of R$^x$ or R$^y$ is independently C$_1$-C$_2$alkyl and the other one is H,
or both R$^x$ and R$^y$ are independently C$_1$-C$_2$alkyl;
or a tautomer thereof,
or a salt thereof.

In one embodiment, the compound of Formula (I-b'), wherein
B is unsubstituted ethenyl;
R$^{A2}$ and R$^A$1 are each independently H or optionally substituted (C$_1$-C$_6$alkyl)oxy-, wherein $C_1$-$C_6$alkyl of said optionally substituted ($C_1$-$C_6$alkyl)oxy- is optionally substituted with one substituent selected from hydroxyl or unsubstituted morpholinyl;

$R^{14}$ is methyl or ethyl;

$R^{C2}$ is methyl or ethyl;

$R^{15}$ is methyl or ethyl; and $R^{17}$ is methyl or ethyl;

at least one of $R^x$ or $R^y$ is independently $C_1$-$C_2$alkyl and the other one is H, or both $R^x$ and $R^y$ are independently $C_1$-$C_2$alkyl;

or a tautomer thereof, or a salt thereof.

In one embodiment, the compound of Formula (I-1),

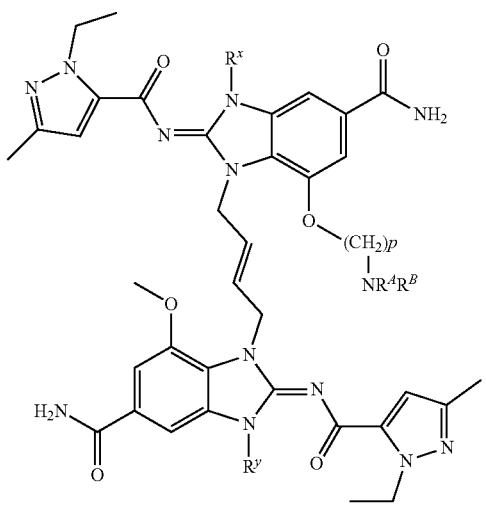

wherein

P is an integer among 1 to 6;

$R^A$ and $R^B$ are independently H, or $C_1$-$C_4$alkyl;

or N, $R^A$ and $R^B$ form an optionally substituted 5 or 6 membered heterocyclic ring, wherein the heterocyclic ring is selected from the group consisting of morpholinyl, piperidinyl, piperazinyl and pyrrolidinyl, and the heterocyclic ring is optionally substituted by one or two substituents independently selected from the group consisting of hydroxyl and $C_1$-$C_3$ alkyl optionally substituted with one or two substituent of hydroxyl or $C_1$-$C_3$ alkoxyl;

at least one of $R^x$ or $R^y$ is independently $C_1$-$C_2$alkyl and the other one is H;

or both $R^x$ and $R^y$ are independently $C_1$-$C_2$alkyl;

or a tautomer thereof, or a salt thereof.

In one embodiment, the compounds of Formula (I-1), wherein $R^x$ and $R^y$ are each independently methyl or ethyl. In another embodiment, the compounds of Formula (I-1), wherein $R^x$ and $R^y$ are both methyl. In a further embodiment, the compounds of Formula (I-1), wherein one of $R^x$ and $R^y$ is methyl and the other one is H.

In one embodiment, the compound of the invention has Formula (I-bc)

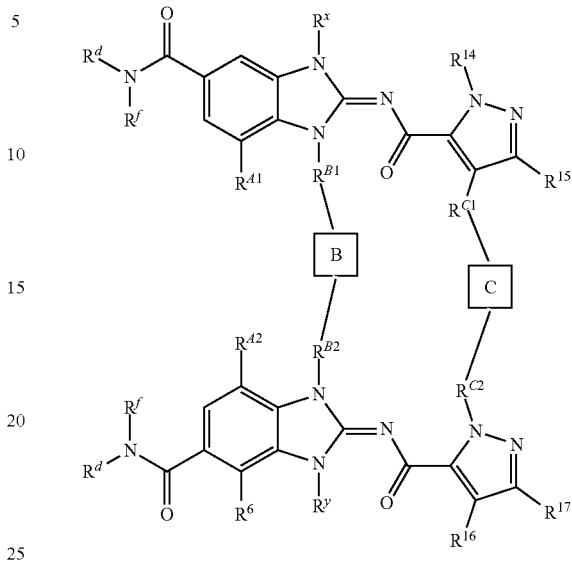

wherein $R^{C1}$ and $R^{C2}$ are each independently —$CH_2$—,

C is -halo($C_1$-$C_6$alkyl), unsubstituted —$C_1$-$C_5$alkyl, or unsubstituted —$C_2$-$C_5$alkenyl-;

$R^{B1}$ and $R^{B2}$ are each independently —$CR^dR^f$—; B is -halo($C_1$-$C_6$alkyl), unsubstituted —$C_1$-$C_5$alkyl, or unsubstituted —$C_2$-$C_5$alkenyl-;

$R^{A2}$ and $R^{A1}$ are each independently H, halogen, hydroxyl, —O—P(O)(OH)$_2$, —O—P(O)($R^I$)($R^{II}$), optionally substituted ($C_1$-$C_6$alkyl), or optionally substituted ($C_1$-$C_6$alkyl)oxy-, wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, —O—P(O)(OH)$_2$, —O—P(O)($R^I$)($R^{II}$), $C_1$-$C_4$alkoxyl, —N($R^e$)($R^f$), —CO$_2$($R^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)($R^I$)($R^{II}$), amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, —($C_1$-$C_4$alkyl)-O—P(O)(OH)$_2$, —($C_1$-$C_4$alkoxyl)-O—P(O)($R^I$)($R^{II}$), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxyl)-O—P(O)($R^I$)($R^{II}$), —($C_1$-$C_6$alkyl)-NH$_2$, and $C_1$-$C_4$alkoxy-($C_1$-$C_4$alkoxy)-;

each $R^d$ is independently H or $C_1$-$C_4$alkyl;

$R^e$ is selected from H, ($C_1$-$C_4$alkyl), —CO($C_1$-$C_4$alkyl), —OCO($C_1$-$C_4$alkyl), —($C_1$-$C_4$alkyl)-NH$_2$, —($C_1$-$C_4$alkyl) $C_1$-$C_4$alkoxy, or —CO$_2$($C_1$-$C_4$alkyl), each $R^1$ is H or ($C_1$-$C_4$alkyl);

$R^6$ is H;

$R^{14}$ is $C_1$-$C_4$alkyl;

$R^{15}$ is $C_1$-$C_4$alkyl;

$R^{16}$ is $C_1$-$C_4$alkyl;
$R^{17}$ is $C_1$-$C_4$alkyl; and
each occurrence of $R^I$ and $R^{II}$ are independently ($C_1$-$C_6$alkyl)oxy-,
at least one of $R^x$ or $R^y$ is independently $C_1$-$C_4$alkyl and the other one is H,
or both $R^x$ and $R^y$ are independently $C_1$-$C_4$alkyl;
or a tautomer thereof;
or a salt thereof, particularly a pharmaceutically acceptable salt thereof.

In one embodiment, the compound of Formula (I-bc), wherein $R^{A2}$ and $R^{A}1$ are each independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —O—P(O)(OH)$_2$, —O—P(O)($R^I$)($R^{II}$), —N($R^e$)($R^f$), $C_1$-$C_4$alkoxyl, phenyl, optionally substituted 5-6 membered heterocycloalkyl containing at least one nitrogen or oxygen as a member of the ring, each $R^e$ is independently selected from H, $C_1$-$C_4$alkyl, —($C_1$-$C_4$alkyl)-NH$_2$, or —($C_1$-$C_4$alkyl) $C_1$-$C_4$alkoxy and each $R^f$ is independently H or ($C_1$-$C_4$alkyl).

In one embodiment, the compound of Formula (I-bc), wherein at least one of $R^{A2}$ or $R^{A}1$ is independently H, halogen, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from —N($R^e$)($R^f$), tetrahydropyran, pyrrolidinyl, piperazinyl, piperidyl and morpholinyl, each $R^e$ is independently selected from H, $C_1$-$C_4$alkyl, —($C_1$-$C_4$alkyl)-NH$_2$, or —($C_1$-$C_4$alkyl) $C_1$-$C_4$alkoxy and each $R^f$ is independently H or $C_1$-$C_4$alkyl.

In one embodiment, the compound of Formula I-2,

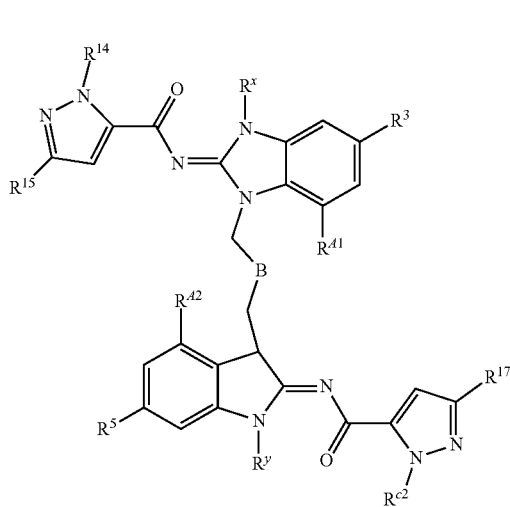

(I-2)

wherein
$R^{14}$, $R^{15}$, $R^{c2}$ and $R^{17}$ are independently $C_1$-$C_3$alkyl;
$R^{A1}$ an $R^{A2}$ are independently H, hydroxy, COOH, or optionally substituted ($C_1$—C/alkyl)oxy-,
wherein the alkyl of optionally substituted ($C_1$-$C_6$alkyl) oxy- is optionally substituted by 1-4 substituents each independently selected from the group consisting of hydroxy, —CO$_2$($R^1$), —N($R^e$)($R^f$), optionally substituted phenyl, and optionally substituted 5-6 membered heterocycloalkyl,
wherein said optionally substituted phenyl, or 5-6 membered heterocycloalkyl is optionally substituted by 1-4 substituents each independently selected from the group consisting of ($C_1$-$C_4$alkyl)oxy- and $C_1$-$C_4$alkyl;
$R^3$ and $R^5$ are each independently —CO—N($R^d$)($R^f$),
each $R^d$, $R^e$ and $R^f$ are independently H or $C_1$-$C_3$alkyl;
B is substituted —$C_1$-$C_4$alkyl- or substituted —$C_2$-$C_4$alkenyl-,
wherein the alkyl moiety of said substituted —$C_1$-$C_4$alkyl-, or substituted —$C_2$-$C_4$alkenyl-, is substituted by 1-4 substituents each independently selected from the group consisting of halogen, hydroxy, ($C_1$-$C_4$alkyl)oxy-, and $C_{1-4}$alkyl,
at least one of $R^X$ or $R^y$ is independently $C_1$-$C_4$alkyl and the other one is H,
or both $R^x$ and $R^y$ are independently $C_1$-$C_4$alkyl;
or a tautomer thereof,
or a salt thereof (particularly a pharmaceutically acceptable salt thereof).

In one embodiment, the compounds of Formula (I-2), $R^{14}$, $R^{15}$, $R^{c2}$ and $R^{17}$ are independently methyl or ethyl.

In one embodiment, the compounds of Formula (I-2), $R^{14}$ and $R^{c2}$ are ethyl and $R^{15}$, and $R^{17}$ are methyl.

In one embodiment, the compounds of of Formula (I-2), $R^{14}$, $R^{15}$, $R^{c2}$ and $R^{17}$ are methyl.

In one embodiment, the compounds of of Formula (I-2), $R^{A}1$ and $R^{A2}$ are independently H, hydroxy or optionally substituted ($C_1$-$C_6$alkyl)oxy-, wherein the alkyl of optionally substituted ($C_1$-$C_6$alkyl)oxy- is optionally substituted by 1-4 substituents each independently selected from the group consisting of hydroxy, COOH, and optionally substituted phenyl, wherein said optionally substituted phenyl is optionally substituted by 1-4 substituents each independently selected from the group consisting of ($C_1$-$C_4$alkyl) oxy-.

In one embodiment, the compounds of of Formula (I-2), one of $R^{A}1$ and $R^{A2}$ is H and the other one of $R^{A}1$ and $R^{A2}$ is hydroxy or optionally substituted ($C_1$-$C_6$alkyl)oxy-,
wherein the alkyl of optionally substituted ($C_1$-$C_6$alkyl) oxy- is optionally substituted by 1-4 substituents each independently selected from the group consisting of hydroxy, COOH, and optionally substituted phenyl,
wherein said optionally substituted phenyl is optionally substituted by 1-4 substituents each independently selected from the group consisting of ($C_1$-$C_4$alkyl) oxy-.

In one embodiment, the compounds of Formula (I-2), one of $R^{A}1$ and $R^{A2}$ is H and the other one of $R^{A}1$ and $R^{A2}$ is hydroxy or optionally substituted ($C_1$-$C_4$alkyl)oxy-,
wherein the alkyl of optionally substituted ($C_1$-$C_4$alkyl) oxy- is optionally substituted by 1-2 substituents each independently selected from the group consisting of hydroxy and optionally substituted phenyl,
wherein said optionally substituted phenyl is optionally substituted by 1-2 substituents each independently selected from the group consisting of ($C_1$-$C_4$alkyl) oxy-.

In one embodiment, the compounds of Formula (I-2), $R^{A1}$ and $R^{A2}$ are both H.

In one embodiment, the compounds of Formula (I-2), wherein at least one of $R^{A1}$ and $R^{A2}$ is not H.

In one embodiment, the compounds of Formula (I-2), $R^{A1}$ and $R^{A2}$ is each independently optionally substituted ($C_1$-

C$_4$alkyl)oxy-, wherein the alkyl of optionally substituted (C$_1$-C$_4$alkyl)oxy- is optionally substituted by 1-2 substituents of hydroxy.

In one embodiment, the compounds of Formula (I-2), R$^3$ and R$^5$ are independently selected from the group consisting of —CO—N(R$^d$)(R$^f$), and each R$^d$ and R$^f$ are independently H or C$_1$-C$_3$alkyl.

In one embodiment, the compounds of Formula (I-2), R$^3$ and R$^5$ are —CO—NH$_2$.

In one embodiment, the compounds of Formula (I-2), B is substituted —C$_1$-C$_4$alkyl- or substituted —C$_2$-C$_4$alkenyl-,
wherein the alkyl moiety of said substituted —C$_1$-C$_4$alkyl- or substituted —C$_2$-C$_4$alkenyl-, is substituted by 1-4 substituents each independently selected from the group consisting of halogen, and C$_{1-4}$alkyl.

In one embodiment, the compounds of Formula (I-2), B is substituted —CH$_2$—CH$_2$— or substituted —CH═CH—,
wherein the substituted —CH$_2$—CH$_2$— or substituted —CH═CH— is substituted by 1-4 substituents each independently selected from the group consisting of halogen and C$_{1-4}$alkyl.

In one embodiment of the compounds of Formula (I-2), B is substituted —CH$_2$—CH$_2$— or substituted —CH═CH—,
wherein the substituted —CH$_2$—CH$_2$— or substituted —CH═CH— is substituted by 1-4 substituents each independently selected from the group consisting of fluoro and C$_{1-2}$alkyl.

In one embodiment of the compounds of Formula (I-2), B is substituted —CH$_2$—CH$_2$— or substituted —CH═CH—,
wherein the substituted —CH$_2$—CH$_2$— or substituted —CH═CH— is substituted by 1-4 substituents of fluoro.

In one embodiment of the compounds of Formula (I-2), B is substituted —CH$_2$—CH$_2$— or substituted —CH═CH—,
wherein the substituted —CH$_2$—CH$_2$— or substituted —CH═CH— is substituted by 1-4 substituents each independently of C$_{1-2}$alkyl.

In one embodiment of the compounds of Formula (I-2), B is substituted —CH$_2$—CH$_2$— or substituted —CH═CH—,
wherein the substituted —CH$_2$—CH$_2$— or substituted —CH═CH— is substituted by 1-4 substituents of hydroxy.

In one embodiment of the compounds of Formula (I-2), B is —CH$_2$—CH$_2$— substituted by 1-2 substituents of hydroxy.

In one embodiment, the compounds of Formula (I-2), wherein R$^x$ and R$^y$ are each independently methyl or ethyl. In another embodiment, the compounds of Formula (I-2), wherein R$^x$ and R$^y$ are both methyl. In a further embodiment, the compounds of Formula (I-2), wherein one of R$^x$ and R$^y$ is methyl and the other one is H.

In one embodiment, the compounds of Formula (I-2), wherein
R$^4$, R$^{15}$, R$^{c2}$ and R$^{17}$ are independently methyl or ethyl;
one of R$^{A1}$ and R$^{A2}$ is H and the other one of R$^{A1}$ and R$^{A2}$ is optionally substituted (C$_1$-C$_4$alkyl)oxy-,
wherein the alkyl of optionally substituted (C$_1$-C$_4$alkyl)oxy- is optionally substituted by 1-2 substituents each independently selected from the group consisting of hydroxy and optionally substituted phenyl,
wherein said optionally substituted phenyl is optionally substituted by 1-2 substituents each independently selected from the group consisting of (C$_1$-C$_4$alkyl)oxy-;
R$^3$ and R$^5$ are both —CO—NH$_2$; and
B is substituted —CH$_2$—CH$_2$— or substituted —CH═CH—,
wherein the substituted —CH$_2$—CH$_2$— or substituted —CH═CH— is substituted by 1-4 substituents each independently selected from the group consisting of fluoro and C$_{1-2}$alkyl; and
at least one of R$^x$ or R$^y$ is independently C$_1$-C$_4$alkyl and the other one is H,
or both R$^x$ and R$^y$ are independently C$_1$-C$_4$alkyl.

In one embodiment, the compounds of Formula (I-2), wherein
R$^{14}$, R$^{15}$, R$^{c2}$ and R$^{17}$ are independently methyl or ethyl;
one of R$^{A1}$ and R$^{A2}$ is H and the other one of R$^{A1}$ and R$^{A2}$ is optionally substituted (C$_1$-C$_4$alkyl)oxy-,
wherein the alkyl of optionally substituted (C$_1$-C$_4$alkyl)oxy- is optionally substituted by 1-2 substituents of hydroxy;
R$^3$ and R$^5$ are both —CO—NH$_2$; and
B is substituted —CH$_2$—CH$_2$— or substituted —CH═CH—,
wherein the substituted —CH$_2$—CH$_2$— or substituted —CH═CH— is substituted by 1-4 substituents each independently selected from the group consisting of hydroxy and C$_{1-2}$alkyl; and
at least one of R$^x$ or R$^y$ is independently C$_1$-C$_4$alkyl and the other one is H,
or both R$^x$ and R$^y$ are independently C$_1$-C$_4$alkyl.

In one embodiment, the compound of Formula I-3,

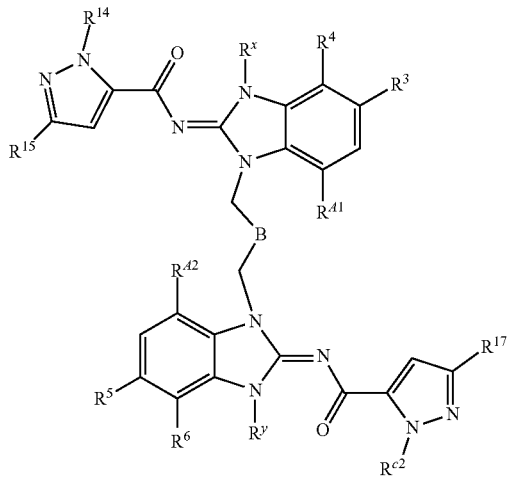

(I-3)

wherein
R$^{14}$, R$^{15}$, R$^{c2}$ and R$^{17}$ are independently C$_1$-C$_3$alkyl;
R$^{A1}$ and R$^{A2}$ are independently H, hydroxy, halogen, COOH, or optionally substituted (C$_1$-C$_6$alkyl)oxy-,
wherein the alkyl of optionally substituted (C$_1$-C$_6$alkyl) oxy- is optionally substituted by 1-4 substituents each independently selected from the group consisting of hydroxy, —CO$_2$(R$^f$), —N(R$^e$)(R$^f$), (C$_1$-C$_4$alkyl)oxy-, optionally substituted phenyl, and optionally substituted 5-6 membered heterocycloalkyl,
wherein said optionally substituted phenyl, or 5-6 membered heterocycloalkyl is optionally substituted by 1-4 substituents each independently selected from the group consisting of halogen, (C$_1$-C$_4$alkyl)oxy- and C$_1$-C$_4$alkyl;

R$^3$ and R$^5$ are each independently —CO—N(R$^d$)(R$^f$), or one of R$^3$ and R$^5$ is —CO—N(R$^d$)(R$^f$), and the other of R$^3$ and R$^5$ is H or CO$_2$(R$^c$);

R$^4$ and R$^6$ are each independently H or halogen, each R$^c$, R$^d$, R$^e$ and R$^f$ are independently H or C$_1$-C$_4$alkyl;

B is optionally substituted —C$_1$-C$_4$alkyl- or optionally substituted —C$_2$-C$_4$alkenyl-,
wherein the alkyl moiety of said optionally substituted —C$_1$-C$_4$alkyl-, or optionally substituted —C$_2$-C$_4$alkenyl-, is optionally substituted by 1-4 substituents each independently selected from the group consisting of halogen, hydroxy, (C$_1$-C$_4$alkyl)oxy-, and C$_1$-$_4$alkyl; and at least one of R$^x$ or R$^y$ is independently C$_1$-C$_4$alkyl and the other one is H, or both R$^x$ and R$^y$ are independently C$_1$-C$_4$alkyl;

or a tautomer thereof, or a salt thereof (particularly a pharmaceutically acceptable salt thereof).

In one embodiment, the compounds of Formula (I-3), R$^{14}$, R$^{15}$, R$^{c2}$ and R$^{17}$ are independently methyl or ethyl.

In one embodiment, the compounds of Formula (I-3), R$^{14}$ and R$^{c2}$ are ethyl and R$^{15}$, and R$^{17}$ are methyl.

In one embodiment, the compounds of of Formula (I-3), R$^{A1}$ and R$^{A2}$ are independently H, hydroxy or optionally substituted (C$_1$-C$_6$alkyl)oxy-,
wherein the alkyl of optionally substituted (C$_1$-C$_6$alkyl)oxy- is optionally substituted by 1-4 substituents each independently selected from the group consisting of hydroxy, COOH, and optionally substituted phenyl,
wherein said optionally substituted phenyl is optionally substituted by 1-4 substituents each independently selected from the group consisting of (C$_1$-C$_4$alkyl)oxy-.

In one embodiment, the compounds of of Formula (I-3), one of R$^{A1}$ and R$^{A2}$ is H and the other one of R$^{A1}$ and R$^{A2}$ is hydroxy or optionally substituted (C$_1$-C$_6$alkyl)oxy-,
wherein the alkyl of optionally substituted (C$_1$-C$_6$alkyl)oxy- is optionally substituted by 1-4 substituents each independently selected from the group consisting of hydroxy, COOH, and optionally substituted phenyl,
wherein said optionally substituted phenyl is optionally substituted by 1-4 substituents each independently selected from the group consisting of (C$_1$-C$_4$alkyl)oxy-.

In one embodiment, the compounds of Formula (I-3), one of R$^{A1}$ and R$^{A2}$ is H and the other one of R$^{A1}$ and R$^{A2}$ is hydroxy or optionally substituted (C$_1$-C$_4$alkyl)oxy-,
wherein the alkyl of optionally substituted (C$_1$-C$_4$alkyl)oxy- is optionally substituted by 1-2 substituents each independently selected from the group consisting of hydroxy and optionally substituted phenyl,
wherein said optionally substituted phenyl is optionally substituted by 1-2 substituents each independently selected from the group consisting of (C$_1$-C$_4$alkyl)oxy-.

In one embodiment, the compounds of Formula (I-3), R$^{A1}$ and R$^{A2}$ is each independently optionally substituted (C$_1$-C$_4$alkyl)oxy-, wherein the alkyl of optionally substituted (C$_1$-C$_4$alkyl)oxy- is optionally substituted by 1-2 substituents of hydroxy.

In one embodiment, the compounds of Formula (I-3), R$^3$ and RS are —CO—NH$_2$.

In one embodiment, the compounds of Formula (I-3), B is substituted —CH$_2$—CH$_2$— or substituted —CH=CH—,
wherein the substituted —CH$_2$—CH$_2$— or substituted —CH=CH— is substituted by 1-4 substituents each independently selected from the group consisting of halogen and C$_1$-$_4$alkyl.

In one embodiment of the compounds of Formula (I-3), B is substituted —CH$_2$—CH$_2$— or substituted —CH=CH—,
wherein the substituted —CH$_2$—CH$_2$— or substituted —CH=CH— is substituted by 1-4 substituents each independently selected from the group consisting of fluoro and C$_1$-$_2$alkyl.

In one embodiment of the compounds of Formula (I-3), B is substituted —CH$_2$—CH$_2$— or substituted —CH=CH—,
wherein the substituted —CH$_2$—CH$_2$— or substituted —CH=CH— is substituted by 1-4 substituents of fluoro.

In one embodiment of the compounds of Formula (I-3), B is substituted —CH$_2$—CH$_2$— or substituted —CH=CH—,
wherein the substituted —CH$_2$—CH$_2$— or substituted —CH=CH— is substituted by 1-4 substituents each independently of C$_1$-$_2$alkyl.

In one embodiment of the compounds of Formula (I-3), B is substituted —CH$_2$—CH$_2$— or substituted —CH=CH—,
wherein the substituted —CH$_2$—CH$_2$— or substituted —CH=CH— is substituted by 1-4 substituents of hydroxy.

In one embodiment of the compounds of Formula (I-3), B is —CH$_2$—CH$_2$— substituted by 1-2 substituents of hydroxy.

In one embodiment, the compounds of Formula (I-3), wherein R$^x$ and R$^y$ are each independently methyl or ethyl. In another embodiment, the compounds of Formula (I-3), wherein R$^x$ and R$^y$ are both methyl. In a further embodiment, the compounds of Formula (I-3), wherein one of R$^x$ and R$^y$ is methyl and the other one is H.

In one embodiment, the compounds of Formula (I-3), wherein

R$^4$, R$^{15}$, R$^{c2}$ and R$^{17}$ are independently methyl or ethyl;
one of R$^{A}$1 and R$^{A2}$ is H and the other one of R$^{A}$1 and R$^{A2}$ is optionally substituted (C$_1$-C$_4$alkyl)oxy-,
wherein the alkyl of optionally substituted (C$_1$-C$_4$alkyl)oxy- is optionally substituted by 1-2 substituents each independently selected from the group consisting of hydroxy and optionally substituted phenyl,
wherein said optionally substituted phenyl is optionally substituted by 1-2 substituents each independently selected from the group consisting of (C$_1$-C$_4$alkyl)oxy-;

R$^3$ and R$^5$ are both —CO—NH$_2$; and

B is substituted —CH$_2$—CH$_2$— or substituted —CH=CH—,
wherein the substituted —CH$_2$—CH$_2$— or substituted —CH=CH— is substituted by 1-4 substituents each independently selected from the group consisting of fluoro and C$_1$-$_2$alkyl; and at least one of R$^x$ or R$^y$ is independently C$_1$-C$_4$alkyl and the other one is H, or both R$^x$ and R$^y$ are independently C$_1$-C$_4$alkyl.

In one embodiment, the compounds of Formula (I-3), wherein

R$^4$, R$^{15}$, R$^{c2}$ and R$^{17}$ are independently methyl or ethyl;
one of R$^{A1}$ and R$^{A2}$ is H and the other one of R$^{A1}$ and R$^{A2}$ is optionally substituted (C$_1$-C$_4$alkyl)oxy-,
wherein the alkyl of optionally substituted (C$_1$-C$_4$alkyl)oxy- is optionally substituted by 1-2 substituents of hydroxy;

$R^3$ and $R^5$ are both —CO—NH$_2$; and

B is substituted —CH$_2$—CH$_2$— or substituted —CH═CH—,
    wherein the substituted —CH$_2$—CH$_2$— or substituted —CH═CH— is substituted by 1-4 substituents each independently selected from the group consisting of hydroxy and C$_{1-2}$alkyl; and at least one of R$^x$ or R$^y$ is independently C$_1$-C$_4$alkyl and the other one is H, or both R$^x$ and R$^y$ are independently C$_1$-C$_4$alkyl.

Representative compounds of this invention include the compounds of the Examples. It will be appreciated that the present invention encompasses compounds of Formula (I) as the free base and as salts thereof, for example as a pharmaceutically acceptable salt thereof. In one embodiment, the invention relates to compounds of Formula (I) in the form of a free base. In another embodiment, the invention relates to compounds of Formula (I) in the form of a salt, particularly, a pharmaceutically acceptable salt. It will be further appreciated that, in one embodiment, the invention relates to compounds of the Examples in the form of a free base. In another embodiment, the invention relates to compounds of the Examples in the form of a salt, particularly, a pharmaceutically acceptable salt.

Specific embodiments of the compounds of this invention include:

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-hydroxy-3-methyl-2,3-dihydro-1H-benzo[d]imidazole-5-carboxamide, (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, (2E,2'E)-1,1'-(pentane-1,5-diyl)bis(2-((1-ethyl-3-methyl-1H-pyrazole-5-carbonyl)imino)-3-methyl-2,3-dihydro-1H-benzo[d]imidazole-5-carboxamide, (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide, (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(3-methoxypropoxy)-3-methyl-2,3-dihydro-1H-benzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, (E)-1-((E)-4-((E)-7-(benzyloxy)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, (E)-1-((E)-4-((E)-4-bromo-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, (E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide, (E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide, (E)-1-(4-((E)-7-bromo-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide, (E)-1-(((4R,5R)-5-(((E)-5-carbamoyl-2-((1-ethyl-3-methyl-1H-pyrazole-5-carbonyl)imino)-3-methyl-2,3-dihydro-1H-benzo[d]imidazol-1-yl)methyl)-2,2-dimethyl-1,3-dioxolan-4-yl)methyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, (E)-2-((1-ethyl-3-methyl-1H-pyrazole-5-carbonyl)imino)-1-(4-((E)-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-7-((4-methoxybenzyl)oxy)-3-methyl-2,3-dihydro-1H-benzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-hydroxy-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, (E)-1-((2S,3S)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide, methyl 4-(((E)-6-carbamoyl-3-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-1-methyl-2,3-dihydro-1H-benzo[d]imidazol-4-yl)oxy)butanoate, (E)-1-((E)-4-((E)-5-carbamoyl-3-ethyl-2-((1-ethyl-3-methyl-1H-pyrazole-5-carbonyl)imino)-2,3-dihydro-1H-benzo[d]imidazol-1-yl)-2,3-dimethylbut-2-en-1-yl)-3-ethyl-2-((1-ethyl-3-methyl-1H-pyrazole-5-carbonyl)imino)-7-((4-methoxybenzyl)oxy)-2,3-dihydro-1H-benzo[d]imidazole-5-carboxamide, (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-(3-(dimethylamino)propoxy)-2-((1-ethyl-3-methyl-1H-pyrazole-5-carbonyl)imino)-3-methyl-2,3-dihydro-1H-benzo[d]imidazole-5-carboxamide, (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-

((3-methoxybenzyl)oxy)-3-methyl-2,3-dihydro-1H-benzo[d]imidazole-5-carboxamide, methyl (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxylate, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-hydroxy-3-methyl-2,3-dihydro-1H-benzo[d]imidazole-5-carboxamide, (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, (E)-7-bromo-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide, (2E,2'E)-1,1'-(2,3-dihydroxybutane-1,4-diyl)bis(2-((1-ethyl-3-methyl-1H-pyrazole-5-carbonyl)imino)-3-methyl-2,3-dihydro-1H-benzo[d]imidazole-5-carboxamide), (2E,2'E)-1,1'-((2S,3S)-2,3-diethoxybutane-1,4-diyl)bis(2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide), (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide, (2E,2'E)-1,1'-((2R,3R)-2,3-diethoxybutane-1,4-diyl)bis(2-((1-ethyl-3-methyl-1H-pyrazole-5-carbonyl)imino)-7-hydroxy-3-methyl-2,3-dihydro-1H-benzo[d]imidazole-5-carboxamide), (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide, (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide, (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-3-methyl-7-phenethyl-2,3-dihydro-1H-benzo[d]imidazole-5-carboxamide, (E)-7-bromo-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-3-methyl-2,3-dihydro-1H-benzo[d]imidazole-5-carboxamide, (E)-1-(5-((E)-5-carbamoyl-3-ethyl-2-((1-ethyl-3-methyl-1H-pyrazole-5-carbonyl)imino)-2,3-dihydro-1H-benzo[d]imidazol-1-yl)pentyl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide, (E)-1-(5-((E)-5-carbamoyl-2-((1-ethyl-3-methyl-1H-pyrazole-5-carbonyl)imino)-2,3-dihydro-1H-benzo[d]imidazol-1-yl)pentyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide, (E)-1-(5-((E)-5-carbamoyl-3-ethyl-2-((1-ethyl-3-methyl-1H-pyrazole-5-carbonyl)imino)-2,3-dihydro-1H-benzo[d]imidazol-1-yl)pentyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide, butyl (E)-1-((E)-4-((E)-5-carbamoyl-2-((1-ethyl-3-methyl-1H-pyrazole-5-carbonyl)imino)-7-((4-methoxybenzyl)oxy)-3-methyl-2,3-dihydro-1Hbenzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1Hbenzo[d]imidazole-5-carboxylate (E)-1-((E)-4-((E)-5-carbamoyl-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxylic acid, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-4-(morpholinomethyl)-2,3-dihydro-1H-benzo[d]imidazol-1-yl)-2,3-dimethylbut-2-en-1-yl)-3-methyl-2,3-dihydro-1H-benzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((2-fluorobenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-fluorobenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((3-fluorobenzyl)oxy)-3-methyl-2,3-dihydro-1H-benzo[d]imidazol-1-yl)-2,3-dimethylbut-2-en-1-yl)-3-methyl-2,3-dihydro-1Hbenzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-isobutoxy-3-methyl-2,3-dihydro-1H-benzo[d]imidazole-5-carboxamide, (E)-7-(3-(dimethylamino)propoxy)-2-((1-ethyl-3-methyl-1H-pyrazole-5-carbonyl)imino)-1-((E)-4-((E)-2-((1-ethyl-3-methyl-1Hpyrazole-5-carbonyl)imino)-3-methyl-2,3-dihydro-1H-benzo[d]imidazol-1-yl)-2,3-dimethylbut-2-en-1-yl)-3-methyl-2,3-dihydro-1Hbenzo[d]imidazole-5-carboxamide, (E)-1-((E)-4-((E)-7-(3-(dimethylamino)propoxy)-2-((1-ethyl-3-methyl-1H-pyrazole-5-carbonyl)imino)-3-methyl-2,3-dihydro-1Hbenzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1Hbenzo[d]imidazole-5-carboxamide, (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-(2-hydroxy-2-methylpropoxy)-3-methyl-2,3-dihydro-1Hbenzo[d]imidazole-5-carboxamide, (2E,2'E)-1,1'-((meso)-2,3-dimethoxybutane-1,4-diyl)bis(2-((1-ethyl-3-methyl-1H-pyrazole-5-carbonyl)imino)-3-methyl-2,3-dihydro-1H-benzo[d]imidazole-5-carboxamide), (E)-1-((E)-4-((E)-7-(3-(4,4-difluoropiperidin-1-yl)propoxy)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, (5aE,21E,29E)-8-ethyl-26-(3-hydroxypropoxy)-5,10,18,22,29,30-hexamethyl-7,20-dioxo-5,7,8,11,12,13,14,15,20,22,28,31-dodecahydrobenzo[4,5]imidazo[1,2-a]benzo[4,5]imidazo[2,1-p]dipyrazolo[5,1-e:4',3'-l][1,3,6,15,17]pentaazacyclohenicosine-3,24-dicarboxamide, or a tautomer thereof;
or a salt thereof, particularly a pharmaceutically acceptable salt, thereof.

In one embodiment, the compounds of formula described above, for example the compounds of Formula (I), Formula (I-2), or Formula (I-3) is (E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide having the structure of

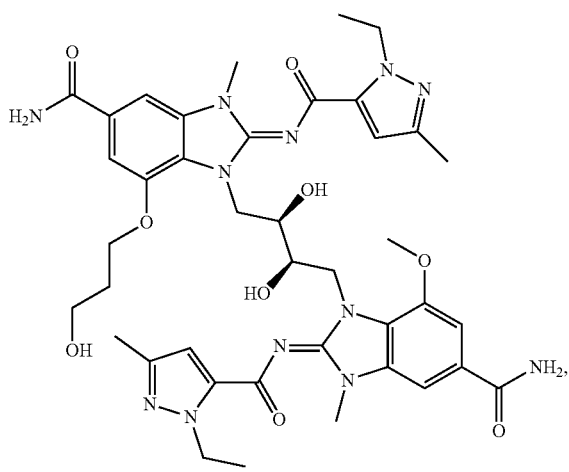 [SMILES: CCn1nc(C)cc1C(=O)/N=c1\n(C)c2cc(C(N)=O)cc(OC)c2n1C[C@@H](O)[C@H](O)Cn1/c(=N/C(=O)c2cc(C)nn2CC)n(C)c2cc(C(N)=O)cc(OCCCO)c21]

or a tautomer thereof;
or a salt thereof, particularly a pharmaceutically acceptable salt thereof.

In one embodiment, the compounds of formula described above, for example the compounds of Formula (I), Formula (I-2), or Formula (I-3) is (E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide having the structure of

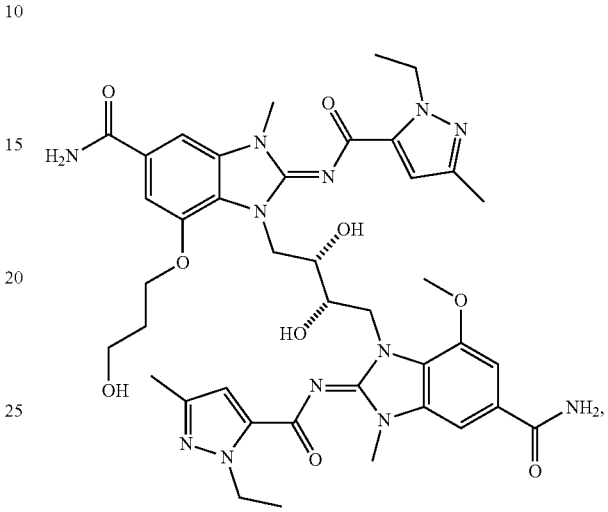

or a tautomer thereof;
or a salt thereof, particularly a pharmaceutically acceptable salt thereof.

In one embodiment, the compounds of formula described above, for example the compounds of Formula (I), Formula (I-2), or Formula (I-3) are not the following compounds:
(E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide having the structure of

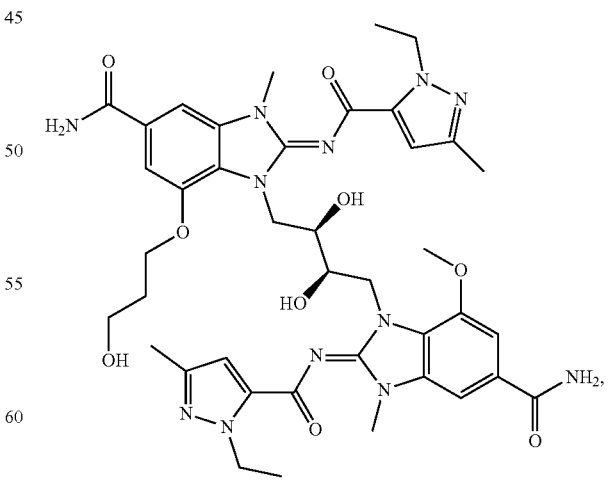

or a tautomer thereof;
or a salt thereof, particularly a pharmaceutically acceptable salt thereof.

In one embodiment, the compounds of formula described above, for example the compounds of Formula (I), Formula (I-2), or Formula (I-3) are not the following compounds: (E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide having the structure of

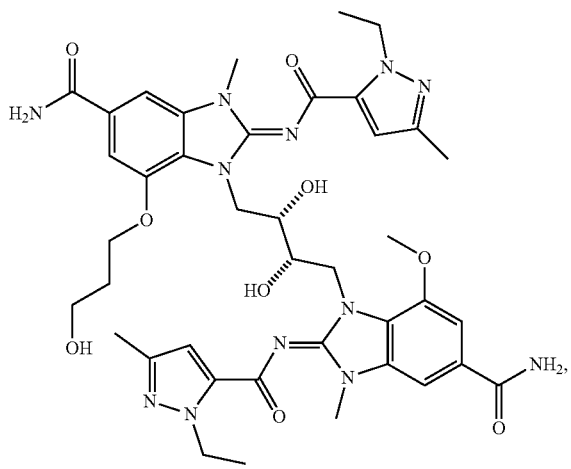 [SMILES: CCn1nc(C)cc1C(=O)/N=c1\n(C)c2cc(C(N)=O)cc(OC)c2n1C[C@H](O)[C@@H](O)Cn1/c(=N/C(=O)c2cc(C)nn2CC)n(C)c2cc(C(N)=O)cc(OCCCO)c21]

or a tautomer thereof;
or a salt thereof, particularly a pharmaceutically acceptable salt thereof.

The compounds of this invention may contain one or more asymmetric centers (also referred to as a chiral center), such as a chiral carbon, or a chiral —SO— moiety. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

The stereochemistry of the chiral center present in compounds of this invention is generally represented in the compound names and/or in the chemical structures illustrated herein. Where the stereochemistry of a chiral center present in a compound of this invention, or in any chemical structure illustrated herein, is not specified, the structure is intended to encompass any stereoisomer and all mixtures thereof. Accordingly, the present invention encompasses all isomers of the compounds of Formula (I), and salts thereof, whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Individual stereoisomers of a compound of this invention may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The invention also includes various deuterated forms of the compounds of this invention. Each available hydrogen atom attached to a carbon atom may be independently replaced with a deuterium atom. A person of ordinary skill in the art will know how to synthesize deuterated forms of the compounds of this invention. For example, α-deuterated α-amino acids are commercially available or may be prepared by conventional techniques (see for example: Elemes, Y. and Ragnarsson, U. *J. Chem. Soc., Perkin Trans.* 1, 1996, 6, 537-40). Employing such compounds may allow for the preparation of compounds in which the hydrogen atom at a chiral center is replaced with a deuterium atom. Other commercially available deuterated starting materials may be employed in the preparation of deuterated analogs of the compounds of this invention (see for example: methyl-$d_3$-amine available from Aldrich Chemical Co., Milwaukee, Wis.), or they may be synthesized using conventional techniques employing deuterated reagents (e.g. by reduction using lithium aluminum deuteride or sodium borodeuteride or by metal-halogen exchange followed by quenching with $D_2O$ or methanol-d).

Suitable pharmaceutically acceptable salts of the compounds of Formula (I) can include acid addition salts or base addition salts. For reviews of suitable pharmaceutically acceptable salts see Berge et al., *J. Pharm. Sci.*, 66:1-19, (1977) and P. H. Stahl and C. G. Wermuth, Eds., *Handbook of Pharmaceutical Salts: Properties, Selection and Use*, Weinheim/Zurich:Wiley-VCH/VHCA (2002).

Salts of the compounds of Formula (I) containing a basic amine or other basic functional group may be prepared by any suitable method known in the art, such as treatment of the free base with a suitable inorganic or organic acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate (hemi-fumarate, etc.), galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride (dihydrochloride, etc.), hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate (diphosphate, etc.), proprionate, pyroglutamate, salicylate, sebacate, stearate, succinate, sulfate, tartrate, thiocyanate, p-toluenesulfonate (tosylate), undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acids such as lysine and arginine.

The invention includes within its scope all possible stoichiometric and non-stoichiometric forms of the salts (e.g., hydrobromide, dihydrobromide, fumarte, hemi-fumarate, etc) of the compounds of Formula (I).

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that the invention includes all polymorphs of any compound of this invention, e.g., all polymorphic forms of any compound named or depicted by structure herein, including any salts and/or solvates (particularly, hydrates) thereof.

Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the conditions used in crystallizing/recrystallizing the compound. Polymorphic forms may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The skilled artisan will appreciate that pharmaceutically acceptable solvates (particularly, hydrates) of a compound of Formula (I), including pharmaceutically acceptable solvates of a pharmaceutically acceptable salt of a compound of Formula (I), may be formed when solvent molecules are incorporated into the crystalline lattice during crystallization. Solvates may involve non-aqueous solvents such as ethanol, or they may involve water as the solvent that is incorporated into the crystalline lattice. Solvates wherein water is the solvent that is incorporated into the crystalline lattice are typically referred to as "hydrates."

The present invention includes within its scope all possible stoichiometric and non-stoichiometric salt and/or hydrate forms.

Salts and solvates (e.g. hydrates and hydrates of salts) of the compounds of the invention which are suitable for use in medicine are those wherein the counterion or associated solvent is pharmaceutically acceptable. Salts having non-pharmaceutically acceptable counterions are within the scope of the present invention, for example, for use as intermediates in the preparation of other compounds of the invention.

Typically, a pharmaceutically acceptable salt may be readily prepared by using a desired acid or base as appropriate. The resultant salt may crystallize or precipitate from solution, or form by trituration, and may be recovered by filtration, or by evaporation of the solvent.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The invention encompasses all prodrugs of the compounds of this invention, which upon administration to the recipient are capable of providing (directly or indirectly) a compound of this invention, or an active metabolite or residue thereof. Such derivatives are recognisable to those skilled in the art, without undue experimentation. Nevertheless, reference is made to the teaching of Burger's Medicinal Chemistry and Drug Discovery, $5^{th}$ Edition, Vol 1: Principles and Practice, which is incorporated herein by reference to the extent of teaching such derivatives.

It is to be further understood that the present invention includes within its scope all tautomeric or isomer forms of any free base form of the compounds of this invention as well as all possible stoichiometric and non-stoichiometric salt forms. The compounds of the invention are useful in the treatment or prevention of diseases and disorders in which modulation of STING is beneficial. Such STING mediated diseases and disorders include inflammation, allergic and autoimmune diseases, infectious diseases, cancer, pre-cancerous syndromes, metabolic diseases, and cardiovascular disease. The compounds of the invention are also useful as an immugenic composition or vaccine adjuvant. Accordingly, this invention is directed to a method of modulating STING comprising contacting a cell with a compound of the invention.

One aspect of the invention provides methods of treatment or prevention of STING mediated diseases and disorders, in which agonizing STING is beneficial. Exemplary diseases/disorders include, but are not limited to, cancer, infectious disease (e.g., HIV, HBV, HCV, HPV, and influenza), vaccine adjuvant.

One aspect of the invention provides methods of treatment or prevention of STING mediated diseases and disorders, in which inhibiting STING is beneficial. Exemplary diseases/disorders include, but are not limited to, systemic lupus erythematosus (SLE), cutaneous lupus, lupus nephritis, psoriasis, diabetes mellitus including insulin-dependent diabetes mellitus (IDDM), obesity related insulin resistance and Nonalcoholic fatty liver disease (NAFLD), dermatomyositis, systemic sclerosis (scleroderma), and Sjögren's syndrome (SS), rheumatoid arthritis, psoriatic arthritis, STING associated vasculitis with onset at infancy (SAVI), Aicardi Goutieres syndrome (AGS), chilblain lupus, mixed connective tissue disease, neuroinflammation linked to Alzheimer's disease, amyotrophic lateral sclerosis (ALS), Parkison's syndrome, Huntington's disease, and multiple sclerosis, as well as inflammation of the heart associated with myocardial infarction.

In one embodiment, this invention provides a compound of the invention for use in therapy. This invention also provides a compound of Formula or a pharmaceutically acceptable salt thereof, for use in therapy. This invention particularly provides a compound of Formula (I), or a pharmaceutically acceptable salt thereof, for use in the treatment of a STING-mediated disease or disorder.

This invention also provides a compound of Formula (I), or a pharmaceutically acceptable salt thereof, for use as a vaccine adjuvant. There is also therefore provided an immunogenic composition or vaccine adjuvant comprising a compound of Formula (I), or a pharmaceutically acceptable salt thereof.

In a further embodiment of the invention, there is provided a composition comprising a compound of Formula (I), or a pharmaceutically acceptable salt thereof, and one or more immunostimulatory agents.

In another embodiment, this invention provides a compound of the invention for use in the treatment of a STING-mediated disease or disorder and/or for use as an immugenic composition or a vaccine adjuvant. In another embodiment, this invention provides a compound of Formula (I), or a pharmaceutically acceptable salt thereof, for use in the amelioration of organ injury or damage sustained as a result of a STING-mediated disease or disorder.

The invention further provides for the use of a compound of the invention in the manufacture of a medicament for treatment of a STING-mediated disease or disorder. The invention further provides for the use of a compound of Formula (I), or a salt thereof, particularly a pharmaceutically acceptable salt thereof, in the manufacture of a medicament for treatment of a STING-mediated disease or disorder, for example the diseases and disorders recited herein.

The invention further provides for the use of a compound of Formula (I), or a salt thereof, particularly a pharmaceutically acceptable salt thereof, in the manufacture of a vaccine. There is further provided the use of a compound of Formula (I), or a pharmaceutically acceptable salt thereof, for the manufacture of an immunogenic composition comprising an antigen or antigenic composition, for the treatment or prevention of disease. There is further provided the use of a compound of Formula (I), or a pharmaceutically acceptable salt thereof, for the manufacture of a vaccine composition comprising an antigen or antigenic composition, for the treatment or prevention of disease.

In another embodiment, the invention is directed to a method of treating a STING-mediated disease or disorder comprising administering a therapeutically effective amount of a compound of this invention to a human in need thereof. In another embodiment, the invention is directed to a method of treating a STING-mediated disease or disorder comprising administering a therapeutically effective amount of a compound of Formula (I) or a salt, particularly a pharmaceutically acceptable salt thereof, to a human in need thereof.

In another embodiment, the invention is directed to a method of treating or preventing disease comprising the administration to a human subject suffering from or susceptible to disease, an immunogenic composition comprising an antigen or antigenic composition and a compound of Formula (I), or a pharmaceutically acceptable salt thereof. In another embodiment, the invention is directed to a method of treating or preventing disease comprising the administration to a patient human subject suffering from or susceptible to disease, a vaccine composition comprising an antigen or antigenic composition and a compound of Formula (I), or a pharmaceutically acceptable salt thereof.

In one embodiment, this invention is directed to a compound of Formula (I), or a pharmaceutically acceptable salt thereof for use in the treatment of inflammation. In a further aspect there is provided a method of treating inflammation comprising administering to a human in need thereof a therapeutically effective amount of a compound of Formula (I), or a pharmaceutically acceptable salt thereof. In a further aspect there is provided a compound of Formula (I) or a pharmaceutically acceptable salt thereof for use in the manufacture of a medicament for the treatment of inflammation.

In one embodiment, this invention is directed to a compound of Formula (I) or a pharmaceutically acceptable salt thereof for use in the treatment of an allergic disease. In a further aspect there is provided a method of treating an allergic disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an allergic disease. Exemplary allergic disease includes allergic rhinitis, hay fever, atopic dermatitis, Urticaria.

In one embodiment, this invention is directed to a compound of Formula (I) or a pharmaceutically acceptable salt thereof for use in the treatment of an autoimmune disease. In a further aspect there is provided a method of treating an autoimmune disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an autoimmune disease.

In one embodiment, this invention is directed to a compound of Formula (I) or a pharmaceutically acceptable salt thereof for use in the treatment of an infectious disease. In a further aspect there is provided a method of treating an infectious disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an infectious disease.

In one embodiment, this invention is directed to a method of treating an HIV infection in a human by administering to the human a therapeutically effective amount of a compound of Formula (I), or a pharmaceutically acceptable salt thereof. In one embodiment, this invention is directed to a method of treating an HIV infection, in a human having or at risk of having the infection by administering to the human a therapeutically effective amount of a compound of Formula (I), or a pharmaceutically acceptable salt thereof. In another embodiment, this invention is directed to a method of treating an AIDS infection, in a human having the infection by administering to the human a therapeutically effective amount of a compound of Formula (I), or a pharmaceutically acceptable salt thereof.

In one embodiment, this invention is directed to a method of treating an HBV infection in a human by administering to the human a therapeutically effective amount of a compound of Formula (I), or a pharmaceutically acceptable salt thereof. In one embodiment, this invention is directed to a method of treating an HBV infection, in a human having or at risk of having the infection by administering to the human a therapeutically effective amount of a compound of Formula (I), or a pharmaceutically acceptable salt thereof.

In one embodiments, the method treating and HBV infection comprising administering a first therapeutic agent. In one embodiment, the methods comprise administering a first therapeutic agent that is a therapeutically effective amount of a compound of Formula (I), or a pharmaceutically acceptable salt thereof, and administering one or more second therapeutic agents. In one embodiment, the first therapeutic agent and one or more second therapeutic agents are co-administered.

In one embodiment, the first therapeutic agent and one or more second therapeutic agents are co-administered sequentially or concomitantly. In one embodiment, the one or more second therapeutic agents are also a compound of Formula (I). In one embodiment, the one or more second therapeutic agents are different from a compound or composition described herein. Examples of one or more second therapeutic agents include, but are not limited to, an anti-inflammatory agent, chemotherapeutic agent or anti-infection agent. In other related embodiments, the additional therapeutic agent may be an HBV agent, an HCV agent, a chemotherapeutic agent, an antibiotic, an analgesic, a non-steroidal anti-inflammatory (NSAID) agent, an antifungal agent, an antiparasitic agent, an anti-nausea agent, an antidiarrheal agent, an immunomodulatory, or an immunosuppressant agent.

In one embodiment, the one or more second therapeutic agents are an HBV agent. In one embodiment, the HBV agent can include, but is not limited to, interferon alpha-2b, interferon 5 alpha-2a, and interferon alphacon-1 (pegylated and unpegylated), ribavirin; an HBV RNA replication inhibitor; an HBV antigen production inhibitor; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In one embodiment, the one or more second therapeutic agents are an HCV agent. In one embodiment, the HCV agent can include, but is not limited to interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

In one embodiment, the one or more second therapeutic agents are an anti-inflammatory agent (i.e., an inflammation lowering therapy). In one embodiment, the inflammation lowering therapy can include, but is not limited to, a therapeutic lifestyle change, a steroid, a NSAID or a DMARD. The steroid can be a corticosteroid. The NSAID can be an aspirin, acetaminophen, ibuprofen, naproxen, COX inhibitors, indomethacin and the like. The DMARD can be a TNF inhibitor, purine synthesis inhibitor, calcineurin inhibitor, pyrimidine synthesis inhibitor, a sulfasalazine, methotrexate and the like.

In one embodiment, the one or more second therapeutic agents are a chemotherapeutic agent (i.e., a cancer treating agent). Chemotherapeutic agents can include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin, gemcitabine and diethylstilbestrol (DES).

In one embodiment, the one or more second therapeutic agents are an immunomodulatory agent known as innate immune activators, check point inhibitors, T-cell stimulatory agents or other agents that restore adaptive immune responses against HBV. Immune-modulators includes, but are not limited to, antibodies or small molecules antagonizing CTLA-4 such as ipilimumab (YERVOY), PD-1 such as Opdivo/nivolumab and Keytruda/pembrolizumab), PDL1 such as TECENTRIQ™ (atezolizumab), LAG3, TIM3, or IDO. Immune-modulators includes, but are not limited to, antibodies or small molecules stimulating ICOS, OX-40, TLRs, IL7R or IL12R.

In one embodiment, the one or more second therapeutic agents are an anti-infection agent. Examples of antiinfection agents include, but are not limited to, antibiotics, antifungal drugs and antiviral drugs.

In one embodiment, this invention is directed to a method of treating an HCV infection in a human by administering to the human a therapeutically effective amount of a compound of Formula (I), or a pharmaceutically acceptable salt thereof. In one embodiment, this invention is directed to a method of treating an HCV infection, in a human having or at risk of having the infection by administering to the human a therapeutically effective amount of a compound of Formula (I), or a pharmaceutically acceptable salt thereof.

In one embodiment, this invention is directed to a method of treating influenza in a human by administering to the human a therapeutically effective amount of a compound of Formula (I), or a pharmaceutically acceptable salt thereof. In one embodiment, this invention is directed to a method of treating influenza, in a human having or at risk of having the infection by administering to the human a therapeutically effective amount of a compound of Formula (I), or a pharmaceutically acceptable salt thereof.

In one embodiment, this invention is directed to a method of treating human papilomavirus (HPV) infection in a human by administering to the human a therapeutically effective amount of a compound of Formula (I), or a pharmaceutically acceptable salt thereof. In one embodiment, this invention is directed to a method of treating HPV infection, in a human having or at risk of having the infection by administering to the human a therapeutically effective amount of a compound of Formula (I), or a pharmaceutically acceptable salt thereof. As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In one embodiment, this invention is directed to a compound of Formula (I) or a pharmaceutically acceptable salt thereof for use in the treatment of cancer and pre-cancerous syndromes. In a further aspect there is provided a method of treating cancer and pre-cancerous syndromes comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of cancer and pre-cancerous syndromes.

Autoimmune diseases associated include, but are not limited to STING associated vasculitis with onset at infancy (SAVI), Aicardi Goutieres syndrome (AGS), chilblain lupus, ataxia telanogiectasia (also referred to as Louis-Bar Syndrome), retinal vasculopathy with cerebral leukodystrophy (RCVL), systemic lupus erythematosus (SLE), cutaneous lupus, lupus nephritis, psoriasis, diabetes mellitus including insulin-dependent diabetes mellitus (IDDM), dermatomyositis, human immunodeficiency virus (HIV), AIDS, polymyositis, systemic sclerosis (scleroderma), and Sjögren's syndrome (SS) rheumatoid arthritis, psoriatic arthritis, polyarthritis, osteoarthritis, myasthenia gravis, polyarteritis nodosa, vasculitis, cutaneous vasculitis, anti-neutrophil cytoplasmic antibody (ANCA)-associated vasculitis, Henoch-Schönlein purpura, autoimmune hepatitis, primary sclerosing cholangitis, Wegener's granulomatosis, microscopi polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Inflammation represents a group of vascular, cellular and neurological responses to trauma. Inflammation can be characterized as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present, and to allow for the physiological process or healing and tissue repair to progress.

The compounds of this invention may be used to treat inflammation of any tissue and organs of the body, including musculoskeletal inflammation, vascular inflammation, neural inflammation, digestive system inflammation, ocular inflammation, cardiac inflammation, adipose tissue inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis, CNS vasculitis, and schizophrenia.

Examples of inflammation associated with neurodegenerative diseases which may be treated with compounds of the invention include Alzheimer's disease and related dementias, amyotrophic lateral sclerosis (ALS) and Frontotmeporal Lobar Degeneration (FTD), Parkinson's disease, and Huntington's disease.

Examples of inflammation of the vasculature or lymphatic system which may be treated with the compounds of the invention include arthrosclerosis, arthritis, phlebitis, vasculitis, and lymphangitis.

Examples of inflammation of the cardiovascular system which may be treated with the compounds of the invention include not limited to myocardial infarction, heart failure, congenital heart defect, coranary artery disease, hypertension, cardiomyopathy, and other related cardiovascular conditions.

Examples of inflammation of the liver which may be treated with the compounds of the invention include but not limited to liver fibrosis, alcoholic liver disease (ALD), Nonalcoholic fatty liver disease (NAFLD) and Nonalcoholic steatohepatitis, and biliary liver disease.

Examples of inflammation of adipose tissue which may be treated with the compounds of the invention include but not limited to obesity and obesity induced insulin resistance.

Examples of inflammation of the liver which may be treated with the compounds of the invention include but not limited to liver fibrosis, and fibrosis-carcinoma alcoholic liver disease (ALD), Nonalcoholic fatty liver disease (NAFLD) and Nonalcoholic steatohepatitis (NASH), and biliary liver disease.

Examples of inflammation of the pancreas which may be treated with the compounds of the invention include but not limited to pancreatitis and metabolic syndrome induced pancreatic beta cells dysfunction.

Examples of inflammation of the kidney which may be treated with the compounds of the invention include but not limited to kidney nephritis.

Examples of inflammation in the lung which may be treated with the compound of the invention include pulmonary fibrosis, COPD, and asthma.

Examples of inflammation in the eye which may be treated with the compound of the invention include dry eye syndromes and age related macular degeneration.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

In one embodiment, the compounds of present invention can be used to treat systemic lupus erythematosus, rheumatoid arthritis, osteoarthritis, inflammatory bowel disease (IBD) (for example, Crohn's disease, Ulcerative colitis).

The compounds of this invention may be used to treat autoimmune conditions having an inflammatory component. Such conditions include acute disseminated alopecia universalise, Behcet's disease, Chagas' disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-associated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, chronic obstructive pulmonary disease, adult respiratory distress syndrome, and vitiligo.

The compounds of this invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the compounds of this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome, Sezary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic pulmonary disease, and inflammation accompanying infectious conditions (e.g., sepsis). In one embodiment, the compounds of this invention may be used to treat asthma.

Examples of cancer diseases and conditions in which a compounds of this invention may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer. In some embodiments, the compounds of the present invention may be used to treat solid or liquid tumors. In some embodiments, the compounds of the present invention may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and/or Non Hodgkin lymphoma (NHL). Suitably the present invention relates to a method for treating or lessening the severity of pre-cancerous syndromes in a mammal, including a human, wherein the pre-cancerous syndrome is selected from: cervical intraepithelial neoplasia, monoclonal gammopathy of unknown significance (MGUS), myelodysplastic syndrome, aplastic anemia, cervical lesions, skin nevi (pre-melanoma), prostatic intraepithelial (intraductal) neoplasia (PIN), Ductal Carcinoma in situ (DCIS), colon polyps and severe hepatitis or cirrhosis.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lymphoblastic leukemia (CLL), follicular lymphoma, acute myeloid leukemia and chronic myelogenous leukemia.

In one embodiment, the compounds of the present invention may be useful for treatment of skin cancers (e.g., non-melanoma skin cancer, squamous cell carcinoma, basal cell carcinoma) or actinic keratosis. In addition to a field effect for clearing superficial skin cancers, the compounds of the present invention may prevent the development of subsequent skin cancers and pre-malignant actinic keratosis in treated patients.

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

The compounds of this invention may be used to treat neurodegenerative diseases. Exemplary neurodegenerative diseases include, but are not limited to, multiple sclerosis, Huntington's disease, Alzheimer's disease, Parkinson's disease, amyotrophic lateral sclerosis (ALS), and Frontotemporal Lobar Degeneration (FTD).

The compounds of this invention may be used to treat or prevent metabolic disease (such as insulin resistance, Non-alcoholic fatty liver disease (NAFLD)/Nonalcoholic steatohepatitis (NASH), obesity, diabetes, high blood pressure, fatty liver and cardiovascular diseases The compounds of this invention may be used to treat an infectious disease, which is any disease instigated by or coincident with an infection from a pathogen. Pathogens are broadly defined as any species of organism that is foreign to a human tissue environment. Common disease-causing pathogens include bacteria (many like TB), viruses (many like HBV, HIV, flu) and parasitic protozoans (like *P falciparum* that causes malaria). The compounds of this invention may be used to treat infectious diseases derived from bacteria, such as TB infection (*Mycobacterium tuberculosis*), Chlamydia, Tularemia infection (*Francisella tularensis*), plasmodium infection or infections from DNA or RNA virus. The compounds of this invention may be used to treat infectious diseases derived from the DNA virus families: Herpesviridae (herpes simplex virus-1, Kaposi's sarcoma-associated virus and Epstein-Barr virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Hepatitis C virus), Orthomyxoviridae (influenza), and Coronaviridae (human coronavirus and SARS coronzvirus).

The compounds of this invention may be employed alone or in combination with other therapeutic agents. As modulators of the immune response, the compounds of this invention may also be used in monotherapy or used in combination with another therapeutic agent in the treatment of diseases and conditions in which modulation of STING is beneficial. Combination therapies according to the present invention thus comprise the administration of a compound of Formula (I) or a pharmaceutically acceptable salt thereof, and at least one other therapeutically active agent. In one embodiment, combination therapies according to the present invention comprise the administration of at least one compound of Formula (I) or a pharmaceutically acceptable salt thereof, and at least one other therapeutic agent. The compound(s) of Formula (I) and pharmaceutically acceptable salts thereof, and the other therapeutic agent(s) may be administered together in a single pharmaceutical composition or separately and, when administered separately this may occur simultaneously or sequentially in any order. The amounts of the compound(s) of Formula (I) and pharmaceutically acceptable salts thereof, and the other therapeutic agent(s) and the relative timings of administration will be selected in order to achieve the desired combined therapeutic effect. Thus, in a further aspect, there is provided a combination comprising a compound of Formula (I), or a pharmaceutically acceptable salt thereof, together with one or more other therapeutic agents.

The compounds of Formula (I) and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The compounds of Formula (I) and pharmaceutically acceptable salts thereof may be used in combination with radiotherapy and/or surgery and/or at least one other therapeutic agent which may be useful in the treatment of cancer and pre-cancerous syndromes. Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; cell cycle signaling inhibitors; immuno-oncology agents and immunostimulatory agents.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β, 13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p.16-23, 1995).

Docetaxel, (2R,3S)- N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin Ill, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of *vinca* alkaloids include, but are not limited to, vinblastine, vincristine, and vinorelbine.

Vinblastine, vincaleukoblastine sulfate, is commercially available as VELBAN© as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosuppression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated for use as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diamine [1,1-cyclobutane-dicarboxylate(2-)—O,O'], is commercially available as PARAPLATIN© as an injectable solution. Carboplatin is primarily indicated in the first and second line treatment of advanced ovarian carcinoma.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated for use as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and for use in combination with other agents for the second line treatment of Hodgkin's Disease.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthracyclines such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-Fluorouracil, 5-fluoro-2,4- (1H,3H) pyrimidinedione, is commercially available as fluorouracil. Administration of 5-fluorouracil leads to inhibition of thymidylate synthesis and is also incorporated into both RNA and DNA. The result typically is cell death. 5-Fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine (EHNA), fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dihydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10, 11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irinotecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents relegation of single strand breaks caused by Topoisomerase I in response to torsional strain of the DNA molecule. Topotecan is indicated for second line treatment of metastatic carcinoma of the ovary and small cell lung cancer.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrozole, vorozole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, and anti-estrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signaling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic therapeutic agents including non-receptor MEK angiogenesis inhibitors may also be useful. Anti-angiogenic agents such as those which inhibit the effects of vascular endothelial growth factor, (for example the anti-vascular endothelial cell growth factor antibody bevacizumab [Avastin™], and compounds that work by other mechanisms (for example linomide, inhibitors of integrin av33 function, endostatin and angiostatin).

Agents used in immunotherapeutic regimens may also be useful in combination with the compounds of Formula (I). Immunotherapy approaches, including for example ex-vivo and in-vivo approaches to increase the immunogenecity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

Therapeutic agents used in proapoptotic regimens (e.g., bcl-2 antisense oligonucleotides) may also be used in the combination of the present invention.

Cell cycle signaling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of Formula (I), or a salt thereof, particularly a pharmaceutically acceptable salt thereof, and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In one embodiment, the combination of the present invention comprises a compound of Formula (I), or a salt thereof, particularly a pharmaceutically acceptable salt thereof, and at least one anti-neoplastic agent which is an anti-microtubule agent selected from diterpenoids and vinca alkaloids.

In a further embodiment, at least one anti-neoplastic agent is a diterpenoid. In a further embodiment, at least one anti-neoplastic agent is a *vinca* alkaloid.

In one embodiment, the combination of the present invention comprises a compound of Formula (I), or a salt thereof, particularly a pharmaceutically acceptable salt thereof, and at least one anti-neoplastic agent, which is a platinum coordination complex.

In a further embodiment, at least one anti-neoplastic agent is paclitaxel, carboplatin, or vinorelbine. In a further embodiment, at least one anti-neoplastic agent is carboplatin. In a further embodiment, at least one anti-neoplastic agent is vinorelbine. In a further embodiment, at least one anti-neoplastic agent is paclitaxel. In one embodiment, the combination of the present invention comprises a compound of Formula (I), or a salt, particularly a pharmaceutically acceptable salt thereof, and at least one anti-neoplastic agent which is a signal transduction pathway inhibitor.

In a further embodiment, the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms. In a further embodiment, the signal transduction pathway inhibitor is an inhibitor of a serine/threonine kinase rafk, akt, or PKC-zeta. In a further embodiment, the signal transduction pathway inhibitor is an inhibitor of a non- receptor tyrosine kinase selected from the src family of kinases. In a further embodiment, the signal transduction pathway inhibitor is an inhibitor of c-src. In a further embodiment, the signal transduction pathway inhibitor is an inhibitor of Ras oncogene selected from inhibitors of farnesyl transferase and geranylgeranyl transferase. In a further embodiment, the signal transduction pathway inhibitor is an inhibitor of a serine/threonine kinase selected from the group consisting of PI3K.

In a further embodiment, the signal transduction pathway inhibitor is a dual EGFr/erbB2 inhibitor, for example N-{3-chloro-4-[(3-fluorobenzyl) oxy]phenyl}-6-[5-({[2-(methanesulphonyl) ethyl]amino}methyl)-2-furyl]-4-quinazolin-amine.

In one embodiment, the combination of the present invention comprises a compound of Formula (I), or a salt, particularly a pharmaceutically acceptable salt thereof, and at least one anti-neoplastic agent which is a cell cycle signaling inhibitor. In further embodiment, cell cycle signaling inhibitor is an inhibitor of CDK2, CDK4 or CDK6.

Additional examples of other therapeutic agents (e.g., anti-neoplastic agent) for use in combination or co-administered with a compound of Formula (I) are immuno-modulators.

As used herein "immuno-modulators" refer to any substance including monoclonal antibodies that affects the immune system. Immuno-modulators can be used as antineoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/ pembrolizumab). Other immuno-modulators include, but are not limited to, ICOS antibodies, OX-40 antibodies, PD-L1 antibodies, LAG3 antibodies, TIM-3 antibodies, 41BB antibodies and GITR antibodies.

Additional examples of other therapeutic agents (antineoplastic agent) for use in combination or co-administered with a compound of this invention are anti-PD-L1 agents. Anti-PD-L1 antibodies and methods of making the same are known in the art. Such antibodies to PD-L1 may be polyclonal or monoclonal, and/or recombinant, and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 20110280877, 2014/0341902 and 20130045201. Additional exemplary antibodies to PD-L1 (also referred to as CD274 or B7-H1) and methods for use are disclosed in U.S. Pat. Nos. 7,943, 743, 8,168,179; and 7,595,048 WO2014055897, WO2016007235 and US Patent Appln. Pub. Nos. 20130034559, 20130034559 and 20150274835. PD-L1 antibodies are in development as immuno-modulatory agents or immuno-modulator for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149. In another embodiment, the antibody to PD-L1 is an antibody disclosed in U.S. Pat. No. 8,779,108. In another embodiment, the anti-PD-L1 antibody comprises the CDRs of an antibody disclosed in U.S. Pat. No. 8,779,108. In another embodiment, the antibody to PD-L1 is an antibody disclosed in US Patent Appln. Pub. No. 20130045201. In another embodiment, the anti-PD-L1 antibody comprises the CDRs of an antibody disclosed in US Patent Appln. Pub. No. 20130045201. In one embodiment, the anti-PD-L1 antibody is BMS-936559 (MDX-1105), which was described in WO 2007/005874. In another embodiment, the anti-PD-L1 antibody is MPDL3280A (RG7446). In another embodiment, the anti-PD-L1 antibody is MED14736, which is an anti-PD-L1 monoclonal antibody described in WO 2011/066389 and US 2013/034559. In another embodiment, the anti-PD-L1 antibody is TECENTRIQ™ (atezolizumab), which is an anti-PDL1 cancer immunotherapy which was approved in the US in May 2016 for specific types of bladder cancer. In another embodiment, anti-PD-L1 antibody is YW243.55.S70 which is an anti-PD-L1 described in WO 2010/077634 and U.S. Pat. No. 8,217,149. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/ 034559.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MED14736, MSB0010718C.

Additional examples of other therapeutic agents (antineoplastic agent) for use in combination or co-administered with a compound of this invention are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521, 051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in Figure 6; nivolumab, a human IgG4 mAb with the structure described in WHO Drug Information, Vol. 27, No. 1, pages 68-69 (2013) and which comprises the heavy and light chain amino acid sequences shown in Figure 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3K/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of other therapeutic agents (antineoplastic agent) for use in combination or co-administered with a compound of Formula (I) are antibodies to ICOS.

ICOS is a co-stimulatory T cell receptor with structural and functional relation to the CD28/CTLA-4-Ig superfamily (Hutloff, et al., "ICOS is an inducible T-cell co-stimulator structurally and functionally related to CD28", Nature, 397: 263-266 (1999)). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao S et al., "B7-H2 is a costimulatory ligand for CD28 in human", Immunity, 34(5); 729-40 (2011)). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naïve $T_H1$ and $T_H2$ effector T cell populations (Paulos C M et al., "The inducible costimulator (ICOS) is critical for the development of human Th17 cells", Sci Transl Med, 2(55); 55ra78 (2010)). ICOS expression is highly induced on CD4+ and CD8+ effector T cells following activation through TCR engagement (Wakamatsu E, et al., "Convergent and divergent effects of costimulatory molecules in conventional and regulatory CD4+ T cells", Proc Natal Acad Sci USA, 110(3); 1023-8 (2013)). CDRs for murine antibodies to human ICOS having agonist activity are shown in PCT/EP2012/055735 (WO 2012/131004). Antibodies to ICOS are also disclosed in WO 2008/137915, WO 2010/056804, EP 1374902, EP1374901, and EP1125585.

Agonist antibodies to ICOS or ICOS binding proteins are disclosed in WO2012/13004, WO 2014/033327, WO2016/120789, US20160215059, and US20160304610. In one embodiment, agonist antibodies to ICOS include ICOS binding proteins or antigen binding portions thereof comprising one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR as disclosed in WO2016/120789, which is incorporated by reference in its entirety herein. In one embodiment, the ICOS binding protein or antigen binding portion thereof is an agonist antibody to ICOS comprising a $V_H$ domain comprising an amino acid sequence at least 90% identical to the amino acid sequence set forth in SEQ ID NO:7 and/or a $V_L$ domain comprising an amino acid sequence at least 90% identical to the amino acid sequence as set forth in SEQ ID NO:8 as set forth in WO2016/120789 wherein said ICOS binding protein specifically binds to human ICOS. In one embodiment, the ICOS binding protein is an agonist antibody to ICOS comprising a $V_H$ domain comprising the amino acid sequence set forth in SEQ ID NO:7 and a $V_L$ domain comprising the amino acid sequence set forth in SEQ ID NO:8 as set forth in WO2016/120789.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in US Patent Nos: U.S. Pat. Nos. 7,504,101; 7,758,852; 7,858,765; 7,550,140; 7,960,515; WO2012027328; WO2013028231.

In one embodiment, the OX40 antigen binding protein is one disclosed in WO2012/027328 (PCT/US2011/048752), international filing date 23 Aug. 2011. In another embodiment, the antigen binding protein comprises the CDRs of an antibody disclosed in WO2012/027328 (PCT/US2011/048752), international filing date 23 Aug. 2011, or CDRs with 90% identity to the disclosed CDR sequences. In a further embodiment the antigen binding protein comprises a VH, a VL, or both of an antibody disclosed in WO2012/027328 (PCT/US2011/048752), international filing date 23 Aug. 2011, or a VH or a VL with 90% identity to the disclosed VH or VL sequences.

In another embodiment, the OX40 antigen binding protein is disclosed in WO2013/028231 (PCT/US2012/024570), international filing date 9 Feb. 2012, which is incorporated by reference in its entirety herein. In another embodiment, the antigen binding protein comprises the CDRs of an antibody disclosed in WO2013/028231 (PCT/US2012/024570), international filing date 9 Feb. 2012, or CDRs with 90% identity to the disclosed CDR sequences. In a further embodiment, the antigen binding protein comprises a VH, a VL, or both of an antibody disclosed in WO2013/028231 (PCT/US2012/024570), international filing date 9 Feb. 2012, or a VH or a VL with 90% identity to the disclosed VH or VL sequences. In one embodiment, the OX40 antigen binding protein is an isolated agonist antibody to OX40 comprising a light chain variable region having a sequence at least 90% identical to the amino acid sequence of SEQ ID NO:10 as set forth in WO2013/028231 and a heavy chain variable region having a sequence at least 90% identical to the amino acid sequence of SEQ ID NO:4 as set forth in WO2013/028231. In one embodiment, the OX40 antigen binding protein is an isolated antibody comprising a light chain variable comprising the amino acid sequence of SEQ ID NO:10 as set forth in WO2013/028231 and a heavy chain variable region comprising the amino acid sequence of SEQ ID NO:4 as set forth in WO2013/028231.

Thus, in one embodiment methods of treating a human in need thereof are provided comprising administering a compound of Formula (I) or a salt thereof and at least one immuno-modulator. In one embodiment, the immuno-modulator is selected from an ICOS agonist antibody, an OX-40 antibody or a PD-1 antibody. In one embodiment, the human has cancer. Also provided herein is the use of a compound of Formula (I), or a salt thereof in combination with at least one immuno-modulator for the treatment of a human in need thereof.

Additional examples of other therapeutic agents for use in combination or co-administered with a compound of Formula (I), or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity. In humans, ten TLR have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidylic acid (Poly 1:C), a TLR3 agonist; polyadenosine-polyuridylic acid (poly AU), a TLR3 agonist; Polyinosinic-Polycytidylic acid stabilized with poly-L-lysine and carboxymethylcellulose (Hiltonol), a TLR3 agonist; bacterial flagellin a TLR5 agonist; imiquimod, a TLR7 agonist; resiquimod, a TLR7/8 agonist; loxoribine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial lipopolysaccharide. Suitably a TLR4 agonist is a non-toxic derivative of lipid A. An example of a semisynthetic non-toxic derivative of lipid A TLR4 agonist is monophosphoryl lipid A, and in particular 3-de-O-acylated monophosphoryl lipid A (3D-MPL). 3D-MPL is sold under the name MPL by GlaxoSmithKline Biologicals S. A. AGPs and their immunomodulating effects via TLR4 are disclosed in patent publications such as WO 2006/016997, WO 2001/090129, and/or U.S. Pat. No. 6,113, 918 and have been reported in the literature. Additional AGP derivatives are disclosed in U.S. Pat. Nos. 7,129,219, 6,525, 028 and 6,911,434. Certain AGPs act as agonists of TLR4, while others are recognized as TLR4 antagonist.

In one embodiment the immunostimulatory agent for use in combination with the compounds of the present invention is a TLR4 agonist. In one embodiment, the TLR4 agonist are referred to as CRX-601 and CRX-527. Their structures are set forth as follows:

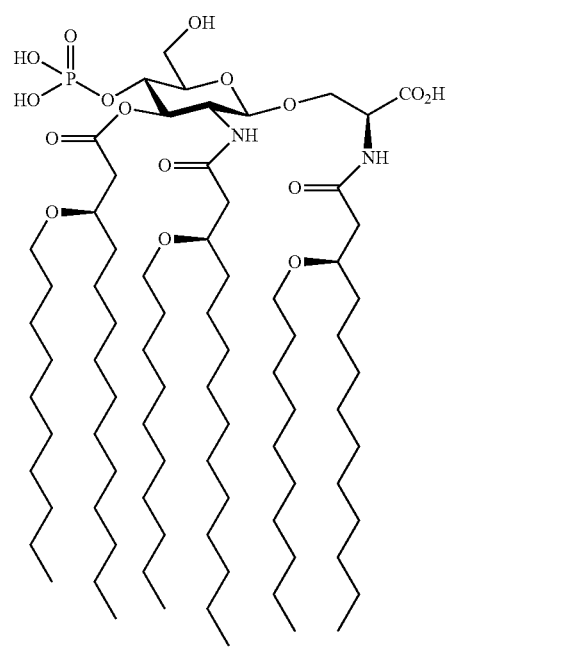

(CRX-601)

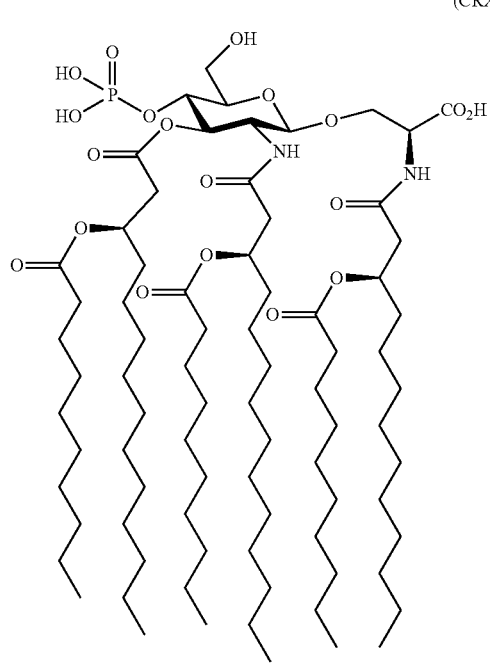

(CRX-527)

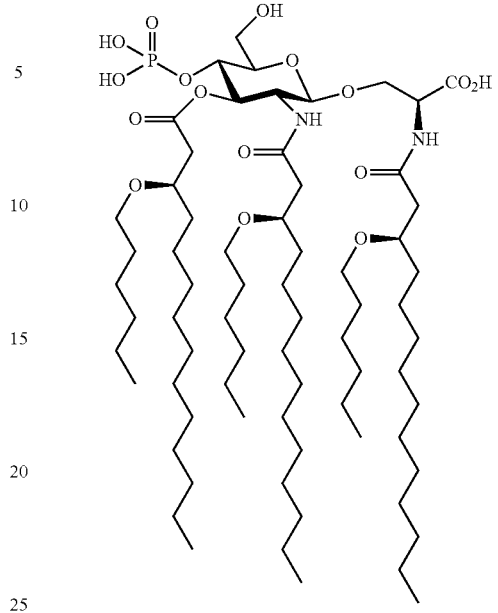

CRX 602

Additionally, another preferred embodiment employs the TLR4 agonist CRX 547 having the structure shown.

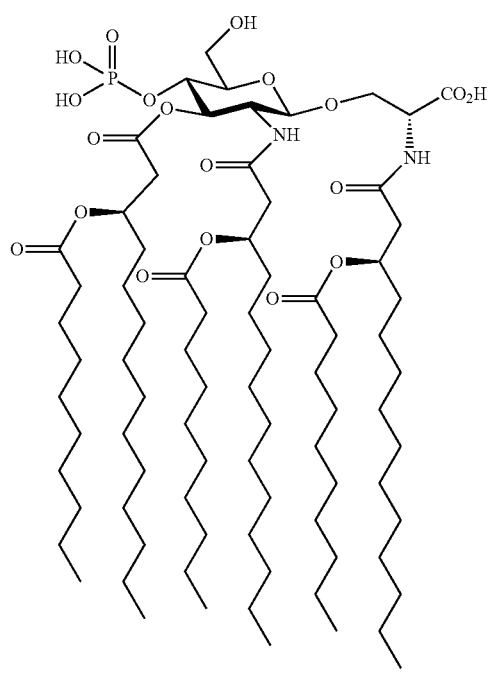

CRX 547

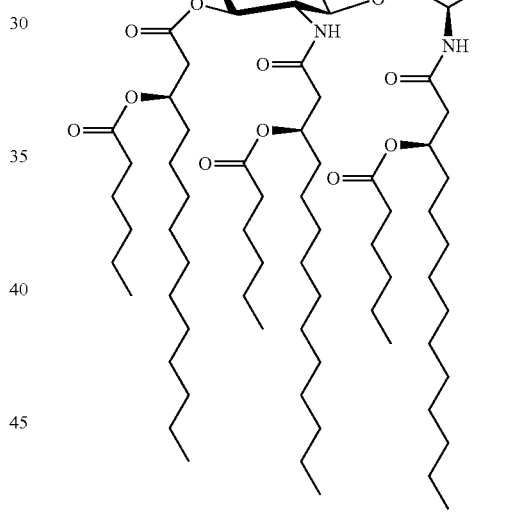

CRX-526

Still other embodiments include AGPs such as CRX 602 or CRX 526 providing increased stability to AGPs having shorter secondary acyl or alkyl chains.

Thus, in one embodiment, methods of treating a human in need thereof are provided comprising administering a compound of Formula (I) or a salt thereof and at least one immunostimulatory agent. In one embodiment, the immunostimulatory agent is a TLR4 agonist. In one embodiment, the immunostimulatory agent is an AGP. In yet another embodiment, the TLR4 agonist is selected from a compound having the formula CRX-601, CRX-527, CRX-547, CRX-602 or CRX-526. In one embodiment, the human has cancer. Also provided herein is the use a compound of Formula (I), or a salt thereof in combination with at least one immunestimulatory agent for the treatment of a human in need thereof.

In addition to the immunostimulatory agents described above, the compositions of the present invention may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacteria. rt.-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula (I) that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance. (Lemos H, et al., Cancer Res. 2016 Apr. 15; 76(8):2076-81), (Munn D H, et at., Trends Immunol. 2016 March; 37(3):193-207). Further active ingredients (antineoplastic agents) for use in combination or co-administered with the presently invented compounds of Formula (I) are IDO inhibitors. Epacadostat, ((Z)—N-(3-bromo-4-fluorophenyl)-N'-hydroxy-4-[2-(sulfamoylamino)ethylamino]-1,2,5-oxadiazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of other therapeutic agents (antineoplastic agent) for use in combination or co-administered with a compound of Formula (I) are CD73 inhibitors and A2a and A2b adenosine antagonists.

In one embodiment, the compound of the invention may be employed with other therapeutic methods of treating infectious disease. In particular, antiviral and antibacterial agents are envisaged.

The compounds of Formula (I) and pharmaceutically acceptable salts thereof may be used in combination with at least one other therapeutic agent useful in the prevention or treatment of bacterial and viral infections. Examples of such agents include, without limitation: polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, rilpivirine and similar agents; entry inhibitors such as enfuvirtide (T-20), T-1249, PRO-542, PRO-140, TNX-355, BMS-806, 5-Helix and similar agents; integrase inhibitors such as dolutegravir, elvitegravir, raltegravir L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; pharmacokinetic enhancers such as cobicistat; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents.

The compounds of Formula (I) and pharmaceutically acceptable salts thereof may also be used in combination with other therapeutic agents which may be useful in the treatment of Kaposi's sarcoma-associated herpesvirus infections (KSHV and KSHV-related) include, without limitation chemotherapeutic agents such as bleomycin, vinblastine, vincristine, cyclophosphamide, prednisone, alitretinoin and liposomal anthracyclines such as doxorubicin, daunorubicin, immunotherapeutics such as Rituximab, Tocilizumab, Siltuximab and others such as Paclitaxel and Rapamycin.

In one embodiment of this invention, the at least one other therapeutic agent is an antimycobacterial agent or a bactericidal antibiotic. The compounds of Formula (I) and pharmaceutically acceptable salts thereof may also be used in combination with at least one other therapeutic agent which may be useful in the treatment of TB infection (*Mycobacterium tuberculosis*) and Tularemia (*Francisella tularensis*) include without limitation to first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amoxicillin/clavulanate thioacetazone imipenem/cilastatin high dose isoniazid clarithromycin, ciprofloxacin. The compounds of Formula (I) and pharmaceutically acceptable salts thereof may also be used in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), PNU-100480, or delamanid (OPC-67683). The compounds of Formula (I) and pharmaceutically acceptable salts thereof may also be used in combination with at least one other therapeutic agent which may be useful in the treatment of Chlamydia include, without limitations Azithromycin, Doxycycline, Erythromycin, Levofloxacin, Ofloxacin.

The compounds of this invention may also be used in combination with at least one other therapeutic agent which may be useful in the treatment of plasmodium infection include, without limitations to chloroquine, atovaquone-proguanil, artemether-lumefantrine, mefloquine, quinine, quinidine, doxycycline, cindamycin, artesunate, primaquine.

In the treatment of amyotrophic lateral sclerosis (ALS), a compound of Formula (I) or a pharmaceutically acceptable salts thereof may be used in combination with a glutamate blocker (Riluzole (Rilutek®)), quinidine (Nuedexta®), anti-cholinergics (amitriptyline®, Artane®, scopolamine patch (Transderm Scop®)), sympathomimetics (pseudoephedrine), mucolytics (guaifenesin), or analgesics (tramadol (Ultram @); ketorolac (Toradol®); morphine; fentanyl patch (Duragesic®)).

In the treatment of multiple sclerosis, a compound of Formula (I) or pharmaceutically acceptable salts thereof may be used in combination with corticosteroids (prednisone, methylprednisolone), Interferon Beta-1A (Avonex®, Extavia®, Rebif®, Betaseron®), peginterferon beta-1A (Plegridy®), Glatiramer acetate (Copaxone@); glatiramer acetate (Glatopa®-generic equivalent of Copaxone); Dimethyl fumarate (Tecfidera®); Fingolimod (Gilenya®)); teriflunomide (Aubagio®); dalfampridine (Ampyra@); daclizumab (Zinbryta); alemtuzumab (Lemtrada®); natalizumab (Tysabri®); or mitoxantrone hydrochloride (Novantrone®).

The compounds of this invention may also be used as adjuvants to improve the immune response raised to any given antigen and/or reduce reactogenicity/toxicity in a patient, particularly a human, in need therof. As such, a compound of this invention may be used in combination with vaccine compositions to modify, especially to enhance, the immune response for example by increasing the level or duration of protection and/or allowing a reduction in the antigenic dose.

The compounds of Formula (I) and pharmaceutically acceptable salts thereof may be used in combination with one or more vaccines or immunogenic antigens useful in the prevention or treatment of viral infections. Such vaccines or immunogenic antigens include, without limitation to pathogen derived proteins or particles such as attenuated viruses, virus particles, and viral proteins typically used as immunogenic substances. Examples of viruses and sources of viral antigens include, without limitation Polioviruses, Cioronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herepesviruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), H1N1 influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

In another aspect, the invention provides methods of curing HIV comprising administering to a subject a compound of the invention. "Cure" or "Curing" in a patient is used to denote the eradication, stoppage, halt or end of the human immunodeficiency virus or symptoms, or the progression of the symptoms or virus, for a defined period. As an example, in one embodiment, "cure" or "curing" refers to a therapeutic administration or a combination of administrations that alone or in combination with one or more agents induces and maintains sustained viral control (undetectable levels of plasma viremia by, e.g., a polymerase chain reaction (PCR) test, a bDNA (branched chain DNA) test or a NASBA (nucleic acid sequence based amplification) test) of human immunodeficiency virus after a minimum of, by way of example, one or two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

In another embodiment of the present invention, there is provided compound of the invention for use in curing an HIV infection.

In another embodiment of the present invention, there is provided the use of a compound of the invention for in the manufacture of a medicament for curing an HIV infection.

In another aspect, there is a combination comprising a compound of the invention and one or more additional pharmaceutical agents active against HIV. Such compounds and agents may be present in a pharmaceutical formulation or composition. Accordingly, the invention also encompasses methods of treating, curing and/or preventing an HIV infection in a subject administering to a subject a combination (or pharmaceutical formulation or composition thereof) comprising a compound of the invention and of one or more additional pharmaceutical agents active against HIV.

In such embodiments, the one or more additional agents active against HIV is/are selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, vicriviroc (Sch-C), Sch-D, TAK779, maraviroc, TAK449, didanosine, tenofovir, lopinavir, and darunavir.

As such, the compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of compounds of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compounds of the present invention and the other pharmaceutically active agent(s) against HIV and the relative timings of administration will be selected in order to achieve the desired combined therapeutic effect.

In addition, the compounds of the present invention may be used in combination with one or more other agents that may be useful in the prevention, treatment or cure of HIV. Examples of such agents include: Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, TDF, TAF and similar agents; Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents; protease inhibitors such as saquinavir, ritonavir, indinavir, nelfinavir, amprenavir, fosamprenavir, brecanavir, darunavir, atazanavir, tipranavir, palinavir, lasinavir, and similar agents; Integrase inhibitors such as raltegravir, elvitegravir, bictegravir, dolutegravir, cabotegravir and similar agents; maturation inhibitors such as PA-344 and PA-457, and similar agents; and GSK2838232.CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents. Further examples where the compounds of the invention may be used in combination with one or more agents useful in the prevention or treatment of HIV are listed in Table A.

TABLE A

| FDA Approval | Brand Name | Generic Name | Manufacturer |
|---|---|---|---|
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| — | — | Cabotegravir | |

The scope of combinations of compounds of this invention with HIV agents is not limited to those mentioned above, but includes in principle any combination with any pharmaceutical composition useful for the cure, treatment and/or prevention of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452. Ritonavir is 10-hydroxy-2-methyl-5-(1-methyethyl)-1-1[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by *Sequoia* Pharmaceuticals of Gaithersburg, Md., as a pharmacological enhancer.

The above other therapeutic agents, when employed in combination with the compound of the invention, may be used, for example, in those amounts indicated in the Physicians' Desk Reference (PDR) or as otherwise determined by one of ordinary skill in the art.

In another embodiment of the invention, there is provided a method of treating an HIV-infection in a subject comprising administering to the subject a combination as set forth herein.

In another embodiment of the invention, there is provided a method of curing an HIV infection in a subject comprising administering to the subject a combination as set forth herein.

In another embodiment of the invention, there is provided a method of preventing an HIV infection in a subject comprising administering to the subject a combination as set forth herein.

In another embodiment of the invention, there is provided a combination as set forth herein, for use as a medicament in treating HIV.

In another embodiment of the invention, there is provided a combination as set forth herein, for use as a medicament in preventing HIV.

In another embodiment of the invention, there is provided a combination as set forth herein, for use as a medicament in curing HIV.

In another embodiment of the invention, there is provided a combination as set forth herein, for use in treating an HIV infection.

In another embodiment of the invention, there is provided a combination as set forth herein, for use in preventing an HIV infection.

In another embodiment of the invention, there is provided a combination as set forth herein, for use in curing an HIV infection.

In another embodiment of the invention, there is provided the use of a combination as set forth herein, in the manufacture of a medicament for treating an HIV infection.

In another embodiment of the invention, there is provided the use of a combination as set forth herein, in the manufacture of a medicament for preventing an HIV infection.

In another embodiment of the invention, there is provided the use of a combination as set forth herein, in the manufacture of a medicament for curing an HIV infection.

Accordingly, this invention provides an immunogenic composition comprising an antigen or antigenic composition and a compound of Formula (I), or a pharmaceutically acceptable salt thereof. There is further provided a vaccine composition comprising an antigen or antigenic composition and a compound of Formula (I), or a pharmaceutically acceptable salt thereof.

The compounds of Formula (I) and pharmaceutically acceptable salts thereof may also be used in combination with at least one other therapeutic agent which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, anti-fibrotic agents, anti-inflammatory agents such as corticosteroids or NSAIDs (non-steroidal anti-inflammatory agents) and similar agents.

A compound that modulate STING, particularly a compound of Formula (I) or a pharmaceutically acceptable salt thereof, may be administered in combination with other anti-inflammatory agents, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, RIPK1 and RIPK2 inhibitors, anti-inflammatory biologic agents, including anti-IL6 biologics, anti-IL1 agents, anti-IL17 biologics, anti-CD22, anti-integrin agents, anti-IFNα, anti-CD20 or CD4 biologics and other cytokine inhibitors or biologics to T-cell or B-cell receptors or interleukins.

For example, in the treatment of systemic lupus erythematosus and related lupus disorders, a compound that modulates STING, particularly a compound of Formula (I), or a pharmaceutically acceptable salt thereof, may be administered in combination with at least one other therapeutic agent, including, a corticosteroid (such as prednisolone (Delatsone®, Orapred, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Cellcept®), Tacrolimus®, Sirolimus®), B-cell therapy (belimumab (Benlysta®), B-cell inhibitor (Atacicept®, Apratuzumab® (anti-CD22), SBI-087 (anti-CD20), an anti-BAFF antibody (LY2127399, A623), Velcade®), azathioprine (Azasan®, Imuran®), triamcinolone (Clinacort®, Kenalog-10$^{th}$), hydroxychloroquine (Plaquenil®), thalidomide (Immunoprin®, Contergan®), immunoglobulin therapy (HyQiva®, Flebogamma®, Gamunex®, Privigen®, Gammagard®), anti-interferon-alpha therapy (Rontalizumab®, Sifalimumab®, AGS-009©, IFN Kinoid), anti-interferon receptor (IFNR) (Anifrolumab®), TLR7 and TLR9 blockers (IMO-3100), anti-cytokine therapies (anti-IL6 (CNTO-136), anti-interferon-gamma (AMG811), immunomodulatory therapy (Lupuzor™, Abatacept, Orencia®, AMG557, Laquinimod, Paquinimod, Leflunomide, anti-ICOS (Medi-570), anti-CD40 ligand antibody (CDP7657)), and/or a platelet aggregation inhibitor (aspirin).

In the treatment of Sjögren's syndrome, a compound that modulates STING, particularly a compound of Formula (I) or a pharmaceutically acceptable salt thereof, may be administered in combination with anti-rheumatic agents (hydroxychloroquine and Plaquenil®, Ridaura®, Kineret®), cholinergic agonists (Salagen®, Evoxac©), a JAK inhibitor (Xelijanz®, and anti-TNFα treatments (Remicade®, Humira®, Enbrel®, Cimzia®, Simponi®).

In treatment of vasculitis and disease with inflammation of small or medium size blood vessels, a compound that modulates STING, particularly a compound of Formula (I), or a pharmaceutically acceptable salt thereof, may be administered in combination with alkylating agents (cyclophosphamide, Cytoxan®), anti-rheumatic anti-CD20 antibody (Rituxan®, Rituximab®), and anti-TNFα inhibitors (Etanrcept®).

In the treatment of psoriasis, a compound that modulates STING, particularly a compound of Formula (I), or a pharmaceutically acceptable salt thereof, may be administered in combination with ixekizumab, tildrakizumab, secukinumab, alefacept, calcipotriene and betamethasone dipropionate, prednisone, tazorac topical gel, methotrexate, cyclosporine, fumaric acid, acitretin, phototherapy (UVA, UVB), psoralen, coal tar, TNF inhibitors (etanercept, infliximab, adalimumab, certolizumab pegol), PDE-4 inhibitors (apremilast), JAK inhibitors (tofacitinib), IL 12/23 (ustekinumab), IL17 (secukinumab, ixekizumab, brodalumab with AMG-827), 1L23 (tildrakizumab with MK-3222, guselkumab, itolizumab, biosimilars of infliximab (Remsima (Inflectra®), Sandoz GP 11111), biosimilars of rituximab (CT-P10 (Mabthera®), PF-05280586 (MabThera®)), biosimilars of etanercept (CHS-2014), biosimilars of adalimumab (GP-2017), M-518101 topical vitamin D; Maruho GK-664, or CT-327 (topical Tropomyosin-receptor kinase A), CF-101, secukinumab (AIN457), or dimethyl fumarate LAS-41008.

In the treatment of rheumatoid arthritis, a compound that modulates STING, particularly a compound of Formula (I), or a pharmaceutically acceptable salt thereof, may be administered in combination with tocilizumab, DMARDs (methotrexate, hydroxychloroquine, sulfasalazine, leflunomide), sulfasalazine delayed release, certolizumab pegol, ibuprofen, naproxen sodium, adalimumab, Kineret; etodolac, naproxen sodium, abatacept, prednisone, infliimimab, golimuma, rofecoxib, tofacitinib, methotrexate, selective JAK1 & JAK2 inhbitor (baracitinib), antisense oligonucleotide (alicafosen), biosimilars for infliximab (Remsima (Inflectra®)), GS-071 infliximab (Aprogen), SB2 infliximab, PF-06438179 infliximab, GP11111, biosimilars for rituximab (CT-P10 rituximab Celltrion), BI-695500, GP-2013, PF-05280586, biosimilars for etanercept (etanercept SB4 (Brenzys™), Benepali®; CHS-0214 etanercept, GP-2015, biosimilars for adalimumab (ABP-501 adalimumab, BI-695501, Samsung SB5, GP-2017. PF-06410293, Momenta M923, or biosimilar for abatacept (M834).

In another embodiment, a compound that modulates STING, particularly a compound of Formula (I), or a pharmaceutically acceptable salt thereof, may be administered to a patient in need thereof, in combination with at least one other therapy and/or with at least one other active therapeutic agent that is considered standard of care (U.S. Department of Health and Human Services, Agency for Healthcare Research and Quality, National Guideline Clearinghouse, https://www.guideline.gov/ and World Health Organization, http://www.who.int/management/quality/standards/en/) for any of the diseases and/or disorders recited herein.

In another embodiment, a compound that modulates STING, particularly a compound of Formula (I), or a pharmaceutically acceptable salt thereof, may be administered to a patient in need thereof, in combination with at least one other therapy, for example, in combination with UVA and/or UVB phototherapy as indicated for the treatment of psoriasis.

In another embodiment, a compound that modulates STING, particularly a compound of Formula (I), or a pharmaceutically acceptable salt thereof, may be administered to a patient in need thereof, in combination with at least one other active therapeutic agent for an indication recited herein, wherein the at least one other active therapeutic agent is: a corticosteroid [administered orally, topically, by injection, or as a suppository; prednisone, methylprednisolone, prednisolone, budesonide, betamethasone, dexamethasone, hydrocortisone, triamcinolone, fluticasone (fluticasone furoate, fluticasone propionate), fludroxycortide (flurandrenolide, flurandrenolone), fluocinonide, clobetasol (clobetasol propionate)], an anti-TNF biologic agent (etanecerpt, adalimumab, infliximab, certolizumab, or golimumab), a PDE-4 inhibitor (apremilast), 5-aminosalicyclic acid (mesalazine/mesalamine; sulfasalazine, balsalazide), a DMARD (a disease-modifying anti-rheumatic drug: methotrexate, hydroxychloroquine, sulfasalazine, leflunomide), a thiopurine (azathioprine, mercaptopurine), a JAK inhibitor (tofacitinib), an NSAID (aspirin, acetaminophen, ibuprofen, naproxen (naproxen sodium), etodolac, celecoxib, diclofenac, meloxicam), an anti-IL6 biologic agent (tocilizumab), an anti-IL1 biologic agent (anakinra, canakinumab, rilonacept), an anti-IL12 or IL23 biologic agent (ustekinumab, risankizumab, guselkumab, tildrakizumab), an anti-CD6 biologic agent (itolizumab), an anti-integrin agent (natalizumab (Tysabri®), etrolizumab), an anti-IL17 biologic agent (secukinumab, ixekizumab, brodalumab), an anti-CD22 biologic agent (epratuzumab), an anti-CD20 biologic agent (rituximab, ofatumumab), an anti-CD20 or CD4 biologic agent and other cytokine inhibitor or biologic to T-cell or B-cell receptors or interleukins, a calcineurin inhibitor (cyclosporine, pimecrolimus, tacrolimus), acitretin, fumaric acid, dimethyl fumarate, cyclophosphamide, cyclosporine (or ciclosporin), methotrexate, mycophenolic acid (or mycophenolate mofetil), topical vitamin D (calcipotriol or calcipotriene), an mTOR inhibitor (temsirolimus, everolimus), a Syk inhibitor (fostamatinib), an anti-IFNa biologic agent (sifalimumab), or, a retinoid (tazarotene). Examples of other suitable biologic agents include abatacept, belimumab, and alicafosen.

In one embodiment of this invention, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, a compound that inhibits STING, particularly a compound of Formula (I) or a pharmaceutically acceptable salt thereof, may be administered in combination with an inhaled corticosteroid ((ICS) such as fluticasone proprionate (Flovent®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-dur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antangonist (AMG 853), indacaterol (Arcapta®Neohaler®), an epinephrine inhalation aerosol (E004), fluticasone furoate/fluticasone proprionate, vinanterol inhalation/fluticasone furoate powder (Relovair™), fluticasone propionate/eformoterol fumarate dehydrate (Flutiform®), reslizumab, salbutamol dry-powder inhalation, tiotropium bromide (Spiriva®HandiHaler®), formoterol/budesonide (Symbicort®SMART®), fluticasone furoate (Veramyst®), Vectura's VR506, lebrikizumab (RG3637), a combination phosphodiesterase (PDE)-3 and (PDE)-4 inhibitor (RPL554).

In one embodiment of this invention, the at least one other therapeutic agent is selected from a long acting beta agonist, a long-acting inhaled anticholinergic or muscarinic antagonist, a phosphodiesterase inhibitor, a combination an inhaled corticosteroid long acting beta agonist, a short acting beta agonist, and an inhaled corticosteroid. For example, in the treatment of COPD, a compound that modulates STING, particularly a compound of Formula (I) or a pharmaceutically acceptable salt thereof, may be administered in combination with a LABA (such as salmeterol xinafoate (Serevent), umeclidinium/vilanterol (Anuro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate(ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In one embodiment of this invention, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of Formula (I) or a pharmaceutically acceptable salt thereof, may be administered in combination with an oral corticosteroid (such as prednisolone (Delatsone®, Oraped, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In one embodiment of this invention, the at least one other therapeutic agent is a ciliary neurotrophic growth factor or a gene transfer agent. For example, in the treatment of retinitis pigmentosa, a compound that modulates STING, particularly a compound of Formula (I) or a pharmaceutically acceptable salt thereof, may be administered in combination with a ciliary neurtotrophic growth factor (NT-501-CNTF) or gene transfer agent, UshStat®.

In one embodiment of this invention, the at least one other therapeutic agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. For example, in the treatment of influenza, a compound that modulates STING, particularly a compound of Formula (I) or a pharmaceutically acceptable salt thereof, may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®

In the treatment of a staphylococcus infection, a compound that modulates STING, particularly a compound of Formula (I) or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In one embodiment of this invention, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, a compound that modulates STING, particularly a compound of Formula (I), or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), anon-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

In the treatment of Parkinson's disease, the compounds of the invention may be administered in combination with L-dopamine based therapies (Carbidopa (Lodosyn)-levodopa), dopamine agonists like pramipexole (Mrapex), ropinirole (Requip), rotigotine (Neupro), and Apomorphine (Apokyn), monoamine oxidase (MAO) B inhibitors like selegiline (Eldepryl, Zelapar), rasagiline (Azilect), and Safinamide (Xadago)), catechol O-methyltransferase (COMT) inhibitors entacapone (Comtan) and Tolcapone (Tasmar), anticholinergics like beztropine (Cogentin) or trihexyphenidyl, and amantadine. A compound of Formula (I) or a pharmaceutically acceptable salt thereof, may be administered in combination with devices implanted in patients that deliver electrical pulses to the brain and reduce Parkinson's disease symptoms known as deep brain stimulation (DBS).

In the treatment of myocardial infarction, the compounds of the invention may be administered in combination with anti-IL1beta antibody therapies (e.g., canakinumab).

The compounds of the invention may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminum salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of Formula (I), or a pharmaceutically acceptable salt thereof. There is further provided a vaccine composition comprising a compound of Formula (I), or a pharmaceutically acceptable salt thereof, and an antigen or antigenic composition.

A therapeutically "effective amount" is intended to mean that amount of a compound that, when administered to a patient in need of such treatment, is sufficient to effective treat or prevent, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art. "Treating" or "treatment" is intended to mean at least the mitigation of a disease or disorder in a patient. The methods of treatment for mitigation of a disease or disorder include the use of the compounds in this invention in any conventionally acceptable manner, for example for retardation, therapy or cure of a STING-mediated disease or disorder, as described hereinabove. In one embodiment, "treat" "treating" or "treatment" in reference to cancer refers to alleviating the cancer, eliminating or reducing one or more symptoms of the cancer, slowing or eliminating the progression of the cancer, and delaying the reoccurrence of the condition in a previously afflicted or diagnosed patient or subject.

"Prevent", "preventing" or "prevention" refers to the prophylactic administration of a drug to diminish the likelihood of the onset of or to delay the onset of a disease or biological manifestation thereof. Prophylactic therapy is appropriate, for example, when a subject is considered at high risk for developing cancer, such as when a subject has a strong family history of cancer or when a subject has been exposed to a carcinogen.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

In addition to the above described routes of administration suitable for treatment of oncology, the pharmaceutical compositions may be adapted for administration by intratumoral or peritumoral injection. The intratumoral or peritumoral injection of a compound of the present invention directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities, (van der Jeught, et al., Oncotarget, 2015, 6(3), 1359-1381). A further advantage of local or intratumoral or peritumoral administration is the ability to achieve equivalent efficacy at much lower doses, thus minimizing or eliminating adverse events that may be observed at much higher systemic doses (Marabelle, A., et al., Clinical Cancer Research, 2014, 20(7), p1747-1756).

The compounds of the invention may be administered via eye drops to treat Sjogren's syndrome.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and at least one pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof).

As provided herein, unit dosage forms (pharmaceutical compositions) containing from 1 mg to 1000 mg of a compound of the invention may be administered one, two, three, or four times per day to effect treatment of a STING-mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional therapeutic agents, (e.g., pharmaceutically active compounds).

As used herein, "pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

It will be understood that the compounds of this invention may also be formulated with vaccines as adjuvants to modulate their activity. Such compositions may contain antibody (antibodies) or antibody fragment(s) or an antigenic component including but not limited to protein, DNA, live or dead bacteria and/or whole, inactivated or split viruses or virus-like particles, recombinant proteins or antigenic fragments thereof, optionally together with one or more other components with adjuvant activity including but not limited to aluminum salts, oil and water emulsions, heat shock proteins, saponins, lipid A preparations and derivatives, glycolipids, liposomes, TLR agonists such as CpG DNA or similar agents, cytokines such as GM-CSF or IL-12, or similar agents.

Certain compounds of the invention may be potent immunomodulators and accordingly, care should be exercised in their handling.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

It will be understood that certain compounds of the invention may be potent immunomodulators and accordingly, care should be exercised in their handling.

The reactions described herein are applicable for producing compounds of the invention having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. Suitable protecting groups and the methods for protecting and de-protecting different substituents using such suitable protecting groups are well known to those skilled in the art; examples of which may be found in T. W. Greene 'Protective Groups in Organic Synthesis' (4th edition, J. Wiley and Sons, 2006). Unless otherwise noted, all starting materials were obtained from commercial suppliers and used without further purification.

Certain intermediate compounds described herein form a yet further aspect of the invention.

General Synthetic Methods

The compounds of this invention may be prepared using synthetic procedures illustrated in the reaction schemes below, which can be readily adapted to prepare other compounds of the invention by drawing on the knowledge of a skilled organic chemist. The syntheses provided in these schemes are applicable for producing compounds of the invention having a variety of different R groups employing appropriate precursors, which are suitably protected if needed, to achieve compatibility with the reactions outlined herein. Subsequent deprotection, where needed, affords compounds of the nature generally disclosed. While the schemes are shown with compounds only of Formula (I), they are illustrative of processes that may be used to make the compounds of the invention. Intermediates (compounds used in the preparation of the compounds of the invention) may also be present as salts.

Method 1

All variables are as defined in Formula (I). A suitably substituted halo-nitrophenyl compound (1A) is reacted with a monoprotected diamine such as (1B) to provide the N-protected nitro-aniline. Removal of the amine protecting group affords amine (1D). Alternatively, amine (1D) can be obtained directly by reaction of halo-nitrophenyl compound (1A) with a symmetrical diamine (1C). Amine (1D) can be reacted with a halo-nitrophenyl compound (1E) to afford bis-nitro compound (1F). In cases where (1A) is identical to (1E), bis-nitro compound (1F) can be obtained directly by reaction of diamine (1C) with excess halo-nitrophenyl compound. Reduction of both nitro groups will provide a tetraaniline (1G). Tetraaniline (1G) can be converted to (1H), an amidobenzimidazole dimer or macrocycle, via one of two methods: 1) Treatment with cyanogen bromide to afford a bis-aminobenzimidazole followed by amide coupling with a pyrazole acid such as (1K) or a linked-pyrazole di-acid (1 L); or 2) Treatment with isothiocyanate (1M) until dithiourea formation is complete, then addition of EDC (or other desulfurization reagent) and triethylamine (or other suitable base) and stirring until cyclodesulfurization is complete. Alkylation of benzimidazole groups of (1H) with an alkylation agent and an appropriate base provides compounds of structure (11). The site and extent of alkylation (i.e. mono-, di-, tri-alkylation) can often be controlled by choice of conditions. When suitable functional groups are present on (11), deprotection or further functionalization of these groups will be possible to afford additional compounds (1J).

Scheme 1
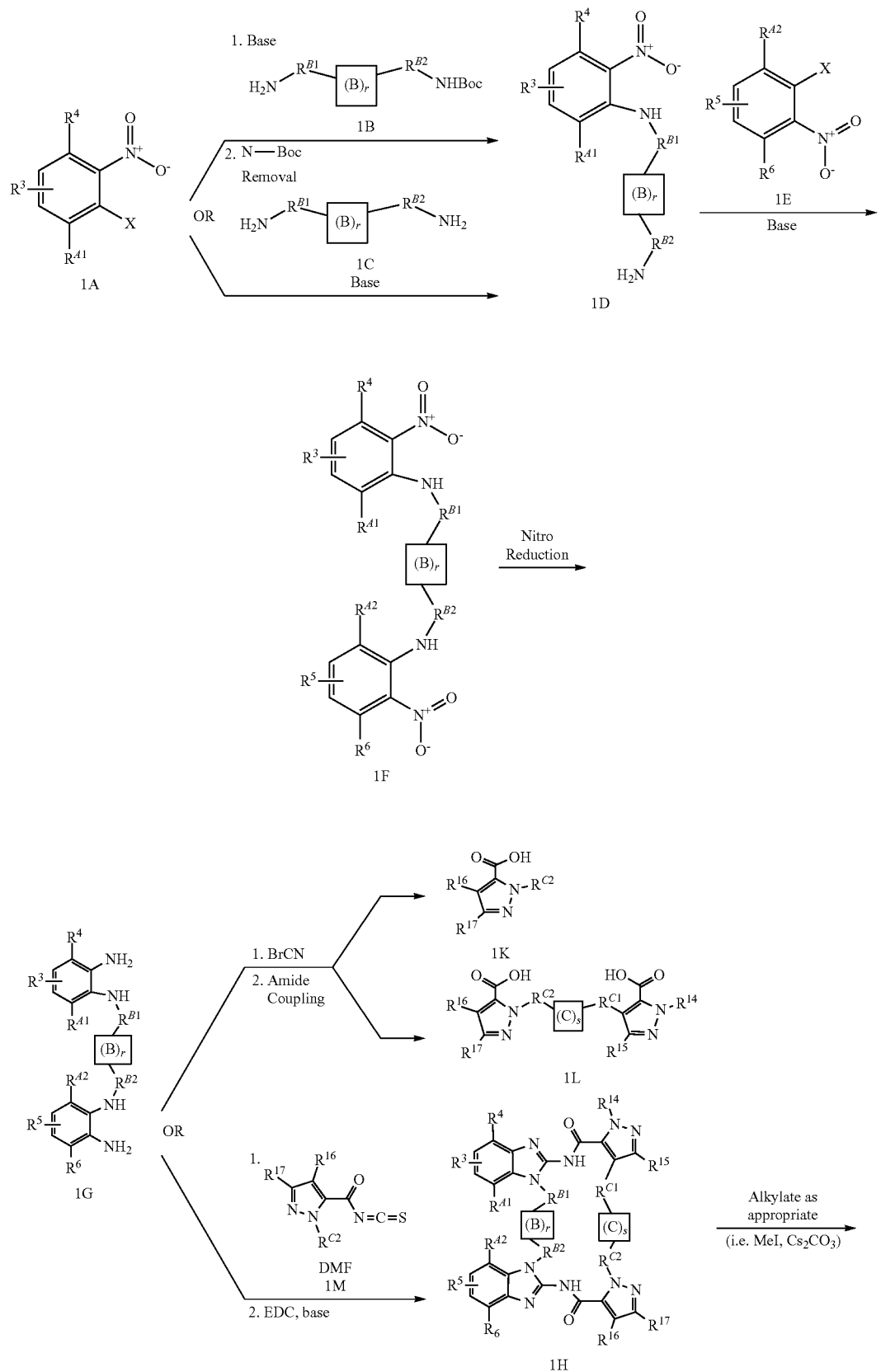

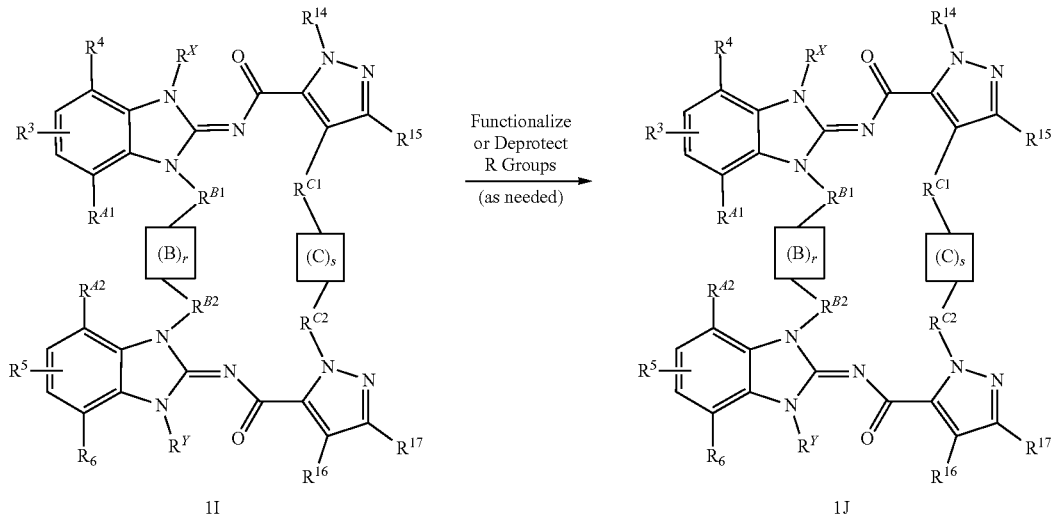

1I → Functionalize or Deprotect R Groups (as needed) → 1J

Method 2

All variables are as defined in Formula (I). A suitably substituted halo-nitrophenyl compound (2A) is reacted with a monoprotected diamine such as (2B) to provide nitro-aniline (2C). Reduction of the nitro group under appropriate conditions will afford dianiline (2D). Dianiline (2D) can be converted to an amidobenzimidazole (2E) via one of two methods: 1) Treatment with cyanogen bromide followed by amide coupling with a pyrazole acid such as (2M); or 2) Treatment with isothiocyanate (2N) until thiourea formation is complete, then addition of EDC (or other suitable desulfurization reagent) and triethylamine (or other suitable base) and stirring until cyclodesulfurization is complete. Removal of the amine protecting group affords amine (2F), which can be reacted with a halo-nitrophenyl compound (2G) to afford nitro aniline (2H). Reduction of the nitro group will provide dianiline (2I). Dianiline (2I) can be converted to an amidobenzimidazole (2J) via one of two methods: 1) Treatment with cyanogen bromide followed by amide coupling with a pyrazole acid such as (2O); or 2) Treatment with isothiocyanate (2P) until thiourea formation is complete, then addition of EDC (or other suitable desulfurization reagent) and triethylamine (or other suitable base) and stirring until cyclodesulfurization is complete. Alkylation of benzimidazole groups of (2J) with an alkylation agent and an appropriate base provides compounds of structure (2K). The site and extent of alkylation (i.e. mono-, di-, tri-alkylation) can often be controlled by choice of conditions. When suitable functional groups are present on (2K), deprotection or further functionalization of these groups will be possible to afford additional compounds (2L).

Scheme 2

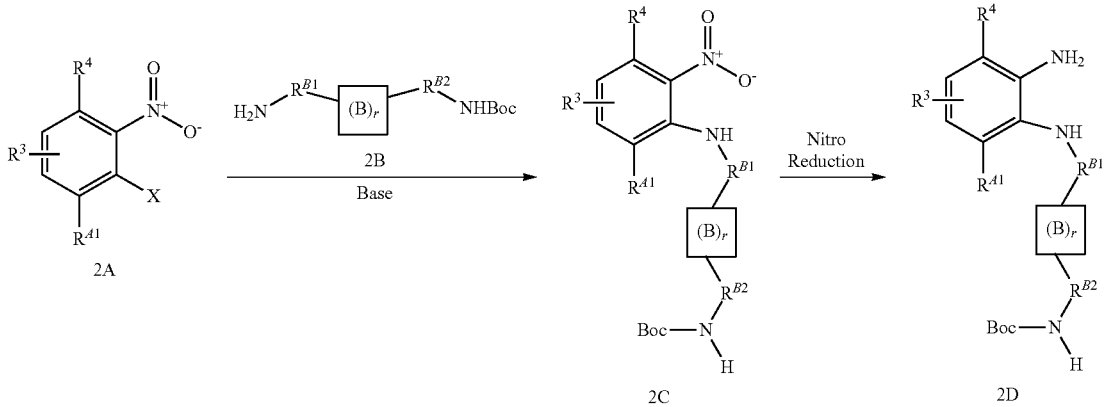

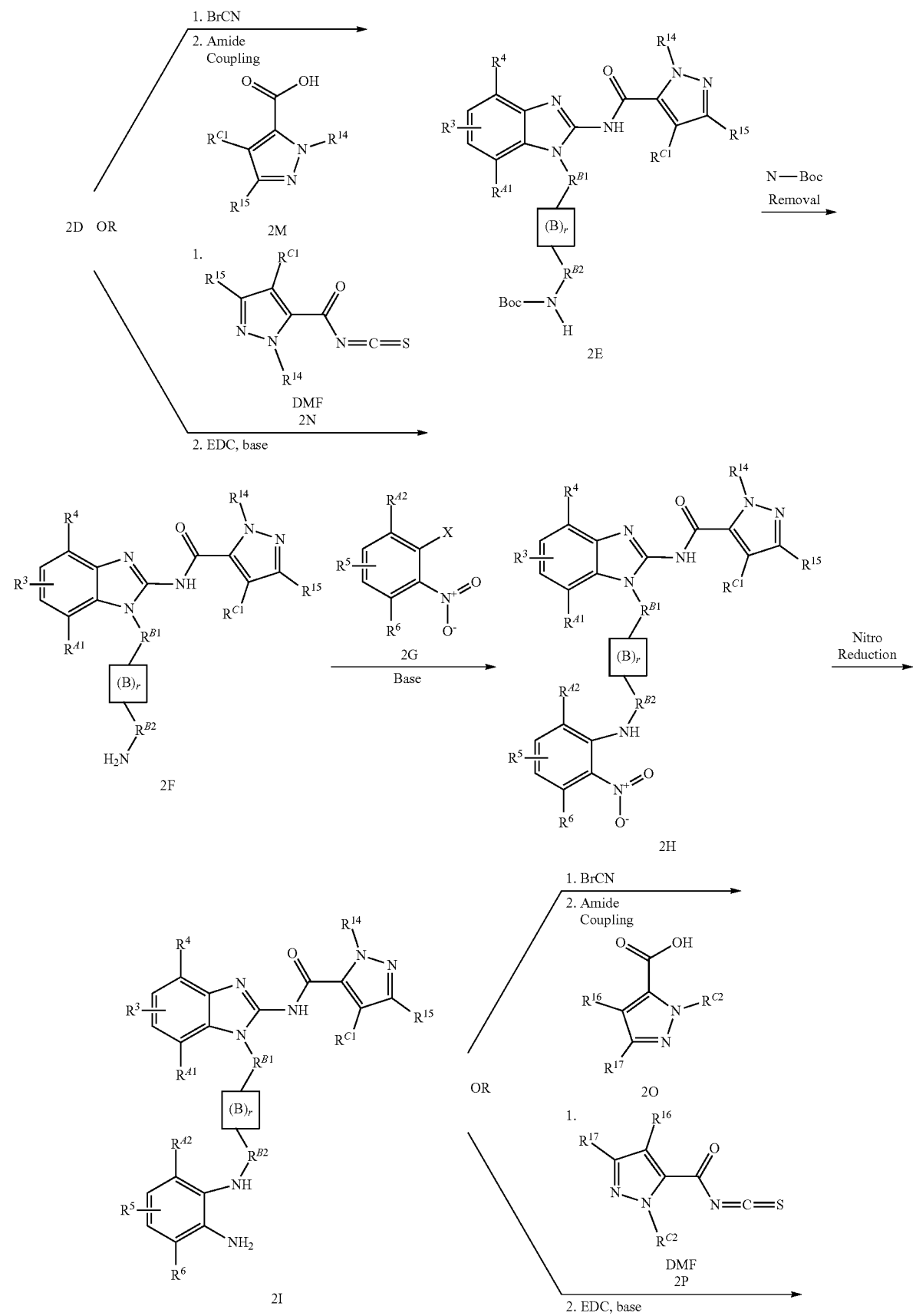

-continued

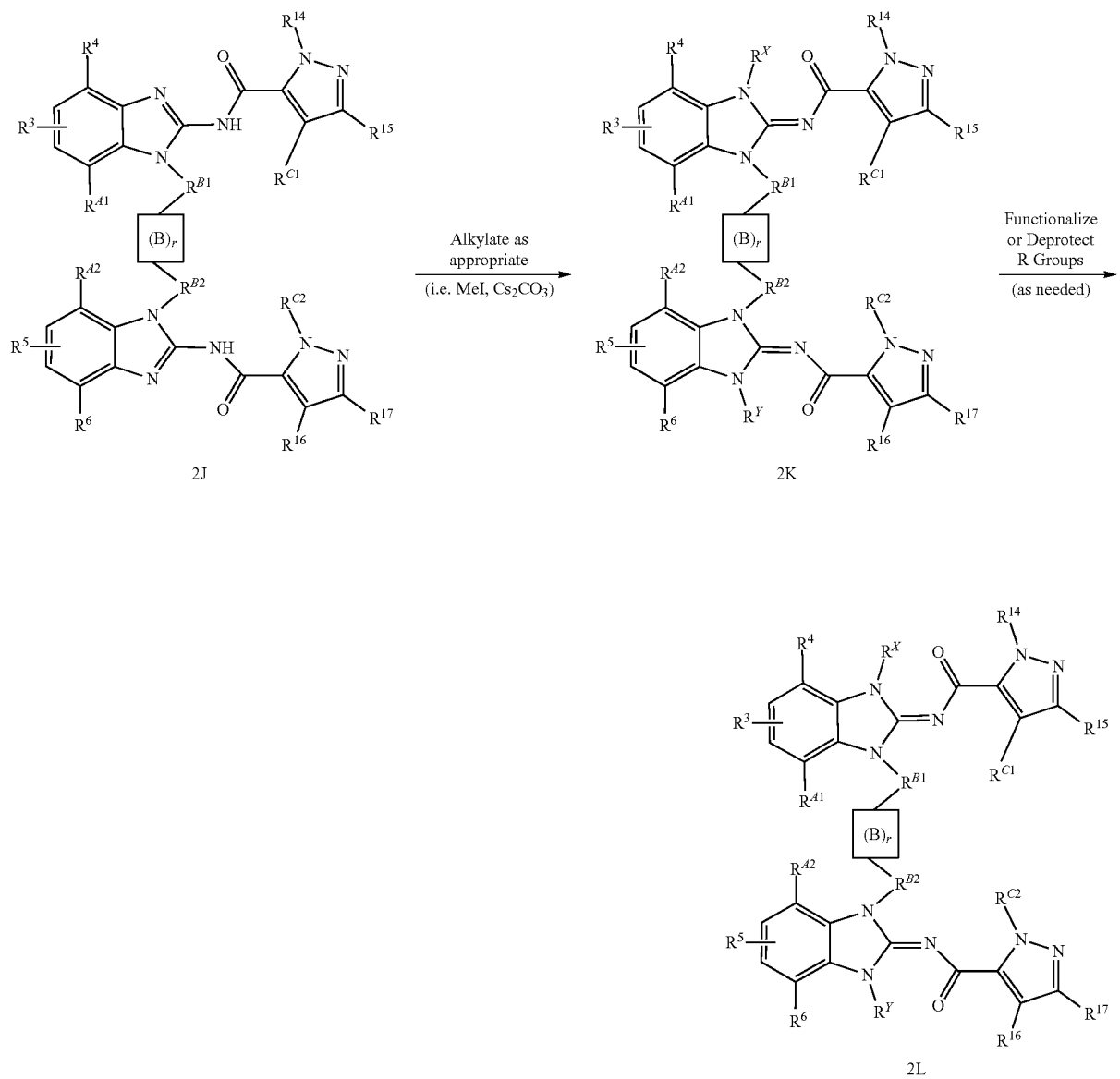

Method 3

All variables are as defined in Formula (I). A suitably substituted halo-nitrophenyl compound (3A) is reacted with a suitable dielectrophile such as dibromide (3B) to provide the nitro-aniline monobromide (3C). Treatment of (3C) with another suitably substituted halo-nitrophenyl compound (3D) affords the linked bis halo-nitrophenyl compound (3E). Reaction of the bis halo-nitrophenyl compound (3E) with a diamine containing a linker group (3F) affords dinitro macrocycle (3G). Reduction of both nitro groups will provide a tetraaniline (3H). Tetraaniline (3H) can be converted to macrocycles (3I) via one of two methods: 1) Treatment with cyanogen bromide to afford a bis-aminobenzimidazole followed by amide coupling with a pyrazole acid such as (3L) or a linked-pyrazole di-acid (3M); or 2) Treatment with isothiocyanate (3N) until dithiourea formation is complete, then addition of EDC (or other desulfurization reagent) and triethylamine (or other suitable base) and stirring until cyclodesulfurization is complete. Alkylation of benzimidazole groups of (3I) with an alkylation agent and an appropriate base provides compounds of structure (3J). The site and extent of alkylation (i.e. mono-, di-, tri-alkylation) can often be controlled by choice of conditions. When suitable functional groups are present on (3J), deprotection or further functionalization of these groups will be possible to afford additional compounds (3K).

Scheme 3
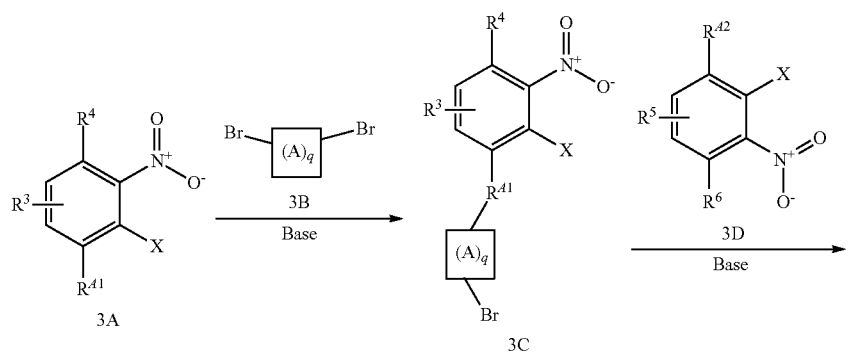
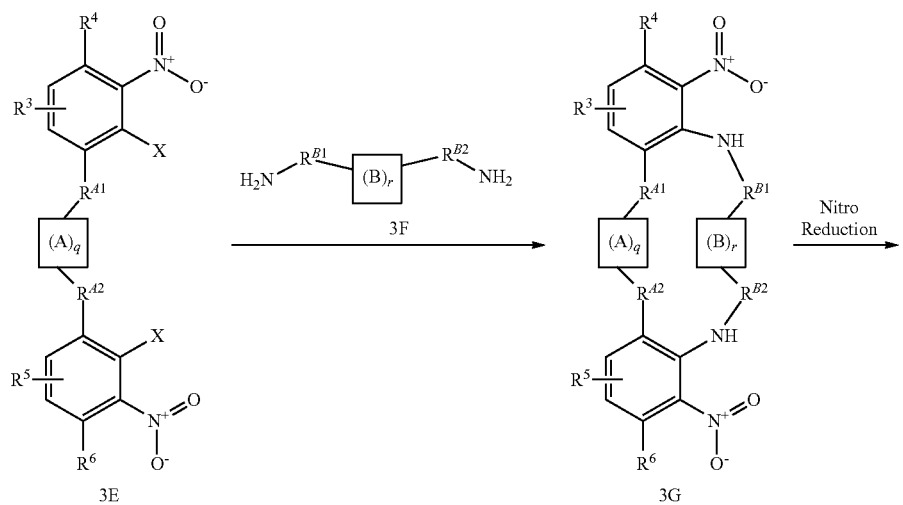
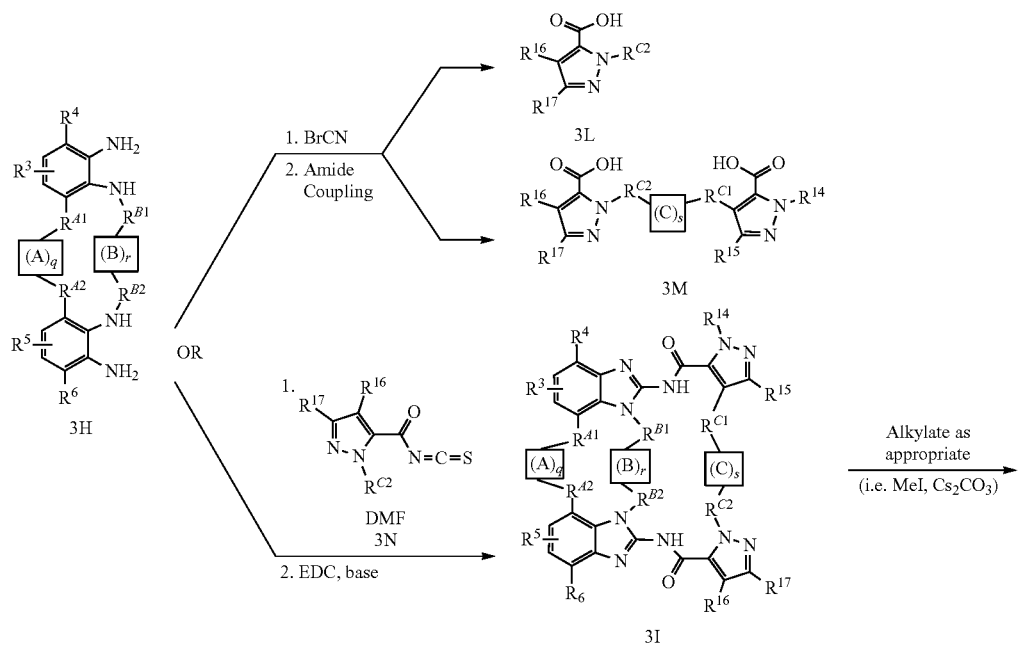

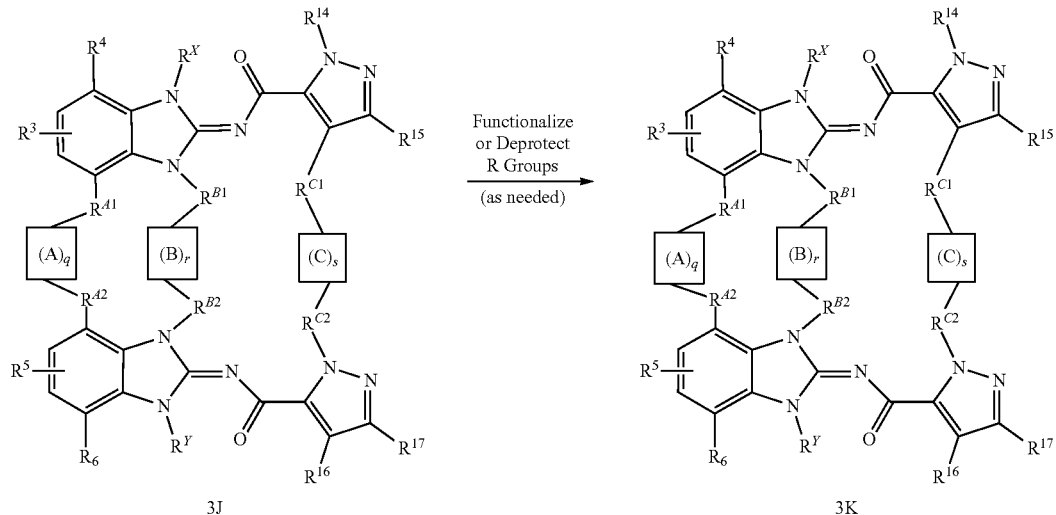

3J → 3K

Functionalize or Deprotect R Groups (as needed)

Method 4

All variables are as defined in Formula (I). A suitably substituted halo-nitrophenyl compound (4A) is reacted with a monoprotected diamine such as (4B) to provide nitroaniline (4C). Reduction of the nitro group under appropriate conditions will afford dianiline (4D). Dianiline (4D) can be converted to an amidobenzimidazole (4E) via one of two methods: 1) Treatment with cyanogen bromide followed by amide coupling with a pyrazole acid such as (4N); or 2) Treatment with isothiocyanate (4O) until thiourea formation is complete, then addition of EDC (or other suitable desulfurization reagent) and triethylamine (or other suitable base) and stirring until cyclodesulfurization is complete. Alkylation of benzimidazole groups of (4E) with an alkylation agent and an appropriate base provides compounds of structure (4F). If needed, deprotect/functionalize R groups.

Removal of the amine protecting group affords amine (4G), which can be reacted with a halo-nitrophenyl compound (4H) to afford nitro aniline (4I). Reduction of the nitro group will provide dianiline (4J). Dianiline (4J) can be converted to an amidobenzimidazole (4K) via one of two methods: 1) Treatment with cyanogen bromide followed by amide coupling with a pyrazole acid such as (4P); or 2) Treatment with isothiocyanate (4Q) until thiourea formation is complete, then addition of EDC (or other suitable desulfurization reagent) and triethylamine (or other suitable base) and stirring until cyclodesulfurization is complete. Alkylation of the newly formed benzimidazole group of (4K) with an alkylation agent and an appropriate base provides compounds of structure (4L). As needed, R groups and/or linker groups can be deprotected or functionalized (i.e. dihydroxylation of linker group containing alkene moiety) to afford additional compounds (4M).

Scheme 4

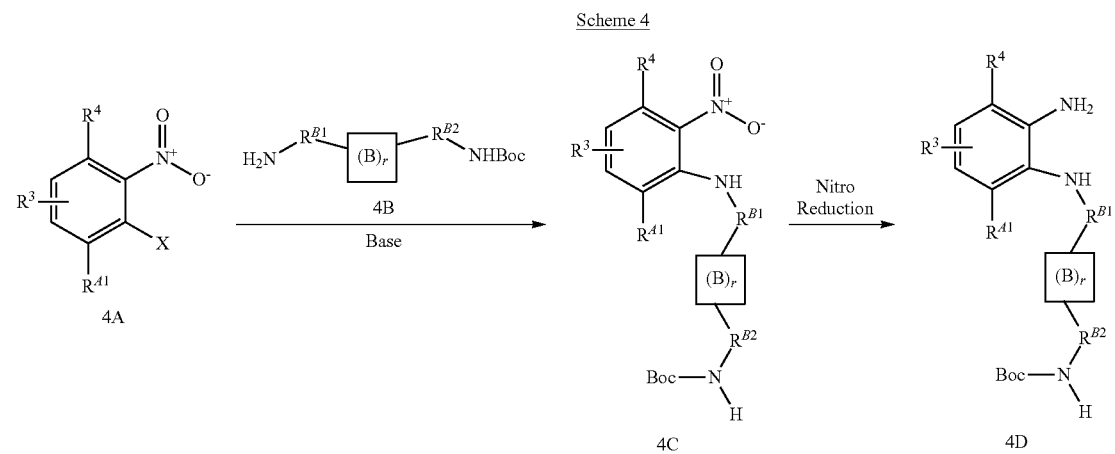

-continued
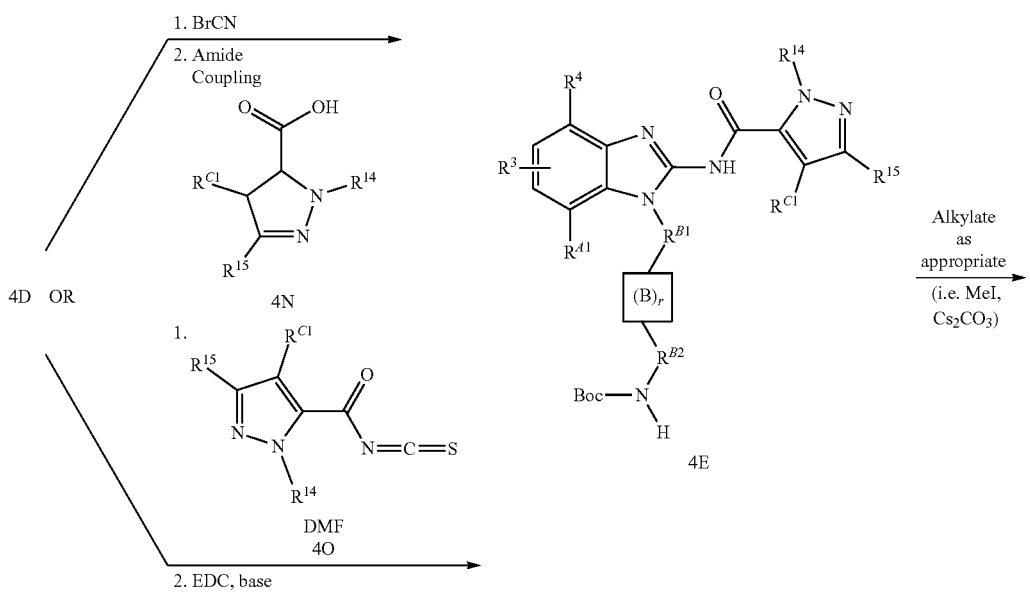
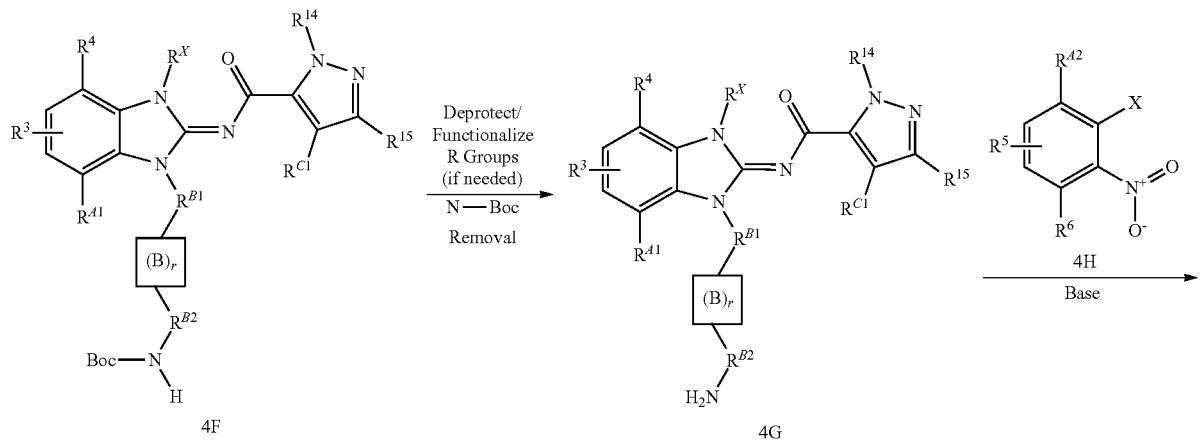
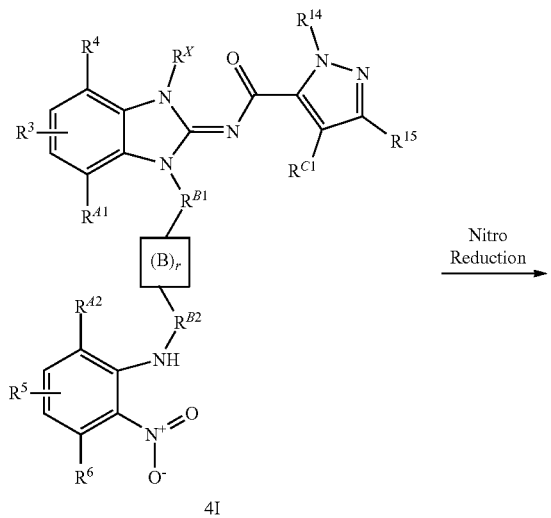

-continued
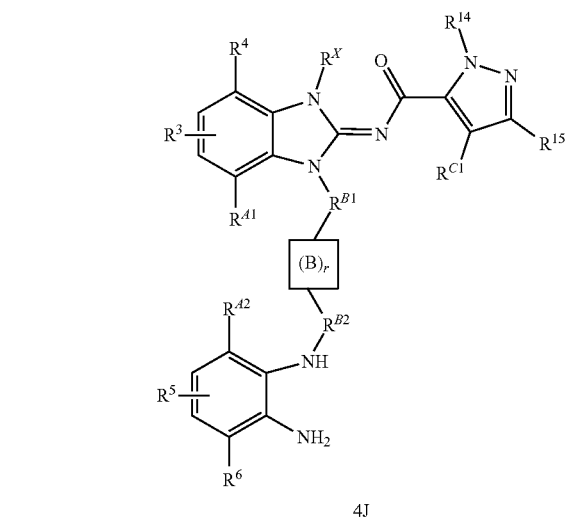
4J
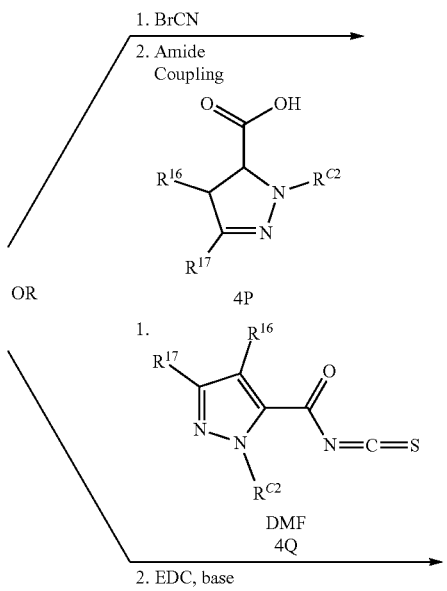
1. BrCN
2. Amide Coupling
4P
OR
1.
4Q
DMF
2. EDC, base
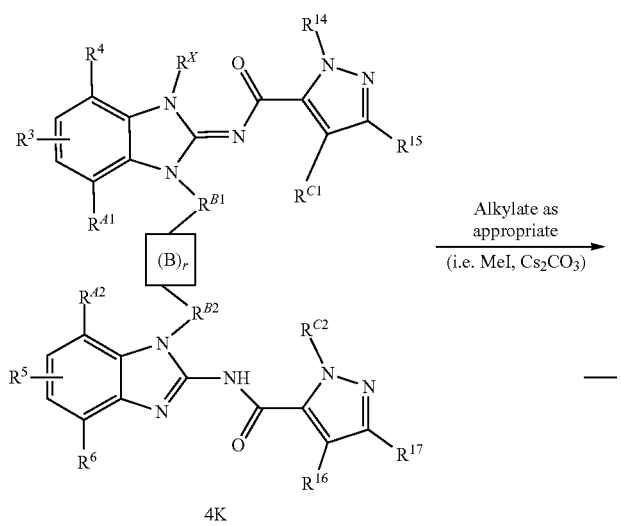
4K
Alkylate as appropriate
(i.e. MeI, Cs₂CO₃)
4L
As needed:
Deprotect/
Functionalize
R Groups
Deprotect/
Functionalize
Linker (B)ᵣ
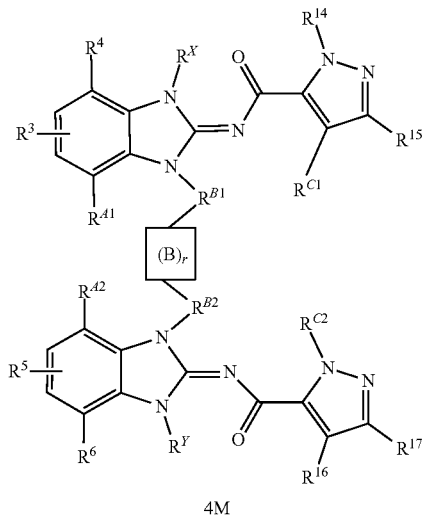
4M

Method 5

All variables are as defined in Formula (I). A suitably substituted halo-nitrophenyl compound (5A) is reacted with a monoprotected diamine such as (5B) to provide the N-protected nitro-aniline. Removal of the amine protecting group affords amine (5D). Alternatively, amine (5D) can be obtained directly by reaction of halo-nitrophenyl compound (5A) with a symmetrical diamine (5C). Amine (5D) can be reacted with a halo-nitrophenyl compound (5E) to afford bis-nitro compound (5F). In cases where (5A) is identical to (5E), bis-nitro compound (5F) can be obtained directly by reaction of diamine (5C) with excess halo-nitrophenyl compound. If needed, deprotect/functionalize R groups (i.e. CC bond formation when $R^{A1}$ group is halide). Reduction of nitro groups will provide a tetraaniline (5H). If present and depending on the conditions employed, other groups present in (5F) may also be reduced (i.e. alkene, aryl halides). Tetraaniline (5H) can be converted to (5I), an amidobenzimidazole dimer or macrocycle, via one of two methods: 1) Treatment with cyanogen bromide to afford a bis-aminobenzimidazole followed by amide coupling with a pyrazole acid such as (5L) or a linked-pyrazole di-acid (5M); or 2) Treatment with isothiocyanate (5N) until dithiourea formation is complete, then addition of EDC (or other desulfurization reagent) and triethylamine (or other suitable base) and stirring until cyclodesulfurization is complete. Alkylation of benzimidazole groups of (5I) with an alkylation agent and an appropriate base provides compounds of structure (5J). The site and extent of alkylation (i.e. mono-, di-, tri-alkylation) can often be controlled by choice of conditions. As needed, R groups and/or linker groups can be deprotected or functionalized (i.e. dihydroxylation of linker group containing alkene moiety) to afford additional compounds (5K).

Scheme 5

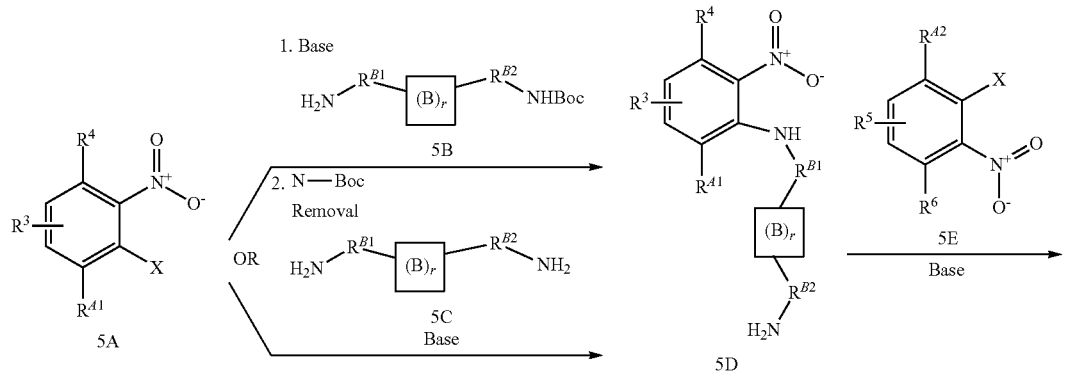

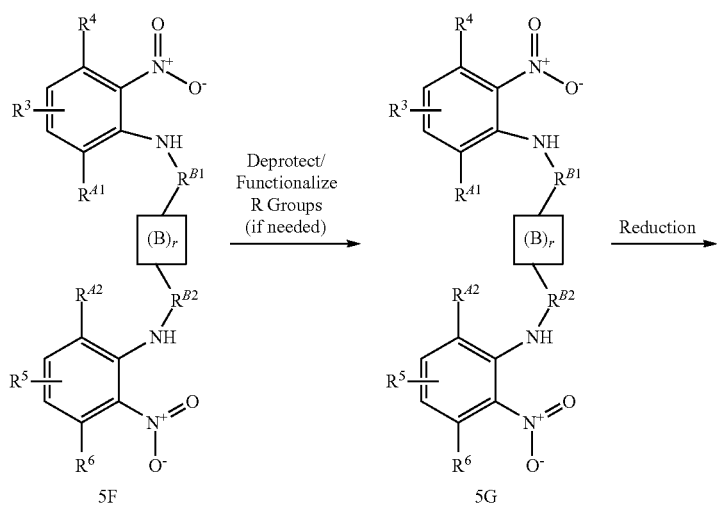

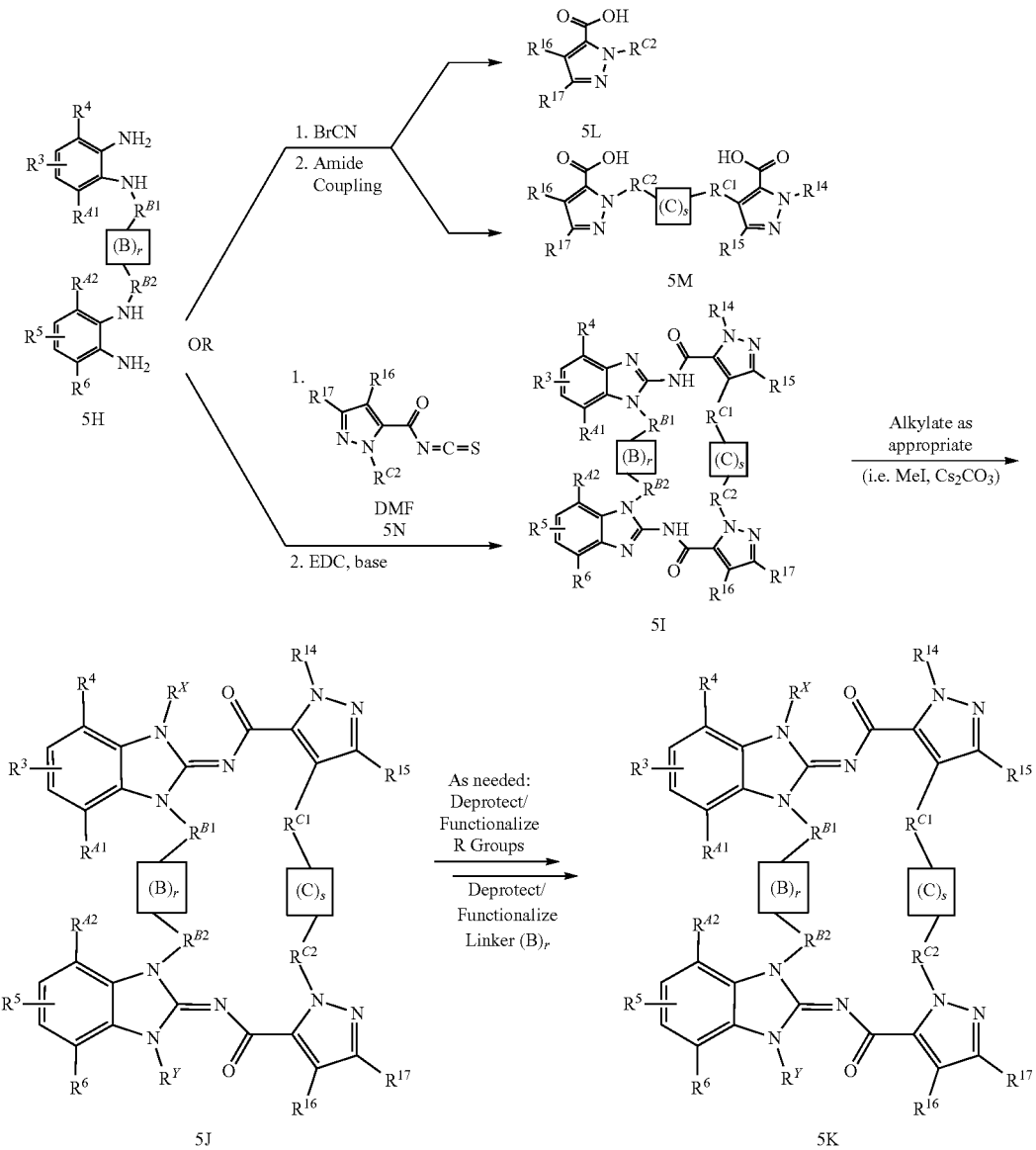

Names for the intermediate and final compounds described herein were generated using the software naming programs ChemDraw Pro 12.0.2.1076 Plug-In inside of Perkin Elmer E-Notebook or MarvinSketch 5.11.4_b82 (Chemaxon).

It will be appreciated by those skilled in the art that in certain instances these programs may name a structurally depicted compound as a tautomer or isomer of that compound. It is to be understood that any reference to a named compound or a structurally depicted compound is intended to encompass all tautomers or isomers of such compounds and any mixtures of tautomers and/or isomers thereof.

The following abbreviations may be used in this specification:

| Abbreviation | Meaning |
| --- | --- |
| AcOH | acetic acid |
| aq. | aqueous |
| BBr3 | boron tribromide |
| BOC, tBOC | tert-butoxycarbonyl |
| brine | saturated aqueous sodium chloride |
| BuOH | butanol |
| CDCl3 | deuterated chloroform |
| CDI | 1,1'-carbonyldiimidazole |
| CH2Cl2 or DCM | methylene chloride or dichloromethane |
| CH3CN or MeCN | acetonitrile |
| CH3NH2 | methylamine |

-continued

| Abbreviation | Meaning |
| --- | --- |
| d | day |
| DAST | diethylaminosulfur trifluoride |
| DCE | 1,2-dichloroethane |
| DCM | Dichloromethane |
| DIEA or DIPEA | diisopropyl ethylamine |
| DMA | dimethylacetamide |
| DMAP | 4-dimethylaminopyridine |
| DMF | N,N-dimethylformamide |
| DMSO | dimethylsulfoxide |
| EDC | 1-ethyl-3-(3-dimethylaminopropyl)carbodiimide |
| equiv | equivalents |
| Et | ethyl |
| Et3N or TEA | triethylamine |
| Et2O | diethyl ether |
| EtOAc | ethyl acetate |
| EtOH | ethanol |
| FCC | flash column chromatography |
| h, hr | hour(s) |
| HATU | O-(7-azabenzotriazol-1yl)-N,N,N',N'-tetramethylyronium hexafluorophosphate |
| HCl | hydrochloric acid |
| HOAt | 1-hydroxy-7-azabenzotriazole |
| HOBt | hydroxybenzotriazole |
| HPLC | high-performance liquid chromatography |
| ICI | iodine monochloride |
| IPA | isopropyl alcohol |
| i-Pr2NEt | N',N'-diisopropylethylamine |
| K2CO3 | potassium carbonate |
| KHMDS | potassium bis(trimethylsilyl)amide |
| KOt-Bu | potassium tert-butoxide |
| KOH | potassium hydroxide |
| LCMS | liquid chromatography-mass spectroscopy |
| LiAlH4 | lithium aluminum hydride |
| LiHDMS | lithium hexamethyldisilazide |
| LiOH | lithium hydroxide |
| Me | methyl |
| MeOH or CH3OH | methanol |
| MgSO4 | magnesium sulfate |
| min | minute(s) |
| MS | mass spectrum |
| µw | microwave |
| NaBH4 | sodium borohydride |
| Na2CO3 | sodium carbonate |
| NaHCO3 | sodium bicarbonate |
| NaOH | sodium hydroxide |
| Na2SO4 | sodium sulfate |
| NBS | N-bromosuccinimide |
| N2H2 | hydrazine |
| NH4Cl | ammonium chloride |
| NH4OH | ammonium hydroxide |
| NiCl2•6H2O | nickel (II) chloride hexahydrate |
| NMO | N-methyl morpholine-N-oxide |
| NMP | N-methyl-2-pyrrolidone |
| NMR | nuclear magnetic resonance |
| Pd/C | palladium on carbon |
| Ph | phenyl |
| POCl3 | phosphoryl chloride |
| PSI | pound-force per square inch |
| RB | round bottom |
| rm or rxn mixture | reaction mixture |
| rt/RT | room temperature |
| satd. | saturated |
| sm | starting material |
| TBAF | tetra-n-butylammonium fluoride |
| TFA | trifluoroacetic acid |
| THF | tetrahydrofuran |
| TMEDA | tetramethylethylenediamine |
| TMSI | trimethylsilyl iodide |
| TMSN3 | trimethylsilyl azide |
| T3P | 2,4,6-tripropyl-1,3,5,2,4,6-trioxatriphosphorinane-2,4,6-trioxide |
| tR or Rf or Rt | retention time |
| TsOH | p-toluenesulfonic acid |

Intermediate 1

(3-bromopropoxy)(tert-butyl)dimethylsilane

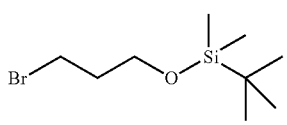

To 1H-imidazole (13.4 g, 197 mmol) in DCM (100 mL) was added 3-bromopropan-1-ol (13.7 g, 99 mmol) followed slowly by tert-butylchlorodimethylsilane (17.8 g, 118 mmol) in DCM (20 ml). After 3 h at room temperature, the reaction was concentrated to ~100 mL and poured in EtOAc (800 mL), washed with 5% aq citric acid (2×200 mL) and brine. The organic layer was dried over MgSO₄, filtered and concentrated to yield the title compound (10.0 g, 39.5 mmol, 40% yield). $^1$H NMR (400 MHz, chloroform-d) δ ppm 3.78 (t, J=5.70 Hz, 2H), 3.56 (t, J=6.46 Hz, 2H), 2.07 (t, J=5.83 Hz, 2H), 0.94 (s, 9H), 0.11 (s, 6H).

Intermediate 2

4-chloro-3-methoxy-5-nitrobenzamide

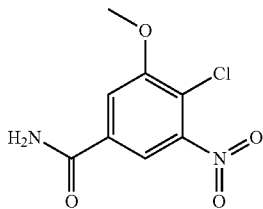

Methyl 4-chloro-3-methoxy-5-nitrobenzoate (1000 mg, 4.07 mmol) was stirred in NH₄OH (10 mL, 77 mmol) at room temperature for 24 h. The reaction temperature was then increased to 50° C. for 2 h. An additional 2 mL (~3.7 eq) of NH₄OH was added to the vessel. After an additional 2 h stirring at 50° C. (4 h total) the reaction was cooled to room temperature. The solid was filtered and rinsed with cold water. The solid was dried under house vacuum and lyophilized to give 4-chloro-3-methoxy-5-nitrobenzamide (710 mg, 2.99 mmol, 73% yield) as a tan solid. $^1$H NMR (400 MHz, DMSO-d₆) δ ppm 8.31 (br. s., 1H), 8.06 (d, J=1.77 Hz, 1H), 7.88 (d, J=1.77 Hz, 1H), 7.81 (br. s., 1H), 4.02 (s, 3H). LCMS [M+H]$^+$=230.9.

Intermediate 3

4-chloro-3-hydroxy-5-nitrobenzamide

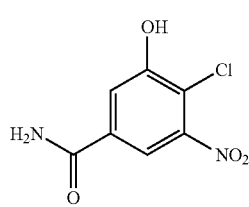 [SMILES: NC(=O)c1cc(O)c(Cl)c([N+](=O)[O-])c1]

4-chloro-3-methoxy-5-nitrobenzamide (1 g, 4.34 mmol) was suspended in dry DCM (15 mL) and stirred at room temperature. To the reaction was added BBr₃ (17.4 mL, 1 M in DCM) dropwise. A slurry rapidly formed which was stirred overnight at room temperature under nitrogen. The reaction was poured into ice water (300 mL) and stirred vigorously for 30 min. The resulting suspension was filtered and the solids dried to afford the title compound (610 mg, 2.82 mmol, 65% yield). $^1$H NMR (400 MHz, DMSO-d₆) δ ppm 11.53 (br. s., 1H), 8.17 (br. s., 1H), 7.92 (s, 1H), 7.72 (s, 1H), 7.66 (br. s., 1H). LCMS [M+H]$^+$=217.

Intermediate 4

3-(3-((tert-butyldimethylsilyl)oxy)propoxy)-4-chloro-5-nitrobenzamide

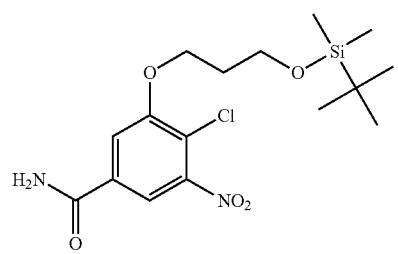 [SMILES: CC(C)(C)[Si](C)(C)OCCCOc1cc(C(N)=O)cc([N+](=O)[O-])c1Cl]

(3-bromopropoxy)(tert-butyl)dimethylsilane (7.3 g, 28.8 mmol) was dissolved in dry DMF (75 mL), 4-chloro-3-hydroxy-5-nitrobenzamide (4.8 g, 22.16 mmol) was added followed by K₂CO₃ (6.13 g, 44.3 mmol) and stirred for 2 h at 100° C. under nitrogen. The reaction was cooled to room temperature, poured into EtOAc (600 mL), washed with water (600 mL), brine, dried with MgSO₄, filtered, and concentrated in vacuo. The residue was purified by silica gel chromatography eluting with 20-80% hexanes/EtOAc to afford the title compound (7.43 g, 19.1 mmol, 86% yield). $^1$H NMR (400 MHz, DMSO-d₆) δ ppm 8.29 (br. s., 1H), 8.05 (d, J=1.71 Hz, 1H), 7.89 (d, J=1.71 Hz, 1H), 7.77 (br. s., 1H), 4.30 (t, J=5.99 Hz, 2H), 3.80 (t, J=5.99 Hz, 2H), 1.98 (quin, J=5.99 Hz, 2H), 0.80-0.90 (m, 9H), 0.02 (s, 6H). LCMS [M+H]$^+$=389.

Intermediate 5

4-chloro-3-(3morpholinopropoxy)-5-nitrobenzamide

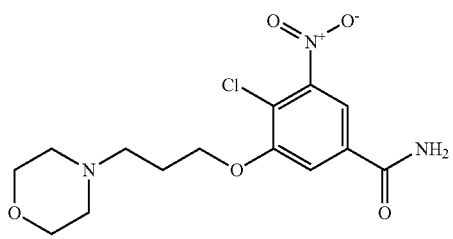 [SMILES: NC(=O)c1cc(OCCCN2CCOCC2)c(Cl)c([N+](=O)[O-])c1]

A mixture of 4-chloro-3-hydroxy-5-nitrobenzamide (5000 mg, 23.09 mmol), 4-(3-chloropropyl)morpholine (4534 mg, 27.7 mmol), K2CO₃ (4148 mg, 30.0 mmol) in DMF (30 mL) was stirred at 70° C. overnight. Solvent was removed in vacuo to give a crude solid product that was purified by silica gel chromatography (12 g column, MeOH:DCM=1:10). Pure fractions were pooled and solvents were removed in vacuo to give 4-chloro-3-(3-morpholinopropoxy)-5-nitrobenzamide (3200 mg, 9.31 mmol, 40.3% yield) as yellow solid. $^1$H NMR (400 MHz, DMSO-d$_6$) δ ppm 8.29 (s, 1H), 8.04 (s, 1H), 7.88 (d, J=1.2 Hz, 1H), 7.77 (s, 1H), 4.28 (t, J=6.2 Hz, 2H), 3.62-3.52 (m, 4H), 2.46-2.44 (m, 2H), 2.37 (br. s., 4H), 2.02-1.90 (m, 2H). LCMS (m/z): 343.8 [M+H]$^+$.

Intermediate 6

(E)-1-(4-Aminobut-2-en-1-yl)-2-(1-ethyl-3-methyl-1H-pyrazole-5-carboxamido)-1H-benzo[d]imidazole-5-carboxamide Hydrochloride

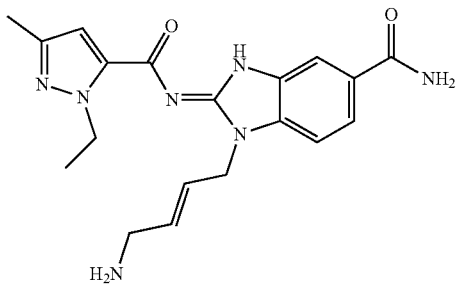

Step 1: (E)-tert-Butyl (4-((4-carbamoyl-2-nitrophenyl)amino)but-2-en-1-yl)carbamate

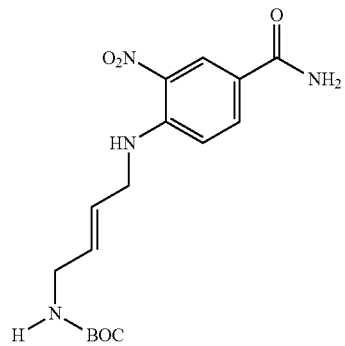 [SMILES: CC(C)(C)OC(=O)NC/C=C/CNc1ccc(C(N)=O)cc1[N+](=O)[O-]]

A mixture of 4-fluoro-3-nitrobenzamide (10.0 g, 54.3 mmol), (E)-tert-butyl (4-aminobut-2-en-1-yl)carbamate (10.62 g, 57.0 mmol) and K$_2$CO$_3$ (15.01 g, 109 mmol) in DMSO (200 mL) was stirred at room temperature overnight. The reaction was poured into water (2000 mL) and stirred for 30 min. The resulting solid was collected by filtration to yield the title compound (18.3 g, 52.2 mmol, 96% yield). LCMS [2M+H]$^+$=700.5

Step 2: (E)-tert-Butyl (4-((2-amino-4-carbamoylphenyl)amino)but-2-en-1-yl)carbamate

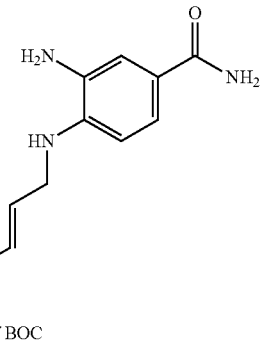

To (E)-tert-butyl (4-((4-carbamoyl-2-nitrophenyl)amino)but-2-en-1-yl)carbamate (18.3 g, 52.2 mmol) in DMF (300 mL) was added stannous chloride dihydrate (58.9 g, 261 mmol). After stirring at room temperature overnight, the reaction was added dropwise to saturated aq NaHCO$_3$ (2000 mL) and extracted with EtOAc (5×500 mL). The combined organic layers were washed with brine (200 mL), dried over Na$_2$SO$_4$, filtered and concentrated to yield the title compound (16.5 g, 51.5 mmol, 99% yield) as a yellow oil. LCMS [M−BOC+H]$^+$=221.1

Step 3: (E)-tert-Butyl (4-(2-amino-5-carbamoyl-1 Hbenzo[d]imidazol-1-yl)but-2-en-1-yl)carbamate

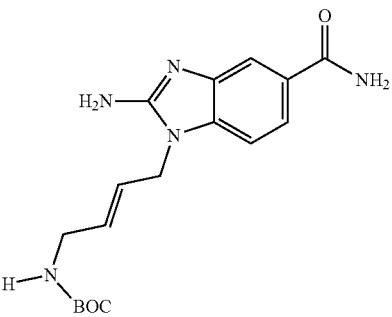 [SMILES: CC(C)(C)OC(=O)NC/C=C/Cn1c(N)nc2cc(C(N)=O)ccc21]

A mixture of (E)-tert-butyl (4-((2-amino-4-carbamoylphenyl)amino)but-2-en-1-yl)carbamate (16.5 g, 51.5 mmol) and cyanogen bromide (8.18 g, 77 mmol) in THF (200 mL) was heated to reflux overnight. The reaction was cooled to room temperature, diluted with saturated aq NaHCO$_3$ (500 mL), and extracted with EtOAc (5×300 mL). The combined organic layers were washed with brine, dried over Na$_2$SO$_4$, filtered and concentrated. The residue was purified over silica gel, eluting with 50:1 to 20:1 DCM in MeOH (+3% NH$_4$OH) to yield the title compound (13.7 g, 39.7 mmol, 77% yield) as an off-white solid. LCMS [M+H]$^+$=346.1

Step 4: (E)-tert-Butyl (4-(5-carbamoyl-2-(1-ethyl-3-methyl-1H-pyrazole-5-carboxamido)-1H-benzo[d]imidazol-1-yl)but-2-en-1-yl)carbamate

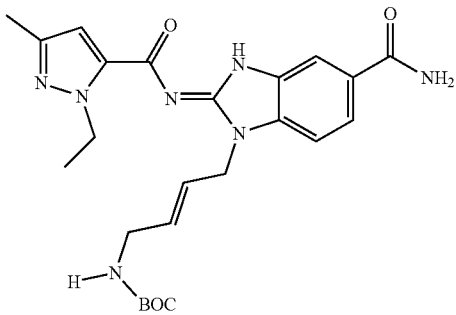 [SMILES: CCn1nc(C)cc1C(=O)/N=c1\[nH]c2cc(C(N)=O)ccc2n1C/C=C/CNC(=O)OC(C)(C)C]

To 1-ethyl-3-methyl-1H-pyrazole-5-carboxylic acid (9.17 g, 59.5 mmol) in DCM (500 mL) at 0° C. was added EDC (20.53 g, 107 mmol) and HOBt (18.22 g, 119 mmol). After 15 min, a mixture of (E)-tert-butyl (4-(2-amino-5-carbamoyl-1H-benzo[d]imidazol-1-yl)but-2-en-1-yl)carbamate (13.7 g, 39.7 mmol) in DMF (50 mL) was added, followed by TEA (27.6 mL, 198 mmol). The reaction was warmed to room temperature, stirred overnight and concentrated. The residue was diluted with water (500 mL) and extracted with EtOAc (3×300 mL), and the combined organic phases were washed with brine, dried over $Na_2SO_4$, filtered and concentrated. The residue was purified over silica gel, eluting with 50:1 to 20:1 DCM: MeOH to give the crude product, which was washed with DCM (300 mL) and collected by filtration to yield the title compound (14.0 g, 29.1 mmol, 73% yield) as an off-white solid. $^1$H NMR (400 MHz, DMSO-$d_6$) δ ppm 12.84 (s, 1H), 8.00-7.97 (m, 2H), 7.80-7.78 (m, 1H), 7.49 (d, J=8.4 Hz, 1H), 7.34 (s, 1H), 6.95 (t, J=5.5 Hz, 1H), 6.66 (s, 1H), 5.73-5.65 (m, 2H), 4.83 (d, J=4.3 Hz, 2H), 4.62 (q, J=7.0 Hz, 2H), 3.52 (s, 2H), 2.18 (s, 3H), 1.38-1.33 (m, 12H); LCMS [M+H]$^+$=482.0

Step 5: (E)-1-(4-Aminobut-2-en-1-yl)-2-(1-ethyl-3-methyl-1H-pyrazole-5-carboxamido)-1H-benzo[d]imidazole-5-carboxamide Hydrochloride

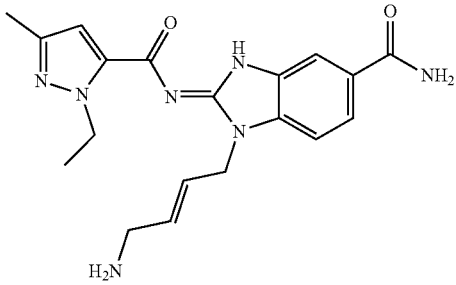 [SMILES: CCn1nc(C)cc1C(=O)/N=c1\[nH]c2cc(C(N)=O)ccc2n1C/C=C/CN]

To a suspension of (E)-tert-butyl (4-(5-carbamoyl-2-(1-ethyl-3-methyl-1H-pyrazole-5-carboxamido)-1H-benzo[d]imidazol-1-yl)but-2-en-1-yl)carbamate (3.00 g, 6.23 mmol) in dioxane (60 mL) was added 4 N HCl in dioxane (15.6 mL, 62.3 mmol), followed by MeOH (15 mL) to dissolve some remaining solid. After 30 min at room temperature, the reaction mixture became cloudy and was allowed to stir for approximately 3 days. The resulting solid was collected by filtration and washed with DCM to yield the title compound (2.0 g, 4.8 mmol, 77% yield) as a white solid. $^1$H NMR (400 MHz, DMSO-$d_6$) δ ppm 7.97-8.09 (br. s., 1H), 7.82 (d, J=8.11 Hz, 1H), 7.50 (d, J=8.11 Hz, 1H), 7.38 (br. s., 1H), 6.70 (s, 1H), 5.97-6.08 (m, 1H), 5.68-5.80 (m, 1H), 4.91 (d, J=4.31 Hz, 2H), 4.60 (q, J=6.67 Hz, 2H), 3.42 (br. s., 2H), 2.18 (s, 3H), 1.36 (t, J=6.97 Hz, 3H); LCMS [M+H]$^+$=382.2

Intermediate 7

(E)-7-(3-((tert-Butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

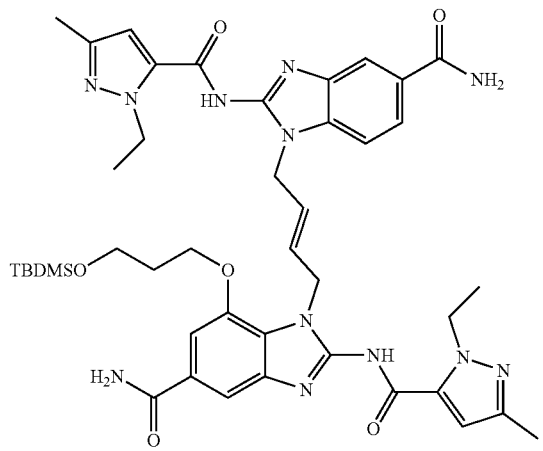

Step 1: (E)-1-(4-((2-(3-((tert-Butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide

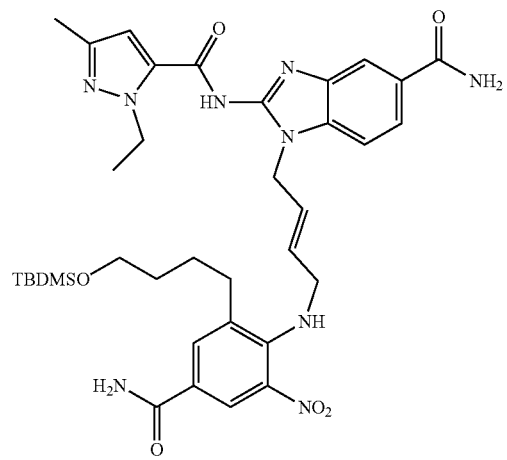

A microwave tube containing (E)-1-(4-aminobut-2-en-1-yl)-2-(1-ethyl-3-methyl-1H-pyrazole-5-carboxamido)-1H-benzo[d]imidazole-5-carboxamide hydrochloride (517 mg, 1.24 mmol, in DMSO (10 mL) was treated with TEA (0.28 mL, 2.0 mmol), followed by $K_2CO_3$ (274 mg, 1.98 mmol) and 3-(3-((tert-butyldimethylsilyl)oxy)propoxy)-4-chloro-5-nitrobenzamide (385 mg, 0.990 mmol). The reaction was heated to 75° C. After 7 h, the mixture was concentrated, and the residue was purified over silica gel, eluting with 10-90% EtOAc to remove impurities, followed by 0-10% MeOH in DCM to yield the title compound (200 mg, 0.273 mmol, 28% yield) as an orange solid. $^1$H NMR (400 MHz, DMSO-$d_6$) δ ppm 8.16 (d, J=1.52 Hz, 1H), 7.94-8.08 (m, 3H), 7.74 (d, J=8.11 Hz, 2H), 7.50 (s, 1H), 7.31-7.43 (m, 3H), 6.62 (s, 1H), 5.74-5.81 (m, 2H), 4.80 (br. s., 2H), 4.59 (d, J=6.84 Hz, 2H), 4.13 (br. s., 2H), 4.01 (t, J=6.08 Hz, 2H), 3.63 (t, J=5.96 Hz, 2H), 2.16 (s, 3H), 1.76-1.88 (m, 2H), 1.33 (t, J=7.10 Hz, 3H), 0.74-0.82 (m, 9H), −0.06 (s, 6H); LCMS [M+H]$^+$=734.6

Step 2: (E)-1-(4-((2-Amino-6-(3-((tert-butyldimethylsilyl)oxy)propoxy)-4-carbamoylphenyl)amino)but-2-en-1-yl)-2-(1-ethyl-3-methyl-1Hpyrazole-5-carboxamido)-1H-benzo[d]imidazole-5-carboxamide

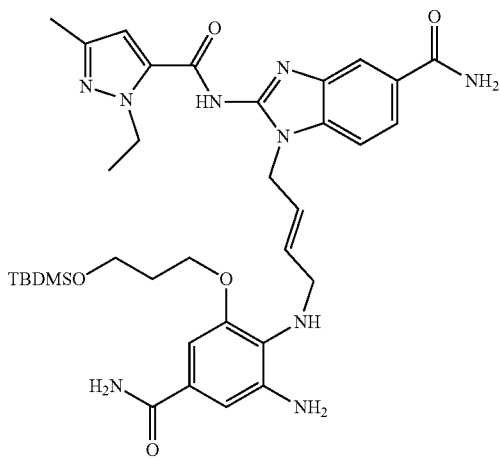 [SMILES: CCn1nc(C)cc1C(=O)Nc1nc2cc(C(N)=O)ccc2n1C/C=C/CNc1c(CCCCO[Si](C)(C)C(C)(C)C)cc(C(N)=O)cc1[N+](=O)[O-]]

(E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide (1 g, 1.363 mmol) was suspended in MeOH (20 mL) and ammonium hydroxide (4.62 mL, 34.1 mmol) was added and stirred for 5 mins at room temperature. Sodium hydrosulfite (1.675 g, 8.18 mmol) in water (5 mL) was then added. After 60 mins, EtOAc (300 ml) was added and the mixture was extracted with water (50 ml×3). The organic phase was separated, dried with $Na_2SO_4$, and concentrated in vacuo to afford title compound (710 mg, 1.009 mmol, 74.0% yield) as light yellow solid which was used without further purification. $^1$H NMR (400 MHz, DMSO-$d_6$) δ ppm 12.80 (br. s., 1H), 8.00 (s, 1H), 7.97 (br. s., 1H), 7.75 (dd, J=8.49, 1.14 Hz, 1H), 7.63 (br. s., 1H), 7.28-7.41 (m, 2H), 7.00 (br. s., 1H), 6.84 (d, J=1.52 Hz, 1H), 6.74 (d, J=1.52 Hz, 1H), 6.65 (s, 1H), 5.79-5.96 (m, 1H), 5.64-5.78 (m, 1H), 4.81 (d, J=4.82 Hz, 2H), 4.68 (br. s., 2H), 4.61 (d, J=7.10 Hz, 2H), 3.92 (t, J=5.83 Hz, 2H), 3.84 (br. s., 1H), 3.63 (t, J=6.08 Hz, 2H), 3.57 (br. s., 2H), 2.17 (s, 3H), 1.70-1.82 (m, 2H), 1.34 (t, J=7.10 Hz, 3H), 0.68-0.83 (m, 9H), −0.06 (s, 6H); LCMS [M+H]$^+$=704.3

Step 3: (E)-2-Amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide

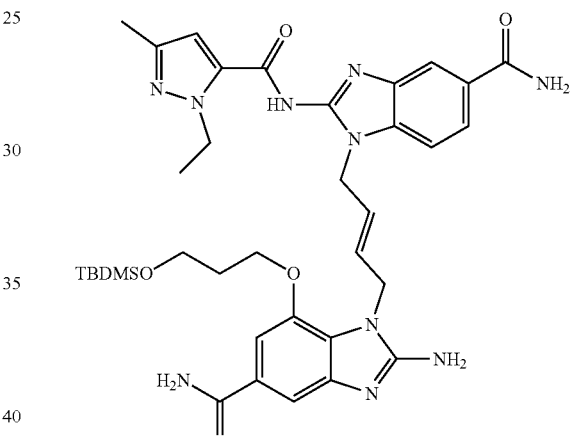

To a solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzo[d]imidazole-5-carboxamide (120 mg, 0.170 mmol) in MeOH (5 mL) was added cyanogen bromide (36 mg, 0.34 mmol) at room temperature. After 2 h, the reaction was concentrated, and EtOAc was added (10 mL). After stirring 30 min, the solid was isolated by filtration, and washed with EtOAc to yield the title compound (120 mg, 0.165 mmol, 97% yield) as a light brown solid, which was used without further purification. $^1$H NMR (400 MHz, MeOH-$d_4$) δ ppm 8.00 (d, J=1.27 Hz, 1H), 7.81 (dd, J=8.36, 1.77 Hz, 1H), 7.49 (d, J=1.27 Hz, 1H), 7.39-7.45 (m, 1H), 7.36 (d, J=1.27 Hz, 1H), 6.61 (s, 1H), 5.82-5.99 (m, 2H), 4.96-5.01 (m, 2H), 4.56-4.65 (m, 2H), 4.12 (t, J=6.21 Hz, 2H), 3.62-3.75 (m, 2H), 2.18-2.29 (m, 3H), 1.79 (t, J=6.21 Hz, 2H), 1.24-1.54 (m, 5H), 0.84-0.98 (m, 9H), −0.01-0.11 (m, 6H); LCMS [M+H]$^+$=729.5

135

Step 4: (E)-7-(3-((tert-Butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

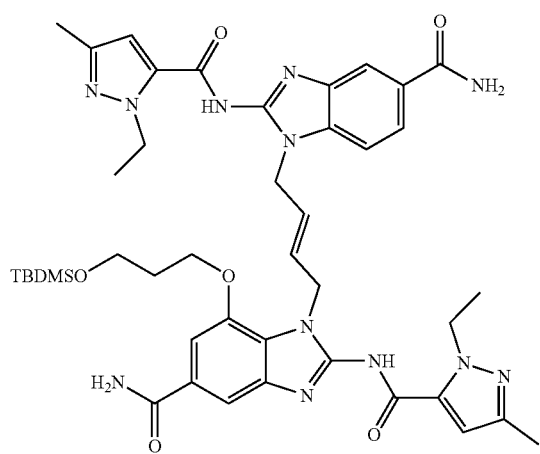

To a solution of 1-ethyl-3-methyl-1H-pyrazole-5-carboxylic acid (33 mg, 0.21 mmol) in DMF (3 mL) was added HATU (75 mg, 0.20 mmol) and HOBt (12.6 mg, 0.082 mmol). After stirring at room temperature for 10 min, triethylamine (0.09 mL, 0.66 mmol) was added, followed by (E)-2-amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide (120 mg, 0.165 mmol) and the reaction was continued at room temperature. After 3 days, a solid was precipitated out of the reaction by the dropwise addition of water. The solid was isolated by filtration and washed with water. The solid was then purified over silica gel (12 g HP Gold column), eluting with 0-20% MeOH in DCM. The desired fractions were combined and concentrated to yield the title compound (29 mg, 0.034 mmol, 20% yield) as an off-white solid. $^1$H NMR (400 MHz, THF-$d_4$) δ ppm 12.53 (br. s., 2H), 8.00 (d, J=1.01 Hz, 1H), 7.61 (d, J=1.01 Hz, 1H), 7.53 (dd, J=8.36, 1.52 Hz, 1H), 7.36 (d, J=6.84 Hz, 2H), 7.29 (d, J=1.01 Hz, 1H), 7.12 (d, J=8.36 Hz, 1H), 6.83 (br. s., 2H), 6.66 (d, J=2.28 Hz, 2H), 6.06 (dt, J=15.46, 5.58 Hz, 1H), 5.87 (dt, J=15.46, 5.83 Hz, 1H), 5.09 (d, J=5.32 Hz, 2H), 4.89 (d, J=5.58 Hz, 2H), 4.59-4.72 (m, 4H), 3.97 (t, J=6.21 Hz, 2H), 3.69 (t, J=5.96 Hz, 2H), 2.20 (s, 6H), 1.73-1.78 (m, 2H), 1.40 (td, J=7.03, 1.14 Hz, 6H), 0.82-0.94 (m, 9H), −0.03-0.09 (m, 6H); LCMS [M/2+H]+=433.6

136

Intermediate 8

1-ethyl-3-methyl-1H-pyrazole-5-carbonyl Isothiocyanate

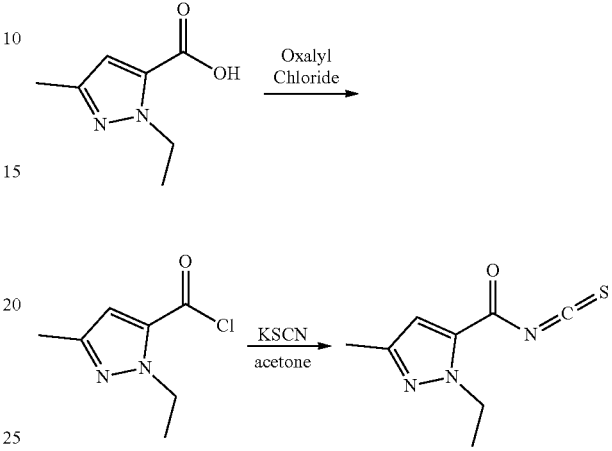

To a 1L round bottom flask was added 1-ethyl-3-methyl-1H-pyrazole-5-carboxylic acid (25 g, 162 mmol) and DCM (500 mL). To this heterogeneous solution was added DMF (0.1 mL, 1.291 mmol) followed by the slow addition of oxalyl chloride (15.61 mL, 178 mmol). After stirring for 1 h at room temperature, the volatiles were removed under vacuum and the crude was co-evaporated twice with dichloromethane (100 mL each). It was assumed 100% yield and the crude (1-ethyl-3-methyl-1H-pyrazole-5-carbonyl chloride (28.0 g, 162 mmol, 100% yield)) was used directly.

To a dry 1L round bottom flask was added KSCN (18.92 g, 195 mmol) and acetone (463 mL). This clear homogenous solution was cooled to 0° C. After 5 min stirring at 0° C., 1-ethyl-3-methyl-1H-pyrazole-5-carbonyl chloride (28 g, 162 mmol) was added as a solution in acetone (25 mL). Once the addition was complete, the reaction was allowed to stir at 0° C. After 1 min additional KSCN was added (~2 g) and the reaction was stirred for an additional 20 min. At this time, hexanes (200 mL) was added to the reaction mixture and the crude heterogeneous solution was concentrated in vacuo to one third of the volume. The process of hexanes addition and concentration was repeated twice (300 mL of hexanes each). After the last concentration, hexanes (200 mL) were added and the solid was removed by filtration, rinsing with hexanes (100 mL). The resulting clear light yellow filtrate was concentrated and purified by chromatography (330 g Gold silica column; eluting with 0-20% EtOAc/hexanes). The desired product elutes at ~7% EtOAc/hexanes. The desired fractions were combined and concentrated yielding 1-ethyl-3-methyl-1H-pyrazole-5-carbonyl isothiocyanate (27.5 g, 139 mmol, 86% yield) as a clear colorless liquid. $^1$H NMR (400 MHz, chloroform-d) δ ppm 6.77 (s, 1H), 4.54 (q, J=7.10 Hz, 2H), 2.34 (s, 3H), 1.44 (t, J=7.22 Hz, 3H); LCMS [M+H]+=196.1. The acylisothiocyanate product degrades over time, and so a ~0.4 M 1,4-dioxane solution was prepared and frozen to avoid/slow decomposition. This solution was thawed and used directly in subsequent reactions.

Intermediate 9 tert-butyl (E)-(4-((4-carbamoyl-2-methoxy-6-nitrophenyl)amino)but-2-en-1-yl)carbamate

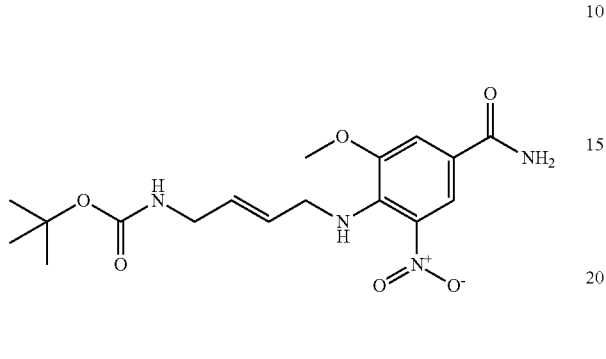

To a suspension of 4-chloro-3-methoxy-5-nitrobenzamide (1.50 g, 6.50 mmol) in EtOH (25 mL) was added (E)-tert-butyl (4-aminobut-2-en-1-yl)carbamate (1.454 g, 7.81 mmol) and DIEA (3.4 mL, 20 mmol). The reaction was stirred at 120° C. in a sealed tube overnight and allowed to cool to room temperature. The resulting orange solid was collected by filtration and washed with EtOH to afford the title compound (2.10 g, 5.52 mmol, 85% yield). $^1$H NMR (400 MHz, DMSO-$d_6$) δ ppm 8.19 (d, J=1.77 Hz, 1H) 8.03 (br. s., 1H) 7.76 (t, J=6.08 Hz, 1H) 7.55 (d, J=1.52 Hz, 1H) 7.34 (br. s., 1H) 6.95 (t, J=5.45 Hz, 1H) 5.53 (br. s., 2H) 4.09 (br. s., 2H) 3.88 (s, 3H) 3.48 (br. s., 2H) 1.35 (s, 9H). LCMS (m/z): 325.1 [M−t−Bu+H]$^+$.

An alternative route of preparing the compound described herein: To a 3-neck 5-liter flask was added 4-chloro-3-methoxy-5-nitrobenzamide (451.10 g, 1956 mmol), n-butanol (2174 mL), N-ethyl-N-isopropylpropan-2-amine (854 mL, 4890 mmol) and tert-butyl (E)-(4-aminobut-2-en-1-yl) carbamate (403.1 g, 2164 mmol). To the flask was attached a condenser and a septum containing a temperature probe. The reaction flask was stirred with an overhead stirrer (300 rpm) and heated to 110° C. using a heating mantle attached to a temperature regulator. The heterogenous mixture became deep red and homogenous after 6 h. The reaction was stirred at 110° C. for 24 h. The mixture was cooled to room temperature. Isopropanol (1200 mL) was added. The solid was filtered on a Buchner funnel. The orange cake was rinsed twice with isopropanol (1200 mL each). The solid was air-dried overnight (~14 h). Tert-butyl (E)-(4-((4-carbamoyl-2-methoxy-6-nitrophenyl)amino)but-2-en-1-yl)carbamate (532 g, 1343 mmol, 68.6% yield) was obtained as an orange solid. The minimum purity of this solid was estimated to be 96% as judged by 1H NMR, HPLC trace and LCMS. $^1$H NMR (400 MHz, DMSO-$d_6$) δ ppm 8.19 (d, J=1.77 Hz, 1H) 8.03 (br. s., 1H) 7.76 (t, J=5.96 Hz, 1H) 7.56 (d, J=1.77 Hz, 1H) 7.35 (br. s., 1H) 6.96 (t, J=5.58 Hz, 1H) 5.53 (br. s., 2H) 4.09 (br. s., 2H) 3.88 (s, 3H) 3.48 (br. s., 2H) 1.09-1.54 (m, 9H). LCMS (m/z): 381.2 [M+H]$^+$.

Intermediate 10

(E)-4-((4-Aminobut-2-en-1-yl)amino)-3-methoxy-5-nitrobenzamide, Hydrochloride

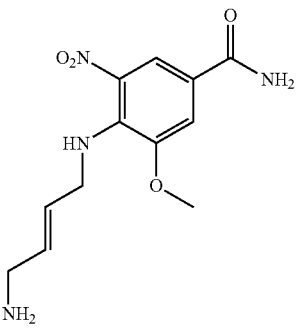 [SMILES: COc1cc(C(N)=O)cc([N+](=O)[O-])c1NC/C=C/CN]

To a suspension of tert-butyl (E)-(4-((4-carbamoyl-2-methoxy-6-nitrophenyl)amino)but-2-en-1-yl)carbamate (20 g, 47.3 mmol) in MeOH (50 mL) was added slowly 4 M HCl in dioxane (100 mL, 400 mmol). The reaction mixture was stirred at room temperature for 1 h, then the resulting solid was isolated by filtration, washed with diethyl ether (3×100 mL), and dried under high vacuum to provide the title compound (13.90 g, 43.9 mmol, 93% yield). $^1$H NMR (400 MHz, DMSO-$d_6$) δ ppm 8.22 (d, J=2.03 Hz, 1H), 7.76-8.16 (br. m., 5H), 7.60 (d, J=2.03 Hz, 1H), 7.37 (br. s., 1H), 5.87 (dt, J=15.52, 5.80 Hz, 1H), 5.62 (dt, J=15.65, 6.37 Hz, 1H), 4.18 (d, J=5.32 Hz, 2H), 3.90 (s, 3H), 3.40 (t, J=5.70 Hz, 2H). LCMS (m/z): 281.1 [M+H]$^+$.

Intermediate 11

(E)-1-((E)-4-aminobut-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 3 Hydrochloride

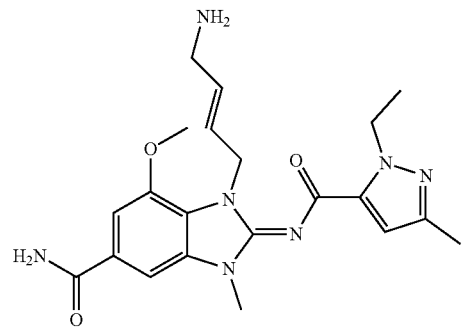 [SMILES: CCn1nc(C)cc1C(=O)/N=c1/n(C)c2cc(C(N)=O)cc(OC)c2n1C/C=C/CN]

139

Step 1: tert-butyl ((E)-4-((E)-5-carbamoyl-2-((1-ethyl-3-methyl-1H-pyrazole5-carbonyl)imino)-7-methoxy-3-methyl-2,3-dihydro-1H-benzo[d]imidazol-1-yl)but-2-en-1-yl)carbamate

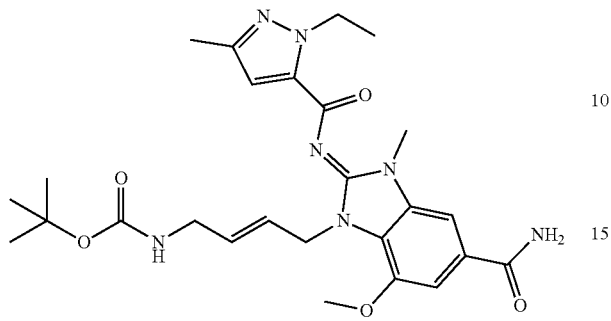

To tert-butyl (E)-(4-(5-carbamoyl-2-(1-ethyl-3-methyl-1H-pyrazole-5-carboxamido)-7-methoxy-1H-benzo[d]imidazol-1-yl) but-2-en-1-yl) carbamate (530 mg, 1.036 mmol) in DMF (5 mL) at room temperature was added cesium carbonate (675 mg, 2.072 mmol) and methyl iodide (0.097 mL, 1.554 mmol). The reaction was stirred at room temperature. After 2 h, the reaction was diluted with 100 mL EtOAc, and washed with 2×100 mL water and 3×100 mL brine. The organic layer was collected and concentrated under vacuum to afford the title compound as a yellow solid (630 mg, 1.04 mmol, 100% yield). LCMS m/z=526 [M+H]+.

Step 2: (E)-1-((E)-4-aminobut-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 3 Hydrochloride

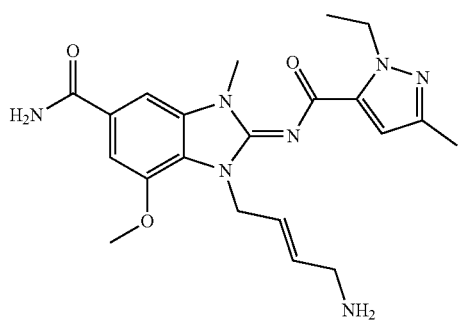 [SMILES: CCn1nc(C)cc1C(=O)/N=c1\n(C)c2cc(C(N)=O)cc(OC)c2n1C/C=C/CN]

To tert-butyl ((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)carbamate (600 mg, 1.142 mmol) in MeOH (5 mL) was added 4 M hydrochloric acid in dioxane (2.85 mL, 11.42 mmol) and the reaction was stirred at room temperature. After 3 h, the volatiles were removed under vacuum to afford the title compound as an orange solid (650 mg, 1.04 mmol, 92% yield). $^1$H NMR (400 MHz, DMSO-$d_6$) δ ppm 1.33 (t, J=7.10 Hz, 3H) 2.20 (s, 3H) 3.32-3.42 (m, 3H) 3.66 (br. s., 3H) 4.03 (s, 3H) 4.54 (q, J=7.10 Hz, 2H) 5.03 (br. s., 2H) 5.60-5.71 (m, 1H) 5.97 (dt, J=15.59, 5.89 Hz, 1H) 6.79 (br. s., 1H) 7.52-7.61 (m, 2H) 7.90 (br. s., 1H) 8.05 (br. s., 3H) 8.22 (br. s., 1H). LCMS m/z=426 [M+H]$^+$.

140

Intermediate 12

(E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

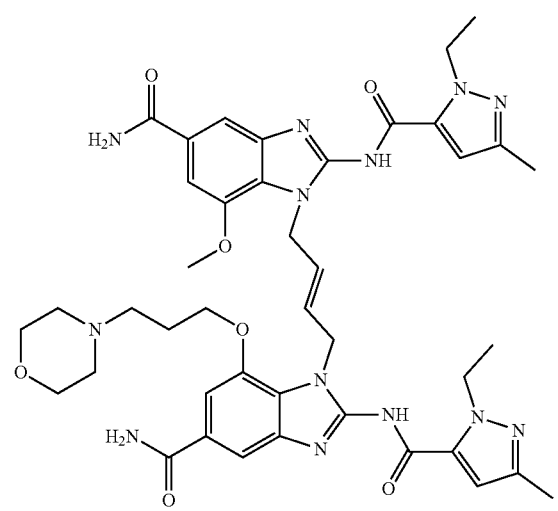 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCN3CCOCC3)c21]

Step 1: (E)-4-((4-((4-Carbamoyl-2-(3-morpholinopropoxy)-6-nitrophenyl)amino)but-2-en-1-yl) amino)-3-methoxy-5-nitrobenzamide

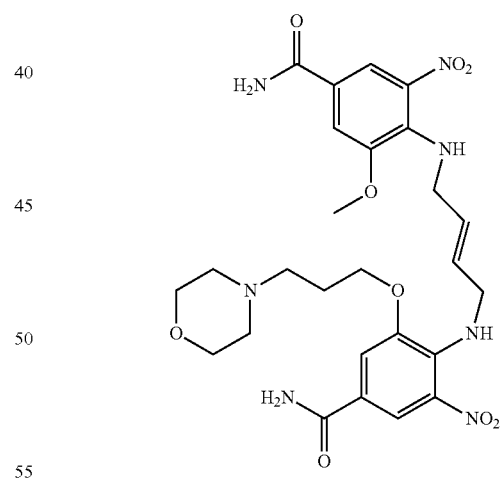

(E)-4-((4-aminobut-2-en-1-yl)amino)-3-methoxy-5-nitrobenzamide, hydrochloride (1.7 g, 5.37 mmol), 4-chloro-3-(3-morpholinopropoxy)-5-nitrobenzamide (1.65 g, 4.81 mmol), isopropanol (15 mL) and DIPEA (2.94 mL, 16.85 mmol) were divided into two 24-mL vials. The vials were capped and heated at 120° C. for 42 h. The resulting solid was isolated by filtration, rinsed with isopropanol (2×3 mL) to afford (E)- 4-((4-((4-carbamoyl-2-(3-morpholinopropoxy)-6-nitrophenyl)amino)but-2-en-1-yl)amino)-3-methoxy-5-nitrobenzamide (1.95 g, 2.79 mmol, 51.9% yield) as a brick red solid. LCMS (m/z): 588.2 [M+H]$^+$.

Step 2: (E)-3-Amino-4-((4-((2-amino-4-carbamoyl-6-(3-morpholinopropoxy)phenyl)amino)but-2-en-1-yl)amino)-5-methoxybenzamide

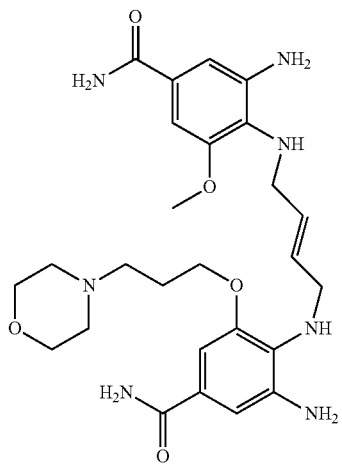 [SMILES: COc1cc(C(N)=O)cc([N+](=O)[O-])c1NC/C=C/CNc1c(OCCCN2CCOCC2)cc(C(N)=O)cc1[N+](=O)[O-]]

To (E)-4-((4-((4-carbamoyl-2-(3-morpholinopropoxy)-6-nitrophenyl)amino)but-2-en-1-yl)amino)-3-methoxy-5-nitrobenzamide (4.6 g, 6.65 mmol) in MeOH (83.0 mL) at room temperature was added sodium hydrosulfite (19.08 g, 93.0 mmol) in water (70 mL). After 15 min, solid sodium bicarbonate (24 grams) was added. After 10 min., the reaction was filtered, and the solid was rinsed with MeOH (4×20 mL). The combined filtrates were concentrated onto Celite, and the was purified by dry-loading onto silica gel (80 g Gold column), eluting with 2-40% (10:1 MeOH: aq NH₄OH) in DCM to afford the title compound (1.81 g, 3.26 mmol, 49% yield) as a dark yellow film. ¹H NMR (400 MHz, DMSO-d₆) δ ppm 7.64 (br. s., 2H), 6.99 (br. s., 2H), 6.85 (dd, J=5.07, 1.77 Hz, 2H), 6.78 (dd, J=4.31, 1.77 Hz, 2H), 5.63-5.72 (m, 2H), 4.66 (d, J=8.11 Hz, 4H), 3.96 (t, J=6.21 Hz, 2H), 3.74 (s, 3H), 3.51-3.60 (m, 6H), 3.17 (br. s., 4H), 2.43 (t, J=7.10 Hz, 2H), 2.35 (br. s., 4H), 1.87 (t, J=6.72 Hz, 2H); LCMS (m/z): 528.4 [M+H]⁺.

Step 3: (E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

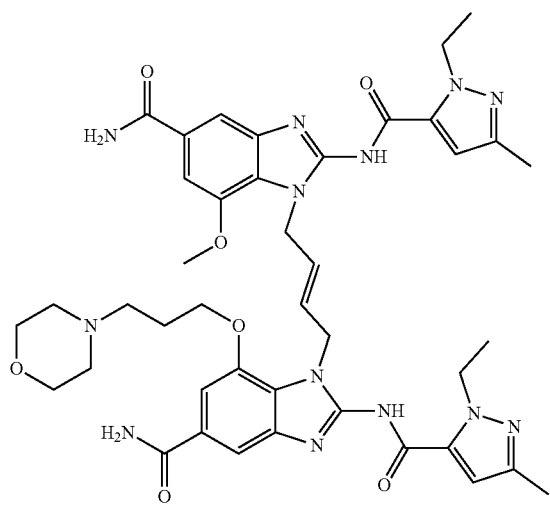 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCN3CCOCC3)c21]

To (E)-3-amino-4-((4-((2-amino-4-carbamoyl-6-(3-morpholinopropoxy)phenyl)amino)-but-2-en-1-yl)amino)-5-methoxybenzamide (368 mg, 0.697 mmol) in DMF (6.97 mL) at 0° C. was added 0.4 M 1-ethyl-3-methyl-1H-pyrazole-5-carbonyl isothiocyanate in dioxane (2.0 mL, 0.80 mmol). After ~10 min, another portion of 0.4 M 1-ethyl-3-methyl-1H-pyrazole-5-carbonyl isothiocyanate in dioxane (0.5 mL, 0.20 mmol) was added, followed ~15 min later by a final portion (0.5 mL, 0.20 mmol). After 35 min total reaction time, EDC (334 mg, 1.74 mmol) was added followed by triethylamine (0.486 mL, 3.49 mmol). The mixture was allowed to warm to room temperature and stirred overnight (~14 hours). The reaction was quenched with 3:1 water: saturated aqueous NH₄Cl solution (40 mL) and extracted with 3:1 chloroform: EtOH (2×40 mL). The combined organic phase was washed with water (20 mL), dried over magnesium sulfate and concentrated. The resulting residue was purified by silica gel chromatography (40 g column, 2-40% gradient of [10:1 MeOH: aq NH₄OH]/DCM) to give the title compound (361 mg, 0.425 mmol, 60.9% yield) as a peach-colored solid. ¹H NMR (400 MHz, DMSO-d₆) δ ppm 1.20-1.35 (m, 6H), 1.55-1.73 (m, 2H), 2.02-2.31 (m, 12H), 3.46 (t, J=4.44 Hz, 4H), 3.70 (s, 3H), 3.93 (t, J=5.96 Hz, 2H), 4.40-4.68 (m, 4H), 4.80-5.00 (m, 4H), 5.69-6.00 (m, 2H), 6.41-6.74 (m, 2H), 7.13-7.51 (m, 4H), 7.56-7.76 (m, 2H), 7.99 (d, J=3.55 Hz, 2H), 12.85 (br. s., 2H). LCMS (m/z): 851.5 [M+H]+.

Intermediate 13

2,2,3,3-Tetrafluorobutane-1,4-diamine

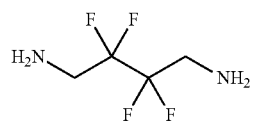

Step 1: 2,2,3,3-Tetrafluorobutane-1,4-diyl bis(4-methylbenzenesulfonate)

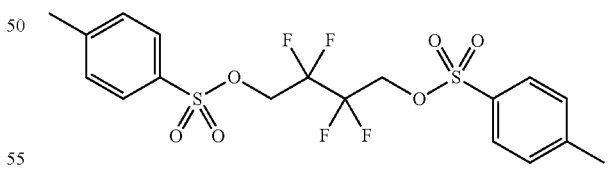

To 2,2,3,3-tetrafluorobutane-1,4-diol (10.0 g, 61.7 mmol) in pyridine (150 mL) at 0° C. was added 4-methylbenzene-1-sulfonyl chloride (29.4 g, 154 mmol) over 5 min, and then the reaction was heated to 55° C. After 1 day, the reaction was quenched with ice water, and the resulting solid was collected by filtration, dissolved in DCM (200 mL) and washed with 5% aq H₂SO₄ (100 mL×3). The organic layer was dried over Na₂SO₄ and concentrated to yield the title compound (27.3 g, 58.0 mmol, 94% yield) as a white solid. LCMS [M+H]⁺=470.9

Step 2: 1,4-Diazido-2,2,3,3-tetrafluorobutane

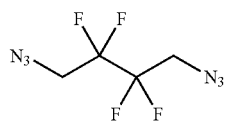 [SMILES: [N-]=[N+]=NCC(F)(F)C(F)(F)CN=[N+]=[N-]]

2,2,3,3-Tetrafluorobutane-1,4-diyl bis(4-methylbenzenesulfonate) (10.0 g, 21.3 mmol) and sodium azide (5.53 g, 85.0 mmol) in DMF (40 mL) was stirred at 110° C. overnight. The reaction was quenched with NaClO (aq) and extracted with DCM (5 mL×3). The combined organic layers were washed with water (10 mL), dried over Na$_2$SO$_4$ and concentrated to yield the title compound (3.5 g, 16.5 mmol, 78% yield). LCMS [M+H]$^+$=213.1

Step 3: 2,2,3,3-Tetrafluorobutane-1,4-diamine

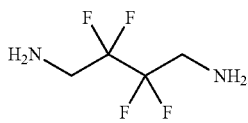

To a solution of 1,4-diazido-2,2,3,3-tetrafluorobutane (36.0 g, 170 mmol) in MeOH (350 mL) was added 10% Pd on carbon (18.1 g, 17.0 mmol). The reaction mixture was stirred at 40° C. under hydrogen (4 atm) for 16 h. The mixture was filtered through a pad of Celite, washed with MeOH and the filtrate was concentrated in vacuo to yield the title compound (22.0 g, 124 mmol, 73% yield). $^1$H NMR (400 MHz, chloroform-d) δ ppm 3.12-3.37 (m, 4H), 1.43 (br. s., 4H).

Intermediates 14A and 14B 7-(3-(((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide Intermediate 14A

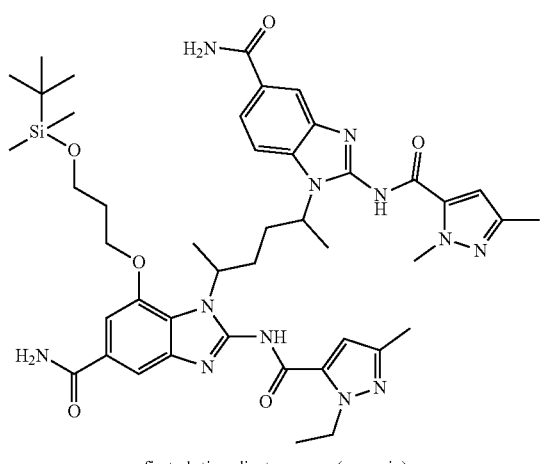

first eluting diastereomer (racemic)

Intermediate 14B

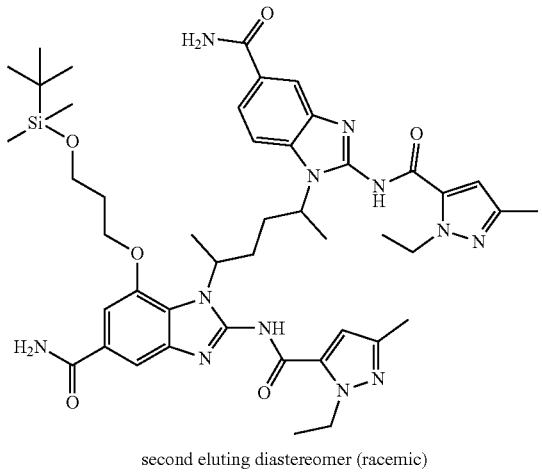

second eluting diastereomer (racemic)

Step 1: 2,5-diazidohexane

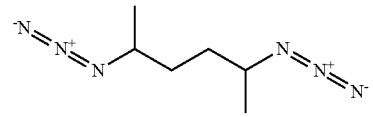

To a 500-mL round bottom flask were added 2,5-dibromohexane (10 g, 41.0 mmol) and DMF (100 mL). To this homogeneous solution was added sodium azide (10.66 g, 164 mmol). The heterogeneous reaction mixture was stirred at 80° C. for 1 h. The mixture was cooled down to room temperature and water (100 mL) was added. The aqueous phase was extracted with diethyl ether (3×100 mL). The combined organic phase was washed with brine (100 mL), dried over sodium sulfate, filtered, and concentrated under vacuum. 2,5-Diazidohexane (8.54 g, 33.5 mmol, 83% yield, 66% purity) was obtained as a yellow oil. 1H NMR (400 MHz, CHLOROFORM-d) δ ppm 1.30 (d, J=6.59 Hz, 6H), 1.40-1.76 (m, 4H), 3.35-3.68 (m, 2H).

Step 2: Hexane-2,5-diamine

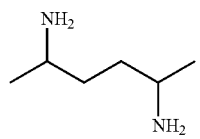

2,5-Diazidohexane (8.54 g, 50.8 mmol) was dissolved in MeOH (300 mL). This solution was hydrogenated in a single pass through a ThalesNano H-Cube® system (35° C., 25 bar hydrogen pressure, 2 mL/min flowrate). The solution was then concentrated, and the crude product used in subsequent reactions. Hexane-2,5-diamine (6.04 g, 49.4 mmol, 97% yield) was obtained as a colorless oil. $^1$H NMR (400 MHz, CHLOROFORM-d) δ ppm 1.09 (dd, J=6.21, 1.65 Hz, 6H), 1.21-1.62 (m, 8H), 2.78-3.02 (m, 2H).

Step 3: 3-(3-((tert-butyldimethylsilyl)oxy)propoxy)-4-((5-((4-carbamoyl-2-nitrophenyl)amino)hexan-2-yl)amino)-5-nitrobenzamide

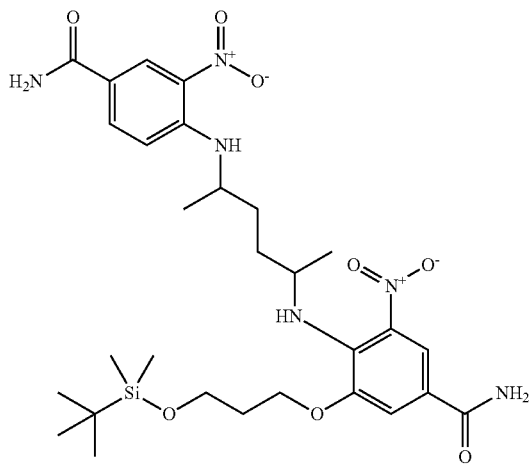 [SMILES: CC(CCC(C)Nc1c(OCCCO[Si](C)(C)C(C)(C)C)cc(C(N)=O)cc1[N+](=O)[O-])Nc1ccc(C(N)=O)cc1[N+](=O)[O-]]

Into a 40-mL vial were placed 3-(3-((tert-butyldimethylsilyl)oxy)propoxy)-4-chloro-5-nitrobenzamide (the compound of intermediate 4) (1.255 g, 3.23 mmol), isopropanol (8 mL) and DIPEA (1.879 mL, 10.76 mmol). To this heterogeneous mixture was added hexane-2,5-diamine (500 mg, 4.30 mmol) as a solution in isopropanol (2 mL). The vial was capped and heated to 110° C. overnight (~14 h). The solution was cooled to room temperature. 4-Fluoro-3-nitrobenzamide (0.594 g, 3.23 mmol) was added followed by DIPEA (1.879 mL, 10.76 mmol). The reaction was again heated to 110° C. for 2 h. The solid formed upon cooling to room temperature. The solid was collected on a filter and rinsed twice with isopropanol (2 mL each). This crude solid was purified by silica gel chromatography (ISCO unit, 80 g SiO₂ cartridge, 2-20% gradient of MeOH/DCM). The corresponding fractions were combined and concentrated. 3-(3-((Tert-butyldimethylsilyl)oxy)propoxy)-4-((5-((4-carbamoyl-2-nitrophenyl)amino)hexan-2-yl)amino)-5-nitrobenzamide (300 mg, 0.450 mmol, 10.47% yield) was obtained as an orange glassy film (mixture of diastereomers). LCMS (m/z): 633.5 [M+H]$^+$.

Step 4: 3-amino-4-((5-((2-amino-4-carbamoylphenyl)amino)hexan-2-yl)amino)-5-(3-((tert-butyldimethylsilyl)oxy)propoxy)benzamide

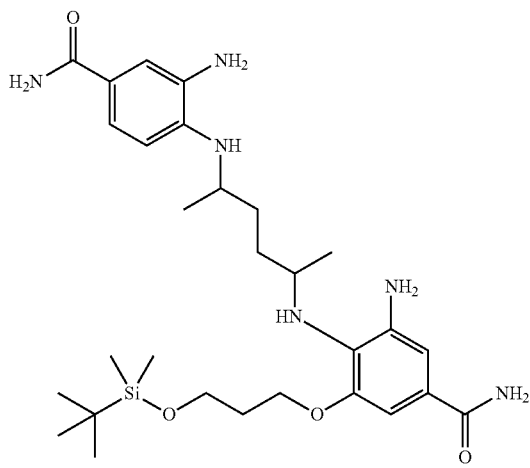 [SMILES: CC(CCC(C)Nc1c(N)cc(C(N)=O)cc1OCCCO[Si](C)(C)C(C)(C)C)Nc1ccc(C(N)=O)cc1N]

To a 125-mL Erlenmeyer flask were added 3-(3-((tert-butyldimethylsilyl)oxy)propoxy)-4-((5-((4-carbamoyl-2-nitrophenyl)amino)hexan-2-yl)amino)-5-nitrobenzamide (386 mg, 0.610 mmol) and MeOH (40 mL). This solution was hydrogenated using a ThalesNano H-Cube® system (5% Pd/C cartridge, 30° C., 10 bar hydrogen pressure, 1.5 mL/min flowrate). After two cycles, the reduction was complete. The solution was concentrated to obtain 3-amino-4-((5-((2-amino-4-carbamoylphenyl)amino)hexan-2-yl)amino)-5-(3-((tert-butyldimethylsilyl)oxy)propoxy)benzamide (352 mg, 0.602 mmol, 99% yield). LCMS (m/z): 573.5 [M+H]$^+$.

Step 5: 7-(3-((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide Intemediate 14A

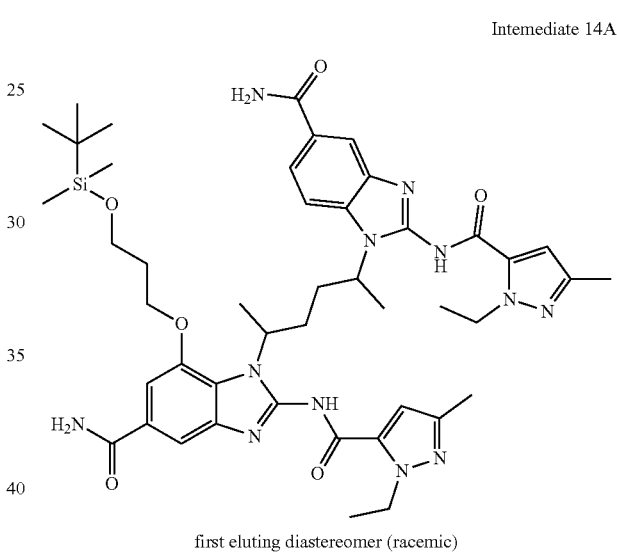

first eluting diastereomer (racemic)

Intemediate 14B

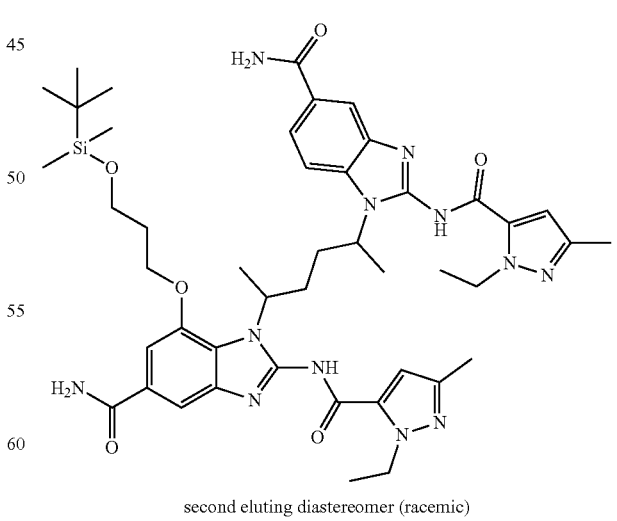

second eluting diastereomer (racemic)

To a 100-mL round bottom flask was added 3-amino-4-((5-((2-amino-4-carbamoylphenyl)amino)hexan-2-yl)amino)-5-(3-((tert-butyldimethylsilyl)oxy)propoxy)benzamide (352 mg, 0.614 mmol) and DMF (6.1 mL). A solution of 1-ethyl-3-methyl-1H-pyrazole-5-carbonyl isothiocyanate (the compound of intermediate 8) (~0.4 M in dioxane, 2.75 mL, 1.100 mmol) was added at 0° C. and the mixture was stirred for 15 min. EDC (295 mg, 1.536 mmol) was then added followed by addition of triethylamine (0.428 mL, 3.07 mmol). The reaction was stirred overnight (~14 h) at room temperature. The reaction was partitioned between 50 mL ethyl acetate and 50 mL of a 1:1 mixture of saturated aqueous ammonium chloride solution and water. The layers were separated. The aqueous layer was extracted with ethyl acetate (2×25 mL). The combined organic phase was washed with brine, dried over sodium sulfate, and concentrated under vacuum. Purification by reverse phase preparative chromatography (Dual phase ISCO system, Gemini C18, 5 um, 50×30 mm column; 40-70% gradient of MeCN/water with NH$_4$OH modifier) enabled separation and characterization of a first eluting diastereomer and a second eluting diastereomer. Each diastereomer is anticipated to be racemic (i.e. pair of enantiomers). Fractions containing first eluting diastereomer and second eluting diastereomer were separately pooled and dried to provide Intermediates XA and XB respectively as white solids.

Intermediate 14A (First Eluting Diastereomer)

Racemic 7-(3-((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide (200 mg, 0.223 mmol, 36.4% yield).

LCMS (m/z): 895.6 [M+H]$^+$; 1.37 min retention time (Acquity UPLC CSH C18, 1.7 um, 50 mm×2.1 mm column; 40° C.; 3-95% gradient over 1.5 min, MeCN/10 mM ammonium bicarbonate in water adjusted to pH 10 with 25% ammonium hydroxide solution).

$^1$H NMR (400 MHz, METHANOL-d$_4$) δ ppm 7.98 (br. s., 0.54), 7.91 (s, 0.51), 7.80 (t, J=7.22 Hz, 1.06), 7.45-7.65 (m, 2.01), 7.40 (s, 0.52), 7.35 (s, 0.54), 6.34-6.79 (m, 2.09), 5.44 (br. s., 1.20), 4.65 (m, 4.10), 4.28 (m, 1.56), 3.99 (br. s., 0.63), 3.79 (m, 1.06), 3.70 (br. s., 0.65), 3.61 (br. s., 0.58), 2.98 (br. s., 2.98), 2.35-2.65 (m, 1.40), 2.28 (s, 1.49), 2.23 (m, 3.16), 2.17 (br. s., 1.47), 1.99 (br. s., 0.98), 1.81 (br. s., 2.70), 1.62 (d, J=6.84 Hz, 1.87), 1.55 (d, J=6.84 Hz, 3.08), 1.50 (d, J=6.59 Hz, 1.46), 1.29-1.47 (m, 6.68), 0.87 (s, 9.20), 0.02 (s, 6.00).

Intermediate 14B (Second Eluting Diastereomer)

Racemic 7-(3-((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide (210 mg, 0.235 mmol, 38.2% yield) as a white solid.

LCMS (m/z): 895.6 [M+H]$^+$; 1.42 min retention time (Acquity UPLC CSH C18, 1.7 um, 50 mm×2.1 mm column; 40° C.; 3-95% gradient over 1.5 min, MeCN/10 mM ammonium bicarbonate in water adjusted to pH 10 with 25% ammonium hydroxide solution).

$^1$H NMR (400 MHz, METHANOL-d$_4$) δ ppm 7.80 (br. s., 2.29), 7.60 (br. s., 3.77), 7.43 (br. s., 3.64), 7.24 (br. s., 3.24), 7.10 (s, 3.41), 6.81 (br. s., 3.41), 5.62-6.31 (br. s., 2.02), 5.35-5.61 (m, 3.60), 5.26 (br. s., 2.06), 4.57-4.84 (m, 11.14), 4.25-4.52 (m, 4.04), 4.11 (br. s., 1.46), 3.96 (t, J=5.96 Hz, 2.56), 3.84 (br. s., 0.87), 3.59 (br. s., 4.64), 2.85 (q, J=12.17 Hz, 0.97), 2.11-2.40 (m, 20.85), 2.06 (s, 5.95), 1.69-1.99 (m, 8.53), 1.20-1.68 (m, 44.08), 0.96 (s, 10.71), 0.86 (s, 21.28), 0.14 (d, J=5.07 Hz, 7.03), 0.01 (d, J=3.80 Hz, 14.00).

Intermediate 15

4-chloro-3-((4-methoxybenzyl)oxy)-5-nitrobenzamide

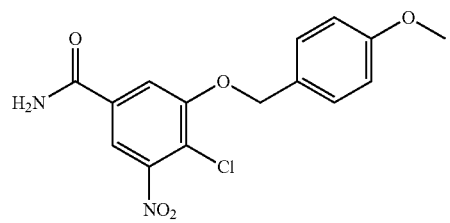 [SMILES: COc1ccc(COc2cc(C(N)=O)cc([N+](=O)[O-])c2Cl)cc1]

To 4-chloro-3-hydroxy-5-nitrobenzamide (942 mg, 4.35 mmol) dissolved in DMF (7 mL), Cs$_2$CO$_3$ (1.559 g, 4.78 mmol) was added followed by 4-methoxybenzyl chloride (0.622 mL, 4.57 mmol). The reaction mixture was stirred for 24 h at room temperature. With vigorous stirring, water (15 mL) was added dropwise and the resulting solid was stirred for 5 minutes, collected by filtration and rinsed with water to afford the title compound (1.26 g, 3.74 mmol, 82% yield) as a light orange solid. $^1$H NMR (400 MHz, CDCl) δ ppm 7.80 (d, J=1.8 Hz, 1H), 7.76 (d, J=1.8 Hz, 1H), 7.43 (d, J=8.6 Hz, 2H), 6.98 (d, J=8.6 Hz, 2H), 6.13 (br. s., 1H), 5.82 (br. s., 1H), 5.25 (s, 2H), 3.87 (s, 3H); LCMS (m/z): 337.1 [M+H]$^+$.

Intermediate 16
(E)-2,3-dimethylbut-2-ene-1,4-diamine, 2Hydrochloride

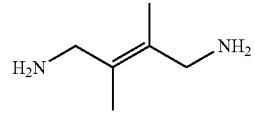

Step 1: (E)-2,2'-(2,3-dimethylbut-2-ene-1,4-diyl)bis(isoindoline-1,3-dione)

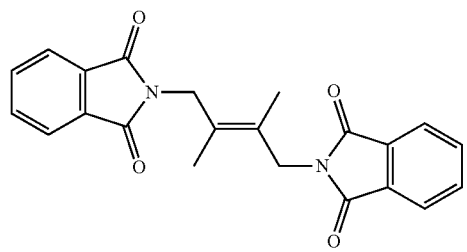

To a solution of (E)-1,4-dibromo-2,3-dimethylbut-2-ene (29.5 g, 122 mmol) in DMF (244 mL) was added phthalimide potassium salt (45.2 g, 244 mmol). The white suspension was stirred at room temperature overnight. The reaction was poured into water (2 L) and the resulting white suspension was filtered. The filtercake was air-dried (48 h) to afford (E)-2,2'-(2,3-dimethylbut-2-ene-1,4-diyl)bis(isoindoline-1,3-dione) (37 g, 99 mmol, 81% yield) as a white solid. The solid was used without further purification. ¹H NMR (400 MHz, CHLOROFORM-d) δ ppm 7.84-7.93 (m, 4H), 7.72-7.81 (m, 4H), 4.39 (s, 4H), 1.95 (s, 6H).

Step 2: (E)-2,3-dimethylbut-2-ene-1,4-diamine, 2Hydrochloride

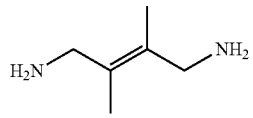

To a mixture of (E)-2,2'-(2,3-dimethylbut-2-ene-1,4-diyl) bis(isoindoline-1,3-dione) (15.3 g, 40.9 mmol) in EtOH (332 mL) was added hydrazine monohydrate (6.01 mL, 123 mmol). The reaction was heated at 80° C. After 3 h the reaction was cooled to room temperature. The thick white mixture was filtered, the filtercake was washed with ethanol, and the filtrate was concentrated to dryness. The resulting white solid from filtrate was partitioned between water (150 mL) and EtOAc (150 mL). The aqueous layer was concentrated to dryness to afford a viscous, yellow-tinted oil. The viscous oil was treated with 1 N HCl (250 mL) and EtOAc (250 mL). The white precipitate that appeared (byproduct) was removed by filtration. The filtrate was transferred to a separatory funnel. The aqueous layer was separated; filtered to remove remaining white solids and concentrated to dryness to afford (E)-2,3-dimethylbut-2-ene-1,4-diamine, 2Hydrochloride (4.2 g, 22.45 mmol, 54.9% yield) as a greyish-pink solid. The material was used without further purification. ¹H NMR (400 MHz, DMSO-d₆) δ ppm 8.23 (br. s., 6H), 3.45 (q, J=5.75 Hz, 4H), 1.83 (s, 6H).

Intermediate 17 tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate

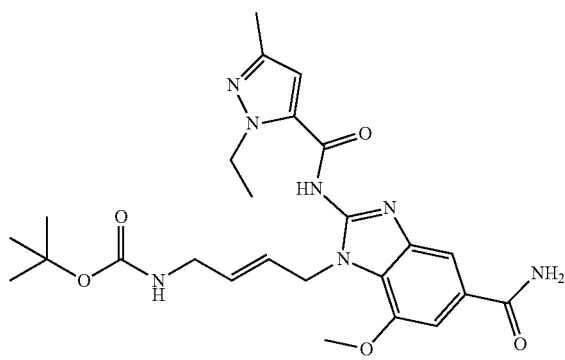 [SMILES: CCn1nc(C)cc1C(=O)Nc1nc2cc(C(N)=O)cc(OC)c2n1C/C=C/CNC(=O)OC(C)(C)C]

Step 1: tert-butyl (E)-(4-((2-amino-4-carbamoyl-6-methoxyphenyl)amino)but-2-en-1-yl)carbamate

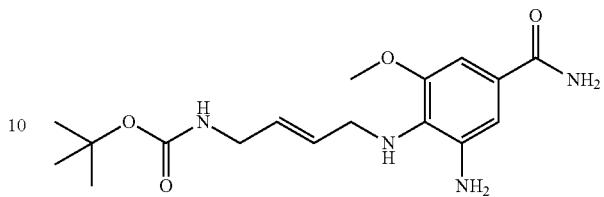

To a 2-L round bottom flask was added tert-butyl (E)-(4-((4-carbamoyl-2-methoxy-6-nitrophenyl)amino)but-2-en-1-yl)carbamate (25.8 g, 67.8 mmol) and methanol (484 mL). This orange heterogenous solution was cooled down to 0° C. After 20 minutes stirring at 0° C., ammonium hydroxide solution (29% wt, 91 mL, 678 mmol) was added followed by sodium hydrosulfite (85% wt, 70.0 g, 342 mmol) as a solution in water (194 mL). The flask was removed from the ice bath and stirred at room temperature. The heterogenous mixture slowly changes color—from orange to off-white. After 3 h of stirring at room temperature, water (~800 mL) was added until a clear solution was obtained. The methanol was evaporated using reduced pressure. The white solid that formed during evaporation was filtered off and washed with water twice (300 mL each). The solid was air-dried for 16 h and then 5 h in the vacuum oven at 50° C. Tert-butyl (E)-(4-((2-amino-4-carbamoyl-6-methoxyphenyl)amino) but-2-en-1-yl)carbamate (19.34 g, 54.1 mmol, 80% yield) was obtained as an off-white solid. The purity of this solid was judged to be 98% by HPLC, LCMS and 1H NMR. ¹H NMR (400 MHz, DMSO-d₆) δ ppm 7.62 (br. s., 1H) 6.98 (br. s., 1H) 6.92 (t, J=5.45 Hz, 1H) 6.87 (d, J=1.77 Hz, 1H) 6.79 (d, J=1.77 Hz, 1H) 5.57 (qt, J=15.27, 5.23 Hz, 2H) 4.67 (br. s., 2H) 3.82 (br. s., 1H) 3.76 (s, 3H) 3.51 (dd, J=12.29, 5.70 Hz, 4H) 1.37 (s, 9H). LCMS (m/z): 351.1 (M+H)⁺.

Step 2: tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate

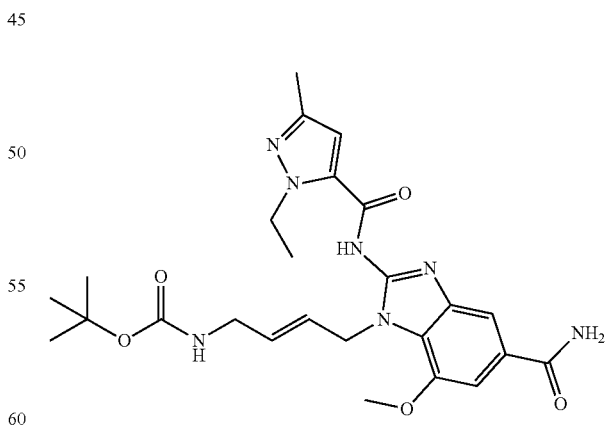

To a 2-Liter round bottom flask was placed tert-butyl (E)-(4-((2-amino-4-carbamoyl-6-methoxyphenyl)amino) but-2-en-1-yl)carbamate (19.34 g, 55.2 mmol) and DMF (184 mL). This solution was cooled down to 0° C. After 20 minutes stirring at 0° C., 1-ethyl-3-methyl-1H-pyrazole-5-carbonyl isothiocyanate (44.2 mL, 44.2 mmol) was added as a ~1.0 M solution in dioxane. After 10 minutes stirring at 0° C., the formation of the intermediate thiourea was complete. EDC (15.87 g, 83 mmol) and DIEA (28.9 mL, 166 mmol) were added. The reaction was warmed to room temperature and stirred overnight (~14 h). To the heterogenous reaction mixture was added a mixture of 250 mL of saturated aqueous ammonium chloride and 750 mL of water. This heterogenous mixture was stirred for 1 h at room temperature. The solid was filtered off and rinsed twice with water (200 mL each). The off-white solid was dried in a vacuum oven at 50° C. for 3 days. Tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate (21.23 g, 41.5 mmol, 75% yield) was obtained as a white solid with a purity ~100% judged by LCMS, HPLC and $^1$H NMR. $^1$H NMR (400 MHz, DMSO-$d_6$) δ ppm 12.84 (br. s., 1H) 8.00 (br. s., 1H) 7.67 (s, 1H) 7.30-7.45 (m, 2H) 6.86-7.00 (m, 1H) 6.64 (s, 1H) 5.54-5.80 (m, 2H) 4.92 (d, J=4.82 Hz, 2H) 4.61 (q, J=7.01 Hz, 2H) 3.97 (s, 3H) 3.50 (br. s., 2H) 2.18 (s, 3H) 1.11-1.41 (m, 12H). LCMS (m/z): 512.5 (M+H)$^+$.

Intermediate 18

(E)-1-(4-aminobut-2-en-1-yl)-2-(1-ethyl-3-methyl-1H-pyrazole-5-carboxamido)-7-methoxy-1H-benzo[d]imidazole-5-carboxamide, 2Hydrochloride

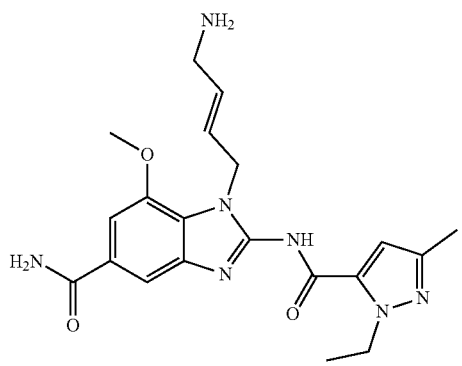 [SMILES: CCn1nc(C)cc1C(=O)Nc1nc2cc(C(N)=O)cc(OC)c2n1C/C=C/CN]

To a 1-liter round bottom flask was added tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate (21.23 g, 41.5 mmol), ethanol (234 mL) and t-butylmethyl ether (96 mL). To this heterogenous solution was added HCl (114 mL, 456 mmol) as a 4M solution in dioxane. During the HCl addition the solution went from heterogenous to homogenous with a clear yellow color. The reaction was stirred at room temperature overnight. By the next morning, a white solid had precipitated. More 4M HCl solution (15.56 mL, 62.2 mmol) was added and the mixture stirred for another 9 h until the reaction was completed. The white solid was filtered off and rinsed with 1:4 mixture of ethanol (200 mL)/TBME (800 mL). The obtained solid was dried in the vacuum oven overnight (50° C.). (E)-1-(4-aminobut-2-en-1-yl)-2-(1-ethyl-3-methyl-1H-pyrazole-5-carboxamido)-7-methoxy-1H-benzo[d]imidazole-5-carboxamide, 2Hydrochloride (22.56 g, 44.2 mmol, 107% yield) was obtained as a white solid with a purity 95% as judged by LCMS, HPLC and $^1$H NMR. $^1$H NMR (400 MHz, DMSO-$d_6$) δ ppm 12.88 (br. s., 1H) 7.77-8.18 (m, 4H) 7.68 (d, J=1.27 Hz, 1H) 7.25-7.51 (m, 2H) 6.68 (s, 1H) 6.04 (dt, J=15.52, 5.80 Hz, 1H) 5.53-5.78 (m, 1H) 4.99 (d, J=5.32 Hz, 2H) 4.61 (q, J=7.10 Hz, 2H) 3.99 (s, 3H) 3.27-3.57 (m, 2H) 2.19 (s, 3H) 1.36 (t, J=7.10 Hz, 3H). LCMS (m/z): 412.3 (M+H)$^+$.

Intermediate 19

(E)-2-(4-amino-2,3-dimethylbut-2-en-1-yl)isoindoline-1,3-dione

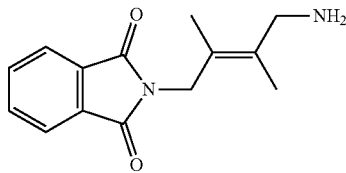 [SMILES: C/C(CN)=C(/C)CN1C(=O)c2ccccc2C1=O]

Step 1: (3r,5r,7r)-1-((E)-4-bromo-2,3-dimethylbut-2-en-1-yl)-1,3,5,7-tetraazaadamantan-1-ium, Bromide

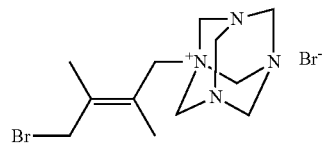 [SMILES: C/C(CBr)=C(/C)C[N+]12CN3CN(CN(C3)C1)C2 ; [Br-]]

To a solution of (E)-1,4-dibromo-2,3-dimethylbut-2-ene (13.59 g, 50.6 mmol) in DCM (200 mL) was added 1,3,5,7-tetraazaadamantane (7.09 g, 50.6 mmol) in portions over 2 min. The reaction was stirred for 25 min and the resulting solid was filtered, rinsed with DCM and dried to afford (3r,5r,7r)-1-((E)-4-bromo-2,3-dimethylbut-2-en-1-yl)-1,3,5,7-tetraazaadamantan-1-ium, Bromide (16.7 g, 43.7 mmol, 86% yield) as a white solid. LCMS (m/z): 301.1 [M]$^+$.

Step 2: (3r,5r,7r)-1-((E)-4-(1,3-dioxoisoindolin-2-yl)-2,3-dimethylbut-2-en-1-yl)-1,3,5,7-tetraazaadamantan-1-ium, Bromide

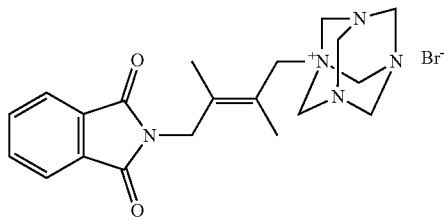 [SMILES: C/C(CN1C(=O)c2ccccc2C1=O)=C(/C)C[N+]12CN3CN(CN(C3)C1)C2 ; [Br-]]

To a suspension of (3r,5r,7r)-1-((E)-4-bromo-2,3-dimethylbut-2-en-1-yl)-1,3,5,7-tetraazaadamantan-1-ium, Bromide (16.7 g, 43.7 mmol) in acetone (200 mL) was added potassium 1,3-dioxoisoindolin-2-ide (8.09 g, 43.7 mmol). The reaction mixture was heated at 55° C. for 1.5 h. Over the next 2.5 h, the reaction was treated with additional potassium phthalimide until the the starting material was consumed. The reaction mixture was removed from heat, stirred for 10 min and then filtered while still warm. The solid was rinsed with acetone and dried to afford 20.4 g of crude product. The crude product was stirred in cold water (ice bath) for 5 min. The solid was collected on a filter, rinsed with cold water, and dried to give (3r,5r,7r)-1-((E)-4-(1,3-dioxoisoindolin-2-yl)-2,3-dimethylbut-2-en-1-yl)-1,3,5,7-tetraazaadamantan-1-ium, Bromide (10.3 g, 22.9 mmol, 52.6% yield) as a light yellow solid. LCMS (m/z): 368.2 [M]+.

Step 3: (E)-2-(4-amino-2,3-dimethylbut-2-en-1-yl)isoindoline-1,3-dione

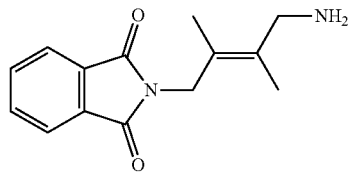 [SMILES: C/C(CN)=C(/C)CN1C(=O)c2ccccc2C1=O]

To a suspension of (3r,5r,7r)-1-((E)-4-(1,3-dioxoisoindolin-2-yl)-2,3-dimethylbut-2-en-1-yl)-1,3,5,7-tetraazaadamantan-1-ium, Bromide (10.3 g, 22.97 mmol) in EtOH (100 mL) at room temperature was added concentrated hydrogen chloride (7.55 mL, 92 mmol). The reaction mixture turned from light yellow to light orange in color. The reaction was heated at 80° C. for 55 min. The color became darker orange over time. The reaction mixture was cooled to room temperature and saturated NaHCO$_3$ solution was added to raise the pH of the solution (~20 mL). The mixture was stirred for 5 min, diluted with 20 mL of water and extracted with 3:1 chloroform:EtOH (3×75 mL). The organic extracts were dried over sodium sulfate, concentrated and dried to give (E)-2-(4-amino-2,3-dimethylbut-2-en-1-yl)isoindoline-1,3-dione (5.77 g, 22.4 mmol, 98% yield) as a light brown solid. $^1$H NMR (400 MHz, DMSO-d$_6$) δ ppm 7.71-8.09 (m, 6H), 4.25 (s, 2H), 3.45 (s, 2H), 1.95 (d, J=1.27 Hz, 3H), 1.65 (d, J=1.27 Hz, 3H). LCMS (m/z): 245.2 [M+H]+.

Intermediate 20 tert-butyl (E)-(4-amino-2,3-dimethylbut-2-en-1-yl)carbamate

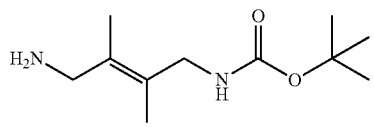

Step 1: tert-butyl Dichlorocarbamate

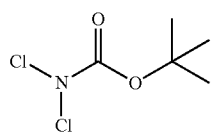

To a solution of tert-butyl carbamate (20.1 g, 172 mmol) in DCM (400 mL) at 0° C. were added calcium hypochlorite (technical grade, available chlorine 65%) (75 g, 343 mmol) and then 6 M hydrochloric acid (143 mL, 858 mmol) dropwise over 35 min (internal temperature 5-10° C. during addition). The resulting yellow suspension was then stirred for 20 min. The layers were separated, the organic layer washed with water and brine, and dried over sodium sulfate. The solution was carefully concentrated under reduced pressure (23° C., 80 mbar) to provide tert-butyl dichlorocarbamate (33.4 g, 172 mmol, 100%) as a light yellow liquid. $^1$H NMR (400 MHz, CDCl) δ ppm 1.56 (s, 9H).

Step 2: tert-butyl (E)-(4-chloro-2,3-dimethylbut-2-en-1-yl)carbamate

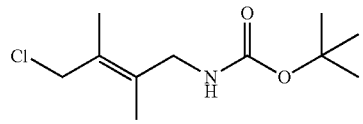

Nitrogen was bubbled through 300 mL chloroform for 10 min. 2,3-dimethylbuta-1,3-diene (24.79 mL, 219 mmol) was then added and the solution was cooled to 0° C. under nitrogen atmosphere. A solution of tert-butyl dichlorocarbamate (41 g, 220 mmol) in chloroform (150 mL) was added over 80 min to generate a mixture of (E)-tert-butyl chloro(4-chloro-2,3-dimethylbut-2-en-1-yl)carbamate and tert-butyl (E)-(4-chloro-2,3-dimethylbut-2-en-1-yl)carbamate. After 15 min of additional stirring in an ice bath, a freshly-prepared aqueous solution of sodium sulfite (3M, 219 mL, 657 mmol) was added quickly dropwise at a rate that maintained the internal temperature below room temperature (caution: exothermic reaction with gas evolution). The ice bath was removed and the reaction stirred an additional 15 min. The layers were separated. The organic layer was washed with water and brine, dried over sodium sulfate, and concentrated to provide tert-butyl (E)-(4-chloro-2,3-dimethylbut-2-en-1-yl)carbamate (45.4 g, 184 mmol, 84% yield) as a white solid. $^1$H NMR (400 MHz, CHLOROFORM-d) δ ppm 4.49 (br. s., 1H), 4.10 (s, 2H), 3.80 (br. s., 2H), 1.86 (s, 3H), 1.82 (d, J=1.25 Hz, 3H), 1.47 (s, 9H).

Step 3: tert-butyl (E)-(4-(1,3-dioxoisoindolin-2-yl)-2,3-dimethylbut-2-en-1-yl)carbamate

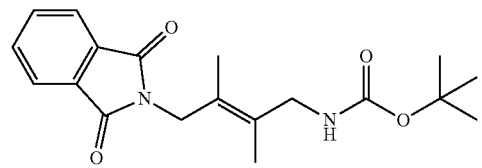 [SMILES: C/C(CNC(=O)OC(C)(C)C)=C(/C)CN1C(=O)c2ccccc2C1=O]

To a solution of tert-butyl (E)-(4-chloro-2,3-dimethylbut-2-en-1-yl)carbamate (40.4 g, 164 mmol) in DMF (300 mL) was added potassium 1,3-dioxoisoindolin-2-ide (30.4 g, 164 mmol) and the reaction mixture was stirred at room temperature for 3 h. The mixture was cooled in an ice/water bath and water (450 mL) was added to provide a thick precipitate. After stirring at room temperature for 10 min, the solids were filtered, rinsed with water, and dried to provide tert-butyl (E)-(4-(1,3-dioxoisoindolin-2-yl)-2,3-dimethylbut-2-en-1-yl)carbamate (50.08 g, 137 mmol, 84% yield) as a white solid. $^1$H NMR (400 MHz, CHLOROFORM-d) δ ppm 7.87 (dd, J=5.40, 3.14 Hz, 2H), 7.74 (dd, J=5.27, 3.01 Hz, 2H), 4.41-4.48 (m, 1H), 4.35 (s, 2H), 3.78 (br. s., 2H), 1.97 (s, 3H), 1.70 (d, J=1.25 Hz, 3H), 1.47 (s, 9H).

Step 4: tert-butyl (E)-(4-amino-2,3-dimethylbut-2-en-1-yl)carbamate

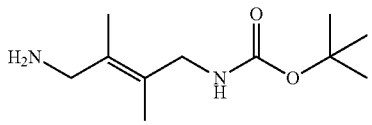

Two identical reactions were set up in parallel. To a mixture of tert-butyl (E)-(4-(1,3-dioxoisoindolin-2-yl)-2,3-dimethylbut-2-en-1-yl)carbamate (25 g, 69.0 mmol) in ethanol (400 mL) was added hydrazine monohydrate (6.69 mL, 138 mmol). The mixture was stirred at 80° C. for 4.5 h. After heating for 30 min, a thick precipitate began to form and stirring became difficult. The two reactions were combined and concentrated to remove ethanol and gave a white solid. This material was stirred in water (450 mL). 1M HCl (50 mL) and 6M HCl (14 mL) solutions were added to adjust the pH to ~5 and the suspension was stirred for 10 min. The solid was filtered off and rinsed with water. The aqueous filtrate was extracted with DCM (100 mL) to remove any impurities/color. The aqueous phase was then adjusted to pH 13 with 1M sodium hydroxide and extracted with 3:1 CHCl₃:EtOH (3×300 mL). The combined organic layer was dried over sodium sulfate, filtered, and concentrated to give a pale orange oil, which quickly solidified. The solids were triturated with 5% diethyl ether/heptane (200 mL) for 5 min then filtered and rinsed with heptane (crop 1). The filtrate was concentrated and stirred in 5 mL of diethyl ether. The solids were rinsed with minimal diethyl ether and filtered to give a second crop. Combination and drying in vacuo provided tert-butyl (E)-(4-amino-2,3-dimethylbut-2-en-1-yl)carbamate (23.9 g, 111 mmol, 80% yield) as an off-white solid. ¹H NMR (400 MHz, METHANOL-d₄) δ ppm 3.70 (s, 2H), 3.24 (s, 2H), 1.81 (d, J=1.00 Hz, 3H), 1.73 (s, 3H), 1.46 (s, 9H). LCMS (m/z): 215.3 [M+H]⁺.

Intermediate 21

(E)-4-((4-amino-2,3-dimethylbut-2-en-1-yl)amino)-3-nitrobenzamide, Hydrochloride

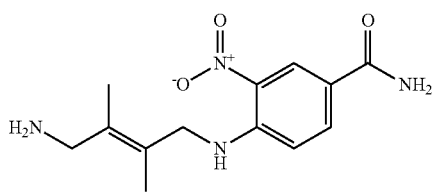

Step 1: tert-butyl (E)-(4-((4-carbamoyl-2-nitrophenyl)amino)-2,3-dimethylbut-2-en-1-yl)carbamate

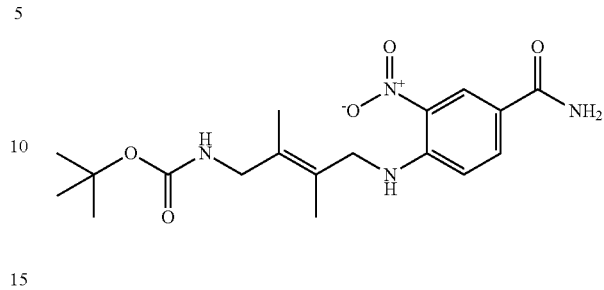

To a solution of tert-butyl (E)-(4-amino-2,3-dimethylbut-2-en-1-yl)carbamate (1.92 g, 8.96 mmol) and 4-fluoro-3-nitrobenzamide (1.650 g, 8.96 mmol) in DMSO (25 mL) was added potassium carbonate (1.486 g, 10.75 mmol). The bright orange mixture was stirred at room temperature for 2 h. The mixture was added dropwise into rapidly stirring ice water (200 mL) and stirred 1 h. The resulting precipitate was filtered, rinsed with water, and dried to give tert-butyl (E)-(4-((4-carbamoyl-2-nitrophenyl)amino)-2,3-dimethylbut-2-en-1-yl)carbamate (2.9 g, 7.5 mmol, 84% yield) as a bright yellow solid. ¹H NMR (400 MHz, DMSO-d₆) δ ppm 8.66 (d, J=2.28 Hz, 1H), 8.36 (t, J=5.32 Hz, 1H), 7.99 (dd, J=8.87, 2.03 Hz, 2H), 7.31 (br. s., 1H), 7.02 (t, J=5.70 Hz, 1H), 6.92 (d, J=9.12 Hz, 1H), 4.02 (d, J=5.07 Hz, 2H), 3.60 (d, J=5.58 Hz, 2H), 1.75 (s, 3H), 1.68 (s, 3H), 1.38 (s, 9H).

Step 2: (E)-4-((4-amino-2,3-dimethylbut-2-en-1-yl)amino)-3-nitrobenzamide, Hydrochloride

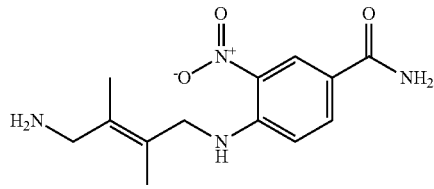

To a suspension of tert-butyl (E)-(4-((4-carbamoyl-2-nitrophenyl)amino)-2,3-dimethylbut-2-en-1-yl)carbamate (2.9 g, 7.66 mmol) in DCM (LARA to update) was added 4M HCl in dioxane (9.58 mL, 38.3 mmol). The reaction was stirred at room temperature for 2 h. The resulting solids were filtered, rinsed with DCM, and dried to give (E)-4-((4-amino-2,3-dimethylbut-2-en-1-yl)amino)-3-nitrobenzamide, hydrochloride (2.4 g, 7.28 mmol, 95% yield) as a bright yellow solid. ¹H NMR (400 MHz, DMSO-d₆) δ ppm 8.68 (d, J=2.28 Hz, 1H), 8.44 (t, J=5.45 Hz, 1H), 8.01 (dd, J=9.00, 2.15 Hz, 5H), 7.33 (br. s., 1H), 6.90 (d, J=9.12 Hz, 1H), 4.10 (d, J=5.07 Hz, 2H), 3.48 (d, J=5.58 Hz, 2H), 1.90 (s, 3H), 1.72 (s, 3H). LCMS (m/z): no prominent [M+H]⁺.

Intermediate 22

(2S,3S)-2,3-diethoxybutane-1,4-diamine

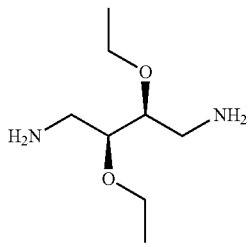

Step 1: (4S,5S)-4,5-bis(azidomethyl)-2,2-dimethyl-1,3-dioxolane

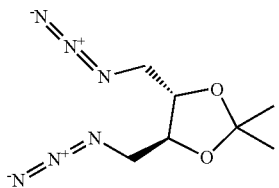

To a solution of ((4S,5S)-2,2-dimethyl-1,3-dioxolane-4,5-diyl)bis(methylene) bis(4-methylbenzenesulfonate) (5.23 g, 11.11 mmol) in DMF (20 mL) was added sodium azide (2.89 g, 44.5 mmol). The mixture was stirred at 80° C. for 18 h. The mixture was diluted with water (100 mL) and extracted with EtOAc (2×100 mL). The organic phase was washed with water (2×100 mL), brine (100 mL), dried with magnesium sulfate and concentrated to give (4S,5S)-4,5-bis(azidomethyl)-2,2-dimethyl-1,3-dioxolane (2.3 g, 10.8 mmol, 98% yield) as clear oil. $^1$H NMR (400 MHz, CHLOROFORM-d) δ ppm 1.51 (s, 6H), 3.30-3.43 (m, 2H), 3.54-3.66 (m, 2H), 4.10 (td, J=2.8, 1.3 Hz, 2H). LCMS (m/z): no prominent [M+H]$^+$.

Step 2: (2S,3S)-1,4-diazidobutane-2,3-diol

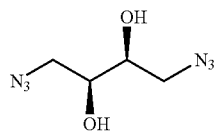 [SMILES: [N-]=[N+]=NC[C@H](O)[C@@H](O)CN=[N+]=[N-]]

To the solution of (4S,5S)-4,5-bis(azidomethyl)-2,2-dimethyl-1,3-dioxolane (2.3 g, 10.84 mmol) in THF (50 mL) was added para-toluenesulfonic acid (0.103 g, 0.542 mmol). The reaction mixture was heated at 60° C. for 18 h. The reaction mixture was cooled to room temperature and partitioned between EtOAc (50 mL) and water (30 mL). The aqueous phase was extracted with EtOAc (2×50 mL). The combined organic phase was washed with brine (30 mL), dried with magnesium sulfate, and concentrated. NMR analysis indicates no reaction had occurred. To the mixture was added 1.25 M HCl in methanol (34.7 mL, 43.4 mmol). The reaction was heated at 60° C. for 18 h. The reaction mixture was concentrated to give (2S,3S)-1,4-diazidobutane-2,3-diol (2.01 g, 10.5 mmol, 97% yield) as light yellow clear oil. $^1$H NMR (400 MHz, CHLOROFORM-d) δ ppm 3.35-3.59 (m, 4H), 3.71-3.90 (m, 2H).

Step 3: (2S,3S)-2,3-diethoxybutane-1,4-diamine

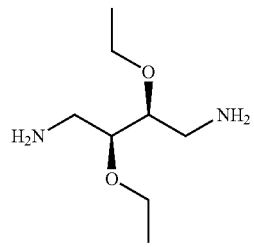

To the mixture of (2S,3S)-1,4-diazidobutane-2,3-diol (2.01 g, 11.68 mmol) in DMF (50 mL) was added sodium hydride (1.167 g, 29.2 mmol) at 0° C. The mixture was stirred at room temperature for 5 min, then iodoethane (2.36 mL, 29.2 mmol) was added. The mixture was stirred at room temperature for 18 h. The mixture was partitioned between EtOAc (100 mL) and water (100 mL). The organic phase was washed with brine (3×30 mL), dried with magnesium sulfate and concentrated to give crude (2S,3S)-1,4-diazido-2,3-diethoxybutane (2.47 g) as a clear oil. $^1$H NMR (400 MHz, CHLOROFORM-d) δ ppm 1.27 (t, J=7.0 Hz, 6H), 3.31-3.47 (m, 4H), 3.56-3.82 (m, 6H). A mixture of crude (2S,3S)-1,4-diazido-2,3-diethoxybutane (2.47 g) and palladium on carbon (0.3 g, 2.8 mmol) in methanol (30 mL) was purged with nitrogen and exchanged for an atmosphere of hydrogen (balloon). The mixture was stirred at room temperature for 18 h. Hydrogen was exchanged with nitrogen and the mixture was filtered through Celite and concentrated to give (2S,3S)-2,3-diethoxybutane-1,4-diamine (1.86 g, 90% yield) as a clear oil. $^1$H NMR (400 MHz, DMSO-d$_6$) δ ppm 1.07-1.13 (m, 6H), 2.31-2.49 (m, 2H), 2.57-2.68 (m, 2H), 3.20-3.27 (m, 2H), 3.50-3.60 (m, 4H).

Intermediate 23

4-chloro-3-nitro-5-(trifluoromethyl)benzamide

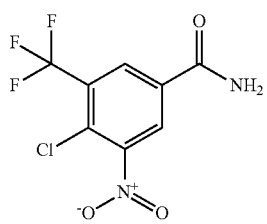

To a solution of 4-chloro-3-nitro-5-(trifluoromethyl)benzoic acid (3.94 g, 14.62 mmol) in DCM (97 mL) was added at room temperature oxalyl chloride (2.047 mL, 23.39 mmol) and 4 drops of DMF. After stirring for 1 h, 30% ammonium hydroxide solution (9.49 mL, 73.1 mmol) was added and stirred for 18 h. The resulting white precipitate was filtered, washed first with water then DCM, and dried to provide 4-chloro-3-nitro-5-(trifluoromethyl)benzamide (3.32 g, 12.36 mmol, 85% yield) as a white solid. $^1$H NMR (400 MHz, DMSO-$d_6$) δ ppm 8.77 (d, J=2.0 Hz, 1H), 8.57 (d, J=1.8 Hz, 1H), 7.97 (br. s., 2H). LCMS (m/z): 269.1 [M+H]$^+$.

Intermediate 24

Ethyl 3-(5-carbamoyl-2-fluoro-3-nitrophenyl)propanoate

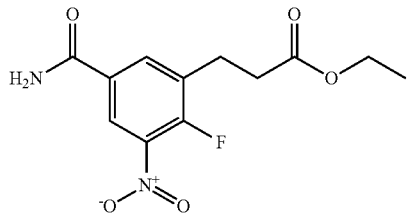

To 3-bromo-4-fluoro-5-nitrobenzamide (5 g, 18.25 mmol) in DMF (60.8 mL) was added tetra-n-butylammonium chloride (5.18 g, 18.25 mmol) and Pd(OAc)$_2$ (0.418 g, 1.825 mmol). Nitrogen was bubbled through the mixture for 2 min then 3,3-diethoxyprop-1-ene (8.69 mL, 54.7 mmol) and tributylamine (8.83 mL, 36.5 mmol) were added. The vessel was sealed and the mixture heated at 125° C. for 16 h. The mixture was partitioned between ethyl acetate (200 mL) and saturated aqueous ammonium chloride (200 mL). The aqueous phase was extracted again with ethyl acetate. The pooled organic layer was washed with brine (2×150 mL), dried with magnesium sulfate, filtered, and concentrated in vacuo. The residue was purified by silica gel chromatography (120 g silica, 30-100% gradient of EtOAc/hexane) to provide ethyl 3-(5-carbamoyl-2-fluoro-3-nitrophenyl)propanoate (1.77 g, 5.42 mmol, 29.7% yield). $^1$H NMR (400 MHz, DMSO-$d_6$) δ ppm 8.48 (dd, J=6.7, 2.2 Hz, 1H), 8.18-8.33 (m, 2H), 7.71 (br. s., 1H), 4.05 (q, J=7.3 Hz, 2H), 2.94-3.06 (m, 2H), 2.73 (t, J=7.5 Hz, 2H), 1.15 (t, J=7.3 Hz, 3H). LCMS (m/z): 285.1 [M+H]$^+$.

Intermediate 25

2-Fluoro-1-((4-methoxybenzyl)oxy)-3-nitrobenzene

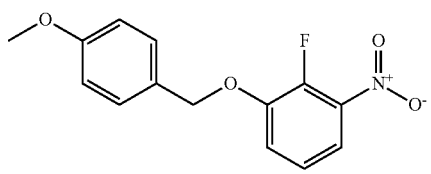 [SMILES: COc1ccc(COc2cccc([N+](=O)[O-])c2F)cc1]

To a brown solution of 2-fluoro-3-nitrophenol (4.75 g, 30.2 mmol) in DMF (40 mL) at room temperature was added cesium carbonate (10.84 g, 33.3 mmol) and 4-methoxybenzyl chloride (4.32 mL, 31.7 mmol). The mixture was stirred at room temperature for 16 h. Water (150 mL) was added to the vigorously stirred reaction mixture and stirred 10 min to produce a precipitate. The solids were filtered, rinsed with water, and dried to give 2-fluoro-1-((4-methoxybenzyl)oxy)-3-nitrobenzene (8.1 g, 28.1 mmol, 93% yield). $^1$H NMR (400 MHz, DMSO-$d_6$) δ ppm 7.63-7.75 (m, 2H), 7.42 (d, J=8.62 Hz, 2H), 7.36 (d, J=1.77 Hz, 1H), 6.92-7.02 (m, 2H), 5.21 (s, 2H), 3.77 (s, 3H). LCMS (m/z): no [M+H]$^+$ observed.

Intermediate 26

(2R,3S)-2,3-dimethoxybutane-1,4-diamine

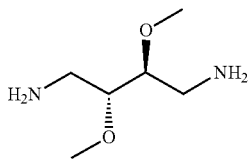

Step 1: dimethyl (2R,3S)-2,3-dimethoxysuccinate

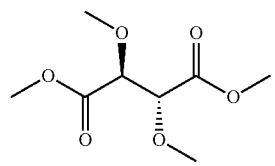

To the mixture of dimethyl (2R,3S)-2,3-dihydroxysuccinate (5.86 g, 32.9 mmol) and silver oxide (22.87 g, 99 mmol) was added iodomethane (41.1 mL, 658 mmol). The mixture was heated at 45° C. for 6 h and room temperature for 18 h. The mixture was filtered, washed with DCM and concentrated to give the title compound (5.8 g, 28.3 mmol, 86% yield) as clear oil which solidified upon storage. $^1$H NMR (400 MHz, METHANOL-$d_4$) δ ppm 4.26 (s, 2H) 3.76 (s, 6H) 3.46 (s, 6H).

Step 2: (2R,3S)-2,3-dimethoxybutane-1,4-diol

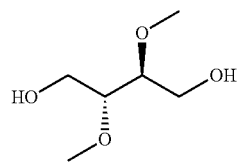

A solution of dimethyl (2R,3S)-2,3-dimethoxysuccinate (5.1 g, 24.73 mmol) in THF (30 mL) was added to the mixture of LAH (2.065 g, 54.4 mmol) in THF (150 mL) at 0° C. The mixture was warmed to room temperature for 2 h. The reaction was quenched with sat. sodium sulfate solution (9.1 mL). The mixture was filtered, dried with magnesium sulfate and concentrated to give the title compound (3.6 g, 24.0 mmol, 97% yield) as clear oil. $^1$H NMR (400 MHz, DMSO-$d_6$) δ ppm 4.51 (t, J=5.58 Hz, 2H) 3.51-3.59 (m, 2H) 3.38-3.45 (m, 2H) 3.32 (s, 6H) 3.19-3.26 (m, 2H).

Step 3: (2R,3S)-2,3-dimethoxybutane-1,4-diyl bis(4-methylbenzenesulfonate)

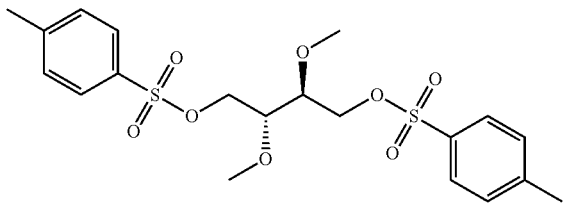

To a solution of (2R,3S)-2,3-dimethoxybutane-1,4-diol (3.3 g, 21.97 mmol) in pyridine (40 mL) at −78° C. was added TsCl (12.57 g, 65.9 mmol). The mixture was allowed to warm to room temperature and stirred for 18 h. Water (150 mL) was added and the mixture was cooled to 0° C. for 2 h. The resulting precipitate was filtered, rinsed with water and dried to give the title compound (7.52 g, 16.4 mmol, 74.6% yield) as white solid. $^1$H NMR (400 MHz, CHLOROFORM-d) δ ppm 7.69-7.86 (m, 4H) 7.35-7.44 (m, 4H) 4.08-4.33 (m, 4H) 3.33-3.45 (m, 2H) 3.25 (s, 6H) 2.49 (s, 6H).

Step 4: (2R,3S)-1,4-diazido-2,3-dimethoxybutane

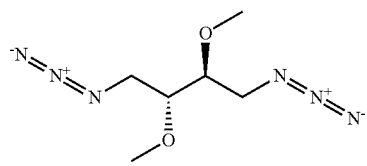

To a solution of (2R,3S)-2,3-dimethoxybutane-1,4-diyl bis(4-methylbenzenesulfonate) (7.52 g, 16.40 mmol) in DMF (40 mL) was added sodium azide (4.26 g, 65.6 mmol). The mixture was stirred at 80° C. for 18 h. The mixture was diluted with water (200 mL) and extracted with EtOAc (2×200 mL). The organic phase was washed with water (2×200 mL) and brine (100 mL), dried with magnesium sulfate and concentrated to give the title compound (3.16 g, 15.8 mmol, 96% yield) as a clear oil. $^1$H NMR (400 MHz, CHLOROFORM-d) δ ppm 3.60-3.68 (m, 2H) 3.48 (s, 6H) 3.37-3.45 (m, 4H).

Step 5: (2R,3S)-2,3-dimethoxybutane-1,4-diamine

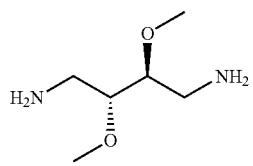

To a mixture of (2R,3S)-1,4-diazido-2,3-dimethoxybutane (3.16 g, 15.8 mmol) and palladium on carbon (0.672 g, 6.31 mmol) in methanol (30 mL) was added hydrogen (balloon). The mixture was stirred at room temperature for 60 h. After removal of hydrogen, the mixture was filtered through celite and concentrated to give the title compound (2.33 g, 15.7 mmol, 100% yield) as clear oil. $^1$H NMR (400 MHz, CHLOROFORM-d) δ ppm 3.49 (s, 6H) 3.25-3.35 (m, 2H) 2.83-2.96 (m, 4H).

Intermediate 27

((1S,2S)-cyclopropane-1,2-diyl)dimethanamine, 2 Hydrochloride

Step 1: (1S,2S)-cyclopropane-1,2-dicarboxamide

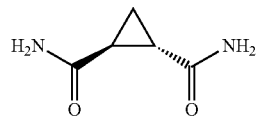

Into a 250-mL round-bottom flask was added diethyl (1S,2S)-cyclopropane-1,2-dicarboxylate (38 g, 204 mmol) and ammonium hydroxide solution (28% wt aqueous solution; 380 mL, 3035 mmol). The mixture was stirred at 25° C. for 48 h. The mixture was filtered, and the filter cake was subsequently washed with EtOAc (100 mL). The solid was dried under vacuum to obtained (1S,2S)-cyclopropane-1,2-dicarboxamide (14.5 g, 108 mmol, 53% yield) as a white solid. $^1$H NMR (300 MHz, DMSO-d$_6$) δ ppm 7.65 (s, 2H), 6.90 (s, 2H), 1.86 (m, 2H), 0.97 (m, 2H).

Step 2: di-tert-butyl (((1S,2S)-cyclopropane-1,2-diyl)bis(methylene))dicarbamate

Into a mixture of (1S,2S)-cyclopropane-1,2-dicarboxamide (14.5 g, 113 mmol) and THF (300 mL) at 0° C. was added LiAlH$_4$ (17.18 g, 453 mmol) batchwise. The mixture was then stirred at 25° C. for 48 h. The mixture was quenched by addition of crushed ice (200 g) at 0° C. The mixture was filtered, and the filtrate was used directly to the next step. To the filtrate was added LiOH (10.52 g, 4.39 mmol) and water (200 mL). Boc anhydride (56.1 mL, 242 mmol) was added and the mixture was stirred overnight at room temperature. The reaction mixture was then extracted three times with DCM (100 mL×3). The combined organic layer was dried with sodium sulfate, filtered, and concentrated under reduced pressure. The residue was purified by normal phase silica gel chromatography (80 g silica, 1:4 EtOAc/petroleum ether) to provide di-tert-butyl ((((1S,2S)-cyclopropane-1,2-diyl)bis(methylene))dicarbamate (10 g, 31.6 mmol, 29% yield over two steps) as a colorless oil. $^1$H NMR (300 MHz, Methanol-d$_4$) δ ppm 3.03 (m, 2H), 2.85 (m, 2H), 0.83 (m, 2H), 0.41 (m, 2H).

Step 3:
((1S,2S)-cyclopropane-1,2-diyl)dimethanamine, 2Hydrochloride

Into a 500-mL round-bottom flask was added di-tert-butyl ((((1S,2S)-cyclopropane-1,2-diyl)bis(methylene))dicarbamate (10 g, 33.3 mmol) and HCl (4 M in 1,4-dioxane, 100 mL, 400 mmol). After stirring at 25° C. for 30 min, the mixture was concentrated under reduced pressure. The residue was then dissolved in water (100 mL) and freeze-dried. ((1S,2S)-cyclopropane-1,2-diyl)dimethanamine, 2Hydrochloride (5.3 g, 29.1 mmol, 87% yield) was obtained as an off-white solid. $^1$H NMR (400 MHz, Methanol-d$_4$) δ ppm 3.05 (m, 2H), 2.81 (m, 2H), 1.27-1.18 (m, 2H), 0.87-0.79 (m, 2H). LCMS (m/z): 101.2 [M+H]$^+$, no UV peak observed.

Example 1

(E)-1-((E)-4-((Z)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide

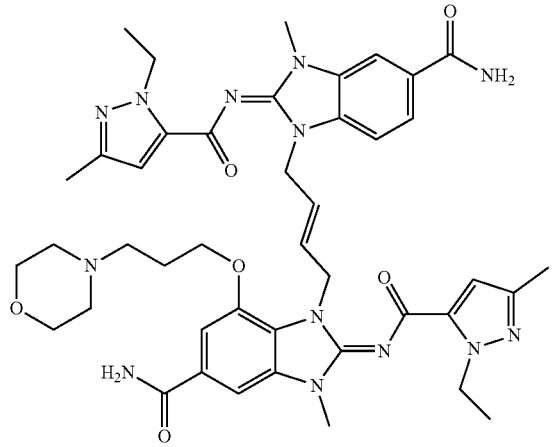 [SMILES: CCn1nc(C)cc1C(=O)/N=c1/n(C)c2cc(C(N)=O)ccc2n1C/C=C/Cn1/c(=N\C(=O)c2cc(C)nn2CC)n(C)c2cc(C(N)=O)cc(OCCCN3CCOCC3)c21]

Step 1: (E)-1-(4-((4-carbamoyl-2-(3-morpholinopropoxy)-6-nitrophenyl)amino)but-2-en-1-yl)-2-(1-ethyl-3-methyl-1H-pyrazole-5-carboxamido)-1H-benzo[d]imidazole-5-carboxamide

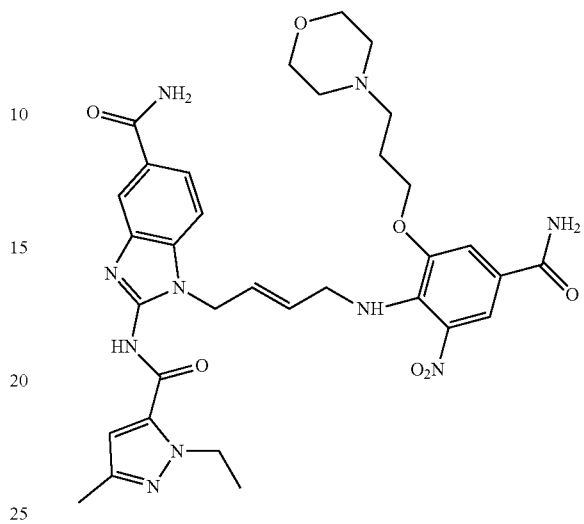

To a suspension of the (E)-1-(4-aminobut-2-en-1-yl)-2-(1-ethyl-3-methyl-1H-pyrazole-5-carboxamido)-1H-benzo[d]imidazole-5-carboxamide hydrochloride (535 mg, 1.280 mmol) in EtOH (5 mL) was added triethylamine (471 mg, 4.65 mmol) and 4-chloro-3-(3-morpholinopropoxy)-5-nitrobenzamide (400 mg, 1.164 mmol). The reaction vessel was sealed and heated at 120° C. for 20 h. Upon cooling, an orange solid precipitated out of the dark solution. The solid was washed with EtOAc and dried to provide (E)-1-(4-((4-carbamoyl-2-(3-morpholinopropoxy)-6-nitrophenyl)amino)but-2-en-1-yl)-2-(1-ethyl-3-methyl-1H-pyrazole-5-carboxamido)-1H-benzo[d]imidazole-5-carboxamide (457 mg, 0.664 mmol, 57.0% yield). The reaction was repeated 3 times to provide 1.37 g of title compound. LCMS m/z=689 [M+H]$^+$.

Step 2: (E)-1-(4-((2-amino-4-carbamoyl-6-(3-morpholinopropoxy)phenyl)amino)but-2-en-1-yl)-2-(1-ethyl-3-methyl-1H-pyrazole-5-carboxamido)-1H-benzo[d]imidazole-5-carboxamide

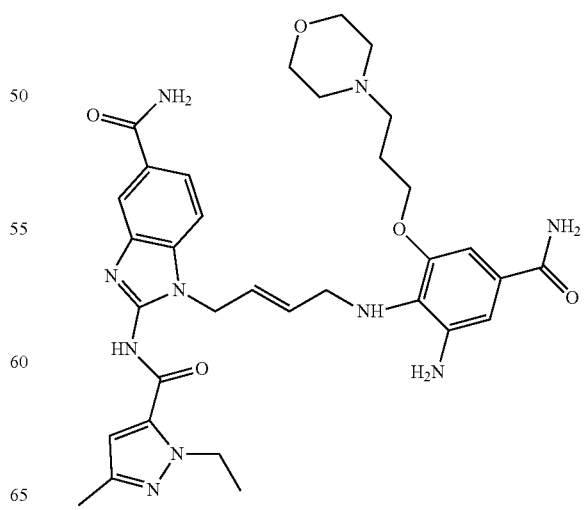

(E)-1-(4-((4-carbamoyl-2-(3-morpholinopropoxy)-6-nitrophenyl)amino)but-2-en-1-yl)-2-(1-ethyl-3-methyl-1H-pyrazole-5-carboxamido)-1H-benzo[d]imidazole-5-carboxamide (1.05 g, 1.525 mmol) was suspended in MeOH (16 mL) and 28% ammonium hydroxide (5.17 mL, 38.1 mmol). After 5 min stirring, a solution of sodium hydrosulfite (1.593 g, 9.15 mmol) in water (4.00 mL) was added and subsequently stirred at room temperature for 2 h.

EtOAc was added and the organic layer washed with water and brine. The organic phase was then dried and concentrated to afford crude (E)-1-(4-((2-amino-4-carbamoyl-6-(3-morpholinopropoxy)phenyl)amino)but-2-en-1-yl)-2-(1-ethyl-3-methyl-1H-pyrazole-5-carboxamido)-1H-benzo[d]imidazole-5-carboxamide (330 mg, 0.501 mmol, 32.9% yield) as an off-white solid. The crude material was used without further purification. LCMS m/z=659 [M+H]$^+$.

Step 3: (E)-2-amino-1-(4-(5-carbamoyl-2-(1-ethyl-3-methyl-1H-pyrazole-5-carboxamido)-1H-benzo[d]imidazol-1-yl)but-2-en-1-yl)-7-(3-morpholinopropoxy)-1H-benzo[d]imidazole-5-carboxamide

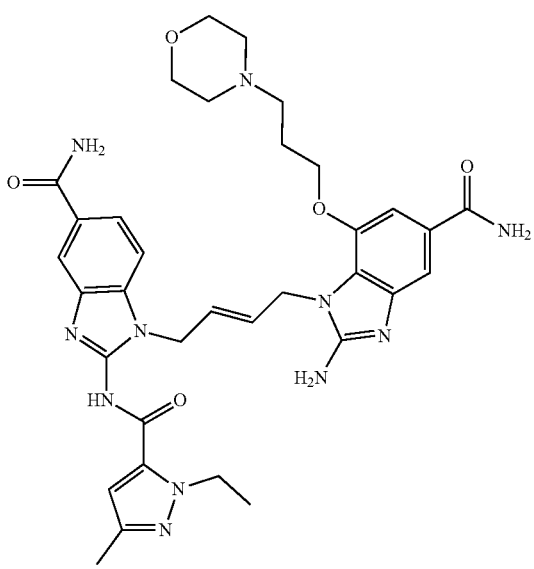 [SMILES: CCn1nc(C)cc1C(=O)Nc1nc2cc(C(N)=O)ccc2n1C/C=C/Cn1c(N)nc2cc(C(N)=O)cc(OCCCN3CCOCC3)c21]

To a solution of (E)-1-(4-((2-amino-4-carbamoyl-6-(3-morpholinopropoxy)phenyl)amino)but-2-en-1-yl)-2-(1-ethyl-3-methyl-1H-pyrazole-5-carboxamido)-1H-benzo[d]imidazole-5-carboxamide (330 mg, 0.501 mmol) in MeOH (15 mL) was added cyanogen bromide (159 mg, 1.503 mmol) and the reaction mixture was stirred at room temperature for 3 h. Precipitation of product was achieved by addition of EtOAc and subsequent stirring for 1 h. The solid was filtered, washed with EtOAc and dried to provide as (E)-2-amino-1-(4-(5-carbamoyl-2-(1-ethyl-3-methyl-1H-pyrazole-5-carboxamido)-1H-benzo[d]imidazol-1-yl)but-2-en-1-yl)-7-(3-morpholinopropoxy)-1H-benzo[d]imidazole-5-carboxamide (284 mg, 0.416 mmol, 83% yield) as a light brown solid. The material was used without further purification. LCMS m/z=684 [M+H]$^+$.

Step 4: (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide

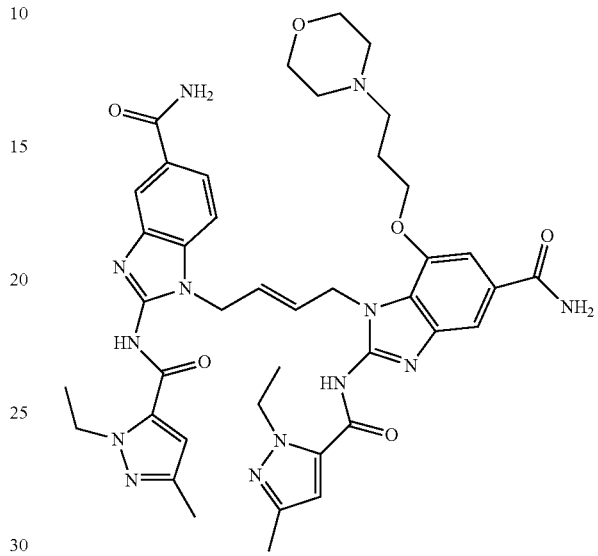

To a suspension of (E)-2-amino-1-(4-(5-carbamoyl-2-(1-ethyl-3-methyl-1H-pyrazole-5-carboxamido)-1H-benzo[d]imidazol-1-yl)but-2-en-1-yl)-7-(3-morpholinopropoxy)-1H-benzo[d]imidazole-5-carboxamide (260 mg, 0.380 mmol) in DMF (4 mL) was added at room temperature a solution of 1-ethyl-3-methyl-1H-pyrazole-5-carboxylic acid (117 mg, 0.760 mmol) and 1H-benzo[d][1,2,3]triazol-1-ol hydrate (58.2 mg, 0.380 mmol) and 2-(3H-[1,2,3]triazolo[4,5-b]pyridin-3-yl)-1,1,3,3-tetramethylisouronium hexafluorophosphate(V) (289 mg, 0.760 mmol) and triethylamine (0.212 mL, 1.521 mmol) in DMF (4 mL). The mixture was stirred at room temperature overnight. Water (10 mL) was then added and the resulting cloudy solution was put in refrigerator for 3 h. The resulting precipitate was filtered (180 mg) and combined with 80 mg additional crude solid from an earlier reaction. The crude product was further purified by silica gel chromatography (ISCO 24 g column, gradient 0-35% of MeOH in DCM) to provide after removal of solvents (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide (140 mg, 0.171 mmol). H NMR (METHANOL-d$_4$, 600 MHz): δ ppm 7.96 (s, 1H), 7.71 (dd, J=8.3, 1.6 Hz, 1H), 7.56 (s, 1H), 7.35 (d, J=8.4 Hz, 1H), 7.27 (s, 1H), 6.62 (s, 1H), 6.55 (s, 1H), 5.95 (dt, J=15.5, 5.1 Hz, 1H), 5.76-5.83 (m, 1H), 5.06 (br d, J=4.6 Hz, 2H), 4.86 (br d, J=5.3 Hz, 2H), 4.63 (s, 2H), 4.56 (q, J=7.0 Hz, 2H), 3.99 (t, J=6.1 Hz, 2H), 3.64 (br t, J=4.2 Hz, 4H), 2.43-2.48 (m, 2H), 2.40 (br s, 4H), 2.21 (s, 3H), 2.19 (s, 3H), 1.75-1.81 (m, 2H), 1.37 (t, J=7.1 Hz, 3H), 1.32 (t, J=7.2 Hz, 3H). LCMS m/z=820.9 [M+H]$^+$.

Step 5: (E)-1-((E)-4-((Z)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide The compound prepared by the above process may exist in a tautomeric/isomeric e.g., (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide

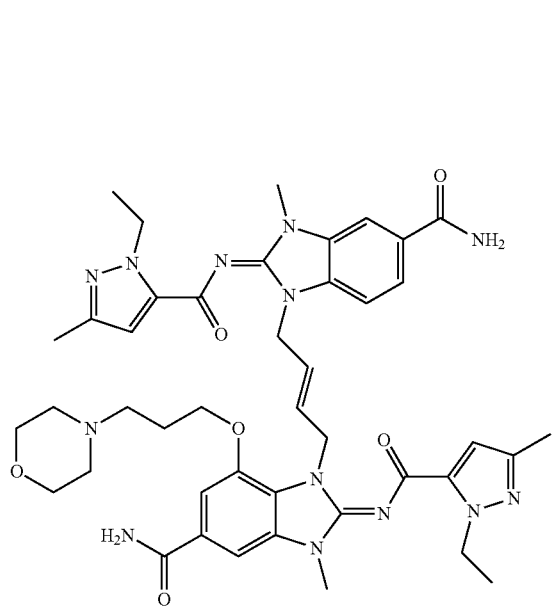 [SMILES: CCn1nc(C)cc1C(=O)/N=c1/n(C)c2cc(C(N)=O)ccc2n1C/C=C/Cn1/c(=N\C(=O)c2cc(C)nn2CC)n(C)c2cc(C(N)=O)cc(OCCCN3CCOCC3)c21]

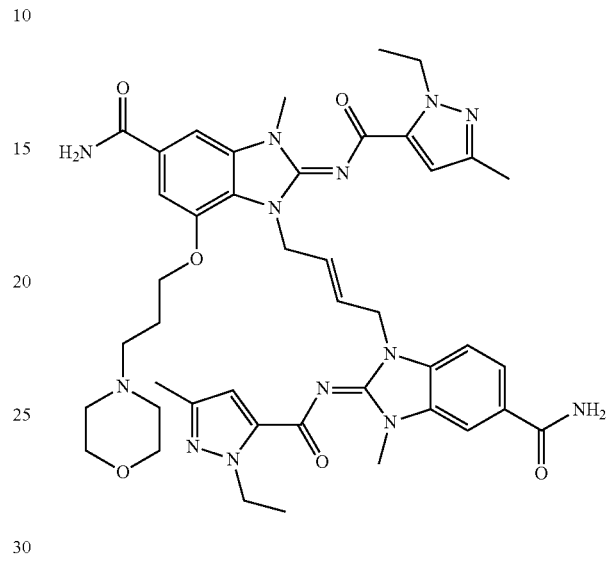

Example 2

(E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)butyl)-2-((1-ethyl-3-methyl-1H-pyrazole-5-carbonyl)imino)-7-methoxy-3-methyl-2,3-dihydro-1H-benzo[d]imidazole-5-carboxamide To a suspension of (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide (52 mg, 0.063 mmol) in DMF (2 mL) was added cesium carbonate (62.0 mg, 0.190 mmol) and methyl iodide (9.91 μl, 0.159 mmol). The reaction mixture was stirred at room temperature for 12 h. Solvent was evaporated and the residue was purified by silica gel chromatography (gradient of 0-25% of MeOH/DCM, silica gel column 12 g) to afford the clean product as (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide (44 mg, 0.052 mmol, 82% yield). $^1$H NMR (DMSO-$d_6$, 600 MHz): δ ppm 8.07 (br s, 1H), 7.80 (br d, J=8.3 Hz, 1H), 7.74 (br s, 1H), 7.48 (br d, J=8.4 Hz, 1H), 7.41 (s, 1H), 6.29-6.44 (m, 2H), 5.83-5.99 (m, 1H), 5.60-5.76 (m, 1H), 4.81-4.94 (m, 2H), 4.75 (br d, J=5.1 Hz, 2H), 4.38-4.55 (m, 4H), 4.06 (br s, 2H), 3.54 (br s, 3H), 3.45-3.59 (m, 7H), 2.25-2.30 (m, 2H), 2.15-2.37 (m, 4H), 2.11 (br d, J=7.0 Hz, 6H), 1.72 (br s, 2H), 1.19-1.24 (m, 3H), 1.14-1.26 (m, 3H). LCMS m/z=848 [M+H]$^+$.

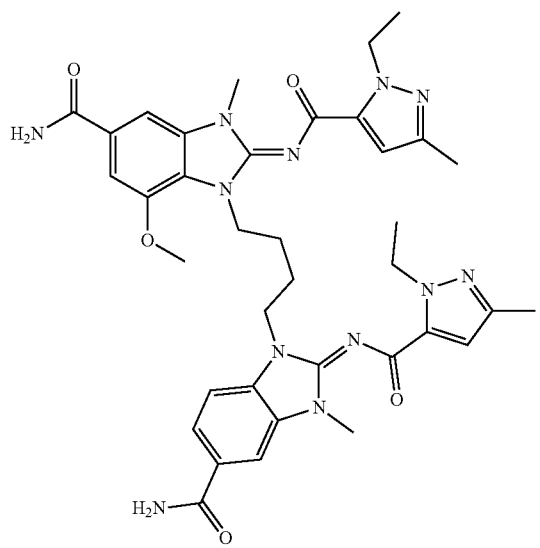 [SMILES: CCn1nc(C)cc1C(=O)/N=c1\n(C)c2cc(C(N)=O)ccc2n1CCCCn1/c(=N/C(=O)c2cc(C)nn2CC)n(C)c2cc(C(N)=O)cc(OC)c21]

Step 1: tert-butyl (4-((4-carbamoyl-2-nitrophenyl)amino)butyl)carbamate

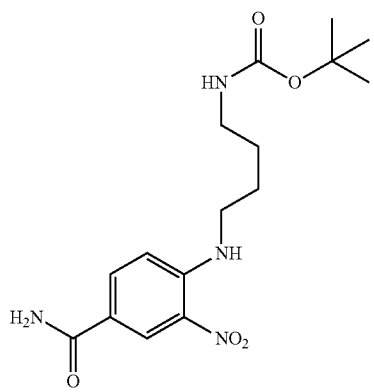 [SMILES: CC(C)(C)OC(=O)NCCCCNc1ccc(C(N)=O)cc1[N+](=O)[O-]]

A mixture of tert-butyl (4-aminobutyl)carbamate (5.00 g, 26.6 mmol), 4-fluoro-3-nitrobenzamide (4.89 g, 26.6 mmol), and K$_2$CO$_3$ (4.04 g, 29.2 mmol) in DMSO (25 mL) was stirred at 70° C. for 2 h. The reaction was cooled to room temperature and slowly diluted with 125 mL of water via addition funnel. The resulting solid was isolated by filtration, dried, and placed in a vacuum oven at 56° C. for 3 days to give the title compound (9.2 g, 26.1 mmol, 98% yield) as a yellow solid. $^1$H NMR (400 MHz, DMSO-d$_6$) δ ppm 8.67 (d, J=2.02 Hz, 1H) 8.40 (t, J=5.43 Hz, 1H) 8.01 (d, J=6.82 Hz, 2H) 7.30 (br. s., 1H) 7.12 (d, J=9.09 Hz, 1H) 6.87 (br. s., 1H) 3.42 (q, J=6.57 Hz, 2H) 2.91-3.01 (m, 2H) 1.60 (d, J=6.57 Hz, 2H) 1.43-1.54 (m, 2H) 1.38 (s, 9H). LCMS [M+H]$^+$=353.

Step 2: tert-butyl (4-((2-amino-4-carbamoylphenyl)amino)butyl)carbamate

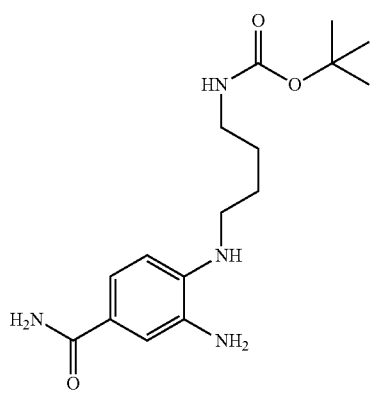 [SMILES: CC(C)(C)OC(=O)NCCCCNc1ccc(C(N)=O)cc1N]

A 500 mL round bottomed flask was charged with tert-butyl (4-((4-carbamoyl-2-nitrophenyl)amino)butyl)carbamate (9.2 g, 26.1 mmol), 10% Pd/C (0.920 g, 8.64 mmol) (Degussa wet type), EtOH (100 mL) and MeOH (100 mL). The flask was evacuated and placed under a balloon of hydrogen with stirring. A condenser was placed on top of the flask and the hydrogen balloon was placed atop the condenser. The mixture was stirred at room temperature for 20 h, then the flask was evacuated and the suspension was filtered through a bed of Celite using EtOH to aid in rinsing. The filtrate was concentrated in vacuo and placed under high vacuum to give the title compound (8.4 g, 26.1 mmol, 100% yield) as a black solid. $^1$H NMR (400 MHz, DMSO-d$_6$) δ ppm 7.44 (br. s., 1H) 7.04-7.15 (m, 2H) 6.85 (t, J=5.43 Hz, 1H) 6.74 (br. s., 1H) 6.37 (d, J=8.08 Hz, 1H) 4.89 (t, J=5.18 Hz, 1H) 4.60 (br. s., 2H) 3.07 (q, J=6.48 Hz, 2H) 2.97 (q, J=6.40 Hz, 2H) 1.45-1.64 (m, 4H) 1.39 (s, 9H). LCMS [M+H]$^+$=323.1

Step 3: tert-butyl (4-(2-amino-5-carbamoyl-1H-benzo[d]imidazol-1-yl)butyl)carbamate, Hydrobromide

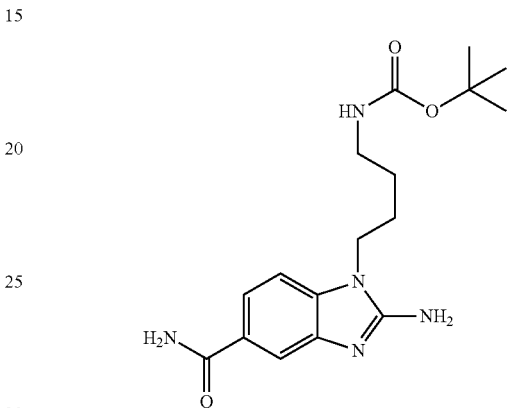

tert-Butyl (4-((2-amino-4-carbamoylphenyl)amino)butyl)carbamate (8.40 g, 26.1 mmol) was dissolved in MeOH (110 mL) and a solution of 5 M cyanogen bromide in CH$_3$CN (5.73 mL, 28.7 mmol) was added via syringe. The dark reaction was capped and stirred for 15 h at room temperature. The reaction was concentrated in vacuo and placed under high vacuum to give the title compound (11.17 g, 26.1 mmol, 100% yield) as a dark solid. $^1$H NMR (400 MHz, DMSO-d$_6$) b ppm 12.85 (br. s., 1H) 8.74 (br. s., 2H) 8.08 (br. s., 1H) 7.80-7.90 (m, 2H) 7.64 (d, J=8.34 Hz, 1H) 7.44 (br. s., 1H) 6.89 (t, J=5.56 Hz, 1H) 4.15 (t, J=7.20 Hz, 2H) 2.96 (q, J=6.32 Hz, 2H) 1.66 (d, J=7.07 Hz, 2H) 1.42-1.50 (m, 2H) 1.38 (s, 9H). LCMS [M+H]$^+$=348.1

Step 4: tert-butyl (4-(5-carbamoyl-2-(1-ethyl-3-methyl-1H-pyrazole-5-carboxamido)-1H-benzo[d]imidazol-1-yl)butyl)carbamate

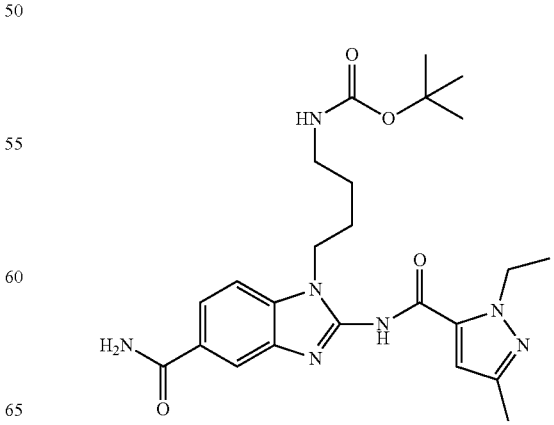

A mixture of tert-butyl (4-(2-amino-5-carbamoyl-1H-benzo[d]imidazol-1-yl)butyl)carbamate, hydrobromide (11.17 g, 26.1 mmol), 1-ethyl-3-methyl-1H-pyrazole-5-carboxylic acid (4.82 g, 31.3 mmol), HATU (11.90 g, 31.3 mmol), DIPEA (18.22 mL, 104 mmol), and HOBt (1.997 g, 13.04 mmol) in DMF (100 mL) was stirred at room temperature for 21 h. The reaction was diluted with 300 mL of water and 300 mL of EtOAc, transferred to a separatory funnel, and the layers were separated, and the aqueous layer was extracted with EtOAc (2×150 mL). The combined EtOAc layers were washed with saturated $NH_4Cl$ (2×200 mL), water (1×200 mL), and brine (2×200 mL). The organic layer was dried over $Na_2SO_4$, filtered, concentrated in vacuo, and placed under high vacuum. The solid was purified via chromatography on silica gel (ISCO® Combiflash, 0-20% MeOH: DCM, 330 g column, loaded in 50 mL of DCM). The desired fractions were combined, concentrated in vacuo, and placed under high vacuum to give the title compound as a purple solid, (9.53 g, 19.71 mmol, 76% yield). $^1$H NMR (400 MHz, DMSO-$d_6$) δ ppm 12.85 (s, 1H) 8.01 (br. s., 2H) 7.81 (d, J=8.34 Hz, 1H) 7.59 (d, J=8.34 Hz, 1H) 7.36 (br. s., 1H) 6.80-6.86 (m, 1H) 6.68 (s, 1H) 4.64 (q, J=6.82 Hz, 2H) 4.23 (t, J=6.44 Hz, 2H) 2.98 (d, J=5.81 Hz, 2H) 2.19 (s, 3H) 1.76 (d, J=6.57 Hz, 2H) 1.40-1.48 (m, 2H) 1.30-1.40 (m, 13H). LCMS [M+H]$^+$=484.3

Step 5: 1-(4-aminobutyl)-2-(1-ethyl-3-methyl-1H-pyrazole-5-carboxamido)-1H-benzo[d]imidazole-5-carboxamide, 2 Hydrochloride

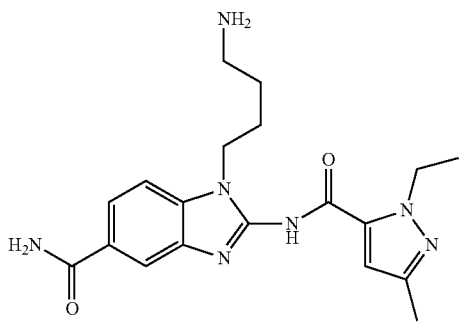 [SMILES: CCn1nc(C)cc1C(=O)Nc1nc2cc(C(N)=O)ccc2n1CCCCN]

An ice-cooled 500 mL round bottomed flask containing tert-butyl (4-(5-carbamoyl-2-(1-ethyl-3-methyl-1H-pyrazole-5-carboxamido)-1H-benzo[d]imidazol-1-yl)butyl)carbamate (9.53 g, 19.71 mmol) was treated with 4 M HCl in 1,4-dioxane (42.0 mL, 168 mmol). The ice bath was removed and the purple slurry was stirred at room temperature for 2.5 h. The reaction was then concentrated in vacuo, placed under high vacuum, and the resulting solid was placed in a vacuum oven at 50° C. for 15 h and cooled under high vacuum to afford impure title compound as a grey solid which also contained 1,4-dioxane (11.89 grams, assumed 19.7 mmol, 100% yield). Material was used as is without further purification. $^1$H NMR (400 MHz, DMSO-$d_6$) b ppm 12.91 (br. s, 1H) 8.03 (d, J=1.26 Hz, 2H) 7.77-7.87 (m, 4H) 7.62 (d, J=8.34 Hz, 1H) 7.38 (br. s., 1H) 6.70 (s, 1H) 6-5 (br. s, 1H), 4.63 (q, J=7.07 Hz, 2H) 4.28 (t, J=6.57 Hz, 2H) 2.77-2.87 (m, 2H) 2.20 (s, 3H) 1.81-1.91 (m, 2H) 1.52-1.60 (m, 2H) 1.38 (t, J=7.07 Hz, 3H). LCMS [M+H]$^+$=384.2

Step 6: Methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate

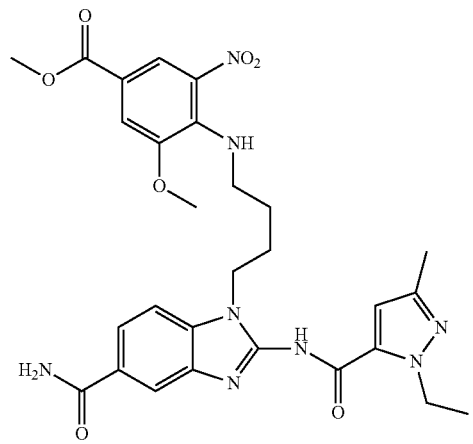

A 250 mL 3-neck round bottomed flask equipped with a condenser, a large stir bar, and an internal thermometer was charged with 1-(4-aminobutyl)-2-(1-ethyl-3-methyl-1H-pyrazole-5-carboxamido)-1H-benzo[d]imidazole-5-carboxamide, 2 hydrochloride (9.38 g, 20.55 mmol) and methyl 4-chloro-3-methoxy-5-nitrobenzoate (5.048 g, 20.55 mmol). DMSO (50 mL) was added followed by DIPEA (17.95 mL, 103 mmol) and the dark suspension was heated at 100° C. for approximately 24 h, cooled, and added dropwise to 500 mL of stirred water. After the addition was complete, the resulting orange suspension was stirred for 20 min and filtered. The isolated orange-red paste was washed with water and hexanes, dried in the Buchner funnel, and then in a vacuum oven at 56° C. for 20 h. The reddish solid was then triturated with $Et_2O$ (60 mL) and isolated by filtration. The trituration and filtration was repeated. The resulting solid was placed in a vacuum oven at 56° C. for 3 days to give afford the title compound (11.17 g, 18.85 mmol, 92% yield) as a reddish solid. $^1$H NMR (400 MHz, DMSO-$d_6$) δ ppm 12.78 (br. s., 1H) 8.12 (s, 1H) 7.99 (s, 1H) 7.93 (d, J=7.53 Hz, 2H) 7.79 (d, J=8.28 Hz, 1H) 7.53 (d, J=7.78 Hz, 1H) 7.36 (s, 1H) 7.31 (br. s., 1H) 6.60 (s, 1H) 4.60 (d, J=7.03 Hz, 2H) 4.23 (br. s., 2H) 3.84 (s, 3H) 3.80 (s, 3H) 3.53 (d, J=5.77 Hz, 2H) 2.15 (s, 3H) 1.82 (br. s., 2H) 1.62 (br. s., 2H) 1.35 (t, J=7.03 Hz, 3H). LCMS [M+H]$^+$=711.6

173

Step 7: Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate

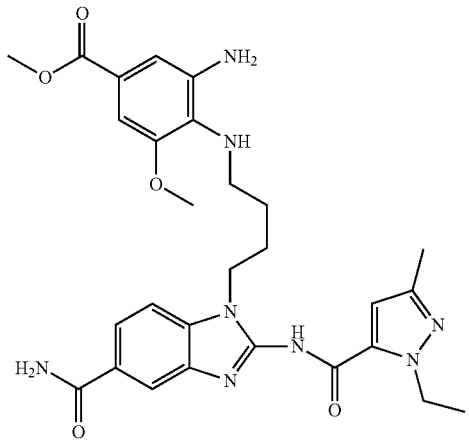 [SMILES: CCn1nc(C)cc1C(=O)Nc1nc2cc(C(N)=O)ccc2n1CCCCNc1c(OC)cc(C(=O)OC)cc1[N+](=O)[O-]]

Methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate (5.0 g, 8.44 mmol) was mostly dissolved in DMF (50 mL) with stirring at room temperature in a 250 mL round bottomed flask. Raney nickel (Raney 2800 nickel in water, ca. 10 mL of slurry, Aldrich) was added and a condenser was added atop the flask. A 3-way stopcock adapter with an attached hydrogen balloon was placed on top of the condenser and the setup was evacuated, filled with hydrogen, evacuated, and finally filled with hydrogen. The reaction was heated at 70° C. for 7 h. An additional 8 mL of Raney nickel slurry were added and the reaction was heated at 70° C. for 14 h. The reaction was cooled and filtered through Celite while washing with DMF. The filtrate, a solution of about 100 mL DMF and 20 mL water from the Raney nickel slurry, containing the desired product was used as a solution directly in the next reaction. Assumed quantitative yield. LCMS [M+H]$^+$=563.4

Step 8: Methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, Hydrobromide

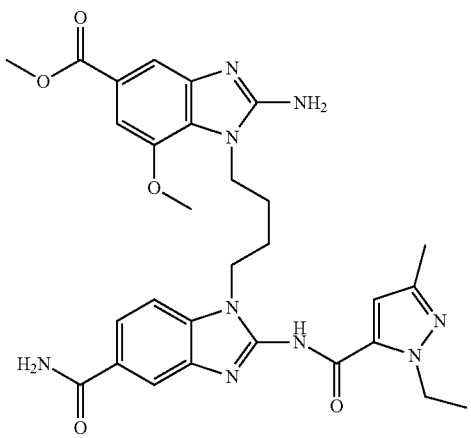 [SMILES: CCn1nc(C)cc1C(=O)Nc1nc2cc(C(N)=O)ccc2n1CCCCn1c(N)nc2cc(C(=O)OC)cc(OC)c21]

174

Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate (solution in DMF/water from previous step) was treated with 5 M cyanogen bromide in CH$_3$CN (1.875 mL, 9.37 mmol) and the resulting solution was stirred at room temperature for 22 h. The reaction was concentrated in vacuo and placed under high vacuum to give a brown semi-solid. The semi-solid was triturated with EtOAc, stirred vigorously for 30 min, and the resulting solid was isolated by filtration and dried in a Buchner funnel to provide impure title product as a tan solid (5.08 g). This impure material was used without purification. LCMS [M+H]$^+$=588.5.

Step 9: Methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate

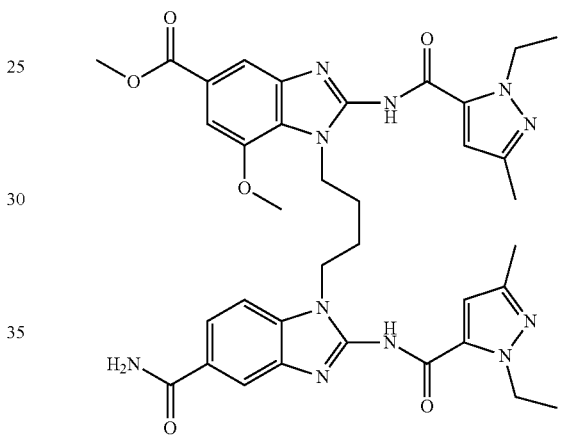

A mixture of methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, hydrobromide (5.073 g, 7.59 mmol), 1-ethyl-3-methyl-1H-pyrazole-5-carboxylic acid (1.287 g, 8.35 mmol), HATU (3.46 g, 9.11 mmol), and DIPEA (3.98 mL, 22.76 mmol) in DMF (30 mL) was stirred at room temperature for 17 h. The reaction was concentrated in vacuo then the resulting residue was triturated with water (100 mL) and stirred for 30 min. The resulting suspension was filtered and partially dried in a Buchner funnel to give a dark tan solid. The solid was mostly dissolved in 150 mL of 10% IPA:chloroform, diluted with water and filtered. The filtrate layers were then separated and the organic layer was dried over Na$_2$SO$_4$, filtered, concentrated, and placed under high vacuum to give a tan solid. The solid was triturated with warm 10% IPA: chloroform (100 mL) and filtered. The filtrate layers were separated, the organic layer was dried over Na$_2$SO$_4$, filtered, added to the original tan solid, concentrated in vacuo and placed under high vacuum. The solid was purified via chromatography on silica gel (Biotage® Isolera, 120 gm Gold column, 0-10% MeOH: DCM over 30 min, loaded as a solution in DCM/MeOH). The desired product fractions were combined, concentrated, and placed under high vacuum to give a light tan solid. The solid was triturated with DCM (50 mL) and isolated by filtration, and placed in a vacuum oven at 56° C. for 30 h to provide methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate as a white solid (1.0 g, 1.4 mmol, 18% yield). $^1$H NMR (400 MHz, DMSO-$d_6$) δ ppm 12.89 (s, 1H) 12.82 (s, 1H) 7.90-8.01 (m, 2H) 7.70-7.81 (m, 2H) 7.53 (d, J=8.28 Hz, 1H) 7.30-7.40 (m, 2H) 6.59 (d, J=5.02 Hz, 2H) 4.50-4.64 (m, 4H) 4.38 (br. s., 2H) 4.27 (br. s., 2H) 3.87 (d, J=3.76 Hz, 6H) 2.10 (s, 6H) 1.86 (br. s., 4H) 1.23-1.39 (m, 6H). LCMS [M+H]$^+$=724.5.

Step 10: 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylic Acid Step 11: 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide

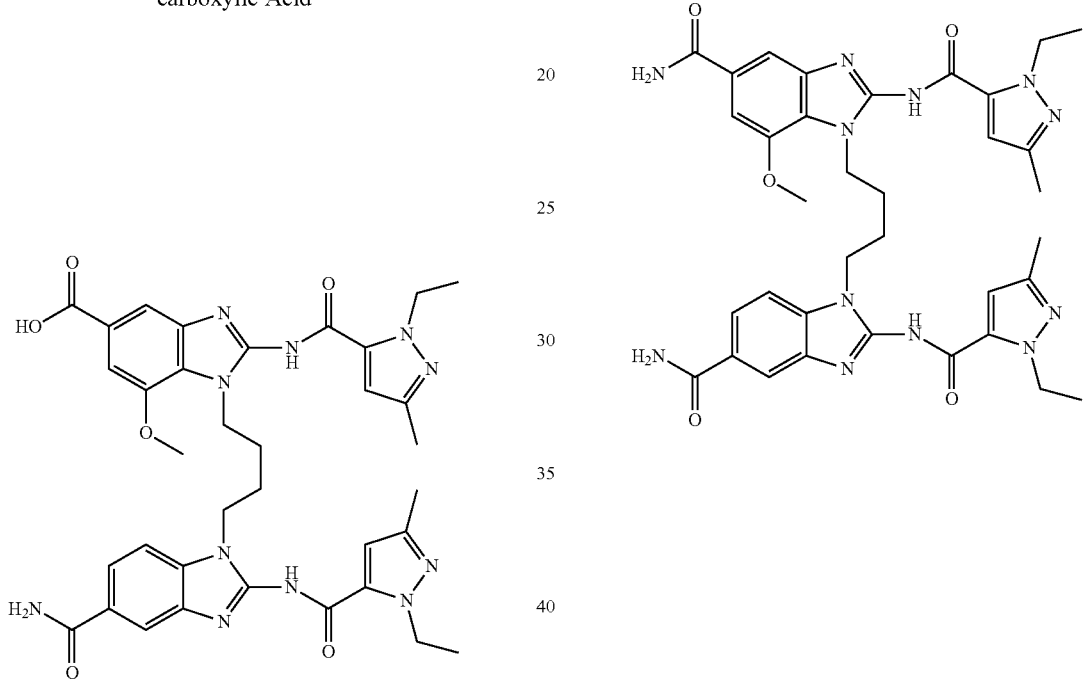

To a suspension of methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylate (550 mg, 0.760 mmol) in MeOH (11 mL) and water (11 mL) was added NaOH (304 mg, 7.60 mmol). The reaction was stirred at room temperature overnight. The MeOH was removed in vacuo and the resulting solution was treated with 1 N HCl until pH ~3. The resulting slurry was filtered and the filtercake was dried in a vacuum oven to afford 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylic acid (650 mg, 0.687 mmol, 90% yield) as white solid. The compound was used for next step without further purification. LCMS m/z=710 [M+H]$^+$.

To a solution of 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxylic acid (320 mg, 0.338 mmol) and HATU (154 mg, 0.406 mmol) in DMF (3.381 mL) was added DIEA (295 μL, 1.691 mmol). After 20 min, ammonium chloride (54.3 mg, 1.014 mmol) was added to the reaction mixture and the reaction was stirred at room temperature for 3 days. Additional HATU (50 mg, 0.132 mmol) and DIEA (58.9 μl, 0.338 mmol) were added. The reaction was stirred for 10 min at room temperature and ammonium chloride (18.26 mg, 0.338 mmol) was added. To drive reaction to completion, HOBt hydrate (51.7 mg, 0.338 mmol) was added and the reaction was stirred at room temperature for 90 min. The reaction was dry-loaded onto silica gel and purified by silica gel chromatography (ISCO-Rf 12 g column, gradient 0%-30% MeOH/DCM) to afford 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide (175 mg, 0.244 mmol, 72.3% yield) as a white solid. LCMS m/z=709 [M+H]$^+$.

Step 12: (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)butyl)-2-((1-ethyl-3-methyl-1H-pyrazole-5-carbonyl)imino)-7-methoxy-3-methyl-2,3-dihydro-1H-benzo[d]imidazole-5-carboxamide

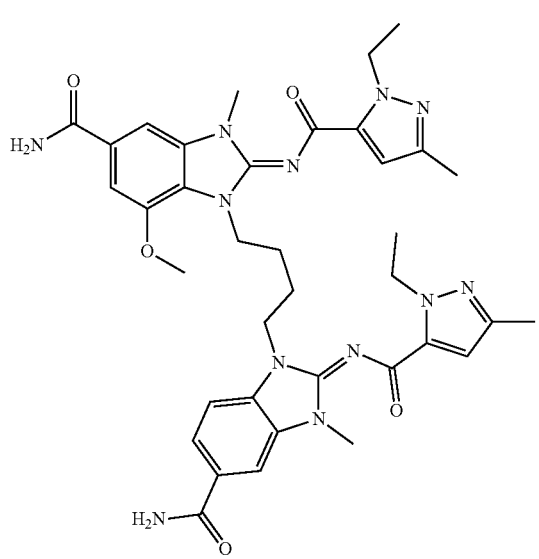 [SMILES: CCn1nc(C)cc1C(=O)/N=c1\n(C)c2cc(C(N)=O)ccc2n1CCCCn1/c(=N/C(=O)c2cc(C)nn2CC)n(C)c2cc(C(N)=O)cc(OC)c21]

To a suspension of 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-7-methoxy-1H-benzo[d]imidazole-5-carboxamide (100 mg, 0.141 mmol) in DMF (4 mL) was added cesium carbonate (138 mg, 0.423 mmol) and methyl iodide (50.1 mg, 0.353 mmol, 100 uL of a stock solution (220 uL methyl iodide in 780 uL DMF). The reaction was stirred at room temperature for 2 h, dry-loaded onto silica gel and purified by silica gel chromatography (ISCO-Rf, 12 g column, gradient 0%-30% MeOH/DCM) to afford 100 mg solid (~93% pure by LCMS). The resulting residue (100 mg) was dissolved in MeOH, dry-loaded onto silica gel and re-purified (ISCO-Rf, 12 g column, gradient 0%-20% MeOH/DCM). Pure fractions were pooled and concentrated to dryness to afford (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)butyl)-2-((1-ethyl-3-methyl-1H-pyrazole-5-carbonyl)imino)-7-methoxy-3-methyl-2,3-dihydro-1H-benzo[d]imidazole-5-carboxamide (33 mg, 0.044 mmol, 31.4% yield). $^1$H NMR (400 MHz, DMSO-$d_6$) δ ppm 7.98-8.13 (m, 3H) 7.84 (dd, J=8.36, 1.52 Hz, 1H) 7.69 (d, J=1.01 Hz, 1H) 7.58 (d, J=8.62 Hz, 1H) 7.47 (d, J=14.19 Hz, 2H) 7.42 (s, 1H) 6.46 (d, J=6.84 Hz, 2H) 4.42-4.55 (m, 4H) 4.11-4.28 (m, 4H) 3.83 (s, 3H) 3.51 (s, 3H) 3.47 (s, 3H) 2.12 (s, 6H) 1.74 (br. s., 4H) 1.24 (td, J=7.10, 1.52 Hz, 6H). LCMS m/z=737 [M+H]$^+$.

Example 3

(5aE,21E)-8-ethyl-5,10,18,22-tetramethyl-7,20-dioxo-5,7,8,11,12,13,14,15,20,22,28,29,30,31-tetradecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide

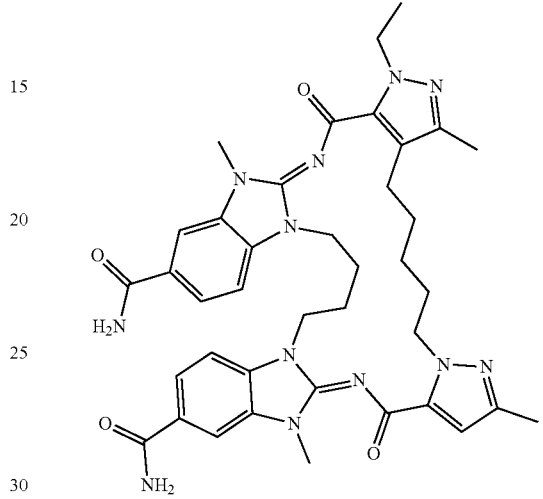

Step 1: ethyl 3-methyl-1-(5-(trimethylsilyl)pent-4-yn-1-yl)-1H-pyrazole-5-carboxylate

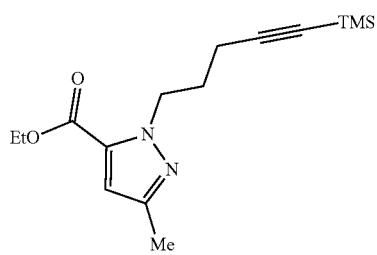 [SMILES: CCOC(=O)c1cc(C)nn1CCCC#C[Si](C)(C)C]

A mixture of ethyl 3-methyl-1H-pyrazole-5-carboxylate (22 g, 143 mmol), (5-chloropent-1-yn-1-yl)trimethylsilane (24.94 g, 143 mmol), $K_2CO_3$ (39.4 g, 285 mmol), and DMF (4 mL) was stirred at 60° C. overnight under a nitrogen gas atmosphere. The mixture was then dissolved in DCM and washed with water. The organic phase was dried over anhydrous $Na_2SO_4$, filtered, concentrated under reduced pressure, and purified by column chromatography on silica gel (petroleum ether/EtOAc=10:1) to afford ethyl 3-methyl-1-(5-(trimethylsilyl)pent-4-yn-1-yl)-1H-pyrazole-5-carboxylate (12.5 g, 42.7 mmol, 30% yield) as a colorless oil. LCMS [M+H]$^+$=293.

Step 2: ethyl 3-methyl-1-(pent-4-yn-1-yl)-1H-pyrazole-5-carboxylate

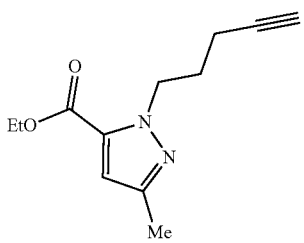 [SMILES: C#CCCCn1nc(C)cc1C(=O)OCC]

A mixture of ethyl 3-methyl-1-(5-(trimethylsilyl)pent-4-yn-1-yl)-1H-pyrazole-5-carboxylate (37.7 g, 129 mmol), $K_2CO_3$ (44.5 g, 322 mmol), and EtOH (800 mL) was stirred at room temperature overnight. The mixture was then filtered and the filtrate was concentrated under reduced pressure. The residue was dissolved in DCM, washed with water, dried over anhydrous $Na_2SO_4$, filtered, and concentrated under reduced pressure to afford ethyl 3-methyl-1-(pent-4-yn-1-yl)-1H-pyrazole-5-carboxylate (20 g, 91 mmol, 70.4% yield) as a colorless oil. LCMS $[M+H]^+$=221.

Step 3: benzyl 1-ethyl-3-methyl-1H-pyrazole-5-carboxylate

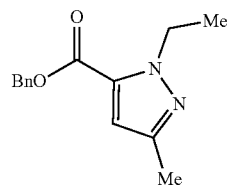 [SMILES: CCn1nc(C)cc1C(=O)OCc1ccccc1]

A mixture of 1-ethyl-3-methyl-1H-pyrazole-5-carboxylic acid (20 g, 130 mmol), (bromomethyl)benzene (22.2 g, 130 mmol), $K_2CO_3$ (26.9 g, 195 mmol), and DMF (200 mL) was stirred at 60° C. overnight. The mixture was then dissolved in DCM, washed with water, dried over anhydrous $Na_2SO_4$, filtered, concentrated under reduced pressure, and purified by column chromatography on silica gel (petroleum ether/EtOAc=10:1) to afford benzyl 1-ethyl-3-methyl-pyrazole-5-carboxylate (31.4 g, 129 mmol, 99% yield) as a colorless oil. LCMS $[M+H]^+$=245.

Step 4: benzyl 1-ethyl-4-iodo-3-methyl-1H-pyrazole-5-carboxylate

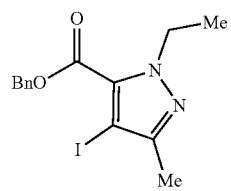 [SMILES: CCn1nc(C)c(I)c1C(=O)OCc1ccccc1]

A mixture of benzyl 1-ethyl-3-methyl-1H-pyrazole-5-carboxylate (31.6 g, 129 mmol), 1-iodopyrrolidine-2,5-dione (34.9 g, 155 mmol) and DMF (400 mL) was stirred at 90° C. for 2 days. The mixture was then allowed to cool to room temperature, dissolved in DCM, and washed with a saturated aqueous sodium thiosulfate solution. The organic layer was dried over anhydrous $Na_2SO_4$, filtered, concentrated under reduced pressure, and purified by column chromatography (petroleum ether/EtOAc=10:1) to afford benzyl 1-ethyl-4-iodo-3-methyl-1H-pyrazole-5-carboxylate (42.6 g, 115 mmol, 89% yield). LCMS $[M+H]^+$=371.

Step 5: Benzyl 4-(5-(5-(ethoxycarbonyl)-3-methyl-1H-pyrazol-1-yl)pent-1-yn-1-yl)-1-ethyl-3-methyl-1H-pyrazole-5-carboxylate

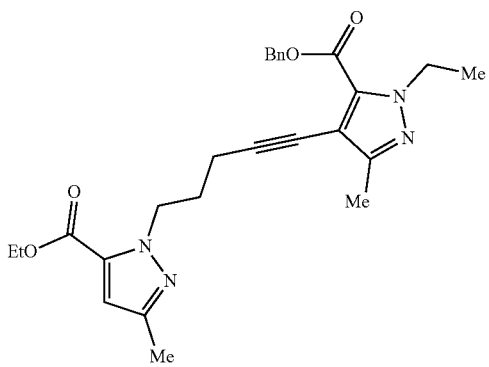 [SMILES: CCOC(=O)c1cc(C)nn1CCCC#Cc1c(C)nn(CC)c1C(=O)OCc1ccccc1]

A mixture of ethyl 3-methyl-1-(pent-4-yn-1-yl)-1H-pyrazole-5-carboxylate (10.0 g, 45.4 mmol), benzyl 1-ethyl-4-iodo-3-methyl-1H-pyrazole-5-carboxylate (16.8 g, 45.4 mmol), copper(I) iodide (0.864 g, 4.54 mmol), bis(triphenylphosphine)palladium(II) chloride (0.319 g, 0.454 mmol), and $Et_3N$ (200 mL) was stirred at 60° C. overnight under a nitrogen gas atmosphere. The mixture was then dissolved in DCM and washed with water. The organic phase was dried over anhydrous $Na_2SO_4$, filtered, concentrated under reduced pressure, and purified by column chromatography on silica gel (petroleum ether/EtOAc=5:1) to afford benzyl 4-(5-(5-(ethoxycarbonyl)-3-methyl-1H-pyrazol-1-yl)pent-1-yn-1-yl)-1-ethyl-3-methyl-1H-pyrazole-5-carboxylate (9.5 g, 20.5 mmol, 45.3% yield) as a yellow solid. LCMS $[M+H]^+$=463.

Step 6: 4-(5-(5-(ethoxycarbonyl)-3-methyl-1H-pyrazol-1-yl)pentyl)-1-ethyl-3-methyl-1H-pyrazole-5-carboxylic Acid

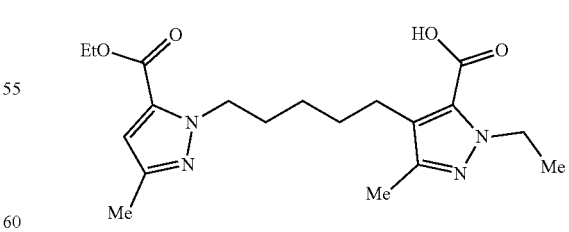

A mixture of benzyl 4-(5-(5-(ethoxycarbonyl)-3-methyl-1H-pyrazol-1-yl)pent-1-yn-1-yl)-1-ethyl-3-methyl-1H-pyrazole-5-carboxylate (19.0 g, 41.10 mmol), 10% Pd/C (0.22 g, 2.05 mmol), and THF (500 mL) was stirred at room temperature under a hydrogen gas atmosphere (4 atm) for 2 days. The reaction mixture was then filtered and concentrated under reduced pressure. The residue obtained was recrystallized from EtOAc/petroleum ether (1:5, v/v) to afford 4-(5-(5-(ethoxycarbonyl)-3-methyl-pyrazol-1-yl)pentyl)-1-ethyl-3-methyl-pyrazole-5-carboxylic acid (10.5 g, 27.90 mmol, 67.9% yield). $^1$H-NMR (400 MHz, CDCl$_3$) δ ppm 6.63 (s, 1H), 4.57-4.48 (m, 4H), 4.38-4.32 (m, 2H), 2.74-2.62 (m, 2H), 2.32 (s, 3H), 2.23 (s, 3H), 1.91-1.86 (m, 2H), 1.59-1.54 (m, 2H), 1.45-1.37 (m, 8H). LCMS [M+H]$^+$=377.

Step 7: 4-4-(7-(5-carboxy-3-methyl-1H-pyrazol-1-yl)heptyl)-1-ethyl-3-methyl-1H-pyrazole-5-carboxylic Acid

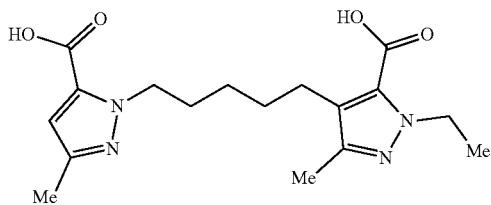 [SMILES: CCn1nc(C)c(CCCCCn2nc(C)cc2C(=O)O)c1C(=O)O]

To a suspension of 4-(5-(5-(ethoxycarbonyl)-3-methyl-1H-pyrazol-1-yl)pentyl)-1-ethyl-3-methyl-1H-pyrazole-5-carboxylic acid (9.0 g, 23.9 mmol) in MeOH (120 mL) and water (120 mL) stirred at room temperature was added a 2 M aq. NaOH solution (60 mL, 119.5 mmol). The reaction mixture was stirred at room temperature for 30 min. The mixture was then acidified to pH 4 with the addition of a 6 M HCl solution upon which a solid precipitated from the reaction mixture. The solid was collected by filtration and dried under reduced pressure to afford 4-(5-(5-carboxy-3-methyl-1H-pyrazol-1-yl)pentyl)-1-ethyl-3-methyl-1H-pyrazole-5-carboxylic acid (6.5 g, 18.7 mmol, 78.1% yield) as a white solid. $^1$H-NMR (400 MHz, DMSO-d$_6$) δ ppm 6.57 (s, 1H), 4.40-4.34 (m, 4H), 2.53 (t, J=7.6 Hz, 2H), 2.16 (s, 3H), 2.09 (s, 3H), 1.74-1.67 (m, 2H), 1.44-1.37 (m, 2H), 1.27-1.16 (m, 5H). LCMS [M+H]$^+$=349.

Step 8: 1-allyl-2-amino-1H-benzo[d]imidazole-5-carboxamide, Hydrobromide

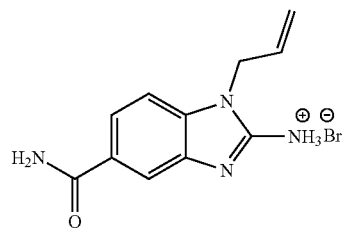 [SMILES: C=CCn1c([NH3+])nc2cc(C(N)=O)ccc21 ; [Br-]]

To a solution of 4-fluoro-3-nitrobenzamide (10.0 g, 54.3 mmol) in DMF (60 mL) was added allylamine (36.6 mL, 489 mmol) dropwise at room temperature and the mixture was stirred for 5 min. After this period, K$_2$CO$_3$ (15.01 g, 109 mmol) was added in one portion and the mixture was stirred at room temperature for 30 min. DMF was then removed in vacuo. The residue was suspended in 500 mL of water, the resulting orange precipitate was filtered off, washed with water, and dried in vacuo.

The above precipitate was dissolved in AcOH (600 mL) and the flask was placed into a 20° C. water bath. Zinc (10.65 g, 163 mmol) was added carefully in small portions. The reaction was monitored by LCMS and additional zinc (approximately 3 eq) was added in small portions as needed until the reduction was complete. Upon reaction completion by LCMS, the solids were filtered off and the filtrate concentrated in vacuo. The evaporation residue was taken up in DCM (500 mL) and EtOH (150 mL) and washed with 15% aq. K$_2$CO$_3$ (100 mL). The organic layer was separated, dried over Na$_2$SO$_4$, filtered, and concentrated in vacuo.

The above evaporation residue was dissolved in MeOH (200 mL), 5.0 M cyanogen bromide in CH$_3$CN (11.95 mL, 59.7 mmol) was added rapidly in one portion, and the mixture was stirred at room temperature for 18 h. After this period, the reaction mixture was concentrated in vacuo, then dissolved again in MeOH (200 mL). A mixture of toluene (100 mL) and CH$_3$CN (100 mL) was added and the resulting mixture was concentrated to dryness at 40° C. (0-1 mbar) and dried in vacuo for 16 h to afford 1-allyl-2-amino-1H-benzo[d]imidazole-5-carboxamide, hydrobromide (11.3 g, 38.0 mmol, 70.0% yield) as a dark purple powder. $^1$H NMR (400 MHz, DMSO-d$_6$) δ ppm 8.83 (s, 2H), 8.07 (br. s., 1H), 7.88 (d, J=1.00 Hz, 1H), 7.82 (dd, J=8.41, 1.38 Hz, 1H), 7.52 (d, J=8.53 Hz, 1H), 7.43 (br. s., 1H), 5.87-6.02 (m, 1H), 5.25 (dd, J=10.42, 0.88 Hz, 1H), 5.17 (dd, J=17.32, 1.00 Hz, 1H), 4.84 (d, J=5.02 Hz, 2H); LCMS [M+H]$^+$=216.9.

Step 9: 1-allyl-2-(1-(5-(5-((1-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide

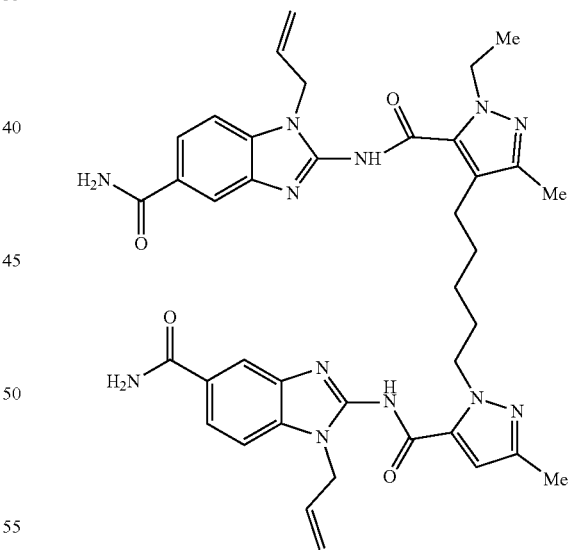

A 5.0 mL Biotage® sealed tube was charged with 4-(5-(5-carboxy-3-methyl-1H-pyrazol-1-yl)pentyl)-1-ethyl-3-methyl-1H-pyrazole-5-carboxylic acid (634 mg, 1.820 mmol), 1-allyl-2-amino-1H-benzo[d]imidazole-5-carboxamide, hydrobromide (1352 mg, 4.55 mmol), HATU (1730 mg, 4.55 mmol), and NMP (13 mL). After 1 minute of stirring at room temperature, DIPEA (3.17 mL, 18.20 mmol) was added and the mixture was stirred at room temperature for 5 min, then heated in a microwave reactor at 140° C. for 1 h. After this period, 5.0 mL of water was added and the mixture was stirred at room temperature for 5 min. It was then poured into 250 mL of ice-cold water and stirred vigorously for 1 h. The resulting solid was filtered off, washed with water, dissolved from the filter using MeOH/DCM, concentrated in vacuo, and subjected to silica gel chromatography (Biotage® Ultra SNAP 100 g SiO$_2$ column: 0-40% MeOH/EtOAc) to yield 1-allyl-2-(1-(5-(5-((I-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide (840 mg, 1.128 mmol, 62% yield) as a pink solid. $^1$H NMR (400 MHz, DMSO-d$_6$) δ ppm 12.88 (s, 1H), 12.81 (s, 1H), 7.99-8.02 (m, 2H), 7.97 (br. s., 2H), 7.77 (ddd, J=8.34, 3.66, 1.39 Hz, 2H), 7.41 (dd, J=16.93, 8.34 Hz, 2H), 7.34 (br. s., 2H), 6.65 (s, 1H), 5.87-6.02 (m, 2H), 4.99-5.22 (m, 4H), 4.82 (dd, J=11.62, 4.80 Hz, 4H), 4.50-4.61 (m, 4H), 2.73 (t, J=7.45 Hz, 2H), 2.15 (s, 3H), 2.08 (s, 3H), 1.71-1.85 (m, 2H), 1.45-1.55 (m, 2H), 1.27-1.34 (m, 5H); LCMS [M+H]$^+$=745.7.

Step 10: 8-ethyl-10,18-dimethyl-7,20-dioxo-6,7,8,
11,12,13,14,15,20,21,28,31-dodecahydrobenzo[4,5]
imidazo[1,2-a]benzo[4,5]imidazo[2,1-p]dipyrazolo
[5,1-e:4',3'-1][1,3,6,15,17]pentaazacyclohenicosine-
3,24-dicarboxamide

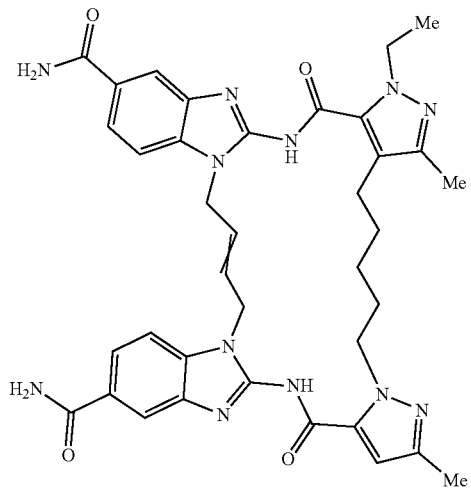 [SMILES: CCn1nc(C)c2c1C(=O)Nc1nc3cc(C(N)=O)ccc3n1CC=CCn1c(nc3cc(C(N)=O)ccc31)NC(=O)c1cc(C)nn1CCCCC2]

Four 20 mL Biotage® microwave sealed tubes were charged with a total of 1-allyl-2-(1-(5-(5-((I-allyl-5-carbamoyl-1H-benzo[d]imidazol-2-yl)carbamoyl)-1-ethyl-3-methyl-1H-pyrazol-4-yl)pentyl)-3-methyl-1H-pyrazole-5-carboxamido)-1H-benzo[d]imidazole-5-carboxamide (160 mg, 0.215 mmol), Hoveyda-Grubbs II catalyst (26.9 mg, 0.043 mmol), and freshly degassed 1,2-dichloroethane (DCE) (80 mL). The sealed tubes were heated in a microwave reactor for 4 h at 100° C. After the mixture cooled to room temperature, MeOH (1.0 mL) was added to each tube and the resulting clear solution was stirred at room temperature for 5 min. A solution of potassium 2-isocyanoacetate (15 mg in 1.5 mL of MeOH) was added to each tube and the resulting mixture was stirred at room temperature for 5 min. The tubes were combined, concentrated in vacuo, then the evaporation residue was taken up in a minimal volume of DCM/MeOH, and purified by silica gel chromatography (Biotage® Ultra SNAP 100 g SiO$_2$ column; 0-40% MeOH/EtOAc) to afford the desired product (61 mg) as a pale green solid with a mixture of alkene isomers. The product was further purified (Biotage® Ultra SNAP 25 g SiO$_2$ column; 0-20% MeOH/DCM gradient) to yield 8-ethyl-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide as a 7:1 trans:cis mixture (54 mg, 0.075 mmol, 35% yield). Characterization of the trans isomer: $^1$H NMR (400 MHz, DMSO-d$_6$) δ ppm 12.87 (s, 1H), 12.84 (s, 1H), 7.98 (br. s., 4H), 7.77 (dd, J=7.71, 3.16 Hz, 2H), 7.33-7.48 (m, 4H), 6.55 (s, 1H), 5.89-5.98 (m, 1H), 5.66-5.75 (m, 1H), 4.90 (d, J=7.83 Hz, 4H), 4.73 (t, J=6.95 Hz, 2H), 4.47 (q, J=6.99 Hz, 2H), 2.72-2.80 (m, 2H), 2.17 (s, 3H), 2.10 (s, 3H), 1.72 (br. s., 2H), 1.44 (br. s., 2H), 1.30 (t, J=7.07 Hz, 5H); LCMS [M+H]$^+$=717.6.

Step 11: 8-ethyl-10,18-dimethyl-7,20-dioxo-6,7,8,
11,12,13,14,15,20,21,28,29,30,31-tetradecahyd-
robenzo[4,5]imidazo[1,2-a]benzo[4,5]imidazo[2,1-p]
dipyrazolo[5,1-e:4',3'-1][1,3,6,15,17]
pentaazacyclohenicosine-3,24-dicarboxamide

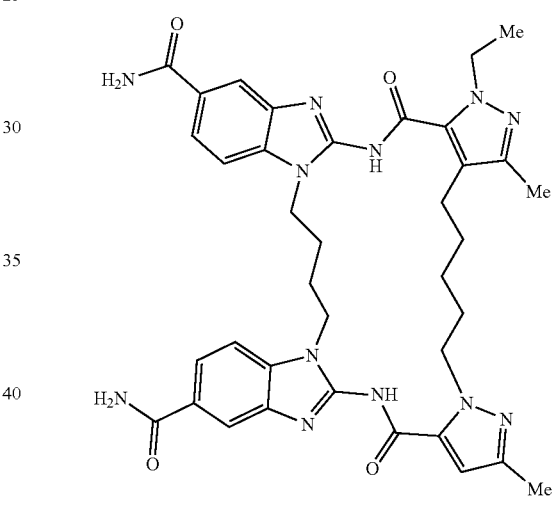

A round bottomed flask was charged with 10% Pd/C (200 mg, 0.188 mmol) and purged with nitrogen. A solution of 8-ethyl-10,18-dimethyl-7,20-dioxo-6,7,8,11,12,13,14,15,20,21,28,31-dodecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide (100 mg, 0.140 mmol, 7:1 trans:cis mixture) in a mixture of MeOH (20.0 mL) and THF (20.0 mL) was added, the flask was purged with hydrogen, and the reaction mixture was stirred under hydrogen atmosphere (1 atm) for 23 h. The flask was then opened to air, stirred vigorously for 15 min and filtered, the Pd/C washed with MeOH/THF, the filtrate concentrated in vacuo, and subjected to silica gel chromatography (Biotage® Ultra SNAP 25 g SiO$_2$ column; 0-20% MeOH/DCM) to yield 8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide (56 mg, 0.078 mmol, 55.8% yield) as a pale pink solid. $^1$H NMR (400 MHz, DMSO-d$_6$) δ ppm 12.88 (br. s., 2H), 8.02 (s, 4H), 7.79-7.87 (m, 2H), 7.67 (d, J=8.34 Hz, 1H), 7.63 (d, J=8.34 Hz, 1H), 7.37 (br. s., 2H), 6.57 (s, 1H), 4.74 (t, J=6.57 Hz, 2H), 4.48 (q, J=6.99 Hz, 2H), 4.19-4.31 (m, 4H), 2.78-2.86 (m, 2H), 2.16 (s, 3H), 2.08 (s, 3H), 1.91 (br. s., 4H), 1.77-1.86 (m, 2H), 1.44-1.54 (m, 2H), 1.35-1.42 (m, 2H), 1.29 (t, J=7.07 Hz, 3H); LCMS (m/z): 719.7 [M+H]$^+$.

Step 12: (5aE,21E)-8-ethyl-5,10,18,22-tetramethyl-7,20-dioxo-5,7,8,11,12,13,14,15,20,22,28,29,30,31-tetradecahydrobenzo[4,5]imidazo[1,2-a]benzo[4,5]imidazo[2,1-p]dipyrazolo[5,1-e:4',3'-]][1,3,6,15,17]pentaazacyclohenicosine-3,24-dicarboxamide

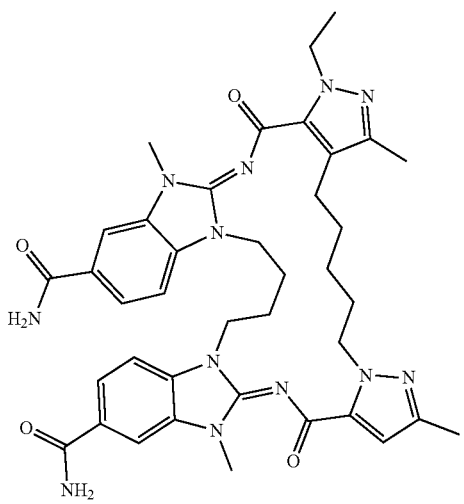 [SMILES: CCn1nc(C)c2c1C(=O)/N=C1\N(C)c3cc(C(N)=O)ccc3N1CCCCN1/C(=N/C(=O)c3cc(C)nn3CCCCC2)N(C)c2cc(C(N)=O)ccc21]

To a solution of 8-ethyl-10,18-dimethyl-7,20-dioxo-6,7,8,11,12,13,14,15,20,21,28,29,30,31-tetradecahydrobenzo[4,5]imidazo[1,2-a]benzo[4,5]imidazo[2,1-p]dipyrazolo[5,1-e:4',3'-I][1,3,6,15,17]pentaazacyclohenicosine-3,24-dicarboxamide (85 mg, 0.118 mmol) in DMF (3 mL) was added methyl iodide (0.015 mL methyl iodide, 0.236 mmol, 83 uL of a stock solution of 180 uL methyl iodide in 820 uL DMF). The reaction was stirred at room temperature for 3 h. The reaction was dry-loaded onto silica gel and purified by silica gel chromatography (ISCO-Rf, 12 g column, gradient 0%-30% MeOH/DCM) to afford a pale yellow solid. The material was suspended in MeCN and concentrated to dryness under a stream of air over the weekend to afford (5aE,21E)-8-ethyl-5,10,18,22-tetramethyl-7,20-dioxo-5,7,8,11,12,13,14,15,20,22,28,29,30,31-tetradecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide (58 mg, 0.077 mmol, 65.0% yield) as a white solid. $^1$H NMR (400 MHz, METHANOL-d$_4$) δ ppm 8.08 (dd, J=6.97, 1.39 Hz, 2H), 7.87-7.99 (m, 2H), 7.63 (d, J=8.62 Hz, 1H), 7.51 (d, J=8.62 Hz, 1H), 6.53 (s, 1H), 4.63 (t, J=6.97 Hz, 2H), 4.52 (q, J=7.18 Hz, 2H), 4.20-4.32 (m, 4H), 3.61 (s, 6H), 2.73-2.84 (m, 2H),2.26 (s, 3H), 2.21 (s, 3H), 1.87 (br. s., 6H), 1.53-1.63 (m, 2H), 1.30-1.40 (m, 5H). LCMS m/z=747 [M+H]$^+$.

Example 4

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2hydrochloride

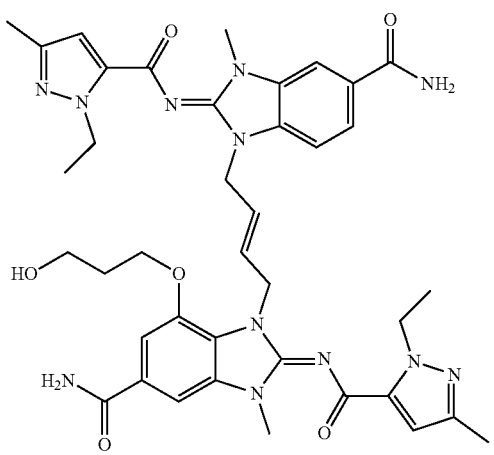

Step 1: (E)-7-(3-((tert-butyldimethylsilyl)oxy)propoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide

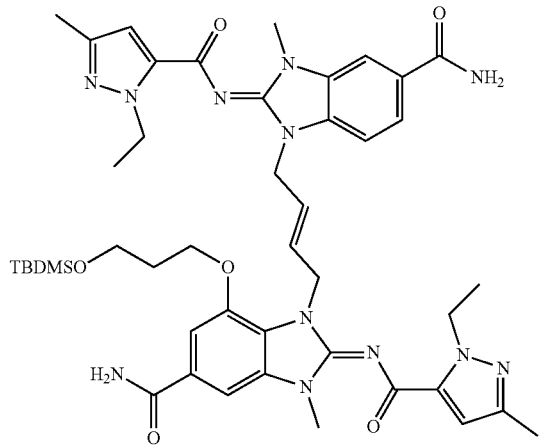

To a suspension of (E)-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (78 mg, 0.068 mmol) in DMF (3 mL) was added cesium carbonate (66.1 mg, 0.203 mmol) and 2.5 eq of methyl iodide (50 uL of a stock solution made of 220 uL methyl iodide in 780 uL DMF). The reaction was stirred at room temperature for 4h. A white precipitate formed in the yellow reaction mixture. Additional methyl iodide was added (2.5 eq) and the reaction immediately lost its yellow color. The reaction was stirred at room temperature over the weekend. Additional cesium carbonate (66 mg, 0.20 mmol) and methyl iodide solution (2.5 eq) were required to drive reaction to completion. Water was added and the aqueous layer was extracted with DCM (3×) then with ~15% EtOH/DCM (2×). The combined organic extracts were washed with brine, dried over sodium sulfate and concentrated to dryness. The resulting residue was dry-loaded onto 12 g silica gel column and eluted with a gradient of 0-20% MeOH/DCM to afford (E)-7-(3-((tert-butyldimethylsilyl)oxy)propoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide (20 mg, 0.022 mmol, 33.1% yield) as a white solid. LCMS m/z=893 [M+H]$^+$.

Step 2: (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2 Hydrochloride

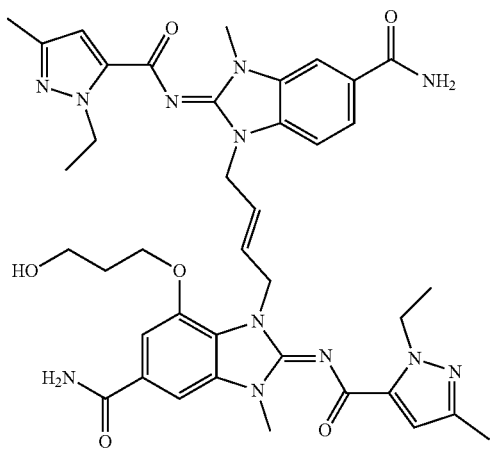

To a solution of (E)-7-(3-((tert-butyldimethylsilyl)oxy)propoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide (20 mg, 0.022 mmol) in 1,4-dioxane (0.5 mL) was added 4 M HCl in dioxane (0.011 mL, 0.045 mmol). Additional 4 M HCl in dioxane was added as needed to drive the deprotection. When complete, the reaction was filtered and the filter cake was washed with dioxane and dried in a vacuum oven at 45° C. overnight. The resulting pale yellow solid was submitted as (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2Hydrochloride (17 mg, 0.020 mmol, 87% yield). $^1$H NMR (400 MHz, DMSO-d$_6$) δ ppm 8.01-8.13 (m, 3H) 7.78-7.84 (m, 1H) 7.75 (s, 1H) 7.35-7.52 (m, 4H) 6.42 (s, 2H), 5.88-5.97 (m, 1H), 5.60-5.68 (m, 1H), 4.88 (d, J=5.07 Hz, 2H) 4.76 (d, J=5.58 Hz, 2H) 4.36-4.48 (m, 4H) 4.11 (t, J=6.34 Hz, 2H) 3.56 (s, 3H) 3.53 (s, 3H) 3.46 (s, 2H) 2.12 (s, 6H) 1.75 (d, J=6.08 Hz, 2H) 1.21 (t, J=7.10 Hz, 6H). LCMS m/z=779 [M+H]$^+$.

Example 5

(E)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide, 2 Hydrochloride

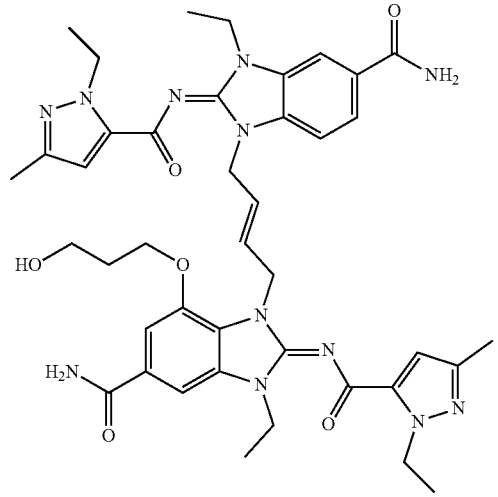

Step 1: (E)-7-(3-((tert-butyldimethylsilyl)oxy)propoxy)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-2,3-dihydro-1H-benzo[d]imidazole-5-carboxamide

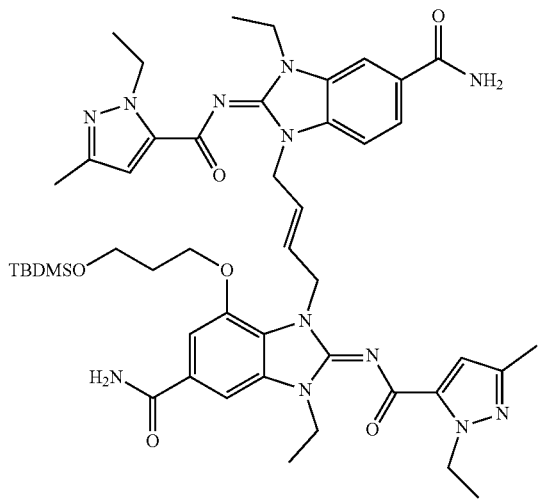

To a suspension of (E)-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (50 mg, 0.058 mmol) in DMF (2 mL) was added cesium carbonate (75 mg, 0.231 mmol) and iodoethane (27.0 mg, 0.173 mmol). After 3 h, additional ethyl iodide (15 uL) was added and the reaction stirred for 15 min. The reaction was partitioned between DCM and water. The aqueous layer was extracted with DCM/EtOH (3×). The combined organics were washed with brine, dried over sodium sulfate, dry-loaded onto silica gel and purified by silica gel chromatography (12 g column, 0-20% MeOH/DCM gradient) to afford (E)-7-(3-((tert-butyldimethylsilyl)oxy)propoxy)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-2,3-dihydro-1H-benzo[d]imidazole-5-carboxamide (18 mg, 0.020 mmol, 33.8% yield). LCMS m/z=921 [M+H]$^+$.

Step 2: (E)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide, 2Hydrochloride

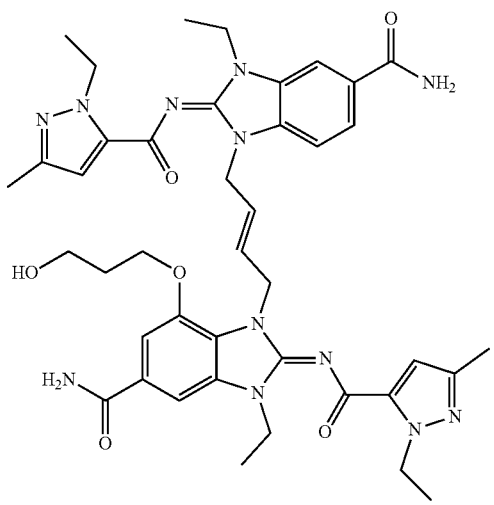

To a solution of (E)-7-(3-((tert-butyldimethylsilyl)oxy)propoxy)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-2,3-dihydro-1H-benzo[d]imidazole-5-carboxamide (17 mg, 0.018 mmol) in 1,4-dioxane (923 µL) was added HCl in dioxane (27.7 µL, 0.111 mmol). After 1h at room temperature, the reaction was filtered and the filtercake was washed with diethylether and dried in a vacuum oven at 55° C. overnight to afford (E)-1-((E)-4-((Z)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide, 2 hydrochloride (14 mg, 0.015 mmol, 81% yield) as a white solid. $^1$H NMR (400 MHz, DMSO-d$_6$) δ ppm 8.03-8.14 (m, 3H), 7.68-7.87 (m, 2H), 7.42-7.52 (m, 4H), 6.38 (s, 2H), 5.80-5.97 (m, 1H), 5.41-5.68 (m, 1H), 4.81-4.94 (m, 2H), 4.67-4.78 (m, 2H), 4.34-4.45 (m, 4H), 4.01-4.22 (m, 7H), 3.32-3.51 (m, 2H), 2.12 (s, 3H), 2.10 (s, 3H), 1.68-1.76 (m, 2H), 1.11-1.32 (m, 12H). LCMS m/z=807 [M+H]$^+$.

The compound prepared by the above process may exist in a tautomeric/isomeric form, e.g., (E)-1-((E)-4-((E)-5-carbamoyl-3-ethyl-2-((1-ethyl-3-methyl-1H-pyrazole-5-carbonyl)imino)-2,3-dihydro-1H-benzo[d]imidazol-1-yl)but-2-en-1-yl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide, 2 hydrochloride

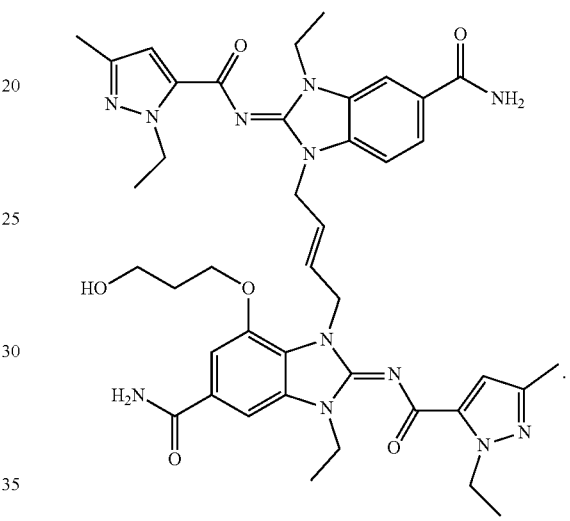

Example 6

(2E,2'E)-1,1'-(2,2,3,3-tetrafluorobutane-1,4-diyl)bis(2-((1-ethyl-3-methyl-1H-pyrazole-5-carbonyl)imino)-3-methyl-2,3-dihydro-1H-benzo[d]imidazole-5-carboxamide), Trifluoroacetic Acid Salt

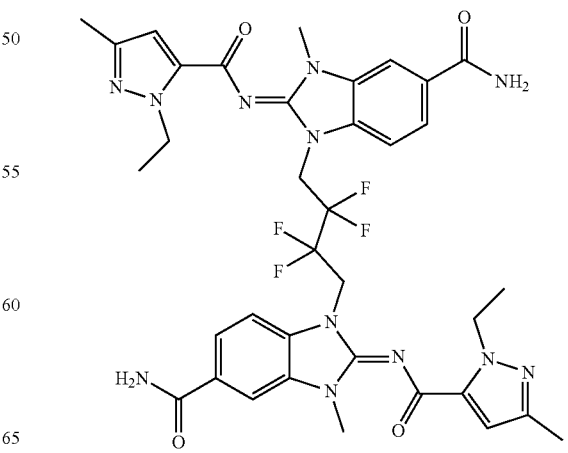

Step 1: 4,4'-((2,2,3,3-Tetrafluorobutane-1,4-diyl)bis(azanediyl))bis(3-nitrobenzamide)

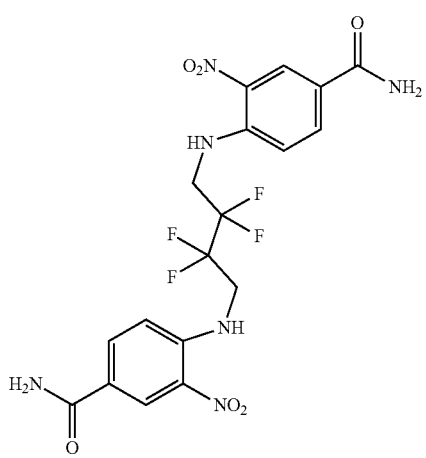 [SMILES: NC(=O)c1ccc(NCC(F)(F)C(F)(F)CNc2ccc(C(N)=O)cc2[N+](=O)[O-])c([N+](=O)[O-])c1]

To 2,2,3,3-tetrafluorobutane-1,4-diamine (1.25 g, 7.81 mmol), and potassium carbonate (3.24 g, 23.4 mmol) in DMF (50 mL) at room temperature was added 4-fluoro-3-nitrobenzamide (3.59 g, 19.5 mmol) over 5 min, and the reaction was stirred overnight. The mixture was quenched with water, and the resulting solid was collected by filtration and triturated with MeOH to afford the title compound (600 mg, 1.23 mmol, 16% yield) as a yellow solid. LCMS [M+H]$^+$=489.

Step 2: 4,4'-((2,2,3,3-Tetrafluorobutane-1,4-diyl)bis(azanediyl))bis(3-aminobenzamide)

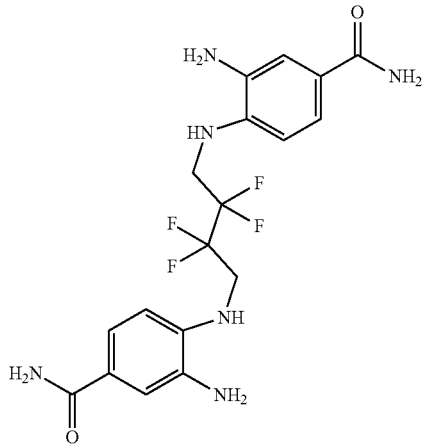

4,4'-((2,2,3,3-tetrafluorobutane-1,4-diyl)bis(azanediyl))bis(3-nitrobenzamide) (1.15 g, 2.36 mmol) and Pd on carbon (0.251 g, 2.36 mmol) in MeOH (100 mL) were stirred under H$_2$ at 30° C. overnight. The reaction was filtered, and the filtrate concentrated to afford the title compound (250 mg, 0.584 mmol, 25% yield). LCMS [M+H]$^+$=429.1

Step 3: 1,1'-(2,2,3,3-Tetrafluorobutane-1,4-diyl)bis(2-amino-1H-benzo[d]imidazole-5-carboxamide)

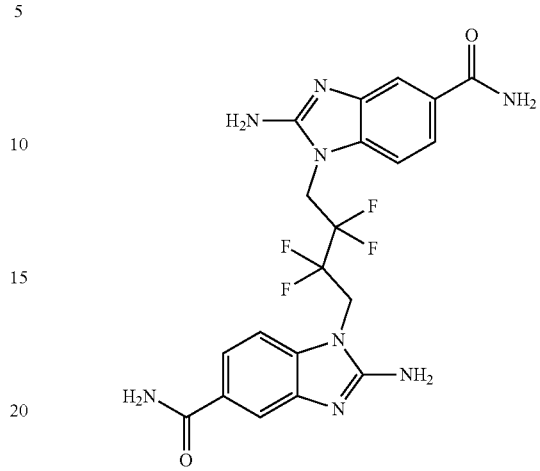

To 4,4'-((2,2,3,3-tetrafluorobutane-1,4-diyl)(azanediyl))bis(3-aminobenzamide) (20 mg, 0.047 mmol) in MeOH (1 mL) and water (2 mL) was added cyanogen bromide (29.7 mg, 0.280 mmol), and the reaction was stirred at 30° C. overnight. The MeOH was removed in vacuo and the resulting solid was collected by filtration to afford the title compound (15 mg, 0.031 mmol, 67% yield). LCMS [M+H]$^+$=479.0

Step 4: 1,1'-(2,2,3,3-Tetrafluorobutane-1,4-diyl)bis(2-(1-ethyl-3-methyl-1H-pyrazole-5-carboxamido)-1H-benzo[d]imidazole-5-carboxamide)

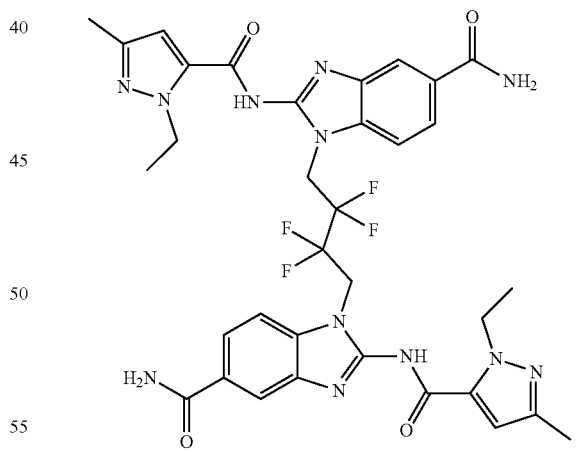

To HATU (763 mg, 2.01 mmol) and 1-ethyl-3-methyl-1H-pyrazole-5-carboxylic acid (227 mg, 1.47 mmol) in DMF (20 mL) at room temperature was added EDC (385 mg, 2.01 mmol), 1,1'-(2,2,3,3-tetrafluorobutane-1,4-diyl)bis(2-amino-1H-benzo[d]imidazole-5-carboxamide) (320 mg, 0.667 mmol) and DIEA (0.467 mL, 2.68 mmol) in one charge. The reaction was heated to 70° C. for 12 h, concentrated and purified to yield the title compound (8 mg, 0.01 mmol, 2% yield). $^1$H NMR (400 MHz, DMSO-d$_6$) δ ppm 13.05 (s, 2H), 8.01 (d, J=8.6 Hz, 4H), 7.81 (d, J=8.2 Hz, 2H), 7.53 (d, J=8.3 Hz, 2H), 7.38 (s, 2H), 6.73 (s, 2H), 5.32 (t, J=16.0 Hz, 4H), 4.59 (dd, J=14.0, 6.9 Hz, 4H), 2.06 (s, 6H), 1.33 (t, J=7.1 Hz, 6H); LCMS [M+H]$^+$=751.1

Step 5: (2E,2'E)-1,1'-(2,2,3,3-tetrafluorobutane-1,4-diyl)bis(2-((1-ethyl-3-methyl-1H-pyrazole-5-carbonyl)imino)-3-methyl-2,3-dihydro-1H-benzo[d]imidazole-5-carboxamide), Trifluoroacetic Acid Salt

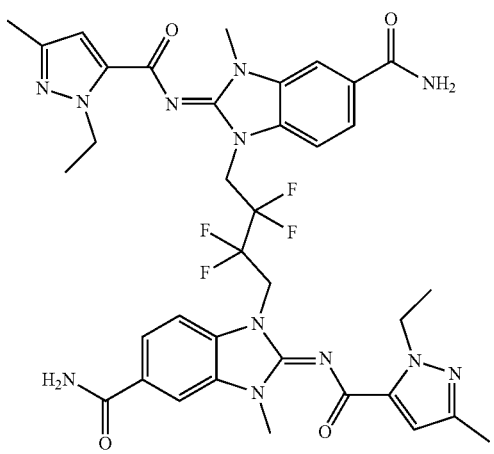

To a 100 mL round bottom flask was added 1,1'-(2,2,3,3-tetrafluorobutane-1,4-diyl)bis(2-(1-ethyl-3-methyl-1H-pyrazole-5-carboxamido)-1H-benzo[d]imidazole-5-carboxamide) (49 mg, 0.065 mmol) and DMF (0.653 mL). To this solution was added cesium carbonate (63.8 mg, 0.196 mmol) followed by methyl iodide (10.20 µL, 0.163 mmol). The mixture was stirred at room temperature. After 30 minutes, more methyl iodide was added (10 uL; 0.16 mmol) and the mixture was stirred overnight (~14 hours) at room temperature. This clear crude mixture was directly injected into a reverse phase preparative HPLC system and purified (Dual Phase ISCO, 20-50% CH$_3$CN/H$_2$O gradient, TFA modifier). Pure fractions were combined and concentrated to yield (2E,2'E)-1,1'-(2,2,3,3-tetrafluorobutane-1,4-diyl)bis(2-((1-ethyl-3-methyl-1H-pyrazole-5-carbonyl)imino)-3-methyl-2,3-dihydro-1H-benzo[d]imidazole-5-carboxamide), trifluoroacetic acid salt (3 mg, 3.19 µmol, 4.89% yield) as an off-white, semi-solid. $^1$H NMR (400 MHz, METHANOL-d4) δ ppm 1.34 (t, J=7.10 Hz, 6H) 2.25 (s, 6H) 3.70 (s, 6H) 4.60 (q, J=7.10 Hz, 4H) 5.19 (t, J=15.33 Hz, 4H) 6.66 (s, 2H) 7.60 (d, J=8.36 Hz, 2H) 7.96 (dd, J=8.36, 1.52 Hz, 2H) 8.11 (d, J=1.27 Hz, 2H). LCMS m/z=779 [M+H]$^+$.

Example 7

1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamidoan)-1H-benzo[d]imidazole-5-carboxamide, 2 Trifluoroacetic Acid Salt

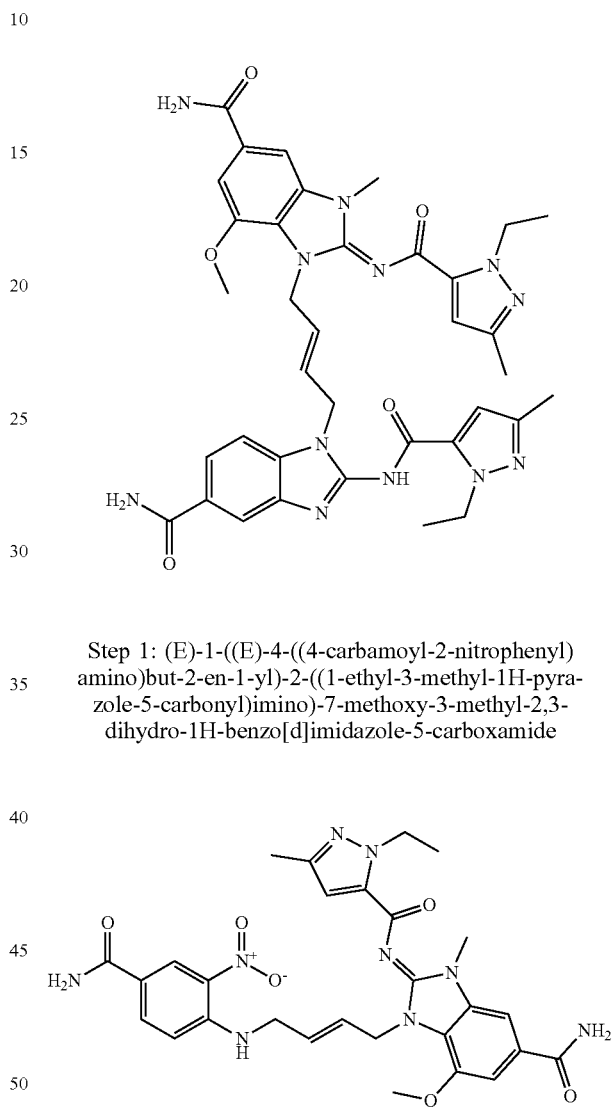

Step 1: (E)-1-((E)-4-((4-carbamoyl-2-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide 4-Fluoro-3-nitrobenzamide (86 mg, 0.467 mmol), (E)-1-((E)-4-aminobut-2-en-1-yl)-2-((1-ethyl-3-methyl-1H-pyrazole-5-carbonyl) imino)-7-methoxy-3-methyl-2,3-dihydro-1H-benzo[d]imidazole-5-carboxamide, 3Hydrochloride (name used in PU66420P: (Z)-1-((E)-4-aminobut-2-en-1-yl)-2-((1-ethyl-3-methyl-1H-pyrazole-5-carbonyl) imino)-7-methoxy-3-methyl-2,3-dihydro-1H-benzo[d]imidazole-5-carboxamide, 3 hydrochloride (250 mg, 0.467 mmol) and DIPEA (0.245 mL, 1.402 mmol) were suspended in isopropanol (2 mL) and heated at 120° C. in a sealed vial. After 18 h, the reaction was diluted with 25 mL EtOAc and washed with 2×25 mL water, 25 mL saturated sodium bicarbonate solution and 25 mL brine. The aqueous layers were back-extracted with 25 mL EtOAc. The organic layers were collected, and concentrated under vacuum to provide the crude solid product. The crude product was dissolved in 6 mL DMSO, filtered, and purified by mass-directed prep-HPLC. The pure fractions were combined, the organics were removed under vacuum, and the compound was extracted from the aqueous solvent with 2×50 mL DCM. The volatiles were removed under vacuum to provide the title compound as a yellow solid (102 mg, 0.173 mmol, 37% yield). LCMS m/z=590 [M+H]$^+$.

Step 2: (E)-1-((E)-4-((2-amino-4-carbamoylphenyl) amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

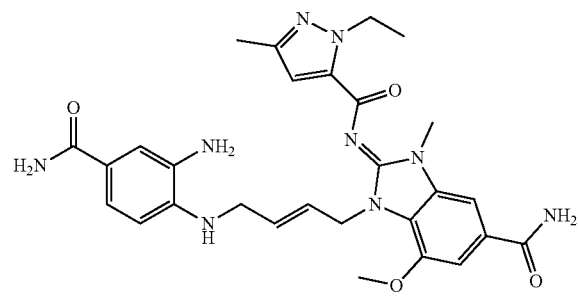 [SMILES: CCn1nc(C)cc1C(=O)/N=c1\n(C)c2cc(C(N)=O)cc(OC)c2n1C/C=C/CNc1ccc(C(N)=O)cc1N]

To a suspension of (E)-1-((E)-4-((4-carbamoyl-2-nitrophenyl) amino) but-2-en-1-yl)-2-((1-ethyl-3-methyl-1H-pyrazole-5-carbonyl) imino)-7-methoxy-3-methyl-2,3-dihydro-1H-benzo[d]imidazole-5-carboxamide (105 mg, 0.178 mmol) in acetic acid (0.500 mL) and MeOH (0.5 mL) was added 1 weight % Pt and 2 weight % vanadium on activated carbon, 50-70% wetted powder (34.7 mg, 1.781 μmol, Strem, 78-1536). The flask was evacuated and purged with nitrogen, and this was repeated two more times. The flask was evacuated and flushed with a hydrogen balloon, and was stirred at room temperature under a hydrogen atmosphere. Owing to incomplete conversion after 5 h, the reaction mixture was filtered through a small Celite plug using MeOH. The reaction mixture was concentrated under vacuum and stored in a freezer. The crude was redissolved in acetic acid (0.500 mL) and MeOH (0.5 mL), and 1 weight % Pt and 2 weight % vanadium V on activated carbon, 50-70% wetted powder (34.7 mg, 1.781 μmol) was added. The flask was evacuated and purged with nitrogen, and this was repeated a further two times. The flask was evacuated and flushed with a hydrogen balloon, and was stirred at room temperature under a hydrogen atmosphere. After 2 h, the reaction mixture was filtered through a small Celite plug using MeOH then was concentrated under vacuum to afford the title compound as a red oil (163 mg, 0.148 mmol, 82% yield). LCMS m/z=280 [M+2H/2]$^+$.

Step 3: 1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl) but-2-en-1-yl)-2-(1-ethyl-3-methyl-1H-pyrazole-5-carboxamidoan)-1H-benzo[d]imidazole-5-carboxamide, 2 Trifluoroacetic Acid Salt

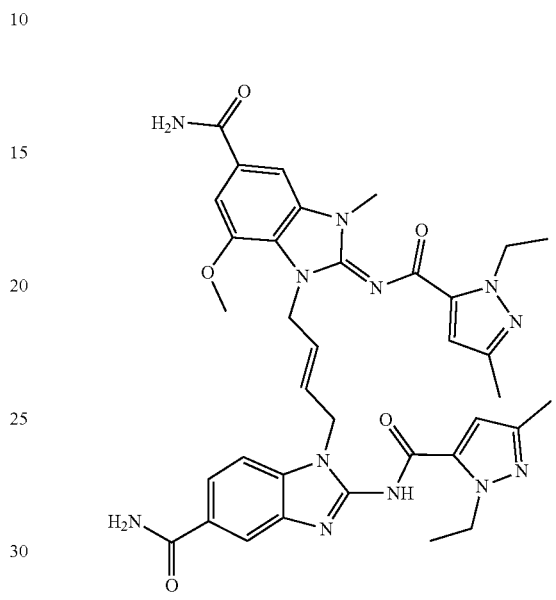

To (E)-1-((E)-4-((2-amino-4-carbamoylphenyl) amino) but-2-en-1-yl)-2-((1-ethyl-3-methyl-1H-pyrazole-5-carbonyl) imino)-7-methoxy-3-methyl-2,3-dihydro-1H-benzo[d] imidazole-5-carboxamide (100 mg, 0.179 mmol) in DMF (1 mL) at 0° C. was added 1-ethyl-3-methyl-1H-pyrazole-5-carbonyl isothiocyanate (0.491 mL, 0.197 mmol, 0.4 M in dioxane) and stirred at 0° C. for 1 h. After 1 h, EDC (51.4 mg, 0.268 mmol) and triethylamine (0.075 mL, 0.536 mmol) were added, and the reaction was stirred at 40° C. for 3 h and overnight at room temperature. The reaction was diluted with 1.5 mL DMSO and the title compound purified by mass directed preparative HPLC (basic modifier). The pure fractions were collected and the organics were removed under vacuum. The compound was then extracted with 2×25 mL DCM, and the organic layers washed with 10 mL brine. The volatiles were removed under vacuum to provide the title compound (~80% purity by LCMS). The compound was diluted with 2.0 mL DMSO and repurified by mass directed preparative HPLC (TFA modifier). The pure fractions were collected and the solvents removed under vacuum to provide the title compound as a yellow oil (15 mg, 0.016 mmol, 8.8% yield). $^1$H NMR (400 MHz, METHANOL-$d_4$) δ ppm 1.31-1.38 (m, 6H), 2.24-2.26 (m, 6H), 3.71 (s, 3H), 3.88 (s, 3H), 4.50 (q, J=7.10 Hz, 2H), 4.60 (q, J=7.10 Hz, 2H), 4.88 (d, J=5.83 Hz, 2H), 5.11 (d, J=5.07 Hz, 2H), 5.78 (dt, J=15.40, 5.73 Hz, 1H), 5.95-6.03 (m, 1H), 6.63 (s, 1H), 6.65 (s, 1H), 7.36 (d, J=8.36 Hz, 1H), 7.51 (d, J=1.27 Hz, 1H), 7.74 (dd, J=8.36, 1.52 Hz, 1H), 7.79 (d, J=1.01 Hz, 1H), 8.00 (d, J=1.52 Hz, 1H). LCMS m/z=721 [M+H]$^+$.

Example 8

1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2 Trifluoroacetic Acid Salt

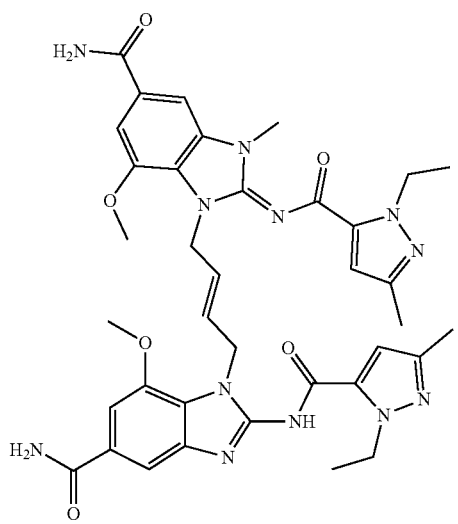 [SMILES: CCn1nc(C)cc1C(=O)/N=c1\n(C)c2cc(C(N)=O)cc(OC)c2n1C/C=C/Cn1c(NC(=O)c2cc(C)nn2CC)nc2cc(C(N)=O)cc(OC)c21]

Step 1: (E)-1-((E)-4-((4-carbamoyl-2-methoxy-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

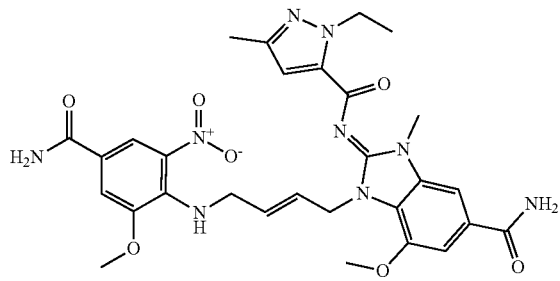 [SMILES: CCn1nc(C)cc1C(=O)/N=c1\n(C)c2cc(C(N)=O)cc(OC)c2n1C/C=C/CNc1c(OC)cc(C(N)=O)cc1[N+](=O)[O-]]

4-chloro-3-methoxy-5-nitrobenzamide (108 mg, 0.467 mmol), (E)-1-((E)-4-aminobut-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 3Hydrochloride (250 mg, 0.467 mmol) and DIPEA (0.245 mL, 1.402 mmol) were suspended in isopropanol (2 mL) and heated at 120° C. in a sealed vial. After 22 h, the reaction was diluted with 25 mL EtOAc and washed with 2×25 mL water, 25 mL saturated sodium bicarbonate solution and 25 mL brine. The aqueous layers were extracted with 25 mL EtOAc. The organic layers were collected, and concentrated under vacuum to provide crude product as an orange solid. The crude product was dissolved in 12 mL DMSO, filtered and purified directly by mass directed prepHPLC (high pH modifier, multiple injections). The pure fractions were combined, the organics were removed under vacuum, and the title compound was extracted from the aqueous solvent with 2×50 mL DCM. The volatiles were removed under vacuum to provide the title compound as an orange solid (53 mg, 0.086 mmol, 18.3% yield). LCMS m/z=620 [M+H]$^+$.

Step 2: (E)-1-((E)-4-((2-amino-4-carbamoyl-6-methoxyphenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

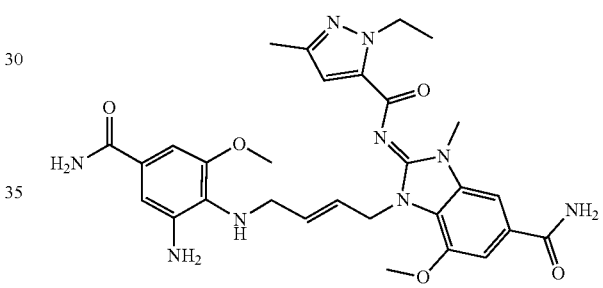

To a suspension of (E)-1-((E)-4-((4-carbamoyl-2-methoxy-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (name used in PU66420P: (Z)-1-((E)-4-((4-carbamoyl-2-methoxy-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (50 mg, 0.081 mmol) in acetic acid (0.500 mL) and MeOH (0.5 mL) was added 1 weight % Pt and 2 weight % vanadium on activated carbon, 50-70% wetted powder (15.74 mg, 0.807 µmol, Strem, 78-1536). The vial was evacuated and purged with nitrogen, and this was repeated two more times. The vial was evacuated and flushed with a hydrogen balloon then stirred at room temperature under a hydrogen atmosphere. After 4 h, the reaction mixture was filtered through a small Celite plug using MeOH then was concentrated under vacuum to provide a crude product mixture as a pale red solid (52 mg). LCMS m/z=590 [M+H]$^+$.

Step 3: 1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2 Trifluoroacetic Acid Salt

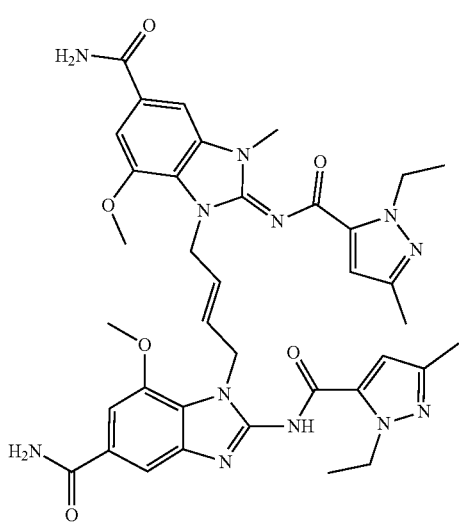 [SMILES: CCn1nc(C)cc1C(=O)/N=c1\n(C)c2cc(C(N)=O)cc(OC)c2n1C/C=C/Cn1c(NC(=O)c2cc(C)nn2CC)nc2cc(C(N)=O)cc(OC)c21]

To (E)-1-((E)-4-((2-amino-4-carbamoyl-6-methoxyphenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (60 mg, 0.102 mmol) in DMF (1 mL) at 0° C. was added 1-ethyl-3-methyl-1H-pyrazole-5-carbonyl isothiocyanate (0.280 mL, 0.112 mmol) as a 0.4 M solution in dioxane and stirred at 0° C. for 1 h. After 1 h, EDC (29.3 mg, 0.153 mmol) and triethylamine (0.043 mL, 0.305 mmol) were added, and the reaction was stirred at 40° C. for 2 h then room temperature for 18 h. The reaction mixture was diluted with 1.5 mL DMSO and purified on a mass-directed prep HPLC (high pH modifier). A second prepHPLC purification step was needed (using TFA-modifier) to provide pure title compound as an off-white solid (5.0 mg, 5.11 mmol, 5.0% yield). $^1$H NMR (400 MHz, DMSO-d$_6$) δ ppm 1.21 (t, J=7.10 Hz, 3H) 1.26 (t, J=7.10 Hz, 3H) 2.10 (s, 3H) 2.12 (s, 3H) 3.50 (s, 3H) 3.75 (s, 3H) 3.80 (s, 3H) 4.43 (q, J=7.18 Hz, 2H) 4.53 (q, J=7.01 Hz, 2H) 4.82-4.91 (m, 4H) 5.76-5.80 (m, 2H) 6.36 (s, 1H) 6.52 (s, 1H) 7.33 (d, J=1.01 Hz, 1H) 7.38 (br. s., 1H) 7.43 (d, J=0.76 Hz, 1H) 7.48 (br. s, 1H) 7.65 (d, J=1.27 Hz, 1H) 7.72 (d, J=1.01 Hz, 1H) 7.99 (br. s., 1H) 8.05 (br. s, 1H) 12.85 (s, 1H). LCMS m/z=751 [M+H]$^+$.

Example 9

1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide, 2 Hydrochloride

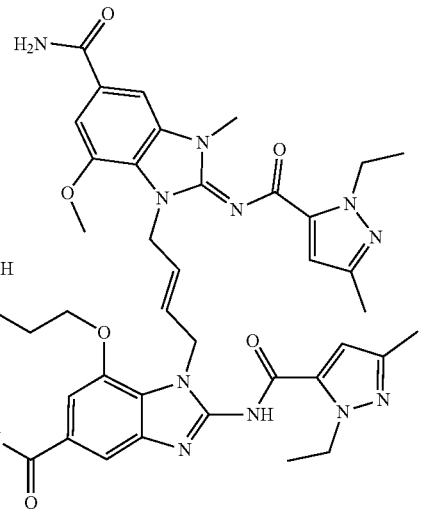

Step 1: ((E)-1-((E)-4-((2-(3-((tert-butyldimethylsilyl)oxy)propoxy)-4-carbamoyl-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

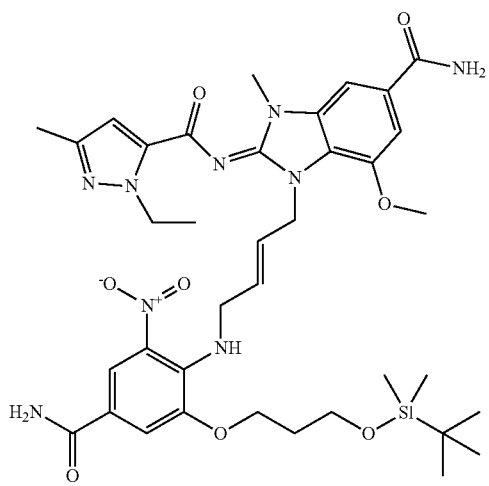

3-(3-((tert-butyldimethylsilyl)oxy)propoxy)-4-chloro-5-nitrobenzamide (182 mg, 0.467 mmol), (E)-1-((E)-4-aminobut-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 3Hydrochloride (250 mg, 0.467 mmol) and DIPEA (0.245 mL, 1.402 mmol) were suspended in isopropanol (2 mL) and heated at 120° C. in a sealed vial. After 22 h, the reaction was diluted with 25 mL EtOAc and washed with, 2×25 mL water, 25 mL saturated sodium bicarbonate solution and 25 mL brine. The aqueous layers were back-extracted with 25 mL EtOAc. The organic layers were collected, and concentrated under vacuum. The crude product was dissolved in 6 mL DMSO, filtered and purified by mass-directed prep HPLC (high pH modifier). The pure fractions were combined, the organics were removed under vacuum, and the compound was extracted from the aqueous solvent with 2×50 mL DCM. Evaporation of solvents provided the title compound as an orange solid (80 mg, 0.103 mmol, 22% yield). LCMS m/z=778 [M+H]$^+$.

Step 2: (E)-1-((E)-4-((2-amino-6-(3-((tert-butyldimethylsilyl)oxy)propoxy)-4-carbamoylphenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

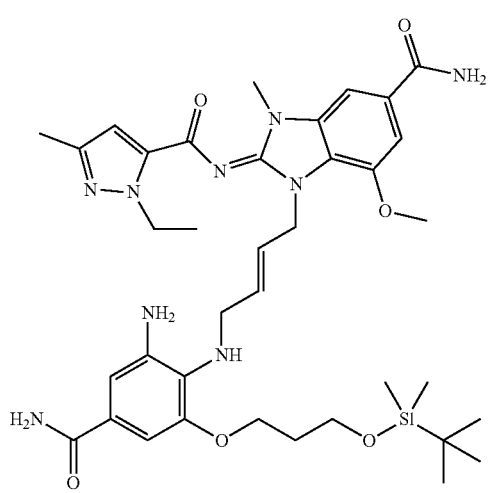

To a suspension of (E)-1-((E)-4-((2-(3-((tert-butyldimethylsilyl)oxy)propoxy)-4-carbamoyl-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (name used in PU66420P: (Z)-1-((E)-4-((2-(3-((tert-butyldimethylsilyl)oxy)propoxy)-4-carbamoyl-6-nitrophenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide) (80 mg, 0.103 mmol) in acetic acid (0.500 mL) and MeOH (0.5 mL) was added 1 weight % Pt and 2 weight % vanadium on activated carbon, 50-70% wetted powder (20.06 mg, 1.028 µmol, Strem 78-1536). The vial was evacuated and purged with nitrogen, and this was repeated two more times. The vial was evacuated and flushed with a hydrogen balloon, and was stirred at room temperature under a hydrogen atmosphere. After 4 h, the reaction mixture was filtered through a small Celite plug using MeOH then was concentrated and dried under vacuum to provide the title compound (77 mg, 0.072 mmol, 70% yield). LCMS m/z=748 [M+H]$^+$.

Step 3: 7-(3-((tert-butyldimethylsilyl)oxy)propoxy)-1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-1H-benzo[d]imidazole-5-carboxamide

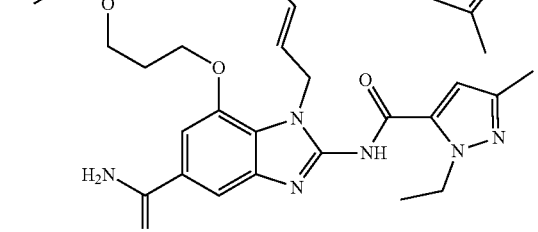

To (E)-1-((E)-4-((2-amino-6-(3-((tert-butyldimethylsilyl)oxy)propoxy)-4-carbamoylphenyl)amino)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (80 mg, 0.107 mmol) in DMF (1 mL) at 0° C. was added 1-ethyl-3-methyl-1H-pyrazole-5-carbonyl isothiocyanate (0.294 mL, 0.118 mmol, 0.4 M) in dioxane and stirred at 0° C. for 1 h. EDC (30.8 mg, 0.160 mmol) and triethylamine (0.045 mL, 0.321 mmol) were added, and the reaction was stirred at 40° C. for 2 h and room temperature for 18 h. The reaction was diluted with 1.5 mL DMSO and purified using mass-directed prepHPLC (high pH modifier). The pure fractions were collected and the organics were removed under vacuum. The compound was then extracted with 2×25 mL DCM, and the organic layers washed with 10 mL brine. The volatiles were removed under vacuum to provide the title compound as an off-white solid (25 mg, 0.027 mmol, 26% yield). LCMS m/z=909 [M+H]$^+$.

Step 4: 1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide, 2 Hydrochloride

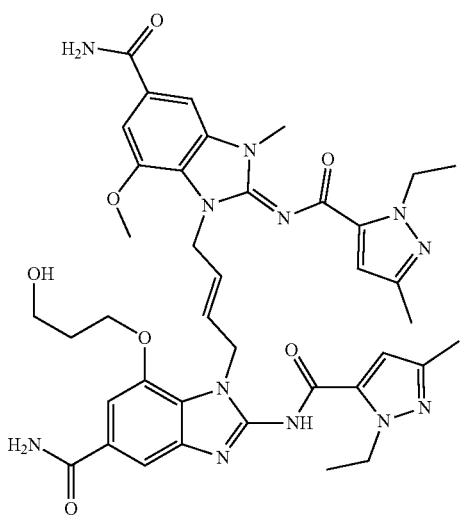 [SMILES: CCn1nc(C)cc1C(=O)/N=c1\n(C)c2cc(C(N)=O)cc(OC)c2n1C/C=C/Cn1c(NC(=O)c2cc(C)nn2CC)nc2cc(C(N)=O)cc(OCCCO)c21]

To 7-(3-((tert-butyldimethylsilyl)oxy)propoxy)-1-((E)-4-((E)-5-carbamoyl-2-((1-ethyl-3-methyl-1H-pyrazole-5-carbonyl)imino)-7-methoxy-3-methyl-2,3-dihydro-1H-benzo[d]imidazol-1-yl)but-2-en-1-yl)-2-(1-ethyl-3-methyl-1H-pyrazole-5-carboxamido)-1H-benzo[d]imidazole-5-carboxamide (25 mg, 0.027 mmol) in MeOH (1 mL) was added hydrochloric acid (0.069 mL, 0.275 mmol, 4 M) in dioxane and the reaction was stirred at room temperature. After 10 min, the volatiles were removed under vacuum to afford the title compound as a white solid (22 mg, 0.025 mmol, 92% yield). $^1$H NMR (400 MHz, METHANOL-d$_4$) δ ppm 1.29-1.36 (m, 3H), 1.45 (t, J=6.72 Hz, 3H), 1.85-1.91 (m, 2H), 2.29 (s, 3H), 2.36 (s, 3H), 3.64 (t, J=5.45 Hz, 2H), 3.89 (s, 3H), 3.91 (s, 3H), 4.18 (t, J=5.32 Hz, 2H), 4.38 (q, J=6.51 Hz, 2H), 4.69 (q, J=6.80 Hz, 2H), 5.19 (br. s., 2H), 5.30 (br. s., 2H), 5.85-6.06 (m, 2H), 6.80 (s, 1H), 6.99 (s, 1H), 7.43 (s, 1H), 7.61 (s, 1H), 7.74 (s, 1H), 8.00 (s, 1H). LCMS m/z=795 [M+H]$^+$.

Example 10

(E)-1-((E)-4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 2 Trifluoroacetic Acid Salt

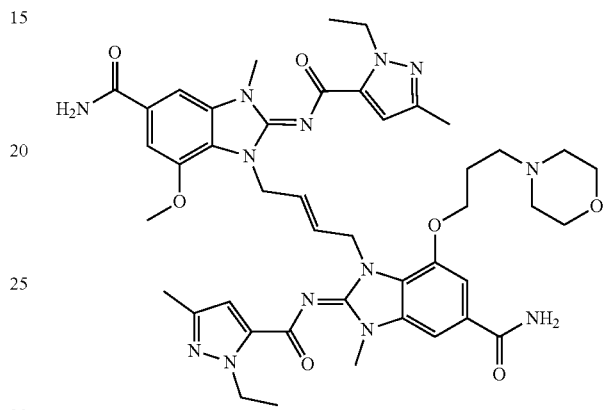

To a 20-mL vial were placed (E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (200 mg, 0.235 mmol) and DMF (2.35 mL). To this solution were added cesium carbonate (230 mg, 0.706 mmol) and methyl iodide (37 μL, 0.588 mmol). The solution was stirred at room temperature for 15 min. DMF (2 mL) and water (2 mL) were added directly to the vial. This mixture was directly purified using mass-directed preparative HPLC (15-55% gradient of MeCN/water with NH$_4$OH as modifier). The corresponding fractions were combined and concentrated. The concentrated mixture was further purified by mass-directed preparative HPLC (5-35% gradient of MeCN/water with TFA as modifier). The corresponding fractions were combined and concentrated to provide (E)-1-((E)-4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 2 trifluoroacetic acid salt (3 mg, 2.69 umol, 1.14% yield) as a clear oil. $^1$H NMR (400 MHz, DMSO-d$_6$) δ ppm 9.94 (br. s., 2H), 8.09 (br. s., 2H), 7.81 (s, 1H), 7.78 (s, 1H), 7.53 (br. s., 2H), 7.42 (d, J=6.08 Hz, 2H), 6.42 (m, 2H), 5.51-5.85 (m, 2H), 4.72-4.99 (m, 4H), 4.42 (q, J=6.84 Hz, 4H), 4.05 (t, J=5.58 Hz, 2H), 3.95 (d, J=11.66 Hz, 2H), 3.69 (s, 3H), 3.62 (t, J=11.91 Hz, 2H), 3.56 (s, 3H), 3.54 (s, 3H), 3.34 (d, J=11.91 Hz, 2H), 3.19 (d, J=7.10 Hz, 2H), 3.02 (br. s., 2H), 2.12 (s, 6H), 1.94 (m, 2H), 1.21 (m, 6H). LCMS (m/z): 878.7 [M+H]$^+$.

Example 11

(E)-1-((E)-4-((E)-5-carbamoyl-2-((1-ethyl-3-methyl-1H-pyrazole-5-carbonyl)imino)-3-methyl-7-(3-(4-methyl-414-morpholino)propoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide, 2 Trifluoroacetic Acid Salt, Trifluoroacetate

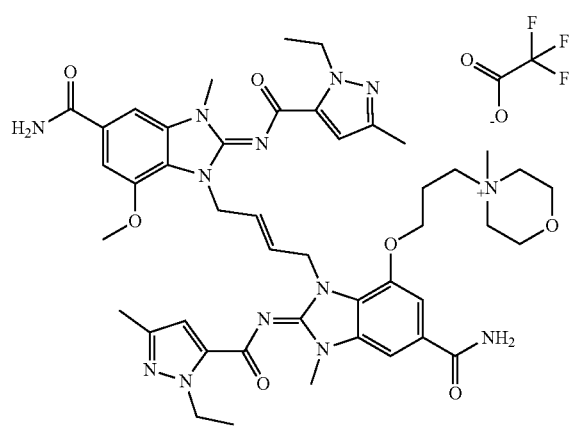

To a 20-mL vial were placed (E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (200 mg, 0.235 mmol) and DMF (2.35 mL). To this solution were added cesium carbonate (230 mg, 0.706 mmol) and methyl iodide (37 µL, 0.588 mmol). The solution was stirred at room temperature for 15 min. DMF (2 mL) and water (2 mL) were added directly to the vial. This mixture was directly purified using mass-directed preparative HPLC (15-55% gradient of MeCN/water with NH$_4$OH as modifier. The corresponding fractions were combined and concentrated. The concentrated mixture was purified by reverse phase preparative HPLC (5-35% gradient of MeCN/water with TFA as modifier) using an acidic modifier. The corresponding fractions were combined and concentrated to provide the title compound (6 mg, 4.81 umol, 2.04% yield) as a clear oil. $^1$H NMR (400 MHz, DMSO-d$_6$) δ ppm 8.08 (br. s., 2H), 7.81 (s, 2H), 7.77 (s, 1H), 7.53 (br. s., 3H), 7.39-7.40 (m, 3H), 6.41 (s, 1H), 6.40 (s, 1H), 5.60-5.75 (m, 2H), 4.74-4.97 (m, 4H), 4.35-4.51 (m, 4H), 4.02 (t, J=5.32 Hz, 2H), 3.82-3.98 (m, 4H), 3.67 (s, 3H), 3.50-3.54 (m, 8H), 3.08 (s, 3H), 2.12 (s, 6H), 1.95-2.05 (m., 2H), 1.24-1.20 (m, 6H). LCMS (m/z): 892.7 [M]$^+$

Example 12

(2E,2'E)-1,1'-(pentane-1,4-diyl)bis(2-((1-ethyl-3-methyl-1H-pyrazole-5-carbonyl)imino)-3-methyl-2,3-dihydro-1H-benzo[d]imidazole-5-carboxamide)

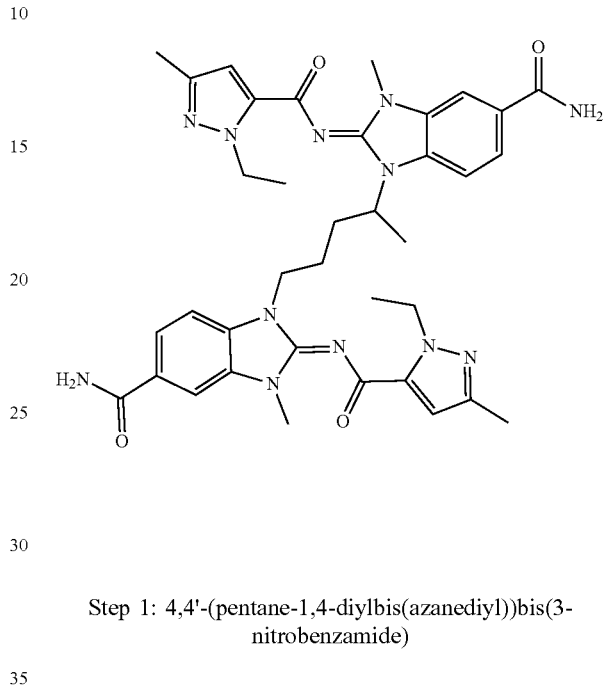

Step 1: 4,4'-(pentane-1,4-diylbis(azanediyl))bis(3-nitrobenzamide)

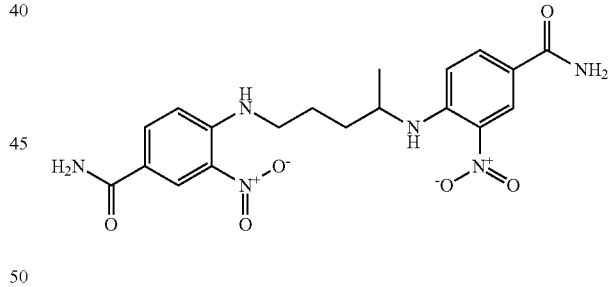

Into a reaction flask was placed pentane-1,4-diamine, 2 hydrochloride (1 g, 5.71 mmol) and isopropanol (9.52 mL). To this solution was added 4-fluoro-3-nitrobenzamide (1.052 g, 5.71 mmol) followed by DIPEA (4.49 mL, 25.7 mmol). The flask was capped and the reaction was heated to 105° C. After 4 hours, more 4-fluoro-3-nitrobenzamide (1.052 g, 5.71 mmol) and isopropanol (10 mL) were added. The mixture was stirred overnight (~14 h) at 105° C. The formed precipitate was filtered off and rinsed with isopropanol twice (5 mL each). 4,4'-(Pentane-1,4-diylbis(azanediyl))bis(3-nitrobenzamide) (2.6 g, 5.80 mmol, 100% yield) was obtained as a yellow solid. LCMS (m/z): 431.3 [M+H]$^+$

Step 2: 4,4'-(pentane-1,4-diylbis(azanediyl))bis(3-aminobenzamide)

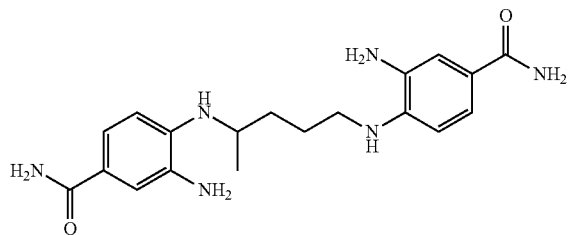 [SMILES: CC(CCCNc1ccc(C(N)=O)cc1N)Nc1ccc(C(N)=O)cc1N]

To a 100-mL round bottom flask was added 4,4'-(pentane-1,4-diylbis(azanediyl))bis(3-nitrobenzamide) (500 mg, 1.162 mmol) and MeOH (11.6 mL). To this solution was added ammonium chloride (249 mg, 4.65 mmol) and 5.5 mL of a saturated aqueous ammonium chloride solution. To this solution was added zinc (759 mg, 11.62 mmol). The heterogeneous mixture was stirred at room temperature for 15 min. The mixture was filtered and the collected solid was rinsed with MeOH (10 mL). To the combined filtrates was added Celite and the crude product was purified by flash chromatography (dry loading technique, 12 g SiO₂ cartridge, 2-40% MeOH/DCM as the eluent containing NH₄OH as a modifier). The corresponding fractions were combined and concentrated. 4,4'-(Pentane-1,4-diylbis(azanediyl))bis(3-aminobenzamide) (368 mg, 0.944 mmol, 81% yield) was obtained as a colorless oil. LCMS (m/z): 371.2 [M+H]⁺

Step 3: 1,1'-(pentane-1,4-diyl)bis(2-(1-ethyl-3-methyl-1H-pyrazole-5-carboxamido)-1H-benzo[d]imidazole-5-carboxamide)

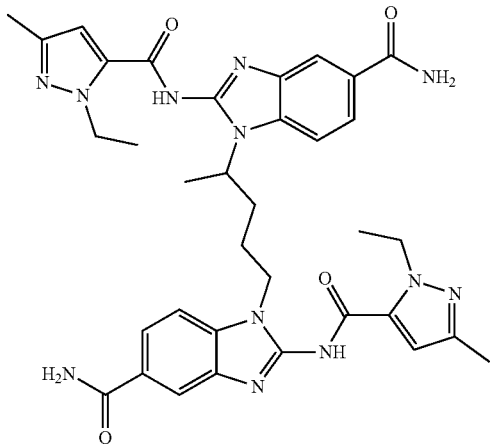

To a 100-mL round bottom flask was added 4,4'-(pentane-1,4-diylbis(azanediyl))bis(3-aminobenzamide) (368 mg, 0.993 mmol) and DMF (9.9 mL). This solution was cooled to 0° C. After 5 min stirring at 0° C., 1-ethyl-3-methyl-1H-pyrazole-5-carbonyl isothiocyanate (3 mL of a ~0.4 M dioxane solution, ~1.2 mmol) was added. After 15 min, more 1-ethyl-3-methyl-1H-pyrazole-5-carbonyl isothiocyanate (1 mL of a ~0.4 M dioxane solution, ~0.4 mmol) was added. The reaction was allowed to stir for another 15 min at 0° C. EDC (476 mg, 2.483 mmol) and triethylamine (0.692 mL, 4.97 mmol) were then added. The reaction mixture was warmed up to room temperature and allowed to stir overnight (~14 h). The reaction mixture was poured into 4:1 water/saturated aqueous ammonium chloride (25 mL). The product was extracted with ethyl acetate (3×15 mL). The combined organic phase was washed with water (20 mL), brine (20 mL) and dried over magnesium sulfate. The crude was concentrated and purified by flash chromatography (24 g SiO₂ cartridge, 2-40% MeOH/DCM as the eluent containing NH₄OH as a modifier). The corresponding fractions were combined and concentrated. 1,1'-(Pentane-1,4-diyl)bis(2-(1-ethyl-3-methyl-1H-pyrazole-5-carboxamido)-1H-benzo[d]imidazole-5-carboxamide) (303 mg, 0.429 mmol, 43.1% yield) was obtained as a white powder. ¹H NMR (400 MHz, DMSO-d₆) δ ppm 12.88 (br. s, 1H), 12.80 (br. s, 1H), 7.95-7.99 (m, 4H), 7.70-7.73 (m, 2H), 7.61 (d, J=8.62 Hz, 1H), 7.34-7.42 (m, 3H), 6.61 (m, 2H), 5.20 (br. s., 1H), 4.53-4.60 (m, 4H), 4.32 (br. s, 1H), 4.11-4.16 (m, 1H), 2.34 (br. s, 1H), 2.10 (s, 3H), 2.09 (s, 3H), 1.92 (m, 1H), 1.70 (m, 1H), 1.61 (m, 1H), 1.52 (d, J=6.84 Hz, 3H), 1.28-1.34 (m, 6H); LCMS (m/z): 693.6 [M+H]⁺.

Step 4: (2E,2'E)-1,1'-(pentane-1,4-diyl)bis(2-((1-ethyl-3-methyl-1H-pyrazole-5-carbonyl)imino)-3-methyl-2,3-dihydro-1H-benzo[d]imidazole-5-carboxamide)

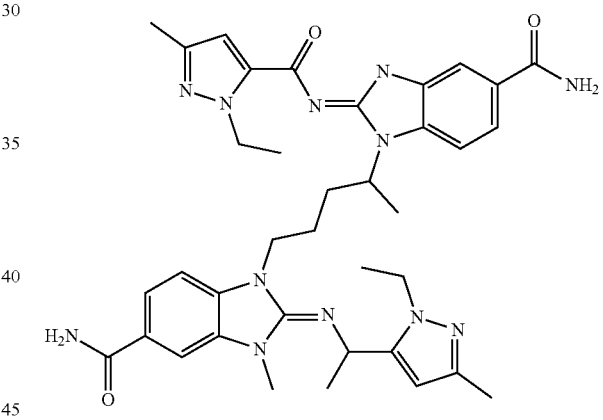

To a 10-mL vial was placed 1,1'-(pentane-1,4-diyl)bis(2-(1-ethyl-3-methyl-1H-pyrazole-5-carboxamido)-1H-benzo[d]imidazole-5-carboxamide) (50 mg, 0.072 mmol) and DMF (1.4 mL). To the heterogeneous solution was added cesium carbonate (70.5 mg, 0.217 mmol) followed by addition of methyl iodide (0.011 mL, 0.180 mmol). The vial was capped and the mixture was stirred overnight (~14 h) at room temperature. The mixture was diluted with DMSO (1 mL) and water (1 mL) to form a clear homogenous solution. This solution was directly purified by reverse phase preparative HPLC (Dual Phase ISCO system, 5-35% gradient of MeCN/water with 0.1% NH₄OH modifier). The corresponding fractions were combined and concentrated. The product was lyophilized with MeCN and water (~30 mL). (2E,2'E)-1,1'-(pentane-1,4-diyl)bis(2-((1-ethyl-3-methyl-1H-pyrazole-5-carbonyl)imino)-3-methyl-2,3-dihydro-1H-benzo[d]imidazole-5-carboxamide) (25 mg, 0.035 mmol, 48.1% yield) was obtained as a white fluffy solid. ¹H NMR (400 MHz, METHANOL-d₄) δ ppm 7.87 (d, J=2.28 Hz, 2H), 7.82 (dd, J=8.36, 1.52 Hz, 1H), 7.73-7.80 (m, 1H), 7.54 (d, J=8.36 Hz, 1H), 7.41 (d, J=8.62 Hz, 1H), 6.63 (s, 2H), 4.85 (m, 1H), 4.63 (q, J=7.18 Hz, 4H), 4.25-4.41 (m, 1H), 4.06-4.20 (m, 1H), 3.57 (s, 3H), 3.55 (s, 3H), 2.25 (s, 6H), 2.23 (m, 1H), 1.81-2.03 (m, 2H), 1.68 (m., 1H), 1.58 (d, J=6.84 Hz, 3H), 1.39 (t, J=7.10 Hz, 6H). LCMS (m/z): 721.6 [M+H]⁺

Example 13

(2E,2'E)-1,1'-(4-methylpentane-1,4-diyl)bis(2-((1-ethyl-3-methyl-1H-pyrazole-5-carbonyl)imino)-3-methyl-2,3-dihydro-1H-benzo[d]imidazole-5-carboxamide)

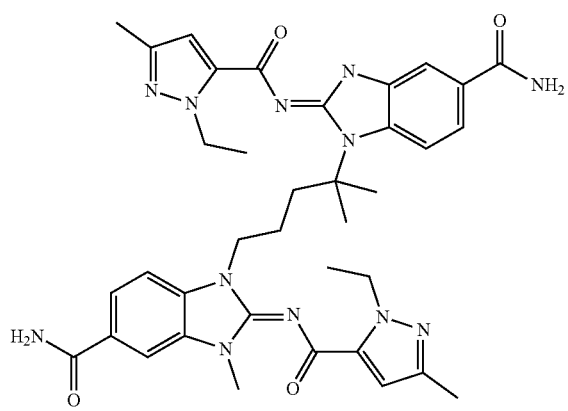 [SMILES: CCn1nc(C)cc1C(=O)/N=c1\n(C)c2cc(C(N)=O)ccc2n1CCCC(C)(C)n1/c(=N/C(=O)c2cc(C)nn2CC)[nH]c2cc(C(N)=O)ccc21]

Step 1: 4,4'-((4-methylpentane-1,4-diyl)bis(azanediyl))bis(3-nitrobenzamide)

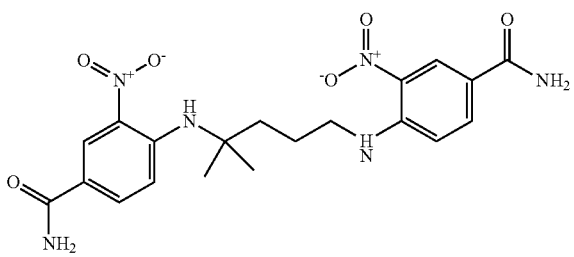

To a 24-mL vial was placed 4-methylpentane-1,4-diamine (0.49 g, 4.22 mmol) and isopropanol (14.0 mL). To this solution was added 4-fluoro-3-nitrobenzamide (1.63 g, 8.85 mmol) followed by addition of DIPEA (2.58 ml, 14.76 mmol). The vial was capped and the heterogeneous solution was stirred overnight (~14 h) at 105° C. A precipitate was filtered off and rinsed with isopropanol (2×5 mL). 4,4'-((4-methylpentane-1,4-diyl)bis(azanediyl))bis(3-nitrobenzamide) (1.46 g, 3.02 mmol, 71.7% yield, 92% purity) was obtained as an orange solid. LCMS (m/z): 445.3 [M+H]⁺.

Step 2: 4,4'-((4-methylpentane-1,4-diyl)bis(azanediyl))bis(3-aminobenzamide)

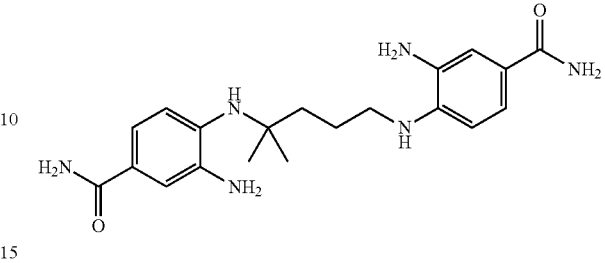

To a 100-mL round bottom flask were added 4,4'-((4-methylpentane-1,4-diyl)bis(azanediyl))bis(3-nitrobenzamide) (500 mg, 1.035 mmol) and MeOH (15 mL). To this solution were added ammonium chloride (1107 mg, 20.70 mmol), 10 mL of a saturated aqueous ammonium chloride solution and zinc (677 mg, 10.35 mmol). The heterogenous mixture was stirred at room temperature. After 20 min, more zinc (350 mg, 5.35 mmol) and ammonium chloride (600 mg, 11.22 mmol) were added. After stirring for a total of 90 min at room temperature, the mixture was filtered. The remaining solid was rinsed with MeOH (20 mL). To the combined filtrate was added Celite and the crude product was purified by silica gel chromatography (dry loading technique, 12 g SiO₂ cartridge, 2-40% gradient of MeOH/DCM containing NH₄OH as the modifier). The corresponding fractions were combined and concentrated. 4,4'-((4-Methylpentane-1,4-diyl)bis(azanediyl))bis(3-aminobenzamide) (247 mg, 0.610 mmol, 59.0% yield) was obtained as a white film. LCMS (m/z): 385.4 [M+H]⁺

Step 3: 1,1'-(4-methylpentane-1,4-diyl)bis(2-(1-ethyl-3-methyl-1H-pyrazole-5-carboxamido)-1H-benzo[d]imidazole-5-carboxamide)

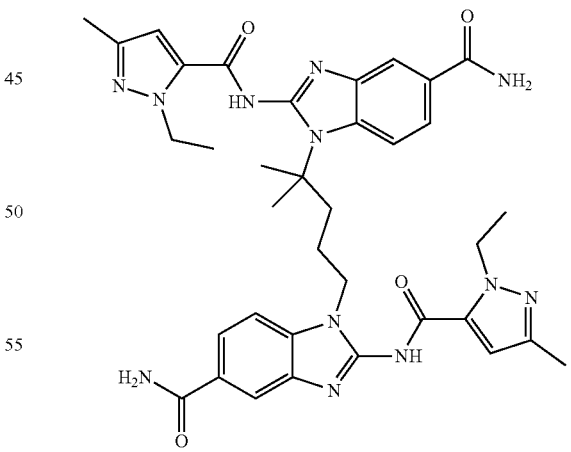

To a 100-mL round bottom flask were added 4,4'-((4-methylpentane-1,4-diyl)bis(azanediyl))bis(3-aminobenzamide) (247 mg, 0.642 mmol) and DMF (6.42 mL). This solution was cooled down to 0° C. After 5 min stirring at 0° C., 1-ethyl-3-methyl-1H-pyrazole-5-carbonyl isothiocyanate (~0.4 M in dioxane, 2.5 mL; ~1.0 mmol) was added as a solution. After 20 min, more 1-ethyl-3-methyl-1H-pyrazole-5-carbonyl isothiocyanate (~0.4 M in dioxane, 0.45 mL; 0.18 mmol) was added to ensure complete thiourea formation. After stirring for an additional 20 min at 0° C., EDC (308 mg, 1.606 mmol) was added followed by triethylamine (0.448 mL, 3.21 mmol). The reaction mixture was raised to room temperature and stirred overnight (~14 h). The reaction was poured into a beaker containing 25 mL of a 3:1 water/saturated aqueous ammonium chloride solution and stirred for 10 min. The resulting white precipitate was filtered off and rinsed with water (3×5 mL). The solid was dried in the vacuum oven for 6 h at 50° C. 1,1'-(4-Methylpentane-1,4-diyl)bis(2-(1-ethyl-3-methyl-1H-pyrazole-5-carboxamido)-1H-benzo[d]imidazole-5-carboxamide) (341 mg, 0.473 mmol, 73.6% yield) was obtained as an off-white solid. $^1$H NMR (400 MHz, DMSO-d$_6$) δ ppm 7.93 (m, 3H), 7.84 (s, 1H), 7.73 (d, J=8.87 Hz, 1H), 7.67 (d, J=8.36 Hz, 1H), 7.60 (d, J=8.62 Hz, 1H), 7.24-7.44 (m, 2H), 6.40 (s, 1H), 6.25 (br. s., 1H), 4.39-4.64 (m, 4H), 4.11 (t, J=6.46 Hz, 2H), 2.44 (br. s., 2H), 2.10 (s, 3H), 2.07 (s, 3H), 1.90 (br. s., 6H), 1.68 (br. s., 2H), 1.31 (t, J=7.10 Hz, 3H), 1.24 (t, J=7.10 Hz, 3H). LCMS (m/z): 707.6 [M+H]$^+$ Step 4: (2E,2'E)-1,1'-(4-methylpentane-1,4-diyl)bis(2-((1-ethyl-3-methyl-1H-pyrazole-5-carbonyl)imino)-3-methyl-2,3-dihydro-1H-benzo[d]imidazole-5-carboxamide)

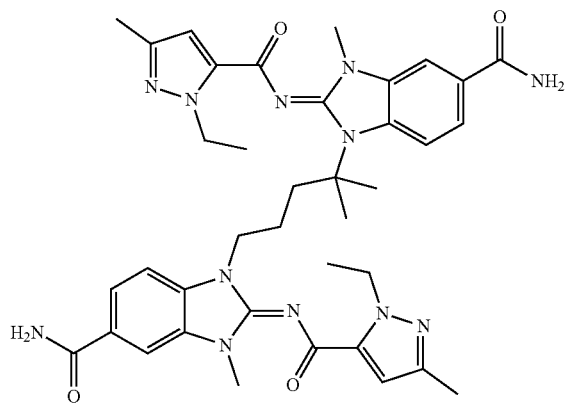 [SMILES: CCn1nc(C)cc1C(=O)/N=c1\n(C)c2cc(C(N)=O)ccc2n1CCCC(C)(C)n1/c(=N/C(=O)c2cc(C)nn2CC)n(C)c2cc(C(N)=O)ccc21]

To a 10-mL vial was placed 1,1'-(4-methylpentane-1,4-diyl)bis(2-(1-ethyl-3-methyl-1H-pyrazole-5-carboxamido)-1H-benzo[d]imidazole-5-carboxamide) (49 mg, 0.069 mmol) and DMF (0.693 mL). To this solution was added cesium carbonate (67.8 mg, 0.208 mmol) followed by addition of methyl iodide (10.84 μL, 0.173 mmol). The vial was capped and the mixture was stirred overnight (~14 h) at room temperature. The mixture was diluted with DMSO (1 mL) and water (1 mL) to form a clear homogeneous solution. This solution was directly injected and purified by reverse phase preparative HPLC (Dual Phase ISCO system, 5-35% gradient of MeCN/water with 0.1% NH$_4$OH modifier). The corresponding fractions were combined and concentrated. (2E,2'E)-1,1'-(4-methylpentane-1,4-diyl)bis(2-((1-ethyl-3-methyl-1H-pyrazole-5-carbonyl)imino)-3-methyl-2,3-dihydro-1H-benzo[d]imidazole-5-carboxamide) (15.8 mg, 0.022 mmol, 31.0% yield) was obtained as a clear oil. $^1$H NMR (400 MHz, METHANOL-d$_4$) δ ppm 7.64-7.85 (m, 5H), 7.34 (d, J=8.36 Hz, 1H), 6.65 (s, 1H), 6.57 (s, 1H), 4.64 (m, 4H), 4.20 (t, J=5.96 Hz, 2H), 3.54 (s, 3H), 3.40 (s, 3H), 2.24-2.31 (m, 5H), 2.23 (s, 3H), 1.82-1.95 (m, 8H), 1.41 (m, 6H). LCMS (m/z): 735.4 [M+H]$^+$.

Example 14

(E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)-2-methylpentan-2-yl)-2-((1-ethyl-3-methyl-1H-pyrazole-5-carbonyl)imino)-N,3-dimethyl-2,3-dihydro-1H-benzo[d]imidazole-5-carboxamide

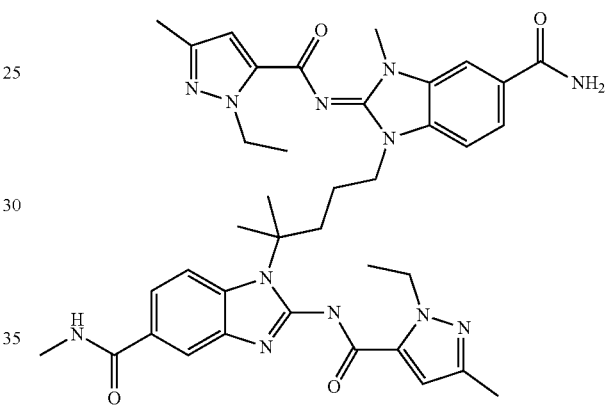

To a 10-mL vial were added 1,1'-(4-methylpentane-1,4-diyl)bis(2-(1-ethyl-3-methyl-1H-pyrazole-5-carboxamido)-1H-benzo[d]imidazole-5-carboxamide) (a synthetic intermediate of Example 13) (100 mg, 0.141 mmol) and DMF (1.415 mL). To this solution were added cesium carbonate (138 mg, 0.424 mmol) followed by addition of methyl iodide (0.044 mL, 0.707 mmol). The vial was capped and the mixture was stirred overnight (~14 h) at room temperature. This mixture was purified directly by reverse phase preparative HPLC (Dual Phase ISCO system, gradient of MeCN/water with 0.1% NH$_4$OH modifier). The corresponding fractions were combined and concentrated. (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)-2-methylpentan-2-yl)-2-((1-ethyl-3-methyl-1H-pyrazole-5-carbonyl)imino)-N,3-dimethyl-2,3-dihydro-1H-benzo[d]imidazole-5-carboxamide (7.1 mg, 0.0087 mmol, 6.16% yield) was obtained as a white film. $^1$H NMR (400 MHz, METHANOL-d$_4$) δ ppm 7.56-7.85 (m, 5H), 7.25-7.37 (m, 1H), 6.66 (s, 1H), 6.58 (s, 1H), 4.54-4.76 (m, 4H), 4.20 (t, J=5.96 Hz, 2H), 3.55 (d, J=5.58 Hz, 3H), 3.40 (s, 3H), 3.02 (s, 3H), 2.26 (s, 3H), 2.26 (m, 1H), 2.23 (s, 3H), 2.23 (m, 1H), 1.87 (s, 6H), 1.87 (m, 2H), 1.42 (m, 6H). LCMS (m/z): 749.4 [M+H]$^+$.

Example 15

(E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide (Diastereomer 1)

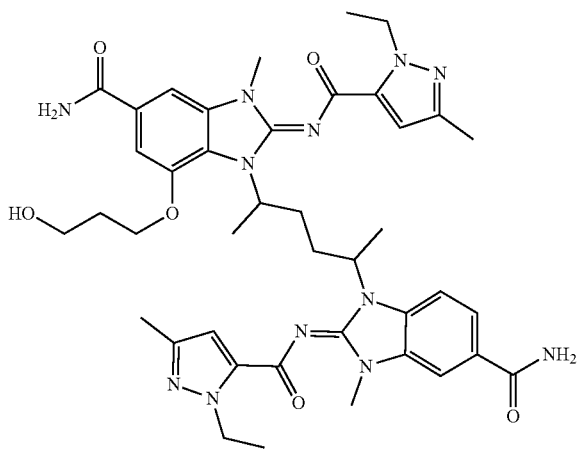 [SMILES: CCn1nc(C)cc1C(=O)/N=c1\n(C)c2cc(C(N)=O)ccc2n1C(C)CCC(C)n1/c(=N/C(=O)c2cc(C)nn2CC)n(C)c2cc(C(N)=O)cc(OCCCO)c21]

Step 1: (E)-7-(3-((tert-butyldimethylsilyl)oxy)propoxy)-1-(-5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-3-methyl-2,3-dihydro-1H-benzo[d]imidazole-5-carboxamide

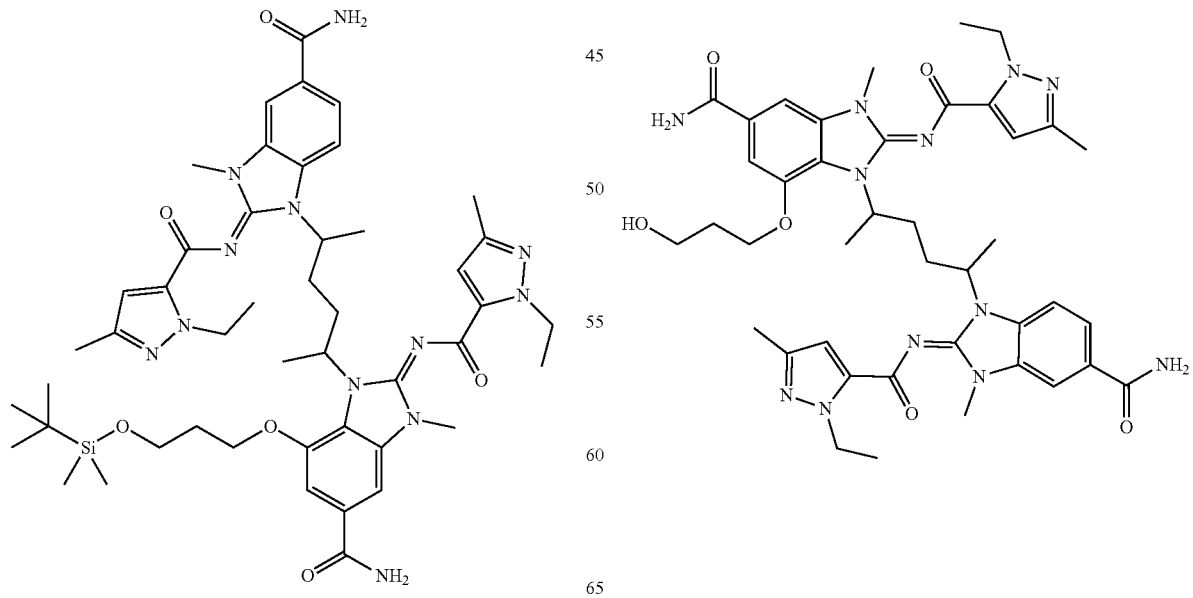

Into a 10-mL vial were placed 7-(3-((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide (25 mg, 0.028 mmol, for example, intermediate 14B, second eluting diastereomer) and DMF (559 µL). To this heterogeneous solution was added cesium carbonate (27.3 mg, 0.084 mmol) followed by methyl iodide (4.37 µL, 0.070 mmol). The vial was capped and the mixture was stirred overnight (~14 h) at room temperature. The mixture was diluted with DMSO (1 mL) and water (1 mL) to form a clear homogeneous solution. This solution was directly injected and purified by reverse phase preparative HPLC (Dual Phase ISCO system, 3-35% gradient of MeCN/water with 0.1% NH$_4$OH modifier). The corresponding fractions were combined and concentrated to provide (E)-7-(3-((tert-butyldimethylsilyl)oxy)propoxy)-1-(-5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-3-methyl-2,3-dihydro-1H-benzo[d]imidazole-5-carboxamide (18 mg, 0.019 mmol, 66.3% yield) as a white solid. LCMS: 923.4 [M+H]$^+$, 1.30 min retention time (Acquity UPLC CSH C18, 1.7 um, 50 mm×2.1 mm column; 3-95% gradient over 1.5 min, MeCN/10 mM ammonium bicarbonate in water adjusted to pH 10 with 25% ammonium hydroxide solution).

Step 2: (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide

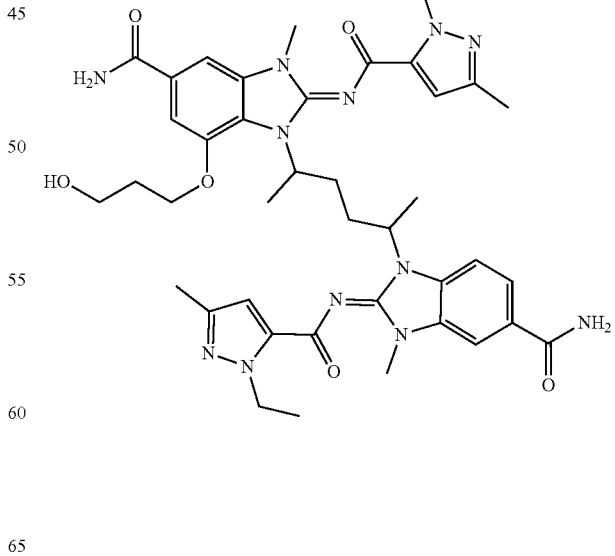

Into a 20-mL vial were placed (E)-7-(3-((tert-butyldimethylsilyl)oxy)propoxy)-1-(-5-((E)-5-carbamoyl-2-((1- ethyl-3-methyl-1H-pyrazole-5-carbonyl)imino)-3-methyl-2,
3-dihydro-1H-benzo[d]imidazol-1-yl)hexan-2-yl)-2-((1-
ethyl-3-methyl-1H-pyrazole-5-carbonyl)imino)-3-methyl-2,
3-dihydro-1H-benzo[d]imidazole-5-carboxamide (25 mg,
0.027 mmol) and MeOH (2 mL). To this solution was added
HCl (3 M CPME solution, 300 μL, 0.900 mmol). The
reaction mixture was stirred at room temperature overnight.
The volatiles were removed under an N₂ blow down unit.
The crude product was purified by reverse phase preparative
HPLC (Dual Phase ISCO system, 20-50% gradient of
MeCN/water with 0.1% NH₄OH modifier). The corresponding fractions were combined and concentrated to provide
(E)-1-(5-((E)-5-carbamoyl-2-((1-ethyl-3-methyl-1H-pyrazole-5-carbonyl)imino)-3-methyl-2,3-dihydro-1H-benzo[d]
imidazol-1-yl)hexan-2-yl)-2-((1-ethyl-3-methyl-1H-pyrazole-5-carbonyl)imino)-7-(3-hydroxypropoxy)-3-methyl-2,
3-dihydro-1H-benzo[d]imidazole-5-carboxamide (5.5 mg,
6.46 μmol, 23.85% yield) as a glassy white solid. $^1$H NMR
(400 MHz, METHANOL-d₄) δ ppm 8.01 (s, 1.17) 7.88 (br.
s., 3.21) 7.49-7.73 (m, 8.82) 7.42 (br. s., 2.89) 7.29 (br. s.,
0.86) 7.20 (s, 2.93) 6.70 (s, 3.36) 6.64 (br. s., 2.95) 4.98-5.11
(m, 4.53) 4.81 (br. s., 3.36) 4.55-4.75 (m, 14.25) 4.29-4.55
(m, 3.26) 4.08 (m, 2.84) 3.82 (m, 2.33) 3.41-3.75 (m, 28.77)
3.23 (br. s., 4.09) 2.19-2.36 (m, 21.72) 2.00-2.18 (m, 11.47)
1.76-2.00 (m, 13.31) 1.54 (m, 23.37) 1.35-1.50 (m, 24.00);
LCMS: 809.5 [M+H]⁺, 0.74 min retention time (Acquity
UPLC CSH C18 50 mm×2.1 mm column, 1.7 um; 5-95%
gradient over 1.5 min; MeCN/water with 0.1% TFA modifier).

Example 16

(E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide (Diastereomer 2)

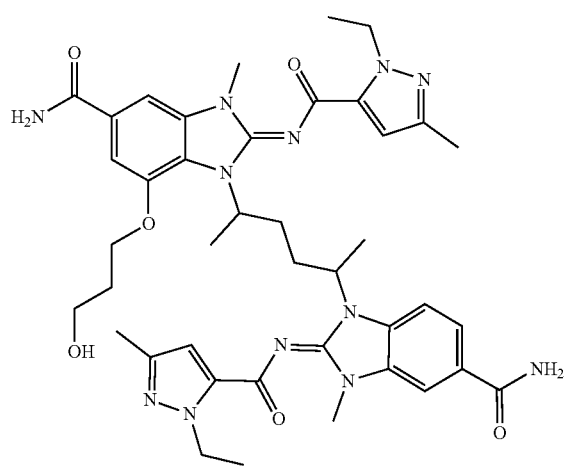 [SMILES: CCn1nc(C)cc1C(=O)/N=c1\n(C)c2cc(C(N)=O)ccc2n1C(C)CCC(C)n1/c(=N/C(=O)c2cc(C)nn2CC)n(C)c2cc(C(N)=O)cc(OCCCO)c21]

Step 1: (E)-7-(3-((tert-butyldimethylsilyl)oxy)
propoxy)-1-(5-((E)-5-carbamoyl-2-((1-ethyl-3-
methyl-1H-pyrazole-5-carbonyl)imino)-3-methyl-2,
3-dihydro-1H-benzo[d]imidazol-1-yl)hexan-2-yl)-2-
((1-ethyl-3-methyl-1H-pyrazole-5-carbonyl)imino)-
3-methyl-2,3-dihydro-1H-benzo[d]imidazole-5-
carboxamide

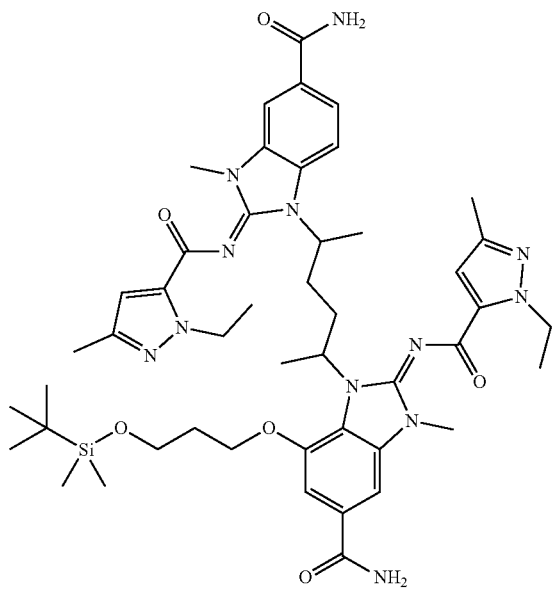 [SMILES: CCn1nc(C)cc1C(=O)/N=c1\n(C)c2cc(C(N)=O)ccc2n1C(C)CCC(C)n1/c(=N/C(=O)c2cc(C)nn2CC)n(C)c2cc(C(N)=O)cc(OCCCO[Si](C)(C)C(C)(C)C)c21]

Into a 10-mL vial were placed 7-(3-((tert-butyldimethylsilyl)oxy)propoxy)-1-(5-(5-carbamoyl-2-(1-ethyl-3-methyl-1H-pyrazole-5-carboxamido)-1H-benzo[d]imidazol-1-yl)hexan-2-yl)-2-(1-ethyl-3-methyl-1H-pyrazole-5-carboxamido)-1H-benzo[d]imidazole-5-carboxamide (25 mg, 0.028 mmol, for example Intermediate 14A, first eluting diastereomer) and DMF (559 μL). To this heterogeneous solution were added cesium carbonate (27.3 mg, 0.084 mmol) and methyl iodide (4.37 μl, 0.070 mmol). The vial was capped and the mixture was stirred overnight (~14 h) at room temperature. The mixture was diluted with DMSO (1 mL) and water (1 mL) to form a clear homogeneous solution. This solution was directly injected and purified by reverse phase preparative HPLC (Dual Phase ISCO system, 5-35% gradient of MeCN/water with 0.1% NH₄OH modifier). The corresponding fractions were combined and concentrated to provide (E)-7-(3-((tert-butyldimethylsilyl)oxy) propoxy)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-3-methyl-2,3-dihydro-1H-benzo[d]imidazole-5-carboxamide (15 mg, 0.014 mmol, 49.5% yield, 85% purity) as a white solid. LCMS: 923.5 [M+H]⁺, 1.24 min retention time (Acquity UPLC CSH C18, 1.7 um, 50 mm×2.1 mm column; 3-95% gradient over 1.5 min, MeCN/10 mM ammonium bicarbonate in water adjusted to pH 10 with 25% ammonium hydroxide solution).

217

Step 2: (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide

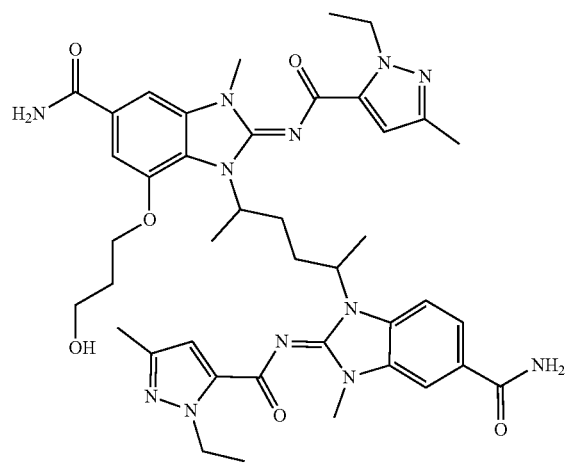 [SMILES: CCn1nc(C)cc1C(=O)/N=c1\n(C)c2cc(C(N)=O)ccc2n1C(C)CCC(C)n1/c(=N/C(=O)c2cc(C)nn2CC)n(C)c2cc(C(N)=O)cc(OCCCO)c21]

Into a 20-mL vial were placed (E)-7-(3-((tert-butyldimethylsilyl)oxy)propoxy)-1-(-5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-3-methyl-2,3-dihydro-1H-benzo[d]imidazole-5-carboxamide (15 mg, 0.016 mmol) and MeOH (2 mL). To this solution was added HCl (3 M CPME solution, 300 μL, 0.900 mmol). The reaction mixture was stirred at room temperature overnight. The volatiles were removed using a stream of nitrogen. The residue was purified by reverse phase preparative HPLC (Dual phase ISCO system; 20-50% gradient of MeCN/water with 0.1% NH$_4$OH modifier). The corresponding fractions were combined and concentrated to provide racemic (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)hexan-2-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide (5 mg, 5.87 μmol, 36.1% yield) as a glassy white solid. $^1$H NMR (400 MHz, METHANOL-d$_4$) δ ppm 8.07 (m, 2.61), 7.86 (m, 2.78), 7.58-7.81 (m, 4.92), 7.52 (s, 2.38), 6.48-6.73 (m, 4.98), 5.47 (br. s., 1.43), 4.75 (br. s., 2.43), 4.49-4.69 (m, 10.33), 4.26-4.40 (m, 4.06), 4.21 (br. s., 1.08), 3.50-3.76 (m, 20.52), 2.68 (s, 1.17), 2.49 (br. s., 0.84), 2.15-2.41 (m, 18.94), 1.94-2.07 (m, 2.86), 1.78-1.94 (m, 3.63), 1.70 (m., 3.14), 1.46-1.63 (m, 16.31), 1.26-1.42 (m, 17.00). LCMS: 809.5 [M+H]$^+$, 0.71 min retention time (Acquity UPLC CSH C18, 1.7 um, 50 mm×2.1 mm column; 5-95% gradient over 1.5 min; MeCN/water with 0.1% TFA modifier).

218

Example 17

(E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2 Trifluoroacetic Acid Salt Step 1:
3-(3-(benzyloxy)propoxy)-4-chloro-5-nitrobenzamide

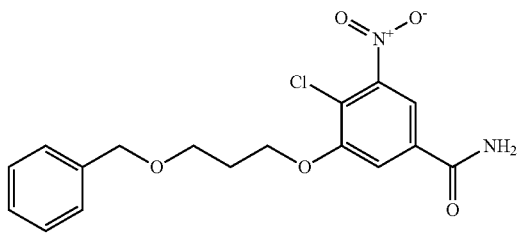 [SMILES: NC(=O)c1cc(OCCCOCc2ccccc2)c(Cl)c([N+](=O)[O-])c1]

To a stirred suspension of 4-chloro-3-hydroxy-5-nitrobenzamide (30 g, 139 mmol) and potassium carbonate (57.4 g, 416 mmol) in DMF (200 mL) under nitrogen was added at room temperature a solution of ((3-bromopropoxy)methyl)benzene (47.6 g, 208 mmol) dropwise during 1 minute. The reaction mixture was stirred at 80° C. overnight. The reaction mixture was cooled to room temperature and quenched by the addition of 200 mL of water. The aqueous phase was then extracted with DCM (3×100 mL). The combined organic layer was washed with water (4×200 mL) and brine (200 mL), dried, and concentrated under vacuum. The crude product was purified by silica gel chromatography (100 g column, 1:2 petroleum ether/EtOAc). The appropriate fractions were pooled and concentrated to afford 3-(3-(benzyloxy)propoxy)-4-chloro-5-nitrobenzamide (33 g, 90 mmol, 65.3% yield) as a yellow solid. LCMS (m/z): 365 [M+H]$^+$.

Step 2: 4-((4-amino-2,2,3,3-tetrafluorobutyl)amino)-3-(3-(benzyloxy)propoxy)-5-nitrobenzamide

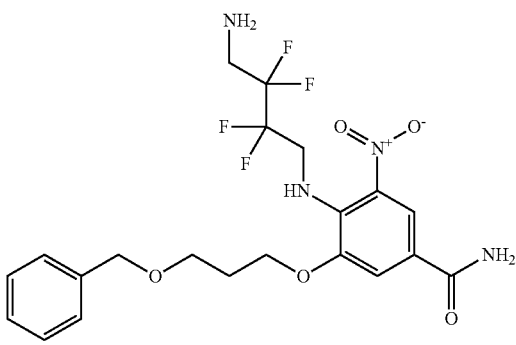 [SMILES: NCC(F)(F)C(F)(F)CNc1c(OCCCOCc2ccccc2)cc(C(N)=O)cc1[N+](=O)[O-]]

A suspension of 2,2,3,3-tetrafluorobutane-1,4-diamine (4 g, 24.98 mmol), 3-(3-(benzyloxy)propoxy)-4-chloro-5-nitrobenzamide (4.56 g, 12.49 mmol) and DIPEA (6 mL, 34.4 mmol) in isopropanol (18 mL) was stirred overnight in a sealed tube at 135° C. When cooled, volatiles were removed in vacuo. The crude product was purified by silica gel chromatography (20 g column, 60-100% gradient of EtOAc/petroleum ether. The appropriate fractions were pooled and concentrated to afford 4-((4-amino-2,2,3,3-tetrafluorobutyl)amino)-3-(3-(benzyloxy)propoxy)-5-nitrobenzamide (3 g, 6.14 mmol, 24.6% yield) as a reddish brown oil. LCMS (m/z): 489 [M+H]$^+$.

Step 3: 3-(3-(benzyloxy)propoxy)-4-((4-((4-carbamoyl-2-nitrophenyl)amino)-2,2,3,3-tetrafluorobutyl)amino)-5-nitrobenzamide

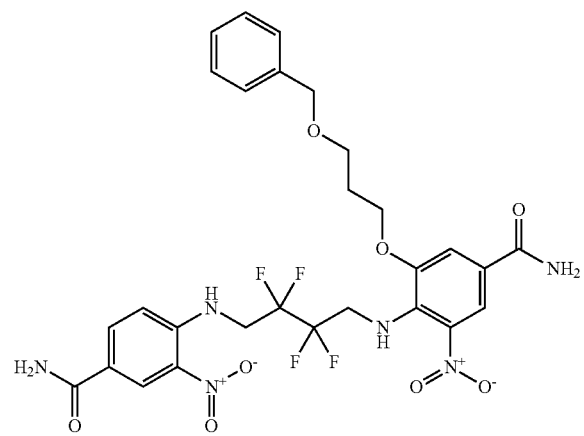 [SMILES: NC(=O)c1ccc(NCC(F)(F)C(F)(F)CNc2c(OCCCOCc3ccccc3)cc(C(N)=O)cc2[N+](=O)[O-])c([N+](=O)[O-])c1]

A suspension of 4-((4-amino-2,2,3,3-tetrafluorobutyl)amino)-3-(3-(benzyloxy)propoxy)-5-nitrobenzamide (3 g, 6.14 mmol), 4-fluoro-3-nitrobenzamide (1.696 g, 9.21 mmol) and potassium carbonate (1.698 g, 12.28 mmol) in DMF (30 mL) was stirred under nitrogen at 60° C. overnight. When cooled, water was added (50 mL) and the aqueous phase was extracted with EtOAc (2×100 mL). The combined organic layer was washed with water (3×200 mL) and brine (200 mL), dried, and concentrated under vacuum. The crude product was purified by silica gel chromatography (10 g column, 30-100% gradient of EtOAc/petroleum ether).

The appropriate fractions were pooled and concentrated to afford 3-(3-(benzyloxy)propoxy)-4-((4-((4-carbamoyl-2-nitrophenyl)amino)-2,2,3,3-tetrafluorobutyl)amino)-5-nitrobenzamide (2 g, 3.06 mmol, 49.9% yield) as a yellow solid. LCMS (m/z): 653 [M+H]$^+$.

Step 4: 3-amino-4-((4-((2-amino-4-carbamoylphenyl)amino)-2,2,3,3-tetrafluorobutyl)amino)-5-(3-(benzyloxy)propoxy)benzamide

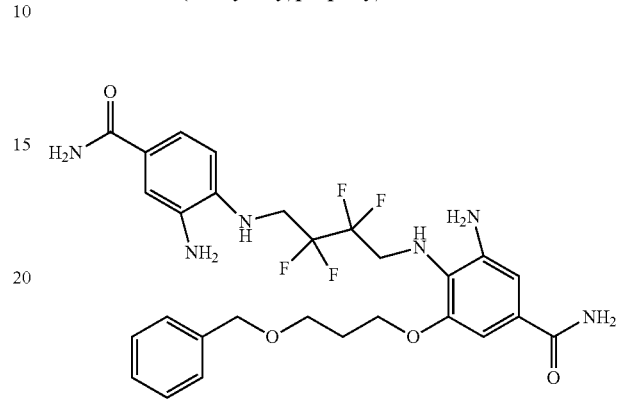

To a stirred suspension of 3-(3-(benzyloxy)propoxy)-4-((4-((4-carbamoyl-2-nitrophenyl)amino)-2,2,3,3-tetrafluorobutyl)amino)-5-nitrobenzamide (1.9 g, 2.91 mmol) in acetic acid (20 mL) under nitrogen was added solid zinc (1.904 g, 29.1 mmol) in one portion. The reaction mixture was stirred at 25° C. for 2 h. The reaction solution was then filtered and the filtrate was concentrated under vacuum to give 3-amino-4-((4-((2-amino-4-carbamoylphenyl)amino)-2,2,3,3-tetrafluorobutyl)amino)-5-(3-(benzyloxy)propoxy)benzamide (1.5 g, 2.53 mmol, 87% yield) as a blown solid. LCMS (m/z): 593 [M+H]$^+$.

Step 5: 2-amino-1-(4-(2-amino-5-carbamoyl-1H-benzo[d]imidazol-1-yl)-2,2,3,3-tetrafluorobutyl)-7-(3-(benzyloxy)propoxy)-1H-benzo[d]imidazole-5-carboxamide

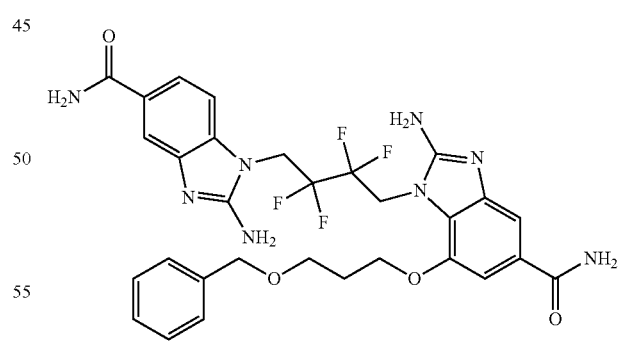

To a solution of 3-amino-4-((4-((2-amino-4-carbamoylphenyl)amino)-2,2,3,3-tetrafluorobutyl)amino)-5-(3-(benzyloxy)propoxy)benzamide (2.1 g, 3.54 mmol) in MeOH (20 mL) was added cyanogen bromide (1.126 g, 10.63 mmol). The reaction mixture was stirred at 25° C. for 16 h. The mixture was diluted with diethyl ether (30 mL). The mixture was filtered and the filter cake washed with diethyl ether. The filtrate was concentrated under reduced pressure to afford 2-amino-1-(4-(2-amino-5-carbamoyl-1H- benzo[d]imidazol-1-yl)-2,2,3,3-tetrafluorobutyl)-7-(3-(benzyloxy)propoxy)-1H-benzo[d]imidazole-5-carboxamide (1.8 g, 2.381 mmol, 67.2% yield, ~85% purity) as a grey solid. The product was used directly without further purification. LCMS (m/z): 643 [M+H]⁺.

Step 6: 7-(3-(benzyloxy)propoxy)-1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-1H-benzo[d]imidazole-5-carboxamide

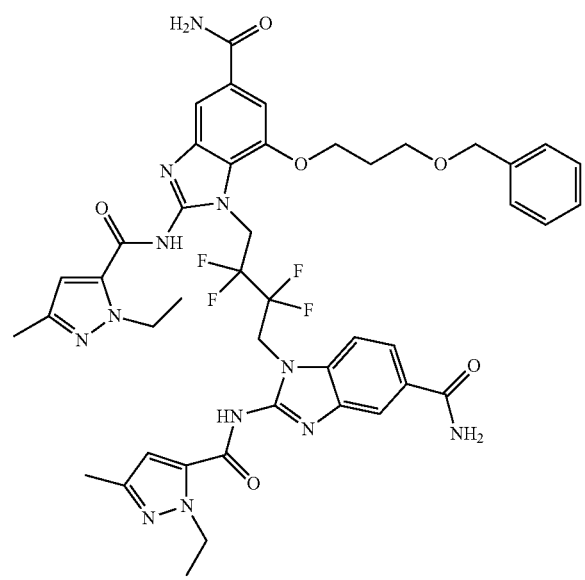 [SMILES: CCn1nc(C)cc1C(=O)Nc1nc2cc(C(N)=O)ccc2n1CC(F)(F)C(F)(F)Cn1c(NC(=O)c2cc(C)nn2CC)nc2cc(C(N)=O)cc(OCCCOCc3ccccc3)c21]

To a solution of 1-ethyl-3-methyl-1H-pyrazole-5-carboxylic acid (0.864 g, 5.60 mmol), 2-amino-1-(4-(2-amino-5-carbamoyl-1H-benzo[d]imidazol-1-yl)-2,2,3,3-tetrafluorobutyl)-7-(3-(benzyloxy)propoxy)-1H-benzo[d]imidazole-5-carboxamide (1.8 g, 2.80 mmol) and DIPEA (1.957 mL, 11.20 mmol) in DMF (20 mL) was added HATU (2.66 g, 7.00 mmol). The reaction mixture was stirred at 60° C. for 16 h. The mixture was poured into water. The precipitate was collected by filtration, washed with water, MeCN and diethyl ether, and then dried under vacuum to afford 7-(3-(benzyloxy)propoxy)-1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-1H-benzo[d]imidazole-5-carboxamide (1.1 g, 1.05 mmol, 37.3% yield, ~87% purity) as a light brown solid. The product was used without further purification. LCMS (m/z): 915 [M+H]⁺.

Step 7: 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-(3-hydroxypropoxy)-1H-benzo[d]imidazole-5-carboxamide

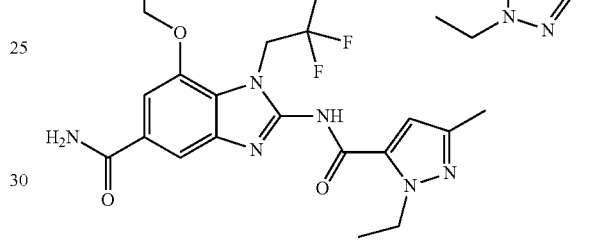

To a solution of 7-(3-(benzyloxy)propoxy)-1-(4-(5-carbamoyl-2-(1-ethyl-3-methyl-11H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-1H-benzo[d]imidazole-5-carboxamide (1.1 g, 1.2 mmol) in MeOH (30 mL) and NMP (10.0 mL) was added Pd on carbon (1.279 g). The reaction was hydrogenated using the H-cube system (4 atm hydrogen) at 60° C. for 72 h. The mixture was diluted with DMF (20 mL). The catalyst was then removed by filtration and the filtrate was concentrated under reduced pressure. The crude product was purified by preparative HPLC (Gemini-C18, 5p silica, 21×150 mm column, 10-60% gradient of MeCN/water with 0.1% TFA modifier). Pure fractions were pooled and evaporated to dryness to afford 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-(3-hydroxypropoxy)-1H-benzo[d]imidazole-5-carboxamide (75 mg, 0.086 mmol, 7.19% yield) as a pink solid. ¹H NMR (400 MHz, DMSO) δ 13.06-13.04 (m, 2H), 8.06-8.03 (m, 3H), 7.84 (d, J=8.4 Hz, 1H), 7.70 (s, 1H), 7.53 (d, J=8.4 Hz, 1H), 7.46 (s, 1H), 7.40 (s, 2H), 6.66-6.65 (m, 2H), 5.27-2.20 (m, 4H), 4.62-4.50 (m, 5H), 4.26 (t, J=6.1 Hz, 2H), 3.55 (t, J=5.7 Hz, 2H), 2.06 (s, 6H), 1.98-1.82 (m, 2H), 1.33 (t, J=7.0 Hz, 6H). LCMS (m/z): 824.4 [M+H]⁺.

Step 8: (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2trifluoroacetic Acid Salt

Example 18

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide

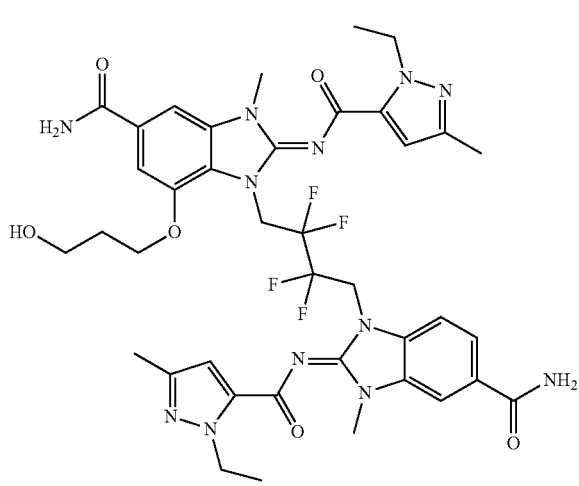 [SMILES: CCn1nc(C)cc1C(=O)/N=c1\n(C)c2cc(C(N)=O)ccc2n1CC(F)(F)C(F)(F)Cn1/c(=N/C(=O)c2cc(C)nn2CC)n(C)c2cc(C(N)=O)cc(OCCCO)c21]

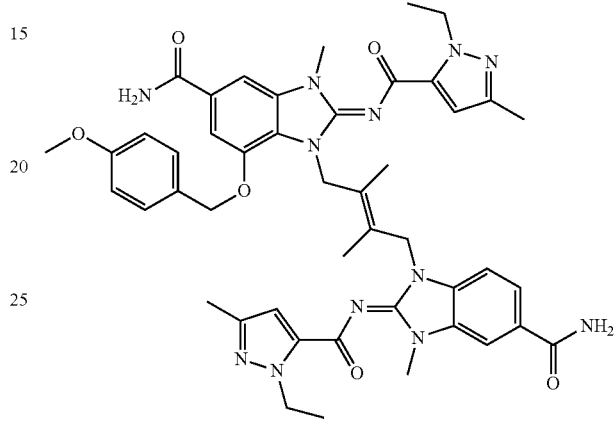

Step 1: (E)-4-((4-(1,3-dioxoisoindolin-2-yl)-2,3-dimethylbut-2-en-1-yl)amino)-3-nitrobenzamide

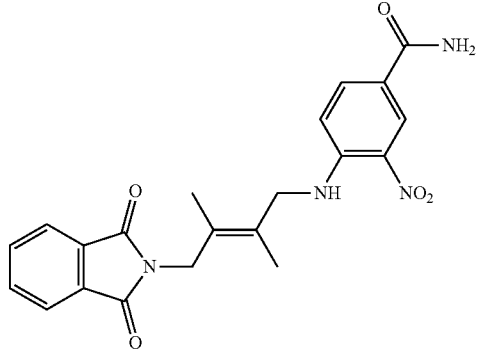 [SMILES: C/C(CNc1ccc(C(N)=O)cc1[N+](=O)[O-])=C(/C)CN1C(=O)c2ccccc2C1=O]

Into an 8-mL vial were placed 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-(3-hydroxypropoxy)-1H-benzo[d]imidazole-5-carboxamide (25 mg, 0.030 mmol), cesium carbonate (49.4 mg, 0.152 mmol), and DMF (1 mL). To this solution was added methyl iodide (4.26 µL, 0.068 mmol). The vial was capped and the mixture was stirred at room temperature overnight (~14 hours). The sample was diluted with more DMF and directly purified by mass-directed preparative HPLC (XSELECT CSH C18, 5 um packing, 150×30 mm column, 15-55% gradient of MeCN/water with 0.1% TFA modifier). The corresponding fractions were pooled and concentrated in vacuo to provide (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide, 2 trifluoroacetic acid salt (2 mg, 1.702 µmol, 5.62% yield) as a clear solid. $^1$H NMR (DMSO-$d_6$, 600 MHz): δ ppm 8.09 (s, 2H), 8.05 (br. s., 1H), 7.89 (dd, J=8.4, 1.2 Hz, 1H), 7.75 (s, 1H), 7.57 (d, J=8.3 Hz, 1H), 7.51 (s, 1H), 7.48 (br. s., 1H), 7.46 (br. s., 1H), 6.52 (s, 1H), 6.51 (s, 1H), 5.15-5.30 (m, 4H), 4.51-4.48 (m, 4H), 4.22 (br. t., J=6.5 Hz, 2H), 3.60 (s, 3H), 3.57 (s, 3H), 3.51 (br. t., J=6.0 Hz, 2H), 2.15 (s, 3H), 2.12 (s, 3H), 1.84 (br. t., J=6.3 Hz, 2H), 1.24-1.26 (m, 6H). LCMS (m/z): 853.4 [M+H]$^+$.

To a solution of (E)-2-(4-amino-2,3-dimethylbut-2-en-1-yl)isoindoline-1,3-dione (5.7 g, 23.33 mmol) and 4-fluoro-3-nitrobenzamide (3.9 g, 21.18 mmol) in DMSO (65 mL) was added potassium carbonate (6.44 g, 46.6 mmol). The reaction was stirred at room temperature for 3 h. The reaction mixture was poured into a flask containing 300 mL of rapidly stirred water. The mixture was stirred for 5 min, filtered and the filtered solids were rinsed sequentially with water, diethyl ether (2×), and ethyl acetate (2×). The solid was collected, stirred in hexanes (30 mL), filtered and dried to afford (E)-4-((4-(1,3-dioxoisoindolin-2-yl)-2,3-dimethylbut-2-en-1-yl)amino)-3-nitrobenzamide (6.77 g, 16.6 mmol, 78% yield) as a bright yellow solid. LCMS (m/z): 409.2 [M+H]$^+$.

Step 2: (E)-4-((4-((4-carbamoyl-2-nitrophenyl)amino)-2,3-dimethylbut-2-en-1-yl)amino)-3-((4-methoxybenzyl)oxy)-5-nitrobenzamide Step 3: (E)-3-amino-4-((4-((2-amino-4-carbamoylphenyl)amino)-2,3-dimethylbut-2-en-1-yl)amino)-5-((4-methoxybenzyl)oxy)benzamide

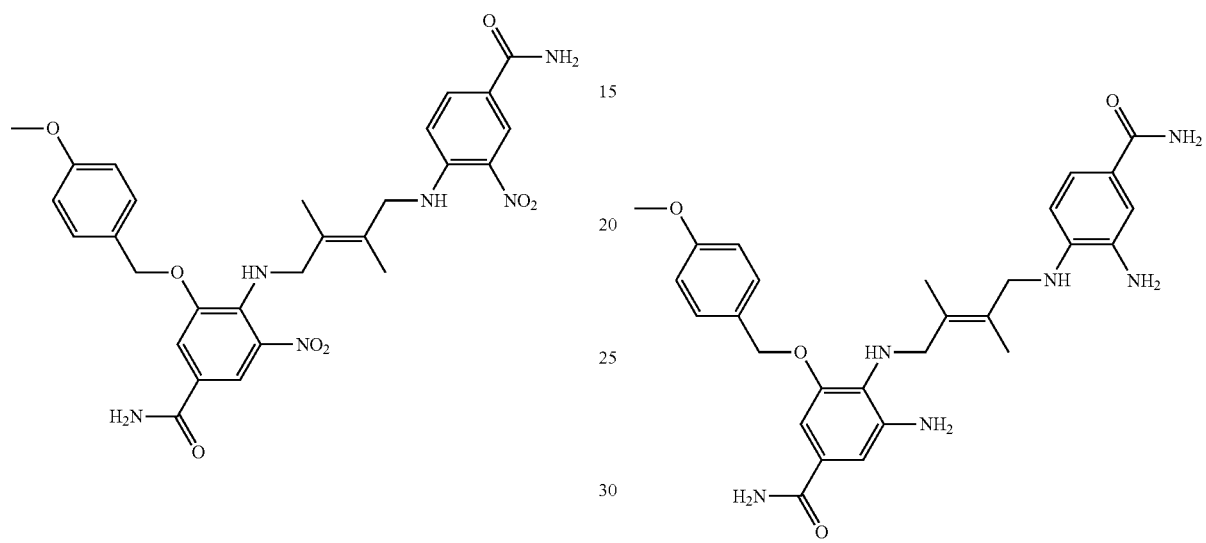

To a suspension of (E)-4-((4-(1,3-dioxoisoindolin-2-yl)-2,3-dimethylbut-2-en-1-yl)amino)-3-nitrobenzamide (6.4 g, 15.67 mmol) in EtOH (100 mL) was added hydrazine monohydrate (0.84 mL, 17.2 mmol). After 10 min, EtOH (50 ml) was added to facilitate stirring. The reaction mixture was heated at 80° C. for 20 h. The reaction was filtered while still warm and desired product was found in both solids and filtrate. The solids and filtrate were combined, concentrated to dryness and used crude in the next reaction.

To a bright yellow suspension of (E)-4-((4-amino-2,3-dimethylbut-2-en-1-yl)amino)-3-nitrobenzamide (4.65 g, 10.53 mmol) and 4-chloro-3-((4-methoxybenzyl)oxy)-5-nitrobenzamide (3.30 g, 9.80 mmol) in 1-butanol (100 mL) was added sodium bicarbonate (2.47 g, 29.4 mmol). The mixture was heated at 120° C. After 18 h, the reaction mixture was cooled to room temperature, stirred for 15 min and the solids were filtered and rinsed with n-butanol (2×25 mL). One portion of a saturated NaHCO$_3$ solution was diluted with one portion of water. Solids were washed with the diluted NaHCO$_3$ solution (2×25 mL), water (1×25 mL), diluted NaHCO$_3$ solution (50 mL) and water (30 mL). The solid was collected in a round bottom flask and stirred in the diluted bicarb solution (100 mL) at room temperature for 2 h. The solids were filtered, washed with water and dried in a vacuum oven to afford (E)-4-((4-((4-carbamoyl-2-nitrophenyl)amino)-2,3-dimethylbut-2-en-1-yl)amino)-3-((4-methoxybenzyl)oxy)-5-nitrobenzamide (3.62 g, 6.3 mmol, 63.8% yield) as an orange solid. LCMS (m/z): 579.3 [M+H]$^+$.

To a suspension of (E)-4-((4-((4-carbamoyl-2-nitrophenyl)amino)-2,3-dimethylbut-2-en-1-yl)amino)-3-((4-methoxybenzyl)oxy)-5-nitrobenzamide (3.46 g, 5.98 mmol) in MeOH (25 mL) and acetic acid (20 mL) was added 1% Pt with 2% V on activated carbon (50-70% wetted powder, 1.167 g, 0.060 mmol). The flask was stirred under a hydrogen atmosphere (hydrogen balloon) at room temperature for 6 h. MeOH (10 mL) was used to rinse solids off the sides of the flask and stirring was continued for another 16 h. After removal of hydrogen, the reaction was filtered through Celite, rinsed with MeOH and concentrated to afford a thick, orange oil. DCM (15 mL) was added and, with stirring, the resulting mixture was treated with saturated NaHCO$_3$ solution (in 1 mL portions until bubbling stopped and aqueous layer was basic). The liquid was decanted away, and the remaining solid was partitioned between 3:1 CHCl$_3$:EtOH and brine. The organic layer was dried over sodium sulfate and concentrated to provide a light brown foam. The foam was triturated with MeOH to afford (E)-3-amino-4-((4-((2-amino-4-carbamoylphenyl)amino)-2,3-dimethylbut-2-en-1-yl)amino)-5-((4methoxybenzyl)oxy)benzamide (1.4 g, 2.70 mmol, 45.1% yield). LCMS (m/z): 519.4 [M+H]$^+$.

Step 4: (E)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-7-((4-methoxybenzyl)oxy)-1H-benzo[d]imidazole-5-carboxamide Step 5: (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide

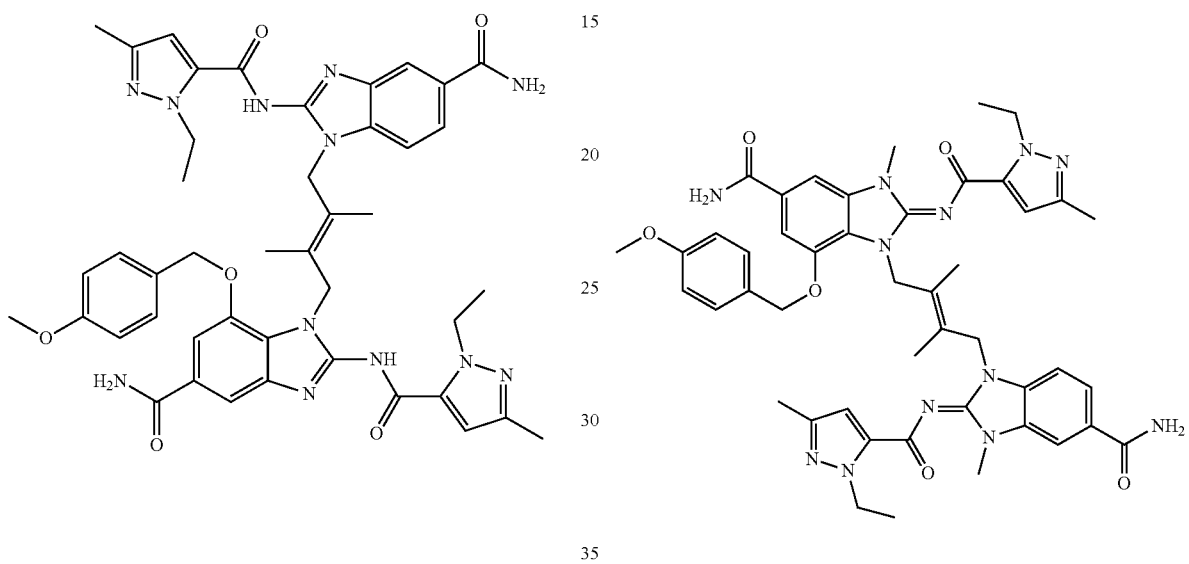

To an ice-cold solution of (E)-3-amino-4-((4-((2-amino-4-carbamoylphenyl)amino)-2,3-dimethylbut-2-en-1-yl)amino)-5-((4-methoxybenzyl)oxy)benzamide (1.40 g, 2.70 mmol) in DMF (18 mL) was added dropwise over 2 minutes 1-ethyl-3-methyl-1H-pyrazole-5-carbonyl isothiocyanate (~1 M in dioxane, 5.40 mL, 5.40 mmol). After 15 min, EDC (1.29 g, 6.75 mmol) and TEA (1.881 mL, 13.50 mmol) were added. The reaction was warmed to room temperature and heated at 40° C. for 22 h. The reaction was cooled to room temperature and poured into a rapidly stirred solution of 3:1 water:saturated aqueous NH$_4$Cl solution (100 mL). Fine solids formed immediately and the mixture was stirred another 10 min. The solid was filtered, washed twice with water (50 mL) and dried in a vacuum oven at 50° C. overnight to give (E)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-7-((4-methoxybenzyl)oxy)-1H-benzo[d]imidazole-5-carboxamide (2.20 g, 2.48 mmol, 92% yield) as a light tan solid. $^1$H NMR (DMSO-d$_6$) δ: 12.97 (d, J=3.3 Hz, 2H), 8.08 (s, 1H), 8.03 (br. s., 1H), 7.96 (br. s., 1H), 7.68-7.75 (m, 2H), 7.50 (s, 1H), 7.40 (d, J=9.6 Hz, 2H), 7.16 (d, J=8.4 Hz, 1H), 7.06-7.12 (m, 2H), 6.72 (s, 1H), 6.70 (s, 1H), 6.56 (s, 1H), 6.50 (s, 1H), 5.04 (br. s., 2H), 4.96 (s, 2H), 4.88 (br. s., 2H), 4.53-4.62 (m, 4H), 3.59 (s, 3H), 2.10 (s, 3H), 2.05 (s, 3H), 1.66 (s, 3H), 1.32 (t, J=7.0 Hz, 6H), 1.17 (s, 3H). LCMS (m/z): 841.5 [M+H]$^+$.

To a solution of (E)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-7-((4-methoxybenzyl)oxy)-1H-benzo[d]imidazole-5-carboxamide (1.30 g, 1.546 mmol) in DMF (12 mL) were added cesium carbonate (1.511 g, 4.64 mmol) and methyl iodide (0.242 mL, 3.86 mmol). The reaction mixture was stirred at room temperature for 1 h. Water (120 mL) was slowly added to the reaction mixture. The mixture was vigorously stirred for 30 min. The resulting solids were collected on a filter and dried. The crude product was purified by silica gel chromatography (80 g column, 30-80% gradient of (3:1 EA:EtOH with 1% ammonium hydroxide)/hexanes) to provide the title compound (1.01 g, 1.16 mmol, 74% yield) as a light yellow solid. $^1$H NMR (DMSO-d$_6$) δ: 8.15 (s, 1H), 8.10 (br. s., 1H), 8.05 (br. s., 1H), 7.77-7.82 (m, 2H), 7.62 (s, 1H), 7.52 (br. s., 1H), 7.49 (br. s., 1H), 7.22 (d, J=8.6 Hz, 1H), 7.17 (d, J=8.6 Hz, 2H), 6.68 (d, J=8.9 Hz, 2H), 6.41 (s, 1H), 6.38 (s, 1H), 5.09 (s, 2H), 4.96 (s, 2H), 4.77 (s, 2H), 4.48 (q, J=7.0 Hz, 4H), 3.58-3.63 (m, 6H), 3.56 (s, 3H), 2.07-2.11 (m, 6H), 1.55 (s, 3H), 1.22-1.28 (m, 6H), 1.16 (s, 3H). LCMS (m/z): 869.6 [M+H]$^+$.

Example 19

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-hydroxy-3-methyl-2,3-dihydro-1H-benzo[d]imidazole-5-carboxamide

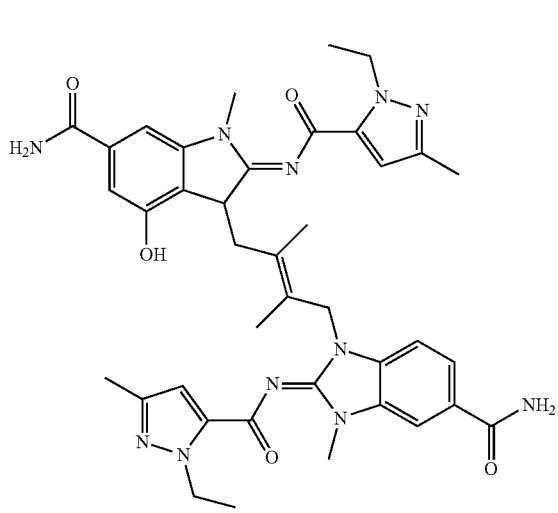 [SMILES: CCn1nc(C)cc1C(=O)/N=C1/C(C/C(C)=C(\C)Cn2/c(=N/C(=O)c3cc(C)nn3CC)n(C)c3cc(C(N)=O)ccc32)c2c(O)cc(C(N)=O)cc2N1C]

To a suspension of (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide (930 mg, 1.070 mmol) in DCM (15 mL) was added HCl (4 M in dioxane, 1.34 mL, 5.35 mmol). Reaction mixture became thick. DCM (10 mL) and MeOH (2 mL) was added to obtain a homogeneous solution. The reaction was stirred at room temperature for 16 h. Owing to incomplete reaction, the reaction mixture was concentrated and the solid residue suspended in DCM (15 mL) and TFA (0.412 mL, 5.35 mmol). In 30 min, the deprotection was complete. The reaction mixture was concentrated and the residue partitioned between 3:1 CHCl$_3$:EtOH and saturated NaHCO$_3$ solution. The solids present were filtered and dried to provide the title compound (427 mg, 0.57 mmol). The remaining organic phase was concentrated and the residue purified by silica gel chromatography (12 g silica column, 1-8% gradient of MeOH/DCM) to provide addition amounts of the title compound (130 mg, 0.17 mmol) as an off-white solid. $^1$H NMR (DMSO-d$_6$) δ ppm 10.68 (s, 1H), 8.10 (s, 1H), 8.01 (br. s., 1H), 7.96 (br. s., 1H), 7.80 (d, J=8.4 Hz, 1H), 7.62 (s, 1H), 7.46 (br. s., 1H), 7.38 (br. s., 1H), 7.32 (s, 1H), 7.22 (d, J=8.4 Hz, 1H), 6.47 (s, 1H), 6.33 (s, 1H), 5.07 (s, 2H), 4.83 (s, 2H), 4.44-4.56 (m, 4H), 3.58 (s, 3H), 3.53 (s, 3H), 2.14 (s, 3H), 2.07 (s, 3H), 1.65 (s, 3H), 1.48 (s, 3H), 1.31-1.24 (m, 6H). LCMS (m/z): 749.5 [M+H]$^+$.

Example 20

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide

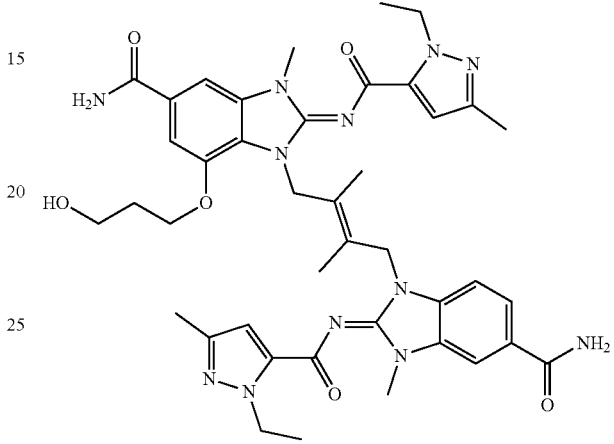

Step 1: (E)-4-((4-amino-2,3-dimethylbut-2-en-1-yl)amino)-3-nitrobenzamide

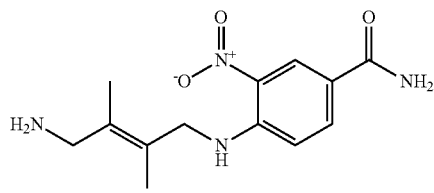

To (E)-2,3-dimethylbut-2-ene-1,4-diamine, 2Hydrochloride (4.4 g, 23.52 mmol) and ethanol (81 ml) and was added a solution of potassium carbonate (6.76 g, 48.9 mmol) in water (81 ml). Once all solids were dissolved, 4-fluoro-3-nitrobenzamide (3.0 g, 16.29 mmol) was added in one portion to the purple-brown solution at room temperature. The reaction mixture was stirred at room temperature for 105 min, then heated at 50° C. for 90 min and filtered. The filtrate was acidified with 6N HCl. The aqueous layer was washed with DCM (2×). The combined organics were extracted with water (1×). The combined aqueous layers were basified with 6N NaOH and sat. sodium bicarbonate and extracted with 3:1 chloroform/ethanol mixture (3×). The combined organic extracts were dried over sodium sulfate, filtered, and concentrated to dryness to afford (E)-4-((4-amino-2,3-dimethylbut-2-en-1-yl)amino)-3-nitrobenzamide (1.8 g, 5.30 mmol, 32.5% yield) as a brownish-yellow residue. LCMS (m/z): 279.1 [M+H]$^+$.

Step 2: (E)-3-(3-((tert-butyldimethylsilyl)oxy) propoxy)-4-((4-((4-carbamoyl-2-nitrophenyl)amino)-2,3-dimethylbut-2-en-1-yl)amino)-5-nitrobenzamide

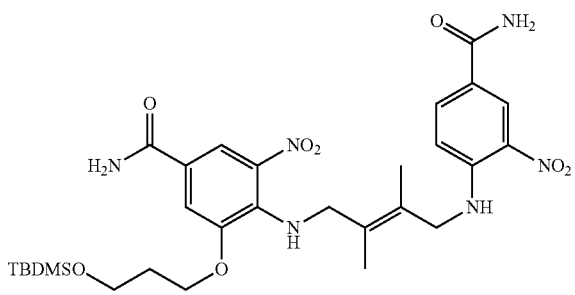

To a suspension of crude (E)-4-((4-amino-2,3-dimethylbut-2-en-1-yl)amino)-3-nitrobenzamide (715 mg, 2.312 mmol) in 1-butanol (10.9 mL) was added DIE (1.14 mL, 6.56 mmol). The mixture was stirred for 10 min, then 3-(3-((tert-butyldimethylsilyl)oxy)propoxy)-4-chloro-5-nitrobenzamide (850 mg, 2.186 mmol) was added. The reaction mixture was heated at 120° C. overnight. The reaction was cooled to room temperature and an orange solid precipitated. The mixture was filtered and the filtercake was washed with ethyl acetate to afford crude (E)-3-(3-((tert-butyldimethylsilyl)oxy)propoxy)-4-((4-((4-carbamoyl-2-nitrophenyl)amino)-2,3-dimethylbut-2-en-1-yl)amino)-5-nitrobenzamide (786 mg, 1.022 mmol, 46.8% yield) as a bright orange solid that still contained residual n-BuOH, but was carried on as is. LCMS (m/z): 631.3 [M+H]$^+$.

Step 3: (E)-3-amino-4-((4-((2-amino-4-carbamoylphenyl)amino)-2,3-dimethylbut-2-en-1-yl) amino)-5-(3-((tert-butyldimethylsilyl)oxy)propoxy) benzamide

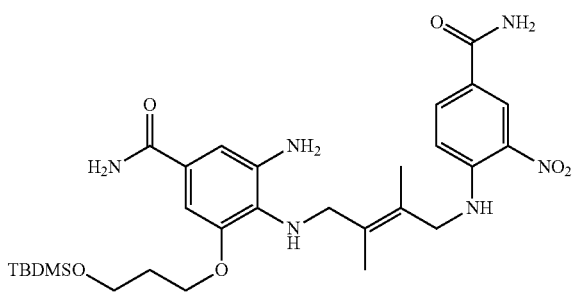 [SMILES: C/C(CNc1ccc(C(N)=O)cc1[N+](=O)[O-])=C(/C)CNc1c(OCCCO[Si](C)(C)C(C)(C)C)cc(C(N)=O)cc1[N+](=O)[O-]]

To a mixture of (E)-3-(3-((tert-butyldimethylsilyl)oxy) propoxy)-4-((4-((4-carbamoyl-2-nitrophenyl)amino)-2,3-dimethylbut-2-en-1-yl)amino)-5-nitrobenzamide (1.82 g, 2.453 mmol) in methanol (53.3 ml) was added ammonium chloride (2.62 g, 49.1 mmol) followed by addition of zinc (3.21 g, 49.1 mmol). The heterogeneous mixture was stirred at rt for 10 min. The reaction mixture was filtered and the filtercake was washed with methanol. The filtrate was dry-loaded onto silica gel and purified silica gel chromatography (80 g column, 0%-20% methanol, DCM with 0.1% NH$_4$OH modifier). Desired fractions were concentrated to dryness to afford (E)-3-amino-4-((4-((2-amino-4-carbamoylphenyl) amino)-2,3-dimethylbut-2-en-1-yl)amino)-5-(3-((tert-butyldimethylsilyl)oxy)propoxy)benzamide (503 mg, 0.881 mmol, 35.9% yield) as a white solid. LCMS (m/z): 571.5 [M+H]$^+$.

Step 4: (E)-7-(3-((tert-butyldimethylsilyl)oxy) propoxy)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d] imidazole-5-carboxamide

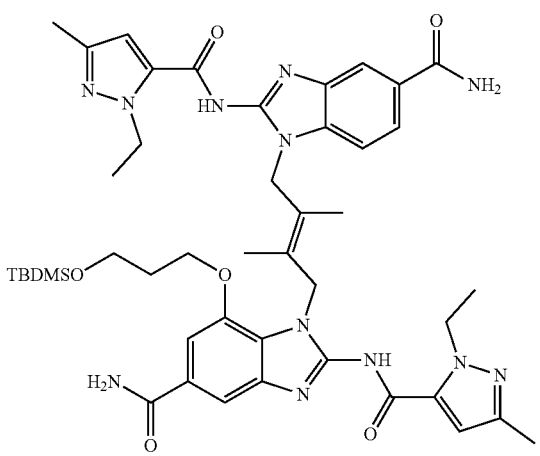

To a solution of (E)-3-amino-4-((4-((2-amino-4-carbamoylphenyl)amino)-2,3-dimethylbut-2-en-1-yl)amino)-5-(3-((tert-butyldimethylsilyl)oxy)propoxy)benzamide (500 mg, 0.876 mmol) in DMF (8.8 mL) at 0° C. was added dropwise and portionwise 1-ethyl-3-methyl-1H-pyrazole-5-carbonyl isothiocyanate in dioxane (~0.4 M, 4.82 mL, 1.93 mmol). After 15 min, additional isothiocyanate was added (~0.4 M, 400 μL) and the reaction mixture was stirred for 10 min. The reaction was treated with EDC (420 mg, 2.190 mmol) and TEA (610 μl, 4.38 mmol) and stirred at room temperature over the weekend. The reaction mixture was poured into 4:1 water/saturated ammonium chloride (200 mL) and the resulting suspension was filtered. The filtercake was dried under a stream of nitrogen to afford (E)-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide (614 mg, 0.687 mmol, 78% yield). $^1$H NMR (400 MHz, DMSO-d$_6$) δ ppm 12.92 (d, J=11.66 Hz, 2H), 7.99-8.08 (m, 2H), 7.90 (br. s., 1H), 7.70 (s, 1H), 7.65 (d, J=8.11 Hz, 1H), 7.31-7.43 (m, 3H), 7.16 (d, J=8.36 Hz, 1H), 6.60 (s, 1H), 6.42 (s, 1H), 5.14 (br. s., 2H), 4.98 (br. s., 2H), 4.48-4.66 (m, 4H), 4.14 (t, J=5.58 Hz, 2H), 3.65 (t, J=5.96 Hz, 2H), 2.02-2.14 (m, 6H), 1.61-1.74 (m, 6H), 1.33 (t, 7.13 Hz, 3H), 1.32 (t, 7.13 Hz, 3H), 0.80 (s, 11H), ~0.03 (s, 6H). LCMS (m/z): 893.4 [M+H]$^+$.

233

Step 5: (E)-7-(3-((tert-butyldimethylsilyl)oxy)
propoxy)-1-((E)-4-((E)-5-carbamoyl-2-((1-ethyl-3-
methyl-1H-pyrazole-5-carbonyl)imino)-3-methyl-2,
3-dihydro-1H-benzo[d]imidazol-1-yl)-2,3-
dimethylbut-2-en-1-yl)-2-((1-ethyl-3-methyl-1H-
pyrazole-5-carbonyl)imino)-3-methyl-2,3-dihydro-
1H-benzo[d]imidazole-5-carboxamide

234

Step 6: (E)-1-((E)-4-((E)-5-carbamoyl-2-((1-ethyl-3-
methyl-1H-pyrazole-5-carbonyl)imino)-3-methyl-2,
3-dihydro-1H-benzo[d]imidazol-1-yl)-2,3-dimethyl-
but-2-en-1-yl)-2-((1-ethyl-3-methyl-1H-pyrazole-5-
carbonyl)imino)-7-(3-hydroxypropoxy)-3-methyl-2,
3-dihydro-1H-benzo[d]imidazole-5-carboxamide

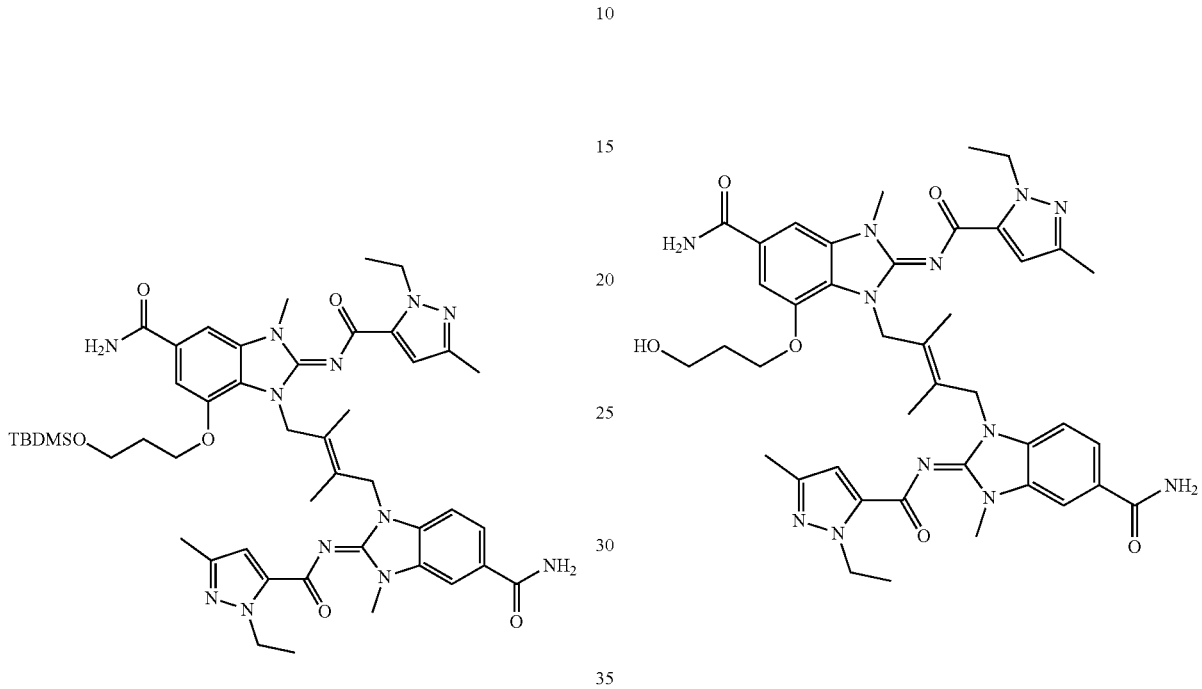

A mixture of (E)-7-(3-((tert-butyldimethylsilyl)oxy)
propoxy)-1-(4-(5-carbamoyl-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide (0.245 g, 0.274 mmol), cesium carbonate (0.268 g, 0.823 mmol) and methyl iodide (0.043 mL, 0.686 mmol) in DMF (2 mL) was stirred at room temperature for 18 h. The reaction mixture was partitioned between EtOAc (20 mL) and brine (20 mL). The aqueous layer was extracted with EtOAc (2×10 mL). The combined EtOAc layer was dried over magnesium sulfate, filtered and concentrated in vacuo. The crude product was purified by silica gel chromatography (RediSepRf High Performance Gold 40 g HP silica column, 40-80% gradient of (3:1 ethanol/ethyl acetate)/hexane with 2% NH$_4$OH modifier) to yield (E)-7-(3-((tert-butyldimethylsilyl)oxy)propoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide (0.040 g, 0.033 mmol, 11.9% yield). LCMS (m/z): 921.7 [M+H]$^+$.

To a mixture of (E)-7-(3-((tert-butyldimethylsilyl)oxy) propoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide (0.030 g, 0.033 mmol) in MeOH (0.5 mL) was added HCl in dioxane (4 M, 0.163 mL, 0.651 mmol), stirred at room temperature for 16 h. The reaction mixture was concentrated in vacuo. The crude product was purified by silica gel chromatography (RediSepRf High Performance Gold 40 g HP silica column, 40-90% gradient of (3:1 ethanol/ethyl acetate)/hexane with 2% NH$_4$OH modifier) to yield (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide (0.007 g, 7.72 µmol, 23.7% yield). $^1$H NMR (600 MHz, DMSO-d$_6$) δ 8.12 (s, 2H), 8.03 (br s, 1H), 7.81 (d, J=8.66 Hz, 1H), 7.78 (s, 1H), 7.50 (s, 1H), 7.47 (s, 1H), 7.45 (br s, 1H), 7.24 (d, J=8.85 Hz, 1H), 6.68 (br s, 1H), 6.45 (s, 1H), 6.34 (s, 1H), 5.06 (br s, 2H), 4.85 (s, 2H), 4.49-4.53 (m, 2H), 4.49 (br s, 2H), 4.19 (br t, J=6.36 Hz, 2H), 3.58 (s, 3H), 3.56 (s, 3H), 3.44 (br t, J=5.99 Hz, 2H), 2.10 (s, 3H), 2.07 (s, 3H), 1.72 (quin, J=6.27 Hz, 2H), 1.61 (s, 3H), 1.48 (s, 3H), 1.27 (t, J=7.10 Hz, 3H), 1.24 (t, J=7.09 Hz, 3H). LCMS (m/z): 807.6 [M+H]$^+$.

Table 1 show Examples 21-28, which can be prepared according to methods illustrated below:

| Example Number | Scheme | Name/Structure | $^1$H NMR LCMS (m/z) [M + H]$^+$ |
|---|---|---|---|
| Example 21 | Method 1 | (E)-1-(4-(5-carbamoyl-2-((1-ethyl-3-methyl-1H-pyrazol-5-carbonyl)imino)-3-methyl-2,3-dihydro-1H-benzo[d]imidazol-1-yl)-2,2,3,3-tetrafluorobutyl)-2-(1-ethyl-3-methyl-1H-pyrazole-5-carboxamido)-1H-benzo[d]imidazole-5-carboxamide, trifluoroacetic acid salt | $^1$H NMR (400 MHz, METHANOL-d$_4$) δ ppm 1.37 (dt, J = 11.15, 7.10 Hz, 6H) 2.22 (s, 6H) 3.72 (s, 3H) 4.54-4.72 (m, 4 H) 5.12-5.43 (m, 4H) 6.68 (s, 1H) 6.74 (s, 1H) 7.54 (d, J = 8.87 Hz, 1H) 7.62 (d, J = 8.11 Hz, 1H) 7.88 (d, J = 8.36 Hz, 1H) 7.97 (d, J = 8.62 Hz, 1H) 8.03 (s, 1H) 8.12 (s, 1H) LCMS (m/z) [M + H]$^+$ 765.5 |
| Example 22 | Method 1 | (2E,2'E)-1,1'-(2,3-dimethylbutane-1,4-diyl)bis(2-((1-ethyl-3-methyl-1H-pyrazol-5-carbonyl)imino)-3-methyl-2,3-dihydro-1H-benzo[d]imidazole-5-carboxamide | $^1$H NMR (METHANOL-d$_4$) δ ppm 8.34 (s, 2H), 8.11 (d, J = 8.6 Hz, 2H), 7.88 (d, J = 8.6 Hz, 2H), 6.98 (s, 2H), 4.56-4.66 (m, 6 H), 4.36-4.46 (m, 2H), 3.88 (s, 6H), 2.35 (br. s., 2H), 2.32 (s, 6H), 1.42 (t, J = 7.1 Hz, 6H), 0.97 (s, 3 H), 0.95 (s, 3H) LCMS (m/z) [M + H]$^+$ 735.4 |

| Example Number | Scheme | Name/Structure | ¹H NMR<br>LCMS (m/z)<br>[M + H]⁺ |
|---|---|---|---|
| Example 23 | Method 5 | (2E,2′E)-1,1′-((2R,3R)-2,3-dihydroxybutane-1,4-diyl)bis(2-((1-ethyl-3-methyl-1H-pyrazole-5-carbonyl)imino)-3-methyl-2,3-dihydro-1H-benzo[d]imidazole-5-carboxamide)<br>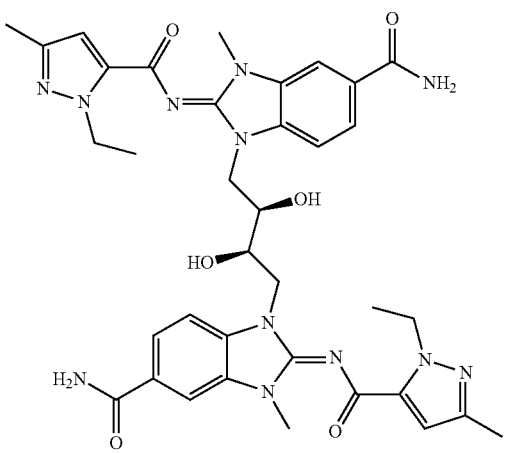 | ¹H NMR (400 MHz, METHANOL-d₄) δ ppm 8.07 (d, J = 1.27 Hz, 2H) 7.93 (dd, J = 8.62, 1.52 Hz, 2H) 7.66 (d, J = 8.36 Hz, 2 H) 6.52 (s, 2H) 4.55 (dd, J = 6.97, 5.70 Hz, 4H) 4.38 (d, J = 6.34 Hz, 4H) 4.05 (t, J = 6.21 Hz, 2H) 3.65 (s, 6H) 2.21 (s, 6H) 1.34 (t, J = 7.10 Hz, 6H)<br>LCMS (m/z) [M + H]⁺ 739.4 |
| Example 24 | Method 1 | (2E,2′E)-1,1′-(pentane-1,5-diyl)bis(2-((1-ethyl-3-methyl-1H-pyrazole-5-carbonyl)imino)-3-methyl-2,3-dihydro-1H-benzo[d]imidazole-5-carboxamide)<br>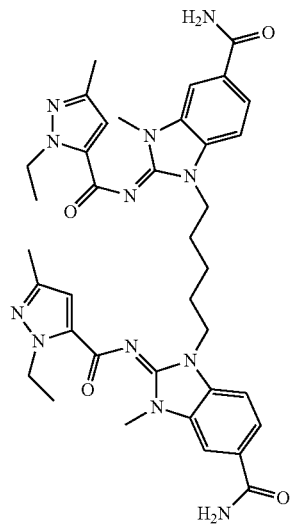 | ¹H NMR (DMSO-d₆) δ ppm 8.01-8.09 (m, 4H), 7.84 (dd, J = 8.4, 1.3 Hz, 2 H), 7.58 (d, J = 8.6 Hz, 2 H), 7.46 (br. s., 2H), 6.48 (s, 2H), 4.51 (q, J = 7.1 Hz, 4H), 4.11 (t, J = 7.0 Hz, 4H), 3.55 (s, 6H), 2.13 (s, 6H), 1.65-1.77 (m, 4H), 1.26 (t, J = 7.1 Hz, 8H)<br>LCMS (m/z) [M + H]⁺ 721.5 |

| Example Number | Scheme | Name/Structure | $^1$H NMR LCMS (m/z) [M + H]$^+$ |
|---|---|---|---|
| Example 25 | Method 1 | (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide | $^1$H NMR (DMSO-d$_6$) δ ppm 8.13 (s, 1H), 8.10 (br. s., 1H), 8.03 (br. s., 1 H), 7.77-7.83 (m, 2H), 7.45-7.54 (m, 3H), 7.24 (d, J = 8.4 Hz, 1H), 6.44 (s, 1H), 6.38 (s, 1H), 5.06 (s, 2H), 4.86 (s, 2 H), 4.45-4.56 (m, 4H), 4.12 (t, J = 6.2 Hz, 2H), 3.59 (s, 3H), 3.57 (s, 3 H), 3.46 (t, J = 4.4 Hz, 4H), 2.25 (t, J = 7.1 Hz, 2H), 2.18 (br. s., 4H), 2.10 (s, 3H), 2.09 (s, 3H), 1.64-1.71 (m, 2H), 1.61 (s, 3 H), 1.51 (s, 3H), 1.22-1.31 (m, 6H) LCMS (m/z) [M + H]$^+$ 876.7 |
| Example 26 | Method 1 | 4-(((E)-6-carbamoyl-3-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-1-methyl-2,3-dihydro-1H-benzo[d]imidazol-4-yl)oxy)butanoic acid | $^1$H NMR (DMSO-d$_6$) δ ppm 8.13 (br. s., 2H), 8.04 (br. s., 1H), 7.78-7.84 (m, 2H), 7.45-7.55 (m, 3H), 7.27 (d, J = 8.4 Hz, 1H), 6.48 (s, 1H), 6.41 (br. s., 1H), 5.09 (br. s., 2H), 4.87 (br. s., 2H), 4.44-4.54 (m, 4H), 4.12 (t, J = 6.2 Hz, 2H), 2.27 (t, J = 7.2 Hz, 2H), 2.10 (s, 3 H), 2.09 (s, 3H), 1.74-1.83 (m, 2H), 1.61 (s, 3 H), 1.50 (s, 3H), 1.21-1.31 (m, 6H) LCMS (m/z) [M + H]$^+$ 835.7 |

| Example Number | Scheme | Name/Structure | ¹H NMR<br>LCMS (m/z)<br>[M + H]⁺ |
|---|---|---|---|
| Example 27 | Method 1 | (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(3-methoxypropoxy)-3-methyl-2,3-dihydro-1H-benzo[d]imidazole-5-carboxamide<br>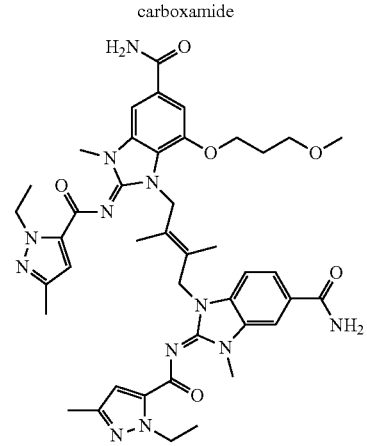 | ¹H NMR (DMSO-$d_6$) δ ppm 8.08-8.13 (m, 2H), 8.03 (br. s., 1H), 7.76-7.82 (m, 2H), 7.44-7.52 (m, 3H), 7.24 (t, J = 8.6 Hz, 1H), 6.45 (s, 1H), 6.37 (s, 1H), 5.06 (s, 2H), 4.86 (s, 2H), 4.44-4.55 (m, 4H), 4.15 (t, J = 6.5 Hz, 2H), 3.58 (s, 3H), 3.56 (s, 3H), 3.28-3.34 (m, 2H), 3.15 (s, 3H), 2.10 (s, 3H), 2.08 (s, 3H), 1.79 (quin, J = 6.2 Hz, 2H), 1.62 (s, 3H), 1.49 (s, 3H), 1.21-1.31 (m, 6H)<br>LCMS (m/z) [M + H]⁺ 821.7 |
| Example 28 | Method 1 | Methyl (E)-1-((E)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxylate<br>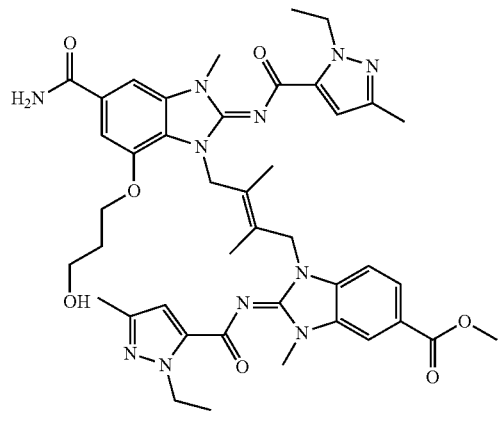 | ¹H NMR (DMSO-$d_6$) δ ppm 8.11 (m, 1H), 7.99-8.10 (m, 1H), 7.76-7.87 (m, 2H), 7.43-7.53 (m, 2H), 7.26 (m, 1H), 6.46 (m, 1H), 6.34 (m, 1H), 5.07 (s, 2H), 4.86 (m, 2H), 4.56-4.62 (m, 1H), 4.45-4.54 (m, 4H), 4.17-4.23 (m, 2H), 3.89-3.95 (m, 3H), 3.55-3.62 (m, 6H), 3.42-3.48 (m, 2H), 2.06-2.13 (m, 6H), 1.69-1.77 (m, 2H), 1.60-1.66 (m, 3H), 1.49 (s, 3H), 1.22-1.31 (m, 6H)<br>LCMS (m/z) [M + H]⁺ 822.6 |

Example 29

(E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide

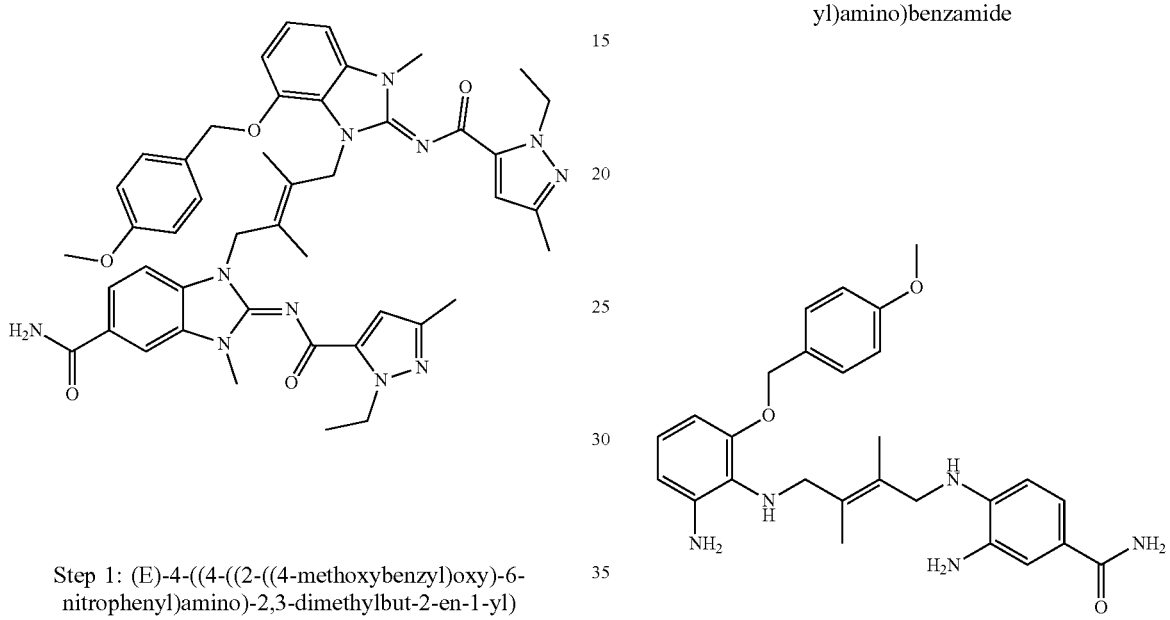

Step 1: (E)-4-((4-((2-((4-methoxybenzyl)oxy)-6-nitrophenyl)amino)-2,3-dimethylbut-2-en-1-yl)amino)-3-nitrobenzamide

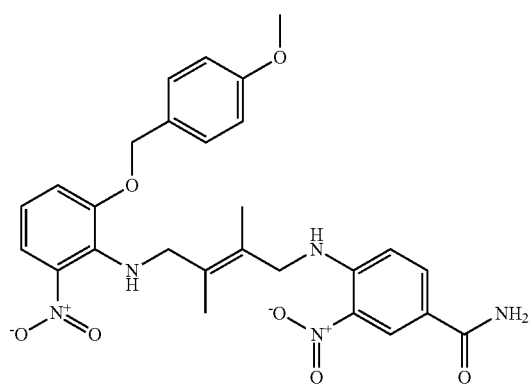

To a bright yellow/orange suspension of (E)-4-((4-amino-2,3-dimethylbut-2-en-1-yl)amino)-3-nitrobenzamide, hydrochloride (2.4 g, 7.62 mmol) and 2-fluoro-1-((4-methoxybenzyl)oxy)-3-nitrobenzene (2.114 g, 7.62 mmol) in DMF (20 mL) was added TEA (3.19 mL, 22.87 mmol). The thick mixture was stirred at room temperature for 2 h, then heated at 50° C. for 18 h. The reaction mixture was added slowly to rapidly stirring water (350 mL). A solid precipitated as clumps. Sonication (30 min) and stirring for 1 h provided a free flowing solid. The solid was filtered, rinsed with water and diethylether (3×30 mLs), and dried to give (E)-4-((4-((2-((4-methoxybenzyl)oxy)-6-nitrophenyl)amino)-2,3-dimethylbut-2-en-1-yl)amino)-3-nitrobenzamide (3.52, 6.25 mmol, 82% yield) as a bright orange solid. LCMS (m/z): 536.2 [M+H]$^+$.

Step 2: (E)-3-amino-4-((4-((2-amino-6-((4-methoxybenzyl)oxy)phenyl)amino)-2,3-dimethylbut-2-en-1-yl)amino)benzamide To a suspension of (E)-4-((4-((2-((4-methoxybenzyl)oxy)-6-nitrophenyl)amino)-2,3-dimethylbut-2-en-1-yl)amino)-3-nitrobenzamide (3.52 g, 6.57 mmol) in methanol (15 mL) and acetic acid (10 mL) was added 1% Pt with 2% V, on activated carbon, 50-70% wetted powder (1.282 g, 0.066 mmol). The atmosphere of the flask was exchanged with nitrogen and then hydrogen (balloon). After stirring 20 h at room temperature, the atmosphere was exchanged for nitrogen. Owing to incomplete reaction, the reaction mixture was stirred under a hydrogen atmosphere for an additional 5 h and then nitrogen reintroduced. The reaction mixture was passed and rinsed through Celite with 10% methanol/DCM. Concentration in vacuo provided a thick orange oil. The oil was taken up in DCM (100 mL) and saturated aqueous sodium bicarbonate solution was added until bubbing stopped. Separation and concentration of the organic layer provided a brown foam. A filterable solid was obtained from ethyl acetate containing small amounts of DCM and MeOH. The resulting solid was filtered and dried to provide (E)-3-amino-4-((4-((2-amino-6-((4-methoxybenzyl)oxy)phenyl)amino)-2,3-dimethylbut-2-en-1-yl)amino)benzamide (1.95 g, 3.90 mmol, 59.3% yield) as a light brown solid. LCMS (m/z): 476.3 [M+H]$^+$.

Step 3: (E)-2-(1-ethyl-3-methyl-1H-pyrazole-5-carboxamido)-1-(4-(2-(1-ethyl-3-methyl-1H-pyrazole-5-carboxamido)-7-((4-methoxybenzyl)oxy)-1H-benzo[d]imidazol-1-yl)-2,3-dimethylbut-2-en-1-yl)-1H-benzo[d]imidazole-5-carboxamide Step 4: (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide

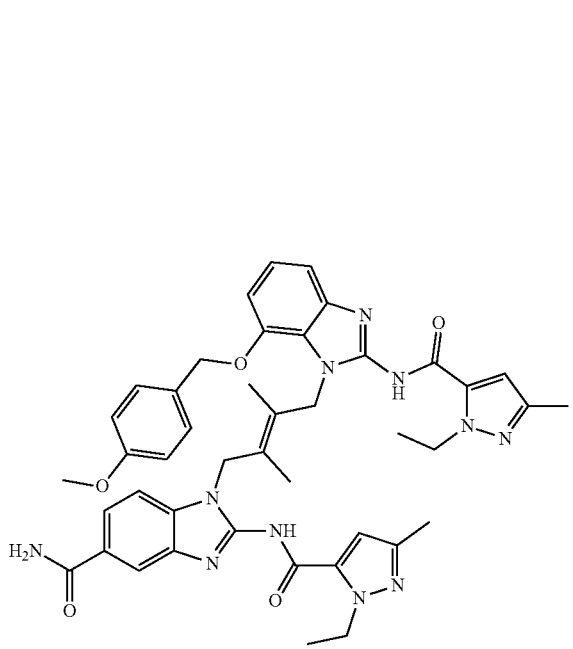 [SMILES: CCn1nc(C)cc1C(=O)Nc1nc2cc(C(N)=O)ccc2n1C/C(C)=C(\C)Cn1c(NC(=O)c2cc(C)nn2CC)nc2cccc(OCc3ccc(OC)cc3)c21]

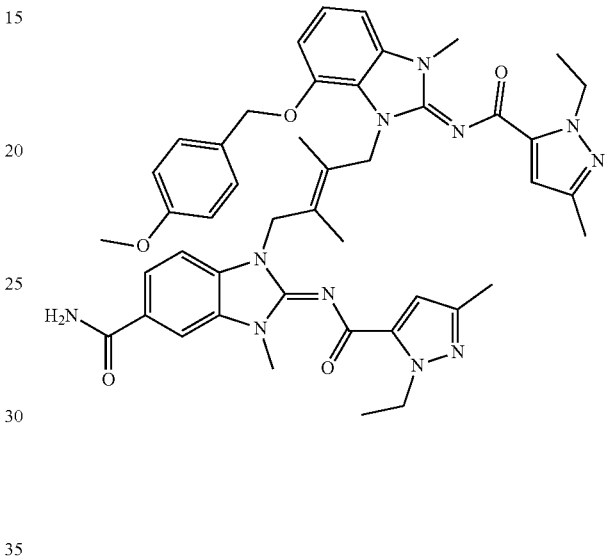

To a light brown solution of (E)-3-amino-4-((4-((2-amino-6-((4-methoxybenzyl)oxy)phenyl)amino)-2,3-dimethylbut-2-en-1-yl)amino)benzamide (1.93 g, 3.86 mmol) in DMF (20 mL) cooled in an ice/water bath was added 1-ethyl-3-methyl-1H-pyrazole-5-carbonyl isothiocyanate (~1M in dioxane, 7.71 mL, 7.71 mmol) quickly dropwise (over ~1 minute). The reaction mixture was stirred for 25 min. EDC (1.848 g, 9.64 mmol) and TEA (2.69 mL, 19.28 mmol) were added and the reaction was warmed to room temperature and stirred for 18 h. The reaction mixture was poured into rapidly stirring 1:1 saturated aqueous NH$_4$Cl solution:water (100 mL) to provide a fine precipitate. The precipitate was washed with water (2×15 mL), triturated twice with ethyl acetate (20 mL), and dried to provide (E)-2-(1-ethyl-3-methyl-1H-pyrazole-5-carboxamido)-1-(4-(2-(1-ethyl-3-methyl-1H-pyrazole-5-carboxamido)-7-((4-methoxybenzyl)oxy)-1H-benzo[d]imidazol-1-yl)-2,3-dimethylbut-2-en-1-yl)-1H-benzo[d]imidazole-5-carboxamide (2.32 g, 2.83 mmol, 73% yield) as a tan solid. LCMS (m/z): 798.4 [M+H]$^+$.

To a solution of (E)-2-(1-ethyl-3-methyl-1H-pyrazole-5-carboxamido)-1-(4-(2-(1-ethyl-3-methyl-1H-pyrazole-5-carboxamido)-7-((4-methoxybenzyl)oxy)-1H-benzo[d]imidazol-1-yl)-2,3-dimethylbut-2-en-1-yl)-1H-benzo[d]imidazole-5-carboxamide (1.09 g, 1.366 mmol) in DMF (15 mL) was added cesium carbonate (1.335 g, 4.10 mmol) and methyl iodide (0.214 mL, 3.42 mmol). The reaction mixture was stirred at room temperature for 5 h. Additional methyl iodide (0.060 mL, 0.956 mmol) was added and the mixture was stirred for another 18 h. Additional methyl iodide (0.060 mL, 0.956 mmol) and cesium carbonate (1.335 g, 4.10 mmol) were added and the mixture was heated at 50° C. for 4 h. The mixture was diluted with water (30 mL) and a sticky solid precipitated. Vigorous stirring provided a filterable solid that was subsequently collected on a filter and rinsed with water. Silica gel chromatography (40 g silica, 10-90% gradient of [3:1 EtOAc:EtOH]/heptane) provided (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide (430 mg, 0.509 mmol, 37% yield) as a tan foam. $^1$H NMR (400 MHz, DMSO-d$_6$) δ ppm 8.14 (s, 1H), 8.01 (br. s., 1H), 7.78 (dd, J=8.4, 1.4 Hz, 1H), 7.45 (br. s., 1H), 7.25-7.32 (m, 1H), 7.13-7.23 (m, 4H), 7.08 (d, J=8.0 Hz, 1H), 6.71 (d, J=8.5 Hz, 2H), 6.43 (s, 1H), 6.37 (s, 1H), 5.03 (s, 2H), 4.97 (s, 2H), 4.78 (s, 2H), 4.45-4.53 (m, 4H), 3.63 (s, 3H), 3.60 (s, 3H), 3.54 (s, 3H), 2.10 (s, 3H), 2.09 (s, 3H), 1.56 (s, 3H), 1.19-1.31 (m, 6H), 1.18 (s, 3H). LCMS (m/z): 826.5 [M+H]$^+$.

Example 30

(E)-1-((E)-4-((E)-7-(benzyloxy)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide

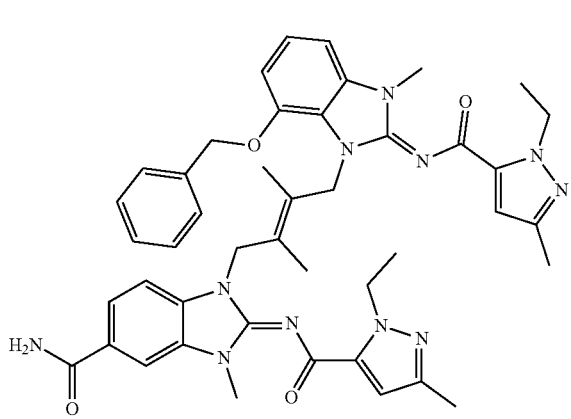 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2cccc(OCc3ccccc3)c21]

To a suspension of (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-hydroxy-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide (45 mg, 0.055 mmol) in DMF (1 mL) was added (bromomethyl)benzene (7.26 μL, 0.061 mmol) followed by potassium carbonate (9.97 mg, 0.072 mmol). The reaction mixture was initially stirred at 50° C. for 3 h and then at room temperature for 16 h. The mixture was diluted with water. The aqueous layer was extracted several times with 3:1 CHCl$_3$:EtOH. Solvents were evaporated in vacuo and the residue was purified by mass-directed HPLC (XSELECT CSH C18, 5 um packing, 150×30 mm column, 30-85% gradient of MeCN/water with 0.1% TFA modifier). A few drops of saturated sodium bicarbonate solution were added to each clean fraction. The ACN was removed using a stream of nitrogen. The suspended solids were filtered, rinsed with water, and dried to provide pure (E)-1-((E)-4-((E)-7-(benzyloxy)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide (30 mg, 0.037 mmol, 67%) as a white solid. $^1$H NMR (400 MHz, DMSO-d$_6$) δ ppm 8.12 (s, 1H), 8.01 (br. s., 1H), 7.76 (dd, J=8.4, 1.4 Hz, 1H), 7.44 (br. s., 1H), 7.12-7.32 (m, 8H), 7.07 (d, J=7.8 Hz, 1H), 6.47 (s, 1H), 6.38 (s, 1H), 5.13 (s, 2H), 4.99 (s, 2H), 4.78 (s, 2H), 4.45-4.55 (m, 4H), 3.59 (s, 3H), 3.56 (s, 3H), 2.13 (s, 3H), 2.10 (s, 3H), 1.59 (s, 3H), 1.19-1.31 (m, 6H), 1.19 (s, 3H). LCMS (m/z): 796.6 [M+H]$^+$.

Example 31

(E)-1-((E)-4-((E)-4-bromo-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide

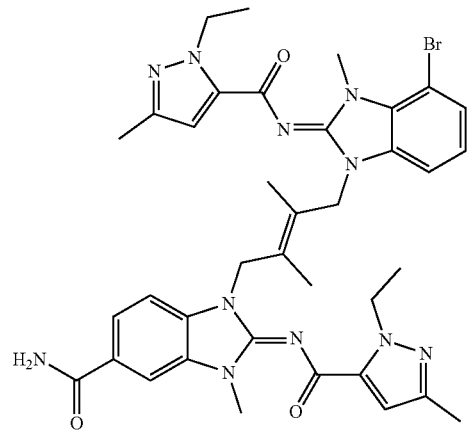 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2c(Br)cccc21]

Step 1: tert-butyl (E)-(4-((3-bromo-2-nitrophenyl)amino)-2,3-dimethylbut-2-en-1-yl)carbamate

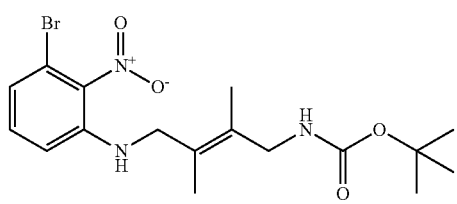 [SMILES: C/C(CNC(=O)OC(C)(C)C)=C(/C)CNc1cccc(Br)c1[N+](=O)[O-]]

To tert-butyl (E)-(4-amino-2,3-dimethylbut-2-en-1-yl)carbamate (0.5 g, 2.33 mmol) in ethanol (11.67 mL) were added 1-bromo-3-fluoro-2-nitrobenzene (0.529 g, 2.33 mmol) and DIEA (1.22 mL, 7.00 mmol). The mixture was stirred at 80° C. for 18 h. The mixture was partitioned between ethyl acetate (50 mL) and brine (20 mL). The aqueous layer was extracted with EtOAc (2×10 mL). The combined EtOAc layers were dried over magnesium sulfate, filtered and concentrated. The residue was purified by silica gel chromatography (40 g silica, gradient of 10-20% ethyl acetate/hexane) to yield tert-butyl (E)-(4-((3-bromo-2-nitrophenyl)amino)-2,3-dimethylbut-2-en-1-yl)carbamate (0.740 g, 1.78 mmol, 77% yield). LCMS (m/z): 414.1 [M+H]$^+$.

Step 2: (E)-4-((4-((3-bromo-2-nitrophenyl)amino)-2,3-dimethylbut-2-en-1-yl)amino)-3-nitrobenzamide

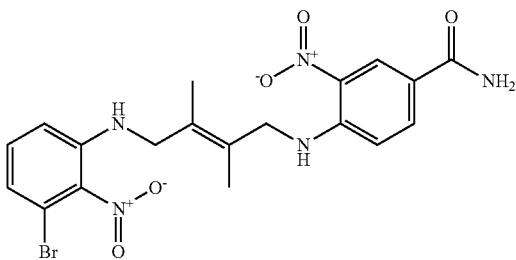

To tert-butyl (E)-(4-((3-bromo-2-nitrophenyl)amino)-2,3-dimethylbut-2-en-1-yl)carbamate (0.44 g, 1.06 mmol) in methanol (5 mL) was added 4 M HCl in dioxane (1.06 mL, 4.25 mmol). The mixture was stirred at room temperature for 3 h. Additional 4 M HCl in dioxane (1.0 mL, 4.0 mmol) was added and stirred 3 more hours. The reaction mixture was concentrated in vacuo to remove HCl and solvents. To this residue, 4-fluoro-3-nitrobenzamide (0.214 g, 1.16 mmol), DIEA (0.927 mL, 5.31 mmol) and 1-butanol (15 ml) were added and the mixture was stirred at 110° C. for 16 h. The mixture was partitioned between ethyl acetate (50 mL) and brine (20 mL). The aqueous layer was extracted with EtOAc (2×10 mL). The combined EtOAc layers were dried over magnesium sulfate, filtered and concentrated. Concentration provided a precipitate that was filtered and dried to provide (E)-4-((4-((3-bromo-2-nitrophenyl)amino)-2,3-dimethylbut-2-en-1-yl)amino)-3-nitrobenzamide (0.40 g, 0.836 mmol, 79% yield) as a solid. LCMS (m/z): 478.1 [M+H]$^+$.

Step 3: (E)-3-amino-4-((4-((2-amino-3-bromophenyl)amino)-2,3-dimethylbut-2-en-1-yl)amino)benzamide

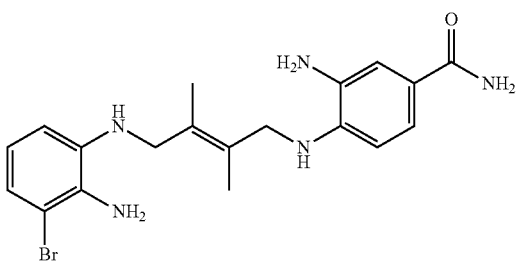 [SMILES: C/C(CNc1ccc(C(N)=O)cc1N)=C(/C)CNc1cccc(Br)c1N]

To (E)-4-((4-((3-bromo-2-nitrophenyl)amino)-2,3-dimethylbut-2-en-1-yl)amino)-3-nitrobenzamide (0.050 g, 0.105 mmol) in methanol (1.6 mL) were added 28-30% ammonium hydroxide solution (0.102 mL, 2.61 mmol) and sodium dithionite solution (0.214 g, 1.045 mmol, in 0.8 mL water). The mixture was stirred at room temperature for 2 h. The reaction mixture was partitioned between ethyl acetate (20 mL) and brine (20 mL). The aqueous layer was extracted with EtOAc (2×10 mL). The combined EtOAc layers were dried over magnesium sulfate, filtered and concentrated. Purification by silica gel chromatography (12 g silica, gradient of 10-40% (3:1 ethanol/ethyl acetate)/heptane using 2% NH$_4$OH modifier) provided (E)-3-amino-4-((4-((2-amino-3-bromophenyl)amino)-2,3-dimethylbut-2-en-1-yl)amino)benzamide (0.030 g, 0.070 mmol, 67.2% yield). $^1$H NMR (400 MHz, DMSO-d$_6$) δ ppm 7.42 (br. s., 1H), 7.01-7.15 (m, 2H), 6.70 (d, J=7.10 Hz, 2H), 6.38-6.47 (m, 1H), 6.32 (dd, J=7.86, 14.95 Hz, 2H), 5.01 (t, J=5.07 Hz, 1H), 4.93 (t, J=5.07 Hz, 1H), 4.74 (s, 2H), 4.63 (s, 2H), 3.76 (d, J=4.82 Hz, 2H), 3.71 (d, J=5.07 Hz, 2H), 1.78 (br. s., 3H), 1.77 (br. s., 3H).

Step 4: (E)-1-(4-(4-bromo-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide

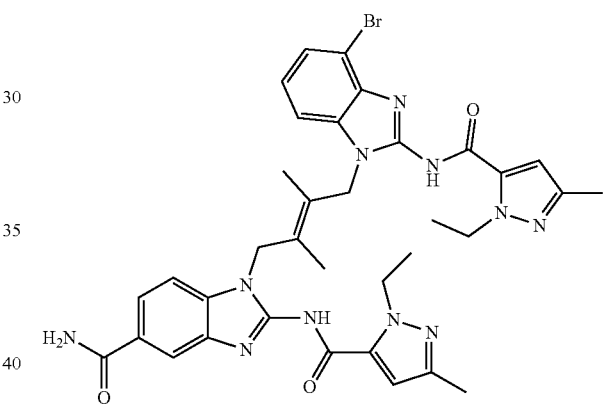

To (E)-3-amino-4-((4-((2-amino-3-bromophenyl)amino)-2,3-dimethylbut-2-en-1-yl)amino)benzamide (0.030 g, 0.072 mmol) in DMF (0.72 mL) at 0° C. was added a solution of 1-ethyl-3-methyl-1H-pyrazole-5-carbonyl isothiocyanate (1 M in dioxane, 0.158 mL, 0.158 mmol). The reaction mixture was stirred for 1 h at 0° C. EDC (0.043 g, 0.215 mmol) and triethylamine (0.060 mL, 0.430 mmol) were added and the mixture was stirred at room temperature for 16 h. The reaction was poured into water (10 mL) and stirred. The resulting solids were filtered and dried at 50° C. in vacuum oven overight to yield (E)-1-(4-(4-bromo-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide (0.043 g, 0.056 mmol, 79% yield). LCMS (m/z): 740.5 [M+H]$^+$.

Step 5: (E)-1-((E)-4-((E)-4-bromo-2-((1-ethyl-3-methyl-1H-pyrazole-5-carbonyl)imino)-3-methyl-2,3-dihydro-1H-benzo[d]imidazol-1-yl)-2,3-dimethyl-but-2-en-1-yl)-2-((1-ethyl-3-methyl-1H-pyrazole-5-carbonyl)imino)-3-methyl-2,3-dihydro-1H-benzo[d]imidazole-5-carboxamide

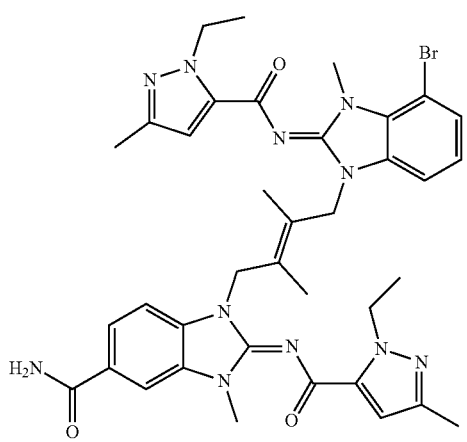 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2c(Br)cccc21]

To (E)-1-(4-(4-bromo-2-(1-ethyl-3-methyl-1H-pyrazole-5-carboxamido)-1H-benzo[d]imidazol-1-yl)-2,3-dimethyl-but-2-en-1-yl)-2-(1-ethyl-3-methyl-1H-pyrazole-5-carboxamido)-1H-benzo[d]imidazole-5-carboxamide (0.040 g, 0.054 mmol) in DMF (0.54 mL) was added cesium carbonate (0.053 g, 0.162 mmol) and iodomethane (7.4 µL, 0.12 mmol). The mixture was stirred at room temperature for 16 h. The mixture was partitioned between ethyl acetate (10 mL) and brine (5 mL). The aqueous layer was extracted with EtOAc (10 mL). The combined EtOAc layers were dried over magnesium sulfate, filtered and concentrated. The residue was purified by mass-directed preparative HPLC (XSELECT CSH C18, 5 um packing, 150×30 mm column, 30-85% gradient of MeCN/water with 0.075% NH$_4$OH, 10 mM ammonium bicarbonate, pH 10) to yield (E)-1-((E)-4-((E)-4-bromo-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide (0.013 g, 0.016 mmol, 30% yield). $^1$H NMR (400 MHz, DMSO-d$_6$) δ ppm 8.11 (d, J=1.27 Hz, 1H), 8.04 (br. s., 1H), 7.80 (dd, J=1.39, 8.49 Hz, 1H), 7.49-7.53 (m, 1H), 7.46 (br. s., 1H), 7.28 (t, J=8.49 Hz, 2H), 7.11-7.18 (m, 1H), 6.45 (s, 1H), 6.42 (s, 1H), 4.85 (br. s., 4H), 4.51 (dq, J=3.68, 6.97 Hz, 4H), 3.78 (s, 3H), 3.59 (s, 3H), 2.128 (s, 3H), 2.125 (s, 3H), 1.59 (s, 6H), 1.25-1.35 (m, 6H). LCMS (m/z): 768.4 [M+H]$^+$.

Examples 32 and 33

Example 32: (E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (Early Eluting Enantiomer)

Example 33: (E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (Late Eluting Enantiomer)

Example 32

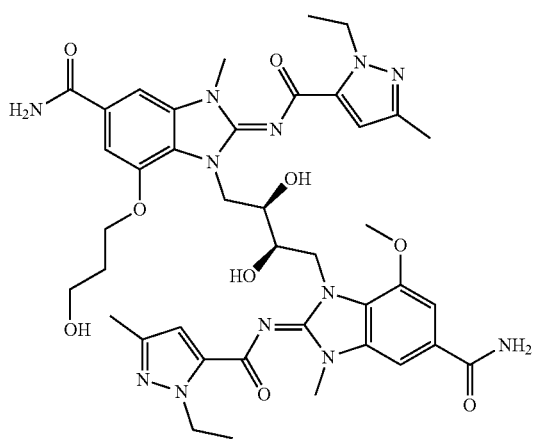

first eluting enantiomer
(E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide Example 33

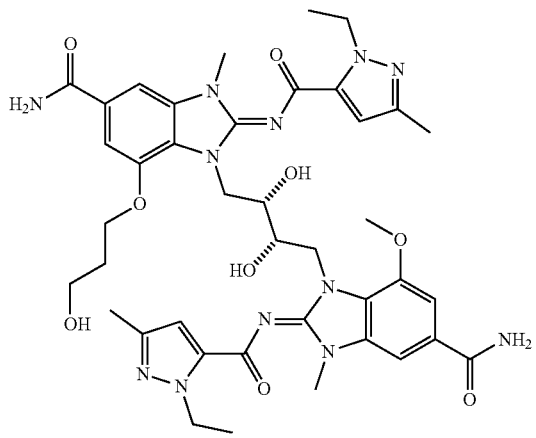

second eluting enantiomer
(E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide

Step 1: (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide

Step 2: (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-7-methoxy-1H-benzo[d]imidazole-5-carboxamide

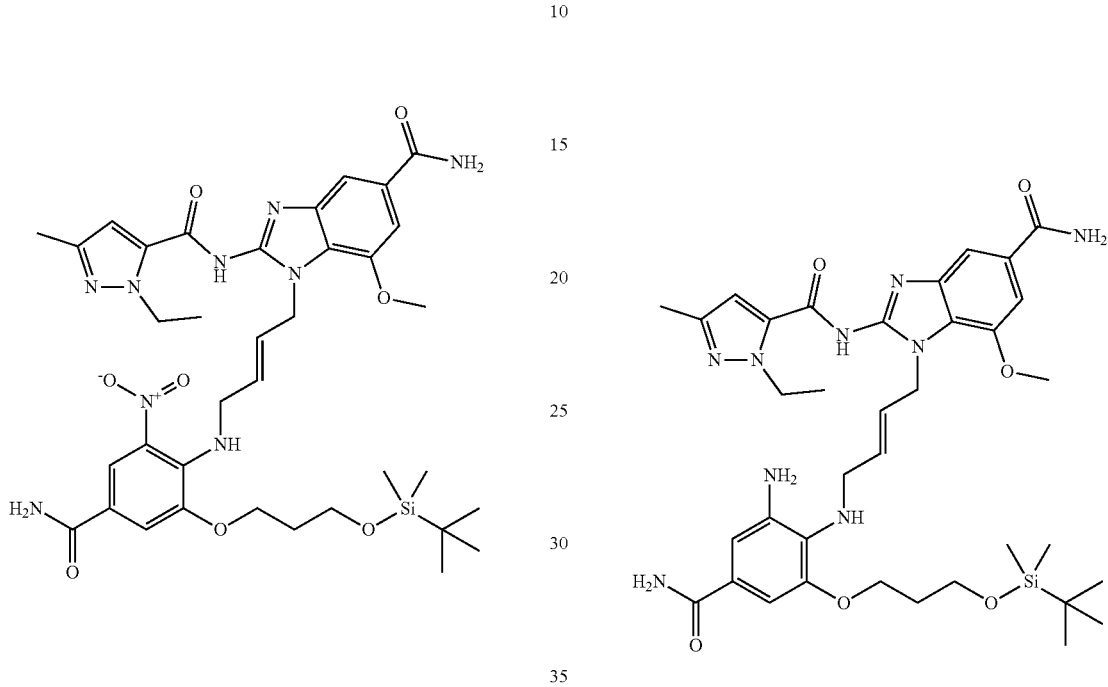

To a suspension of (E)-1-(4-aminobut-2-en-1-yl)-2-(1-ethyl-3-methyl-1H-pyrazole-5-carboxamido)-7-methoxy-1H-benzo[d]imidazole-5-carboxamide, 2 hydrochloride (10.4 g, 21.47 mmol) in 1-butanol (150 mL) at room temperature was added DIEA (7.50 mL, 42.9 mmol). The reaction mixture was then stirred at room temperature for 2 h. The 3-(3-((tert-butyldimethylsilyl)oxy)propoxy)-4-chloro-5-nitrobenzamide (10.9 g, 28.0 mmol) and then sodium bicarbonate (5.41 g, 64.4 mmol) were added. The reaction mixture was then stirred at 100° C. for 4 days. The reaction mixture was cooled to room temperature and concentrated. The resulting orange sludge was suspended in acetonitrile and then filtered. The solid was washed with acetonitrile and water. The solid was then dried to obtain (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide (10.94 g, 14.32 mmol, 67% yield) as an red-orange solid. $^1$H NMR (400 MHz, DMSO-$d_6$) δ ppm 13.27-12.18 (m, 1H), 8.14 (d, J=1.8 Hz, 1H), 7.97 (br. s., 2H), 7.78-7.62 (m, 2H), 7.49 (d, J=1.8 Hz, 1H), 7.38-7.24 (m, 3H), 6.60 (s, 1H), 5.92-5.63 (m, 2H), 4.90 (d, J=5.3 Hz, 2H), 4.58 (q, J=7.1 Hz, 2H), 4.13 (t, J=5.4 Hz, 2H), 4.00 (t, J=6.0 Hz, 2H), 3.87 (s, 3H), 3.64 (t, J=6.1 Hz, 2H), 2.16 (s, 3H), 1.82 (quin, J=6.0 Hz, 2H), 1.33 (t, J=7.0 Hz, 3H), 0.79 (s, 9H), ~0.05 (s, 6H). LCMS (m/z): 764.7 [M+H]$^+$.

To a suspension of (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-7-methoxy-1H-benzo[d]imidazole-5-carboxamide (10.1 g, 13.22 mmol) in methanol (200 mL) stirring at 60° C. was added a solution of sodium dithionite (25.0 g, 121 mmol) in water (200 mL). The reaction mixture was then stirred at the same temperature for 1 h. The reaction mixture was then cooled to room temperature and quenched with 500 mL of water. The resulting mixture was filtered. The collected solid was washed with water (500 mL×3) and then rinsed with diethyl ether (300 mL). The solid was then dried in the vacuum oven to yield partially pure (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-7-methoxy-1H-benzo[d]imidazole-5-carboxamide (7.36 g, 10 mmol, ~76% yield) as a light brown solid. The approximate purity of the title compound by LCMS was 63% (UV, m/z=734.6 [M+H]$^+$) along with 20% (UV, m/z=620.5 [M+H]$^+$) of the silyl-deprotected byproduct. The mixture was used in the next reaction without further purification.

Step 3: (E)-7-(3-((tert-butyldimethylsilyl)oxy)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide

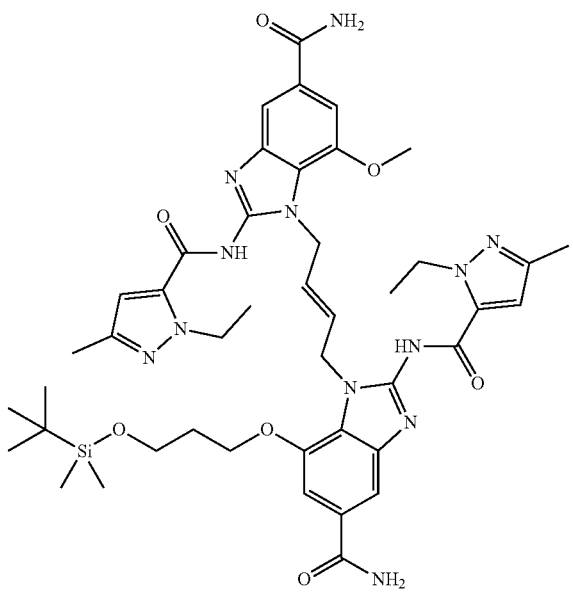 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCO[Si](C)(C)C(C)(C)C)c21]

To a solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-7-methoxy-1H-benzo[d]imidazole-5-carboxamide (7.36 g, 10.03 mmol, ~76% purity) in DMF (60 mL) at room temperature was added dropwise via addition funnel a 1M solution of 1-ethyl-3-methyl-1H-pyrazole-5-carbonyl isothiocyanate (15.1 mL, 15.10 mmol) in 1,4 dioxane. The reaction mixture was then stirred at room temperature for 1 h. To the reaction mixture were then added EDC (3.84 g, 20.06 mmol) and TEA (5.6 mL, 40.2 mmol) at room temperature. The reaction mixture was stirred at room temperature for 48 h. The reaction mixture was diluted with EtOAc and washed with water. A solid was removed by filtration and identified as the silyl-deprotected alcohol derivative. The organic layer was then washed a second time. The combined aqueous layers were back extracted with EtOAc (1×). The combined organic layers were washed with brine, dried with magnesium sulfate, and concentrated. The crude product and solid isolated earlier in the workup were suspended in EtOH and filtered. The solid was washed with EtOH and then dried to obtain an off-white solid (6.0 g). A second crop of solid was also obtained (824 mg). The composition of the combined mixture (6.824 g, ~7.6 mmol, ~76%) was characterized by LCMS and NMR as approximately a 3:1 mixture of (E)-7-(3-((tert-butyldimethylsilyl)oxy)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (LCMS (m/z): 895.8 [M+H]$^+$) and alcohol derivative (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (LCMS (m/z): 781.7 [M+H]$^+$). The mixture was used in the next reaction without further purification.

Step 4: (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2 hydrochloride

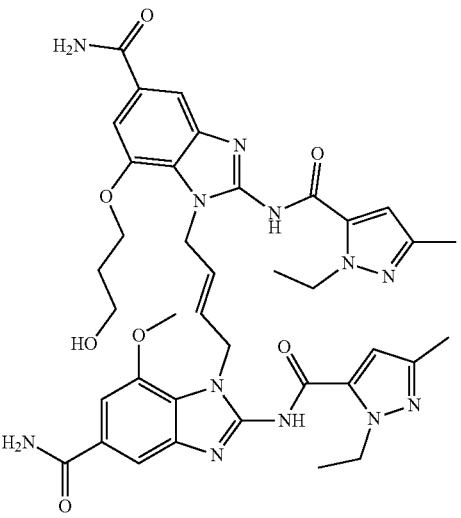 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCO)c21]

To a solution of (E)-7-(3-((tert-butyldimethylsilyl)oxy)propoxy)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide (6.0 g, 6.70 mmol, as a 3:1 mixture of silyl ether/alcohol) in THF (50 mL) at room temperature was added 4M HCl solution in dioxane (8.4 mL, 33.6 mmol). The reaction mixture was then stirred at room temperature for 5 h. Additional HCl solution (4.2 mL, 16.80 mmol) was added and the reaction mixture stirred overnight. Additional HCl solution (4.2 mL, 16.80 mmol) was added and the reaction mixture was stirred for 24 h. Additional HCl solution (8.4 mL, 33.6 mmol) was added. The mixture stirred at room temperature for 1 h and then at 40° C. for 5 h. Additional HCl solution (8.4 mL, 33.6 mmol) was added and the reaction mixture was stirred at 40° C. over the weekend. The reaction mixture was cooled to room temperature then filtered. The solid was washed with THF and dried to yield (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2hydrochloride (5.6 g, 6.56 mmol, 98% yield) as a white solid. $^1$H NMR (400 MHz, DMSO-$d_6$) 5 ppm 7.98 (br. s., 2H), 7.65 (dd, J=1.1, 3.6 Hz, 2H), 7.33 (s, 4H), 6.53 (d, J=1.5 Hz, 2H), 5.86-5.81 (m, 2H), 4.93 (dd, J=3.8, 6.8 Hz, 4H), 4.57-4.47 (m, 4H), 4.07 (t, J=6.4 Hz, 2H), 3.75 (s, 3H), 3.49-3.42 (m, 2H), 2.11 (two s, 6H), 1.80-1.64 (m, 2H), 1.27 (two t, J=7.2 Hz, 6H). LCMS (m/z): 781.7 [M+H]$^+$.

257

Step 5: (E)-1-((E)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

258

Step 6: (E)-1-(4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide

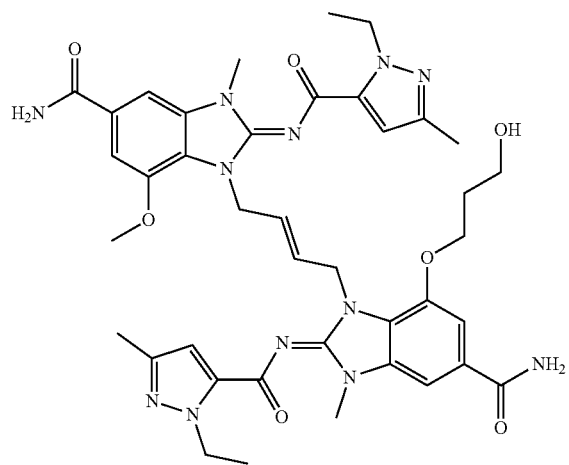 [SMILES: CCn1nc(C)cc1C(=O)/N=c1\n(C)c2cc(C(N)=O)cc(OC)c2n1C/C=C/Cn1/c(=N/C(=O)c2cc(C)nn2CC)n(C)c2cc(C(N)=O)cc(OCCCO)c21]

To a suspension of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, 2 hydrochloride (5.45 g, 6.38 mmol) and cesium carbonate (10.40 g, 31.9 mmol) in DMF (35 mL) at 0° C. by using ice-bath was added methyl iodide (0.918 mL, 14.68 mmol). The ice-bath was removed and the mixture was stirred at room temperature for 16 h. The mixture was partitioned between water and 3:1 chloroform/ethanol. The layers were separated. The aqueous layer was extracted with 3:1 chloroform/ethanol (6×). The organic layer was washed with water. This aqueous wash solution was again extracted with 3:1 chloroform/ethanol. The combined organic layer was dried with sodium sulfate, filtered, and concentrated to provide the title compound (6 g). The approximate purity of the title compound by LCMS was 76% (UV210-350 nm, m/z=809.3 [M+H]$^+$). This compound was used without further purification in the next reaction.

To a suspension of (E)-1-((E)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (5.2 g, 6.43 mmol) in tert-butanol (52 mL) and water (13 mLl) was added NMO (1.130 g, 9.64 mmol). After stirring for 5 min at room temperature, 2.5% osmium tetroxide in tert-butanol (4.04 mL, 0.321 mmol) was added and the mixture was stirred for 18 h. After concentration, the residue was suspended in water and filtered. The collected solid was rinsed with water and dried in vacuo to provide (E)-1-(4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (4.0 g, 73.8% yield) as a mixture of stereoisomers. LCMS (~90% purity by UV210-350 nm; m/z): 843.2 [M+H]$^+$.

Step 7: Purification of Early Eluting Enantiomer Example 33 (E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide and Late Eluting Enantiomer Example 34 (E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide Example 32

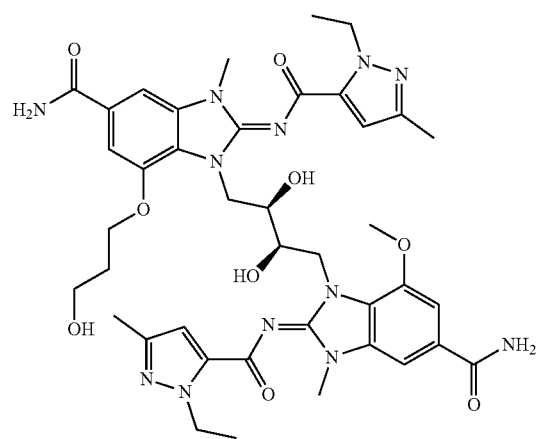

first eluting enantiomer
(E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide Example 33

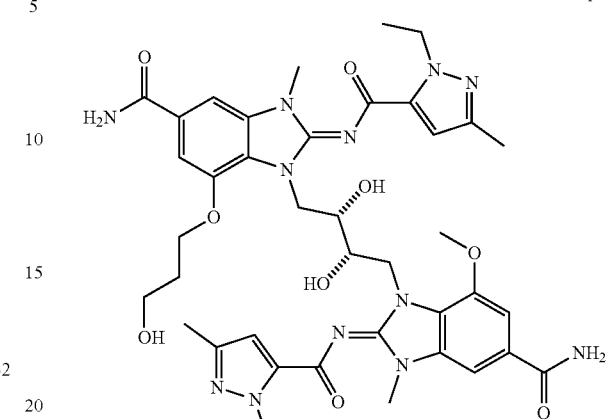

second eluting enantiomer
(E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide For registration and screening, a 1500 mg portion of crude product was separated into discrete enantiomers by a sequence of two preparative HPLC purification steps.

First Purification Step

The purpose of this step was to separate the desired racemic mixture of enantiomer from several minor byproducts that eluted close to the co-eluting pair of enantiomers. The following methods were employed:

| Preparative HPLC Method | Analytical HPLC Method 1 | Analytical HPLC Method 2 |
|---|---|---|
| Input: 1500 mg of crude product (mixture of stereoisomers) | System: Agilent 1100 prep HPLC | System: Agilent 1100 HPLC |
| System: Agilent 1200 prep HPLC system | Column: Chiralpak IC (2) 3u, 4.6 × 150 mm | Column: Phenomenex Luna C18 (2) 3u, 4.6 × 150 mm |
| Column: Chiralpak IC 5u 30 × 250 mm | 5u 4.6 × 150 mm | Solvents: A = $H_2O$ (0.1% TFA); B = $CH_3CN$ (0.1% TFA) |
| Solvent: 100% methanol | Solvents: 100% methanol | Gradient: |
| Flowrate: 45 mL/min | Flowrate: 1.0 mL/min | Time (min); % B |
| Detector: uv 254 nm | Detector: uv 254 nm | 0 min; 20% B |
| Termperature: ambient temperature | Temperature: ambient temperature | 7 min; 20% B |
| Injection: 30 injections of 50 mg crude product in 4 mL methanol | Injection: 5 uL | 20 min; 90% B |
| Retention time: 7.1 min | Retention time: Racemic enantiomers: 4.9 min | 21 min; 20% B |
| | | Flowrate: 1.0 mL/min |
| | | Detector: uv 254 nm |
| | | Temperature: ambient temperature |
| | | Injection: 5 uL |
| | | Retention time: 5.08 min desired product |

Outcome: The purest fractions were combined and concentrated to 10 mL volume. The resulting precipitate was filtered and dried at 35° C. to provide a racemic mixture of enantiomers (600 mg, 0.71 mmol). A 018 HPLC method (Method 2) was also used to demonstrate effectiveness of the purification (purity 98.95%). LMS (m/z): 843.3 [M+H]. Similar treatment of fractions with slightly lower purity (i.e. front and tail fractions) provided additional quantities of the racemic mixture of enantiomers (310 mg).

Second purification step: The purpose of this step was to separate and isolate each enantiomer. The following methods were employed:

| Preparative HPLC Method | Analytical HPLC Method |
|---|---|
| Input: 520 mg of purified racemic mixture of enantiomers | System: Agilent 1100 prep HPLC |
| System: Agilent 1100 prep HPLC | Column: Chiralpak IC 5u 4.6 × 150 mm |
| Column: Chiralpak IC 5u 30 × 250 mm | Solvents: A = DCM; B = EtOH; 12% B, 88 % A |
| Solvents: A = DCM; B = EtOH; 12% B, 88% A | Flowrate: 1.0 mL/min |
| Flowrate: 45 mL/min | Detector: uv 254 nm |
| Detector: uv 254 nm | Temperature: ambient temperature |
| Temperature: ambient temperature | Injection: 10 uL |
| Injection: 10 injections of 52 mg (in 2 mL EtOH and 3 mL DCM) | Retention times: |
| | First eluting enantiomer: 4.6 min |
| | Second eluting enantiomer: 5.9 min |
| Retention times: | |
| First eluting enantiomer: 7.6 min | |
| Second eluting enantiomer: 10.8 min | |

Outcome: The pure fractions of each enantiomer were concentrated and dried under high vacuum at 40° C. to provide the following solids. Assignment of absolute stereochemistry was enabled by subsequent resynthesis from chiral building blocks Example 32 (First Eluting Isomer)

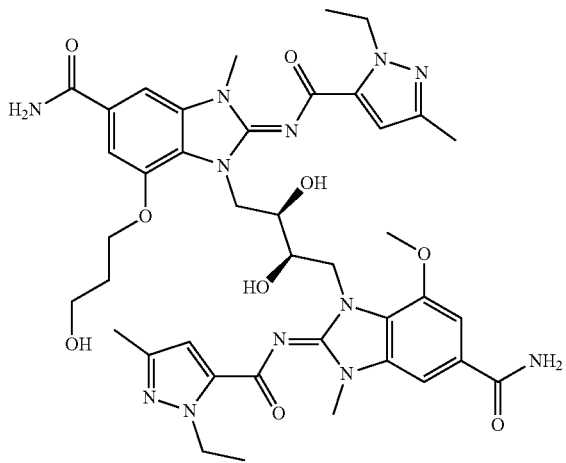 [SMILES: CCn1nc(C)cc1C(=O)/N=c1\n(C)c2cc(C(N)=O)cc(OC)c2n1C[C@@H](O)[C@H](O)Cn1/c(=N/C(=O)c2cc(C)nn2CC)n(C)c2cc(C(N)=O)cc(OCCCO)c21]

(E)-1-((2R,3R)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (247 mg, 0.293 mmol) as a white solid. $^1$H NMR (400 MHz, DMSO-d$_6$) δ ppm 1.26 (t, J=7.1 Hz, 3H) 1.27 (t, J=7.1 Hz, 3H) 1.83 (quin, J=6.15 Hz, 2H) 2.10 (s, 3H) 2.11 (s, 3H) 3.50 (s, 3H) 3.50-3.55 (m, 5H) 3.80 (s, 3H) 3.81-3.91 (m, 2H) 4.18 (t, J=6.46 Hz, 2H) 4.24-4.33 (m, 2H) 4.44-4.53 (m, 5H) 4.53-4.60 (m, 2H) 4.97 (d, J=6.84 Hz, 1H) 5.06 (d, J=6.34 Hz, 1H) 6.41 (s, 1H) 6.44 (s, 1H) 7.41-7.50 (m, 4H) 7.71 (dd, J=2.66, 1.14 Hz, 2H) 8.06 (br. s., 2H). LCMS (100% purity by UV210-350 nm; m/z): 843.3 [M+H]$^+$. Enantiomeric excess >98% ee by chiral analytical HPLC. □D$^{20}$-24 (c 0.1, MeOH).

Example 33 (Second Eluting Isomer)

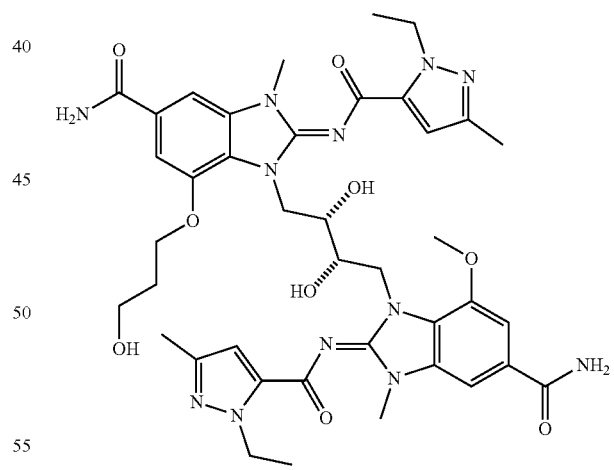

(E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (227 mg, 0.269 mmol) as a white solid. $^1$H NMR (400 MHz, DMSO-d$_6$) δ ppm 1.26 (t, J=7.1 Hz, 3H) 1.27 (t, J=7.1 Hz, 3H) 1.83 (quin, J=6.21 Hz, 2H) 2.10 (s, 3H) 2.11 (s, 3H) 3.50 (s, 3H) 3.50-3.56 (m, 5H) 3.80 (s, 3H) 3.81-3.92 (m, 2H) 4.18 (t, J=6.34 Hz, 2H) 4.24-4.33

(m, 2H) 4.44-4.52 (m, 5H) 4.53-4.61 (m, 2H) 4.97 (d, J=6.84 Hz, 1H) 5.06 (d, J=6.34 Hz, 1H) 6.41 (s, 1H) 6.44 (s, 1H) 7.41-7.50 (m, 4H) 7.71 (dd, J=2.53, 1.01 Hz, 2H) 8.06 (br. s., 2H). LCMS (100% purity by UV210-350 nm; m/z): 843.3 [M+H]⁺. Enantiomeric excess 98% ee by chiral analytical HPLC. □D²⁰+23 (c 0.1, MeOH).

Example 34

(E)-1-(4-((E)-7-bromo-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide

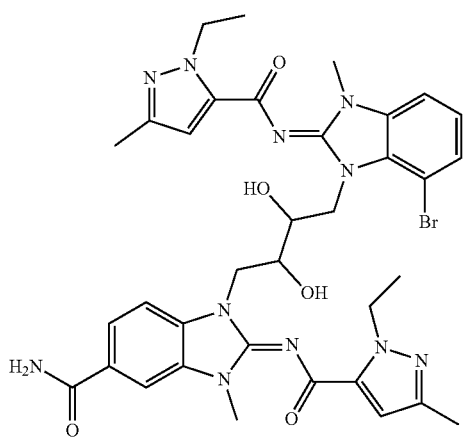 [SMILES: CCn1nc(C)cc1C(=O)/N=c1\n(C)c2cc(C(N)=O)ccc2n1CC(O)C(O)Cn1/c(=N/C(=O)c2cc(C)nn2CC)n(C)c2cccc(Br)c21]

Step 1: tert-butyl (E)-(4-((2-bromo-6-nitrophenyl)amino)but-2-en-1-yl)carbamate

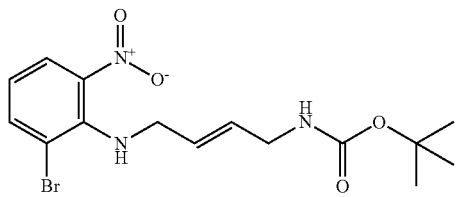 [SMILES: CC(C)(C)OC(=O)NC/C=C/CNc1c(Br)cccc1[N+](=O)[O-]]

To a solution of tert-butyl (E)-(4-aminobut-2-en-1-yl)carbamate (2.2 g, 11.81 mmol) and DIEA (4.37 mL, 25.00 mmol) in isopropanol (30 mL) at 25° C. was added 1-bromo-2-fluoro-3-nitrobenzene (2.5 g, 11.36 mmol). The reaction mixture was then stirred at 25° C. for 4 days. The reaction mixture was concentrated. The resulting material was partitioned between water and EtOAc. The aqueous layer was separated and extracted with EtOAc (1×). The combined organic layers were then washed with brine, dried with magnesium sulfate, and concentrated to obtain the tert-butyl (E)-(4-((2-bromo-6-nitrophenyl)amino)but-2-en-1-yl)carbamate (4.6 g, 12 mmol, 100% yield) as a yellow solid. The isolated material was used without any further purification. LCMS (m/z): 332.0 ([M+H]⁺- t-butyl).

Step 2: tert-butyl (E)-(4-((2-amino-6-bromophenyl)amino)but-2-en-1-yl)carbamate

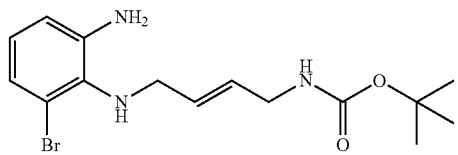 [SMILES: CC(C)(C)OC(=O)NC/C=C/CNc1c(N)cccc1Br]

To a mixture of tert-butyl (E)-(4-((2-bromo-6-nitrophenyl)amino)but-2-en-1-yl)carbamate (4.4 g, 11.39 mmol) and ammonium chloride (6.09 g, 114 mmol) in methanol (50 mL) was added zinc (7.45 g, 114 mmol). The reaction mixture was then stirred at room temperature for 30 min. The reaction mixture was filtered and concentrated. The isolated residue was partitioned between EtOAc and water. The aqueous layer was separated and the organic layer was washed with water a second time. The combined aqueous layer was extracted with EtOAc (1×). The combined organic layer was then washed with brine, dried with magnesium sulfate, filtered and concentrated to obtain crude title compound (4.0 g, ~11.23 mmol) as a light brown oil. LCMS (77% purity by UV210-350 nm; m/z): 356.1 [M+H]⁺. The product was taken on without any further purification.

Step 3: tert-butyl (E)-(4-(7-bromo-2-(1-ethyl-3-methyl-1H-pyrazole-5-carboxamido)-1H-benzo[d]imidazol-1-yl)but-2-en-1-yl)carbamate

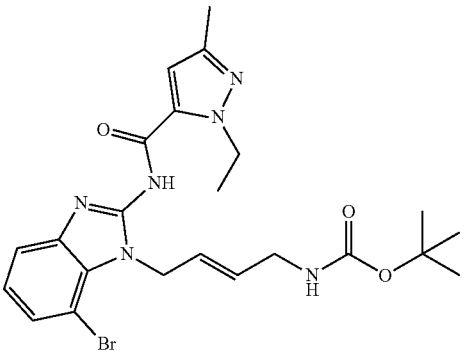 [SMILES: CCn1nc(C)cc1C(=O)Nc1nc2cccc(Br)c2n1C/C=C/CNC(=O)OC(C)(C)C]

To a solution of tert-butyl (E)-(4-((2-amino-6-bromophenyl)amino)but-2-en-1-yl)carbamate (4.0 g, 11.23 mmol) in DMF (40 mL) at room temperature was added a solution of 1-ethyl-3-methyl-1H-pyrazole-5-carbonyl isothiocyanate (1 M in 1,4-dioxane, 12.4 mL, 12.40 mmol). The reaction mixture was then stirred for 45 min. To the reaction mixture were then added EDC (3.23 g, 16.84 mmol) and TEA (4.7 mL, 33.7 mmol) at room temperature. After stirring for 2 h, the mixture was diluted with EtOAc and washed with water (2×). The combined aqueous layer was again extracted with EtOAc (1×). The combined organic layer was washed with brine, dried with magnesium sulfate, filtered, and concentrated. The residue was purified by normal phase chromotagraphy (ISCO CombiFlash, 120 g Gold column, DCM/MeOH) to obtain the title compound (4.5 g, 8.70 mmol, 77% yield) as an off-white solid after evaporation of solvents. LCMS (m/z): 517.2 [M+H]⁺.

Step 4: (E)-N-(1-(4-aminobut-2-en-1-yl)-7-bromo-1H-benzo[d]imidazol-2-yl)-1-ethyl-3-methyl-1H-pyrazole-5-carboxamide, Hydrochloride

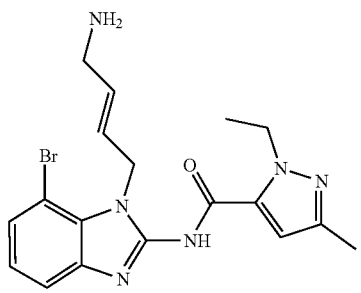 [SMILES: CCn1nc(C)cc1C(=O)Nc1nc2cccc(Br)c2n1C/C=C/CN]

To a solution of tert-butyl (E)-(4-(7-bromo-2-(1-ethyl-3-methyl-1H-pyrazole-5-carboxamido)-1H-benzo[d]imidazol-1-yl)but-2-en-1-yl)carbamate (1.1 g, 2.126 mmol) in methanol (10 mL) at room temperature was added HCl (4 M in dioxane, 5.00 mL, 20 mmol). The reaction mixture was then stirred at room temperature overnight. The reaction mixture was concentrated in vacuo and suspended in diethylether. The resulting solid was filtered, washed with diethylether, and then dried to obtain (E)-N-(1-(4-aminobut-2-en-1-yl)-7-bromo-1H-benzo[d]imidazol-2-yl)-1-ethyl-3-methyl-1H-pyrazole-5-carboxamide, Hydrochloride (1.06 g) as a white solid. The isolated material was taken on without any further purification. LCMS (m/z): 417.1 [M+H]$^+$.

Step 5: (E)-N-(7-bromo-1-(4-((4-carbamoyl-2-nitrophenyl)amino)but-2-en-1-yl)-1H-benzo[d]imidazol-2-yl)-1-ethyl-3-methyl-1H-pyrazole-5-carboxamide

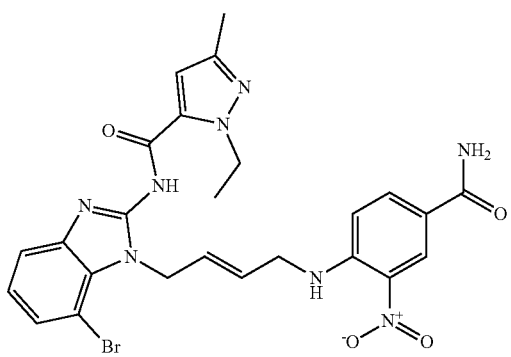

To a suspension of (E)-N-(1-(4-aminobut-2-en-1-yl)-7-bromo-1H-benzo[d]imidazol-2-yl)-1-ethyl-3-methyl-1H-pyrazole-5-carboxamide, hydrochloride (0.965 g, 2.126 mmol) and 4-fluoro-3-nitrobenzamide (0.431 g, 2.339 mmol) in isopropanol (10 mL) at room temperature was added DIEA (0.780 mL, 4.46 mmol). The reaction mixture was stirred at 70° C. overnight. The reaction mixture was then cooled to room temperature and solids collected on a filter. The solid was washed with isopropanol and dried to obtain (E)-N-(7-bromo-1-(4-((4-carbamoyl-2-nitrophenyl)amino)but-2-en-1-yl)-1H-benzo[d]imidazol-2-yl)-1-ethyl-3-methyl-1H-pyrazole-5-carboxamide (1.2 g, 2.06 mmol, 97% yield) as a yellow solid. The isolated material was taken on without any further purification. LCMS (m/z): 581.1 [M+H]$^+$.

Step 6: (E)-N-(1-(4-((2-amino-4-carbamoylphenyl)amino)but-2-en-1-yl)-7-bromo-1H-benzo[d]imidazol-2-yl)-1-ethyl-3-methyl-1H-pyrazole-5-carboxamide

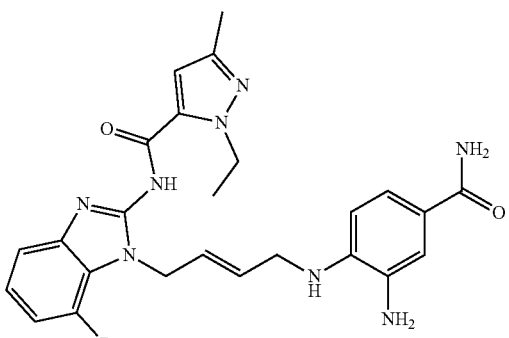

To a solution of (E)-N-(7-bromo-1-(4-((4-carbamoyl-2-nitrophenyl)amino)but-2-en-1-yl)-1H-benzo[d]imidazol-2-yl)-1-ethyl-3-methyl-1H-pyrazole-5-carboxamide (1.2 g, 2.064 mmol) and ammonium chloride (1.1 g, 20.56 mmol) in methanol (15 mL) was added zinc (1.3 g, 19.88 mmol). The reaction mixture was then stirred at room temperature for 8 h. An additional 10 eq of ammonium chloride (1.1 g, 20.56 mmol) and zinc (1.3 g, 19.88 mmol) were added and the mixture stirred at room temperature overnight. As the reduction was still incomplete, acetic acid (1.5 mL) was added then stirred at room temperature for 30 min.

The reaction mixture was filtered and the filtrate was concentrated. The isolated material was partitioned between EtOAc and water. The solid that appears was collected on a filter, washed with EtOAc and water. The filtrate was then placed in a separatory funnel. The aqueous layer was extracted with EtOAc (1×). The combined organic layers were then washed with brine, dried (MgSO4), and concentrated. The residue and solids isolated above were dissolved in MeOH and evaporated onto Celite. Silica gel chromatography (dry loaded, 40 g column, gradient of 0-10% MeOH/DCM) provided an off-white solid (911 mg, ~1.6 mmol) as a ~3:1 mixture of (E)-N-(1-(4-((2-amino-4-carbamoylphenyl)amino)but-2-en-1-yl)-7-bromo-1H-benzo[d]imidazol-2-yl)-1-ethyl-3-methyl-1H-pyrazole-5-carboxamide (LCMS (m/z): 551.2 [M+H]$^+$) and the debrominated byproduct. The isolated material was used directly in the next reaction.

Step 7: (E)-1-(4-(7-bromo-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

Step 8: (E)-1-((E)-4-((E)-7-bromo-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide

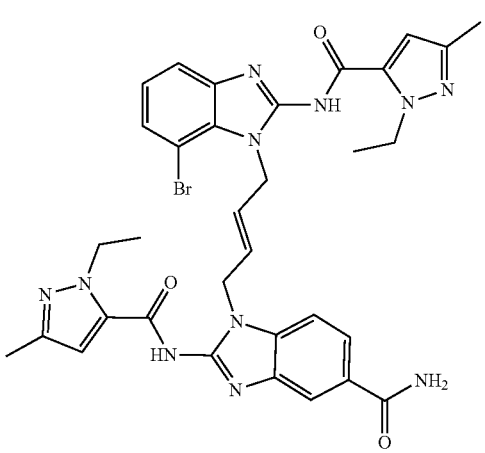

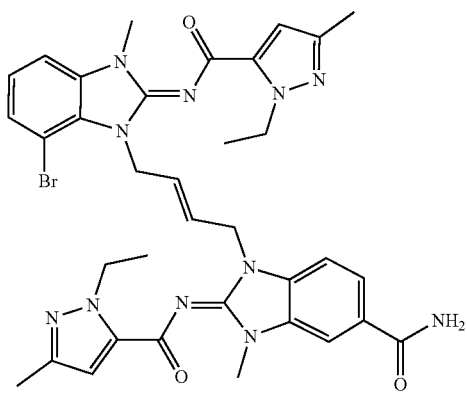 [SMILES: CCn1nc(C)cc1C(=O)/N=c1\n(C)c2cc(C(N)=O)ccc2n1C/C=C/Cn1/c(=N/C(=O)c2cc(C)nn2CC)n(C)c2cccc(Br)c21]

To a solution of (E)-N-(1-(4-((2-amino-4-carbamoylphenyl)amino)but-2-en-1-yl)-7-bromo-1H-benzo[d]imidazol-2-yl)-1-ethyl-3-methyl-1H-pyrazole-5-carboxamide (911 mg, ~1.6 mmol, containing ~25% lacking bromine atom) in DMF (10 mL) at room temperature was added a 1 M solution of 1-ethyl-3-methyl-1H-pyrazole-5-carbonyl isothiocyanate (1.82 mL, 1.82 mmol) in 1,4 dioxane. The reaction mixture was then stirred at room temperature for 1.5 h. EDC (633 mg, 3.30 mmol) and TEA (0.921 mL, 6.61 mmol) were then added at room temperature. After stirring overnight at room temperature, the reaction mixture was diluted with EtOAc and water. Suspended solids were filtered and washed with EtOAc, water, EtOAc, and then diethylether. Drying the off-white solid provided an 85:15 mixture of (E)-1-(4-(7-bromo-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (883 mg, ~1.2 mmol, 75% yield, LCMS (m/z): 712.2 [M+H]$^+$) and the corresponding des-bromide analog. The material was used without further purification.

To a mixture of (E)-1-(4-(7-bromo-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (816 mg, 1.145 mmol, ~ 15% des bromide impurity) and cesium carbonate (1.5 g, 4.60 mmol) in DMF (10 mL) at room temperature was added iodomethane (0.143 mL, 2.29 mmol). The reaction mixture was then stirred at room temperature for 4 h. Additional iodomethane (0.143 mL, 2.290 mmol) was added and the reaction mixture stirred for 45 h at room temperature. Water and EtOAc were added to produce a solid (345 mg, unreacted starting material). The filtrate was separated and the aqueous phase was extracted with EtOAc. The combined organic layer was washed with brine, dried over magnesium sulfate, and concentrated. Purification by preparative HPLC (30 mm×50 mm Gemini C18, gradient of ACN/water with 0.1% TFA modifier) provided (E)-1-((E)-4-((E)-7-bromo-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide (107 mg, 0.144 mmol, 12.6% yield) as a white solid. $^1$H NMR (400 MHz, DMSO-$d_6$) δ ppm 8.09 (d, J=1.3 Hz, 1H), 8.03 (br. s., 1H), 7.81 (dd, J=1.5, 8.3 Hz, 1H), 7.60 (dd, J=0.8, 8.0 Hz, 1H), 7.50 (d, J=8.3 Hz, 1H), 7.45 (dd, J=0.8, 8.0 Hz, 2H), 7.23 (t, J=8.2 Hz, 1H), 6.45 (s, 1H), 6.39 (s, 1H), 5.95 (td, J=4.8, 15.7 Hz, 1H), 5.56 (td, J=5.8, 15.7 Hz, 1H), 5.01 (d, J=3.8 Hz, 2H), 4.78 (d, J=5.5 Hz, 2H), 4.49-4.38 (m, 4H), 3.97 (s, 2H), 3.51 (s, 3H), 2.13 (s, 3H), 2.11 (s, 3H), 1.15-1.28 (m, 6H). LCMS (m/z): 740.3 [M+H]$^+$.

Step 9: (E)-1-(4-((E)-7-bromo-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide

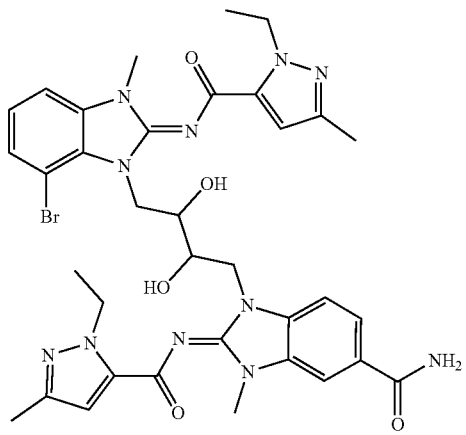 [SMILES: CCn1nc(C)cc1C(=O)/N=c1\n(C)c2cc(C(N)=O)ccc2n1CC(O)C(O)Cn1/c(=N/C(=O)c2cc(C)nn2CC)n(C)c2cccc(Br)c21]

To a suspension of (E)-1-((E)-4-((E)-7-bromo-2-((1-ethyl-3-methyl-1H-pyrazole-5-carbonyl)imino)-3-methyl-2,3-dihydro-1H-benzo[d]imidazol-1-yl)but-2-en-1-yl)-2-((1-ethyl-3-methyl-1H-pyrazole-5-carbonyl)imino)-3-methyl-2,3-dihydro-1H-benzo[d]imidazole-5-carboxamide (54 mg, 0.073 mmol) in tert-butanol (0.8 mL) and water (0.2 mL) was added NMO (26 mg, 0.22 mmol). After stirring for 5 min at room temperature, 2.5% osmium tetroxide in tert-butanol (0.183 mL, 0.015 mmol) was added and stirring was continued for 2 h at room temperature. The reaction mixture was filtered and the filtrate directly purified by reversed phase HPLC (30 mm×50 mm Gemini C18, gradient of ACN/water with 0.1% ammonium hydroxide modifier). (E)-1-(4-((E)-7-bromo-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide (37 mg, 0.48 mmol, 65% yield) was obtained as a white solid. $^1$H NMR (400 MHz, DMSO-$d_6$) δ ppm 8.09-8.00 (m, 2H), 7.85 (dd, J=1.5, 8.4 Hz, 1H), 7.61-7.56 (m, 2H), 7.48-7.39 (m, 2H), 7.23 (t, J=8.0 Hz, 1H), 6.47 (d, J=7.1 Hz, 2H), 5.36 (d, J=6.6 Hz, 1H), 5.11 (d, J=6.6 Hz, 1H), 4.71 (dd, J=9.1, 14.4 Hz, 1H), 4.50 (quin, J=6.7 Hz, 4H), 4.38 (dd, J=3.8, 14.4 Hz, 1H), 4.30-4.15 (m, 2H), 4.04-3.89 (m, 2H), 3.57 (s, 3H), 3.51 (s, 3H), 2.11 (s, 3H), 2.15 (s, 3H), 1.34-1.21 (m, 6H). LCMS (m/z): 774.3 [M+H]$^+$).

Example 35

(2E,2'E)-1,1'-((2S,3S)-2,3-diethoxybutane-1,4-diyl)bis(2-((1-ethyl-3-methyl-1H-pyrazole-5-carbonyl)imino)-3-methyl-2,3-dihydro-1H-benzo[d]imidazole-5-carboxamide)

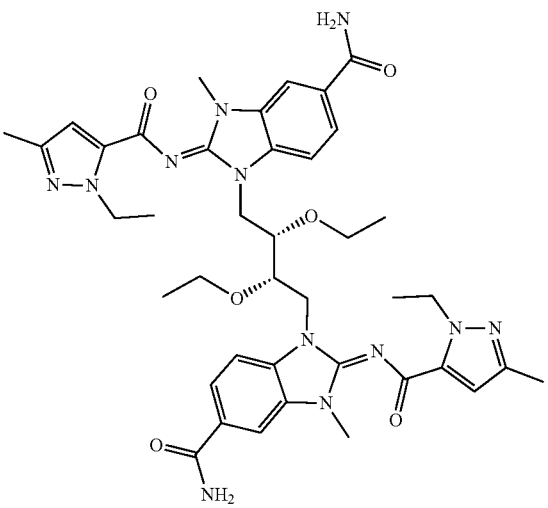

Step 1: 4,4'-(((2S,3S)-2,3-diethoxybutane-1,4-diyl)bis(azanediyl))bis(3-nitrobenzamide)

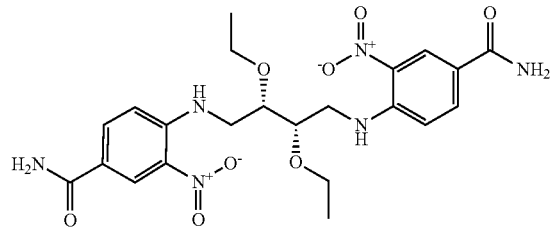

To the mixture of 4-fluoro-3-nitrobenzamide (0.985 g, 5.35 mmol) in 1-butanol (10 mL) was added (2S,3S)-2,3-diethoxybutane-1,4-diamine (0.46 g, 2.61 mmol) and DIEA (1.82 mL, 10.4 mmol). The mixture was stirred at 110° C. for 2 h. When cooled to room temperature, the solids were collected on a filter, washed with a mixture of diethyl ether and 2-propanol (1:1) and dried to provide 4,4'-(((2S,3S)-2,3-diethoxybutane-1,4-diyl)bis(azanediyl))bis(3-nitrobenzamide) (0.63 g, 1.25 mmol, 48% yield) as an orange solid. $^1$H NMR (400 MHz, DMSO-$d_6$) δ ppm 1.13 (t, J=7.0 Hz, 6H), 3.45-3.74 (m, 8H), 3.79-3.89 (m, 2H), 7.17 (d, J=9.1 Hz, 2H), 7.31 (br. s., 2H), 8.02 (dd, J=8.9, 2.0 Hz, 4H), 8.56 (t, J=5.2 Hz, 2H), 8.66 (d, J=2.0 Hz, 2H). LCMS (m/z): 505.1 [M+H]$^+$.

Step 2: 4,4'-(((2S,S)-2,3-diethoxybutane-1,4-diyl)bis(azanediyl))bis(3-aminobenzamide)

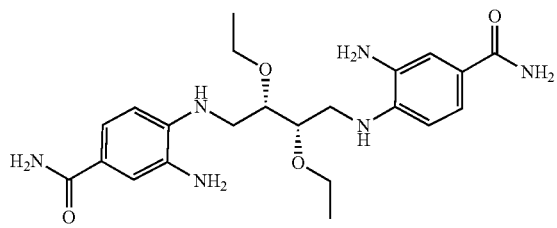 [SMILES: CCO[C@@H](CNc1ccc(C(N)=O)cc1N)[C@H](CNc1ccc(C(N)=O)cc1N)OCC]

To a 100 mL round bottom flask was added 4,4'-(((2S,3S)-2,3-diethoxybutane-1,4-diyl)bis(azanediyl))bis(3-nitrobenzamide) (0.63 g, 1.25 mmol) and methanol (20 mL). To this mixture was added 10 mL saturated aqueous ammonium chloride solution. To this mixture was added zinc (0.812 g, 12.5 mmol) and the heterogenous mixture was stirred at room temperature for 15 min. The mixture was passed and rinsed through a filter using MeOH then concentrated. Silica gel chromatography (24 g column, gradient of 6-20% MeOH/DCM with 1% ammonium hydroxide as modifier) provided 4,4'-(((2S,3S)-2,3-diethoxybutane-1,4-diyl)bis(azanediyl))bis(3-aminobenzamide) (0.446 g, 1.00 mmol, 80% yield) as light yellow solid. LCMS (m/z): 445.4 [M+H]$^+$.

Step 3: 1,1'-((2S,3S)-2,3-diethoxybutane-1,4-diyl)bis(2-(1-ethyl-3-methyl-1H-pyrazole-5-carboxamido)-1H-benzo[d]imidazole-5-carboxamide)

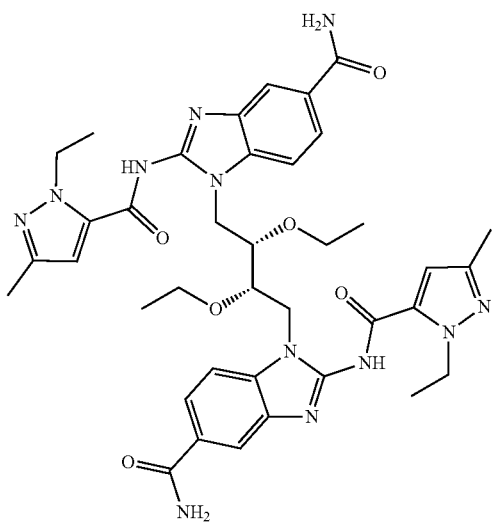

To the solution of 4,4'-(((2S,3S)-2,3-diethoxybutane-1,4-diyl)bis(azanediyl))bis(3-aminobenzamide) (0.446 g, 1.00 mmol) in DMF (20 mL) was added 1-ethyl-3-methyl-1H-pyrazole-5-carbonyl isothiocyanate (~0.4 M in dioxane, 5.02 mL, 2.00 mmol). The mixture was stirred for 15 min. EDC (0.481 g, 2.51 mmol) and TEA (0.699 mL, 5.02 mmol) were added and the reaction mixture was stirred at room temperature for 18 h. The mixture was poured into 3:1 water:saturated aqueous ammonium chloride solution (100 mL). Fine solids immediately formed and stirring was continued for another 10 min. The resulting solids were filtered, washed with water, and dried to provide 1,1'-((2S,3S)-2,3-diethoxybutane-1,4-diyl)bis(2-(1-ethyl-3-methyl-1H-pyrazole-5-carboxamido)-1H-benzo[d]imidazole-5-carboxamide) (0.539 mg, 0.701 mmol, 70% yield) as a white solid. LCMS (m/z): 767.5 [M+H]$^+$.

Step 4: (2E,2'E)-1,1'-((2S,3S)-2,3-diethoxybutane-1,4-diyl)bis(2-(((1-ethyl-3-methyl-1H-pyrazole-5-carbonyl)imino)-3-methyl-2,3-dihydro-1H-benzo[d]imidazole-5-carboxamide)

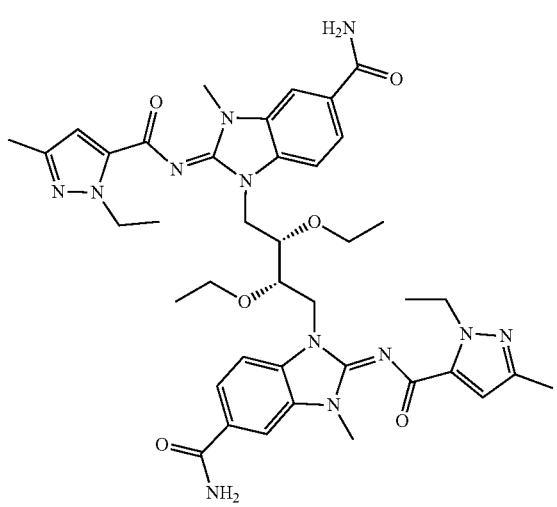

To a solution of 1,1'-((2S,3S)-2,3-diethoxybutane-1,4-diyl)bis(2-(1-ethyl-3-methyl-1H-pyrazole-5-carboxamido)-1H-benzo[d]imidazole-5-carboxamide) (0.09 g, 0.117 mmol) in DMF (5 mL) were added cesium carbonate (0.103 g, 0.317 mmol) and methyl iodide (0.018 mL, 0.282 mmol). The reaction mixture was stirred at room temperature for 18 h. More cesium carbonate (0.019 g, 0.059 mmol) and methyl iodide (0.015 mL, 0.235 mmol) were added. The mixture was stirred for 1 h at 50° C. The reaction was diluted with water and extracted with EtOAc (3×50 mL). The organic phase was washed with brine (10 mL), dried with magnesium sulfate, and concentrated. Mass-directed HPLC (XSelect CSH Prep C18, 5 um, gradient of 15-55% ACN/water with 0.1% TFA as modifier) was used to purify the product. The fractions were combined and ACN was removed. The aqueous phase was basified with saturated ammonium bicarbonate solution. The resulting solids were filtered and dried on a freeze dryer to give (2E,2'E)-1,1'-((2S,3S)-2,3-diethoxybutane-1,4-diyl)bis(2-((1-ethyl-3-methyl-1H-pyrazole-5-carbonyl)imino)-3-methyl-2,3-dihydro-1H-benzo[d]imidazole-5-carboxamide) (13 mg, 0.016 mmol, 14% yield) as a white solid. $^1$H NMR (400 MHz, DMSO-d$_6$) δ ppm 8.01-8.15 (m, 4H) 7.80-7.93 (m, 2H) 7.61 (d, J=8.36 Hz, 2H) 7.46 (br. s., 2H) 6.51 (s, 2H) 4.46-4.62 (m, 6H) 4.38 (dd, J=14.45, 8.87 Hz, 2H) 3.78-3.93 (m, 2H) 3.60 (s, 6H) 3.25-3.33 (m, 2H) 3.02 (dd, J=9.38, 7.10 Hz, 2H) 2.12 (s, 6H) 1.31 (t, J=7.10 Hz, 6H) 0.59 (t, J=6.97 Hz, 6H). LCMS (m/z): 795.3 [M+H]$^+$.

Example 36

(E)-1-(((4R,5R)-5-(((E)-5-carbamoyl-2-((1-ethyl-3-methyl-1H-pyrazole-5-carbonyl)imino)-3-methyl-2,3-dihydro-1H-benzo[d]imidazol-1-yl)methyl)-2,2-dimethyl-1,3-dioxolan-4-yl)methyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide

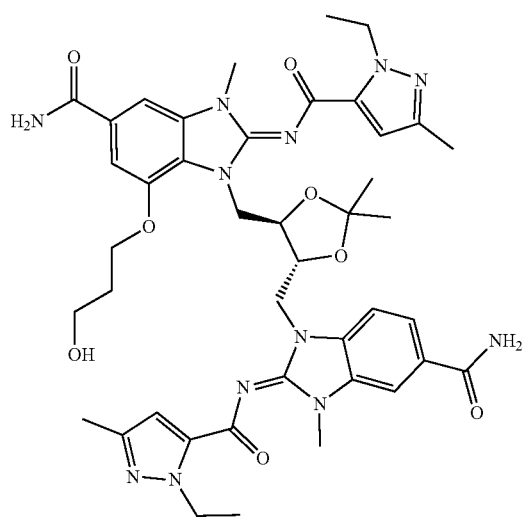 [SMILES: CCn1nc(C)cc1C(=O)/N=c1\n(C)c2cc(C(N)=O)ccc2n1C[C@H]1OC(C)(C)O[C@@H]1Cn1/c(=N/C(=O)c2cc(C)nn2CC)n(C)c2cc(C(N)=O)cc(OCCCO)c21]

Step 1: 4-((((4R,5R)-5-(aminomethyl)-2,2-dimethyl-1,3-dioxolan-4-yl)methyl)amino)-3-(3-(benzyloxy)propoxy)-5-nitrobenzamide

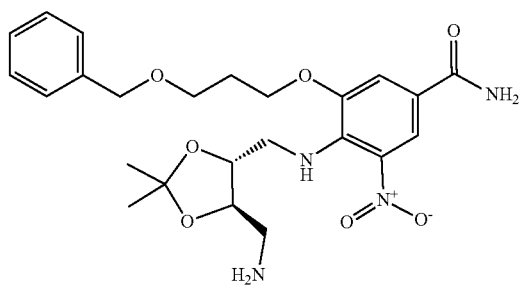 [SMILES: CC1(C)O[C@H](CN)[C@@H](CNc2c(OCCCOCc3ccccc3)cc(C(N)=O)cc2[N+](=O)[O-])O1]

To a solution of ((4R,5R)-2,2-dimethyl-1,3-dioxolane-4,5-diyl)dimethanamine (1 g, 6.24 mmol) and 3-(3-(benzyloxy)propoxy)-4-chloro-5-nitrobenzamide (2.049 g, 5.62 mmol) in 1-butanol (20 mL) was added DIEA (3.27 mL, 18.72 mmol). The reaction mixture was stirred at 120° C. for 16 h. The mixture was concentrated under vacuum to afford crude product. The crude product was purified by silica gel chromatography (elution gradient 0 to 30% MeOH in DCM). Pure fractions were evaporated to dryness to afford 4-((((4R,5R)-5-(aminomethyl)-2,2-dimethyl-1,3-dioxolan-4-yl)methyl)amino)-3-(3-(benzyloxy)propoxy)-5-nitrobenzamide (1.5 g, 2.76 mmol, 44.3% yield) as a red gum. LCMS (m/z): 489 [M+H]⁺.

Step 2: 3-(3-(benzyloxy)propoxy)-4-((((4R,5R)-5-(((4-carbamoyl-2-nitrophenyl)amino)methyl)-2,2-dimethyl-1,3-dioxolan-4-yl)methyl)amino)-5-nitrobenzamide

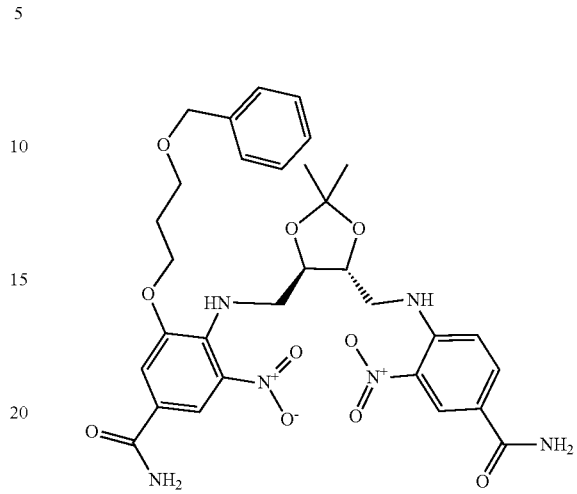

To a solution of 4-((((4R,5R)-5-(aminomethyl)-2,2-dimethyl-1,3-dioxolan-4-yl)methyl)amino)-3-(3-(benzyloxy)propoxy)-5-nitrobenzamide (1.4 g, 2.87 mmol) and 4-fluoro-3-nitrobenzamide (0.580 g, 3.15 mmol) in DMSO (15 mL) was added K2CO₃ (0.792 g, 5.73 mmol). The reaction mixture was stirred at 25° C. for 16 h. The mixture was poured into water (100 mL). The precipitate was collected by filtration, washed with water and dried under vacuum to afford 3-(3-(benzyloxy)propoxy)-4-((((4R,5R)-5-(((4-carbamoyl-2-nitrophenyl)amino)methyl)-2,2-dimethyl-1,3-dioxolan-4-yl)methyl)amino)-5-nitrobenzamide (1.4 g, 1.931 mmol, 67.4% yield) as an orange solid. LCMS (m/z): 653 [M+H]⁺.

Step 3: 3-amino-4-((((4R,5R)-5-(((2-amino-4-carbamoylphenyl)amino)methyl)-2,2-dimethyl-1,3-dioxolan-4-yl)methyl)amino)-5-(3-(benzyloxy)propoxy)benzamide

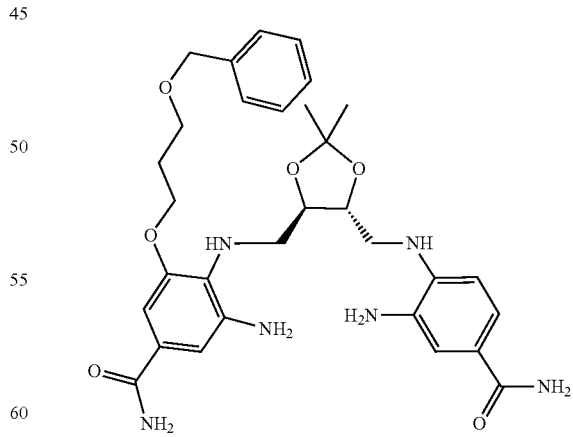

To a solution of 3-(3-(benzyloxy)propoxy)-4-((((4R,5R)-5-(((4-carbamoyl-2-nitrophenyl)amino)methyl)-2,2-dimethyl-1,3-dioxolan-4-yl)methyl)amino)-5-nitrobenzamide (1.35 g, 2.068 mmol) in acetic acid (20 mL) was added zinc (1.352 g, 20.68 mmol). The reaction mixture was stirred at 25° C. for 3 h. The mixture was diluted with DCM (50 mL) and filtered. The filtrate was concentrated under reduced pressure to afford crude 3-amino-4-((((4R,5R)-5-(((2-amino-4-carbamoylphenyl)amino)methyl)-2,2-dimethyl-1,3-dioxolan-4-yl)methyl)amino)-5-(3-(benzyloxy)propoxy) benzamide (1.3 g, 1.755 mmol, 85% yield) as a grey solid. LCMS (m/z): 593 [M+H]⁺.

Step 4: 2-amino-1-(((4R,5R)-5-((2-amino-5-carbamoyl-1H-benzo[d]imidazol-1-yl)methyl)-2,2-dimethyl-1,3-dioxolan-4-yl)methyl)-7-(3-(benzyloxy)propoxy)-1H-benzo[d]imidazole-5-carboxamide

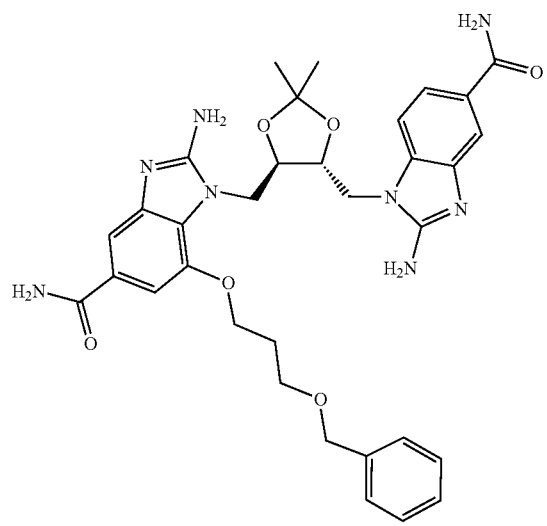 [SMILES: CC1(C)O[C@H](Cn2c(N)nc3cc(C(N)=O)ccc32)[C@@H](Cn2c(N)nc3cc(C(N)=O)cc(OCCCOCc4ccccc4)c32)O1]

To a solution of 3-amino-4-((((4R,5R)-5-(((2-amino-4-carbamoylphenyl)amino)methyl)-2,2-dimethyl-1,3-dioxolan-4-yl)methyl)amino)-5-(3-(benzyloxy)propoxy)benzamide (1.35 g, 2.278 mmol) in methanol (20 mL) was added cyanogen bromide (0.724 g, 6.83 mmol). The reaction mixture was stirred at 25° C. for 16 h. The mixture was diluted with diethyl ether (30 mL). The mixture was filtered and washed with diethyl ether. The filtrate was concentrated under reduced pressure to afford 2-amino-1-(((4R,5R)-5-((2-amino-5-carbamoyl-1H-benzo[d]imidazol-1-yl)methyl)-2,2-dimethyl-1,3-dioxolan-4-yl)methyl)-7-(3-(benzyloxy)propoxy)-1H-benzo[d]imidazole-5-carboxamide (800 mg, 1.12 mmol, 49.2% yield) as a grey solid. LCMS (m/z): 643 [M+H]⁺.

Step 5: 7-(3-(benzyloxy)propoxy)-1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-1H-benzo[d]imidazole-5-carboxamide

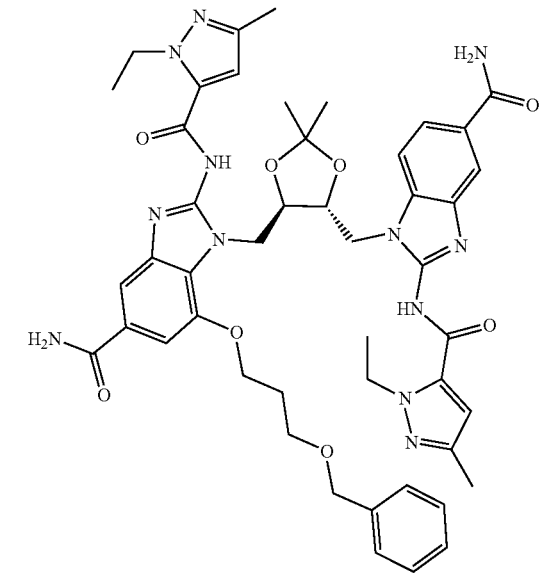 [SMILES: CCn1nc(C)cc1C(=O)Nc1nc2cc(C(N)=O)ccc2n1C[C@H]1OC(C)(C)O[C@@H]1Cn1c(NC(=O)c2cc(C)nn2CC)nc2cc(C(N)=O)cc(OCCCOCc3ccccc3)c21]

To a mixture of 1-ethyl-3-methyl-1H-pyrazole-5-carboxylic acid (336 mg, 2.178 mmol), 2-amino-1-(((4R,5R)-5-((2-amino-5-carbamoyl-1H-benzo[d]imidazol-1-yl)methyl)-2,2-dimethyl-1,3-dioxolan-4-yl)methyl)-7-(3-(benzyloxy)propoxy)-1H-benzo[d]imidazole-5-carboxamide (700 mg, 1.089 mmol) and DIPEA (0.951 mL, 5.45 mmol) in DMF (10 mL) was added HATU (1035 mg, 2.72 mmol). The reaction mixture was stirred at 60° C. for 16 h. The mixture was poured into water. The precipitate was collected by filtration, washed with water and diethyl ether, and then dried under vacuum to afford 7-(3-(benzyloxy)propoxy)-1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-1H-benzo[d]imidazole-5-carboxamide (800 mg, 0.743 mmol, 68.2% yield) as a brown solid. LCMS (~85% purity by UV, m/z): 915 [M+H]⁺.

Step 6: 1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-7-(3-hydroxypropoxy)-1H-benzo[d]imidazole-5-carboxamide Step 7: (E)-1-(((4R,5R)-5-(((E)-5-carbamoyl-2-((1-ethyl-3-methyl-1H-pyrazole-5-carbonyl)imino)-3-methyl-2,3-dihydro-1H-benzo[d]imidazol-1-yl)methyl)-2,2-dimethyl-1,3-dioxolan-4-yl)methyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide

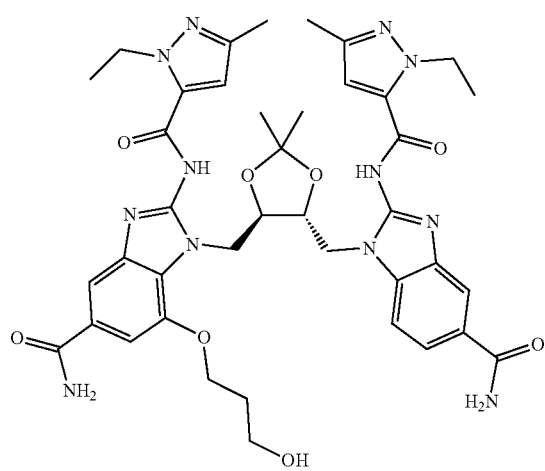 [SMILES: CCn1nc(C)cc1C(=O)Nc1nc2cc(C(N)=O)ccc2n1C[C@H]1OC(C)(C)O[C@@H]1Cn1c(NC(=O)c2cc(C)nn2CC)nc2cc(C(N)=O)cc(OCCCO)c21]

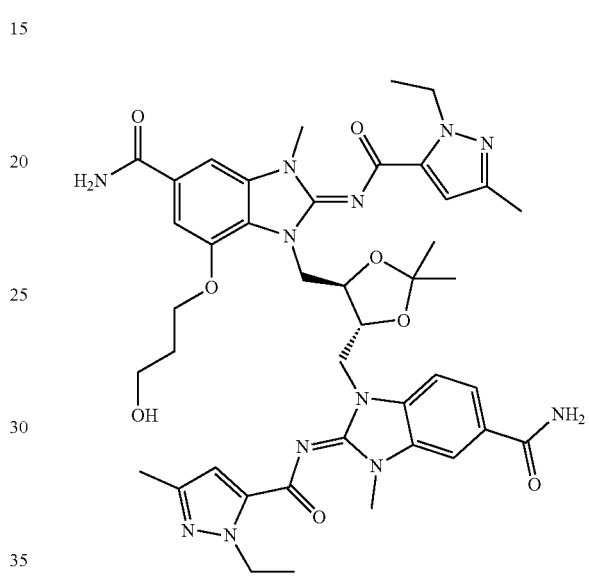

To a solution of 7-(3-(benzyloxy)propoxy)-1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-1H-benzo[d]imidazole-5-carboxamide (650 mg, 0.710 mmol) in methanol (20 mL) was added Pd—C (756 mg, 7.10 mmol). The reaction was hydrogenated using the H-cube (4 atm) at 60° C. for 72 h. The mixture was diluted with DMF (20 mL). The mixture was filtered and the filtrate was concentrated under reduced pressure to afford crude product. The crude product was purified by preparative HPLC (Gemini-C18 column, 5p silica, 21×150 mm; 30-40% gradient of ACN/water with 0.1% TFA modifier) to provide 1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-7-(3-hydroxypropoxy)-1H-benzo[d]imidazole-5-carboxamide (30 mg, 0.035 mmol, 4.9% yield) as an off-white solid. $^1$H NMR (400 MHz, MeOH-d4) δ 7.58 (s, 1H), 7.48 (d, J=8.4 Hz, 1H), 7.33 (s, 1H), 7.17 (d, J=8.4 Hz, 1H), 6.89 (s, 1H), 6.58 (s, 2H), 5.11-4.99 (m, 1H), 4.93 (s, 1H), 4.61 (dqd, J=26.0, 13.2, 6.9 Hz, 5H), 4.46-4.36 (m, 1H), 4.31 (dd, J=13.4, 3.2 Hz, 1H), 4.19 (dd, J=14.0, 3.4 Hz, 1H), 4.03 (dd, J=15.1, 6.4 Hz, 1H), 3.88 (dd, J=14.9, 6.4 Hz, 1H), 3.83-3.72 (m, 1H), 2.23 (s, 3H), 2.18 (s, 3H), 2.05 (dd, J=11.5, 5.9 Hz, 2H), 1.64 (d, J=10.3 Hz, 6H), 1.50-1.28 (m, 6H). LCMS (m/z): 825 [M+H]$^+$.

To a ice-bath cooled mixture of 1-(((4R,5R)-5-((5-carbamoyl-2-(1-ethyl-3-methyl-1H-pyrazole-5-carboxamido)-1H-benzo[d]imidazol-1-yl)methyl)-2,2-dimethyl-1,3-dioxolan-4-yl)methyl)-2-(1-ethyl-3-methyl-1H-pyrazole-5-carboxamido)-7-(3-hydroxypropoxy)-1H-benzo[d]imidazole-5-carboxamide (21 mg, 0.025 mmol) and cesium carbonate (24.88 mg, 0.076 mmol) in DMF (0.5 mL) was added methyl iodide (4 μL, 0.064 mmol). The ice-bath was removed and the mixture was stirred at room temperature for 16 h. After filtration, the filtrate was purified directly by mass-directed preparative HPLC (XSELECT CSH C18, 5 um packing, 150×30 mm column, 30-85% gradient of MeCN/10 mM ammonium bicarbonate adjusted to pH10 with ammonia). Concentration of pure fractions provided title compound (12 mg, 0.014 mmol, 55% yield). $^1$H NMR (400 MHz, DMSO-d$_6$) δ ppm 1.28-1.35 (m, 12H) 1.89-1.94 (m, 2H) 2.08 (s, 3H) 2.13 (s, 3H) 3.28 (s, 3H) 3.30 (s, 3H) 3.53-3.57 (m, 2H) 4.01-4.07 (m, 1H) 4.11-4.16 (m, 1H) 4.27-4.31 (m, 2H) 4.37 (dd, J=12.67, 4.31 Hz, 1H) 4.49-4.56 (m, 6H) 4.60-4.66 (m, 2H) 6.59 (d, J=7.10 Hz, 2H) 7.27 (s, 1H) 7.42-7.50 (m, 4H) 7.72 (dd, J=8.49, 1.39 Hz, 1H) 7.79 (s, 1H) 8.05 (d, J=16.48 Hz, 2H). LCMS (m/z): 853.4 [M+H]$^+$.

Example 37

(E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-isopropyl-3-methyl-2,3-dihydro-1H-benzo[d]imidazole-5-carboxamide

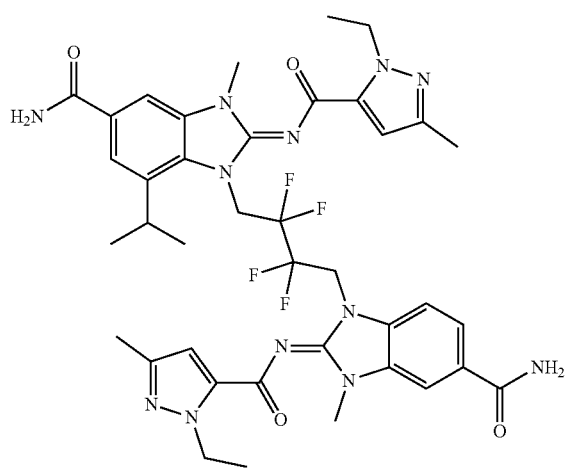 [SMILES: CCn1nc(C)cc1C(=O)/N=c1\n(C)c2cc(C(N)=O)ccc2n1CC(F)(F)C(F)(F)Cn1/c(=N/C(=O)c2cc(C)nn2CC)n(C)c2cc(C(N)=O)cc(C(C)C)c21]

Step 1: 4-((4-amino-2,2,3,3-tetrafluorobutyl)amino)-3-bromo-5-nitrobenzamide

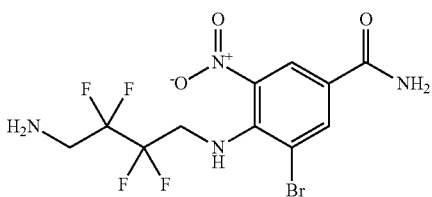

To a solution of 3-bromo-4-fluoro-5-nitrobenzamide (1.4 g, 5.32 mmol) and 2,2,3,3-tetrafluorobutane-1,4-diamine, 2 hydrochloride (1.3 g, 5.58 mmol) in ethanol (30 mL) at room temperature was added DIEA (3.53 mL, 20.23 mmol). The reaction mixture was then warmed to 70° C. and stirred for 4 h. The reaction mixture was cooled to room temperature and then concentrated. The resulting material was partitioned between water and EtOAc. The aqueous layer was separated and extracted with EtOAc (1×). The combined organic layers were then washed with brine, dried with magnesium sulfate and concentrated to obtain 4-((4-amino-2,2,3,3-tetrafluorobutyl)amino)-3-bromo-5-nitrobenzamide (2.15 g, 5.3 mmol, 100% yield) as a yellow solid. The solid was used without further purification. LCMS (m/z): 403.0 [M+H]$^+$.

Step 2: 3-bromo-4-((4-((4-carbamoyl-2-nitrophenyl)amino)-2,2,3,3-tetrafluorobutyl)amino)-5-nitrobenzamide

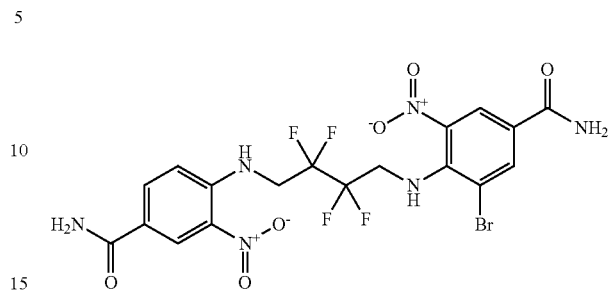

To a suspension of 4-fluoro-3-nitrobenzamide (1.5 g, 8.15 mmol) and 4-((4-amino-2,2,3,3-tetrafluorobutyl)amino)-3-bromo-5-nitrobenzamide (2.15 g, 5.3 mmol) in ethanol (25 mL) at room temperature was added DIEA (2.8 mL, 16.03 mmol). The reaction mixture was then warmed to 80° C. and stirred for 48 h. The reaction mixture was then cooled to room temperature and filtered. The solid was washed with EtOH and then dried to obtain 3-bromo-4-((4-((4-carbamoyl-2-nitrophenyl)amino)-2,2,3,3-tetrafluorobutyl)amino)-5-nitrobenzamide (2.6 g, 4.58 mmol, 86% yield) as a yellow solid. LCMS (m/z): 567.0 [M+H]$^+$.

Step 3: 4-((4-((4-carbamoyl-2-nitrophenyl)amino)-2,2,3,3-tetrafluorobutyl)amino)-3-nitro-5-(prop-1-en-2-yl)benzamide

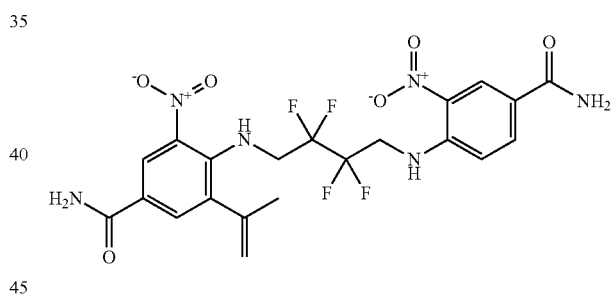

To a 40-mL scintillation vial containing 3-bromo-4-((4-((4-carbamoyl-2-nitrophenyl)amino)-2,2,3,3-tetrafluorobutyl)amino)-5-nitrobenzamide (300 mg, 0.529 mmol), trifluoro(prop-1-en-2-yl)-14-borane, potassium salt (196 mg, 1.322 mmol) and K$_3$PO$_4$ (393 mg, 1.851 mmol) in DMF (2.5 mL) and water (0.25 mL) at room temperature was added PdCl$_2$(dppf)-CH$_2$Cl adduct (44 mg, 0.054 mmol). The reaction vessel was then evacuated and backfilled with nitrogen. The reaction mixture was then warmed to 80° C. and stirred overnight. When cooled to room temperature, the mixture was diluted with EtOAc and water. The biphasic mixture was filtered through a pad of Celite. The aqueous layer was then separated and the organic layer washed with water (2 more times). The combined aqueous layers were then back extracted with EtOAc (1×). The combined organic layers were washed with saturated brine, dried with magnesium sulfate and concentrated. The residue was purified by normal phase silica gel chromatography (0-20% gradient of MeOH/DCM) to provide 4-((4-((4-carbamoyl-2-nitrophenyl)amino)-2,2,3,3-tetrafluorobutyl)amino)-3-nitro-5-(prop-1-en-2-yl)benzamide (111 mg, 0.211 mmol, 40%

Step 4: 3-amino-4-((4-((2-amino-4-carbamoylphenyl)amino)-2,2,3,3-tetrafluorobutyl)amino)-5-isopropylbenzamide

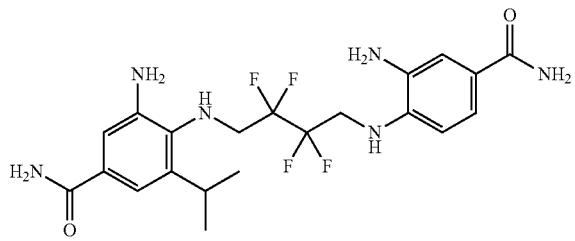 [SMILES: CC(C)c1cc(C(N)=O)cc(N)c1NCC(F)(F)C(F)(F)CNc1ccc(C(N)=O)cc1N]

To a solution of 4-((4-((4-carbamoyl-2-nitrophenyl)amino)-2,2,3,3-tetrafluorobutyl)amino)-3-nitro-5-(prop-1-en-2-yl)benzamide (121 mg, 0.229 mmol) in methanol (20 mL) under nitrogen was added 10% Pd/C (26 mg, 0.024 mmol). The atmosphere of the vessel was exchanged for hydrogen (balloon) and the mixture was stirred overnight. After removal of the hydrogen, LCMS analysis revealed incomplete reduction of the olefin. The Pd catalyst was removed by filtration and the mixture was concentrated. The residue was then dissolved in methanol (20 mL) and further reduced (H-Cube, 50 psi hydrogen, 30° C., 1 h, Pd/C cartridge). After evaporation of solvents, a light brown solid of low purity (~40% by UV) was obtained (72 mg) and used without further purification. LCMS (m/z): 471.1 [M+H]$^+$.

Step 5: 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-isopropyl-1H-benzo[d]imidazole-5-carboxamide

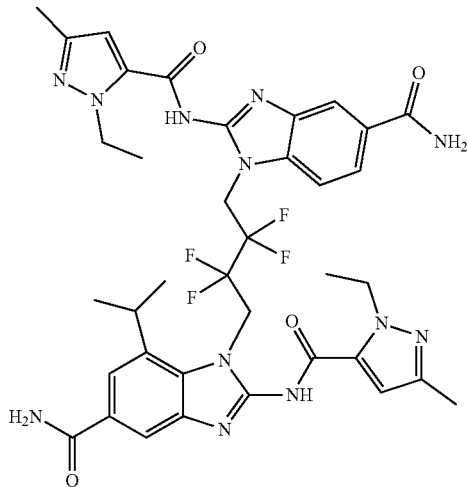 [SMILES: CCn1nc(C)cc1C(=O)Nc1nc2cc(C(N)=O)ccc2n1CC(F)(F)C(F)(F)Cn1c(NC(=O)c2cc(C)nn2CC)nc2cc(C(N)=O)cc(C(C)C)c21]

To a solution of 3-amino-4-((4-((2-amino-4-carbamoylphenyl)amino)-2,2,3,3-tetrafluorobutyl)amino)-5-isopropylbenzamide (72 mg, ~ 40% purity) in DMF (1.5 mL) at room temperature was added a solution of 1-ethyl-3-methyl-1H-pyrazole-5-carbonyl isothiocyanate (1 M in 1,4-dioxane, 0.306 mL, 0.306 mmol). The reaction mixture was then stirred at room temperature for 1 h. To the mixture were then added EDC (110 mg, 0.574 mmol) and TEA (0.160 mL, 1.148 mmol) at room temperature. After stirring overnight, the mixture was filtered and the filtrate was directly purified by mass-directed reverse phase HPLC (XSELECT CSH C18, 5 um packing, 150×30 mm column, 30-85% gradient of MeCN/water with 0.1% TFA modifier) to provide 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-isopropyl-1H-benzo[d]imidazole-5-carboxamide (31 mg, 0.039 mmol, 26% yield). LCMS (m/z): 793.4 [M+H]$^+$.

Step 6: (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-isopropyl-3-methyl-2,3-dihydro-1H-benzo[d]imidazole-5-carboxamide

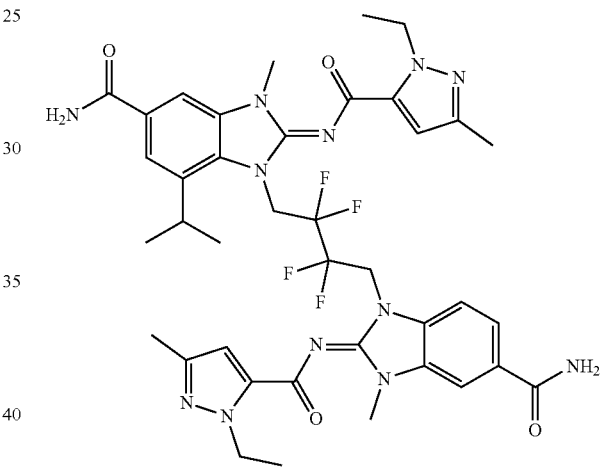

To a mixture of 1-(4-(5-carbamoyl-2-(1-ethyl-3-methyl-1H-pyrazole-5-carboxamido)-1H-benzo[d]imidazol-1-yl)-2,2,3,3-tetrafluorobutyl)-2-(1-ethyl-3-methyl-1H-pyrazole-5-carboxamido)-7-isopropyl-1H-benzo[d]imidazole-5-carboxamide (22 mg, 0.028 mmol) and cesium carbonate (46 mg, 0.141 mmol) in DMF (1 mL) at room temperature was added iodomethane (5 μL, 0.080 mmol). The reaction mixture was then stirred for 5 h. The mixture was filtered and the filtrate was directly purified by mass-directed reverse phase HPLC (XSELECT CSH C18, 5 um packing, 150×30 mm column, 15-55% gradient of MeCN/water with 0.075% NH$_4$OH, 10 mM ammonium bicarbonate, pH 10) to obtain (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-isopropyl-3-methyl-2,3-dihydro-1H-benzo[d]imidazole-5-carboxamide (6 mg, 7.3 umol, 26% yield) as a white solid. $^1$H NMR (400 MHz, DMSO-d$_6$) δ ppm 8.14-8.05 (m, 3H), 7.97-7.85 (m, 3H), 7.66-7.57 (m, 1H), 7.54-7.43 (m, 2H), 6.52 (s, 2H), 5.33-5.12 (m, 4H), 4.55-4.45 (m, 4H), 3.61 (s, 3H), 3.56 (s, 3H), 2.13 (s, 3H), 2.12 (s, 3H), 1.30-1.19 (m, 13H). LCMS (m/z): 821.4 [M+H]$^+$.

Example 38

(E)-2-((1-ethyl-3-methyl-1H-pyrazole-5-carbonyl)imino)-1-(4-((E)-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-7-((4-methoxybenzyl)oxy)-3-methyl-2,3-dihydro-1H-benzo[d]imidazole-5-carboxamide

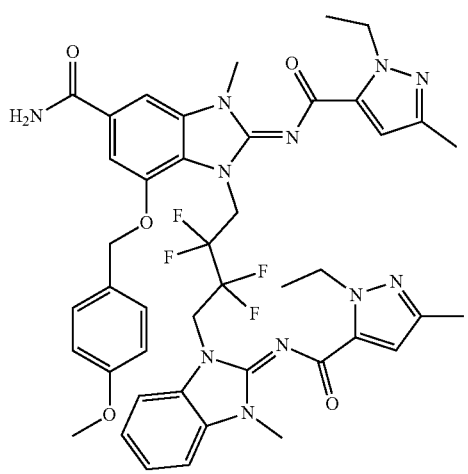 [SMILES: CCn1nc(C)cc1C(=O)/N=c1\n(C)c2ccccc2n1CC(F)(F)C(F)(F)Cn1/c(=N/C(=O)c2cc(C)nn2CC)n(C)c2cc(C(N)=O)cc(OCc3ccc(OC)cc3)c21]

Step 1: 4-((4-amino-2,2,3,3-tetrafluorobutyl)amino)-3-((4-methoxybenzyl)oxy)-5-nitrobenzamide

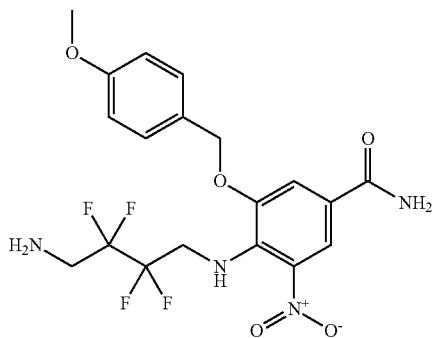 [SMILES: COc1ccc(COc2cc(C(N)=O)cc([N+](=O)[O-])c2NCC(F)(F)C(F)(F)CN)cc1]

To a suspension of 4-chloro-3-((4-methoxybenzyl)oxy)-5-nitrobenzamide (1.2 g, 3.56 mmol) and 2,2,3,3-tetrafluorobutane-1,4-diamine, 2Hydrochloride (1 g, 4.29 mmol) in 1-butanol (40 mL) at room temperature was added sodium bicarbonate (1.078 g, 12.83 mmol). The reaction mixture was then warmed to 120° C. and stirred for 5 days. The mixture was cooled to room temperature and quenched with water. The aqueous phase was extracted with EtOAc (3×). The emulsion that formed was filtered through a cake of Celite. The combined organic layers were washed with brine, dried, and concentrated onto Celite. Normal phase chromatography (40 g column, gradient of 0-8% MeOH/DCM) provided 4-((4-amino-2,2,3,3-tetrafluorobutyl)amino)-3-((4-methoxybenzyl)oxy)-5-nitrobenzamide (349 mg, 0.758 mmol, 21.3% yield) as an orange solid LCMS (m/z): 461.2 [M+H]$^+$.

Step 2: 3-((4-methoxybenzyl)oxy)-5-nitro-4-((2,2,3,3-tetrafluoro-4-((2-nitrophenyl)amino)butyl)amino)benzamide

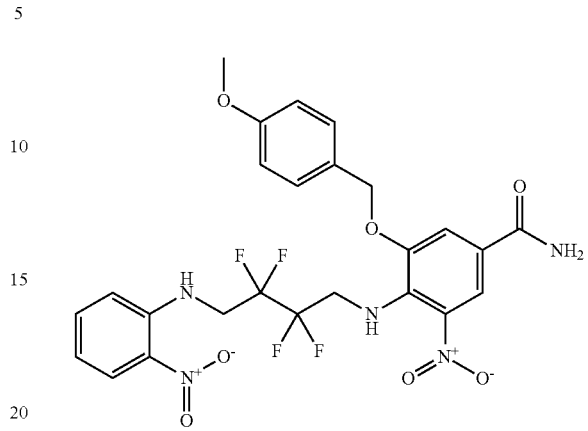

To a suspension of 1-fluoro-2-nitrobenzene (0.16 mL, 1.52 mmol) and 1-fluoro-2-nitrobenzene (0.16 mL, 1.52 mmol) in 1-butanol (4 mL) at room temperature was added sodium bicarbonate (191 mg, 2.27 mmol). The reaction mixture was then warmed to 80° C. and stirred for 12 days. The mixture was cooled to room temperature and quenched with water. The aqueous layer was extracted with EtOAc (3×). The combined organic layers were washed with brine, dried, and concentrated. The residue was suspended in DCM. The solids were then filtered, washed with DCM and dried to obtain 3-((4-methoxybenzyl)oxy)-5-nitro-4-((2,2,3,3-tetrafluoro-4-((2-nitrophenyl)amino)butyl)amino)benzamide (330 mg, 0.569 mmol, 75% yield) as an orange solid. LCMS (m/z): 582.2 [M+H]$^+$.

Step 3: 3-amino-4-((4-((2-aminophenyl)amino)-2,2,3,3-tetrafluorobutyl)amino)-5-((4-methoxybenzyl)oxy)benzamide

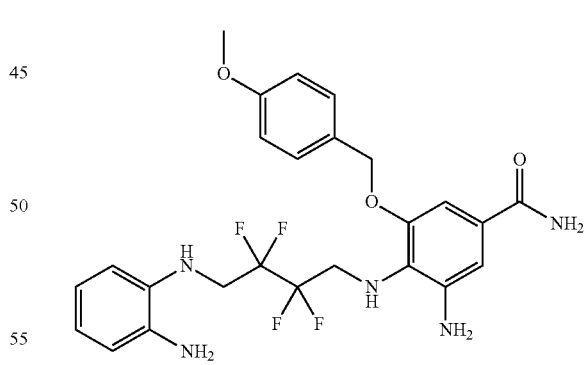

To a solution of 3-((4-methoxybenzyl)oxy)-5-nitro-4-((2,2,3,3-tetrafluoro-4-((2-nitrophenyl)amino)butyl)amino)benzamide (328 mg, 0.564 mmol) and ammonium chloride (302 mg, 5.64 mmol) in methanol (5 mL) at room temperature was added zinc (369 mg, 5.64 mmol). The reaction mixture was then stirred at room temp overnight. The mixture was filtered through Celite, concentrated, and partitioned between water and EtOAc. The aqueous layer was separated and extracted with EtOAc (1×). The combined organic layer was then washed with brine, dried over magnesium sulfate, and concentrated. The residue was suspended in DCM. The solids were filtered, washed with DCM and dried to provide impure title compound (70 mg, ~24% yield). The filtrate was concentrated and the residue purified by mass-directed preparative HPLC (XSELECT CSH C18, 5 um packing, 150×30 mm column, 15-55% gradient of MeCN/water with 0.075% NH4OH, 10 mM ammonium bicarbonate, pH 10) to provide pure 3-amino-4-((4-((2-aminophenyl)amino)-2,2,3,3-tetrafluorobutyl)amino)-5-((4-methoxybenzyl)oxy)benzamide (92 mg, 0.18 mmol, 31% yield) as a light brown solid. LCMS (m/z): 522.3 [M+H]$^+$.

Step 4: 2-(1-ethyl-3-methyl-1H-pyrazole-5-carboxamido)-1-(4-(2-(1-ethyl-3-methyl-1H-pyrazole-5-carboxamido)-1H-benzo[d]imidazol-1-yl)-2,2,3,3-tetrafluorobutyl)-7-((4-methoxybenzyl)oxy)-1H-benzo[d]imidazole-5-carboxamide

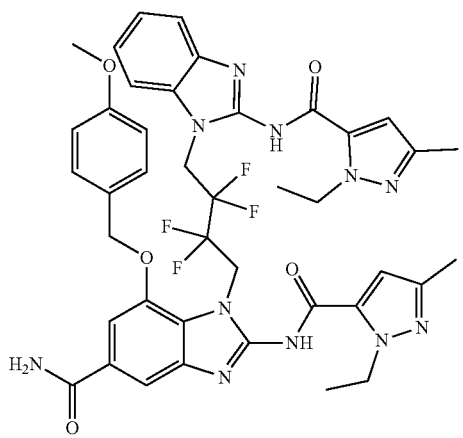 [SMILES: CCn1nc(C)cc1C(=O)Nc1nc2ccccc2n1CC(F)(F)C(F)(F)Cn1c(NC(=O)c2cc(C)nn2CC)nc2cc(C(N)=O)cc(OCc3ccc(OC)cc3)c21]

To a solution of 3-amino-4-((4-((2-aminophenyl)amino)-2,2,3,3-tetrafluorobutyl)amino)-5-((4-methoxybenzyl)oxy) benzamide (92 mg, 0.176 mmol) in DMF (1 mL) at 0° C. was added a solution of 1-ethyl-3-methyl-1H-pyrazole-5-carbonyl isothiocyanate (1 M in 1,4-dioxane, 0.370 mL, 0.370 mmol). The reaction mixture was then stirred at room temperature for 1 h. To the reaction mixture were then added EDC (127 mg, 0.662 mmol) and TEA (0.184 mL, 1.323 mmol) at room temperature. The reaction mixture was then stirred for 2 h. The mixture was diluted with water. The solids were filtered, washed with DCM and water, and dried to obtain 2-(1-ethyl-3-methyl-1H-pyrazole-5-carboxamido)-1-(4-(2-(1-ethyl-3-methyl-1H-pyrazole-5-carboxamido)-1H-benzo[d]imidazol-1-yl)-2,2,3,3-tetrafluorobutyl)-7-((4-methoxybenzyl)oxy)-1H-benzo[d]imidazole-5-carboxamide (85 mg, 0.10 mmol, 57% yield) as an off-white solid. LCMS (m/z): 844.4 [M+H]$^+$.

Step 5: (E)-2-((1-ethyl-3-methyl-1H-pyrazole-5-carbonyl)imino)-1-(4-((E)-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-7-((4-methoxybenzyl)oxy)-3-methyl-2,3-dihydro-1H-benzo[d]imidazole-5-carboxamide To a mixture of 2-(1-ethyl-3-methyl-1H-pyrazole-5-carboxamido)-1-(4-(2-(1-ethyl-3-methyl-1H-pyrazole-5-carboxamido)-1H-benzo[d]imidazol-1-yl)-2,2,3,3-tetrafluorobutyl)-7-((4-methoxybenzyl)oxy)-1H-benzo[d]imidazole-5-carboxamide (65 mg, 0.077 mmol) and cesium carbonate (125 mg, 0.385 mmol) in DMF (1 mL) at room temperature was added iodomethane (0.012 mL, 0.19 mmol). The reaction mixture was then stirred overnight. The reaction mixture was filtered and the filtrate directly purified by mass-directed reverse phase HPLC (XSELECT CSH C18, 5 um packing, 150×30 mm column, 50-99% gradient of MeCN/water with 0.075% NH$_4$OH, 10 mM ammonium bicarbonate, pH 10) to provide (E)-2-((1-ethyl-3-methyl-1H-pyrazole-5-carbonyl)imino)-1-(4-((E)-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-7-((4-methoxybenzyl)oxy)-3-methyl-2,3-dihydro-1H-benzo[d]imidazole-5-carboxamide (33 mg, 0.038 mmol, 49% yield) as an off-white solid. $^1$H NMR (400 MHz, DMSO-d$_6$) δ ppm 8.10 (s, 1H), 7.78 (d, J=1.0 Hz, 1H), 7.68-7.65 (m, 1H), 7.61 (dd, J=1.9, 7.0 Hz, 1H), 7.52 (s, 1H), 7.48-7.33 (m, 5H), 6.77 (d, J=8.6 Hz, 2H), 6.49 (d, J=0.8 Hz, 2H), 5.25-5.09 (m, 4H), 4.72 (t, J=16.6 Hz, 2H), 4.49 (q, J=7.0 Hz, 4H), 3.58 (s, 6H), 3.49 (s, 3H), 2.12 (s, 3H), 2.11 (s, 3H), 1.23 (t, J=7.1 Hz, 3H), 1.24 (t, J=7.1 Hz, 3H). LCMS (m/z): 872.4 [M+H]$^+$.

Example 39

(E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-7-((tetrahydrofuran-3-yl)methoxy)-2,3-dihydro-1H-benzo[d]imidazole-5-carboxamide

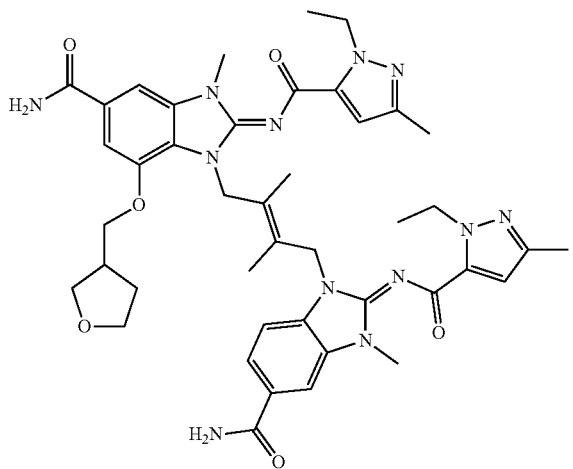 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2cc(C(N)=O)cc(OCC3CCOC3)c21]

To a solution of (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-hydroxy-3-methyl-2,3-dihydro-1H-benzo[d]imidazole-5-carboxamide (49 mg, 0.063 mmol) in DMF (1 mL) was added 3-(bromomethyl)tetrahydrofuran (20.95 mg, 0.127 mmol) followed by potassium carbonate (11.40 mg, 0.083 mmol). The reaction mixture was stirred at 90° C. for 24 h. The mixture was directly purified by preparative HPLC (Phenomenex Eclipse, 5 um packing, 50×30 mm column, 25-55% gradient of MeCN/water with 0.1% TFA modifier). The corresponding fractions were pooled and concentrated in vacuo. The residue was partitioned between EtOAc and an aqueous solution of sodium bicarbonate. The organic layer was separated, dried over sodium sulfate and evaporated in vacuo to provide (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-7-((tetrahydrofuran-3-yl)methoxy)-2,3-dihydro-1H-benzo[d]imidazole-5-carboxamide (22.5 mg, 0.027 mmol, 42.6% yield) as a white solid. $^1$H NMR (400 MHz, DMSO-$d_6$) δ ppm 8.11-8.15 (m, 1H), 8.05-8.11 (m, 1H), 7.99-8.05 (m, 1H), 7.79 (s, 2H), 7.50 (br. s., 3H), 7.18-7.28 (m, 1H), 6.46 (s, 1H), 6.37 (s, 1H), 5.06 (br. s., 2H), 4.86 (br. s., 2H), 4.42-4.56 (m, 4H), 3.97-4.12 (m, 2H), 3.65-3.73 (m, 1H), 3.59 (s, 3H), 3.57 (s, 3H), 3.45-3.53 (m, 2H), 2.11 (s, 3H), 2.08 (s, 3H), 1.62 (br. s., 4H), 1.48 (br. S., 4H), 1.15-1.36 (m, 8H). LCMS (m/z): 833.5 [M+H]$^+$.

Example 40

(E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-hydroxy-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide

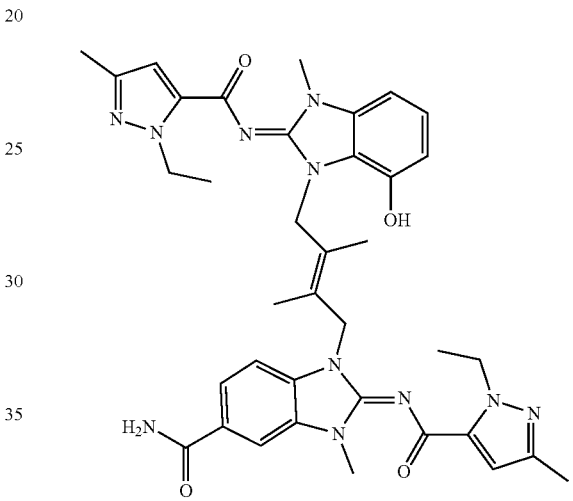

To a solution of (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide (400 mg, 0.484 mmol) in DCM (8 mL) was added a solution of HCl (4M in dioxane, 0.726 mL, 2.91 mmol) dropwise. Most DCM was removed in vacuo. 1,4-dioxane (8 mL) and more HCl solution (4M in dioxane, 0.726 mL, 2.91 mmol) were added. The vessel was sonicated and stirred vigorously for 2.5 h (gum still present and reaction incomplete). The mixture was again concentrated in vacuo and resuspended in THF (6 mL) and water (1 mL). More HCl solution (4M in dioxane, 0.726 mL, 2.91 mmol) was added and the mixture was stirred for 3 h. Reaction mixture was concentrated and dissolved in 20% methanol/DCM (6 mL). To this homogeneous solution was added HCl solution (4M in dioxane, 0.726 mL, 2.91 mmol) and the mixture was stirred for 30 min. Owing to byproduct formation, the solvents were again evaporated and replaced with a mixture of 3:1 DCM:ethanol (8 mL) and more HCl solution (4M in dioxane, 0.726 mL, 2.91 mmol). The reaction mixture was stirred at room temperature for 48 h.

The mixture was concentrated and partitioned between 10% methanol/DCM and saturated aqueous sodium bicarbonate solution. The aqueous layer was extracted twice with 3:1 CHCl₃:EtOH. The combined organic phase was concentrated. The residue was partially purified by silica gel chromatography (12 g silica; 10-90% [3:1 EA:EtOH]/heptane). The crude solids were suspended in several mLs of DMSO. The undissolved solids were filtered, washed with DCM, dried and found sufficiently pure (~90%, 149 mg) for synthesis of additional analogs. The dissolved material was subsequently purified by mass-directed HPLC (XSELECT CSH C18, 5 um packing, 150×30 mm column, 15-55% gradient of MeCN/water with 0.1% TFA modifier). A few drops of saturated sodium bicarbonate solution was added to each clean fraction. The ACN was removed using a stream of nitrogen. The suspended solids were filtered, rinsed with water, and dried to provide pure (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-hydroxy-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide (11.2 mg, 0.016 mmol, 3.2%) as a white solid. ¹H NMR (DMSO-d₆) δ ppm 8.10 (s, 1H), 7.99 (br. s., 1H), 7.78 (dd, J=8.4, 1.4 Hz, 1H), 7.42 (br. s., 1H), 7.20 (d, J=8.5 Hz, 1H), 7.12 (t, J=8.0 Hz, 1H), 7.01 (d, J=7.8 Hz, 1H), 6.75 (d, J=8.0 Hz, 1H), 6.48 (s, 1H 6.32 (s, 1H), 5.08 (s, 2H), 4.82 (s, 2H), 4.44-4.57 (m, 4H), 3.58 (s, 3H), 3.51 (s, 3H), 2.14 (s, 3H), 2.07 (s, 3H), 1.65 (s, 3H), 1.48 (s, 3H), 1.30 (t, J=7.2 Hz, 3H), 1.25 (t, J=7.2 Hz, 3H). LCMS (m/z): 706.4 [M+H]⁺.

Example 41

(E)-1-((2S,3S)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide

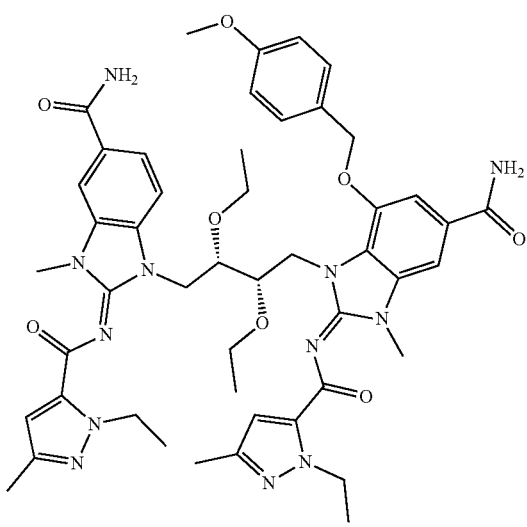 [SMILES: CCO[C@@H](Cn1/c(=N/C(=O)c2cc(C)nn2CC)n(C)c2cc(C(N)=O)ccc21)[C@H](Cn1/c(=N/C(=O)c2cc(C)nn2CC)n(C)c2cc(C(N)=O)cc(OCc3ccc(OC)cc3)c21)OCC]

Step 1: 4-(((2S,3S)-4-((4-carbamoyl-2-nitrophenyl)amino)-2,3-diethoxybutyl)amino)-3-((4-methoxybenzyl)oxy)-5-nitrobenzamide

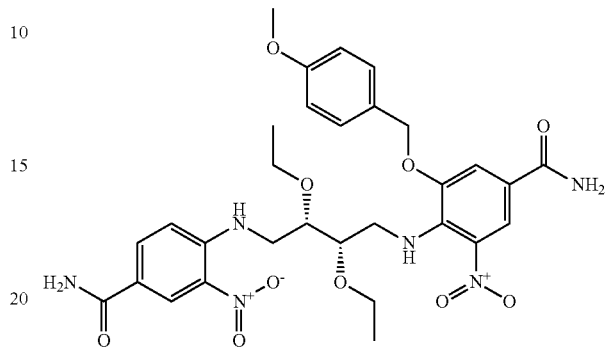

To the mixture of 4-chloro-3-((4-methoxybenzyl)oxy)-5-nitrobenzamide (1.55 g, 4.60 mmol) in 1-butanol (15 mL) were added (2S,3S)-2,3-diethoxybutane-1,4-diamine (1.01 g, 5.75 mmol) and DIEA (2.41 mL, 13.8 mmol). The mixture was stirred at 120° C. for 2 h. 4-fluoro-3-nitrobenzamide (0.848 g, 4.60 mmol) was then added. The mixture was stirred at 120° C. for 18 h. The mixture was cooled and filtered to remove suspended solids. After removal of solvents, silica gel chromatography (40 g silica, gradient of 5-20% MeOH/DCM) provided 4-(((2S,3S)-4-((4-carbamoyl-2-nitrophenyl)amino)-2,3-diethoxybutyl)amino)-3-((4-methoxybenzyl)oxy)-5-nitrobenzamide (0.86 g, ~25% yield, contaminated by ~20% symmetrical bis-PMB-protected byproduct) as an orange solid. LCMS (m/z): 641.2 [M+H]⁺.

The collected precipitate provided 4,4'-(((2S,3S)-2,3-diethoxybutane-1,4-diyl)bis(azanediyl))bis(3-((4-methoxybenzyl)oxy)-5-nitrobenzamide) (423 mg, 0.545 mmol, 12% yield, LCMS (m/z): 777.5 [M+H]⁺) that can be used to prepare other examples.

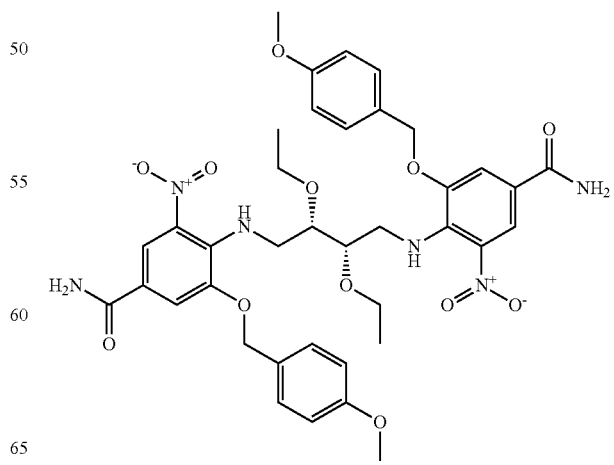

Step 2: 3-amino-4-(((2S,3S)-4-((2-amino-4-carbamoylphenyl)amino)-2,3-diethoxybutyl)amino)-5-((4-methoxybenzyl)oxy)benzamide

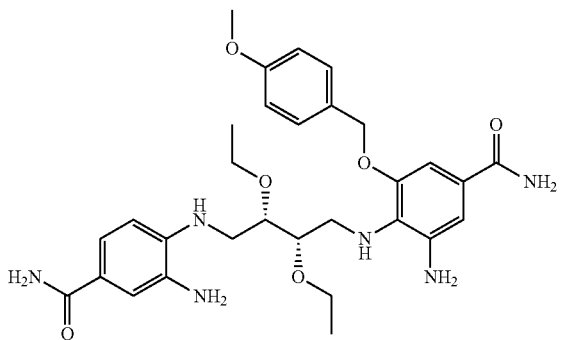 [SMILES: CCO[C@@H](CNc1ccc(C(N)=O)cc1N)[C@H](CNc1c(N)cc(C(N)=O)cc1OCc1ccc(OC)cc1)OCC]

To a 100 mL round bottom flask were added 4-(((2S,3S)-4-((4-carbamoyl-2-nitrophenyl)amino)-2,3-diethoxybutyl)amino)-3-((4-methoxybenzyl)oxy)-5-nitrobenzamide (0.86 g, 1.342 mmol) and methanol (20 mL). To this mixture was added 10 mL saturated aqueous ammonium chloride solution. To this mixture was added zinc (0.878 g, 13.42 mmol) and the heterogenous mixture was stirred at room temperature for 15 min. The mixture was filtered and the filtercake was rinsed with MeOH. The filtrate was concentrated.

The crude product was purified by silica gel chromatography (24 gram silica, gradient of 6-20% MeOH/DCM with 1% NH$_4$OH as modifier) to provide 3-amino-4-(((2S,3S)-4-((2-amino-4-carbamoylphenyl)amino)-2,3-diethoxybutyl)amino)-5-((4-methoxybenzyl)oxy)benzamide (0.127 g, 16%) as a light yellow solid. LCMS (m/z): 581.3 [M+H]$^+$.

Step 3: 1-((2S,3S)-4-(5-carbamoyl-2-(1-ethyl-3-methyl-1H-pyrazole-5-carboxamido)-1H-benzo[d]imidazol-1-yl)-2,3-diethoxybutyl)-2-(1-ethyl-3-methyl-1H-pyrazole-5-carboxamido)-7-((4-methoxybenzyl)oxy)-1H-benzo[d]imidazole-5-carboxamide

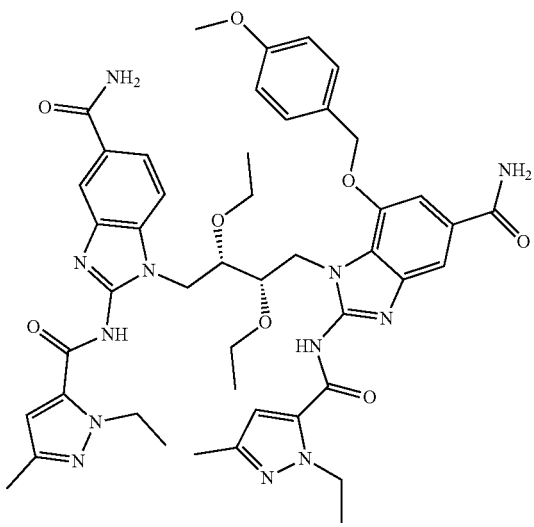 [SMILES: CCO[C@@H](Cn1c(NC(=O)c2cc(C)nn2CC)nc2cc(C(N)=O)ccc21)[C@H](Cn1c(NC(=O)c2cc(C)nn2CC)nc2cc(C(N)=O)cc(OCc3ccc(OC)cc3)c21)OCC]

To the solution of 3-amino-4-(((2S,3S)-4-((2-amino-4-carbamoylphenyl)amino)-2,3-diethoxybutyl)amino)-5-((4-methoxybenzyl)oxy)benzamide (0.127 g, 0.219 mmol) in DMF (6 mL) was added 1-ethyl-3-methyl-1H-pyrazole-5-carbonyl isothiocyanate (~0.4 in dioxane, 1.094 mL, 0.437 mmol). The mixture was stirred for 15 minutes. EDC (0.105 g, 0.547 mmol) and TEA (0.152 mL, 1.094 mmol) were added and the reaction was stirred at 50° C. for 18 h. The reaction mixture was poured into 3:1 water:saturated aqueous ammonium chloride solution (20 mL). The resulting solid was filtered, washed with water, and dried to provide 1-((2S,3S)-4-(5-carbamoyl-2-(1-ethyl-3-methyl-1H-pyrazole-5-carboxamido)-1H-benzo[d]imidazol-1-yl)-2,3-diethoxybutyl)-2-(1-ethyl-3-methyl-1H-pyrazole-5-carboxamido)-7-((4-methoxybenzyl)oxy)-1H-benzo[d]imidazole-5-carboxamide (0.142 g, 0.157 mmol, 72% yield) as a solid. LCMS (m/z): 903.3 [M+H]$^+$.

Step 4: (E)-1-((2S,3S)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide

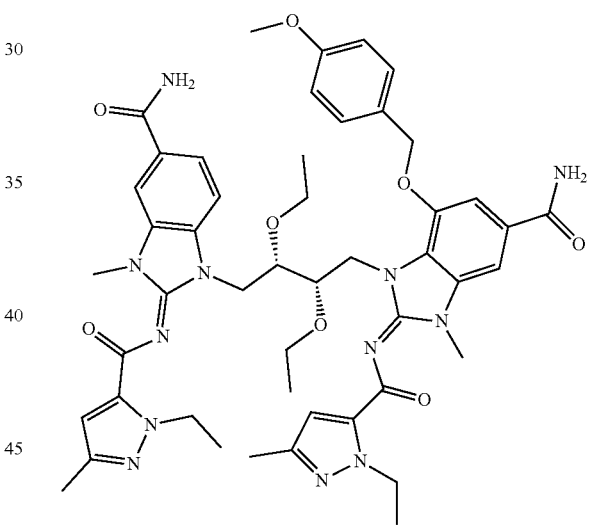

To a solution of 1-((2S,3S)-4-(5-carbamoyl-2-(1-ethyl-3-methyl-1H-pyrazole-5-carboxamido)-1H-benzo[d]imidazol-1-yl)-2,3-diethoxybutyl)-2-(1-ethyl-3-methyl-1H-pyrazole-5-carboxamido)-7-((4-methoxybenzyl)oxy)-1H-benzo[d]imidazole-5-carboxamide (0.112 g, 0.124 mmol) in DMF (5 mL) were added cesium carbonate (0.121 g, 0.372 mmol) and methyl iodide (0.031 mL, 0.496 mmol). The reaction mixture was stirred at room temperature for 18 h. The reaction mixture was diluted with water and extracted with EtOAc (3×50 mL). The organic phase was washed with brine (10 mL), dried with magnesium sulfate$_4$ filtered, and concentrated. The crude product was purified using mass-directed reversed phase HPLC (XSELECT CSH C18, 5 um packing, 150×30 mm column, 15-55% gradient of MeCN/water with 0.075% NH4OH, 10 mM ammonium bicarbonate, pH 10). Pure fractions were combined and concentrated to give the (E)-1-((2S,3S)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide (34 mg, 0.36 mmol, 29% yield) as white solid. $^1$H NMR (400 MHz, DMSO-$d_6$) δ ppm 8.00-8.25 (m, 3H) 7.86 (dd, J=8.49, 1.39 Hz, 1H) 7.77 (d, J=1.01 Hz, 1H) 7.62 (s, 1H) 7.36-7.53 (m, 5H) 6.75 (d, J=8.62 Hz, 2H) 6.49 (d, J=6.84 Hz, 2H) 5.22 (d, J=10.39 Hz, 1H) 5.11 (d, J=10.65 Hz, 1H) 4.44-4.69 (m, 5H) 4.29-4.42 (m, 1H) 3.93-4.06 (m, 1H) 3.63-3.84 (m, 3H) 3.58 (s, 3H) 3.58 (s, 3H) 3.40 (s, 3H) 3.09-3.28 (m, 2H) 2.80-2.94 (m, 2H) 2.12 (s, 3H) 2.10 (s, 3H) 1.30 (t, J=7.10 Hz, 6H) 0.58 (t, J=6.97 Hz, 3H) 0.47 (t, J=6.97 Hz, 3H). LCMS (m/z): 931.4 [M+H]$^+$.

Table 2 show Examples 43-92, which can be prepared according to methods illustrated below:

| Example Number | Scheme | Name/Structure | $^1$H NMR LCMS (m/z) [M + H]$^+$ |
|---|---|---|---|
| Example 42 | Method 1 | (2E,2'E)-1,1'-((E)-2,3-dimethylbut-2-ene-1,4-diyl)bis(2-((1-ethyl-3-methyl-1H-pyrazole-5-carbonyl)imino)-3-methyl-2,3-dihydro-1H-benzo[d]imidazole-5-carboxamide) | $^1$H NMR (400 MHz, METHANOL-$d_4$) δ ppm 8.13 (d, J = 1.27 Hz, 2H) 7.86 (dd, J = 8.36, 1.52 Hz, 2H) 7.36 (d, J = 8.62 Hz, 2H) 6.59 (s, 2H) 4.97 (s, 4H) 4.62 (q, J = 7.10 Hz, 4H) 3.71 (s, 6H) 2.23 (s, 6H) 1.73 (s, 6H) 1.39 (t, J = 7.10 Hz, 6H) LCMS (m/z) [M + H]$^+$ 733.6 |
| Example 43 | Method 1 | (E)-7-bromo-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide | $^1$H NMR (400 MHz, METHANOL-$d_4$) δ ppm 8.10-8.12 (m, 1H) 8.08-8.10 (m, 1H) 7.57 (d, J = 7.86 Hz, 1H) 7.36-7.42 (m, 1H) 7.31-7.37 (m, 1H) 7.24-7.30 (m, 1H) 6.63 (s, 1H) 6.58 (s, 1H) 5.34 (s, 2H) 4.95 (s, 2H) 4.63 (dq, J = 18.00, 7.10 Hz, 4H) 3.69 (s, 3H) 3.68 (s, 3H) 2.25 (s, 3H) 2.22 (s, 3H) 1.72 (s, 3H) 1.59 (s, 3H) 1.39 (dt, J = 15.40, 7.13 Hz, 6H) LCMS (m/z) [M + H]$^+$ 768/770 |

-continued

| Example Number | Scheme | Name/Structure | $^1$H NMR<br>LCMS (m/z) [M + H]$^+$ |
|---|---|---|---|
| Example 44 | Method 1 | (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-hydroxy-3-methyl-2,3-dihydro-1H-benzo[d]imidazole-5-carboxamide | $^1$H NMR (400 MHz, DMSO-d$_6$) δ ppm 10.71 (br. s., 1 H), 7.99-8.12 (m, 2H), 7.95 (br. s., 1H), 7.84 (dd, J = 8.49, 1.39 Hz, 1H), 7.51-7.62 (m, 2H), 7.44 (br. s., 1H), 7.37 (br. s., 1H), 7.32 (s, 1H), 6.50 (s, 1H), 6.48 (s, 1H), 4.27-4.69 (m, 8 H), 3.87-4.00 (m, 1H), 3.69-3.80 (m, 1H), 3.57 (s, 3H), 3.53 (s, 3H), 3.21-3.32 (m, 2H), 3.05-3.17 (m, 1H), 2.88-3.01 (m, 1 H), 2.13 (s, 3H), 2.11 (s, 3 H), 1.23-1.34 (m, 6H), 0.68 (t, J = 6.97 Hz, 3H), 0.52 (t, J = 6.84 Hz, 3H)<br>LCMS (m/z) [M + H]$^+$ 811.6 |
| Example 45 | Method 1 | Methyl 4-(((E)-6-carbamoyl-3-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-1-methyl-2,3-dihydro-1H-benzo[d]imidazol-4-yl)oxy)butanoate | $^1$H NMR (DMSO-d$_6$) δ ppm 8.07-8.13 (m, 2H), 8.01 (br. s., 1H), 7.76-7.82 (m, 2H), 7.45-7.53 (m, 3H), 7.26 (d, J = 8.4 Hz, 1H), 6.44 (s, 1 H), 6.38 (s, 1H), 5.05 (s, 2 H), 4.86 (s, 2H), 4.43-4.56 (m, 4H), 4.11 (t, J = 6.5 Hz, 2H), 3.58 (s, 3H), 3.57 (s, 3H), 3.49 (s, 3H), 2.33 (t, J = 7.5 Hz, 2H), 2.10 (s, 3 H), 2.08 (s, 3H), 1.76-1.85 (m, 2H), 1.61 (s, 3H), 1.50 (s, 3H), 1.22-1.31 (m, 6H)<br>LCMS (m/z) [M + H]$^+$ 849.7 |
| Example 46 | Method 1 | (E)-1-((E)-4-((E)-5-carbamoyl-2-((1-ethyl-3-methyl-1H-pyrazole-5-carbonyl)imino)-3-propyl-2,3-dihydro-1H-benzo[d]imidazol-1-yl)-2,3-dimethylbut-en-1-yl)-2-((1-ethyl-3-methyl-1H-pyrazole-5-carbonyl)imino)-7-((4-methoxybenzyl)oxy)-3-propyl-2,3-dihyd(E)-1-(4-(5-carbamoyl-2-(1-ethyl-3-methyl-1H-pyrazole-5-carboxamido)- | $^1$H NMR (400 MHz, CHLOROFORM-d) δ ppm 7.93-8.11 (m, 1H), 7.43-7.58 (m, 2H), 7.33-7.41 (m, 1H), 7.02-7.16 (m, 3 H), 6.87 (d, J = 8.36 Hz, 3 H), 6.65-6.82 (m, 3H), 5.09-5.28 (m, 2H), 4.75-4.89 (m, 3H), 4.57-4.74 |

| Example Number | Scheme | Name/Structure | ¹H NMR<br>LCMS (m/z) [M + H]⁺ |
|---|---|---|---|
| | | 1H-benzo[d]imidazol-1-yl)-2,3-dimethylbut-2-en-1-yl)-2-(1-ethyl-3-methyl-1H-pyrazole-5-carboxamido)-7-((4-methoxybenzyl)oxy)-1H-benzo[d]imidazole-5-carboxamidero-1H-benzo[d]imidazole-5-carboxamide<br>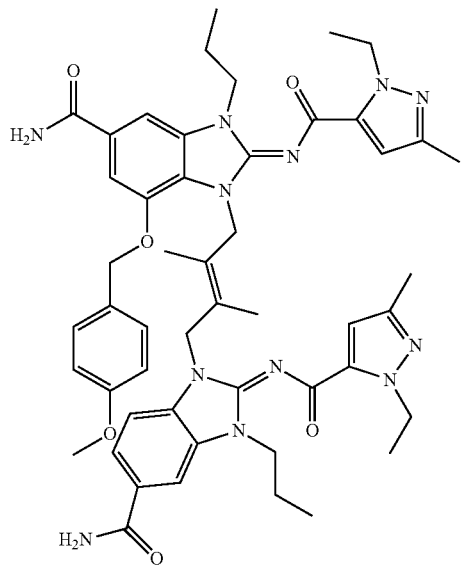 [SMILES: CCCn1/c(=N\C(=O)c2cc(C)nn2CC)n(C/C(C)=C(\C)Cn2/c(=N/C(=O)c3cc(C)nn3CC)n(CCC)c3cc(C(N)=O)cc(OCc4ccc(OC)cc4)c32)c2ccc(C(N)=O)cc21] | (m, 5H), 4.21-4.32 (m, 3 H), 3.79 (s, 3H), 2.32-2.41 (m, 3H), 2.26-2.32 (m, 3 H), 2.02-2.07 (m, 2H), 1.89-1.97 (m, 4H), 1.65-1.84 (m, 2H), 1.59 (br. s., 4 H), 1.47 (s, 3H), 1.38-1.44 (m, 3H), 1.19 (br. s., 2H), 0.95-1.06 (m, 4H), 0.54-0.55 (m, 1H)<br>LCMS (m/z) [M + H]⁺ 925.8 |
| Example 47 | Method 1 | (E)-1-((E)-4-((E)-5-carbamoyl-3-ethyl-2-((1-ethyl-3-methyl-1H-pyrazole-5-carbonyl)imino)-2,3-dihydro-1H-benzo[d]imidazol-1-yl)-2,3-dimethylbut-2-en-1-yl)-3-ethyl-2-((1-ethyl-3-methyl-1H-pyrazole-5-carbonyl)imino)-7-((4-methoxybenzyl)oxy)-2,3-dihydro-1H-benzo[d]imidazole-5-carboxamide<br>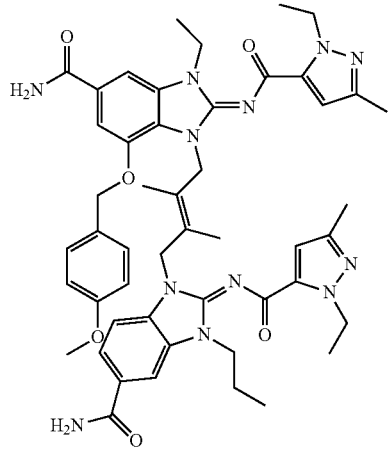 | ¹H NMR (400 MHz, CHLOROFORM-d) δ ppm 8.04 (br. s., 1H), 7.33-7.79 (m, 2H), 7.16 (d, J = 8.11 Hz, 1H), 6.94 (s, 2 H), 6.85 (d, J = 8.62 Hz, 2 H), 6.66 (d, J = 8.62 Hz, 3 H), 5.10 (br. s., 2H), 4.60-4.88 (m, 8H), 4.48 (br. s., 2 H), 4.32 (d, J = 6.59 Hz, 5 H), 3.57-3.92 (m, 4H), 2.18-2.44 (m, 6H), 1.93 (br. s., 2H), 1.43-1.75 (m, 12H), 1.14 (s, 3H)<br>LCMS (m/z) [M + H]⁺ 897.5 |

| Example Number | Scheme | Name/Structure | ¹H NMR<br>LCMS (m/z) [M + H]⁺ |
|---|---|---|---|
| Example 48 | Method 1 | (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-(3-(dimethylamino)propoxy)-2-((1-ethyl-3-methyl-1H-pyrazole-5-carbonyl)imino)-3-methyl-2,3-dihydro-1H-benzo[d]imidazole-5-carboxamide<br>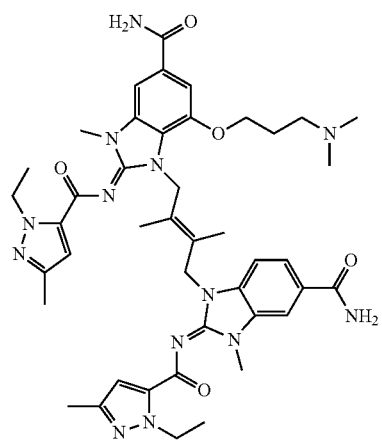 | ¹H NMR (DMSO-$d_6$) δ ppm 8.09-8.15 (m, 2H), 8.02 (br. s., 1H), 7.76-7.82 (m, 2H), 7.45-7.53 (m, 3H), 7.22 (d, J = 8.4 Hz, 1H), 6.45 (s, 1 H), 6.37 (s, 1H), 5.07 (s, 2 H), 4.86 (s, 2H), 4.44-4.56 (m, 4H), 4.12 (t, J = 6.5 Hz, 2H), 3.59 (s, 3H 3.57 (s, 3 H), 2.21 (br. s., 2H), 2.11 (s, 3H), 2.08 (s, 3H), 2.02 (br. s., 6H), 1.64-1.72 (m, 2 H), 1.62 (s, 3H), 1.50 (s, 3 H), 1.22-1.31 (m, 6H)<br>LCMS (m/z) [M + H]⁺ 834.6 |
| Example 49 | Method 1 | (E)-7-(benzyloxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide<br>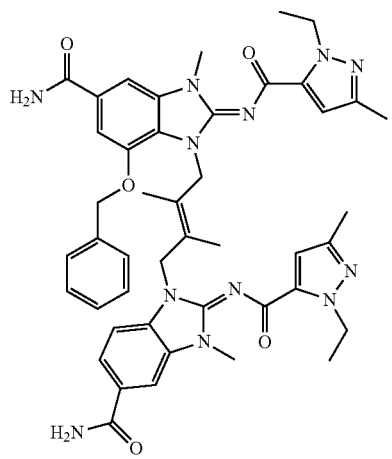 | ¹H NMR (400 MHz, DMSO-$d_6$) δ ppm 8.09-8.17 (m, 2 H), 7.96-8.07 (m, 1H), 7.81 (s, 1H), 7.76 (d, J = 9.38 Hz, 1H), 7.62 (s, 1 H), 7.53 (br. s., 1H), 7.49 (br. s., 1H), 7.25-7.33 (m, 2H), 7.12-7.23 (m, 4H), 6.46 (s, 1H), 6.38 (s, 1H), 5.19 (s, 2H), 4.98 (br. s., 2 H), 4.77 (br. s., 2H), 4.41-4.55 (m, 4H), 3.59 (s, 3H), 3.58 (s, 3H), 2.12 (s, 3H), 2.10 (s, 3H), 1.59 (s, 3H), 1.28 (t, J = 7.10 Hz, 3H), 1.23 (t, J = 7.10 Hz, 3H), 1.17 (s, 3H)<br>LCMS (m/z) [M + H]⁺ 839.6 |

| Example Number | Scheme | Name/Structure | ¹H NMR<br>LCMS (m/z) [M + H]⁺ |
|---|---|---|---|
| Example 50 | Method 1 | (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-((3-methoxybenzyl)oxy)-3-methyl-2,3-dihydro-1H-benzo[d]imidazole-5-carboxamide<br>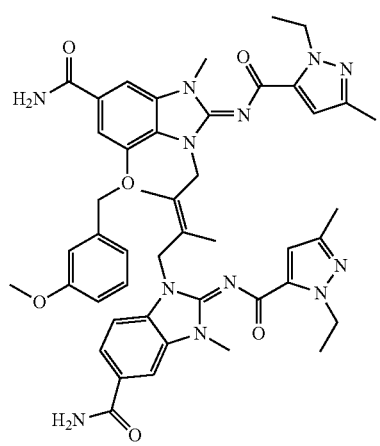 | ¹H NMR (400 MHz, DMSO-$d_6$) δ ppm 8.12 (s, 1H), 8.06-8.10 (m, 1H), 7.97-8.05 (m, 1H), 7.81 (s, 1H), 7.71-7.78 (m, 1H), 7.61 (s, 1H), 7.49-7.54 (m, 1 H), 7.42-7.48 (m, 1H), 7.08-7.23 (m, 2H), 6.91 (s, 1H), 6.84 (d, J = 7.10 Hz, 1H), 6.77 (dd, J = 7.86, 2.53 Hz, 1H), 6.45 (s, 1H), 6.37 (s, 1H), 5.18 (s, 2H), 5.02 (s, 2H), 4.78 (s, 2H), 4.43-4.56 (m, 4H), 3.67 (s, 3H), 3.58 (s, 3H), 3.57 (s, 3H), 2.11 (s, 3H), 2.08 (s, 3H), 1.60 (s, 3H), 1.21-1.31 (m, 9H)<br>LCMS (m/z) [M + H]⁺ 869.5 |
| Example 51 | Method 1 | (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-(4-methoxyphenethoxy)-3-methyl-2,3-dihydro-1H-benzo[d]imidazole-5-carboxamide<br>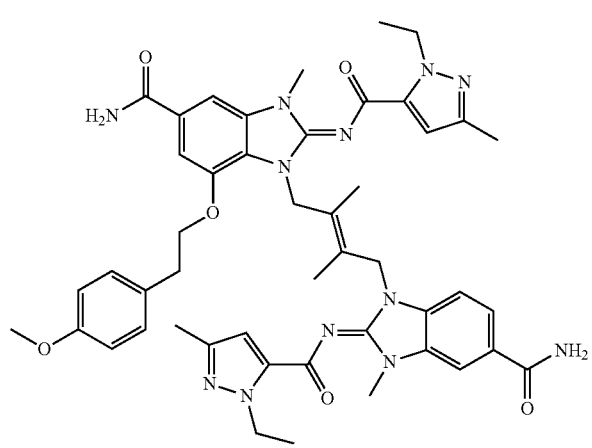 | ¹H NMR (DMSO-$d_6$) δ ppm 8.11 (s, 1H), 8.08 (br. s., 1 H), 8.02 (br. s., 1H), 7.81 (d, J = 8.4 Hz, 1H), 7.77 (s, 1H), 7.52 (s, 1H), 7.45-7.49 (br. m., 2H), 7.23 (d, J = 8.6 Hz, 1H), 7.06 (d, J = 8.6 Hz, 2H), 6.78 (d, J = 8.6 Hz, 2H), 6.46 (s, 1 H), 6.29 (s, 1H), 4.91 (s, 2 H), 4.83 (s, 2H), 4.42-4.55 (m, 4H), 4.32 (t, J = 6.6 Hz, 2H), 3.67 (s, 3H), 3.57 (s, 3H), 3.55 (s, 3H), 2.83-2.89 (m, 2H), 2.09 (s, 3H), 2.05 (s, 3H), 1.53 (s, 3H), 1.43 (s, 3H), 1.24-1.30 (m, 6H)<br>LCMS (m/z) [M + H]⁺ 883.7 |

| Example Number | Scheme | Name/Structure | $^1$H NMR<br>LCMS (m/z) [M + H]$^+$ |
|---|---|---|---|
| Example 52 | Method 1 | (2E,2′E)-1,1′-((E)-2,3-dimethylbut-2-ene-1,4-diyl)bis(2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide)<br>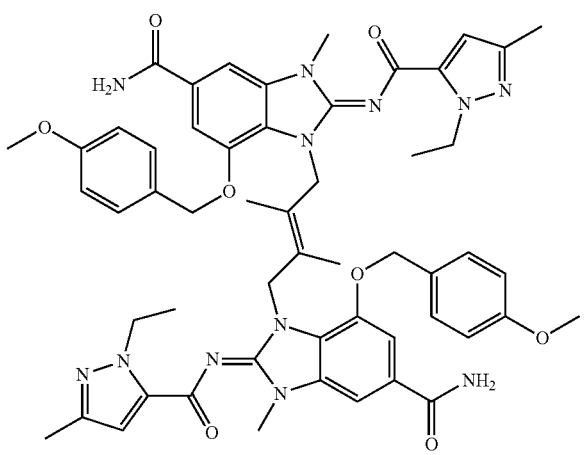 | $^1$H NMR $^1$H NMR (400 MHz, METHANOL-d$_4$) δ ppm 7.81-7.87 (m, 2H) 7.68 (d, J = 1.27 Hz, 2H) 7.23 (d, J = 8.62 Hz, 4H) 6.61 (d, J = 8.62 Hz, 4H) 6.44 (s, 2 H) 5.13 (s, 4H) 5.02 (s, 4 H) 4.44-4.62 (m, 4H) 3.68 (s, 6H) 3.62 (s, 6H) 2.15 (s, 6H) 1.31 (t, J = 7.10 Hz, 6H) 1.15 (s, 6H)<br>LCMS (m/z) [M + H]$^+$ 1005.4 |
| Example 53 | Method 1 | Methyl (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxylate, Trifluoroacetic acid salt<br>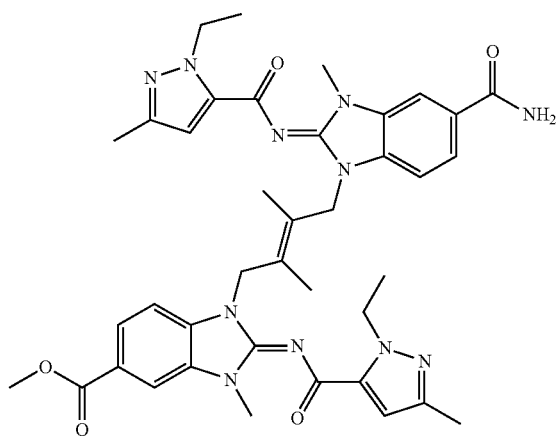 | $^1$H NMR (400 MHz, METHANOL-d$_4$) δ ppm 8.27 (d, J = 1.01 Hz, 1H) 8.20 (d, J = 1.27 Hz, 1H) 7.98 (dd, J = 8.62, 1.52 Hz, 1H) 7.88 (dd, J = 8.49, 1.65 Hz, 1H) 7.41 (dd, J = 14.95, 8.36 Hz, 2H) 6.65 (s, 2H) 5.02 (d, J = 7.35 Hz, 4H) 4.62 (qd, J = 7.10, 3.04 Hz, 4H) 3.99 (s, 3H) 3.77 (d, J = 7.60 Hz, 6H) 2.25 (d, J = 2.79 Hz, 6 H) 1.73 (s, 6H) 1.40 (t, J = 7.10 Hz, 6H)<br>LCMS (m/z) [M + H]$^+$ 748.6 |

| Example Number | Scheme | Name/Structure | ¹H NMR<br>LCMS (m/z) [M + H]⁺ |
|---|---|---|---|
| Example 54 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-hydroxy-3-methyl-2,3-dihydro-1H-benzo[d]imidazole-5-carboxamide<br>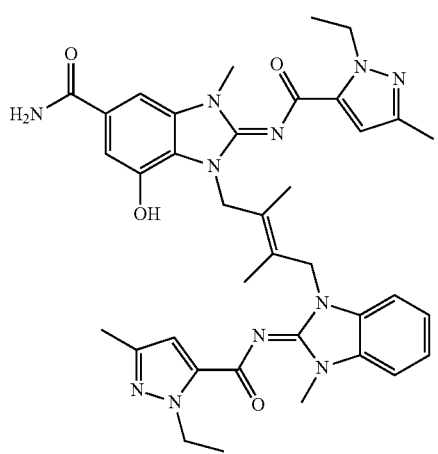 | ¹H NMR (DMSO-$d_6$) δ ppm 10.64 (s, 1H), 7.93 (br. s., 1 H), 7.56-7.63 (m, 2H), 7.29-7.38 (m, 3H), 7.17-7.23 (m, 2H), 6.47 (s, 1H), 6.33 (s, 1 H), 5.07 (s, 2H), 4.81 (s, 2 H), 4.46-4.56 (m, 4H), 3.56 (s, 3H), 3.53 (s, 3H), 2.14 (s, 3H), 2.08 (s, 3H), 1.65 (s, 3H), 1.48 (s, 3H), 1.23-1.31 (m, 6H)<br>LCMS (m/z) [M + H]⁺ 706.4 |
| Example 55 | Method 1 | Ethyl 3-((E)-6-carbamoyl-3-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-1-methyl-2,3-dihydro-1H-benzo[d]imidazol-4-yl)propanoate<br>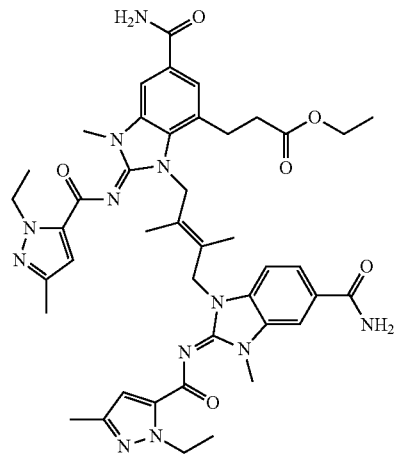 | ¹H NMR (METHANOL-$d_4$) δ ppm 8.13 (d, J = 1.3 Hz, 1 H), 8.02 (d, J = 1.5 Hz, 1H), 7.86 (dd, J = 8.5, 1.6 Hz, 1 H), 7.77 (d, J = 1.3 Hz, 1H), 7.42 (d, J = 8.4 Hz, 1H), 6.65 (s, 1H), 6.52 (s, 1H), 5.23 (s, 2H), 5.01 (s, 2H), 4.58-4.68 (m, 4H), 3.94 (q, J = 7.3 Hz, 2H), 3.71 (s, 6 H), 3.13-3.19 (m, 2H), 2.69-2.75 (m, 2H), 2.26 (s, 3H), 2.17 (s, 3H), 1.69 (br. s., 6H), 1.36-1.42 (m, 6H), 1.11 (t, J = 7.1 Hz, 3H)<br>LCMS (m/z) [M + H]⁺ 833.5 |

| Example Number | Scheme | Name/Structure | ¹H NMR LCMS (m/z) [M + H]⁺ |
| --- | --- | --- | --- |
| Example 56 | Method 5 | (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide 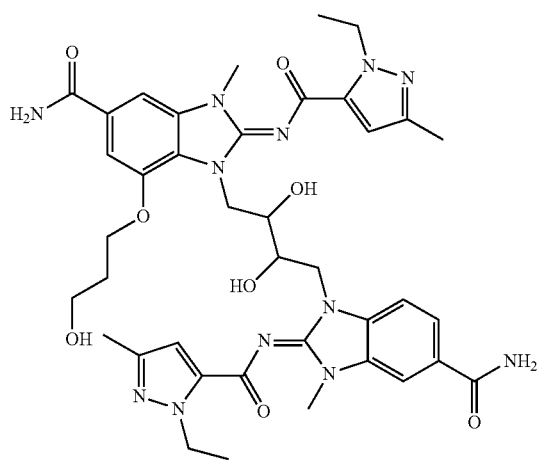 | ¹H NMR (400 MHz, DMSO-$d_6$) δ ppm 1.26 (dt, J = 15.52, 7.19 Hz, 6H) 1.80 (quin, J = 6.15 Hz, 2H) 2.09-2.13 (m, 6H) 3.48-3.55 (m, 8 H) 3.82-3.94 (m, 2H) 4.09-4.14 (m, 2H) 4.16-4.22 (m, 1H) 4.24-4.32 (m, 2 H) 4.43-4.59 (m, 6H) 5.08 (d, J = 6.84 Hz, 1H) 5.40 (d, J = 6.08 Hz, 1H) 6.43 (s, 2 H) 7.39-7.48 (m, 3H) 7.57 (d, J = 8.36 Hz, 1H) 7.72 (d, J = 1.01 Hz, 1H) 7.86 (dd, J = 8.49, 1.39 Hz, 1H) 8.01-8.10 (m, 3H) LCMS (m/z) [M + H]⁺ 813.5 |
| Example 57 | Method 4 | (E)-7-bromo-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dihydroxybutyl)-2-((1-ethyl-3-methyl-1H-pyrazole-5-carbonyl)imino)-3-methyl-2,3-dihydro-1H-benzo[d]imidazole-5-carboxamide 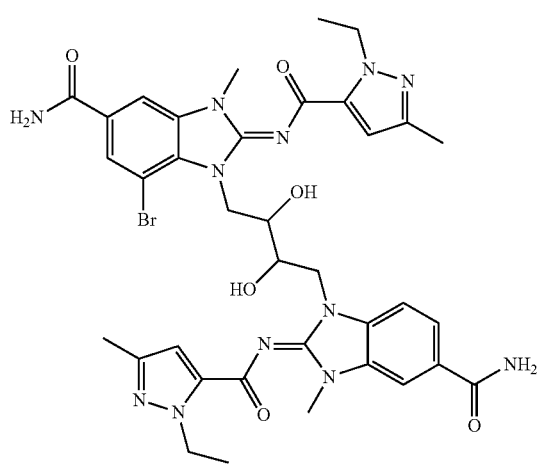 | ¹H NMR (400 MHz, DMSO-$d_6$) δ ppm 1.26-1.31 (m, 6 H) 2.12 (s, 3H) 2.15 (s, 3 H) 3.53 (s, 3H) 3.57 (s, 3 H) 3.95 (br. s., 1H) 4.03 (br. s., 1H) 4.19-4.31 (m, 2H) 4.39 (dd, J = 14.31, 3.51 Hz, 1H) 4.51 (q, J = 6.94 Hz, 4H) 4.75 (dd, J = 14.31, 9.29 Hz, 1H) 5.10 (d, J = 6.27 Hz, 1H) 5.31 (d, J = 6.53 Hz, 1 H) 6.47 (s, 2H) 7.39 (br. s., 1H) 7.54 (br. s., 1H) 7.58 (d, J = 8.53 Hz, 1H) 7.85 (dd, J = 8.53, 1.51 Hz, 1H) 7.98 (d, J = 1.25 Hz, 1H) 8.01 (br. s., 1H) 8.05-8.08 (m, 2H) 8.12 (br. s., 1H) LCMS (m/z) [M + H]⁺ 817.3 |

| Example Number | Scheme | Name/Structure | ¹H NMR<br>LCMS (m/z) [M + H]⁺ |
|---|---|---|---|
| Example 58 | Method 4 | (2E,2'E)-1,1'-(2,3-dihydroxybutane-1,4-diyl)bis(2-((1-ethyl-3-methyl-1H-pyrazole-5-carbonyl)imino)-3-methyl-2,3-dihydro-1H-benzo[d]imidazole-5-carboxamide)<br>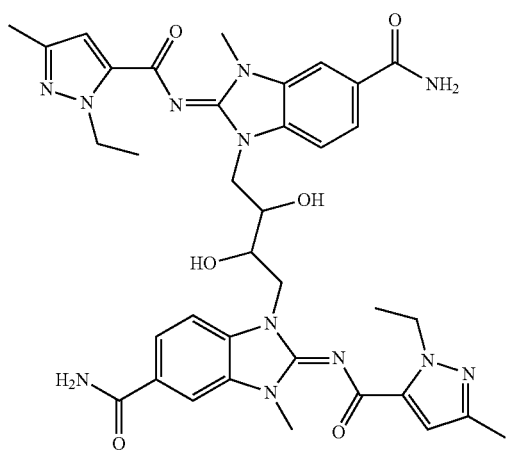 | ¹H NMR (400 MHz, DMSO-$d_6$) δ ppm 1.24-1.28 (m, 6 H) 2.11 (s, 6H) 3.56 (s, 6 H) 3.91-3.97 (m, 2H) 4.22-4.31 (m, 4H) 4.45-4.52 (m, 4H) 5.38 (d, J = 6.53 Hz, 2H) 6.44 (s, 2H) 7.40 (br. s., 2H) 7.59 (d, J = 8.53 Hz, 2H) 7.86 (dd, J = 8.53, 1.51 Hz, 2H) 7.99-8.08 (m, 4 H)<br>LCMS (m/z) [M + H]⁺ 739.3 |
| Example 59 | Method 5 | (E)-1-(4-((E)-5-carbamoyl-3-ethyl-2-((1-ethyl-3-methyl-1H-pyrazole-5-carbonyl)imino)-7-(3-hydroxypropoxy)-2,3-dihydro-1H-benzo[d]imidazol-1-yl)-2,3-dihydroxybutyl)-3-ethyl-2-((1-ethyl-3-methyl-1H-pyrazole-5-carbonyl)imino)-7-methoxy-2,3-dihydro-1H-benzo[d]imidazole-5-carboxamide<br>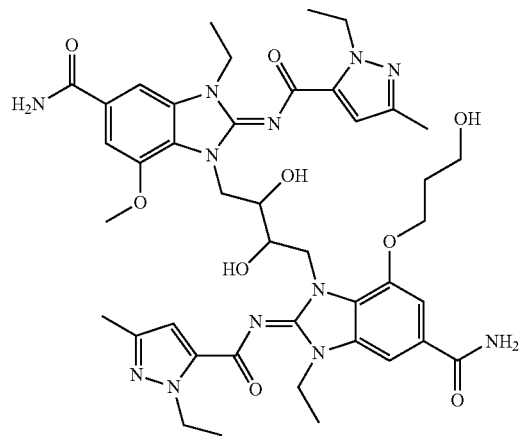 | ¹H NMR (400 MHz, DMSO-$d_6$) δ ppm 1.19-1.28 (m, 12 H) 1.74-1.82 (m, 2H) 2.10 (s, 3H) 2.11 (s, 3H) 3.46-3.55 (m, 2H) 3.72-3.82 (m, 5H) 4.07-4.19 (m, 6 H) 4.22-4.31 (m, 2H) 4.42-4.60 (m, 7H) 5.00 (d, J = 6.84 Hz, 1H) 5.10 (d, J = 6.59 Hz, 1H) 6.36 (s, 1 H) 6.40 (s, 1H) 7.42-7.51 (m, 4H) 7.73-7.77 (m, 2 H) 8.09 (br. s., 2H)<br>LCMS (m/z) [M + H]⁺ 871.3 |

| Example Number | Scheme | Name/Structure | ¹H NMR<br>LCMS (m/z) [M + H]⁺ |
|---|---|---|---|
| Example 60 | Method 1 | (2E,2'E)-1,1'-((2S,3S)-2,3-diethoxybutane-1,4-diyl)bis(2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide)<br>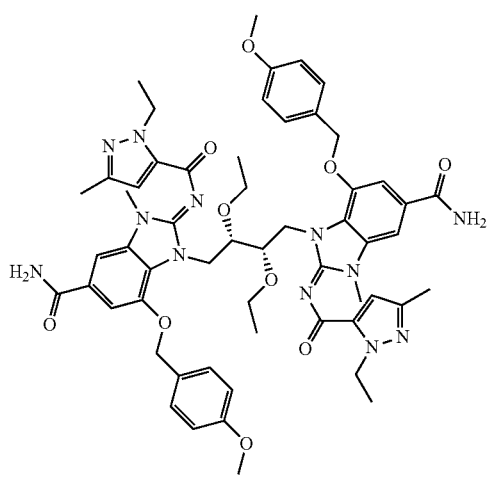 | ¹H NMR (400 MHz, DMSO-d₆) δ ppm 8.10 (br. s., 2H) 7.76 (d, J = 0.76 Hz, 2H) 7.60 (s, 2H) 7.33-7.54 (m, 6H) 6.72 (d, J = 8.62 Hz, 4 H) 6.47 (s, 2H) 5.17 (d, J = 10.39 Hz, 2H) 5.04 (d, J = 10.39 Hz, 2H) 4.40-4.64 (m, 4H) 3.86-4.10 (m, 2H) 3.62-3.76 (m, 2 H) 3.50-3.60 (m, 8H) 3.32 (s, 6H) 3.05-3.21 (m, 2H) 2.70-2.82 (m, 2H) 2.11 (s, 6H) 1.29 (t, J = 7.10 Hz, 6 H) 0.50 (t, J = 6.84 Hz, 6H)<br>LCMS (m/z) [M + H]⁺ 1067.4 |
| Example 61 | Method 5 | (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dihydroxy-2,3-dimethylbutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide<br>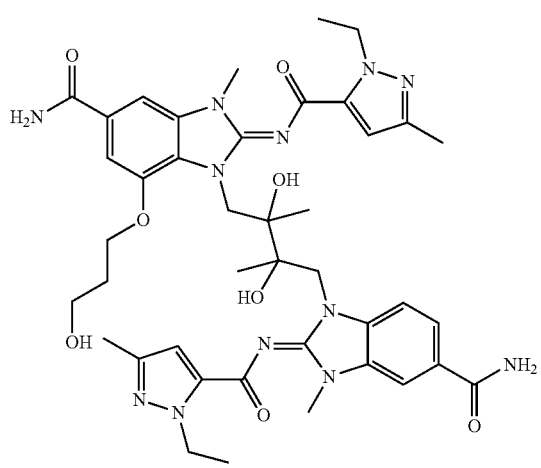 | ¹H NMR (400 MHz, DMSO-d₆) δ ppm 1.05-1.10 (m, 6 H) 1.28-1.33 (m, 6H) 1.95-2.03 (m, 2H) 2.10-2.14 (m, 6H) 3.57-3.63 (m, 8 H) 4.26-4.33 (m, 2H) 4.34-4.41 (m, 1H) 4.51-4.56 (m, 4H) 4.65 (br. s., 1H) 4.69-4.76 (m, 1H) 4.85 (br. s., 1H) 5.28 (br. s., 1H) 6.49 (s, 1H) 6.54 (s, 1H) 7.21-7.24 (m, 1H) 7.41-7.51 (m, 2H) 7.54 (s, 1H) 7.69 (d, J = 8.36 Hz, 1H) 7.79-7.83 (m, 2H) 7.87 (dd, J = 8.49, 1.39 Hz, 1H) 8.06 (br. s., 1H) 8.09-8.15 (m, 2H)<br>LCMS (m/z) [M + H]⁺ 841.4 |

| Example Number | Scheme | Name/Structure | ¹H NMR<br>LCMS (m/z) [M + H]⁺ |
|---|---|---|---|
| Example 62 | Method 1 | (2E,2'E)-1,1'-((2R,3R)-2,3-diethoxybutane-1,4-diyl)bis(2-(((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide)<br>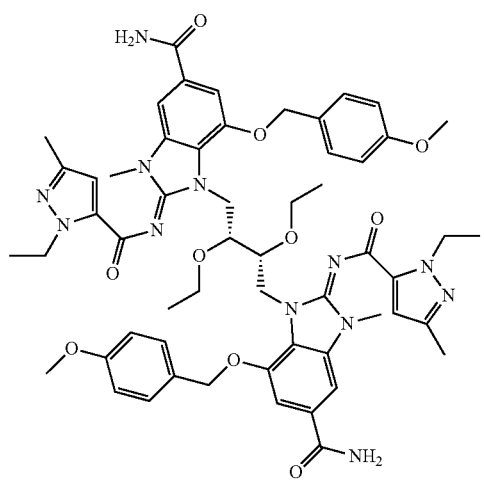 | ¹H NMR (400 MHz, DMSO-$d_6$) δ ppm 8.09 (br. s., 2H) 7.76 (d, J = 0.76 Hz, 2H) 7.60 (s, 2H) 7.50 (br. s., 2 H) 7.40 (d, J = 8.36 Hz, 4H) 6.71 (d, J = 8.62 Hz, 4H) 6.47 (s, 2H) 4.95-5.26 (m, 4H) 4.53 (q, J = 7.18 Hz, 4 H) 3.87-4.03 (m, 2H) 3.48-3.75 (m, 10 H) 3.32 (s, 6 H) 3.05-3.18 (m, 2H) 2.70-2.80 (m, 2H) 2.11 (s, 6H) 1.29 (t, J = 7.10 Hz, 6H) 0.50 (t, J = 6.84 Hz, 6H) LCMS (m/z) [M + H]⁺ 1067.7 |
| Example 63 | Method 1 | (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide<br>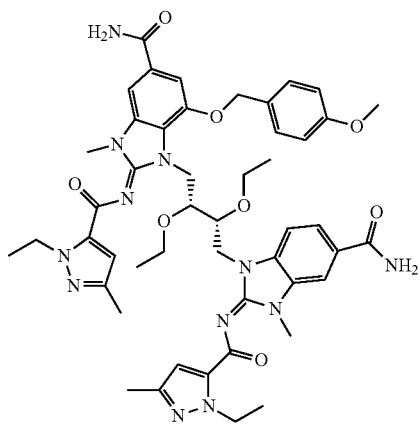 | ¹H NMR (400 MHz, DMSO-$d_6$) δ ppm 8.00-8.16 (m, 3 H) 7.86 (dd, J = 8.49, 1.39 Hz, 1H) 7.77 (d, J = 1.01 Hz, 1H) 7.62 (d, J = 1.01 Hz, 1 H) 7.41-7.53 (m, 4H) 7.38 (d, J = 8.36 Hz, 1H) 6.72-6.79 (m, 2H) 6.50 (s, 1H) 6.49 (s, 1H) 5.06-5.27 (m, 2H) 4.47-4.65 (m, 5H) 4.37 (dd, J = 13.69, 4.06 Hz, 1H) 3.99 (d, J = 12.42 Hz, 1 H) 3.62-3.85 (m, 3H) 3.52-3.61 (m, 6H) 3.40 (s, 3H) 3.21-3.27 (m, 1H) 3.11-3.19 (m, 1H) 2.79-2.96 (m, 2H) 2.12 (s, 3H) 2.10 (s, 3H) 1.30 (t, J = 7.10 Hz, 6H) 0.58 (t, J = 6.84 Hz, 3 H) 0.47 (t, J = 6.97 Hz, 3H) LCMS (m/z) [M + H]⁺ 931.7 |

| Example Number | Scheme | Name/Structure | ¹H NMR<br>LCMS (m/z) [M + H]⁺ |
|---|---|---|---|
| Example 64 | Method 1 | (2E,2′E)-1,1′-((2R,3R)-2,3-diethoxybutane-1,4-diyl)bis(2-((1-ethyl-3-methyl-1H-pyrazole-5-carbonyl)imino)-3-methyl-2,3-dihydro-1H-benzo[d]imidazole-5-carboxamide<br>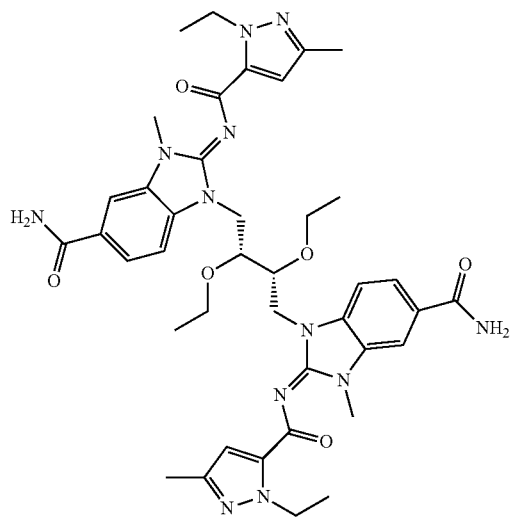 | ¹H NMR (400 MHz, DMSO-$d_6$) δ ppm 8.00-8.14 (m, 4 H) 7.88 (dd, J = 8.49, 1.39 Hz, 2H) 7.61 (d, J = 8.62 Hz, 2H), 7.45 (br. s., 2H) 6.51 (s, 2H) 4.46-4.61 (m, 6H) 4.39 (br. s., 2H) 3.81-3.98 (m, 2H) 3.59 (s, 6H) 3.25-3.32 (m, 2H) 2.95-3.10 (m, 2H) 2.12 (s, 6H) 1.31 (t, J = 7.10 Hz, 6H) 0.59 (t, J = 6.97 Hz, 6H)<br>LCMS (m/z) [M + H]⁺ 795.6 |
| Example 65 | Method 1 | (2E,2′E)-1,1′-((2R,3R)-2,3-diethoxybutane-1,4-diyl)bis(2-((1-ethyl-3-methyl-1H-pyrazole-5-carbonyl)imino)-7-hydroxy-3-methyl-2,3-dihydro-1H-benzo[d]imidazole-5-carboxamide<br>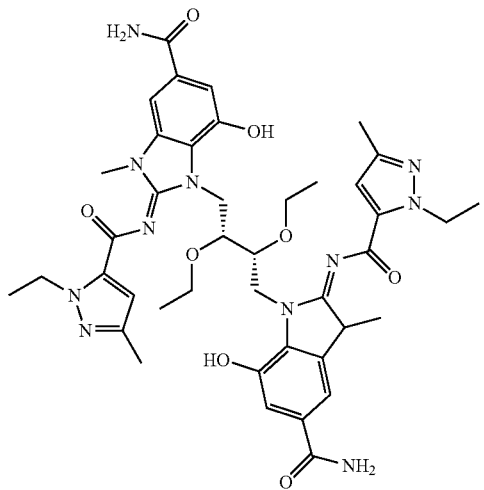 | ¹H NMR (400 MHz, DMSO-$d_6$) δ ppm 10.69 (br. s., 2H) 7.94 (br. s., 2H) 7.53 (br. s., 2H) 7.14-7.42 (m, 4H) 6.47 (s, 2H) 4.36-4.69 (m, 8H) 3.72-3.89 (m, 2H) 3.49 (s, 6H) 3.29 (d, J = 6.84 Hz, 2H) 3.05 (dd, J = 9.25, 7.22 Hz, 2H) 2.07-2.18 (m, 6H) 1.30 (t, J = 7.10 Hz, 6H) 0.65 (t, J = 6.97 Hz, 6 H)<br>LCMS (m/z) [M + H]⁺ 827.6 |

| Example Number | Scheme | Name/Structure | ¹H NMR<br>LCMS (m/z) [M + H]⁺ |
|---|---|---|---|
| Example 66 | Method 1 | (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide<br>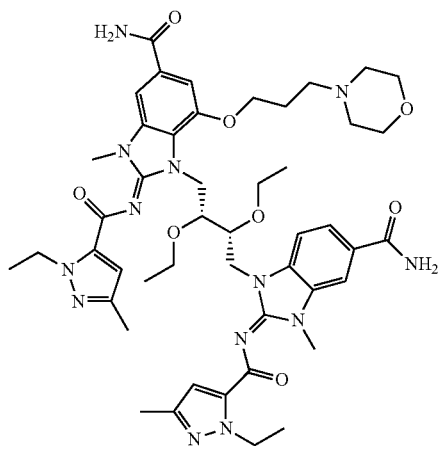 | ¹H NMR (400 MHz, DMSO-d₆) δ ppm 8.03-8.11 (m, 3 H), 7.86 (dd, J = 8.5, 1.4 Hz, 1H), 7.75 (s, 1H), 7.55 (d, J = 8.4 Hz, 1H), 7.42-7.51 (m, 3H), 6.51 (s, 1H), 6.50 (s, 2H), 4.72 (dd, J = 13.9, 9.4 Hz, 1H), 4.44-4.58 (m, 6H), 4.15-4.36 (m, 3H), 3.86 (m, 1H), 3.76 (m, 1H), 3.57 (s, 6H), 3.38-3.44 (br. m., 4H), 3.20-3.30 (m, 1H), 2.93-3.04 (m, 2H), 2.32-2.45 (m, 3H), 2.27 (br. s., 4 H), 2.12 (s, 6H), 1.90-1.98 (m, 2H), 1.30 (q, J = 7.1, 6 H), 0.62 (t, J = 6.8 Hz, 3H), 0.52 (t, J = 7.0 Hz, 3H)<br>LCMS (m/z) [M + H]⁺ 938.6 |
| Example 67 | Method 1 | (E)-1-((2R,3R)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-diethoxybutyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide<br>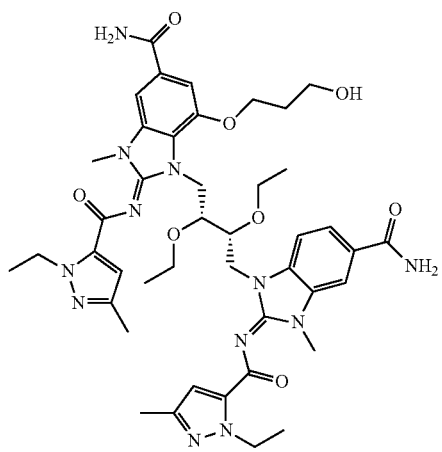 | ¹H NMR (400 MHz, DMSO-d₆) δ ppm 7.98-8.20 (m, 2 H) 7.86 (dd, J = 8.36, 1.52 Hz, 1H) 7.74 (d, J = 1.01 Hz, 1H) 7.39-7.59 (m, 4H) 6.41-6.53 (m, 2H) 4.41-4.75 (m, 8H) 4.16-4.38 (m, 3H) 3.81-3.91 (m, 1 H) 3.68-3.76 (m, 1H) 3.50-3.64 (m, 8H) 3.32 (d, J = 2.53 Hz, 1H) 3.22 (dd, J = 9.25, 6.97 Hz, 1H) 2.88-3.06 (m, 2H) 2.05-2.19 (m, 6H) 1.85-1.99 (m, 2 H) 1.20-1.37 (m, 6H) 0.62 (t, J = 6.97 Hz, 3H) 0.49 (t, J = 6.97 Hz, 3H)<br>LCMS (m/z) [M + H]⁺ 869.5 |

| Example Number | Scheme | Name/Structure | ¹H NMR<br>LCMS (m/z) [M + H]⁺ |
|---|---|---|---|
| Example 68 | Method 1 | (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-hydroxy-3-methyl-2,3-dihydro-1H-benzo[d]imidazole-5-carboxamide | ¹H NMR (400 MHz, DMSO-$d_6$) δ ppm 10.86 (br. s., 1 H), 8.10 (d, J = 1.3 Hz, 1H), 8.06 (s, 1H), 7.96 (br. s., 1 H), 7.89 (dd, J = 1.4, 8.5 Hz, 1H), 7.63-7.57 (m, 2H), 7.48 (br. s., 1H), 7.38 (br. s., 1H) 7.30 (s, 1H), 6.52 (s, 2H), 5.37-5.12 (m, 4 H), 4.57-4.44 (m, 4H), 3.55 (s, 3H), 3.60 (s, 3H), 2.15-2.09 (m, 6H), 1.31-1.19 (m, 6H)<br>LCMS (m/z) [M + H]⁺ 795.4 |
| Example 69 | Method 1 | (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide | ¹H NMR (400 MHz, DMSO-$d_6$) δ ppm 8.14-8.05 (m, 3 H), 7.92 (dd, J = 1.5, 8.6 Hz, 1H) ,7.79 (d, J = 1.0 Hz, 1 H), 7.66 (s, 1H), 7.55-7.46 (m, 3H), 7.41 (d, J = 8.6 Hz, 2H), 6.77 (d, J = 8.9 Hz, 2 H), 6.50 (d, J = 7.1 Hz, 2H), 5.23-5.09 (m, 4H), 4.71 (t, J = 16.6 Hz, 2H), 4.50 (q, J = 7.1 Hz, 4H), 3.60 (d, J = 9.1 Hz, 6H), 3.31 (s, 3 H), 2.12 (s, 3H 2.11 (s, 3H 1.25 (dt, J = 0.8, 7.1 Hz, 6H)<br>LCMS (m/z) [M + H]⁺ 915.3 |

| Example Number | Scheme | Name/Structure | ¹H NMR<br>LCMS (m/z) [M + H]⁺ |
|---|---|---|---|
| Example 70 | Method 5 | (E)-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-3-methyl-7-phenethyl-2,3-dihydro-1H-benzo[d]imidazole-5-carboxamide 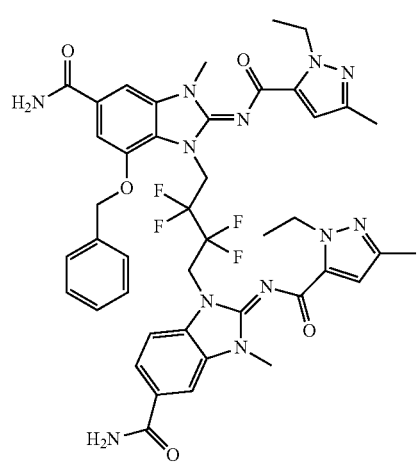 | ¹H NMR (400 MHz, DMSO-$d_6$) δ ppm 8.12-8.09 (m, 1 H), 8.05 (br. s., 2H), 8.00 (d, J = 1.3 Hz, 1H), 7.90 (dd, J = 1.3, 8.5 Hz, 1H), 7.85-7.81 (m, 1H), 7.56 (d, J = 8.5 Hz, 1H), 7.46 (br.s., 2H), 7.28-7.15 (m, 5H), 6.48 (s, 1H), 6.51 (s, 1H), 5.28-5.05 (m, 4H), 4.56-4.43 (m, 4H), 3.60 (d, J = 4.5 Hz, 6H), 3.22-3.13 (m, 2H), 3.01-2.91 (m, 2H), 2.10 (s, 3H), 2.13 (s, 3H), 1.30-1.16 (m, 6H)<br>LCMS (m/z) [M + H]⁺ 883.5 |
| Example 71 | Method 1 | (E)-7-bromo-1-(4-((E)-5-carbamoyl-2-((1-ethyl-3-methyl-1H-pyrazole-5-carbonyl)imino)-3-methyl-2,3-dihydro-1H-benzo[d]imidazol-1-yl)-2,2,3,3-tetrafluorobutyl)-2-((1-ethyl-3-methyl-1H-pyrazole-5-carbonyl)imino)-3-methyl-2,3-dihydro-1H-benzo[d]imidazole-5-carboxamide 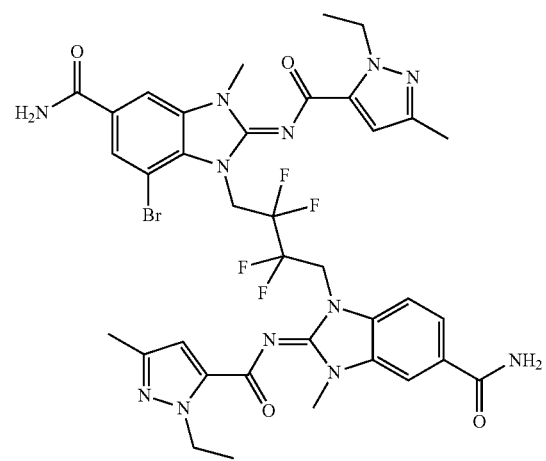 | ¹H NMR (400 MHz, DMSO-$d_6$) δ ppm 8.17 (s, 1H), 8.11 (dd, J = 1.3, 7.1 Hz, 2H), 8.06 (d, J = 1.3 Hz, 2H), 7.90 (dd, J = 1.5, 8.4 Hz, 1H), 7.67-7.60 (m, 2H), 7.48 (br.s., 1 H), 6.53 (d, J = 7.9 Hz, 2H), 5.43 (t, J = 15.3 Hz, 2H), 5.25 (t, J = 16.6 Hz, 2H), 4.50 (q, J = 6.8 Hz, 4H), 3.59 (s, 3H), 3.61 (s, 3H), 2.13 (s, 6H), 1.32-1.20 (m, 6H)<br>LCMS (m/z) [M + H]⁺ 857.3, 859.3 |

| Example Number | Scheme | Name/Structure | ¹H NMR<br>LCMS (m/z) [M + H]⁺ |
|---|---|---|---|
| Example 72 | Method 1 | rel-(2E,2'E)-1,1'-(((1R,2R)-cyclopropane-1,2-diyl)bis(methylene))bis(2-((1-ethyl-3-methyl-1H-pyrazole-5-carbonyl)imino)-3-methyl-2,3-dihydro-1H-benzo[d]imidazole-5-carboxamide<br>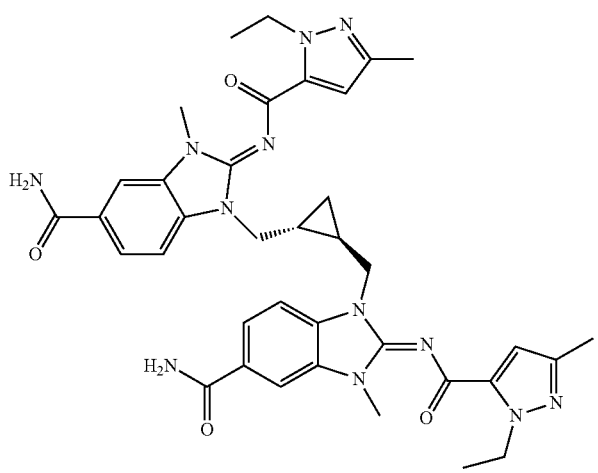 | ¹H NMR (DMSO-d₆) δ ppm 8.06 (br. s., 2H), 7.69 (s, 2 H), 7.61 (dd, J = 8.4, 1.3 Hz, 2H), 7.48 (br. s., 2H), 7.33 (d, J = 8.4 Hz, 2H), 6.54 (s, 2H), 4.56 (q, J = 7.1 Hz, 4 H), 4.35 (dd, J = 14.3, 3.4 Hz, 2H), 3.63 (dd, J = 14.3, 9.8 Hz, 2H), 3.24 (s, 6H), 2.16 (s, 6H), 1.50 (br. s., 2 H), 1.34 (t, J = 7.1 Hz, 6H), 0.76 (t, J = 7.0 Hz, 2H)<br>LCMS (m/z) [M + H]⁺ 719.5 |
| Example 73 | Method 1 | (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)pentyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide<br>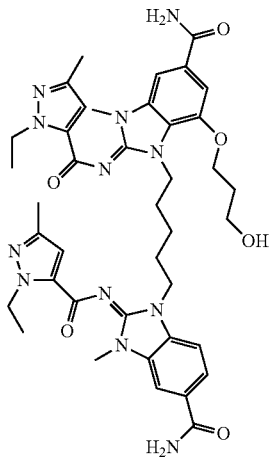 | ¹H NMR (400 MHz, DMSO-d₆) δ ppm 1.22-1.30 (m, 8 H) 1.68-1.77 (m, 4H) 1.80-1.87 (m, 2H) 2.12 (s, 6H) 3.48-3.58 (m, 8H) 4.08-4.15 (m, 2H) 4.16-4.26 (m, 4H) 4.50 (q, J = 7.10 Hz, 4H) 4.60-4.69 (m, 1H) 6.46 (s, 1H) 6.48 (s, 1H), 7.42-7.51 (m, 3H) 7.58 (d, J = 8.36 Hz, 1H) 7.72 (br. s, 1H) 7.82-7.87 (m, 1H) 8.01-8.12 (m, 3H)<br>LCMS (m/z) [M + H]⁺ 795.5 |

| Example Number | Scheme | Name/Structure | $^1$H NMR<br>LCMS (m/z) [M + H]$^+$ |
|---|---|---|---|
| Example 74 | Method 1 | (E)-1-(5-((E)-5-carbamoyl-3-ethyl-2-((1-ethyl-3-methyl-1H-pyrazole-5-carbonyl)imino)-2,3-dihydro-1H-benzo[d]imidazol-1-yl)pentyl)-3-ethyl-2-((1-ethyl-3-methyl-1H-pyrazole-5-carbonyl)imino)-7-(3-hydroxypropoxy)-2,3-dihydro-1H-benzo[d]imidazole-5-carboxamide<br>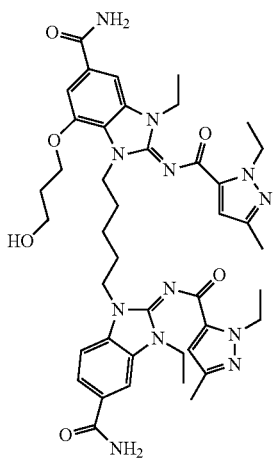 | $^1$H NMR (400 MHz, DMSO-d$_6$) δ ppm 1.20-1.26 (m, 12 H) 1.64-1.75 (m, 4H) 1.83 (quin, J = 6.08 Hz, 2H) 2.11 (s, 3H) 2.12 (s, 3H) 3.38-3.44 (m, 2H) 3.51 (q, J = 5.83 Hz, 2H) 4.06-4.24 (m, 10 H) 4.48 (q, J = 7.10 Hz, 4H) 4.64 (t, J = 5.07 Hz, 1H), 6.44 (s, 1H) 6.46 (s, 1 H) 7.42-7.53 (m, 3H) 7.60 (d, J = 8.62 Hz, 1H) 7.72-7.77 (m, 1H) 7.85 (d, J = 8.36, 1.52 Hz, 1H) 8.04-8.17 (m, 3H)<br>LCMS (m/z) [M + H]$^+$ 823.6 |
| Example 75 | Method 1 | (E)-1-(5-((E)-5-carbamoyl-2-((1-ethyl-3-methyl-1H-pyrazole-5-carbonyl)imino)-3-methyl-2,3-dihydro-1H-benzo[d]imidazol-1-yl)pentyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide<br>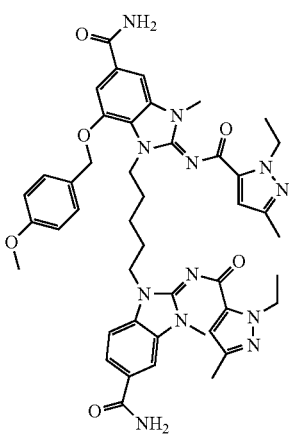 | $^1$H NMR (400 MHz, DMSO-d$_6$) δ ppm 1.06-1.13 (m, 2 H) 1.24 (td, J = 7.10, 2.03 Hz, 6H) 1.53-1.68 (m, 4 H) 2.10 (s, 3H) 2.11 (s, 3 H) 3.51 (s, 3H) 3.54 (s, 3 H) 3.70 (s, 3H) 3.99 (t, J = 6.97 Hz, 2H) 4.12 (t, J = 7.10 Hz, 2H) 4.49 (q, J = 6.84 Hz, 4H) 5.17 (s, 2 H) 6.45 (d, J = 6.84 Hz, 2H) 6.89 (d, J = 8.62 Hz, 2H) 7.38 (d, J = 8.62 Hz, 2H) 7.44 (br. s., 1H) 7.47-7.54 (m, 2H) 7.59-7.63 (m, 1 H) 7.73-7.77 (m, 1H) 7.84 (dd, J = 8.36, 1.52 Hz, 1H) 8.04 (br. s., 1H) 8.06-8.11 (m, 2H)<br>LCMS (m/z [M + H]$^+$ 857.3 |

| Example Number | Scheme | Name/Structure | ¹H NMR<br>LCMS (m/z) [M + H]⁺ |
|---|---|---|---|
| Example 76 | Method 2 | (E)-1-(5-((E)-5-carbamoyl-2-((1-ethyl-3-methyl-1H-pyrazole-5-carbonyl)imino)-2,3-dihydro-1H-benzo[d]imidazol-1-yl)pentyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide<br>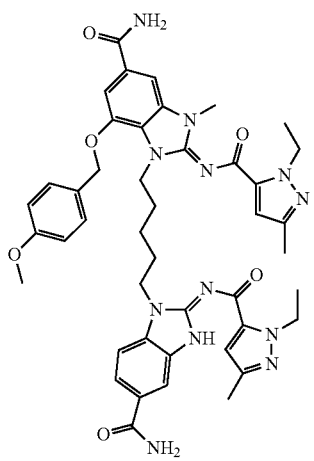 | ¹H NMR (400 MHz, DMSO-d₆) δ ppm 1.13-1.19 (m, 2 H) 1.22-1.31 (m, 6H) 1.61-1.76 (m, 4H) 2.08 (s, 3H) 2.11 (s, 3H) 3.52 (s, 3H) 3.69 (s, 3H) 4.05 (t, J = 6.90 Hz, 2H) 4.18 (t, J = 7.28 Hz, 2H) 4.46-4.59 (m, 4H) 5.17 (s, 2H) 6.44 (s, 1H) 6.54 (s, 1H) 6.86-6.91 (m, 2H) 7.32 (br. s., 1H) 7.37-7.42 (m, 3H) 7.46 (br. s., 1 H) 7.60 (s, 1H) 7.73-7.77 (m, 2H) 7.95 (br. s., 1H) 8.00 (s, 1H) 8.05 (br. s., 1 H) 12.79 (s, 1H)<br>LCMS (m/z) [M + H]⁺ 843.5 |
| Example 77 | Method 2 | (E)-1-(5-((E)-5-carbamoyl-3-ethyl-2-((1-ethyl-3-methyl-1H-pyrazole-5-carbonyl)imino)-2,3-dihydro-1H-benzo[d]imidazol-1-yl)pentyl)-2-((1-ethyl-3-methyl-1H-pyrazole-5-carbonyl)imino)-7-((4-methoxybenzyl)oxy)-3-methyl-2,3-dihydro-1H-benzo[d]imidazole-5-carboxamide<br>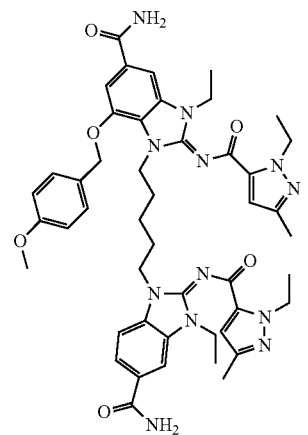 | ¹H NMR (400 MHz, DMSO-d₆) δ ppm 1.03-1.11 (m, 2 H) 1.20-1.28 (m, 9H) 1.51-1.66 (m, 4H) 2.10 (s, 3H) 2.11 (s, 3H) 3.51 (s, 3H) 3.70 (s, 3H) 4.00 (t, J = 7.22 Hz, 2H) 4.07-4.19 (m, 4H) 4.43-4.52 (m, 4H) 5.17 (s, 2H) 6.44 (s, 1H) 6.45 (s, 1 H) 6.86-6.91 (m, 2H) 7.36-7.41 (m, 2H) 7.45 (br.s., 1 H) 7.47-7.54 (m, 2H) 7.59-7.63 (m, 1H) 7.73-7.76 (m, 1H) 7.85 (dd, J = 8.49, 1.39 Hz, 1H) 8.08 (s, 3H)<br>LCMS (m/z) [M + H]⁺ 871.4 |

-continued

| Example Number | Scheme | Name/Structure | ¹H NMR<br>LCMS (m/z) [M + H]⁺ |
|---|---|---|---|
| Example 78 | Method 1 | Butyl (E)-1-((E)-4-((E)-5-carbamoyl-2-((1-ethyl-3-methyl-1H-pyrazole-5-carbonyl)imino)-7-((4-methoxybenzyl)oxy)-3-methyl-2,3 dihydro-1Hbenzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1Hbenzo[d]imidazole-5-carboxylate<br>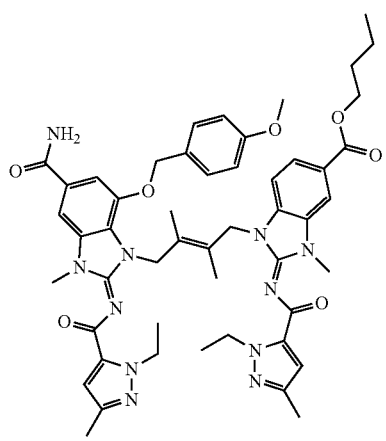 | ¹H NMR (400 MHz, DMSO-$d_6$) δ ppm 8.12 (d, J = 1.3 Hz, 1H), 8.09 (br. s., 1H), 7.78-7.89 (m, 2H), 7.62 (s, 1 H), 7.50 (br. s., 1H), 7.18-7.24 (m, 3H), 6.64-6.76 (m, 2H), 6.44 (s, 1H), 6.35 (s, 1H), 5.10 (s, 2H), 4.97 (s, 2H), 4.78 (s, 2H), 4.43-4.53 (m, 4H), 4.31-4.37 (m, 2H), 3.62 (s, 6H), 3.56 (s, 3H), 2.10 (s, 3H), 2.08 (s, 3H), 1.72-1.81 (m, 2H), 1.57 (s, 3H), 1.40-1.49 (m, 2H), 1.22-1.29 (m, 6 H), 1.20 (s, 3H), 0.96 (t, J = 7.4 Hz, 3H)<br>LCMS (m/z) [M + H]⁺ 926.7 |
| Example 79 | Method 1 | (E)-1-(4-((E)-5-carbamoyl-2-((1-ethyl-3-methyl-1H-pyrazole-5-carbonyl)imino)-7-((4-methoxybenzyl)oxy)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxylic acid<br>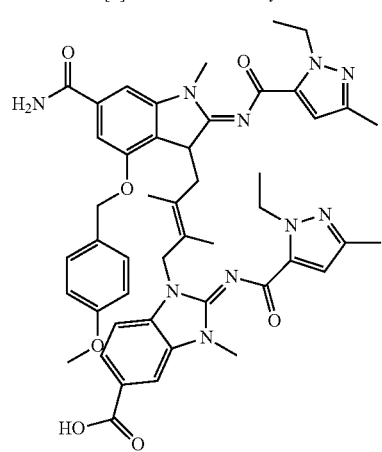 | ¹H NMR (400 MHz, DMSO-$d_6$) δ ppm 13.03 (br. s., 1H), 8.13 (d, J = 1.0 Hz, 1H), 8.08 (br. s., 1H), 7.84 (dd, J = 8.4, 1.4 Hz, 1H), 7.80 (s, 1H), 7.63 (s, 1H), 7.47 (br. s., 1 H), 7.17-7.22 (m, 3H), 6.71 (d, J = 8.8 Hz, 2H), 6.44 (s, 1 H), 6.37 (s, 1H), 5.11 (s, 2 H), 4.98 (s, 2H), 4.78 (s, 2 H), 4.44-4.53 (m, 4H), 3.63 (s, 3H), 3.62 (s, 3H), 3.57 (s, 3H), 2.10 (s, 3H), 2.09 (s, 3H), 1.57 (s, 3H), 1.22-1.29 (m, 6H), 1.20 (s, 3H)<br>LCMS (m/z) [M + H]⁺ 870.5 |

-continued

| Example Number | Scheme | Name/Structure | ¹H NMR LCMS (m/z) [M + H]⁺ |
|---|---|---|---|
| Example 80 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-4-(morpholinomethyl)-2,3-dihydro-1H-benzo[d]imidazol-1-yl)-2,3-dimethylbut-2-en-1-yl)-3-methyl-2,3-dihydro-1H-benzo[d]imidazole-5-carboxamide 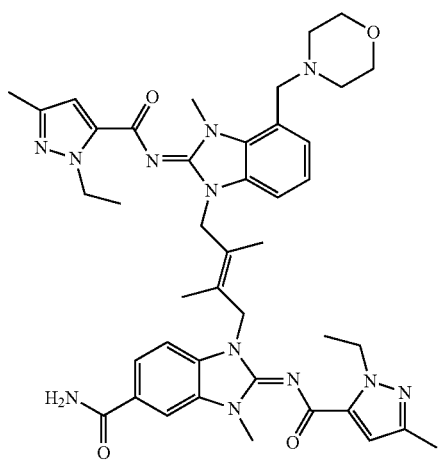 | ¹H NMR (400 MHz, DMSO-$d_6$) δ ppm 8.11 (s, 1H), 8.04 (br. s., 1H), 7.80 (dd, J = 1.52, 8.36 Hz, 1H), 7.46 (br. s., 1H), 7.28 (d, J = 8.62 Hz, 1H), 7.20-7.24 (m, 1H), 7.14-7.18 (m, 2H), 6.46 (s, 1H), 6.43 (s, 1H), 4.85 (br. s., 4H), 4.47-4.55 (m, 4H), 3.89 (s, 3H), 3.79 (s, 2H), 3.59 (s, 3H), 3.53-3.58 (m, 4H), 2.38-2.44 (m, 4H), 2.13 (d, J = 1.01 Hz, 6H), 1.58 (br. s., 6H), 1.28 (t, J = 7.0 Hz, 6H). LCMS (m/z) [M + H]⁺ 789.5 |
| Example 81 | Method 4 | (E)-2-((1-ethyl-3-methyl-1H-pyrazole-5-carbonyl)imino)-1-(4-((E)-2-((1-ethyl-3-methyl-1H-pyrazole-5-carbonyl)imino)-7-fluoro-3-methyl-2,3-dihydro-1H-benzo[d]imidazol-1-yl)-2,3-dihydroxybutyl)-3-methyl-2,3-dihydro-1H-benzo[d]imidazole-5-carboxamide 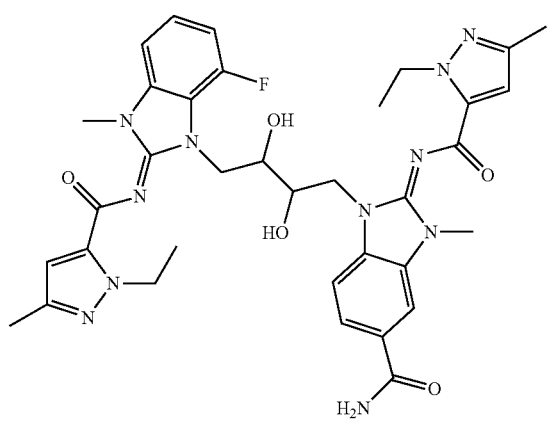 | ¹H NMR (400 MHz, DMSO-$d_6$) δ ppm 8.06 (d, J = 1.3 Hz, 1H), 8.02 (br. s., 1H), 7.85 (dd, J = 1.4, 8.4 Hz, 1H), 7.58 (d, J = 8.5 Hz, 1H), 7.45-7.36 (m, 2H), 7.30 (dt, J = 4.6, 8.2 Hz, 1H), 7.15 (dd, J = 8.3, 11.3 Hz, 1H), 6.46 (s, 1H), 6.43 (s, 1H), 5.31 (d, J = 6.3 Hz, 1H), 5.25 (d, J = 6.3 Hz, 1H), 4.55-4.45 (m, 4H), 4.40 (dd, J = 8.8, 14.1 Hz, 1H), 4.32-4.16 (m, 3H), 3.99-3.85 (m, 2H), 3.57 (s, 3H), 3.54 (s, 3H), 2.13 (s, 3H), 2.11 (s, 3H), 1.27 (t, J = 7.2 Hz, 6H) LCMS (m/z) [M + H]⁺ 714.4 |

| Example Number | Scheme | Name/Structure | ¹H NMR<br>LCMS (m/z) [M + H]⁺ |
|---|---|---|---|
| Example 82 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-((4-fluorobenzyl)oxy)-3-methyl-2,3-dihydro-1Hbenzo[d]imidazole-5-carboxamide<br>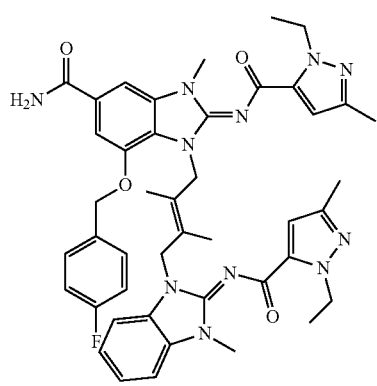 | ¹H NMR (300 MHz, DMSO-d₆) δ ppm 8.09 (s, 1H), 7.82 (s, 1H), 7.58-7.69 (m, 2H), 7.51 (s, 1H), 7.26-7.42 (m, 3H), 7.10-7.25 (m, 2H), 6.95-7.03 (m, 2H), 6.45 (s, 1H), 6.34 (s, 1H), 5.15 (s, 2H), 4.98 (s, 2H), 4.77 (s, 2H), 4.42-4.52 (m, 4H), 3.54 (s, 3H), 3.50 (s, 3H), 2.11 (s, 3H), 2.10 (s, 3H), 1.57 (s, 3H), 1.20-1.30 (m, 6H), 1.18 (s, 3H)<br>LCMS (m/z) [M + H]⁺ 814.4 |
| Example 83 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((2-fluorobenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide<br>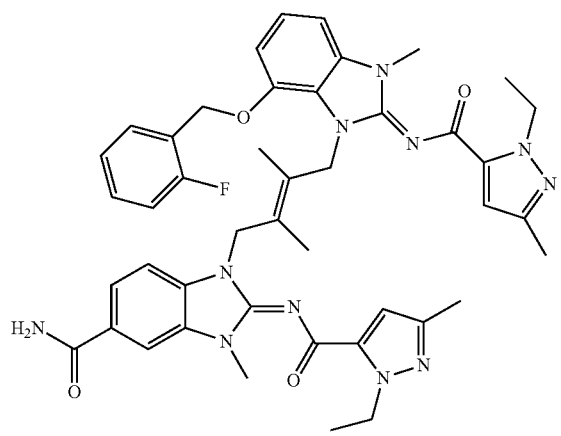 | ¹H NMR (400 MHz, DMSO-d₆) δ ppm 8.11 (s, 1H), 8.02 (s, 1H), 7.75 (d, J = 8.4 Hz, 1H), 7.46 (s, 1H), 7.20-7.51 (m, 4H), 7.10-7.16 (m, 3H), 7.00 (t, J = 7.6 Hz, 1H), 6.48 (s, 1H), 6.37 (s, 1H), 5.18 (s, 2H), 4.94 (s, 2H), 4.74 (s, 2H), 4.64-4.53 (m, 4H), 3.58 (s, 3H), 3.55 (s, 3H), 2.13 (s, 3H), 2.09 (s, 3H), 1.57 (s, 3H), 1.29 (t, J = 6.8 HZ, 3H), 1.22 (t, J = 7.2 Hz, 3H), 1.13 (s, 3H)<br>LCMS (m/z) [M + H]⁺ 814.4 |

| Example Number | Scheme | Name/Structure | ¹H NMR<br>LCMS (m/z) [M + H]⁺ |
|---|---|---|---|
| Example 84 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((4-fluorobenzyl)oxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide<br>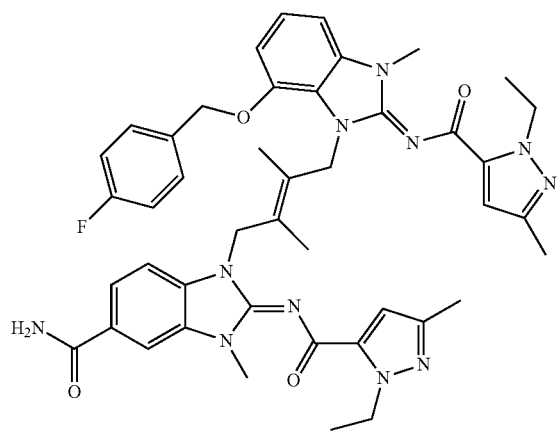 | ¹H NMR (400 MHz, DMSO-d₆) δ ppm 8.12 (s, 1H), 8.02 (s, 1H), 7.75 (d, J = 8.4 Hz, 1H), 7.46 (s, 1H), 7.22-7.33 (m, 4H), 7.15 (d, J = 8.4 Hz, 1H), 6.99-7.07 (m, 3H), 6.44 (s, 1H), 6.37 (s, 1H), 5.10 (s, 2H), 4.98 (s, 2H), 4.78 (s, 2H), 4.46-4.52 (m, 4H), 3.59 (s, 3H), 3.54 (s, 3H), 2.11 (s, 3H), 2.09 (s, 3H), 1.57 (s, 3H), 1.18-1.30 (m, 9H)<br>LCMS (m/z) [M + H]⁺ 814.4 |
| Example 85 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-((3-fluorobenzyl)oxy)-3-methyl-2,3-dihydro-1H-benzo[d]imidazol-1-yl)-2,3-dimethylbut-2-en-1-yl)-3-methyl-2,3-dihydro-1Hbenzo[d]imidazole-5-carboxamide, Trifluoroacetic acid salt<br>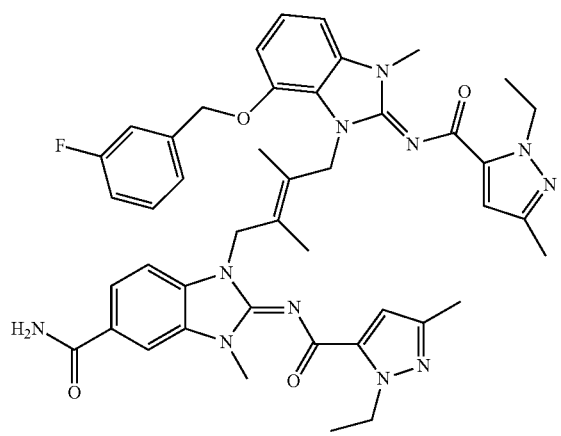 | ¹H NMR (400 MHz, DMSO-d₆) δ ppm 8.11 (s, 1H), 8.04 (s, 1H), 7.74 (d, J = 8.8 Hz, 1H), 7.47 (s, 1H), 7.23-7.33 (m, 3H), 7.05-7.17 (m, 4H), 6.97-7.01 (m, 1H), 6.46 (s, 1H), 6.41 (s, 1H), 5.16 (s, 2H), 5.03 (s, 2H), 4.78 (s, 2H), 4.45-4.53 (m, 4H), 3.58 (s, 3H), 3.57 (s, 3H), 2.12 (s, 3H), 2.09 (s, 3H), 1.59 (s, 3H), 1.23-1.27 (m, 9H)<br>LCMS (m/z) [M + H]⁺ 814.4 |

| Example Number | Scheme | Name/Structure | ¹H NMR<br>LCMS (m/z) [M + H]⁺ |
|---|---|---|---|
| Example 86 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-((3-fluorobenzyl)oxy)-3-methyl-2,3-dihydro-1Hbenzo[d]imidazole-5-carboxamide, trifluoroacetic acid salt<br>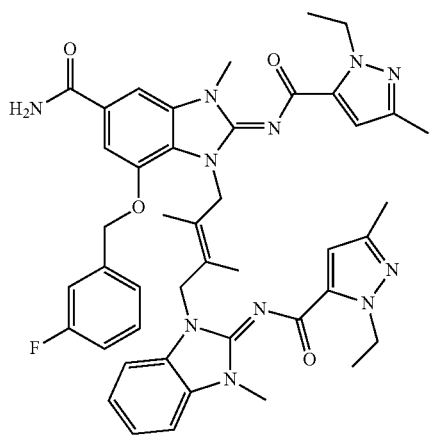 | ¹H NMR (300 MHz, DMSO-d₆) δ ppm 8.09 (s, 1H), 7.84 (s, 1H), 7.57-7.69 (m, 2H), 7.52 (s, 1H), 7.29-7.42 (m, 1H), 7.07-7.29 (m, 5H), 7.00 (t, J = 8.8 Hz, 1H), 6.49 (s, 1H), 6.41 (s, 1H), 5.20 (s, 2H), 5.02 (s, 2H), 4.79 (s, 2H), 4.43-4.53 (m, 4H), 3.61 (s, 3H), 3.59 (s, 3H), 2.13 (s, 3H), 2.10 (s, 3H), 1.60 (s, 3H), 1.18-1.29 (m, 9H)<br>LCMS (m/z) [M + H]⁺ 814.4 |
| Example 87 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-((2-fluorobenzyl)oxy)-3-methyl-2,3-dihydro-1Hbenzo[d]imidazole-5-carboxamide, trifluoroacetic acid salt<br>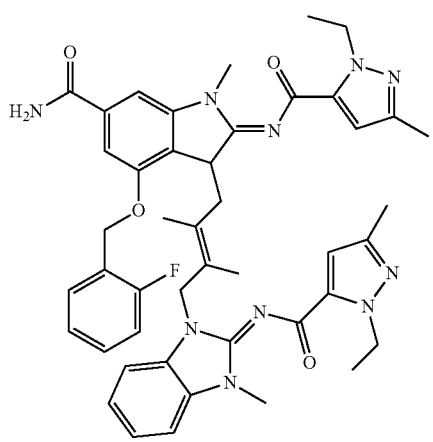 | ¹H NMR (300 MHz, DMSO-d₆) δ ppm 8.14 (s, 1H), 7.84 (s, 1H), 7.65-7.61 (m, 2 H7.55 (s, 1H), 7.38-7.43 (m, 1H), 7.09-7.35 (m, 5H), 6.95-7.02 (m, 1H), 6.58 (s, 1H), 6.41 (s, 1H), 5.24 (s, 2 H), 4.94 (s, 2H), 4.77 (s, 2 H), 4.44-4.53 (m, 4H), 3.63 (s, 3H), 3.59 (s, 3H), 2.16 (s, 3H), 2.10 (s, 3H), 1.57 (s, 3H), 1.20-1.32 (m, 6H), 1.10 (s, 3H)<br>LCMS (m/z) [M + H]⁺ 814.4 |

| Example Number | Scheme | Name/Structure | ¹H NMR<br>LCMS (m/z) [M + H]⁺ |
|---|---|---|---|
| Example 88 | Method 4 | (E)-2-((1-ethyl-3-methyl-1H-pyrazole-5-carbonyl)imino)-1-(4-((E)-2-((1-ethyl-3-methyl-1H-pyrazole-5-carbonyl)imino)-7-methoxy-3-methyl-2,3-dihydro-1H-benzo[d]imidazol-1-yl)-2,3-dihydroxybutyl)-3-methyl-2,3-dihydro-1H-benzo[d]imidazole-5-carboxamide<br>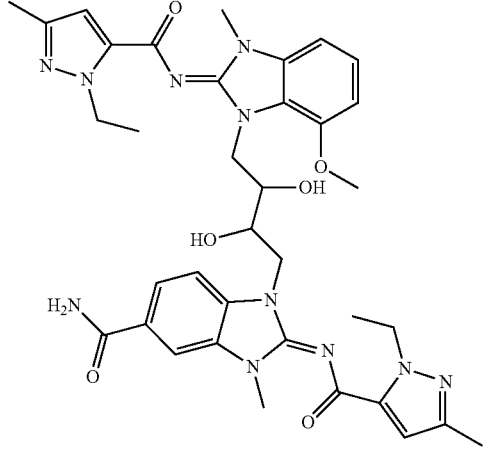 | ¹H NMR (400 MHz, DMSO-d₆) δ ppm 8.06 (d, J = 1.3 Hz, 1H), 8.01 (br. s., 1H), 7.86 (dd, J = 1.4, 8.4 Hz, 1H), 7.58 (d, J = 8.5 Hz, 1H), 7.40 (br. s., 1H), 7.26 (t, J = 8.2 Hz, 1H), 7.16 (d, J = 7.5 Hz, 1H), 6.91 (d, J = 7.8 Hz, 1H), 6.46 (s, 1 H), 6.42 (s, 1H), 5.36 (d, J = 6.0 Hz, 1H), 5.10 (d, J = 6.8 Hz, 1H), 4.54-4.44 (m, 5H), 4.30-4.16 (m, 3 H), 3.91-3.83 (m, 2H), 3.73 (s, 3H), 3.56 (s, 3H), 3.49 (s, 3H), 2.13 (s, 3H), 2.11 (s, 3H), 1.31-1.22 (m, 6H)<br>LCMS (m/z) [M + H]⁺ 726.5 |
| Example 89 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-7-(3-morpholinopropoxy)-2,3-dihydro-1H-benzo[d]imidazol-1-yl)-2,3-dimethylbut-2-en-1-yl)-3-methyl-2,3-dihydro-1H-benzo[d]imidazole-5-carboxamide<br>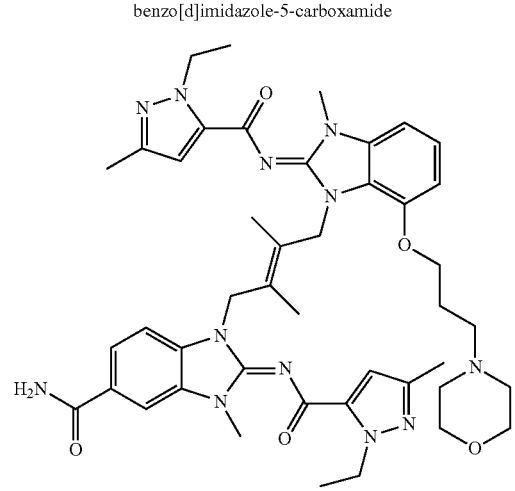 | ¹H NMR (400 MHz, DMSO-d₆) δ ppm 8.12 (s, 1H), 8.02 (s, 1H), 7.77-7.79 (m, 1H), 7.46 (s, 1H), 7.19-7.28 (m, 3H), 6.96 (d, J = 8.0 Hz, 1H), 6.45 (s, 1H), 6.36 (s, 1H), 5.05 (s, 2H), 4.85 (s, 2 H), 4.47-4.52 (m, 4H), 4.05 (t, J = 6.0 Hz, 2H), 3.58 (s, 3 H), 3.54 (s, 3H), 3.45 (t, J = 4.4 Hz, 4H), 2.23 (t, J = 6.8 Hz, 2H), 2.17 (s, 4 H), 2.11 (s, 3H), 2.08 (s, 3 H), 1.61-1.66 (m, 5H), 1.50 (s, 3H), 1.22-1.30 (m, 6H)<br>LCMS (m/z) [M + H]⁺ 833.4 |

Example 90

(E)-1-((E)-4-((E)-7-bromo-2-((1-ethyl-3-methyl-1H-pyrazole-5-carbonyl)imino)-3-methyl-2,3-dihydro-1H-benzo[d]imidazol-1-yl)-2,3-dimethyl but-2-en-1-yl)-2-((1-ethyl-3-methyl- 1H-pyrazole-5-carbonyl)imino)-3-methyl-2,3-dihydro-1H-benzo[d]imidazole-5-carboxamide

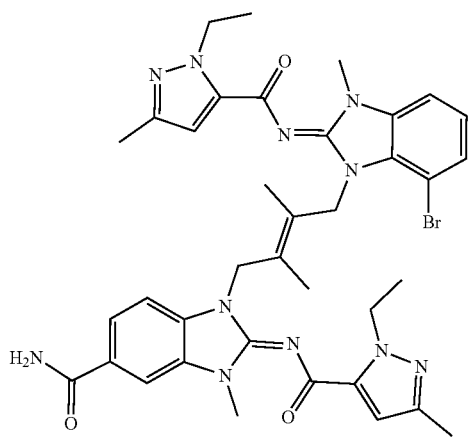 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2cccc(Br)c21]

Step 1: (E)-3-((4-((2-bromo-6-nitrophenyl)amino)-2,3-dimethylbut-2-en-1-yl)amino)-4-nitrobenzamide

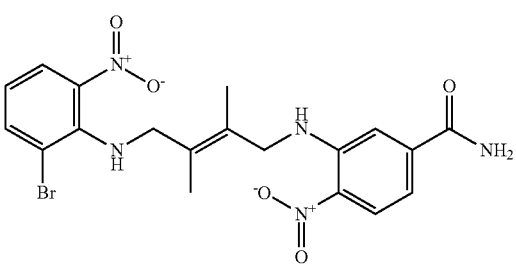

To a bright yellow suspension of (E)-4-((4-amino-2,3-dimethylbut-2-en-1-yl)amino)-3-nitrobenzamide, Hydrochloride (1.05 g, 3.34 mmol) and 1-bromo-2-fluoro-3-nitrobenzene (0.734 g, 3.34 mmol) in 1-butanol (25 mL) was added DIEA (1.75 mL, 10.01 mmol). The reaction was stirred at 80° C. for 5 h and then stirred at room temperature for 16 h. The solids were filtered and rinsed with butanol (20 mL) and water (3×20 mL). Solids were dried to give the title compound (1.16 g, 2.40 mmol, 72% yield) as an orange solid. $^1$H NMR (DMSO-$d_6$, 400 MHz) δ 8.66 (d, J=2.0 Hz, 1H), 8.3-8.4 (m, 1H), 7.99 (br s, 1H), 7.9-8.0 (m, 1H), 7.87 (dd, J=1.5, 7.8 Hz, 1H), 7.81 (dd, J=1.5, 8.3 Hz, 1H), 7.31 (br s, 1H), 6.8-6.9 (m, 1H), 6.77 (d, J=9.0 Hz, 1H), 6.06 (t, J=6.0 Hz, 1H), 3.98 (br d, J=5.8 Hz, 2H), 3.85 (d, J=6.0 Hz, 2H), 1.64 (s, 3H), 1.59 (d, J=1.3 Hz, 3H). LCMS (m/z): 478.2 [M+H]$^+$.

Step 2: (E)-4-amino-3-((4-((2-amino-6-bromophenyl)amino)-2,3-dimethylbut-2-en-1-yl)amino)benzamide

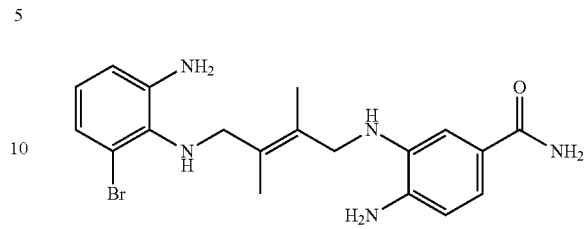

To a mixture of (E)-3-((4-((2-bromo-6-nitrophenyl)amino)-2,3-dimethylbut-2-en-1-yl)amino)-4-nitrobenzamide (1.06 g, 2.216 mmol) and ammonium chloride (1.778 g, 33.2 mmol) in MeOH (50 mL) cooled in an ice/water bath was added zinc (1.449 g, 22.16 mmol) and reaction mixture was stirred at room temperature for 40 min. The mixture was filtered through celite and rinsed with methanol. Filtrate was concentrated and purified by silica gel chromatography (24 g silica column; gradient of 10-60% [3:1 EA:EtOH]/heptane, plus 1% NH$_4$OH solution, 12 min.; 60% [3:1 EA:EtOH]/heptane, 5 min). The purest fractions were combined and concentrated. Mixed fractions were concentrated and repurified (12 g silica column; gradient of 10-55% [3:1 EA:EtOH]/heptane, no NH$_4$OH modifier, 10 min.; 55% [3:1 EA:EtOH]/heptane, 5 min). Fractions were combined and dried to provide the title compound (571 mg, 1.09 mmol, 49.3% yield) as a tan foam. LCMS (m/z): 418.3 [M+H]$^+$, ~80% purity by UV210-350 nm).

Step 3: (E)-1-(4-(7-bromo-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide

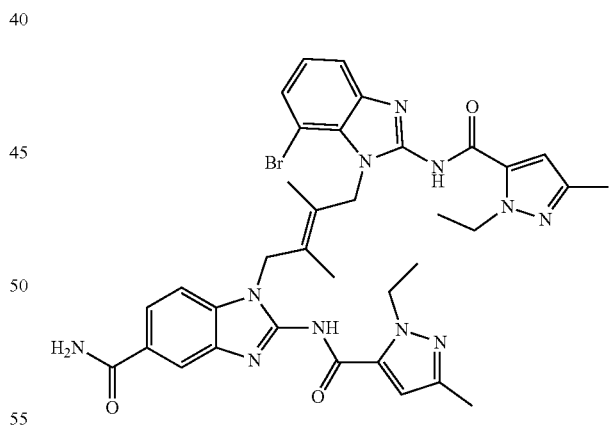

To a light brown solution of (E)-4-amino-3-((4-((2-amino-6-bromophenyl)amino)-2,3-dimethylbut-2-en-1-yl)amino)benzamide (570 mg, 1.090 mmol) in DMF (10 mL) cooled in an ice/water bath was added quickly dropwise 1-ethyl-3-methyl-1H-pyrazole-5-carbonyl isothiocyanate (~1 M in dioxane, 2.18 mL, 2.18 mmol). After stirring for 15 min, EDC (522 mg, 2.73 mmol) and TEA (0.760 mL, 5.45 mmol) were added and the reaction mixture was warmed to room temperature and stirred for 16 h. Into the stirred reaction mixture was quickly added a solution of 5:1 water: saturated aqueous NH$_4$Cl solution (120 mL). The resulting suspension was stirred rapidly for 15 min. The solids were filtered and rinsed with water (3×20 mL). The solids were stirred in diethyl ether (15 mL) for 30 min and then filtered and rinsed with diethyl ether. After drying, the title compound (772 mg, 0.94 mmol, 86% yield) was obtained as a light yellow solid. $^1$H NMR (DMSO-$d_6$) δ: 13.02 (br. s., 1H), 12.90 (s, 1H), 8.02 (s, 1H), 7.94 (br. s., 1H), 7.71 (d, J=8.4 Hz, 1H), 7.61 (d, J=7.9 Hz, 1H), 7.44 (d, J=7.9 Hz, 1H), 7.35 (br. s., 1H), 7.26 (d, J=8.4 Hz, 1H), 7.19 (t, J=8.0 Hz, 1H), 6.64 (s, 1H), 6.52 (s, 1H), 5.26 (br. s., 2H), 5.00 (br. s., 2H), 4.53-4.63 (m, 4H), 2.12 (s, 3H), 2.10 (s, 3H), 1.69 (br. s., 3H), 1.63 (br. s., 3H), 1.35 (t, J=7.1 Hz, 3H), 1.32 (t, J=7.1 Hz, 3H). LCMS (m/z): 740.2/742.4 [M+H]$^+$, ~90% purity by UV210-350 nm).

Step 4: (E)-1-((E)-4-((E)-7-bromo-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide

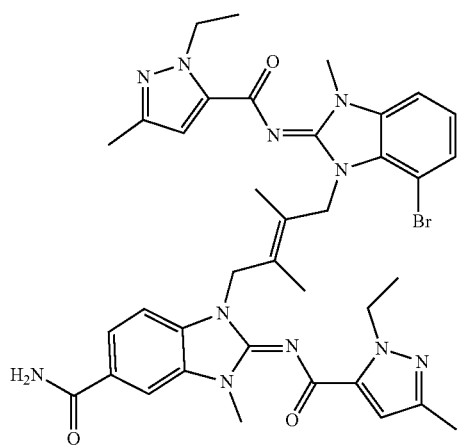 [SMILES: CCn1nc(C)cc1C(=O)/N=c1\n(C)c2cc(C(N)=O)ccc2n1C/C(C)=C(\C)Cn1/c(=N/C(=O)c2cc(C)nn2CC)n(C)c2cccc(Br)c21]

To a solution of (E)-1-(4-(7-bromo-2-(1-ethyl-3-methyl-1H-pyrazole-5-carboxamido)-1H-benzo[d]imidazol-1-yl)-2,3-dimethylbut-2-en-1-yl)-2-(1-ethyl-3-methyl-1H-pyrazole-5-carboxamido)-1H-benzo[d]imidazole-5-carboxamide (760 mg, 0.923 mmol) in DMF (15 mL) was added potassium carbonate (319 mg, 2.309 mmol) and methyl iodide (0.13 mL, 2.12 mmol). The reaction mixture was stirred at room temperature for 3 h. The reaction mixture was diluted with water (30 mL) and clumpy solids formed. The mixture was then partitioned between DCM and water. The organic phase was then washed with brine and concentrated. Purification by silica gel chromatography (24 g silica column; gradient of 10-60% [3:1 EA:EtOH]/heptane, plus 1% NH$_4$OH, 15 min.; 60% [3:1 EA:EtOH]/heptane, plus 1% NH$_4$OH, 10 min.) provided the title compound (386 mg, 0.477 mmol, 51.7% yield) as a light orange foam after solvent evaporation. $^1$H NMR (DMSO-$d_6$) δ: 8.08-8.12 (m, 1H), 8.01 (br. s., 1H), 7.80 (dd, J=8.4, 1.4 Hz, 1H), 7.62-7.67 (m, 1H), 7.49-7.53 (m, 1H), 7.43 (br. s., 1H), 7.25-7.34 (m, 2H), 6.49 (s, 1H), 6.44 (s, 1H), 5.16 (s, 2H), 4.89 (s, 2H), 4.47-4.57 (m, 4H), 3.59 (s, 3H), 3.56 (s, 3H), 2.13 (s, 3H), 2.12 (s, 3H), 1.59 (s, 3H), 1.50 (s, 3H), 1.24-1.33 (m, 6H). LCMS (m/z): 768.5/770.5 [M+H]$^+$.

Example 91

(E)-1-(4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide

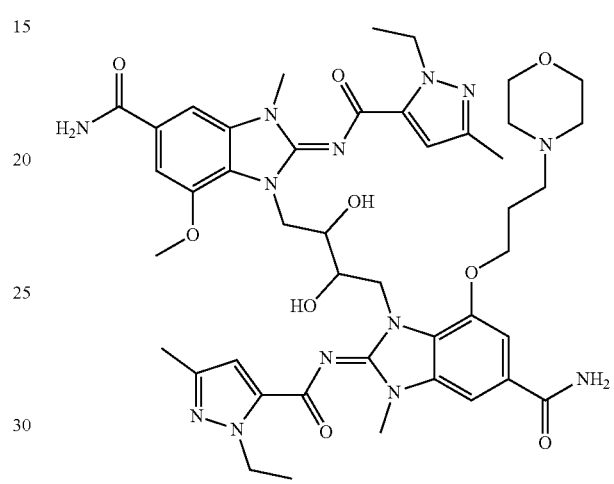

Step 1: (E)-1-((E)-4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide

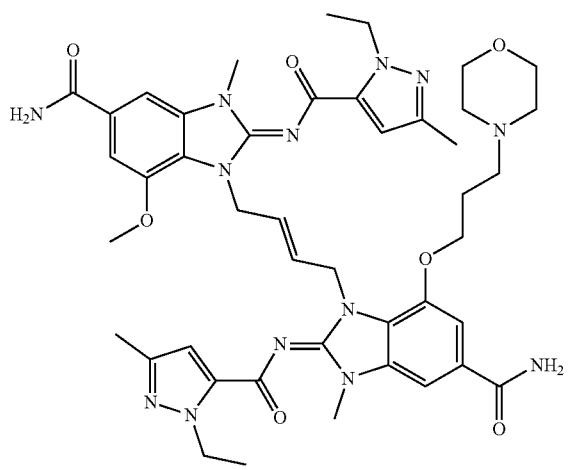

To a suspension of (E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (125 mg, 0.147 mmol, it can be prepared according to preparation described for Example 14 of PCT Int. Appl. WO 2017175147) and potassium carbonate (44.7 mg, 0.324 mmol) in DMF (1.4 mL) was added a solution of methyl iodide (0.019 mL, 0.31 mmol) in DMF (0.4 mL). The mixture was stirred at room temperature for 18 h and then diluted with water. The mixture was extracted with dichloromethane (3×). The combined organic layer was washed with water, dried with sodium sulfate, filtered, and concentrated. The residue was purified by reversed-phase mass-directed preparative HPLC (XSELECT CSH C18, 5 um packing, 150×30 mm column, 15-55% gradient of ACN/water with 0.1% TFA modifier). The fractions containing the desired product were passed through a basic PL-HCO3 MP SPE cartridge. The eluate was concentrated to provide (E)-1-((E)-4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (45 mg, 0.051 mmol, 34.8% yield). ¹H NMR (DMSO-d₆) Q ppm 8.04 (br. s., 2H), 7.71-7.75 (m, 2H), 7.38-7.48 (m, 4H), 6.40 (s, 1H), 6.35 (s, 1H), 5.66-5.80 (m, 2H), 4.79-4.89 (m, 4H), 4.38-4.49 (m, 4H), 4.02 (br. t., J=6.3 Hz, 2H), 3.74 (s, 3H), 3.47-3.54 (m, 10H), 2.18-2.29 (m, 6H), 2.12 (s, 3H), 2.10 (s, 3H), 1.64-1.72 (m, 2H), 1.18-1.25 (m, 6H). LCMS (m/z): 878.3 [M+H]⁺.

Step 2: (E)-1-(4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide To a mixture of (E)-1-((E)-4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-3-methyl-2,3-dihydro-1H-benzo[d]imidazole-5-carboxamide (26 mg, 0.030 mmol) and NMO (5.20 mg, 0.044 mmol) in tert-butanol (1.2 mL) and water (0.3 mL) was added 2.5% osmium tetroxide in tert-butanol (0.019 mL, 1.5 µmol). The mixture was stirred at room temperature for 64 h and then filtered. The filtrate was purified directly by mass-directed preparative HPLC (XSELECT CSH C18, 5 um packing, 150×30 mm column, 15-55% gradient of ACN/water with 0.1% TFA modifier). The fractions containing the title compound were passed through a PL-HCO3 MP SPE cartridge. The eluate was concentrated to provide (E)-1-(4-((E)-5-carbamoyl-2-((1-ethyl-3-methyl-1H-pyrazole-5-carbonyl)imino)-3-methyl-7-(3-morpholinopropoxy)-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide (11 mg, 0.012 mmol, 40.7% yield). 1H NMR (400 MHz, DMSO-d₆) δ ppm 1.24-1.29 (m, 6H) 1.81-1.86 (m, 2H) 2.09-2.12 (m, 6H) 2.27 (br. s., 4H) 2.35-2.39 (m, 2H) 3.47-3.53 (m, 10H) 3.81 (s, 3H) 3.82-3.93 (m, 2H) 4.14 (t, J=6.40 Hz, 2H) 4.26-4.33 (m, 2H) 4.44-4.58 (m, 6H) 4.98 (d, J=6.53 Hz, 1H) 5.07 (d, J=6.02 Hz, 1H) 6.39 (s, 1H) 6.44 (s, 1H) 7.41-7.48 (m, 4H) 7.72 (dd, J=4.52, 1.00 Hz, 2H) 8.05 (br. s., 2H). LCMS (m/z): 912.2 [M+H]⁺.

Example 92

(E)-7-(3-aminopropoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, Formic Acid Salt

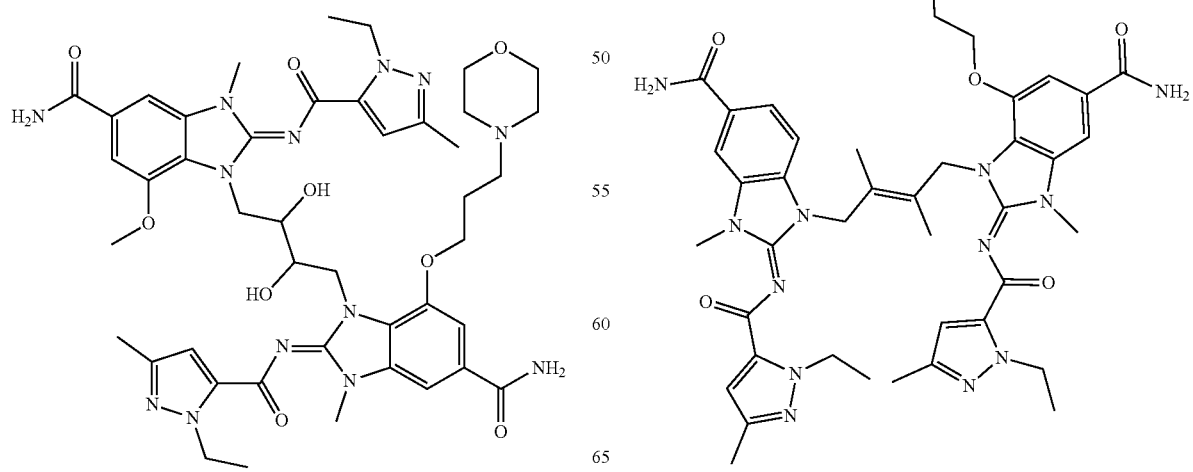

A mixture of (E)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-7-hydroxy-3-methyl-2,3-dihydro-1H-benzo[d]imidazole-5-carboxamide (384 mg, 0.513 mmol), tert-butyl (3-bromopropyl)carbamate (733 mg, 3.08 mmol) and K$_2$CO$_3$ (425 mg, 3.08 mmol) in DMF (10 mL) was heated at 90° C. for nine days. LCMS analysis indicated partial conversion to O-alkylated intermediate increasing over time to reach ca. 50% conversion at 9 days. The reaction mixture was filtered and concentrated. The residue was purified by mass-directed preparative HPLC (XSELECT CSH C18, 5 um packing, 150×30 mm column, 15-55% gradient of ACN/water with 0.1% TFA modifier) to afford 100 mg of a brown residue after solvent evaporation. The residue was a mixture of N-Boc intermediate and title compound (removal of Boc group occurred during solvent evaporation). The residue was dissolved in methanol (1 mL) and 1,4-dioxane (2 mL) and sonicated to a brown solution, then HCl (4 M in dioxane, 1.282 mL, 5.13 mmol) was added. The mixture was sonicated again and the mixture was stirred at room temperature for 3 h. The reaction mixture was concentrated, dissolved in DMSO and then purified by mass-directed preparative HPLC (XSELECT CSH C18, 5 um packing, 150×30 mm column, 15-55% gradient of ACN/water with 0.1% formic acid modifier) to afford (E)-7-(3-aminopropoxy)-1-((E)-4-((E)-5-carbamoyl-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, formic acid salt (8.0 mg, 9.4 μmol, 1.8% yield) as a white solid. $^1$H NMR (400 MHz, DMSO-d$_6$) δ ppm 8.36 (s, 1H), 8.12 (s, 2H), 8.05 (br. s., 1H), 7.76-7.84 (m, 2H), 7.53 (s, 1H), 7.47 (s, 1H), 7.44 (s, 1H), 7.25 (d, J=8.5 Hz, 1H), 6.47 (s, 1H), 6.32 (s, 1H), 5.06 (s, 2H), 4.85 (s, 2H), 4.41-4.57 (m, 4H), 4.22 (t, J=6.4 Hz, 2H), 3.59 (s, 3H), 3.56 (s, 3H), 2.77 (t, J=6.9 Hz, 2H), 2.12 (s, 3H), 2.06 (s, 3H), 1.84 (quin, J=6.5 Hz, 2H), 1.63 (s, 3H), 1.49 (s, 3H), 1.29 (t, J=7.1 Hz, 3H), 1.24 (t, J=7.1 Hz, 3H). LCMS (m/z): 806.3 [M+H]$^+$.

Table 3 show Examples 93-109, which can be prepared according to methods illustrated below:

| Example Number | Scheme | Name/Structure | $^1$H NMR<br>LCMS (m/z) [M + H]$^+$ |
|---|---|---|---|
| Example 93 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-3-methyl-7-(3-morpholinopropoxy)-2,3-dihydro-1Hbenzo[d]imidazole-5-carboxamide, trifluoroacetic acid salt 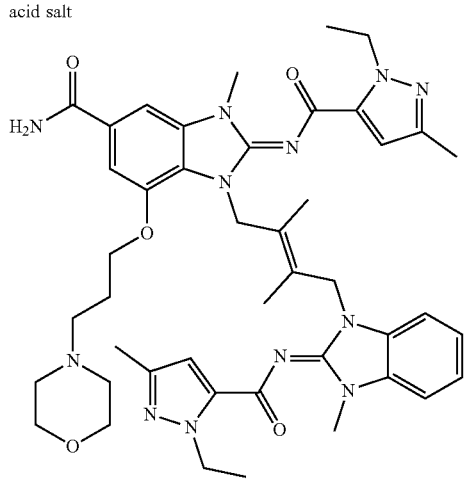 | $^1$H NMR (DMSO-d$_6$) δ ppm 9.67 (br. s., 1H), 8.07 (br. s., 1H), 7.83 (s, 1H), 7.62 (d, J = 8.0 Hz, 1H), 7.51 (s, 2H), 7.34 (ddd, J = 8.1, 6.2, 2.3 Hz, 1H), 7.17-7.24 (m, 2H), 6.47 (s, 1H), 6.31 (s, 1H), 5.07 (s, 2H), 4.84 (s, 2H), 4.44-4.56 (m, 4H), 4.19 (t, J = 6.0 Hz, 2H), 3.93 (br. d., J = 12.5 Hz, 2H), 3.57 (s, 6H), 3.35 (br. d., J = 9.5 Hz, 2H), 3.14-3.21 (br. m., 2H), 2.99 (br. s., 2H), 2.13 (s, 3H), 2.08 (s, 3H), 1.95-2.04 (m, 2H), 1.62 (s, 3H), 1.51 (s, 3H), 1.24-1.31 (m, 6H)<br>LCMS (m/z)[M + H]$^+$ 833.4 |

| Example Number | Scheme | Name/Structure | ¹H NMR<br>LCMS (m/z) [M + H]⁺ |
|---|---|---|---|
| Example 94 | Method 4 | (E)-2-((1-ethyl-3-methyl-1H-pyrazole-5-carbonyl)imino)-1-(4-((E)-2-((1-ethyl-3-methyl-1H-pyrazole-5-carbonyl)imino)-3-methyl-2,3-dihydro-1H-benzo[d]imidazol-1-yl)-2,3-dihydroxybutyl)-7-methoxy-3-methyl-2,3-dihydro-1H-benzo[d]imidazole-5-carboxamide, formic acid salt | ¹H NMR (DMSO-d₆) δ ppm 8.05 (br. s., 1H), 7.73 (s, 1H), 7.52-7.57 (m, 2H), 7.45 (br. s., 1H), 7.41 (s, 1H), 7.26-7.34 (m, 2H), 6.45 (s, 2H), 5.33 (br. s., 1H), 5.08 (br. s., 1H), 4.45-4.55 (m, 5H), 4.14-4.29 (m, 3H), 3.87 (br. s., 2H), 3.76 (s, 3H), 3.54 (s, 3H), 3.52 (s, 3H), 2.12 (s, 6H), 1.23-1.31 (m, 6H)<br>LCMS (m/z)[M + H]⁺ 726.6 |
| Example 95 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-isobutoxy-3-methyl-2,3-dihydro-1H-benzo[d]imidazole-5-carboxamide, trifluoroacetic acid salt | ¹H NMR (400 MHz, CD₃OD) δ ppm 7.82 (s, 1H), 7.71 (d, 1H), 7.58 (s, 1H), 7.44-7.50 (m, 1H), 7.31-7.35 (m, 2H), 6.69 (s, 1H), 6.47 (s, 1H), 5.32 (s, 2H), 4.96 (s, 2H), 4.52-4.62 (m, 4H), 4.00 (d, 2H), 3.79 (s, 3H), 3.73 (s, 3H), 2.27 (s, 3H), 2.17 (s, 3H), 2.06 (m, 1H), 1.76 (s, 3H), 1.56 (s, 3H), 1.38 (t, 3H), 1.31 (t, 3H), 1.02 (s, 3H), 0.98 (s, 3H)<br>LCMS (m/z)[M + H]⁺ 762.4 |

-continued

| Example Number | Scheme | Name/Structure | ¹H NMR<br>LCMS (m/z) [M + H]⁺ |
|---|---|---|---|
| Example 96 | Method 1 | (E)-7-(3-(dimethylamino)propoxy)-2-((1-ethyl-3-methyl-1H-pyrazole-5-carbonyl)imino)-1-((E)-4-((E)-2-((1-ethyl-3-methyl-1Hpyrazole-5-carbonyl)imino)-3-methyl-2,3-dihydro-1H-benzo[d]imidazol-1-yl)-2,3-dimethylbut-2-en-1-yl)-3-methyl-2,3-dihydro-1Hbenzo[d]imidazole-5-carboxamide, Trifluoroacetic acid salt | ¹H NMR (400 MHz, CD₃OD) δ ppm 7.85 (s 1H), 7.67 (d, 1H), 7.58 (s, 1H), 7.42-7.47 (m, 1H), 7.29-7.38 (m, 2H), 6.67 (s, 1H), 6.43 (s, 1H), 5.25 (s, 2H), 4.96 (s, 2H), 4.50-4.63 (m, 4H), 4.28 (t, 2H), 3.73 (s, 3H), 3.68 (s, 3H), 3.24-3.28 (m, 2H), 2.88 (s, 6H), 2.25 (s, 3H), 2.15-2.22 (m, 2H), 2.14 (s, 3H), 1.75 (s, 3H), 1.60 (s, 3H), 1.38 (t, 3H), 1.32 (t, 3H)<br>LCMS (m/z)[M + H]⁺ 791.4 |
| Example 97 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-isobutoxy-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide | 1H NMR (400 MHz, DMSO-d₆) δ ppm 8.11 (s, 1H), 8.02 (s, 1H), 7.76-7.78 (m, 1H), 7.45 (s, 1H), 7.25-7.29 (m, 1H), 7.17-7.21 (m, 2H), 6.96-6.98 (m, 1H), 6.47 (s, 1H), 6.35 (s, 1H), 5.09 (s, 2H), 4.84 (s, 2H), 4.45-4.54 (m, 4H), 3.84 (d, J = 8.0 Hz, 2H), 3.58 (s, 3H), 3.54 (s, 3H), 2.13 (s, 3H), 2.07 (s, 3H), 1.84-1.87 (m, 1H), 1.62 (s, 3H), 1.46 (s, 3H), 1.22-1.30 (m, 6H), 0.88 (s, 3H), 0.86 (s, 3H)<br>LCMS (m/z)[M+H]+ 762.5 |

| Example Number | Scheme | Name/Structure | ¹H NMR LCMS (m/z) [M + H]⁺ |
|---|---|---|---|
| Example 98 | Method 1 | (E)-1-((E)-4-((E)-7-(3-(dimethylamino)propoxy)-2-((1-ethyl-3-methyl-1H-pyrazole-5-carbonyl)imino)-3-methyl-2,3-dihydro-1Hbenzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1Hbenzo[d]imidazole-5-carboxamide, trifluoroacetic acid salt | ¹H NMR (400 MHz, DMSO-d₆) δ ppm 9.65 (br. s., 1H), 8.13 (s, 1H), 8.05 (s, 1H), 7.78-7.80 (m, 1H), 7.48 (s, 1H), 7.22-7.35 (m, 3H), 7.01 (d, J = 8.0 Hz, 1H), 6.48 (s, 1H), 6.33 (s, 1H), 5.08 (s, 2H), 4.84 (s, 2H), 4.43-4.54 (m, 4H), 4.14 (t, J = 6.0 Hz, 2H), 3.59 (s, 3H), 3.57 (s, 3H), 3.09-3.15 (m, 2H), 2.72 (s, 6H), 2.13 (s, 3H), 2.06 (s, 3H), 1.97-2.00 (m, 2H), 1.61 (s, 3H), 1.49 (s, 3H), 1.22-1.31 (m, 6H) LCMS (m/z)[M + Na]⁺ 813.4 |
| Example 99 | Method 1 | (E)-7-(3-(4,4-difluoropiperidin-1-yl)propoxy)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, trifluoroacetic acid salt | ¹H NMR (400 MHz, CD₃OD) δ ppm 7.88 (s, 1H), 7.73 (d, 1H), 7.60 (s, 1H), 7.48-7.53 (m, 1H), 7.35-7.43 (m, 2H), 6.72 (s, 1H), 6.41 (s, 1H), 5.27 (s, 2H), 4.98 (s, 2H), 4.51-4.61 (m, 4H), 4.33 (t, J = 6.2 Hz, 2H), 3.81 (s, 3H), 3.73 (s, 3H), 3.32-3.38 (m, 4H), 2.22-2.40 (m, 9H), 2.12 (s, 3H), 1.75 (s, 3H), 1.59 (s, 3H), 1.38 (t, 3H), 1.32 (t, 3H) LCMS (m/z)[M + H]⁺ 867.5 |

-continued

| Example Number | Scheme | Name/Structure | ¹H NMR LCMS (m/z) [M + H]⁺ |
|---|---|---|---|
| Example 100 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-7-(2-hydroxy-2-methylpropoxy)-3-methyl-2,3-dihydro-1Hbenzo[d]imidazole-5-carboxamide, trifluoroacetic acid salt 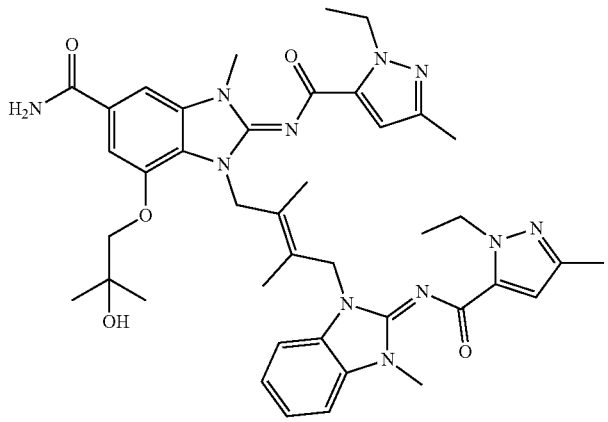 [SMILES: CCn1nc(C)cc1C(=O)/N=c1\n(C)c2ccccc2n1C/C(C)=C(\C)Cn1/c(=N/C(=O)c2cc(C)nn2CC)n(C)c2cc(C(N)=O)cc(OCC(C)(C)O)c21] | ¹H NMR (400 MHz, CD₃OD) δ ppm 7.85 (s, 1H), 7.70 (d, 1H), 7.63 (s, 1H), 7.49 (t, 1H), 7.30-7.39 (m, 2H), 6.72 (s, 1H), 6.44 (s, 1H), 5.40 (s, 2H), 4.95 (s, 2H), 4.50-4.62 (m, 4H), 4.10 (s, 2H), 3.80 (s, 3H), 3.74 (s, 3H), 2.27 (s, 3H), 2.14 (s, 3H), 1.76 (s, 3H), 1.53 (s, 3H), 1.38 (t, 3H), 1.28-1.33 (m, 9H) LCMS (m/z)[M + H]⁺ 778.4 |
| Example 101 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-7-(2-hydroxy-2-methylpropoxy)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide, trifluoroacetic acid salt 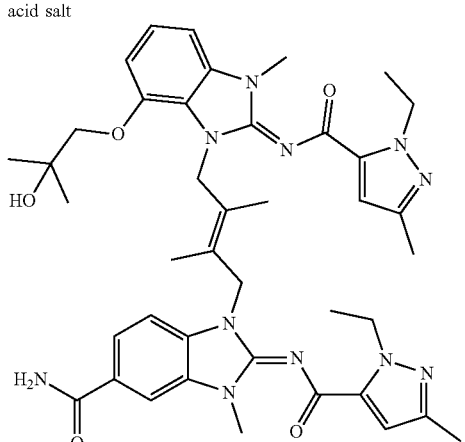 | 1H NMR (400 MHz, DMSO-d₆) δ: 8.11 (s, 1H), 8.01 (s, 1H), 7.76 (d,J = 8.4 Hz, 1H), 7.45 (s , 1H), 7.24-7.33 (m,2H), 7.16 (d, J = 8.4 Hz, 1H), 7.03 (d, J = 8.0 Hz, 1H), 6.47 (s, 1H), 6.35 (s, 1H), 5.20 (s, 2H), 4.81 (s, 2H), 4.42-4.54 (m, 4H), 3.95 (s, 3H), 3.58 (s, 6H), 2.14 (s, 3H), 2.04 (s, 3H), 1.65 (s, 3H), 1.45 (s, 3H), 1.28 (t, J = 7.2 Hz, 3H), 1.21 (t, J = 7.2 Hz, 3H), 1.17 (s, 3H). LCMS (m/z)[M + H]⁺ 778.4 |

| Example Number | Scheme | Name/Structure | ¹H NMR<br>LCMS (m/z) [M + H]⁺ |
|---|---|---|---|
| Example 102 | Method 1 | (2E,2'E)-1,1'-((meso)-2,3-dimethoxybutane-1,4-diyl)bis(2-((1-ethyl-3-methyl-1H-pyrazole-5-carbonyl)imino)-3-methyl-2,3-dihydro-1H-benzo[d]imidazole-5-carboxamide) | ¹H NMR (400 MHz, DMSO-d₆) δ ppm 8.09 (d, J = 1.27 Hz, 2H) 8.05 (br. s., 2H) 7.87 (dd, J = 8.49, 1.39 Hz, 2H) 7.59 (d, J = 8.36 Hz, 2H) 7.44 (br. s., 2H) 6.55 (s, 2H) 4.53 (q, J = 7.01 Hz, 4H) 4.35 (d, J = 5.32 Hz, 4H) 3.88-3.99 (m, 2H) 3.61 (s, 6H) 3.08 (s, 6H) 2.11 (s, 6H) 1.29 (t, J = 7.10 Hz, 6H)<br>LCMS (m/z)[M + H]⁺ 767.7 |
| Example 103 | Method 2 | (E)-1-((E)-4-((E)-4-bromo-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-7-(3-morpholinopropoxy)-2,3-dihydro-1H-benzo[d]imidazole-5-carboxamide | ¹H NMR (600MHz, METHANOL-d₄) δ 7.77 (s, 1H), 7.56 (s, 1H), 7.51 (d, J = 7.7 Hz, 1H), 7.20 (d, J = 8.1 Hz, 1H), 7.09 (t, J = 8.1 Hz, 1H), 6.62 (s, 1H), 6.45 (s, 1H), 5.24 (s, 2H), 4.92 (s, 2H), 4.63 (q, J = 7.0 Hz, 2H), 4.57 (q, J = 7.0 Hz, 2H), 4.25 (br t, J = 6.3 Hz, 2H), 3.94 (s, 3H), 3.68 (s, 3H), 3.64 (br t, J = 4.4 Hz, 4H), 2.45 (br t, J = 7.4 Hz, 2H), 2.39 (br s, 4H), 2.24 (s, 3H), 2.19 (s, 3H), 1.93 (quin, J = 6.8 Hz, 2H), 1.74 (s, 3H), 1.60 (s, 3H), 1.40 (t, J = 7.2 Hz, 3H), 1.35 (t, J = 7.2 Hz, 3H)<br>LCMS (m/z)[M + H]⁺ 911.5/913.5 |

-continued

| Example Number | Scheme | Name/Structure | ¹H NMR<br>LCMS (m/z) [M + H]⁺ |
|---|---|---|---|
| Example 104 | Method 1 | (E)-1-((E)-4-((E)-7-(3-(4,4-difluoropiperidin-1-yl)propoxy)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-2-((1-ethyl-3-methyl-1H-pyrazole-5-carbonyl)imino)-3-methyl-2,3-dihydro-1H-benzo[d]imidazole-5-carboxamide, trifluoroacetic acid salt | ¹H NMR (300 MHz, DMSO-d₆) δ: 8.13 (s, 1H), 8.03 (s, 1H), 7.78 (d, J = 8.3 Hz, 1H), 7.48 (s, 1H), 7.21-7.31 (m, 3H), 7.00 (d, J = 8.3 Hz, 1H), 6.47 (s, 1H), 6.29 (s, 1H), 5.07 (s, 2H), 4.84 (s, 2H), 4.44-4.53 (m, 4H), 4.12-4.13 (m, 2H), 3.55-3.58 (m, 8H), 3.16-3.29 (m, 4H), 1.99-2.27 (m, 12H), 1.61 (s, 3H), 1.49 (s, 3H), 1.21-1.31 (m, 6H).<br>LCMS (m/z)[M + H]⁺ 867.4 |
| Example 105 | Method 1 | (5aE,21E,29E)-8-ethyl-26 hydroxypropoxy)-5,10,18,22,29,30-hexamethyl-7,20-dioxo-5,7,8,11,12,13,14,15,20,22,28,31-dodecahydrobenzo[4,5]imidazo[1,2-a]benzo[4,5]imidazo[2,1-p]dipyrazolo[5,1-e:4',3'-1]][1,3,6,15,17]pentaazacyclo-henicosine-3,24-dicarboxamide | ¹H NMR (400 MHz, DMSO-d₆) δ 8.13 (s, 1H), 8.09 (s, 1H), 8.02 (s, 1H), 7.87 (d, J = 8.4 Hz, 1H), 7.78 (s, 1H), 7.54 (s, 1H), 7.48 (s, 2H), 7.18 (d, J = 8.4 Hz, 1H), 6.47 (s, 1H), 5.09 (s, 2H), 4.92 (s, 2H), 4.63-4.57 (m, 3H), 4.47-4.42 (m, 2H), 4.30 (t, J = 12.8 Hz, 2H), 3.62 (s, 3H), 3.55 (s, 3H), 3.48-3.43 (m, 2H), 2.76-2.66 (m, 2H), 2.14 (s, 3H), 2.11 (s, 3H), 1.83-1.69 (m, 4H), 1.66 (s, 3H), 1.47-1.38 (m, 5H), 1.29 (t, J = 14.4 Hz, 3H), 1.26-1.22 (m, 2H).<br>LCMS (m/z)[M + H]⁺ 847.4;<br>Retention time: 1.33 min |

| Example Number | Scheme | Name/Structure | ¹H NMR<br>LCMS (m/z) [M + H]⁺ |
|---|---|---|---|
| Example 106 | Method 1 | (5aE,21E,29E)-8-ethyl-1-(3-hydroxypropoxy)-5,10,18,22,29,30-hexamethyl-7,20-dioxo-5,7,8,11,12,13,14,15,20,22,28,31-dodecahydrobenzo[4,5]imidazo[1,2-a]benzo[4,5]imidazo[2,1-p]dipyrazolo[5,1-e:4',3'-1][1,3,6,15,17]pentaazacyclohenicosine-3,24-dicarboxamide | 1H NMR (400 MHz, DMSO-$d_6$) δ 8.13 (s, 1H), 8.09 (s, 1H), 8.03 (s, 1H), 7.88 (d, J = 8.4, 1H), 7.76 (s, 1H), 7.52 (s, 1H), 7.48 (s, 2H), 7.28 (d, J = 8.4 Hz, 1H), 6.49 (s, 1H), 5.07 (s, 2H), 4.90 (s, 2H), 4.65-4.54 (m, 3H), 4.48-4.39 (m, 2H), 4.28 (t, J = 12.4 Hz, 2H), 3.61 (s, 3H), 3.56 (s, 3H), 3.48-3.42 (m, 2H), 2.73-2.65 (m, 2H), 2.15 (s, 3H), 2.07 (s, 3H), 1.82-1.64 (m, 4H), 1.55 (s, 3H), 1.44-1.32 (m, 5H), 1.29-1.23 (m, 5H).<br>LCMS (m/z)[M + H]⁺ 847.4;<br>Retention time: 1.32 min |
| Example 107 | Method 1 | (E)-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-N,3-dimethyl-2,3-dihydro-1H-benzo[d]imidazole-5-carboxamide | ¹H NMR (400 MHz, DMSO-$d_6$) δ 8.50 (q, J = 4.3 Hz, 1H), 8.06 (d, J = 1.3 Hz, 1H), 7.75 (dd, J = 8.4, 1.5 Hz, 1H), 7.61 (d, J = 7.9 Hz, 1H), 7.38-7.29 (m, 2H), 7.27-7.20 (m, 2H), 6.48-6.39 (m, 2H), 4.87 (s, 2H), 4.85 (s, 2H), 4.52 (q, J = 7.1 Hz, 4H), 3.59 (s, 3H), 3.57 (s, 3H), 2.84 (d, J = 4.3 Hz, 3H), 2.12 (s, 6H), 1.62 (br s, 3H), 1.61 (br s, 3H), 1.28 (t, J = 7.1 Hz, 6H)<br>LCMS (m/z) [M + H]⁺704.5 |

-continued

| Example Number | Scheme | Name/Structure | $^1$H NMR<br>LCMS (m/z) [M + H]$^+$ |
|---|---|---|---|
| Example 108 | Method 1 | (E)-1-(((1S,2S)-2-(((E)-5-carbamoyl-2-((1-ethyl-3-methyl-1H-pyrazole-5-carbonyl)imino)-3-methyl-2,3-dihydro-1H-benzo[d]imidazol-1-yl)methyl)cyclopropyl)methyl)-2-((1-ethyl-3-methyl-1H-pyrazole-5-carbonyl)imino)-7-(3-hydroxypropoxy)-3-methyl-2,3-dihydro-1H-benzo[d]imidazole-5-carboxamide | $^1$H NMR (400 MHz, Methanol-d$_4$) δ 7.64-7.66 (m, 2H), 7.28-7.32 (m, 2H), 7.17 (s, 1H), 6.62 (s, 1H), 6.64 (s, 1H), 4.57-4.64 (m, 5H), 4.48-4.55 (m, 1H), 4.14-4.26 (m, 2H), 3.71-3.74 (m, 3H), 3.52-3.60 (m, 1H), 3.41 (s, 3H), 3.38 (s, 3H), 2.22 (s, 3H), 2.18 (s, 3H), 2.03-2.11 (m, 2H), 1.61-1.77 (m, 2H), 1.36-1.42 (m, 6H), 0.85-0.87 (m, 2H).<br>LCMS (m/z)[M + H]$^+$ 793.3 |
| Example 109 | Method 1 | (E)-N-ethyl-2-((1-ethyl-3-methyl-1H-pyrazole-5-carbonyl)imino)-1-((E)-4-((E)-2-((1-ethyl-3-methyl-1H-pyrazole-5-carbonyl)imino)-3-methyl-2,3-dihydro-1H-benzo[d]imidazol-1-yl)-2,3-dimethylbut-2-en-1-yl)-3-methyl-2,3-dihydro-1H-benzo[d]imidazole-5-carboxamide | 1H NMR (400 MHz, DMSO-d6) δ 8.52 (t, J = 5.6 Hz, 1H), 8.07 (d, J = 1.5 Hz, 1H), 7.76 (dd, J = 8.4,1.5 Hz, 1H), 7.61 (d, J = 8.1 Hz, 1H), 7.39-7.29 (m, 2H), 7.28-7.18 (m, 2H), 6.44 (d, J = 1.5 Hz, 2H), 4.87 (s, 2H), 4.85 (s, 2H), 4.52 (q, J = 7.1 Hz, 6H), 3.60 (s, 3H), 3.57 (s, 3H), 2.12 (s, 6H), 1.61 (br s, 3H), 1.60 (br s, 3H), 1.28 (t, J = 6.8 Hz, 6H), 1.17 (t, J = 7.2 Hz, 3H)<br>LCMS (m/z)[M + H]$^+$ 718.6 |

AlexaFluor-488 FRET assay ligand
3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic Acid
5
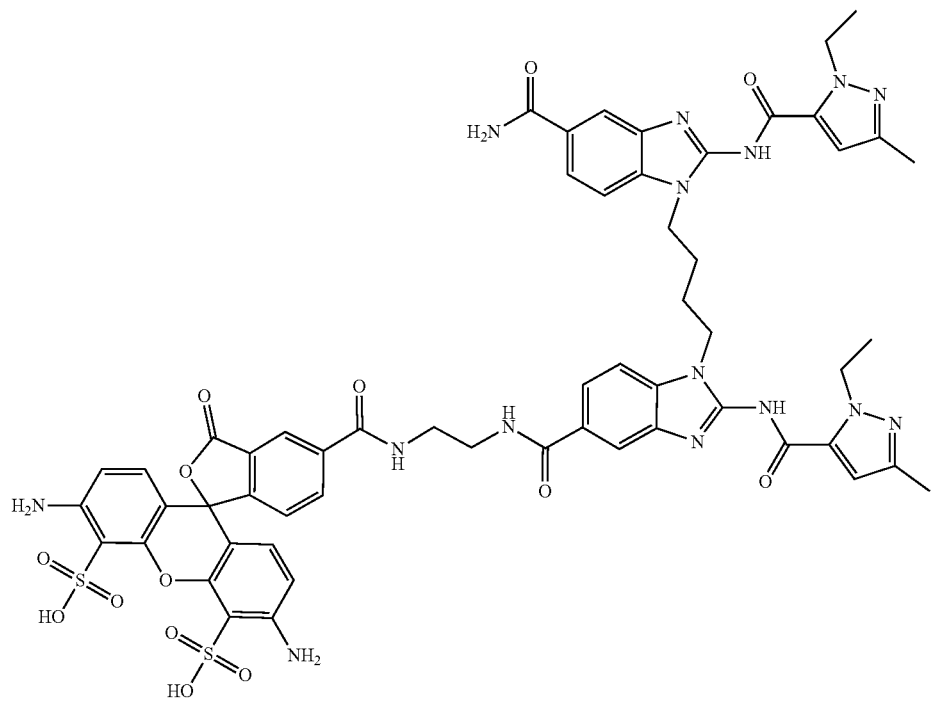 [SMILES: CCn1nc(C)cc1C(=O)Nc1nc2cc(C(N)=O)ccc2n1CCCCn1c(NC(=O)c2cc(C)nn2CC)nc2cc(C(=O)NCCNC(=O)c3ccc4c(c3)C(=O)OC43c4ccc(N)c(S(=O)(=O)O)c4Oc4c3ccc(N)c4S(=O)(=O)O)ccc21]
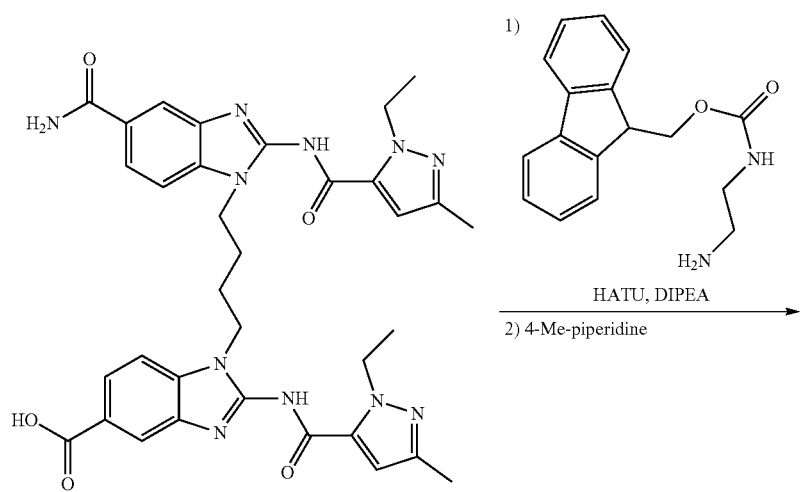

-continued
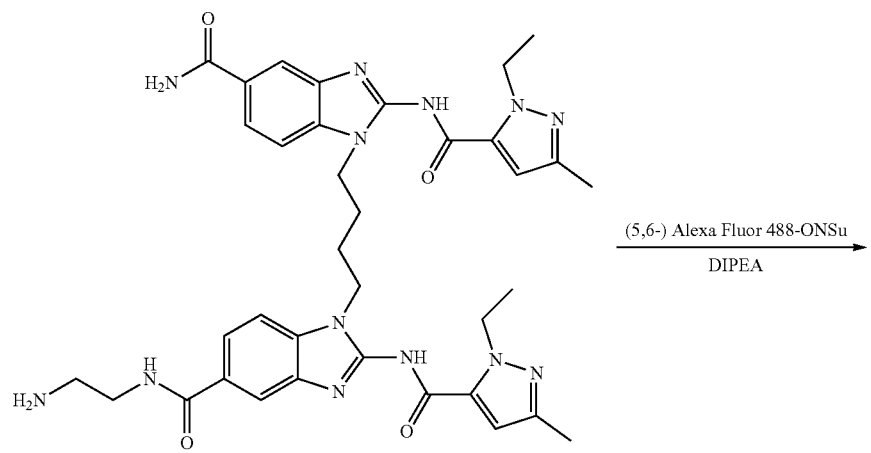
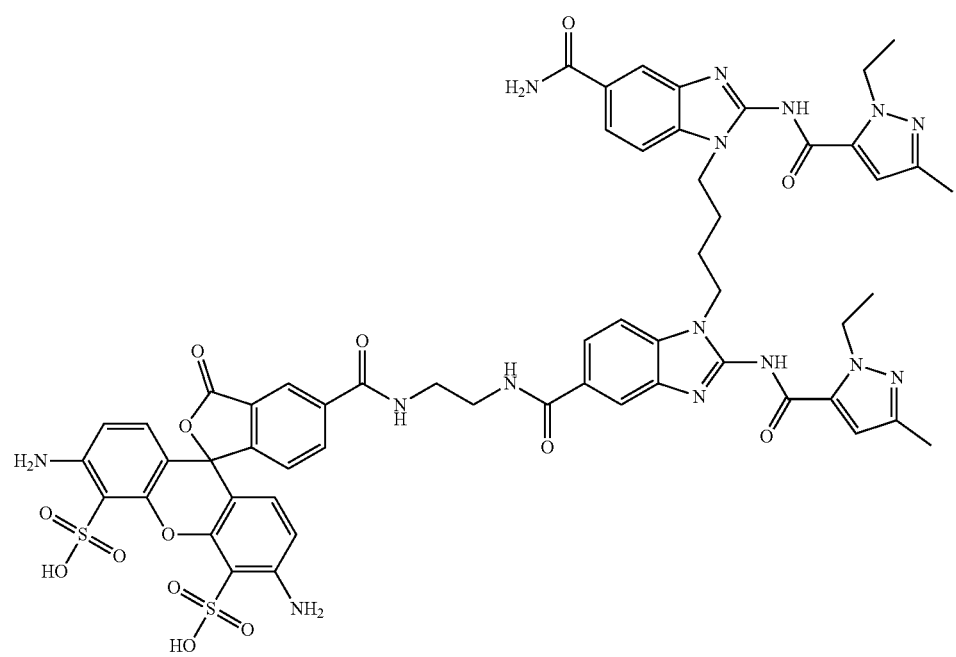

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic acid dihydrochloride Step 1: N-(2-Aminoethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide Trifluoroacetic Acid Salt

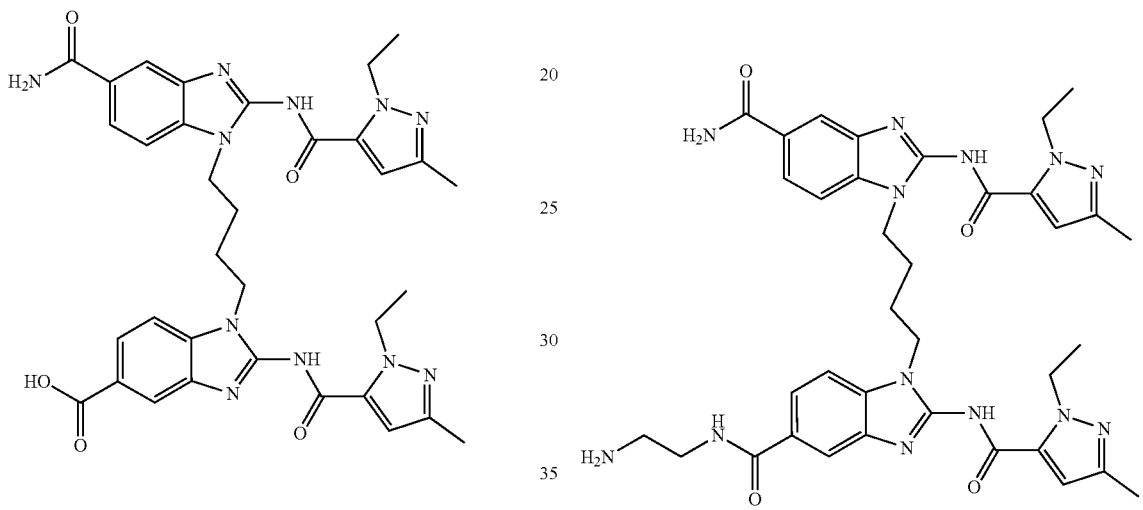

To methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate bis trifluoroacetic acid salt (400 mg, 0.434 mmol, Example 23 described in PCT publication No WO 2017175147) in THF (3.47 mL), MeOH (3.47 mL) and water (1.74 mL) at RT was added 8 M potassium hydroxide (1.09 mL, 8.68 mmol). After stirring overnight, the reaction was concentrated, and water was added. The mixture was acidified to pH 4-5 with 7 N aq HCl, and the resulting grey solid was collected by filtration to yield the title compound (335 mg, 0.423 mmol, 97% yield). $^1$H NMR (400 MHz, DMSO-$d_6$) δ ppm 12.82-12.95 (m, 3H), 8.08 (s, 1H), 7.99 (br. s., 2H), 7.83 (d, J=8.34 Hz, 1H), 7.78 (d, J=8.34 Hz, 1H), 7.58 (t, J=7.33 Hz, 2H), 7.36 (br. s., 1H), 6.60 (d, J=4.80 Hz, 2H), 4.58 (d, J=6.57 Hz, 4H), 4.29 (br. s., 4H) 2.10 (s, 6H), 1.88 (br. s., 4H), 1.31 (t, J=6.95 Hz, 6H); LCMS: Rt=0.83 min, [M+H]$^+$=680.5

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic acid (10 mg, 0.015 mmol) was dissolved (with sonication) in DMSO (300 μL) at 37° C. To this was added a solution of (9H-fluoren-9-yl)methyl (2-aminoethyl) carbamate hydrochloride (6.9 mg, 0.022 mmol) and HATU (7.6 mg, 0.020 mmol) in DMSO (100 μL) followed by DIEA (10 μL, 0.057 mmol). After stirring overnight, the reaction was diluted with DMF (600 μL), 4-methylpiperidine (400 μL) was added and the reaction was stirred at RT 1 hr. The mixture was concentrated, and the resulting residue diluted with 1:1 DMSO: MeOH (<1 mL) and purified by reverse-phase chromatography (Jupiter C18 preparative column, 10 mL/min), eluting with 30-100% (9:1 ACN:water) in water (0.1% TFA additive) to yield the title compound (8.45 mg, 10.1 μmol, 69% yield). LCMS: Rt=0.62 min, [M+H]$^+$=722.4

Step 2: 3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic Acid MeOH (<1 mL) and purified by reverse-phase chromatography (Jupiter C18 preparative column, 10 mL/min), eluting with 15-100% (9:1 ACN:water) in water (0.1% TFA additive). The early eluting positional isomer was obtained in high purity. In contrast, the fractions of the late eluting isomer also contained unreacted starting material. These fractions containing the impure late eluting isomer were pooled and concentrated. This residue was dissolved in 1:1

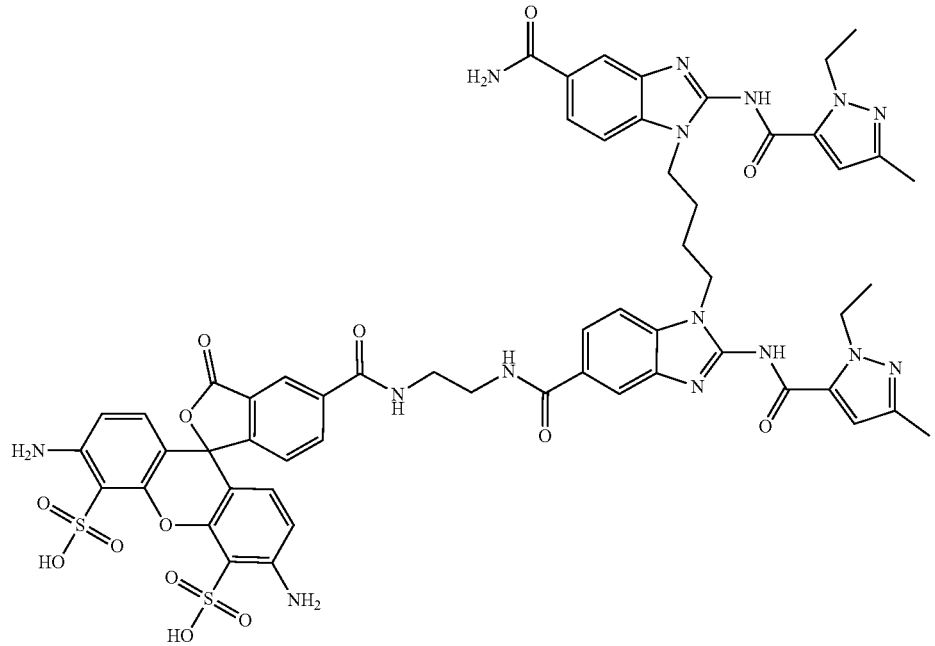 [SMILES: CCn1nc(C)cc1C(=O)Nc1nc2cc(C(N)=O)ccc2n1CCCCn1c(NC(=O)c2cc(C)nn2CC)nc2cc(C(=O)NCCNC(=O)c3ccc4c(c3)C(=O)OC43c4ccc(N)c(S(=O)(=O)O)c4Oc4c3ccc(N)c4S(=O)(=O)O)ccc21]

N-(2-Aminoethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide trifluoroacetic acid salt (8.45 mg, 10.1 µmol) was dissolved in DMF (200 µl) and added to solid (5,6-) Alexa Fluor 488-ONSu (5.00 mg, 7.92 µmol). The commercial Alexa Fluor 488-ONSu reagent was a mixture of the 5- and 6-positional isomers.

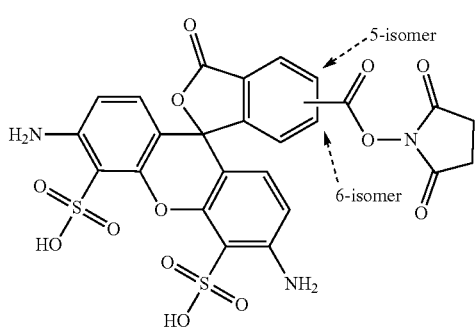

When solution was effected, DIPEA (2 µL, 0.01 mmol) was added, and the mixture was agitated (by vortex action) overnight in the absence of light. LCMS revealed formation of early and late eluting product peaks with the anticipated molecular weight ([M+H] 1238.6). The reaction was concentrated, and the residue was dissolved in 1:1 DMSO:

DMSO:MeOH (<1 mL) and purified by reverse-phase chromatography (Waters SymmetryPrep preparative column, 10 mL/min), eluting with 15-100% (9:1 ACN:water) in water (0.1% TFA additive) to yield the title compound (late eluting isomer, 1.94 mg, 1.49 µmol, 19% yield). LCMS:Rt=0.69 min, [M+H]$^+$=1238.6. Note that the putative structure of the title compound (5-isomer) is not based on rigorous structural determination but instead is based on previous observations that the 5-positional isomer is typically the later eluting isomer by reverse phase HPLC methods.

Biological Assays and Data

As stated above, the compounds of present invention are modulators of STING, and are useful in the treatment of diseases mediated by STING. The biological activities of the compounds of present invention can be determined using any suitable assay for determining the activity of a compound as a modulator of STING, as well as tissue and in vivo models.

The $pIC_{50}$ value for each compound was either reported in at least one experiment or the average of multiple experiments. It is understood that the data described herein may have reasonable variations depending on the specific conditions and procedures used by the person conducting the experiments.

Binding Assays (1) SPA

A radioligand binding assay was developed to measure interactions of compounds of Formula (I) and the carboxy terminal domain (CTD) of STING by competition with 3H-cGAMP (tritium-labeled cyclic guanine (2',5') monophosphate-adenine (3',5') monophosphate). See also Li et al. (*Nature Chemical Biology*, 10, 1043-1048, (2014)). A protein encoding the sequence of human STING spanning residues 149 to 379 (Gene ID 340061) was expressed in bacteria with a carboxy terminal Flag® peptide fused to AviTag™ for biotinylation and hexahistidine tag for affinity purification. The purified STING-Flag-AviTag-6×his protein was biotinylated to completion using the enzyme BirA (Beckett D. et al, *Protein Science*, 1999, 8:921-929). The relative potency of compounds of Formula (I) were determined by competition in equilibrium binding reactions containing 50 nM biotinylated-STING, 50 nM 3H-cGAMP, and 1.25 mg/mL streptavidin-coated scintillation proximity assay beads (Perkin Elmer) in phosphate-buffered saline buffer containing 0.02% (w/v) pluronic F127 and 0.02% (w/v) bovine serum albumin in Greiner white 384-well plates (catalog #784075) pre-stamped with 100-250 nL compound in neat DMSO. Binding reactions were incubated at room temperature for 60 minutes. Luminescence was measured (ViewLux™) and raw counts were expressed as % inhibition using the formula, $$\% I = \left(\frac{U - C1}{C2 - C1}\right) * 100$$

where U is the unknown value, C1 is the average response from complete inhibition by 10 μM cGAMP and C2 is the average of maximum response. Curve fitting was performed using the equation $$Y = A + \left[\frac{(B - A)}{1 + \left(\frac{10^x}{10^C}\right)^D}\right],$$

where A is the minimum response, B is the maximum response, C is the $\log_{10}*XC50$, D is the slope factor, and x is the $\log_{10}$ compound concentration [M] in ABASE XE. Under these conditions, the apparent inhibition constant for positive control compound cGAMP is 250 nM which is approximately fifty-fold greater than its actual affinity of 4-5 nM (Zhang X. et al, *Molecular Cell*, 2013, 51:1-10).

Using the SPA assay described above, the compounds of Examples 1-5 and 7-9, 11-14, 16, and 19, were tested and exhibited $pIC_{50}$ values in the range of 7 to beyond the upper assay limit of 7.4.

(2) FRET Assay

The binding potency of molecules to the C-terminal Domain (CTD) of human STING was determined using a competition binding assay. In this assay, STING (149-379) recombinant protein with a C-terminal biotinylated Avi-tag was employed. When bound to STING, an Alexa488-labeled orthosteric site probe (see pages 347-350 for the synthesis for the FRET assay ligand) accepts the 490 nm emission from Tb-Streptavidin-Avi-STING and an increase in fluorescence is measured at 520 nm. Molecules that compete for the probe binding site will result in a low 520 nm signal. The assay was run in Greiner black 384-well plates (Catalog #784076) containing 100 nL compounds in neat DMSO. A solution of 500 μM STING, 500 μM Streptavidin-Lumi4-Tb, and 100 nM Alexa488 probe in phosphate buffered saline containing 0.02% (w/v) pluronic F127 and 0.02% (w/v) bovine serum albumin was added to the plate using a Combi liquid handler (ThermoFisher). Plates were centrifuged for 1 min at 500 rpm, incubated for 15 min at room temperature, and then fluorescence emission at 520 nm following 337 nm laser excitation on an Envision plate reader (Perkin-Elmer) was measured. The $pIC_{50}$ values were determined using the standard four parameter curve fit in ABASE XE described above.

Using the FRET assay described above, Examples 1-42, 44-89, and 91-108 were tested and exhibited $pIC_{50}$ values in the range of 5.0 to beyond the upper limit of the assay at 9.9.

For example, $pIC_{50}$ of FRET assay for following examples are:

| Example No | FRET assay (pIC50) |
| --- | --- |
| 19 | 9.9 |
| 24 | 9.9 |
| 27 | >9.9 |
| 32 | >9.9 |
| 33 | >9.9 |
| 38 | 9.5 |
| 41 | >9.9 |
| 48 | >9.9 |
| 50 | >9.9 |
| 56 | 9.7 |
| 58 | 9.5 |
| 65 | 9.9 |

Cellular Functional Assays

The function of compounds of Formula (I) may be determined in cellular assays that detect STING specific activation and/or inhibition of IFNβ protein secretion.

(1) Functional Assay I (PBMC antagonist assay): Inhibition of STING by compounds of Formula (I) may be determined by measuring loss of interferon β secreted from peripheral blood mononuclear cells (PBMCs) stimulated with a STING agonist (Example 167 described in PCT publication No WO 2017175147) at the EC80 concentration or 77 nM Bacmam virus, a double stranded DNA virus, following treatment with different doses of compounds of Formula (I). Frozen PBMC cells were thawed and diluted in media (RPMI-1640 with 1.5 g/L NaHCO₃, 4.5 g/L glucose, 10 mM Hepes and 1 mM NaPyruvate, 10% FBS) to a final concentration of 6×10⁵ cells/mL. The PBMC-cell suspension was dispensed into a 384-well tissue culture plate (Griener 781073) at a density of 15,000 cells per well containing 250 nL of compound diluted in DMSO. The PBMC plates were incubated for 30 minutes prior to the addition of the STING agonist. The level of IFNβ protein secreted into the growth media was measured after 4 hours of incubation at 37° C. with the STING agonist using a human IFNβ electrochemiluminescence kit (Meso Scale Diagnostics) following the manufacturer's instructions. Percent inhibition was determined relative to controls that lack compound treatment or STING agonist at EC80 and plotted as a function of compound concentration to determine $PIC_{50}$ using a standard two-state model of receptor-ligand inhibition.

Using the Functional Assay I (PBMC antagonist assay) described above, Examples 1-4, 12, 13, 18-20, 23-25, 27, 29-34, 36, 38, 40, 41, 45, 47, 48, 50, 53, 54, 56-60, 63, 65-67, 69-72, 74, 76-89, 91, and 93-105 were tested. Examples 2, 3, 13, 18-20, 23-25, 27, 29-34, 38, 40, 41, 45, 47, 48, 50, 53, 54, 56-60, 63, 65-67, 69-72, 74, 76-89, 91, and 93-105 exhibited $pIC_{50}$ values in the range of 4.3 to beyond the upper limit of the assay at 8.1.

For example, pIC$_{50}$ of PBMC antagonist assay for following examples are:

| Example No | PE3MC antagonist assay (pIC50) |
|---|---|
| 19 | 6.2 |
| 24 | 6.3 |
| 27 | 6.4 |
| 32 | 5.2 |
| 33 | 5.1 |
| 38 | 8.1 |
| 41 | 7.2 |
| 48 | 5.4 |
| 50 | 7.1 |
| 56 | 5.3 |
| 58 | 5.5 |
| 65 | 5.9 |

(2) Functional Assay II (PBMC agonist assay): Activation of STING by compounds of Formula I was determined by measuring levels of IFNβ secreted from human peripheral blood mononuclear cells (PBMC) treated with different doses of compounds of Formula I. Frozen PBMC cells were thawed, resuspended in media (RPMI-1640 with 1.5 g/L NaHCO$_3$, 4.5 g/L glucose, 10 mM Hepes and 1 mM NaPyruvate, 10% FBS, 10 ng/mL lipopolysaccharide) to a final concentration of 3×10$^5$ cells/mL and dispensed into a 384-well tissue culture plate (Griener 781073) at a density of 15,000 cells per well containing 250 nL of compound diluted in DMSO. The level of IFNβ protein secreted into the growth media was measured after four hours of incubation at 37° C. using a human IFNβ electrochemiluminescence kit (Meso Scale Diagnostics) following the manufacturer's instructions. Percent activation was determined relative to control DMSO treatment and plot as a function of compound concentration to determine pEC50 using a standard model of receptor activation.

Using the Functional Assay II (PBMC agonist assay) described above, Examples 1-4, 12, 13, 18-20, 23-25, 27, 29-34, 36, 38, 40, 41, 45, 47, 48, 50, 53, 54, 56-60, 63, 65-67, 69-72, 74, 76-89, 91, 93, and 94-105 were tested. Examples 1-4, 12, 13, 81 and 88, exhibited pEC50 values in the range of 4.3 to 7.3. All other tested compounds exhibited pEC50 lower than 4.3.

(3) Functional Assay III (HEK WT agonist assay): Activation of STING in cells may be determined using a luciferase reporter assay in human embryonic kidney cells (HEK293T) co-transfected with plasmids expressing STING and the enzyme firefly luciferase driven by the interferon stimulated response element promoter (pISRE-Luc) (Agilent Technologies). Full-length human STING (Gene ID 340061) and full-length human cyclic guanine adenine synthase (cGAS) (reference sequence NM_138441.2) was cloned into mammalian cell expression vectors containing a cytomegalovirus promoter. Transfections were prepared using a cell suspension with Fugene® 6 following the manufacturer's instructions (3:1 Fugene®:DNA). Fifty microliters of the transfection suspension was dispensed into wells of a 384-well plate containing 250 nL of a compound of Formula (I). The final well composition contained 20,000 cells/well, 1 ng STING, 20 ng pISRE-Luc, and empty vector pcDNA3.1 (Invitrogen) to bring the total DNA concentration to 125 ng. Control wells expected to generate maximal activation of STING were cotransfected with a cGAS expression plasmid. Plates were sealed and incubated for 24 hours at 37° C. The expression of firefly luciferase was processed using Steady-Glo® luciferase assay system (Promega) and was analyzed using a standard laboratory luminescence plate reader. Data was normalized to luminescence response in the presence of cGAS, was plotted as a function of compound concentration, and fit using a standard model of receptor activation to derive the pEC$_{50}$.

Using the functional assay Ill (HEK WT agonist assay) described above, Examples 1-9, 11-22, 24-28, 35, 36, 39, 45-52 and 72-74 were tested. Examples 1-9, and 11-16, 24, 26-28, 35, 39, 48, 49, and 73, exhibited pEC$_{50}$ values in the range of 5.1 to beyond the upper limit of the assay at 8.1. Maximum responses ranged from 5 to 139% of the control wells.

(4) Functional assay IV (THP-1 antagonist assay)

Inhibition of STING by compounds of Formula I was determined by measuring loss of interferon β secreted from human PBMCs or immortalized THP-1 cells stimulated with a dsDNA containing baculovirus (Bacmam virus). THP-1 cells plated in round bottom 96-well plate at a density of 1×10$^5$ cells/well in media (RPMI-1640 with 1.5 g/L NaHCO$_3$, 4.5 g/L glucose, 10 mM Hepes and 1 mM NaPyruvate, 10% FBS, 1% PSF, 50 uM p-MeOH) were incubated with varying concentrations of STING antagonists for 60 minutes followed by addition of Bacmam virus (final MOI of 40 pfu/cell). The level IFNβ protein secreted into the growth media was measured after 6 and 20 hours of incubation at 37° C. using a human IFNβ electrochemiluminescence kit (Meso Scale Diagnostics) following the manufacturer's instructions. IFNβ (pg/ml) levels were converted to percent inhibition relative to controls that lack compound treatment (control 1) or Bacmam virus infection (Control 2) and fit using a sigmoidal four parameter least squares fit model to define the compound potency reported as pIC50. 100×(1−(Sample well−(control 2)/(Control 1−Control 2).

Using the functional assay IV (THP-1 antagonist assay) described above, Examples 1, 3-5, 7-9, 12-14, 16-20, 22, 24-26, 27, 29, 30, 35-41, 44, 45-56, 59, 60, and 62-77 were tested. Examples 1, 3, 4, 7-9, 12, 13, 16-20, 22, 24-27, 29, 30, 35, 37-39, 41, 44-56, 60, 62-75, and 77 and exhibited pIC$_{50}$ value of 4.3 to beyond the upper limit of the assay at 9.1.

For example, pIC$_{50}$ of THP-1 antagonist assay for following examples are:

| Example No | THP-1 antagonist assay (pIC50) |
|---|---|
| 19 | 6.7 |
| 24 | 4.6 |
| 27 | 7.3 |
| 38 | 8.9 |
| 41 | 8.6 |
| 48 | 4.9 |
| 50 | 8.9 |
| 56 | 6.9 |
| 65 | 7.6 |

What is claimed is:
1. A compound according to Formula (I):

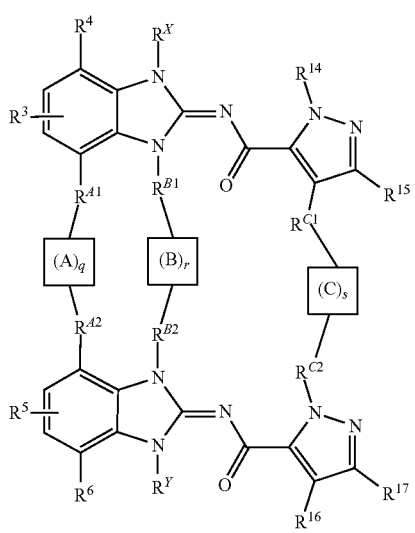

(I)

wherein:
q is 0 or 1;
r is 0 or 1;
s is 0 or 1;
wherein q+r+s=1 or 2;
when q is 0, $R^{A1}$ and $R^{A2}$ are each independently H, halogen, hydroxy, —O—P(O)(OH)$_2$, —O—P(O)(R$^I$)(R$^{II}$), —N(R$^e$)(R$^f$), —CO$_2$R$^f$, —N(R$^f$)COR$^b$, —N(R$^g$)SO$_2$(C$_1$-C$_4$alkyl)-N(R$^e$)(R$^f$), —N(R$^g$)CO(C$_1$-C$_4$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, —O—P(O)(OH)$_2$, —O—P(O)(R$^I$)(R$^{II}$), C$_1$-C$_4$alkoxy-, —N(R$^e$)(R$^f$), —CO$_2$(R), —CON(R$^e$)(R$^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from C$_1$-C$_4$alkyl, halogen, hydroxy, —O—P(O)(OH)$_2$, —O—P(O)(R$^I$)(R$^{II}$), amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)(R$^I$)(R$^{II}$), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$)(R$^{II}$), —C$_1$-C$_4$alkyl-(C$_1$-C$_4$alkoxy) and C$_1$-C$_4$alkoxy-(C$_1$-C$_4$alkoxy)-;
when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(R$^I$)(R$^{II}$), —OR$^c$, —NH, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;
when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR, —NR$^c$R$^d$, —CO$_2$R$^c$, —CONR$^c$R$^d$, —SO$_2$NR$^c$R$^d$, and —OCONR$^c$R$^d$;
when q is 1, $R^{A1}$ and $R^{A2}$ are each independently —CH$_2$—, —NR$^e$—, or —O—, and A, taken together with R$^{A1}$ and R$^{A2}$, forms a linking group, wherein A is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-,
wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —O—P(O)(OH)$_2$, —O—P(O)(R$^I$)(R$^{II}$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$,
and
the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$)(R$^H$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_1$-C$_4$alkoxy)-, —(C$_1$-C$_4$alkoxyl)-O—P(O)(OH)$_2$, —(C$_1$-C$_4$alkoxyl)-O—P(O)(R$^I$)(R$^H$), and C$_1$-C$_4$alkoxy-(C$_1$-C$_4$alkoxy);

when r is 1, R$^{B1}$ and R$^{B2}$ are each independently —CR$^d$R$^f$—, and B, taken together with R$^{B1}$ and R$^{B2}$, forms a linking group, wherein B is a bond or B is -halo(C$_1$-C$_{10}$alkyl)-, optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted C$_3$-C$_6$cycloalkyl, optionally substituted phenyl, optionally substituted 4-6 membered heterocycloalkyl, optionally substituted 5-6 membered heteroaryl, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl)-C$_1$-C$_4$alkyl-, wherein the alkyl moiety of said optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl-C$_1$-C$_4$alkyl)- is optionally substituted by 1-4 substituents each independently selected from —C$_1$-C$_4$alkyl, halogen, halo(C$_1$-C$_4$alkyl), —OH, —O—P(O)(OH)$_2$, —O—P(O)(R$^I$)(R$^H$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted C$_3$-C$_6$cycloalkyl, optionally substituted phenyl, optionally substituted 4-6 membered heterocycloalkyl, optionally substituted 5-6 membered heteroaryl, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl)-C$_1$-C$_4$alkyl- is optionally substituted by 1-4 substituents each independently selected from halogen, hydroxy, —O—P(O)(OH)$_2$, —O—P(O)(R$^I$)(R$^H$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)O—P(O)(OH)$_2$, —(C$_2$-C$_4$alkoxy)-O—P(O)(R$^I$)(R$^H$), and C$_1$-C$_4$alkoxy-(C$_1$-C$_4$alkoxy)-;

when s is 1, R$^{C1}$ and R$^{C2}$ are each —CH$_2$—, and C, taken together with R$^{C1}$ and R$^{C2}$, forms a linking group, wherein C is -halo(C$_1$-C$_{12}$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1 or 2 substituents each independently selected from halogen, halo(C$_1$-C$_4$alkyl), —OH, —O—P(O)(OH)$_2$, —O—P(O)(R$^I$)(R$^H$), —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, —O—P(O)(OH)$_2$, —O—P(O)(R$^I$)(R$^H$), amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)(R$^I$)(R$^H$), and C$_1$-C$_4$alkoxy-(C$_1$-C$_4$alkoxy)-;

R$^3$ and R$^5$ are each independently —CON(R$^d$)(R$^f$), or one of R$^3$ and R$^5$ is —CON(R$^d$)(R$^f$), and the other of R$^3$ and R$^5$ is H, COOH or —CO$_2$(R$^c$);

R$^4$ and R$^6$ are each independently selected from H, halogen, halo(C$_1$-C$_6$alkyl), halo(C$_1$-C$_6$alkoxy)-, hydroxy, —O—P(O)(OH)$_2$, —O—P(O)(R$^I$)(R$^H$), —NH$_2$, —NR$^c$R$^c$, —NR$^c$R$^d$—COR$^c$, —CO$_2$R$^c$, —N(R$^d$)COR$^c$, —N(R$^d$)SO$_2$R$^c$, —N(R$^g$)SO$_2$(C$_1$-C$_2$alkyl)-N(R$^h$)(R$^f$), —N(R$^g$)CO(C$_1$-C$_2$alkyl)-N(R$^h$)(R$^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-, wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from —OH, —O—P $(O)(OH)_2$, —O—$P(O)(R^I)(R^{II})$, —$OR^c$, —$NH_2$, —$NR^cR^e$, —$NR^cR^d$, —$CO_2H$, —$CO_2R^c$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^d SOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—$P(O)(OH)_2$, —O—$P(O)(R^I)(R^{II})$, amino, $(C_1$-$C_4$alkyl)amino-, $(C_1$-$C_4$alkyl)$(C_1$-$C_4$alkyl)amino-, $C_1$-$C_4$alkyl, halo($C_1$-$C_4$alkyl), hydroxy-($C_1$-$C_4$alkyl)-, —($C_1$-$C_4$alkyl)-O—$P(O)(OH)_2$, —($C_1$-$C_4$alkyl)-O—$P(O)(R^I)(R^{II})$, halo($C_1$-$C_4$alkoxy)-, $C_1$-$C_4$alkoxy-, hydroxy-($C_2$-$C_4$alkoxy)-, —($C_2$-$C_4$alkoxy)-O—$P(O)(OH)_2$, —($C_2$-$C_4$alkoxy)-O—$P(O)(R^I)(R^{II})$, $C_1$-$C_4$alkoxy-($C_1$-$C_4$alkoxy)-, —$COR^d$, —$CON(R^d)(R^f)$, and —$CO_2R^d$;

$R^{14}$ is optionally substituted $C_1$-$C_4$alkyl, wherein said optionally substituted $C_1$-$C_4$alkyl is optionally substituted by a substituent selected from —OR, —$NR^cR^d$, —$CO_2R$, —$CONR^cR^d$, —$SO_2NR^cR^d$, and —$OCONR^cR^d$;

$R^{16}$ is H, halogen, or $C_1$-$C_4$alkyl;

$R^{15}$ and $R^{17}$ are each independently H, cyclopropyl, or $C_1$-$C_4$alkyl;

$R^a$ is H, —$R^c$, —$COR^c$, —$CO_2H$, —$CO_2R^c$, —$SOR^c$, —$SO_2R^c$, —$CONH_2$, —$CONR^cR^d$, —$SO_2NH_2$, or —$SO_2NR^cR^d$;

each $R^b$ is independently $C_1$-$C_4$alkyl, halo($C_1$-$C_4$alkyl), —($C_1$-$C_4$alkyl)-OH, —($C_1$-$C_4$alkyl)-O—$P(O)(OH)_2$, —($C_1$-$C_4$alkyl)-O—$P(O)(R^I)(R^{II})$, —($C_1$-$C_4$alkyl)-O—($C_1$-$C_4$alkyl), —($C_1$-$C_4$alkyl)-$N(R^e)(R^f)$, —($C_1$-$C_4$alkyl)-O—$CO(C_1$-$C_4$alkyl), or —($C_1$-$C_4$alkyl)-CO—O—($C_1$-$C_4$alkyl);

each $R^c$ is independently $C_1$-$C_4$alkyl, halo($C_1$-$C_4$alkyl), —($C_1$-$C_4$alkyl)-OH, —($C_1$-$C_4$alkyl)-O—$P(O)(OH)_2$, —($C_1$-$C_4$alkyl)-O—$P(O)(R^I)(R^{II})$, —($C_1$-$C_4$alkyl)-O—($C_1$-$C_4$alkyl), —($C_1$-$C_4$alkyl)-$N(R^e)(R^f)$, —($C_1$-$C_4$alkyl)-O—$CO(C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the $C_3$-$C_6$cycloalkyl, phenyl, 4-6 membered heterocycloalkyl, 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, —O—$P(O)(OH)_2$, —O—$P(O)(R^I)(R^{II})$, amino, —($C_1$-$C_4$alkyl)$NH_2$, ($C_1$-$C_4$alkyl)amino-, ($C_1$-$C_4$alkyl)($C_1$-$C_4$alkyl)amino-, —$C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—$P(O)(OH)_2$, —($C_2$-$C_4$alkoxy)-O—$P(O)(R^I)(R^{II})$, $C_1$-$C_4$alkoxy-($C_1$-$C_4$alkoxy)-, —$COR^d$, —$CON(R^d)(R^f)$, and —$CO_2R^d$;

each $R^d$ is independently H or $C_1$-$C_4$alkyl;

each $R^e$ is independently H, $C_1$-$C_4$alkyl, —$CO(C_1$-$C_4$alkyl), —$OCO(C_1$-$C_4$alkyl), —$CO_2(C_1$-$C_4$alkyl), —($C_1$-$C_4$alkyl)$NH_2$, —($C_1$-$C_4$alkyl) $C_1$-$C_4$alkoxy, —CO-(optionally substituted 5-6 membered heterocycloalkyl), —$CO(C_1$-$C_4$alkyl)-(optionally substituted 5-6 membered heterocycloalkyl), —CO (optionally substituted 5-6 membered heteroaryl), or —$CO(C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—$P(O)(OH)_2$, —O—$P(O)(R^I)(R^{II})$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo ($C_1$-$C_4$alkoxy)-, $C_1$-$C_4$alkoxy-, hydroxy-($C_2$-$C_4$alkoxy)-, —($C_2$-$C_4$alkoxy) O—$P(O)(OH)_2$, —($C_2$-$C_4$alkoxy)-O—$P(O)(R^I)(R^{II})$, $C_1$-$C_4$alkoxy-($C_1$-$C_4$alkoxy)-, —$COR^d$, —$CON(R^d)(R^f)$, and —$CO_2R^d$;

each $R^f$ is independently H or $C_1$-$C_4$alkyl;

$R^g$ and $R^h$ are each independently H or $C_1$-$C_4$alkyl or $R^g$ and $R^h$, taken together with the atom or atoms through which they are connected, form a 5-6 membered ring;

and each occurrence of $R^I$ and $R^{II}$ are independently ($C_1$-$C_6$alkyl)oxy-;

one of $R^x$ and $R^y$ is $C_1$-$C_4$alkyl and the other one is H, or both $R^x$ and $R^y$ are independently $C_1$-$C_4$alkyl;

or a tautomer thereof;

or a salt thereof.

2. The compound or a tautomer or a salt thereof according to claim 1, wherein when s is 0, $R^{C1}$ and $R^{C2}$ are each H.

3. The compound or a tautomer or a salt thereof according to claim 1, wherein $R^4$ and $R^6$ are each H.

4. The compound or a tautomer or a salt thereof according to claim 1, wherein $R^{16}$ is H.

5. The compound or a tautomer or a salt thereof according to claim 1, wherein $R^{14}$, $R^{15}$ and $R^{17}$ are each independently $C_1$-$C_3$alkyl.

6. The compound or a tautomer or a salt thereof according to claim 1, wherein $R^x$ and $R^y$ are each independently methyl or ethyl.

7. The compound or a tautomer or a salt thereof according to claim 1, wherein $R^x$ and $R^y$ are both methyl.

8. The compound or a tautomer or a salt thereof according to claim 1, wherein one of $R^x$ and $R^y$ is methyl and the other one is H.

9. The compound or a tautomer or a salt thereof according to claim 1, having the structure of Formula I-2,

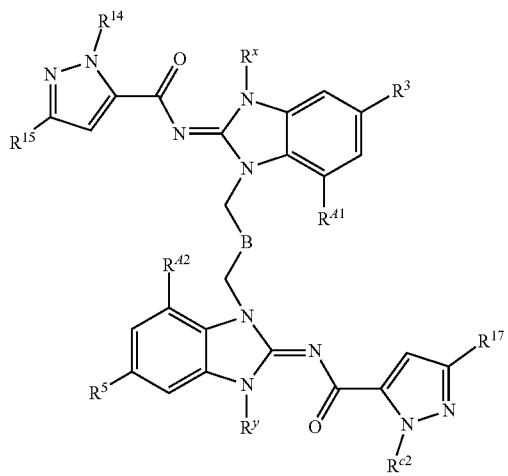

(I-2)

wherein
$R^{14}$, $R^{15}$, $R^{c2}$ and $R^{17}$ are independently $C_1$-$C_3$alkyl;
$R^{41}$ and $R^{42}$ are independently H, hydroxy, COOH, or optionally substituted ($C_1$-$C_6$alkyl)oxy-,
  wherein the alkyl of optionally substituted ($C_1$-$C_6$alkyl)oxy- is optionally substituted by 1-4 substituents each independently selected from the group consisting of hydroxy, —$CO_2(R^f)$, —$N(R^e)(R^f)$, optionally substituted phenyl, and optionally substituted 5-6 membered heterocycloalkyl,
    wherein said optionally substituted phenyl, or 5-6 membered heterocycloalkyl is optionally substituted by 1-4 substituents each independently selected from the group consisting of ($C_1$-$C_4$alkyl)oxy- and $C_1$-$C_4$alkyl;
$R^3$ and $R^5$ are each independently —CO—$N(R^d)(R^f)$,
each $R^d$, $R^e$ and $R^f$ are independently H or $C_1$-$C_3$alkyl;
B is substituted —$C_1$-$C_4$alkyl- or substituted —$C_2$-$C_4$alkenyl-,
  wherein the alkyl moiety of said substituted —$C_1$-$C_4$alkyl-, or substituted —$C_2$-$C_4$alkenyl-, is substituted by 1-4 substituents each independently selected from the group consisting of halogen, hydroxy, ($C_1$-$C_4$alkyl)oxy-, and $C_{1-4}$alkyl,
one of $R^x$ and $R^y$ is $C_1$-$C_4$alkyl and the other one is H, or both $R^x$ and $R^y$ are independently $C_1$-$C_4$alkyl;
or a tautomer thereof,
or a salt thereof.

10. The compound or a tautomer or a salt thereof according to claim 9, wherein $R^{14}$ and $R^{c2}$ are ethyl, and $R^{15}$ and $R^{17}$ are methyl.

11. The compound or a tautomer or a salt thereof according to claim 9, wherein $R^{41}$ and $R^{42}$ are each independently optionally substituted ($C_1$-$C_4$alkyl)oxy-, wherein the alkyl of optionally substituted ($C_1$-$C_4$alkyl)oxy- is optionally substituted by 1-2 substituents of hydroxy.

12. The compound or a tautomer or a salt thereof according to claim 9, wherein $R^3$ and $R^5$ are —CO—$NH_2$.

13. The compound or a tautomer or a salt thereof according to claim 9, wherein B is —$CH_2$—$CH_2$— substituted by 1-2 substituents of hydroxy.

14. The compound or a tautomer or a salt thereof according to claim 9,
wherein $R^{14}$, $R^{15}$, $R^{c2}$ and $R^{17}$ are independently methyl or ethyl;
one of $R^{41}$ and $R^{42}$ is H and the other one of $R^{41}$ and $R^{42}$ is optionally substituted ($C_1$-$C_4$alkyl)oxy-,
  wherein the alkyl of optionally substituted ($C_1$-$C_4$alkyl)oxy- is optionally substituted by 1-2 substituents of hydroxy;
$R^3$ and $R^5$ are both —CO—$NH_2$; and
B is substituted —$CH_2$—$CH_2$— or substituted —CH=CH—,
  wherein the substituted —$CH_2$—$CH_2$— or substituted —CH=CH— is substituted by 1-4 substituents each independently selected from the group consisting of hydroxy and $C_{1-2}$alkyl; and
one of $R^x$ and $R^y$ is $C_1$-$C_4$alkyl and the other one is H, or both $R^x$ and $R^y$ are independently $C_1$-$C_4$alkyl.

15. The compound or a tautomer or a salt thereof according to claim 9, which is
(E)-1-((2S,3S)-4-((E)-5-carbamoyl-2-((1-ethyl-3-methyl-1H-pyrazole-5-carbonyl)imino)-7-(3-hydroxypropoxy)-3-methyl-2,3-dihydro-1H-benzo[d]imidazol-1-yl)-2,3-dihydroxybutyl)-2-((1-ethyl-3-methyl-1H-pyrazole-5-carbonyl)imino)-7-methoxy-3-methyl-2,3-dihydro-1H-benzo[d]imidazole-5-carboxamide having the structure of

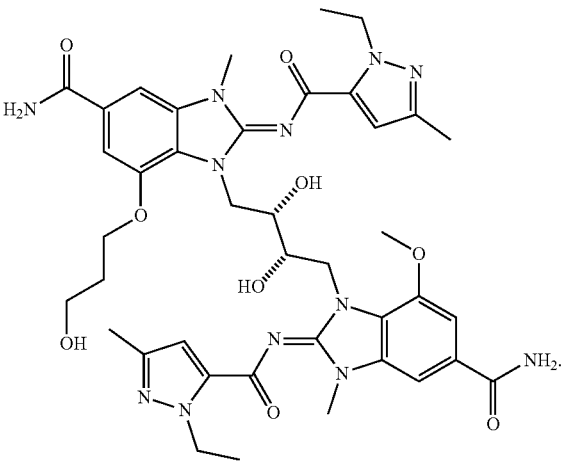 [SMILES: CCn1nc(C)cc1C(=O)/N=c1\n(C)c2cc(C(N)=O)cc(OC)c2n1C[C@H](O)[C@@H](O)Cn1/c(=N/C(=O)c2cc(C)nn2CC)n(C)c2cc(C(N)=O)cc(OCCCO)c21]

16. The compound or a tautomer or a salt thereof according to claim 1, wherein the salt is a pharmaceutically acceptable salt of said compound.

17. A pharmaceutical composition comprising the compound or a tautomer or a pharmaceutically acceptable salt thereof according to claim 16 and at least one pharmaceutically acceptable excipient.

18. A method of treating a STING-mediated disease or disorder comprising administering a therapeutically effective amount of the compound or a tautomer or a pharmaceutically acceptable salt thereof according to claim 16 to a human in need thereof, wherein the STING-mediated disease or disorder is selected from the group consisting of systemic lupus erythematosus (SLE), cutaneous lupus, lupus nephritis, psoriasis, diabetes mellitus including insulin-dependent diabetes mellitus (IDDM), dermatomyositis, systemic sclerosis (scleroderma), and Sjögren's syndrome (SS), rheumatoid arthritis, psoriatic arthritis, STING associated vasculitis with onset at infancy (SAVI), Aicardi Goutieres syndrome (AGS), chilblain lupus, and mixed connective tissue disease.

19. A method of treating a STING-mediated disease or disorder comprising administering a therapeutically effective amount of the compound or a tautomer or a pharmaceutically acceptable salt thereof according to claim 16 to a human in need thereof, wherein the STING-mediated disease or disorder is chronic pulmonary disease, pulmonary fibrosis, or asthma.

* * * * *